(12) United States Patent
Dota et al.

(10) Patent No.: US 11,225,470 B2
(45) Date of Patent: Jan. 18, 2022

(54) TETRAZOLINONE COMPOUNDS AND ITS USE AS PEST CONTROL AGENTS

(71) Applicant: SUMITOMO CHEMICAL COMPANY, LIMITED, Tokyo (JP)

(72) Inventors: Koichiro Dota, Takarazuka (JP); Yuki Sugita, Takarazuka (JP); Yuki Akioka, Takarazuka (JP); Nao Maehata, Takarazuka (JP); Sadayuki Arimori, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 366 days.

(21) Appl. No.: 16/463,505

(22) PCT Filed: Nov. 28, 2017

(86) PCT No.: PCT/JP2017/042660
§ 371 (c)(1),
(2) Date: May 23, 2019

(87) PCT Pub. No.: WO2018/097318
PCT Pub. Date: May 31, 2018

(65) Prior Publication Data
US 2019/0382385 A1    Dec. 19, 2019

(30) Foreign Application Priority Data

Nov. 28, 2016  (JP) .............................. JP2016-229798
Jul. 24, 2017  (JP) .............................. JP2017-142507

(51) Int. Cl.
*C07D 405/12*    (2006.01)
*C07D 257/04*    (2006.01)
(Continued)

(52) U.S. Cl.
CPC ......... *C07D 405/12* (2013.01); *A01N 43/713* (2013.01); *A01N 43/90* (2013.01); *C07D 257/04* (2013.01); *C07D 401/12* (2013.01); *C07D 403/12* (2013.01); *C07D 409/12* (2013.01); *C07D 417/12* (2013.01); *C07D 471/04* (2013.01); *C07D 498/04* (2013.01)

(58) Field of Classification Search
None
See application file for complete search history.

(56) References Cited

U.S. PATENT DOCUMENTS

2011/0130415 A1   6/2011  Singh et al.
2016/0249617 A1   9/2016  Dota

FOREIGN PATENT DOCUMENTS

CN    105683169 A    6/2016
EP    2927218 A1     10/2015
(Continued)

OTHER PUBLICATIONS

Indian Examination Report issued in the Indian Patent Application No. 201947024291 dated Nov. 26, 2020.
(Continued)

*Primary Examiner* — Alton N Pryor
(74) *Attorney, Agent, or Firm* — Birch, Stewart, Kolasch & Birch, LLP

(57) ABSTRACT

The present invention provides a tetrazolinone represented by formula (I) and a pest control agent comprising the same, and their use thereof. Formula (I) [wherein, $W^1$ represents an oxygen atom or a sulfur atom; $W^2$ represents a hydrogen atom, or a C1-C6 chain hydrocarbon group; $R^{15}$ and $R^{16}$ represent a halogen atom and the like; u is 0, 1, 2 or 3; the combination of E, G, $X^1$, $Y^1$ and $Z^1$ represents any one of the combinations of the following a and the like: a: a combination wherein E represents #—C($X^1$)($Y^1$)—O—N=C($Z^1$)—, #—C($X^1$)($Y^1$)—S—N=C($Z^1$)—, #—C($X^1$)($Y^1$)—O—N=C($Z^1$)—O—CH$_2$—, #—C($X^1$)($Y^1$)—O—N=C($Z^1$)—S—CH$_2$—, #—C($X^1$)($Y^1$)—S—N=C($Z^1$)—O—CH$_2$—, #—C($X^1$)($Y^1$)—S—N=C($Z^1$)—S—CH$_2$—, #—C($Z^1$)=N—N=C($Z^2$)—, #—C($X^1$)=C($Y^1$)—C($Z^1$)=N—O—CH$_2$— or #—C($X^1$)=C($Y^1$)—C($Z^1$)=N—S—CH$_2$—; G represents a C1-C6 chain hydrocarbon group, a (C1-C6 alkoxy)C1-C6 alkyl group, a (C1-C6 alkylthio)C1-C6 alkyl group {the C1-C6 chain hydrocarbon group, the (C1-C6 alkoxy)C1-C6 alkyl group, and the (C1-C6 alkylthio)C1-C6 alkyl group may have one or more substituents selected from Group S} or $R^1$-$T^1$-, $X^1$ and $Y^1$, which are identical to or different from each other, independently represents substituents selected from Group T, and $Z^1$ represents a substituent selected from Group V.]

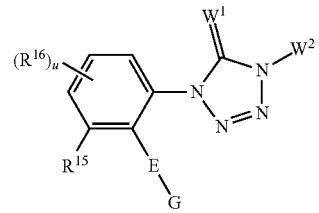

(I)

13 Claims, No Drawings

(51) Int. Cl.
*C07D 401/12* (2006.01)
*C07D 403/12* (2006.01)
*C07D 409/12* (2006.01)
*C07D 417/12* (2006.01)
*C07D 471/04* (2006.01)
*C07D 498/04* (2006.01)
*A01N 43/713* (2006.01)
*A01N 43/90* (2006.01)

(56) References Cited

FOREIGN PATENT DOCUMENTS

| | | |
|---|---|---|
| JP | 9-208565 A | 8/1997 |
| JP | 2016-204377 A | 12/2016 |
| JP | 2017-214366 A | 12/2017 |
| JP | 2018-58810 A | 4/2018 |
| WO | WO 96/36229 A1 | 11/1996 |
| WO | WO 2014/051165 A1 | 4/2014 |
| WO | WO 2015/064727 A1 | 5/2015 |
| WO | WO 2016/088747 A1 | 6/2016 |

OTHER PUBLICATIONS

International Preliminary Report on Patentability and English translation of the Written Opinion of the International Searching Authority for International Application No. PCT/JP2017/042660, dated Jun. 6, 2019.

International Search Report for International Application No. PCT/JP2017/042660, dated Apr. 4, 2018.

Chinese First Office Action and Search Report (including an English translation of thereof) issued in the corresponding Chinese Patent Application No. 201780072998.8 dated Apr. 21, 2021.

Japanese Office Action for Japanese Application No. 2019-526018, dated Aug. 10. 2021, with English translation.

TETRAZOLINONE COMPOUNDS AND ITS USE AS PEST CONTROL AGENTS

TECHNICAL FIELD

This application claims priority to and the benefit of Japanese Patent Application Nos. 2016-229798 filed Nov. 28, 2016 and 2017-142507 filed Jul. 24, 2017, the entire contents of which are incorporated herein by reference.

The present invention relates to an agent for controlling pests and its use.

BACKGROUND ART

Heretofore, various compounds have been developed to control pests (see Patent Document 1).

CITATION LIST

Patent Literature

PTL 1: WO 2014/051165 pamphlet

SUMMARY OF INVENTION

Technical Problem

An object of the present invention is to provide a compound having an excellent efficacy for controlling pests.

Solution to Problem

The present inventors have intensively studied to find a compound having an excellent efficacy for controlling pests, and as a result, found a compound of the below-mentioned formula (I), which has an excellent efficacy for controlling pests, thereby completed the present invention.

That is, the present invention includes the followings.

[1] A compound represented by a formula (I):

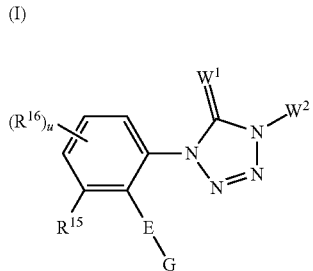

(I)

[Chem.1]

[wherein, $W^1$ represents an oxygen atom or a sulfur atom, $W^2$ represents a hydrogen atom, a C1-C6 chain hydrocarbon group, a C3-C6 cycloalkyl group {the C1-C6 chain hydrocarbon group and the C3-C6 cycloalkyl group may have one or more substituents selected from Group I}, a phenyl group, or a benzyl group {the phenyl group and the benzyl group may have one or more substituents selected from Group O}, $R^{15}$ represents a halogen atom, a nitro group, a cyano group, a C1-C6 chain hydrocarbon group, a C3-C6 cycloalkyl group, a C1-C6 alkoxy group, a C1-C6 alkylthio group, a C3-C6 cycloalkyloxy group, or a C3-C6 cycloalkylthio group {the C1-C6 chain hydrocarbon group, the C3-C6 cycloalkyl group, the C1-C6 alkoxy group, the C1-C6 alkylthio group, the C3-C6 cycloakyloxy group, and the C3-C6 cycloalkylthio group may have one or more substituents selected from Group I}, $R^{16}$ represents a halogen atom, a nitro group, a cyano group, a formyl group, a carboxy group, a hydroxy group, a sulfanyl group, an amino group, a pentafluorosulfanyl group, a C1-C6 chain hydrocarbon group, a C3-C6 cycloalkyl group, a C1-C6 alkoxy group, a C1-C6 alkylthio group, a C3-C6 cycloakyloxy group, a C3-C6 cycloalkylthio group, a C2-C6 alkenyloxy group, a C2-C6 alkynyloxy group, a C2-C6 alkenylthio group, a C2-C6 alkynylthio group, a (C1-C5 alkyl)carbonyl group, a (C1-C5 alkyl)carbonyloxy group, a (C1-C5 alkyl)carbonylthio group, a (C1-C5 alkoxy)carbonyl group, a C1-C6 alkylamino group, a di(C1-C6 alkyl)amino group, a C1-C4 alkylsulfonyl group, a C1-C4 alkylsulfinyl group, a (C1-C6 alkoxy)C1-C6 alkyl group, or a (C1-C6 alkylthio)C1-C6 alkyl group {the C1-C6 chain hydrocarbon group, the C3-C6 cycloalkyl group, the C1-C6 alkoxy group, the C1-C6 alkylthio group, the C3-C6 cycloakyloxy group, the C3-C6 cycloalkylthio group, the C2-C6 alkenyloxy group, the C2-C6 alkynyloxy group, the C2-C6 alkenylthio group, the C2-C6 alkynylthio group, the (C1-C5 alkyl)carbonyl group, the (C1-C5 alkyl)carbonyloxy group, the (C1-C5 alkyl)carbonylthio group, the (C1-C5 alkoxy)carbonyl group, the C1-C6 alkylamino group, the di(C1-C6 alkyl)amino group, the C1-C4 alkylsulfonyl group, the C1-C4 alkylsulfinyl group, the (C1-C6 alkoxy)C1-C6 alkyl group, and the (C1-C6 alkylthio)C1-C6 alkyl group may have one or more substituents selected from Group I}, u is 0, 1, 2 or 3, when u is 2 or 3, a plurality of $R^{16}$ may be independently identical to or different from each other.

The combination of E, G, $X^1$, $Y^1$ and $Z^1$ represents any one of the combinations of the following a to i.

a: a combination wherein E represents #—C($X^1$)($Y^1$)—O—N=C($Z^1$)—, #—C($X^1$)($Y^1$)—S—N=C($Z^1$)—, #—C($X^1$)($Y^1$)—O—N=C($Z^1$)—O—CH$_2$—, #—C($X^1$)($Y^1$)—O—N=C($Z^1$)—S—CH$_2$—, #—C($X^1$)($Y^1$)—S—N=C($Z^1$)—O—CH$_2$—, #—C($X^1$)($Y^1$)—S—N=C($Z^1$)—S—CH$_2$—, #—C($Z^1$)=N—N=C($Z^2$)—, #—C($X^1$)=C($Y^1$)—C($Z^1$)=N—O—CH$_2$— or #—C($X^1$)=C($Y^1$)—C($Z^1$)=N—S—CH$_2$—, G represents a C1-C6 chain hydrocarbon group, a (C1-C6 alkoxy)C1-C6 alkyl group, a (C1-C6 alkylthio)C1-C6 alkyl group {the C1-C6 chain hydrocarbon group, the (C1-C6 alkoxy)C1-C6 alkyl group, and the (C1-C6 alkylthio)C1-C6 alkyl group may have one or more substituents selected from Group S} or $R^1$-$T^1$-, each of $X^1$ and $Y^1$, which are identical to or different from each other, independently represents substituents selected from Group T, and $Z^1$ represents a substituent selected from Group V.

b: a combination wherein E represents an oxygen atom, #—O—N=C($Z^1$)—C($Z^2$)=N—S—CH$_2$—, #—N=C($Z^1$)—S—CH$_2$—, #—N=C($Z^1$)—O—CH$_2$—, #—O—N=C($Z^1$)—S—CH$_2$—, #—O—N=C($Z^1$)—O—CH$_2$—, #—N($X^1$)—O—CH$_2$—, #—O—C($Z^1$)=N—O—CH$_2$—, #—N=C(S$X^3$)—S—CH$_2$—, #—N=C(O$X^3$)—O—CH$_2$—, #—N=C(S$X^3$)—O—CH$_2$— or #—N=C(O$X^3$)—S—CH$_2$—, G represents a C1-C6 chain hydrocarbon group, a (C1-C6 alkoxy)C1-C6 alkyl group, a (C1-C6 alkylthio)C1-C6 alkyl group {the C1-C6 chain hydrocarbon group, the (C1-C6 alkoxy)C1-C6 alkyl group, and the (C1-C6 alkylthio)C1-C6 alkyl group may have one or more substituents selected from Group S} or $R^1$-$T^2$, $X^1$ represents a substituent selected from Group T, and $Z^1$ represents a substituent selected from Group V.

c: a combination wherein E represents a sulfur atom, #—S—N=C($Z^1$)—C($Z^2$)=N—O—CH$_2$— or #—S—N=C($Z^1$)—C($Z^2$)=N—S—CH$_2$—, G represents $R^1$-$T^7$, and $Z^1$ represents a substituent selected from Group V.

d: a combination wherein E represents #—C($Z^1$)=N—N=C($Z^3$)—O—CH$_2$— or #—C($Z^1$)=N—N=C($Z^3$)—S—CH$_2$—,
G represents $R^8$-$T^3$-, $R^9$-$T^4$-, $R^{10}$-$T^5$- or $R^{14}$-$T^6$-, and $Z^1$ represents a substituent selected from Group V.

e: a combination wherein E represents #—C($Z^1$)=N—N=C($V^1$)—O—CH$_2$— or #—C($Z^1$)=N—N=C($V^1$)—S—CH$_2$—, G represents $R^1$-$T^1$, and $Z^1$ represents a substituent selected from Group V.

f: a combination wherein E represents #—C($X^1$)($Y^1$)—O—N=C($Z^1$)—, #—C($X^1$)($Y^1$)—S—N=C($Z^1$)—, #—C($X^1$)($Y^1$)—O—N=C($Z^1$)—O—CH$_2$—, #—C($X^1$)($Y^1$)—O—N=C($Z^1$)—S—CH$_2$—, #—C($X^1$)($Y^1$)—S—N=C($Z^1$)—O—CH$_2$— or #—C($X^1$)($Y^1$)—S—N=C($Z^1$)—S—CH$_2$—, G and $X^1$ together with carbon atom(s) to which they are bound form a C3-C10 alicyclic hydrocarbon group or a 3 to 10 membered non-aromatic heterocyclic group {the C3-C10 alicyclic hydrocarbon group, and the 3 to 10 membered non-aromatic heterocyclic group may have one or more substituents selected from Group J}, $Y^1$ represents a substituent selected from Group T, and $Z^1$ represents a substituent selected from Group V.

g: a combination wherein E represents #—C($X^1$)($Y^1$)—O—N=C($Z^1$)—, #—C($X^1$)($Y^1$)—S—N=C($Z^1$)—, #—C($X^1$)($Y^1$)—O—N=C($Z^1$)—O—CH$_2$—, #—C($X^1$)($Y^1$)—O—N=C($Z^1$)—S—CH$_2$—, #—C($X^1$)($Y^1$)—S—N=C($Z^1$)—O—CH$_2$— or #—C($X^1$)($Y^1$)—S—N=C($Z^1$)—S—CH$_2$—, G, $X^1$ and $Y^1$ together with carbon atoms to which they are bound form a C6-C10 aromatic hydrocarbon group, or 5 to 10 membered aromatic heterocyclic group {the C6-C10 aromatic hydrocarbon group, and the 5 to 10 membered aromatic heterocyclic group may have one or more substituents selected from Group P}, and $Z^1$ represents a substituent selected from Group V.

h: a combination wherein E represents #—C($X^1$)=C($Y^1$)—C($Z^1$)=N—O—CH$_2$—, #—C($X^1$)=C($Y^1$)—C($Z^1$)=N—S—CH$_2$— or #—N($X^1$)—O—CH$_2$—, G and $X^1$ together carbon atoms to which they are bound form, C3-C10 alicyclic hydrocarbon group or 3 to 10 membered non-aromatic heterocyclic group {the C3-C10 alicyclic hydrocarbon group, and the 3 to 10 membered non-aromatic heterocyclic group may have one or more substituents selected from Group J}, $Y^1$ represents a substituent selected from Group T, $Z^1$ represents a substituent selected from Group V.

i: a combination wherein E represents #—C($Z^1$)=N—N=C($Z^3$)—O—CH$_2$—, #—C($Z^1$)=N—N=C($Z^3$)—S—CH$_2$—, #—C($Z^1$)=N—N=C($V^1$)—O—CH$_2$— or #—C($Z^1$)=N—N=C($V^1$)—S—CH$_2$—, G and $Z^1$ together with carbon atoms to which they are bound form a C3-C10 alicyclic hydrocarbon group or a 3 to 10 membered non-aromatic heterocyclic group {the C3-C10 alicyclic hydrocarbon group and the 3 to 10 membered non-aromatic heterocyclic group may have one or more substituents selected from Group U}.

# represents a binding site to G, $Z^2$ represents a hydrogen atom, a halogen atom, a cyano group, an amino group, a nitro group, a C1-C6 chain hydrocarbon group, a C3-C6 cycloalkyl group, a C1-C6 alkoxy group, a C1-C6 alkylthio group, a (C1-C6 alkoxy)C1-C6 alkyl group, a (C1-C6 alkylthio)C1-C6 alkyl group, a C2-C6 cyanoalkyl group, a C1-C6 alkylamino group, a di(C1-C6 alkyl)amino group, a (C1-C5 alkoxy)carbonyl group {the C1-C6 chain hydrocarbon group, the C3-C6 cycloalkyl group, the C1-C6 alkoxy group, the C1-C6 alkylthio group, the (C1-C6 alkoxy)C1-C6 alkyl group, the (C1-C6 alkylthio)C1-C6 alkyl group, the C2-C6 cyanoalkyl group, the C1-C6 alkylamino group, the di(C1-C6 alkyl)amino group and the (C1-C5 alkoxy)carbonyl group may have one or more substituents selected from Group I}, a pyridyl group, an oxetanyl group, a benzyl group {the pyridyl group, the oxetanyl group and the benzyl group may have one or more substituents selected from Group O}, —C(=NOR$^A$)—C(=NOR$^B$)R$^C$ or —CR$^{11}$=N—O—R$^{12}$, $Z^3$ represents a hydrogen atom, a halogen atom, a cyano group, a nitro group, a C1-C6 chain hydrocarbon group, a C3-C6 cycloalkyl group, a C1-C6 alkoxy group, a C1-C6 alkylthio group, a (C1-C6 alkoxy)C1-C6 alkyl group, a (C1-C6 alkylthio)C1-C6 alkyl group, a C2-C6 cyanoalkyl group, (C1-C5 alkoxy)carbonyl group {the C1-C6 chain hydrocarbon group, the C3-C6 cycloalkyl group, the C1-C6 alkoxy group, the C1-C6 alkylthio group, the (C1-C6 alkoxy)C1-C6 alkyl group, the (C1-C6 alkylthio)C1-C6 alkyl group, the C2-C6 cyanoalkyl group and the (C1-C5 alkoxy)carbonyl group may have one or more substituents selected from Group I}, a pyridyl group, an oxetanyl group, a benzyl group {the pyridyl group, the oxetanyl group and the benzyl group may have one or more substituents selected from Group O}, —C(=NOR$^A$)—C(=NOR$^B$)R$^C$ or —CR$^{11}$=N—O—R$^{12}$, $V^1$ represents an amino group, a C1-C6 alkylamino group, a di(C1-C6 alkyl)amino group {the C1-C6 alkylamino group and the di(C1-C6 alkyl)amino group may have one or more substituents selected from Group I} or —CR$^{11}$=N—O—R$^{12}$, $R^{11}$ represents a phenyl group, a benzyl group {the phenyl group and the benzyl group may have one or more substituents selected from Group N}, a hydrogen atom, a halogen atom, a nitro group, a cyano group, a C1-C6 alkyl group, a C3-C6 cycloalkyl group, a C1-C6 alkoxy group or C1-C6 alkylthio group {the C1-C6 alkyl group, the C3-C6 cycloalkyl group, the C1-C6 alkoxy group and the C1-C6 alkylthio group may have one or more halogen atoms}, Each of $R^{12}$, $R^A$, $R^B$, and $R^C$, which are identical to or different from each other, independently represents a phenyl group, a benzyl group, a pyridyl group, a pyrazolyl group, a pyrimidinyl group {the phenyl group, the benzyl group, the pyridyl group, the pyrazolyl group and the pyrimidinyl group may have one or more substituents selected from Group N}, a C1-C6 chain hydrocarbon group, a C3-C6 cycloalkyl group, a (C3-C6 cycloalkyl)C1-C6 alkyl group, a (C1-C6 alkoxy)C2-C6 alkyl group, a (C1-C6 alkylthio)C1-C6 alkyl group, a cyano(C1-C6 alkyl) group {the C1-C6 chain hydrocarbon group, the C3-C6 cycloalkyl group, the (C3-C6 cycloalkyl)C1-C6 alkyl group, the (C1-C6 alkoxy)C2-C6 alkyl group, the (C1-C6 alkylthio)C1-C6 alkyl group and the cyano(C1-C6 alkyl) group may have one or more halogen atoms} or a hydrogen atom, $X^3$ represents a C2-C6 alkenyl group, a C2-C6 alkynyl group, a C3-C6 cycloalkyl group, a (C1-C6 alkoxy)C2-C6 alkyl group, a (C1-C6 alkylthio)C2-C6 alkyl group, a C2-C6 cyanoalkyl group, a [(C1-C6 alkyl)amino]C2-C6 alkyl group, a [di(C1-C6 alkyl)amino]C2-C6 alkyl group {the C2-C6 alkenyl group, the C2-C6 alkynyl group, the C3-C6 cycloalkyl group, the (C1-C6 alkoxy)C2-C6 alkyl group, the (C1-C6 alkylthio)C2-C6 alkyl group, the C2-C6 cyanoalkyl group, the [(C1-C6 alkyl)amino]C2-C6 alkyl group, and the [di(C1-C6 alkyl)amino]C2-C6 alkyl group may have one or more halogen atoms}, a phenyl group, a pyridyl group, a benzyl group {the phenyl group, the pyridyl group and the benzyl group may have one or more substituents selected from Group O} or a hydrogen atom, $R^1$ represents a C3-C10 alicyclic hydrocarbon group, a 3 to 10 membered non-aromatic heterocyclic group {the C3-C10 alicyclic hydrocarbon group and the 3 to 10 membered non-aromatic heterocyclic group may have one or more substituents selected from Group J}, a C6-C10 aromatic hydrocarbon group or a 5 to 10 membered aromatic heterocyclic group {the C6-C10 aromatic hydrocarbon group and the 5 to 10 membered aromatic heterocyclic group may have one or more substituents selected from Group P}, $T^1$ represents a single bond, an oxygen atom, —S(O)$_m$—, —O—S(O)$_m$—*, —NR$^{11}$—, —(CR$^2$R$^3$)$_n$—, —(CR$^2$R$^3$)$_n$—O—*, —O(CR$^2$R$^3$)$_n$—*, —(CR$^2$R$^3$)$_n$S(O)$_m$—*, —S(O)$_m$(CR$^2$R$^3$)$_n$—*, —C(X$^2$)—, —C(X$^2$)—O—*, —O—C(X$^2$)—* or —CR$^4$=CR$^5$—,

* represents a binding site to E, m is 0, 1 or 2, n is 1, 2, 3 or 4, when n is 2, 3 or 4, a plurality of $R^2$ are independently identical to or different from each other, and a plurality of $R^3$ are independently identical to or different from each other.

$X^2$ represents an oxygen atom or a sulfur atom,

Each of $R^2$ and $R^3$, which are identical to or different from each other, independently represents a hydrogen atom, a halogen atom, a nitro group, a cyano group, a C1-C4 chain hydrocarbon group, a C1-C4 alkoxy group, a C1-C4 alkylthio group, a C2-C4 alkenyloxy group, a C2-C4 alkenylthio group, a C2-C4 alkynyloxy group or a C2-C4 alkynylthio group {the C1-C4 chain hydrocarbon group, the C1-C4 alkoxy group, the C1-C4 alkylthio group, the C2-C4 alkenyloxy group, the C2-C4 alkenylthio group, the C2-C4 alkynyloxy group, and the C2-C4 alkynylthio group may have one or more halogen atoms}, Each of $R^4$ and $R^5$, which are identical to or different from each other, independently represents a C1-C4 chain hydrocarbon group which may have one or more halogen atoms, a hydrogen atom, a halogen atom, a nitro group or a cyano group, $T^2$ represents a single bond, —S(O)$_2$—, —(CR$^2$R$^3$)$_n$—, —O—(CR$^2$R$^3$)$_{n+1}$—*, —(CR$^2$R$^3$)$_n$—S(O)$_2$—*, —S(O)$_m$(CR$^2$R$^3$)$_n$—*, —CR$^4$=CR$^5$—, or —CR$^4$=CR$^5$—CR$^2$R$^3$—*, $T^7$ represents a single bond, —(CR$^2$R$^3$)$_n$—, —O—(CR$^2$R$^3$)$_{n+1}$—*, —S(O)$_m$—(CR$^2$R$^3$)$_n$—* or —CR$^4$=CR$^5$—CR$^2$R$^3$—*, $R^8$ represents a 3 to 8 membered non-aromatic heterocyclic group which may have one or more substituents selected from Group M, a partially unsaturated or aromatic 8 to 10 membered fused heterocyclic group, a pyrrolyl group, a furanyl group, a pyrazolyl group, an imidazolyl group, an oxazolyl group, an isoxazolyl group, an isothiazolyl group, a triazolyl group, an oxadiazolyl group, a thiadiazolyl group, a tetrazolyl group, a pyrimidinyl group, a pyrazinyl group, a pyridazinyl group, a tetrahydronaphthyl group, an indanyl group {the 8 to 10 membered fused heterocyclic group, the pyrrolyl group, the furanyl group, the pyrazolyl group, the imidazolyl group, the oxazolyl group, the isoxazolyl group, the isothiazolyl group, the triazolyl group, the oxadiazolyl group, the thiadiazolyl group, the tetrazolyl group, the pyrimidinyl group, the pyrazinyl group, the pyridazinyl group, the tetrahydronaphthyl group and the indanyl group may have one or more substituents selected from Group L}, —CR$^4$=CR$^4$—O—R$^{12}$, —CR$^{11}$=N—N(R$^{19}$R$^{20}$), or —CR$^{11}$=N—O—R$^{12}$, $R^9$ represents a phenyl group which may have one or more substituents selected from Group L, $R^{10}$ represents a pyridyl group which may have one or more substituents selected from Group L, $R^{14}$ represents a thienyl group, a thiazolyl group or a naphthyl group {the thienyl group, the thiazolyl group and the naphthyl group may have one or more substituents selected from Group L}, Each of $R^{19}$ and $R^{20}$, which are identical to or different from each other, independently represents a C1-C4 chain hydrocarbon group which may have one or more halogen atoms, a hydrogen atom, a cyano group, a phenyl group, a benzyl group {the phenyl group and the benzyl group may have one or more substituents selected from Group N}, $T^3$ represents a single bond, an oxygen atom, —S(O)$_m$—, —NR$^{11}$—, —(CR$^2$R$^3$)$_n$—, —(CR$^2$R$^3$)$_n$—O—*, —O—(CR$^2$R$^3$)$_n$—*, —(CR$^2$R$^3$)$_n$—S(O)$_m$—*, —S(O)$_m$—(CR$^2$R$^3$)$_n$—* or —CR$^4$=CR$^5$—, $T^4$ represents an oxygen atom, —S(O)$_m$—, —NR$^{11}$—, —(CR$^2$R$^3$)$_n$—O—*, CR$^2$R$^3$)$_n$—S(O)$_m$—* or —S(O)$_m$—(CR$^2$R$^3$)$_n$—*, $T^5$ represents an oxygen atom, —S(O)$_m$—, —NR$^{11}$—, —(CR$^2$R$^3$)$_n$—, —(CR$^2$R$^3$)$_n$O—*, —O(CR$^2$R$^3$)$_n$—*, —(CR$^2$R$^3$)$_n$S(O)$_m$—* or S(O)$_m$(CR$^2$R$^3$)$_n$—*, $T^6$ represents an oxygen atom, —S(O)$_m$—, —NR$^{11}$—, —(CR$^2$R$^3$)$_n$—, —(CR$^2$R$^3$)$_n$—O—*, —O—(CR$^2$R$^3$)$_n$—*, —(CR$^2$R$^3$)$_n$—S(O)$_m$—*, —S(O)$_m$—(CR$^2$R$^3$)$_n$—* or —CR$^4$=CR$^5$—.

Group I: a group consisting of a halogen atom, a nitro group, a cyano group, an oxo group, a thioxo group, a carboxy group, a formyl group, a hydroxy group, a sulfanyl group, an amino group, a C1-C4 alkoxy group, a C2-C4 alkenyloxy group, a C2-C4 alkynyloxy group, a (C1-C3 alkyl) carbonyloxy group, a phenyl group {the C1-C4 alkoxy group, the C2-C4 alkenyloxy group, the C2-C4 alkynyloxy group, the (C1-C3 alkyl) carbonyloxy group and the phenyl group may have one or more halogen atoms}, —S(Q)$_p$-Y$^2$ and —CR$^{11}$=N—O—R$^{12}$.

Q represents an oxygen atom, =N—CN, =N—NO$_2$, =N—C(O)R$^{13}$ or =N—C(O)OR$^{13}$, $R^{13}$ represents a C1-C6 chain hydrocarbon group which may have one or more substituents selected from Group R, a phenyl group or a pyridyl group {the phenyl group and the pyridyl group may have one or more substituents selected from Group N}, $Y^2$ represents a NR$^{18}$R$^{17}$, a OR$^{18}$, a C1-C6 chain hydrocarbon group, a C3-C6 cycloalkyl group {the C1-C6 chain hydrocarbon group and the C3-C6 cycloalkyl group may have one or more substituents selected from Group R}, a phenyl group or a pyridyl group {the phenyl and the pyridyl group may have one or more substituents selected from Group N}, p is 0, 1 or 2, Each of $R^{18}$ and $R^{17}$, which are identical to or different from each other, independently represents a C1-C6 chain hydrocarbon group, a C3-C6 cycloalkyl group, a (C1-C6 alkoxy)C2-C6 alkyl group, a (C1-C6 alkylthio)C2-C6 alkyl group, a C1-C4 alkylsulfinyl group, a C1-C4 alkylsulfonyl group, a (C1-C5 alkyl)carbonyl group {the C1-C6 chain hydrocarbon group, the C3-C6 cycloalkyl group, the (C1-C6 alkoxy)C2-C6 alkyl group, the (C1-C6 alkylthio)C2-C6 alkyl group, the C1-C4 alkylsulfinyl group, the C1-C4 alkylsulfonyl group and the (C1-C5 alkyl)carbonyl group may have one or more halogen atoms} or a hydrogen atom.

Group J: a group consisting of a 3 to 7 membered non-aromatic heterocyclic group, a 5 to 6 membered aromatic heterocyclic group, a phenyl group, a C3-C10 alicyclic hydrocarbon group {the 3 to 7 membered non-aromatic heterocyclic group, the 5 to 6 membered aromatic heterocyclic group, the phenyl group and the C3-C10 alicyclic hydrocarbon group may have one or more substituents selected from Group K}, a halogen atom, a nitro group, a cyano group, an oxo group, a thioxo group, a formyl group, a carboxy group, a hydroxy group, a sulfanyl group, an amino group, —S(Q)$_p$-Y$^2$, —CR$^{11}$=N—O—R$^{12}$, =N—O—R$^{12}$, a C1-C4 alkoxy group, a C2-C4 alkenyloxy group and a C2-C4 alkynyloxy group {the C1-C4 alkoxy group, the C2-C4 alkenyloxy group and the C2-C4 alkynyloxy group may have one or more halogen atoms}.

Group K: a group consisting of a halogen atom, a nitro group, a cyano group, an oxo group, a thioxo group, a formyl group, a carboxy group, a hydroxy group, a sulfanyl group, an amino group, —S(Q)$_p$-Y$^2$, —CR$^{11}$=N—O—R$^{12}$, a C1-C4 alkoxy group, a C2-C4 alkenyloxy group and a C2-C4 alkynyloxy group {the C1-C4 alkoxy group, the C2-C4 alkenyloxy group and the C2-C4 alkynyloxy group may have one or more halogen atoms}.

Group L: a group consisting of a halogen atom, a nitro group, a cyano group, a formyl group, a hydroxy group, a sulfanyl group, a carboxy group, an amino group, a C1-C6 chain hydrocarbon group, a C3-C6 cycloalkyl group, a C1-C6 alkoxy group, a C2-C6 alkenyloxy group, a C2-C6 alkynyloxy group, a C3-C6 cycloalkoxy group, a C1-C6 alkylthio group, a C2-C6 alkenylthio group, a C2-C6 alkynylthio group, a C1-C6 alkylsulfinyl group, a C2-C6 alkenylsulfinyl group, a C2-C6 alkynylsulfinyl group, a C1-C6 alkylsulfonyl group, a C2-C6 alkenylsulfonyl group, a C2-C6 alkynylsulfonyl group, a C1-C6 alkylamino group, a di(C1-C6 alkyl)amino group, a (C1-C5 alkyl)carbonyl group, a (C1-C5 alkyl)carbonyloxy group, a (C1-C5 alkoxy)carbonyloxy group, an aminocarbony group, a (C1-C6 alkyl)aminocarbony group, a (C1-C6 alkoxy)C1-C6 alkyl group, a (C1-C6 alkylthio)C1-C6 alkyl group, a (C1-C6 alkoxy)C1-C6 alkoxy group, —CR$^{11}$=N—O—R$^{12}$, a phenyl group and a phenoxy group {the C1-C6 chain hydrocarbon group, the C3-C6 cycloalkyl group, the C1-C6 alkoxy group, the C2-C6 alkenyloxy group, the C2-C6 alkynyloxy group, the C3-C6 cycloalkoxy group, the C1-C6 alkylthio group, the C2-C6 alkenylthio group, the C2-C6 alkynylthio group, the C1-C6 alkylsulfinyl group, the C2-C6 alkenylsulfinyl group, the C2-C6 alkynylsulfinyl group, the C1-C6 alkylsulfonyl group, the C2-C6 alkenylsulfonyl group, the C2-C6 alkynylsulfonyl group, the C1-C6 alkylamino group, the di(C1-C6 alkyl)amino group, the (C1-C5 alkyl)carbonyl group, the (C1-C5 alkyl)carbonyloxy group, the (C1-C5 alkoxy)carbonyloxy group, the (C1-C6 alkyl)aminocarbony group, the (C1-C6 alkoxy)C1-C6 alkyl group, the (C1-C6 alkylthio) C1-C6 alkyl group, the (C1-C6 alkoxy)C1-C6 alkoxy group, the phenyl group and the phenoxy group may have one or more halogen atoms}.

Group M: a group consisting of a halogen atom, a nitro group, a cyano group, a formyl group, a hydroxy group, a sulfanyl group, a carboxy group, an amino group, an oxo group, a thioxo group, a C1-C6 chain hydrocarbon group, a C3-C6 cycloalkyl group, a C1-C6 alkoxy group, a C3-C6 cycloalkoxy group, a C1-C6 alkylthio group, a C2-C6 alkenylthio group, a C1-C6 alkylsulfinyl group, a C1-C6 alkylsulfonyl group, a C2-C6 alkenyloxy group, a C2-C6 alkynyloxy group, a (C1-C5 alkyl)carbonyl group, a (C1-C5 alkyl)carbonyloxy group, an aminocarbony group, a (C1-C6 alkyl)aminocarbony group, a (C1-C6 alkoxy)C1-C6 alkyl group, a (C1-C6 alkylthio)C1-C6 alkyl group, a (C1-C6 alkoxy)C1-C6 alkoxy group, a phenyl group and a phenoxy group {the C1-C6 chain hydrocarbon group, the C3-C6 cycloalkyl group, the C1-C6 alkoxy group, the C3-C6 cycloalkoxy group, the C1-C6 alkylthio group, the C2-C6 alkenylthio group, the C1-C6 alkylsulfinyl group, the C1-C6 alkylsulfonyl group, the C2-C6 alkenyloxy group, the C2-C6 alkynyloxy group, the (C1-C5 alkyl)carbonyl group, the (C1-C5 alkyl)carbonyloxy group, the (C1-C6 alkyl)aminocarbony group, the (C1-C6 alkoxy)C1-C6 alkyl group, the (C1-C6 alkylthio)C1-C6 alkyl group, the (C1-C6 alkoxy)C1-C6 alkoxy group, the phenyl group and the phenoxy group may have one or more halogen atoms}.

Group N: a group consisting of a halogen atom, a nitro group, a cyano group, a C1-C6 alkyl group, a C3-C6 cycloalkyl group, a C1-C6 alkoxy group, a C3-C6 cycloalkoxy group, a (C1-C6 alkoxy)C1-C6 alkyl group, a (C1-C6 alkylthio)C1-C6 alkyl group, a (C1-C6 alkoxy)C1-C6 alkoxy group and a C1-C6 alkylthio group {the C1-C6 alkyl group, the C3-C6 cycloalkyl group, the C1-C6 alkoxy group, the C3-C6 cycloalkoxy group, the (C1-C6 alkoxy) C1-C6 alkyl group, the (C1-C6 alkylthio)C1-C6 alkyl group, the (C1-C6 alkoxy)C1-C6 alkoxy group and the C1-C6 alkylthio group may have one or more halogen atoms}.

Group O: a group consisting of a halogen atom, a nitro group, a cyano group, a carboxy group, a hydroxy group, a sulfanyl group, an amino group, a C1-C6 chain hydrocarbon group, a C1-C4 alkoxy group, a C2-C4 alkenyloxy group, a C2-C4 alkynyloxy group, —S(Q)$_p$-Y$^2$, —CR$^{11}$=N—O—R$^{12}$, a (C1-C3 alkyl)carbonyloxy group and a phenyl group {the C1-C6 chain hydrocarbon group, the C1-C4 alkoxy group, the C2-C4 alkenyloxy group, the C2-C4 alkynyloxy group, the (C1-C3 alkyl) carbonyloxy group and the phenyl group may have one or more halogen atoms}.

Group P: a group consisting of a halogen atom, a nitro group, a cyano group, a formyl group, a carboxy group, a hydroxy group, a sulfanyl group, an amino group, —S(Q)$_p$-Y$^2$, —CR$^{11}$=N—O—R$^{12}$, a C1-C6 chain hydrocarbon group, a C1-C4 alkoxy group, a C2-C4 alkenyloxy group, a C2-C4 alkynyloxy group {the C1-C6 chain hydrocarbon group, the C1-C4 alkoxy group, the C2-C4 alkenyloxy group and the C2-C4 alkynyloxy group may have one or more halogen atoms}, a 3 to 7 membered non-aromatic heterocyclic group, a 5 to 6 membered aromatic heterocyclic group, a phenyl group, a phenoxy group and a C3-C10 alicyclic hydrocarbon group {the 3 to 7 membered non-aromatic heterocyclic group, the 5 to 6 membered aromatic heterocyclic group, the phenyl group, the phenoxy group and the C3-C10 alicyclic hydrocarbon group may have one or more substituents selected from Group K.

Group R: a group consisting of a halogen atom, a nitro group, a cyano group, an oxo group, a thioxo group, a carboxy group, a hydroxy group, a sulfanyl group, an amino group, a C1-C4 alkoxy group, a C2-C4 alkenyloxy group, a C2-C4 alkynyloxy group, a (C1-C3 alkyl) carbonyloxy group and a phenyl group{the C1-C4 alkoxy group, the C2-C4 alkenyloxy group and the C2-C4 alkynyloxy group, the (C1-C3 alkyl) carbonyloxy group and the phenyl group may have one or more halogen atoms}.

Group S: a group consisting of a halogen atom, a nitro group, a cyano group, an oxo group, a thioxo group, a carboxy group, a hydroxy group, a sulfanyl group, an amino group, a C1-C4 alkoxy group, a C2-C4 alkenyloxy group, a C2-C4 alkynyloxy group and a (C1-C3 alkyl) carbonyloxy group {the C1-C4 alkoxy group, the C2-C4 alkenyloxy group, the C2-C4 alkynyloxy group and the (C1-C3 alkyl) carbonyloxy group may have one or more halogen atoms}.

Group T: a group consisting of a hydrogen atom, a halogen atom, a cyano group, a nitro group, a formyl group, a carboxy group, a C1-C6 chain hydrocarbon group, a C3-C6 cycloalkyl group, a (C1-C6 alkoxy)C1-C6 alkyl group, a (C1-C6 alkylthio)C1-C6 alkyl group, a C2-C6 cyanoalkyl group, a (C1-C5 alkyl)carbonyl group, a (C1-C5 alkoxy)carbonyl group {the C1-C6 chain hydrocarbon group, the C3-C6 cycloalkyl group, the (C1-C6 alkoxy)C1-C6 alkyl group, the (C1-C6 alkylthio)C1-C6 alkyl group, the C2-C6 cyanoalkyl group, the (C1-C5 alkyl)carbonyl group and the (C1-C5 alkoxy)carbonyl group may have one or more substituents selected from Group I}, a pyridyl group, an oxetanyl group, benzyl group {the pyridyl group, the oxetanyl group and the benzyl group may have one or more substituents selected from Group O}, —C(=NOR$^A$)—C(=NOR$^B$)R$^C$ and —CR$^{11}$=N—O—R$^{12}$.

Group U: a group consisting of a halogen atom, a nitro group, a cyano group, an oxo group, a thioxo group, a carboxy group, a formyl group, a hydroxy group, a sulfanyl group, an amino group, a C1-C4 chain hydrocarbon group, a C3-C6 cycloalkyl group, a C1-C4 alkylthio group, a C1-C4 alkoxy group, a C3-C6 cycloakyloxy group, a C1-C4 alkylsulfonyloxy group, a C3-C6 cycloalkylsulfonyloxy group, a C2-C4 alkenyloxy group, a C2-C4 alkynyloxy group, a (C1-C3 alkyl) carbonyloxy group, a phenyl group {the C1-C4 chain hydrocarbon group, the C3-C6 cycloalkyl group, the C1-C4 alkylthio group, the C1-C4 alkoxy group, the C3-C6 cycloakyloxy group, the C1-C4 alkylsulfonyloxy group, the C3-C6 cycloalkylsulfonyloxy group, the C2-C4 alkenyloxy group, the C2-C4 alkynyloxy group, the (C1-C3 alkyl)carbonyloxy group and the phenyl group may have one or more halogen atoms}, —S(Q)$_p$-Y$^2$, —CR$^{11}$=N—O—R$^{12}$, —C(=NOR$^A$)—C(=NOR$^B$)R$^C$ and =N—O—R$^{12}$.

Group V: a group consisting of a hydrogen atom, a halogen atom, a cyano group, an amino group, a nitro group, a C1-C6 chain hydrocarbon group, a C3-C6 cycloalkyl group, a C1-C6 alkoxy group, a C1-C6 alkylthio group, a (C1-C6 alkoxy)C1-C6 alkyl group, a (C1-C6 alkylthio)C1-C6 alkyl group, a C2-C6 cyanoalkyl group, a C1-C6 alkylamino group, a di(C1-C6 alkyl)amino group, a (C1-C5 alkoxy)carbonyl group {the C1-C6 chain hydrocarbon group, the C3-C6 cycloalkyl group, the C1-C6 alkoxy group, the C1-C6 alkylthio group, the (C1-C6 alkoxy)C1-C6 alkyl group, the (C1-C6 alkylthio)C1-C6 alkyl group, the C2-C6 cyanoalkyl group, the C1-C6 alkylamino group, the di(C1-C6 alkyl)amino group and the (C1-C5 alkoxy)carbonyl group may have one or more substituents selected from Group I}, a pyridyl group, an oxetanyl group, a benzyl group {the pyridyl group, the oxetanyl group and the benzyl group may have one or more substituents selected from Group O}, —C(=NOR$^A$)—C(=NOR$^B$)R$^C$ and —CR$^{11}$=N—O—R$^{12}$]

or its N-oxide compound (hereinafter, the compound represented by formula (I) and its N-oxide compound are referred to as "Present compound" or "Compound of the present invention").

[2] The compound according to [1] wherein

R$^8$ represents a 3 to 8 membered non-aromatic heterocyclic group which may have one or more substituents selected from Group M, a pyrrolyl group, a furanyl group, a pyrazolyl group, an imidazolyl group, an oxazolyl group, an isoxazolyl group, an isothiazolyl group, a triazolyl group, an oxadiazolyl group, a thiadiazolyl group, a tetrazolyl group, a pyrimidinyl group, a pyrazinyl group, a pyridazinyl group, a benzofuranyl group, a benzothienyl group, an indolyl group, an isoindolyl group, an indolizinyl group, an indazolyl group, a benzimidazolyl group, a benzothiazolyl group, a benzoxazolyl group, a benzisothiazolyl group, a benzisoxazolyl group, a dihydrobenzofuranyl group, a dihydrobenzothienyl group, dihydrobenzopyranyl group, a 1,3-benzodioxolyl group, a quinolyl group, an isoquinolyl group, a cinnolinyl group, a phthalazinyl group, a quinazolinyl group, a quinoxalinyl group, a naphthyridinyl group, a tetrahydronaphthyl group, an indanyl group, an oxazolopyridyl group, a thiazolopyridyl group, an isoxazolopyridyl group, isothiazolopyridyl group, a tetrahydroindazoly group, a cyclopentapyrazolyl group {the pyrrolyl group, the furanyl group, the pyrazolyl group, the imidazolyl group, the oxazolyl group, the isoxazolyl group, the isothiazolyl group, the triazolyl group, the oxadiazolyl group, the thiadiazolyl group, the tetrazolyl group, the pyrimidinyl group, the pyrazinyl group, the pyridazinyl group, the benzofuranyl group, the benzothienyl group, the indolyl group, the isoindolyl group, the indolizinyl group, the indazolyl group, the benzimidazolyl group, the benzothiazolyl group, the benzoxazolyl group, the benzisothiazolyl group, the benzisoxazolyl group, the dihydrobenzofuranyl group, the dihydrobenzothienyl group, the dihydrobenzopyranyl group, the 1,3-benzodioxolyl group, the quinolyl group, the isoquinolyl group, the cinnolinyl group, the phthalazinyl group, the quinazolinyl group, the quinoxalinyl group, the naphthyridinyl group, the tetrahydronaphthyl group, the indanyl group, the oxazolopyridyl group, the thiazolopyridyl group, the isoxazolopyridyl group, the isothiazolopyridyl group, the tetrahydroindazoly group and the cyclopentapyrazolyl group may have one or more substituents selected from Group L}, —CR$^A$=CR$^A$—O—R$^{12}$, —CR$^{11}$=N—N(R$^{19}$R$^{20}$), or —CR$^{11}$=N—O—R$^{12}$, and Group U represents a group consisting of a halogen atom, a nitro group, a cyano group, an oxo group, a thioxo group, a carboxy group, a formyl group, a hydroxy group, a sulfanyl group, an amino group, a C1-C4 alkoxy group, a C3-C6 cycloakyloxy group, a C1-C4 alkylsulfonyloxy group, a C3-C6 cycloalkylsulfonyloxy group, a C2-C4 alkenyloxy group, a C2-C4 alkynyloxy group, a (C1-C3 alkyl) carbonyloxy group, a phenyl group {the C1-C4 alkoxy group, the C3-C6 cycloakyloxy group, the C1-C4 alkylsulfonyloxy group, the C3-C6 cycloalkylsulfonyloxy group, the C2-C4 alkenyloxy group, the C2-C4 alkynyloxy group, the (C1-C3 alkyl) carbonyloxy group and the phenyl group may have one or more halogen atoms}, —S(Q)$_p$-Y$^2$, —CR$^{11}$=N—O—R$^{12}$, —C(=NOR$^A$)—C(=NOR$^B$)R$^C$ and =N—O—R$^{12}$.

[3] The compound according to [2] wherein

Each of R$^{12}$, R$^A$, R$^B$ and R$^C$, which are identical to or different from each other, independently represents a phenyl group, a benzyl group, a pyridyl group, a pyrazolyl group or a pyrimidinyl group {the phenyl group, the benzyl group, the pyridyl group, the pyrazolyl group and the pyrimidinyl group may have one or more substituents selected from Group N}, a C1-C6 chain hydrocarbon group, a C3-C6 cycloalkyl group, a (C3-C6 cycloalkyl)C1-C6 alkyl group, a (C1-C6 alkoxy)C2-C6 alkyl group, a (C1-C6 alkylthio)C2-C6 alkyl group {the C1-C6 chain hydrocarbon group, the C3-C6 cycloalkyl group, the (C3-C6 cycloalkyl)C1-C6 alkyl group, the (C1-C6 alkoxy)C2-C6 alkyl group and the (C1-C6 alkylthio)C2-C6 alkyl group may have one or more halogen atoms} or a hydrogen atom, R$^8$ represents a 3 to 8 membered non-aromatic heterocyclic group which may have one or more substituents selected from Group M, a pyrrolyl group, a furanyl group, a pyrazolyl group, an imidazolyl group, an oxazolyl group, an isoxazolyl group, an isothiazolyl group, a triazolyl group, an oxadiazolyl group, a thiadiazolyl group, a tetrazolyl group, a pyrimidinyl group, a pyrazinyl group, a pyridazinyl group, a benzofuranyl group, a benzothienyl group, an indolyl group, an isoindolyl group, an indolizinyl group, an indazolyl group, a benzimidazolyl group, a benzothiazolyl group, a benzoxazolyl group, a benzisothiazolyl group, a benzisoxazolyl group, a 2,3-dihydrobenzofuranyl group, a 2,3-dihydrobenzothienyl group, a 3,4-dihydrobenzopyranyl group, a 1,3-benzodioxolyl group, a quinolyl group, an isoquinolyl group, a cinnolinyl group, a phthalazinyl group, a quinazolinyl group, a quinoxalinyl group, a naphthyridinyl group {the pyrrolyl group, the furanyl group, the pyrazolyl group, the imidazolyl group, the oxazolyl group, the isoxazolyl group, the isothiazolyl group, the triazolyl group, the oxadiazolyl group, the thiadiazolyl group, the tetrazolyl group, the pyrimidinyl group, the pyrazinyl group, the pyridazinyl group, the benzofuranyl group, the benzothienyl group, the indolyl group, the isoindolyl group, the indolizinyl group, the indazolyl group, the benzimidazolyl group, the benzothiazolyl group, the benzoxazolyl group, the benzisothiazolyl group, the benzisoxazolyl group, the 2,3-dihydrobenzofuranyl group, the 2,3-dihydrobenzothienyl group, the 3,4-dihydrobenzopyranyl group, the 1,3-benzodioxolyl group, the quinolyl group, the isoquinolyl group, the cinnolinyl group, the phthalazinyl group, the quinazolinyl group, the quinoxalinyl group and the naphthyridinyl group may have one or more substituents selected from Group L}, $-CR^4=CR^4-O-R^{12}$, $-CR^{11}=N-N(R^{19}R^{20})$, or $-CR^{11}=N-O-R^{12}$, and Group U represents a group consisting of a halogen atom, a nitro group, a cyano group, an oxo group, a thioxo group, a carboxy group, a formyl group, a hydroxy group, a sulfanyl group, an amino group, a C1-C4 alkoxy group, a C2-C4 alkenyloxy group, a C2-C4 alkynyloxy group, a (C1-C3 alkyl) carbonyloxy group, a phenyl group {the C1-C4 alkoxy group, the C2-C4 alkenyloxy group, the C2-C4 alkynyloxy group, the (C1-C3 alkyl) carbonyloxy group and the phenyl group may have one or more halogen atoms}, $-S(Q)_p-Y^2$, $-CR^{11}=N-O-R^{12}$, $-C(=NOR^A)-C(=NOR^B)R^C$ and $=N-O-R^{12}$.

[4] The compound according to [3] wherein $W^2$ represents a C1-C6 chain hydrocarbon group, Each of $R^{15}$ and $R^{16}$, which are identical to or different from each other, independently represents a halogen atom, a C1-C3 alkyl group, a C3-C4 cycloalkyl group or a C1-C3 alkoxy group {the C1-C3 alkyl group, the C3-C4 cycloalkyl group and the C1-C3 alkoxy group may have one or more halogen atoms}, the combination of E, G and $Z^1$ represents a combination wherein E represents #—C($Z^1$)=N—N=C($Z^3$)—O—CH$_2$— or #—C($Z^1$)=N—N=C($Z^3$)—S—CH$_2$—, G represents $R^8$-$T^3$-, $R^9$-$T^4$-, $R^{10}$-$T^5$- or $R^{14}$-$T^6$-, $Z^1$ represents a C1-C6 chain hydrocarbon group, a C3-C6 cycloalkyl group, a C1-C6 alkoxy group, a (C1-C6 alkoxy)C1-C6 alkyl group, a (C1-C6 alkoxy)C1-C6 alkoxy group, a C1-C6 alkylthio group, a (C1-C6 alkylthio)C1-C6 alkyl group, a C1-C6 alkylamino group, a di(C1-C6 alkyl)amino group {the C1-C6 chain hydrocarbon group, the C3-C6 cycloalkyl group, the C1-C6 alkoxy group, the (C1-C6 alkoxy)C1-C6 alkyl group, the (C1-C6 alkoxy)C1-C6 alkoxy group, the C1-C6 alkylthio group, the (C1-C6 alkylthio)C1-C6 alkyl group, the C1-C6 alkylamino group, the di(C1-C6 alkyl)amino group may have one or more halogen atoms}, a hydrogen atom or a halogen atom, $Z^2$ represents a C1-C6 chain hydrocarbon group, a C3-C6 cycloalkyl group, a C1-C6 alkoxy group, a (C1-C6 alkoxy)C1-C6 alkyl group, a (C1-C6 alkoxy)C1-C6 alkoxy group, a C1-C6 alkylthio group, a (C1-C6 alkylthio)C1-C6 alkyl group, a C1-C6 alkylamino group, a di(C1-C6 alkyl)amino group {the C1-C6 chain hydrocarbon group, the C3-C6 cycloalkyl group, the C1-C6 alkoxy group, the (C1-C6 alkoxy)C1-C6 alkyl group, the (C1-C6 alkoxy)C1-C6 alkoxy group, the C1-C6 alkylthio group, the (C1-C6 alkylthio)C1-C6 alkyl group, the C1-C6 alkylamino group and the di(C1-C6 alkyl) amino group may have one or more halogen atoms}, a hydrogen atom or a halogen atom, and $R^2$ and $R^3$ are a hydrogen atom.

[5] The compound according to [2] or its N-oxide compound wherein the combination of E, G, $X^1$, $Y^1$ and $Z^1$ represents any combination of the following a to i:

a: a combination wherein E represents #—C($X^1$)($Y^1$)—O—N=C($Z^1$)—, #—C($X^1$)($Y^1$)—S—N=C($Z^1$)—, #—C($X^1$)($Y^1$)—O—N=C($Z^1$)—O—CH$_2$—, #—C($X^1$)($Y^1$)—O—N=C($Z^1$)—S—CH$_2$—, #—C($X^1$)($Y^1$)—S—N=C($Z^1$)—O—CH$_2$—, #—C($X^1$)($Y^1$)—S—N=C($Z^1$)—S—CH$_2$—, #—C($Z^1$)=N—N=C($Z^2$)—, or #—C($X^1$)=C($Y^1$)—C($Z^1$)=N—S—CH$_2$—, G represents a C1-C6 chain hydrocarbon group, a (C1-C6 alkoxy)C1-C6 alkyl group, a (C1-C6 alkylthio)C1-C6 alkyl group {the C1-C6 chain hydrocarbon group, the (C1-C6 alkoxy)C1-C6 alkyl group and the (C1-C6 alkylthio)C1-C6 alkyl group may have one or more substituents selected from Group S} or $R^1$-$T^1$-, each of $X^1$ and $Y^1$, which are identical to or different from each other, independently represents a substituent selected from Group T, $Z^1$ represents a substituent selected from Group V;

b: a combination wherein E represents an oxygen atom, #—O—N=C($Z^1$)—C($Z^2$)=N—S—CH$_2$—, #—N=C($Z^1$)—S—CH$_2$—, #—N=C($Z^1$)—O—CH$_2$—, #—O—N=C($Z^1$)—S—CH$_2$—, #—O—N=C($Z^1$)—O—CH$_2$—, #—N($X^1$)—O—CH$_2$—, #—N=C($SX^3$)—S—CH$_2$—, #—N=C($OX^3$)—O—CH$_2$—, #—N=C($SX^3$)—O—CH$_2$— or #—N=C($OX^3$)—S—CH$_2$—, G represents a C1-C6 chain hydrocarbon group, a (C1-C6 alkoxy)C1-C6 alkyl group, (C1-C6 alkylthio)C1-C6 alkyl group {the C1-C6 chain hydrocarbon group, the (C1-C6 alkoxy)C1-C6 alkyl group and the (C1-C6 alkylthio)C1-C6 alkyl group may have one or more substituents selected from Group S} or $R^1$-$T^2$-, $X^1$ represents a substituent selected from Group T, and $Z^1$ represents a substituent selected from Group V;

c: a combination wherein E represents a sulfur atom, #—S—N=C($Z^1$)—C($Z^2$)=N—O—CH$_2$— or #—S—N=C($Z^1$)—C($Z^2$)=N—S—CH$_2$—, G represents $R^1$-$T^7$-, and $Z^1$ represents a substituent selected from Group V;

d: a combination wherein E represents #—C($Z^1$)=N—N=C($Z^3$)—O—CH$_2$— or #—C($Z^1$)=N—N=C($Z^3$)—S—CH$_2$—, G represents $R^8$-$T^3$-, $R^9$-$T^4$-, $R^{10}$-$T^5$- or $R^{14}$-$T^6$-, and $Z^1$ represents a substituent selected from Group V;

e: a combination wherein E represents #—C($Z^1$)=N—N=C($V^1$)—O—CH$_2$— or #—C($Z^1$)=N—N=C($V^1$)—S—CH$_2$—, G represents $R^1$-$T^1$-, and $Z^1$ represents a substituent selected from Group V;

f: a combination wherein E represents #—C($X^1$)($Y^1$)—O—N=C($Z^1$)—, #—C($X^1$)($Y^1$)—S—N=C($Z^1$)—, #—C($X^1$)($Y^1$)—O—N=C($Z^1$)—O—CH$_2$—, #—C($X^1$)($Y^1$)—O—N=C($Z^1$)—S—CH$_2$—, #—C($X^1$)($Y^1$)—S—N=C($Z^1$)—O—CH$_2$— or #—C($X^1$)($Y^1$)—S—N=C($Z^1$)—S—CH$_2$—, G and $X^1$ together with carbon atoms to which they are bound form a C3-C10 alicyclic hydrocarbon group or a 3 to 10 membered non-aromatic heterocyclic group {the C3-C10 alicyclic hydrocarbon group and the 3 to 10 membered non-aromatic heterocyclic group may have one or more substituents selected from Group J}, $Y^1$ represents a substituent selected from Group T, and $Z^1$ represents a substituent selected from Group V;

g: a combination wherein E represents #—C($X^1$)($Y^1$)—O—N=C($Z^1$)—, #—C($X^1$)($Y^1$)—S—N=C($Z^1$)—, #—C($X^1$)($Y^1$)—O—N=C($Z^1$)—O—CH$_2$—, #—C($X^1$)($Y^1$)—

O—N=C(Z$^1$)—S—CH$_2$—, #—C(X$^1$)(Y$^1$)—S—N=C(Z$^1$)—O—CH$_2$— or #—C(X$^1$)(Y$^1$)—S—N=C(Z$^1$)—S—CH$_2$—, G, X$^1$ and Y$^1$ together with carbon atoms to which they are bound form a C6-C10 aromatic hydrocarbon group or a 5 to 10 membered aromatic heterocyclic group {the C6-C10 aromatic hydrocarbon group and the 5 to 10 membered aromatic heterocyclic group may have one or more substituents selected from Group P}, and Z$^1$ represents a substituent selected from Group V;

h: a combination wherein E represents #—C(X$^1$)=C(Y$^1$)—C(Z$^1$)=N—O—CH$_2$—, #—C(X$^1$)=C(Y$^1$)—C(Z$^1$)=N—S—CH$_2$— or #—N(X$^1$)—O—CH$_2$—, G and X$^1$ together carbon atoms to which they are bound form a C3-C10 alicyclic hydrocarbon group or a 3 to 10 membered non-aromatic heterocyclic group {the C3-C10 alicyclic hydrocarbon group and the 3 to 10 membered non-aromatic heterocyclic group may have one or more substituents selected from Group J}, Y$^1$ represents a substituent selected from Group T, and Z$^1$ represents a substituent selected from Group V; and i: a combination wherein E represents #—C(Z$^1$)=N—N=C(Z$^3$)—O—CH$_2$—, #—C(Z$^1$)=N—N=C(Z$^3$)—S—CH$_2$—, #—C(Z$^1$)=N—N=C(V$^1$)—O—CH$_2$— or #—C(Z$^1$)=N—N=C(V$^1$)—S—CH$_2$—, G and Z$^1$ together with carbon atoms to which they are bound form a C3-C10 alicyclic hydrocarbon group or a 3 to 10 membered non-aromatic heterocyclic group {the C3-C10 alicyclic hydrocarbon group and the 3 to 10 membered non-aromatic heterocyclic group may have one or more substituents selected from Group U}.

[6] The compound according to [5] wherein
W$^2$ represents a C1-C6 chain hydrocarbon group,
R$^{15}$ represents a C1-C3 alkyl group which may have one or more halogen atoms,
u is 0,
E represents #—C(Z$^1$)=N—N=C(Z$^3$)—O—CH$_2$—,
G represents R$^8$-T$^3$-,
Z$^1$ represents a C1-C6 chain hydrocarbon group which have one or more halogen atoms, or a hydrogen atom,
T$^3$ represents a single bond,
R$^1$ represents a furanyl group, a pyrazolyl group, a pyrimidinyl group, a pyrazinyl group, a benzofuranyl group, a benzothienyl group, an indolyl group, an indazolyl group, a benzimidazolyl group, a benzothiazolyl group, a benzoxazolyl group, a dihydrobenzofuranyl group, a quinolyl group, a quinoxalinyl group, a tetrahydronaphthyl group, an indanyl group, a 1,3-benzodioxolyl group, an oxazolopyridyl group, a thiazolopyridyl group, an isoxazolopyridyl group, an isothiazolopyridyl group, a tetrahydroindazoly group, a cyclopentapyrazolyl group {the furanyl group, the pyrazolyl group, the pyrimidinyl group, the pyrazinyl group, the benzofuranyl group, the benzothienyl group, the indolyl group, the indazolyl group, the benzimidazolyl group, the benzothiazolyl group, the benzoxazolyl group, the dihydrobenzofuranyl group, the quinolyl group, the quinoxalinyl group, the tetrahydronaphthyl group, the indanyl group, the 1,3-benzodioxolyl group, the oxazolopyridyl group, the thiazolopyridyl group, the isoxazolopyridyl group, the isothiazolopyridyl group, the tetrahydroindazoly group and the cyclopentapyrazolyl group may have one or more substituents selected from the group consisting of a C1-C6 chain hydrocarbon group which may have one or more halogen atoms and a halogen atom} or —CR$^{11}$=N—O—R$^{12}$,
R$^{11}$ represents a C1-C6 alkyl group,
R$^{12}$ represents a benzyl group {the benzyl group may have one or more substituents selected from the group consisting of C1-C6 alkyl group and C1-C6 alkoxy group}, a C1-C6 chain hydrocarbon group, a C3-C6 cycloalkyl group, a (C1-C6 alkoxy)C2-C6 alkyl group, a cyano(C1-C6 alkyl) group {the C1-C6 chain hydrocarbon group, the C3-C6 cycloalkyl group, the (C1-C6 alkoxy)C2-C6 alkyl group and the cyano(C1-C6 alkyl) group may have one or more halogen atoms} or a hydrogen atom, and
Z$^3$ represents a C1-C6 chain hydrocarbon group which may have one or more halogen atoms.

[7] The compound according to [5] wherein
W$^2$ represents a C1-C6 chain hydrocarbon group,
R$^{15}$ represents a C1-C3 alkyl group which may have one or more halogen atoms, a C3-C6 cycloalkyl group, a C1-C6 alkoxy group, or halogen atom,
u is 0,
E represents #—C(Z$^1$)=N—N=C(Z$^3$)—O—CH$_2$—,
G and Z$^1$ together with carbon atoms to which they are bound form a C3-C10 alicyclic hydrocarbon group or a 3 to 10 membered non-aromatic heterocyclic group {the C3-C10 alicyclic hydrocarbon group and the 3 to 10 membered non-aromatic heterocyclic group may have one or more substituents selected from Group U}, and
Z$^3$ represents a C1-C6 chain hydrocarbon group which may have one or more halogen atoms.

[8] The compound according to [5] wherein
W$^2$ represents a C1-C6 chain hydrocarbon group,
R$^{15}$ represents a C1-C3 alkyl group which may have one or more halogen atoms,
u is 0,
E represents #—N=C(Z$^1$)—S—CH$_2$—,
G represents a C1-C6 chain hydrocarbon group which may have one or more substituents selected from Group S or R$^1$-T$^2$-,
Z$^1$ represents a C1-C6 alkylthio group,
T$^2$ represents a single bond or —(CR$^2$R$^3$)$_n$—,
R$^1$ represents a tetrahydrofuranyl group, a tetrahydropyranyl group, a cyclopentyl group, a phenyl group, a pyrazolyl group, a benzoxazolyl group, a benzothiazolyl group or an isoxazolopyridyl group {the tetrahydrofuranyl group, the tetrahydropyranyl group, the cyclopentyl group, the phenyl group, the pyrazolyl group, the benzoxazolyl group, the benzothiazolyl group and the isoxazolopyridyl group may have one or more substituents selected from Group P},
n is 1 or 2, and
R$^2$ and R$^3$ represent hydrogen atoms.

[9] The compound according to [1] wherein
R$^{15}$ represents a halogen atom, a methyl group, a cyclopropyl group or a methoxy group,
W$^2$ represents a methyl group,
W$^1$ represents an oxygen atom,
u is 0,
E represents #—C(Z$^1$)=N—N=C(Z$^3$)—O—CH$_2$—,
Z$^3$ represents an ethyl group,
G and Z$^1$ together with carbon atoms to which they are bound form an indan-1-ylidene group, a 1,2,3,4-tetrahydronaphthalen-1-ylidene group, a 2,3-dihydrobenzofuran-3-ylidene group, a 3,4-dihydro-2H-1-benzopyran-4-ylidene group {the indan-1-ylidene group, the 1,2,3,4-tetrahydronaphthalen-1-ylidene group, the 2,3-dihydrobenzofuran-3-ylidene group, and the 3,4-dihydro-2H-1-benzopyran-4-ylidene group may have one or more substituents selected from the group consisting of a halogen atom, a C1-C3 alkyl group which may have one or more halogen atoms, and a C1-C3 alkoxy group which may have one or more halogen atoms}, or a 3,4-dihydro-2H-1-benzothiopyran-4-ylidene group {the 3,4-dihydro-2H-1-benzothiopyran-4-ylidene group may have one or more substituents selected from the group consisting of an oxo group, a halogen atom, a C1-C3 alkyl group which may have one or more halogen atoms, and a C1-C3 alkoxy group which may have one or more halogen atoms}.

[10] The compound according to [1] wherein
$W^1$ represents an oxygen atom,
$W^2$ represents a methyl group,
u is 0,
$R^{15}$ represents a halogen atom, a methyl group, a cyclopropyl group or a methoxy group,
E represents #—C($Z^1$)=N—N=C($Z^3$)—O—CH$_2$—,
G represents $R^8$-$T^3$-,
$Z^1$ represents a C1-C3 alkyl group,
$Z^3$ represents a C1-C3 alkyl group,
$T^3$ represents a single bond,
$R^8$ represents a furanyl group, a pyrazolyl group, a pyrimidinyl group, a pyrazinyl group, a benzofuranyl group, a benzothienyl group, an indolyl group, an indazolyl group, a benzimidazolyl group, a benzothiazolyl group, a benzoxazolyl group, a dihydrobenzofuranyl group, a quinolyl group, a quinoxalinyl group, a tetrahydronaphthyl group, an indanyl group, a 1,3-benzodioxolyl group, a pyrrolopyridyl group {the furanyl group, the pyrazolyl group, the pyrimidinyl group, the pyrazinyl group, the benzofuranyl group, the benzothienyl group, the indolyl group, the indazolyl group, the benzimidazolyl group, the benzothiazolyl group, the benzoxazolyl group, the dihydrobenzofuranyl group, the quinolyl group, the quinoxalinyl group, the tetrahydronaphthyl group, the indanyl group, the 1,3-benzodioxolyl group, and the pyrrolopyridyl group may have one or more substituents selected from the group consisting of C1-C6 chain hydrocarbon group which may have one or more halogen atoms, a (C1-C3 alkoxy)C1-C3 alkyl group, and a halogen atom}, or —C$R^{11}$=N—O—$R^{12}$,
$R^{11}$ represents a C1-C3 alkyl group, and
$R^{12}$ represents a benzyl group {the benzyl group may have one or more substituents selected from the group consisting of a halogen atom, a C1-C6 alkyl group, and a C1-C6 alkoxy group}, a C1-C6 chain hydrocarbon group, a (C3-C6 cycloalkyl)C1-C3 alkyl group, a (C1-C3 alkoxy)C2-C3 alkyl group, a (C1-C3 alkylthio)C1-C3 alkyl group, a cyano(C1-C6 alkyl) group or a hydrogen atom.

[11] An agent for controlling a pest, said agent comprises the compound according to any one of [1] to [10].

[12] A method for controlling a pest, said method comprises applying an effective amount of the compound according to any one of [1] to [10] to plant or soil.

[13] Use of the compound according to any one of [1] to [10] for controlling a pest.

[14] A composition comprising the compound according to any one of [1] to [10] and one or more ingredients selected from the group consisting of a nematode control ingredient, a plant growth regulating ingredient, and other pest control ingredient.

The present invention can control pests.

DESCRIPTION OF EMBODIMENTS

The substituent(s) as described herein is/are explained.
Herein when a substituent has two or more halogen atoms, these halogen atoms may be identical to or different from each other.
The expression of "CX-CY" to be used herein represents that the number of carbon atom is from X to Y. For example, the expression of "C1-C6" represents that the number of carbon atom is 1 to 6.

The term "halogen atom" to be used herein represents, for example, a fluorine atom, a chlorine atom, a bromine atom or an iodine atom,
The term "C2-C6 cyanoalkyl group" to be used herein represents a C1-C5 alkyl group having a cyano group.
The term "chain hydrocarbon group" to be used herein represents an alkyl group, an alkenyl group or an alkynyl group.

Examples of "alkyl group" include a methyl group, an ethyl group, a propyl group, an isopropyl group, a 1,1-dimethylpropyl group, a 1,2-dimethylpropyl group, a 1-ethylpropyl group, a butyl group, an isobutyl group, a tert-butyl group, a pentyl group and a hexyl group.

Examples of "alkenyl group" include a vinyl group, a 1-propenyl group, a 2-propenyl group, a 1-methyl-1-propenyl group, a 1-methyl-2-propenyl group, a 1,2-dimethyl-1-propenyl group, a 1,1-dimethyl-2-propenyl group, a 1-ethyl-1-propenyl group, a 1-ethyl-2-propenyl group, a 3-butenyl group, a 4-pentenyl group, and a 5-hexenyl group.

Examples of "alkynyl group" include an ethynyl group, 1-propynyl group, 2-propynyl group, a 1-methyl-2-propynyl group, a 1,1-dimethyl-2-propynyl group, a 1-ethyl-2-propynyl group, a 2-butynyl group, a 4-pentynyl group, and a 5-hexynyl group.

Examples of "C3-C6 cycloalkyl group" include a cyclopropyl group, a cyclobutyl group, a cyclopentyl group or a cyclohexyl group.

The term "C6-C10 aromatic hydrocarbon group" to be used herein represents, for example, a phenyl group or a naphthyl group.

Examples of "3 to 10 membered non-aromatic heterocyclic group" include an aziridinyl group, an azetidinyl group, a pyrrolidinyl group, a piperidyl group, an azepanyl group, an azacyclooctyl group, a pyrazolidinyl group, an imidazolidinyl group, an oxazolidinyl group, a thiazolidinyl group, an isoxazolidinyl group, a morpholinyl group, a thiomorpholinyl group, a 1,2-oxazinyl group, 1,3-oxazinyl group, a 1,3-thiazinyl group, a piperazinyl group, a tetrahydropyridazinyl group, a hexahydropyridazinyl group, a tetrahydropyrimidinyl group, a hexahydropyrimidinyl group, a 1,4-thiazepanyl group, a 2,3-dihydrobenzofuran ring group, a 3,4-dihydro-2H-1-benzopyran ring group, a 3,4-dihydro-2H-1-benzothiopyran ring group, a 3,4-dihydro-2H-[2,3-b]pyridine ring group, a 3,4-dihydro-2H-pyrano[3,2-b]pyridine ring group, a 3,4-dihydro-2H-pyrano[2,3-c]pyridine group, a 3,4-dihydro-2H-pyrano[3,2-c]pyridine group, and a 7,8-dihydro-6H-pyrano[2,3-c]pyrazine ring group.

The term "3 to 7 membered non-aromatic heterocyclic group" to be used herein represents a monocyclic 3 to 7 membered non-aromatic heterocyclic group.

Examples of "5 to 10 membered aromatic heterocyclic group" include a pyrrolyl group, a furyl group, a thienyl group, a pyrazolyl group, an imidazolyl group, a triazolyl group, a tetrazolyl group, an oxazolyl group, an isoxazolyl group, a thiazolyl group, an isothiazolyl group, an oxadiazolyl group, a thiadiazolyl group, a pyridyl group, a pyridazinyl group, a pyrimidinyl group, a quinolyl group, an indazolyl group and a pyrazinyl group.

Examples of "C1-C6 alkylamino group" include a methylamino group, an ethylamino group, and a hexylamino group.

Examples of "di(C1-C6 alkyl)amino group" include a dimethylamino group, an ethylmethylamino group, a diethylamino group, and a dihexylamino group.

When the (C1-C6 alkoxy)C1-C6 alkyl group and the like have substituent(s), the substituent(s) may bind to any carbon atom thereon.

When the benzyl group have substituent(s), the substituent(s) may be the substituent(s) on benzene ring or the substiutent(s) on methylene group.

Examples of "C3-C6 cycloalkoxy group" include a cyclopropyloxy group and a cyclobutyloxy group.

The term of "a partially unsaturated or aromatic 8 to 10 membered fused heterocyclic group" to be used herein represents a partially unsaturated or aromatic 8 to 10 membered fused heterocyclic group wherein the ring member contains besides a carbon atom, one to three heteroatoms selected from the group consisting of nitrogen atom, oxygen atom and sulfur atom, and includes, for example, a benzofuranyl group, a benzothienyl group, an indolyl group, an isoindolyl group, an indolizinyl group, an indazolyl group, a benzimidazolyl group, a benzothiazolyl group, a benzoxazolyl group, a benzisothiazolyl group, a benzisoxazolyl group, a dihydrobenzofuranyl group, a dihydrobenzothienyl group, a dihydrobenzopyranyl group, a 1,3-benzodioxolyl group, a quinolyl group, an isoquinolyl group, a cinnolinyl group, a phthalazinyl group, a quinazolinyl group, a quinoxalinyl group, a naphthyridinyl group, an oxazolopyridyl group, a thiazolopyridyl group, an isoxazolopyridyl group, an isothiazolopyridyl group, a tetrahydroindazoly group, a cyclopentapyrazolyl group, a dihydroisobenzofuranyl group, a pyrazolopyridyl group, a pyrrolopyridyl group, a furopyridyl group, a thienopyridyl group, an imidazopyridyl group, and an imidazopyrimidinyl group.

The term of "alicyclic hydrocarbon group" to be used herein represents a cycloalkane ring group, a cyloalkene ring group, a cycloalkyne ring group, or a benzocycloalkane ring group. Examples of the cycloalkane ring include a cyclopropane ring and a cyclohexane ring. Examples of the cycloalkene ring include a cyclopropene ring and a cyclohexene ring. Examples of the cycloalkyne ring include a cyclooctyne ring. Examples of the benzocycloalkane ring include an indane ring and a 1,2,3,4-tetrahydronaphthalene ring.

The compound wherein G and $Z^1$ together with carbon atoms to which they are bound form a 1,2,3,4-tetrahydronaphthalen-1-ylidene group represents a compound represented by formula (THN).

Formula (THN):

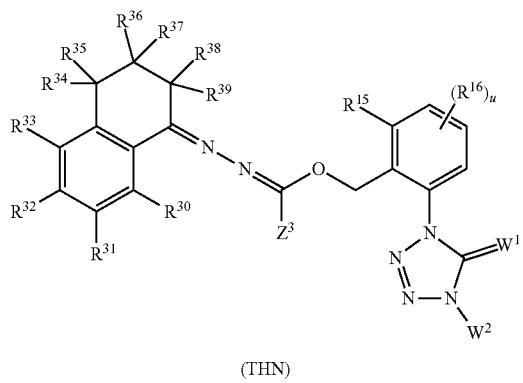

(THN)

wherein $R^{30}$, $R^{31}$, $R^{32}$, $R^{33}$, $R^{34}$, $R^{35}$, $R^{36}$, $R^{37}$, $R^{38}$, and $R^{39}$ represent a substituent selected from Group U or a hydrogen atom, and the other symbols are the same as defined above.

The compound wherein G and $Z^1$ together with carbon atoms to which they are bound form an indan-1-ylidene group represents a compound represented by formula (INDD).

Formula (INDD):

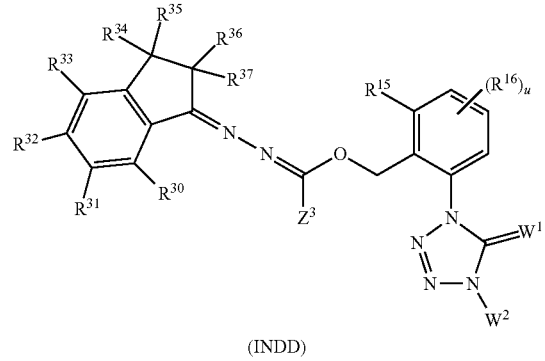

(INDD)

wherein the symbols are the same as defined above.

When G and $Z^1$ together with carbon atoms to which they are bound form a 3 to 10 membered non-aromatic heterocyclic group as a substituent, the substituents include a 2,3-dihydrobenzofuran-3-ylidene group, a 3,4-dihydro-2H-1-benzopyran-4-ylidene group, a 3,4-dihydro-2H-1-benzothiopyran-4-ylidene group, a 3,4-dihydro-2H-pyrano[2,3-b]pyridin-4-ylidene group, a 3,4-dihydro-2H-pyrano[3,2-b]pyridin-4-ylidene group, a 3,4-dihydro-2H-pyrano[2,3-c]pyridin-4-ylidene group, a 3,4-dihydro-2H-pyrano[3,2-c]pyridin-4-ylidene group, and a 7,8-dihydro-6H-pyrano[2,3-b]pyrazin-8-ylidene group.

The compound wherein G and $Z^1$ together with carbon atoms to which they are bound form a 2,3-dihydrobenzofuran-3-ylidene group represents a compound represented by formula (DIF).

Formula (DIF):

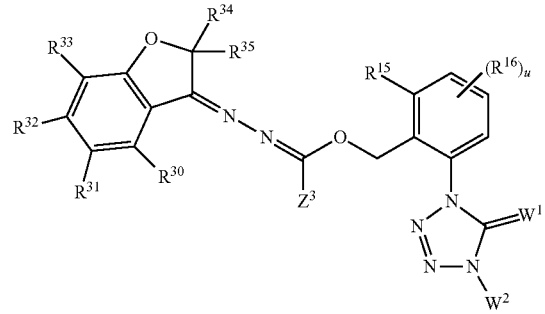

(DIF)

wherein the symbols are the same as defined above.

The compound wherein G and $Z^1$ together with carbon atoms to which they are bound form a 3,4-dihydro-2H-1-benzopyran-4-ylidene group represents a compound represented by formula (DIP).

Formula (DIP):

[Chem.5]

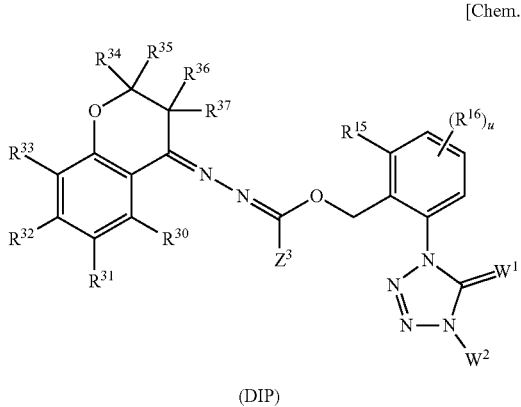

(DIP)

wherein the symbols are the same as defined above.

The compound wherein G and $Z^1$ together with carbon atoms to which they are bound form a 3,4-dihydro-2H-1-benzothiopyran-4-ylidene group represents a compound represented by formula (DIT), formula (DITO) or formula (DIO).

Formula (DIT):

[Chem.6]

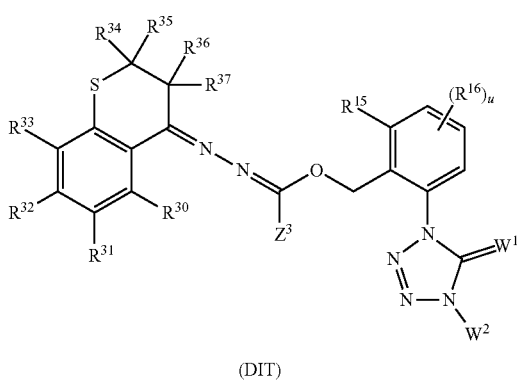

(DIT)

Formula (DITO):

[Chem.7]

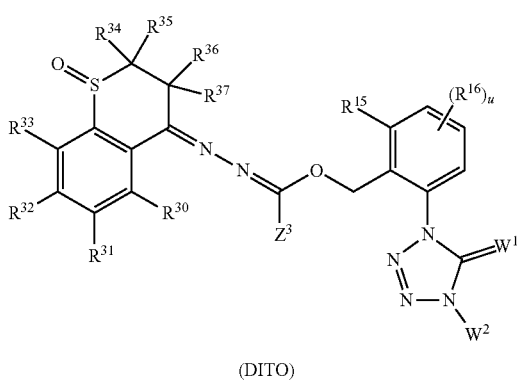

(DITO)

Formula (DIO):

[Chem.8]

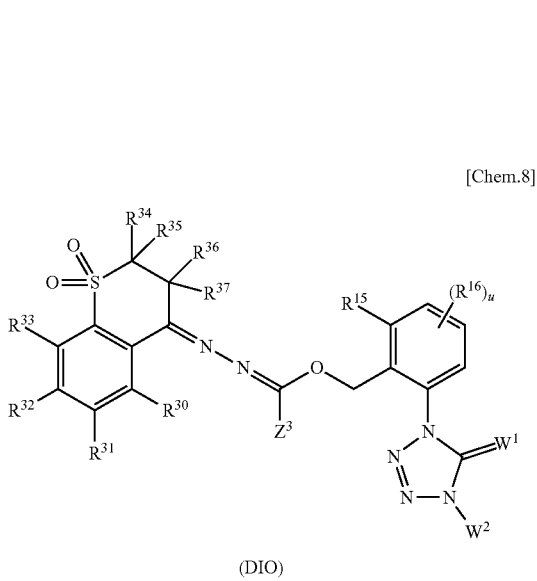

(DIO)

wherein the symbols are the same as defined above.

The compound wherein G and $Z^1$ together with carbon atoms to which they are bound form a 3,4-dihydro-2H-pyrano[2,3-b]pyridin-4-ylidene group represents a compound represented by formula (DIP23bP).

Formula (DIP23bP):

[Chem.9]

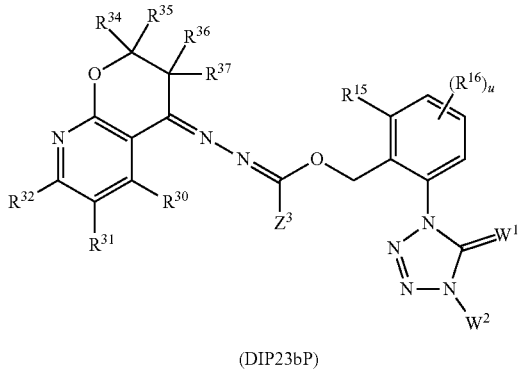

(DIP23bP)

wherein the symbols are the same as defined above.

The compound wherein G and $Z^1$ together with carbon atoms to which they are bound form a 3,4-dihydro-2H-pyrano[3,2-b]pyridin-4-ylidene group represents a compound represented by formula (DIP32bP).

Formula (DIP32bP):

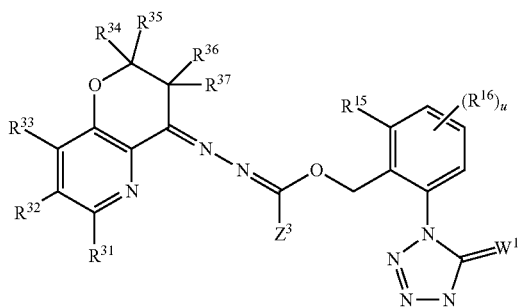

(DIP32bP)

wherein the symbols are the same as defined above.

The compound wherein G and $Z^1$ together with carbon atoms to which they are bound form a 3,4-dihydro-2H-pyrano[2,3-c]pyridin-4-ylidene group represents a compound represented by formula (DIP23 cP).

Formula (DIP23cP):

[Chem.11]

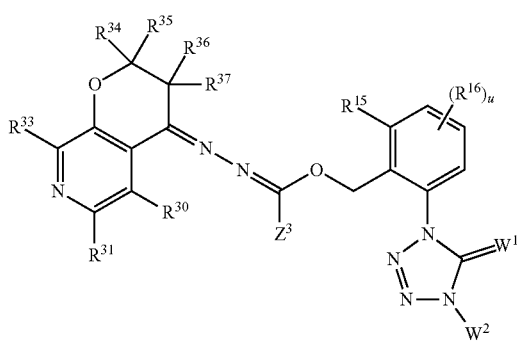

(DIP23cP)

wherein the symbols are the same as defined above.

The compound wherein G and $Z^1$ together with carbon atoms to which they are bound form a 3,4-dihydro-2H-pyrano[3,2-c]pyridin-4-ylidene represents a compound represented by formula (DIP32 cP).

Formula (DIP32cP)

[Chem.12]

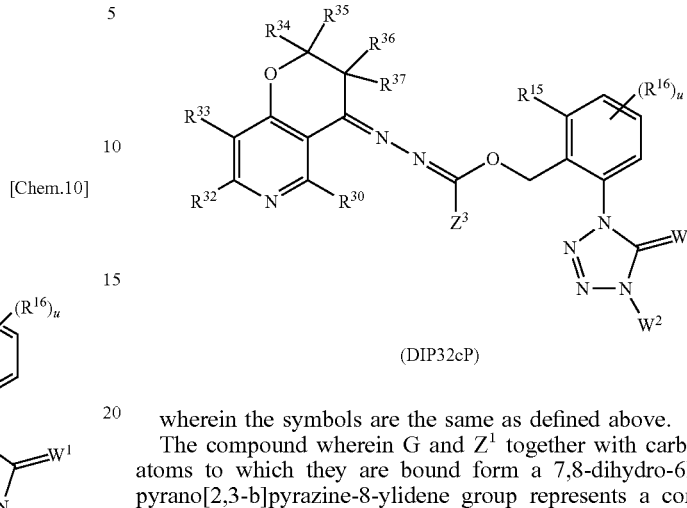

(DIP32cP)

wherein the symbols are the same as defined above.

The compound wherein G and $Z^1$ together with carbon atoms to which they are bound form a 7,8-dihydro-6H-pyrano[2,3-b]pyrazine-8-ylidene group represents a compound represented by formula (DIP23bPR).

Formula (DIP23bPR)

[Chem.13]

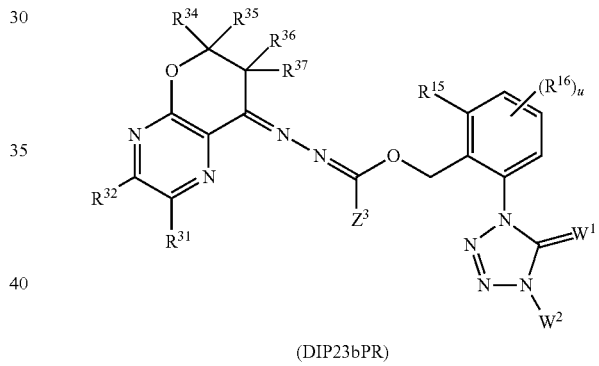

(DIP23bPR)

wherein the symbols are the same as defined above.

When the present compound has one, or two or more asymmetric centers, each optical isomer and mixtures containing the same in optional ratio thereof are encompassed by the present compound. Also, two kinds of geometric isomers due to carbon-carbon double bond or carbon-carbon triple bond, and mixtures containing the same in optional ratio thereof are encompassed by the present compound.

The present compound may be mixed with acids such as hydrochloric acid, sulfuric acid, nitric acid, phosphoric acid, acetic acid, or benzoic acid to form acid addition salts such as hydrochloride salts, sulfates, nitrates, phosphates, acetates, or benzoates.

Examples of the embodiment of the present compound include the following compounds.

Embodiment 1

The present compound wherein $R^{15}$ represents a halogen atom.

Embodiment 2

The present compound wherein $R^{15}$ represents a cyano group.

Embodiment 3

The present compound wherein $R^{15}$ represents a C1-C6 chain hydrocarbon group which may have one or more substituents selected from Group I.

Embodiment 4

The present compound wherein $R^{15}$ represents a C3-C6 cycloalkyl group which may have one or more substituents selected from Group I.

Embodiment 5

The present compound wherein $R^{15}$ represents a C1-C6 alkoxy group which may have one or more substituents selected from Group I.

Embodiment 6

The present compound wherein $R^{15}$ represents a C1-C6 alkylthio group which may have one or more substituents selected from Group I.

Embodiment 7

The present compound wherein $R^{15}$ represents a C3-C6 cycloakyloxy group which may have one or more substituents selected from Group I.

Embodiment 8

The present compound wherein $R^{15}$ represents a C3-C6 cycloalkylthio group which may have one or more substituents selected from Group I.

Embodiment 9

The present compound wherein u is 0.

Embodiment 10

The present compound wherein E represents an oxygen atom.

Embodiment 11

The present compound wherein E represents a sulfur atom.

Embodiment 12

The present compound wherein E represents #—C($X^1$)($Y^1$)—O—N═C($Z^1$)—.

Embodiment 13

The present compound wherein E represents #—C($X^1$)($Y^1$)—S—N═C($Z^1$)—.

Embodiment 14

The present compound wherein E represents #—C($X^1$)($Y^1$)—O—N═C($Z^1$)—O—CH$_2$—.

Embodiment 15

The present compound wherein E represents #—C($X^1$)($Y^1$)—O—N═C($Z^1$)—S—CH$_2$—.

Embodiment 16

The present compound wherein E represents #—C($X^1$)($Y^1$)—S—N═C($Z^1$)—O—CH$_2$—.

Embodiment 17

The present compound wherein E represents #—C($X^1$)($Y^1$)—S—N═C($Z^1$)—S—CH$_2$—.

Embodiment 18

The present compound wherein E represents #—O—N═C($Z^1$)—C($Z^2$)═N—S—CH$_2$—.

Embodiment 19

The present compound wherein E represents #—S—N═C($Z^1$)—C($Z^2$)═N—O—CH$_2$—.

Embodiment 20

The present compound wherein E represents #—S—N═C($Z^1$)—C($Z^2$)═N—S—CH$_2$—.

Embodiment 21

The present compound wherein E represents #—N═C($Z^1$)—S—CH$_2$—.

Embodiment 22

The present compound wherein E represents #—N═C($Z^1$)—O—CH$_2$—.

Embodiment 23

The present compound wherein E represents #—O—N═C($Z^1$)—S—CH$_2$—.

Embodiment 24

The present compound wherein E represents #—O—N═C($Z^1$)—O—CH$_2$—.

Embodiment 25

The present compound wherein E represents #—N($X^1$)—O—CH$_2$—.

Embodiment 26

The present compound wherein E represents #—C($Z^1$)═N—N═C($Z^2$)—.

Embodiment 27

The present compound wherein E represents #—C($Z^1$)═N—N═C($Z^3$)—O—CH$_2$—.

Embodiment 28

The present compound wherein E represents #—C($Z^1$)=N—N=C($Z^3$)—S—$CH_2$—.

Embodiment 29

The present compound wherein E represents #—C($X^1$)=C($Y^1$)—C($Z^1$)=N—O—$CH_2$—.

Embodiment 30

The present compound wherein E represents #—C($X^1$)=C($Y^1$)—C($Z^1$)=N—S—$CH_2$—.

Embodiment 31

The present compound wherein E represents #—N=C($SX^3$)—S—$CH_2$—.

Embodiment 32

The present compound wherein E represents #—N=C($OX^3$)—O—$CH_2$—.

Embodiment 33

The present compound wherein E represents #—N=C($SX^3$)—O—$CH_2$—.

Embodiment 34

The present compound wherein E represents #—N=C($OX^3$)—S—$CH_2$—.

Embodiment 35

The present compound wherein E represents #—O—C($Z^1$)=N—O—$CH_2$—.

Embodiment 36

The present compound wherein E represents #—C($Z^1$)=N—N=C($V^1$)—O—$CH_2$—.

Embodiment 37

The present compound wherein E represents #—C($Z^1$)=N—N=C($V^1$)—S—$CH_2$—.

Embodiment 38

The present compound wherein $R^8$ represents a pyrrolyl group which may have one or more substituents selected from Group L.

Embodiment 39

The present compound wherein $R^8$ represents a furanyl group which may have one or more substituents selected from Group L.

Embodiment 40

The present compound wherein $R^8$ represents a pyrazolyl group which may have one or more substituents selected from Group L.

Embodiment 41

The present compound wherein $R^8$ represents an imidazolyl group which may have one or more substituents selected from Group L.

Embodiment 42

The present compound wherein $R^8$ represents an oxazolyl group which may have one or more substituents selected from Group L.

Embodiment 43

The present compound wherein $R^8$ represents an isoxazolyl group which may have one or more substituents selected from Group L.

Embodiment 44

The present compound wherein $R^8$ represents an isothiazolyl group which may have one or more substituents selected from Group L.

Embodiment 45

The present compound wherein $R^8$ represents a triazolyl group which may have one or more substituents selected from Group L.

Embodiment 46

The present compound wherein $R^8$ represents an oxadiazolyl group which may have one or more substituents selected from Group L.

Embodiment 47

The present compound wherein $R^8$ represents a thiadiazolyl group which may have one or more substituents selected from Group L.

Embodiment 48

The present compound wherein $R^8$ represents a tetrazolyl group which may have one or more substituents selected from Group L.

Embodiment 49

The present compound wherein $R^8$ represents a pyrimidinyl group which may have one or more substituents selected from Group L.

Embodiment 50

The present compound wherein $R^8$ represents a pyrazinyl group which may have one or more substituents selected from Group L.

Embodiment 51

The present compound wherein $R^8$ represents a pyridazinyl group which may have one or more substituents selected from Group L.

Embodiment 52

The present compound wherein $R^8$ represents a benzofuranyl group which may have one or more substituents selected from Group L.

Embodiment 53

The present compound wherein $R^8$ represents a benzothienyl group which may have one or more substituents selected from Group L.

Embodiment 54

The present compound wherein $R^8$ represents an indolyl group which may have one or more substituents selected from Group L.

Embodiment 55

The present compound wherein $R^8$ represents an isoindolyl group which may have one or more substituents selected from Group L.

Embodiment 56

The present compound wherein $R^8$ represents an indolizinyl group which may have one or more substituents selected from Group L.

Embodiment 57

The present compound wherein $R^8$ represents an indazolyl group which may have one or more substituents selected from Group L.

Embodiment 58

The present compound wherein $R^8$ represents a benzimidazolyl group which may have one or more substituents selected from Group L.

Embodiment 59

The present compound wherein $R^8$ represents a benzothiazolyl group which may have one or more substituents selected from Group L.

Embodiment 60

The present compound wherein $R^8$ represents a benzoxazolyl group which may have one or more substituents selected from Group L.

Embodiment 61

The present compound wherein $R^8$ represents a benzisothiazolyl group which may have one or more substituents selected from Group L.

Embodiment 62

The present compound wherein $R^8$ represents a benzisoxazolyl group which may have one or more substituents selected from Group L.

Embodiment 63

The present compound wherein $R^8$ represents a 2,3-dihydrobenzofuranyl group which may have one or more substituents selected from Group L.

Embodiment 64

The present compound wherein $R^8$ represents a 2,3-dihydrobenzothienyl group which may have one or more substituents selected from Group L.

Embodiment 65

The present compound wherein $R^8$ represents a 3,4-dihydrobenzopyranyl group which may have one or more substituents selected from Group L.

Embodiment 66

The present compound wherein $R^8$ represents a 1,3-benzodioxazolyl group which may have one or more substituents selected from Group L.

Embodiment 67

The present compound wherein $R^8$ represents a quinolyl group which may have one or more substituents selected from Group L.

Embodiment 68

The present compound wherein $R^8$ represents an isoquinolyl group which may have one or more substituents selected from Group L.

Embodiment 69

The present compound wherein $R^8$ represents a cinnolinyl group which may have one or more substituents selected from Group L.

Embodiment 70

The present compound wherein $R^8$ represents a phthalazinyl group which may have one or more substituents selected from Group L.

Embodiment 71

The present compound wherein $R^8$ represents a quinazolinyl group which may have one or more substituents selected from Group L.

Embodiment 72

The present compound wherein $R^8$ represents a quinoxalinyl group which may have one or more substituents selected from Group L.

Embodiment 73

The present compound wherein $R^8$ represents a naphthyridinyl group which may have one or more substituents selected from Group L.

Embodiment 74

The present compound wherein $R^8$ represents a 3 to 8 membered non-aromatic heterocyclic group which may have one or more substituents selected from Group M.

Embodiment 75

The present compound wherein $R^8$ represents $-CR^{11}=N-O-R^{12}$.

Embodiment 76

The present compound wherein $R^9$ represents a phenyl group which may have one or more substituents selected from Group L.

Embodiment 77

The present compound wherein $R^{10}$ represents a pyridyl group which may have one or more substituents selected from Group L.

Embodiment 78

The present compound wherein $R^{14}$ represents a thienyl group which may have one or more substituents selected from Group L.

Embodiment 79

The present compound wherein $R^{14}$ represents a thiazolyl group which may have one or more substituents selected from Group L.

Embodiment 80

The present compound wherein $R^{14}$ represents a naphthyl group which may have one or more substituents selected from Group L.

Embodiment 81

The present compound wherein $T^3$ represents a single bond.

Embodiment 82

The present compound wherein $T^3$ represents an oxygen atom.

Embodiment 83

The present compound wherein $T^3$ represents $-S(O)_m-$.

Embodiment 84

The present compound wherein $T^3$ represents $-NR^{11}-$.

Embodiment 85

The present compound wherein $T^3$ represents $-(CR^2R^3)_n-$.

Embodiment 86

The present compound wherein $T^3$ represents $-(CR^2R^3)_n-O-*$.

Embodiment 87

The present compound wherein $T^3$ represents $-O(CR^2R^3)_n-*$.

Embodiment 88

The present compound wherein $T^3$ represents $-(CR^2R^3)_n S(O)_m-*$.

Embodiment 89

The present compound wherein $T^3$ represents $-S(O)_m(CR^2R^3)-$.

Embodiment 90

The present compound wherein $T^3$ represents $-CR^4=CR^5-$.

Embodiment 91

The present compound wherein $T^4$ represents an oxygen atom.

Embodiment 92

The present compound wherein $T^4$ represents $-S(O)_m-$.

Embodiment 93

The present compound wherein $T^4$ represents $-NR^{11}-$.

Embodiment 94

The present compound wherein $T^4$ represents $-(CR^2R^3)_n-O-*$.

Embodiment 95

The present compound wherein $T^4$ represents $-(CR^2R^3)_n-S(O)_m-*$.

Embodiment 96

The present compound wherein $T^4$ represents $-S(O)_m(CR^2R^3)_n-*$.

Embodiment 97

The present compound wherein $T^5$ represents an oxygen atom.

Embodiment 98

The present compound wherein $T^5$ represents $-S(O)_m-$.

Embodiment 99

The present compound wherein $T^5$ represents $-NR^{11}-$.

Embodiment 100

The present compound wherein $T^5$ represents $-(CR^2R^3)_n-$.

Embodiment 101

The present compound wherein $T^5$ represents —$(CR^2R^3)_n$O—*.

Embodiment 102

The present compound wherein $T^5$ represents —$O(CR^2R^3)_n$—*.

Embodiment 103

The present compound wherein $T^5$ represents —$(CR^2R^3)_n$S(O)$_m$—.

Embodiment 104

The present compound wherein $T^5$ represents —S(O)$_m$(CR^2R^3)_n$—*.

Embodiment 105

The present compound wherein $T^6$ represents an oxygen atom.

Embodiment 106

The present compound wherein $T^6$ represents —S(O)$_m$—.

Embodiment 107

The present compound wherein $T^6$ represents —$NR^{11}$—.

Embodiment 108

The present compound wherein $T^6$ represents —$(CR^2R^3)_n$—.

Embodiment 109

The present compound wherein $T^6$ represents —$(CR^2R^3)_n$O—*.

Embodiment 110

The present compound wherein $T^6$ represents —$O(CR^2R^3)_n$—*.

Embodiment 111

The present compound wherein $T^6$ represents —$(CR^2R^3)_n$S(O)$_m$—.

Embodiment 112

The present compound wherein $T^6$ represents —S(O)$_m$(CR^2R^3)_n$—*.

Embodiment 113

The present compound wherein $T^6$ represents —$CR^4$=$CR^5$—.

Embodiment 114

The present compound wherein $W^2$ represents a C1-C6 chain hydrocarbon group, $W^1$ represents an oxygen atom, $R^{15}$ represents a halogen atom, a C1-C3 alkyl group, a C3-C4 cycloalkyl group or a C1-C3 alkoxy group {the C1-C3 alkyl group, the C3-C4 cycloalkyl group and the C1-C3 alkoxy group may have one or more halogen atoms}, u is 0, E represents #—C($Z^1$)=N—N=C($Z^3$)—O—CH$_2$— or #—C($Z^1$)=N—N=C($Z^3$)—S—CH$_2$—, each of $Z^1$ and $Z^3$, which are identical to or different from each other, independently represents a C1-C6 chain hydrocarbon group or a C3-C6 cycloalkyl group {the C1-C6 chain hydrocarbon group and the C3-C6 cycloalkyl group may have one or more halogen atoms}, G represents $R^8$-$T^3$-, and $T^3$ represents a single bond.

Embodiment 115

The compound described in the Embodiment 114 wherein $R^8$ represents a 3 to 8 membered non-aromatic heterocyclic group which may have one or more substituents selected from Group M, a pyrrolyl group, a furanyl group, a pyrazolyl group, an imidazolyl group, an oxazolyl group, an isoxazolyl group, an isothiazolyl group, a triazolyl group, an oxadiazolyl group, a thiadiazolyl group, a tetrazolyl group, a pyrimidinyl group, a pyrazinyl group, a pyridazinyl group, a benzofuranyl group, a benzothienyl group, an indolyl group, an isoindolyl group, an indolizinyl group, an indazolyl group, a benzimidazolyl group, a benzothiazolyl group, a benzoxazolyl group, a benzisothiazolyl group, a benzisoxazolyl group, a 2,3-dihydrobenzofuranyl group, a 2,3-dihydrobenzothienyl group, a 3,4-dihydrobenzopyranyl group, a 1,3-benzodioxolyl group, a quinolyl group, an isoquinolyl group, a cinnolinyl group, a phthalazinyl group, a quinazolinyl group, a quinoxalinyl group, a naphthyridinyl group {the pyrrolyl group, the furanyl group, the pyrazolyl group, the imidazolyl group, the oxazolyl group, the isoxazolyl group, the isothiazolyl group, the triazolyl group, the oxadiazolyl group, the thiadiazolyl group, the tetrazolyl group, the pyrimidinyl group, the pyrazinyl group, the pyridazinyl group, the benzofuranyl group, the benzothienyl group, the indolyl group, the isoindolyl group, the indolizinyl group, the indazolyl group, the benzimidazolyl group, the benzothiazolyl group, the benzoxazolyl group, the benzisothiazolyl group, the benzisoxazolyl group, the 2,3-dihydrobenzofuranyl group, the 2,3-dihydrobenzothienyl group, the 3,4-dihydrobenzopyranyl group, the 1,3-benzodioxolyl group, the quinolyl group, the isoquinolyl group, the cinnolinyl group, the phthalazinyl group, the quinazolinyl group, the quinoxalinyl group and the naphthyridinyl group may have one or more substituents selected from Group L}, —$CR^4$=$CR^4$—O—$R^{12}$, —$CR^{11}$=N—N($R^{19}R^{20}$) or —$CR^{11}$=N—O—$R^{12}$.

Embodiment 116

The compound described in the Embodiment 114 wherein $R^8$ represents a 3 to 8 membered non-aromatic heterocyclic group which may have one or more substituents selected from Group M.

Embodiment 117

The compound described in the Embodiment 114 wherein $R^8$ represents a pyrrolyl group which may have one or more substituents selected from Group L.

Embodiment 118

The compound described in the Embodiment 114 wherein $R^8$ represents a furanyl group which may have one or more substituents selected from Group L.

Embodiment 119

The compound described in the Embodiment 114 wherein $R^8$ represents a pyrazolyl group which may have one or more substituents selected from Group L.

Embodiment 120

The compound described in the Embodiment 114 wherein $R^8$ represents an imidazolyl group which may have one or more substituents selected from Group L.

Embodiment 121

The compound described in the Embodiment 114 wherein $R^8$ represents an oxazolyl group which may have one or more substituents selected from Group L.

Embodiment 122

The compound described in the Embodiment 114 wherein $R^8$ represents an isoxazolyl group which may have one or more substituents selected from Group L.

Embodiment 123

The compound described in the Embodiment 114 wherein $R^8$ represents an isothiazolyl group which may have one or more substituents selected from Group L.

Embodiment 124

The compound described in the Embodiment 114 wherein $R^8$ represents a triazolyl group which may have one or more substituents selected from Group L.

Embodiment 125

The compound described in the Embodiment 114 wherein $R^8$ represents an oxadiazolyl group which may have one or more substituents selected from Group L.

Embodiment 126

The compound described in the Embodiment 114 wherein $R^8$ represents a thiadiazolyl group which may have one or more substituents selected from Group L.

Embodiment 127

The compound described in the Embodiment 114 wherein $R^8$ represents a tetrazolyl group which may have one or more substituents selected from Group L.

Embodiment 128

The compound described in the Embodiment 114 wherein $R^8$ represents a pyrimidinyl group which may have one or more substituents selected from Group L.

Embodiment 129

The compound described in the Embodiment 114 wherein $R^8$ represents a pyrazinyl group which may have one or more substituents selected from Group L.

Embodiment 130

The compound described in the Embodiment 114 wherein $R^8$ represents a pyridazinyl group which may have one or more substituents selected from Group L.

Embodiment 131

The compound described in the Embodiment 114 wherein $R^8$ represents a benzofuranyl group which may have one or more substituents selected from Group L.

Embodiment 132

The compound described in the Embodiment 114 wherein $R^8$ represents a benzothienyl group which may have one or more substituents selected from Group L.

Embodiment 133

The compound described in the Embodiment 114 wherein $R^8$ represents an indolyl group which may have one or more substituents selected from Group L.

Embodiment 134

The compound described in the Embodiment 114 wherein $R^8$ represents an isoindolyl group which may have one or more substituents selected from Group L.

Embodiment 135

The compound described in the Embodiment 114 wherein $R^8$ represents an indolizinyl group which may have one or more substituents selected from Group L.

Embodiment 136

The compound described in the Embodiment 114 wherein $R^8$ represents an indazolyl group which may have one or more substituents selected from Group L.

Embodiment 137

The compound described in the Embodiment 114 wherein $R^8$ represents a benzimidazolyl group which may have one or more substituents selected from Group L.

Embodiment 138

The compound described in the Embodiment 114 wherein $R^8$ represents a benzothiazolyl group which may have one or more substituents selected from Group L.

Embodiment 139

The compound described in the Embodiment 114 wherein $R^8$ represents a benzoxazolyl group which may have one or more substituents selected from Group L.

Embodiment 140

The compound described in the Embodiment 114 wherein $R^8$ represents a benzisothiazolyl group which may have one or more substituents selected from Group L.

Embodiment 141

The compound described in the Embodiment 114 wherein $R^8$ represents a benzisoxazolyl group which may have one or more substituents selected from Group L.

Embodiment 142

The compound described in the Embodiment 114 wherein $R^8$ represents a 2,3-dihydrobenzofuranyl group which may have one or more substituents selected from Group L.

Embodiment 143

The compound described in the Embodiment 114 wherein $R^8$ represents a 2,3-dihydrobenzothienyl group which may have one or more substituents selected from Group L.

Embodiment 144

The compound described in the Embodiment 114 wherein $R^8$ represents a 3,4-dihydrobenzopyranyl group which may have one or more substituents selected from Group L.

Embodiment 145

The compound described in the Embodiment 114 wherein $R^8$ represents a 1,3-benzodioxolyl group which may have one or more substituents selected from Group L.

Embodiment 146

The compound described in the Embodiment 114 wherein $R^8$ represents a quinolyl group which may have one or more substituents selected from Group L.

Embodiment 147

The compound described in the Embodiment 114 wherein $R^8$ represents an isoquinolyl group which may have one or more substituents selected from Group L.

Embodiment 148

The compound described in the Embodiment 114 wherein $R^8$ represents a cinnolinyl group which may have one or more substituents selected from Group L.

Embodiment 149

The compound described in the Embodiment 114 wherein $R^8$ represents a phthalazinyl group which may have one or more substituents selected from Group L.

Embodiment 150

The compound described in the Embodiment 114 wherein $R^8$ represents a quinazolinyl group which may have one or more substituents selected from Group L.

Embodiment 151

The compound described in the Embodiment 114 wherein $R^8$ represents a quinoxalinyl group which may have one or more substituents selected from Group L.

Embodiment 152

The compound described in the Embodiment 114 wherein $R^8$ represents a naphthyridinyl group which may have one or more substituents selected from Group L.

Embodiment 153

The compound described in the Embodiment 114 wherein $R^8$ represents —$CR^4$=$CR^4$—O—$R^{12}$.

Embodiment 154

The compound described in the Embodiment 114 wherein $R^8$ represents —$CR^{11}$=N—N($R^{19}R^{20}$).

Embodiment 155

The compound described in the Embodiment 114 wherein $R^8$ represents —$CR^{11}$=N—O—$R^{12}$.

Embodiment 156

The compound wherein $W^2$ represents a C1-C6 chain hydrocarbon group, $W^1$ represents an oxygen atom, $R^{15}$ represents a halogen atom, a C1-C3 alkyl group, a C3-C4 cycloalkyl group or a C1-C3 alkoxy group {the C1-C3 alkyl group, the C3-C4 cycloalkyl group and the C1-C3 alkoxy group may have one or more halogen atoms}, u is 0, E represents #—C($Z^1$)=N—N=C($Z^3$)—O—$CH_2$—, each of $Z^1$ and $Z^3$, which are identical to or different from each other, independently represents a C1-C6 chain hydrocarbon group or a C3-C6 cycloalkyl group{the C1-C6 chain hydrocarbon group and the C3-C6 cycloalkyl group may have one or more halogen atoms}, G represents $R^8$-$T^3$-, and $T^3$ represents a single bond.

Embodiment 157

The compound described in the Embodiment 156 wherein $R^8$ represents a benzothiazolyl group which may have one or more substituents selected from Group L.

Embodiment 158

The compound described in the Embodiment 156 wherein $R^8$ represents a furanyl group which may have one or more substituents selected from Group L.

Embodiment 159

The compound described in the Embodiment 156 wherein $R^8$ represents a benzothienyl group which may have one or more substituents selected from Group L.

Embodiment 160

The compound described in the Embodiment 156 wherein $R^8$ represents a benzofuranyl group which may have one or more substituents selected from Group L.

Embodiment 161

The compound described in the Embodiment 156 wherein $R^8$ represents a thiazolyl group which may have one or more substituents selected from Group L.

Embodiment 162

The compound described in the Embodiment 156 wherein $R^8$ represents an isothiazolyl group which may have one or more substituents selected from Group L.

Embodiment 163

The compound described in the Embodiment 156 wherein $R^8$ represents a thiadiazolyl group which may have one or more substituents selected from Group L.

Embodiment 164

The compound described in the Embodiment 156 wherein $R^8$ represents a pyrimidinyl group which may have one or more substituents selected from Group L.

Embodiment 165

The compound described in the Embodiment 156 wherein $R^8$ represents a pyridazinyl group which may have one or more substituents selected from Group L.

Embodiment 166

The compound described in the Embodiment 156 wherein $R^8$ represents —$CR^{11}$=N—O—$R^{12}$.

Embodiment 167

The present compound wherein $W^2$ represents a C1-C6 chain hydrocarbon group, $W^1$ represents an oxygen atom, $R^{15}$ represents a C1-C3 alkyl group or a C3-C4 cycloalkyl group {the C1-C3 alkyl group and the C3-C4 cycloalkyl group may have one or more halogen atoms}, u is 0, E represents #—C($Z^1$)=N—N=C($Z^3$)—O—$CH_2$—, each of $Z^1$ and $Z^3$, which are identical to or different from each other, independently represents a C1-C6 chain hydrocarbon group or a C3-C6 cycloalkyl group {the C1-C6 chain hydrocarbon group and the C3-C6 cycloalkyl group may have one or more halogen atoms}, G represents $R^8$-$T^3$-, and $T^3$ represents a single bond.

Embodiment 168

The compound described in the Embodiment 167 wherein $R^8$ represents a benzothiazolyl group which may have one or more substituents selected from Group L.

Embodiment 169

The compound described in the Embodiment 167 wherein $R^8$ represents a furanyl group which may have one or more substituents selected from Group L.

Embodiment 170

The compound described in the Embodiment 167 wherein $R^8$ represents a benzothienyl group which may have one or more substituents selected from Group L.

Embodiment 171

The compound described in the Embodiment 167 wherein $R^8$ represents a benzofuranyl group which may have one or more substituents selected from Group L.

Embodiment 172

The compound described in the Embodiment 167 wherein $R^8$ represents a thiazolyl group which may have one or more substituents selected from Group L.

Embodiment 173

The compound described in the Embodiment 167 wherein $R^8$ represents an isothiazolyl group which may have one or more substituents selected from Group L.

Embodiment 174

The compound described in the Embodiment 167 wherein $R^8$ represents a thiadiazolyl group which may have one or more substituents selected from Group L.

Embodiment 175

The compound described in the Embodiment 167 wherein $R^8$ represents a pyrimidinyl group which may have one or more substituents selected from Group L.

Embodiment 176

The compound described in the Embodiment 167 wherein $R^8$ represents a pyridazinyl group which may have one or more substituents selected from Group L.

Embodiment 177

The compound described in the Embodiment 167 wherein $R^8$ represents —$CR^1$=N—O—$R^{12}$.

Embodiment 178

The present compound wherein $W^2$ represents a C1-C6 chain hydrocarbon group, $W^1$ represents an oxygen atom, $R^{15}$ represents a C1-C3 alkyl group which may have one or more halogen atoms, u is 0, E represents #—C($Z^1$)=N—N=C($Z^3$)—O—$CH_2$—, each of $Z^1$ and $Z^3$ independently represents a C1-C6 chain hydrocarbon group, G represents $R^8$-$T^3$-, and $T^3$ represents a single bond.

Embodiment 179

The compound described in the Embodiment 178 wherein $R^8$ represents a furanyl group which may have one or more substituents selected from Group L.

Embodiment 180

The compound described in the Embodiment 178 wherein $R^8$ represents a pyrazolyl group which may have one or more substituents selected from Group L.

Embodiment 181

The compound described in the Embodiment 178 wherein $R^8$ represents an imidazolyl group which may have one or more substituents selected from Group L.

Embodiment 182

The compound described in the Embodiment 178 wherein $R^8$ represents an oxazolyl group which may have one or more substituents selected from Group L.

Embodiment 183

The compound described in the Embodiment 178 wherein $R^8$ represents an isoxazolyl group which may have one or more substituents selected from Group L.

Embodiment 184

The compound described in the Embodiment 178 wherein $R^8$ represents an isothiazolyl group which may have one or more substituents selected from Group L.

Embodiment 185

The compound described in the Embodiment 178 wherein $R^8$ represents a triazolyl group which may have one or more substituents selected from Group L.

Embodiment 186

The compound described in the Embodiment 178 wherein $R^8$ represents an oxadiazolyl group which may have one or more substituents selected from Group L.

Embodiment 187

The compound described in the Embodiment 178 wherein $R^8$ represents a thiadiazolyl group which may have one or more substituents selected from Group L.

Embodiment 188

The compound described in the Embodiment 178 wherein $R^8$ represents a tetrazolyl group which may have one or more substituents selected from Group L.

Embodiment 189

The compound described in the Embodiment 178 wherein $R^8$ represents a pyrimidinyl group which may have one or more substituents selected from Group L.

Embodiment 190

The compound described in the Embodiment 178 wherein $R^8$ represents a pyrazinyl group which may have one or more substituents selected from Group L.

Embodiment 191

The compound described in the Embodiment 178 wherein $R^8$ represents a pyridazinyl group which may have one or more substituents selected from Group L.

Embodiment 192

The compound described in the Embodiment 178 wherein $R^8$ represents a benzofuranyl group which may have one or more substituents selected from Group L.

Embodiment 193

The compound described in the Embodiment 178 wherein $R^8$ represents an indolyl group which may have one or more substituents selected from Group L.

Embodiment 194

The compound described in the Embodiment 178 wherein $R^8$ represents an isoindolyl group which may have one or more substituents selected from Group L.

Embodiment 195

The compound described in the Embodiment 178 wherein $R^8$ represents an indolizinyl group which may have one or more substituents selected from Group L.

Embodiment 196

The compound described in the Embodiment 178 wherein $R^8$ represents an indazolyl group which may have one or more substituents selected from Group L.

Embodiment 197

The compound described in the Embodiment 178 wherein $R^8$ represents a benzimidazolyl group which may have one or more substituents selected from Group L.

Embodiment 198

The compound described in the Embodiment 178 wherein $R^8$ represents a benzothiazolyl group which may have one or more substituents selected from Group L.

Embodiment 199

The compound described in the Embodiment 178 wherein $R^8$ represents a benzoxazolyl group which may have one or more substituents selected from Group L.

Embodiment 200

The compound described in the Embodiment 178 wherein $R^8$ represents a benzisothiazolyl group which may have one or more substituents selected from Group L.

Embodiment 201

The compound described in the Embodiment 178 wherein $R^8$ represents a benzisoxazolyl group which may have one or more substituents selected from Group L.

Embodiment 202

The compound described in the Embodiment 178 wherein $R^8$ represents a 2,3-dihydrobenzofuranyl group which may have one or more substituents selected from Group L.

Embodiment 203

The compound described in the Embodiment 178 wherein $R^8$ represents a 2,3-dihydrobenzothienyl group which may have one or more substituents selected from Group L.

Embodiment 204

The compound described in the Embodiment 178 wherein $R^8$ represents a 3,4-dihydrobenzopyranyl group which may have one or more substituents selected from Group L.

Embodiment 205

The compound described in the Embodiment 178 wherein $R^8$ represents a 1,3-benzodioxolyl group which may have one or more substituents selected from Group L.

Embodiment 206

The compound described in the Embodiment 178 wherein $R^8$ represents a quinolyl group which may have one or more substituents selected from Group L.

Embodiment 207

The compound described in the Embodiment 178 wherein $R^8$ represents an isoquinolyl group which may have one or more substituents selected from Group L.

Embodiment 208

The compound described in the Embodiment 178 wherein $R^8$ represents a cinnolinyl group which may have one or more substituents selected from Group L.

Embodiment 209

The compound described in the Embodiment 178 wherein $R^8$ represents a phthalazinyl group which may have one or more substituents selected from Group L.

Embodiment 210

The compound described in the Embodiment 178 wherein $R^8$ represents a quinazolinyl group which may have one or more substituents selected from Group L.

Embodiment 211

The compound described in the Embodiment 178 wherein $R^8$ represents a quinoxalinyl group which may have one or more substituents selected from Group L.

Embodiment 212

The compound described in the Embodiment 178 wherein $R^8$ represents a naphthyridinyl group which may have one or more substituents selected from Group L.

Embodiment 213

The compound described in the Embodiment 178 wherein $R^8$ represents a benzothienyl group which may have one or more substituents selected from Group L.

Embodiment 214

The compound described in the Embodiment 178 wherein $R^8$ represents —$CR^4$=$CR^4$—O—$R^{12}$.

Embodiment 215

The compound described in the Embodiment 178 wherein $R^8$ represents —$CR^{11}$=N—N($R^{19}R^{20}$).

Embodiment 216

The compound described in the Embodiment 178 wherein $R^8$ represents —$CR^{11}$=N—O—$R^{12}$.

Embodiment 217

The present compound wherein $W^2$ represents a methyl group, W represents an oxygen atom, $R^{15}$ represents a methyl group, an ethyl group, a fluorine atom, a chlorine atom, a bromine atom or cyclopropyl group, u is 0, E represents #—C($Z^1$)=N—N=C($Z^3$)—O—$CH_2$—, each of $Z^1$ and $Z^3$, which are independently identical to or different from each other, independently represents a methyl group or an ethyl group, G represents $R^8$-$T^3$-, and $T^3$ represents a single bond.

Embodiment 218

The compound described in the Embodiment 217 wherein $R^8$ represents a furanyl group which may have one or more substituents selected from Group L.

Embodiment 219

The compound described in the Embodiment 217 wherein $R^8$ represents a pyrazolyl group which may have one or more substituents selected from Group L.

Embodiment 220

The compound described in the Embodiment 217 wherein $R^8$ represents an imidazolyl group which may have one or more substituents selected from Group L.

Embodiment 221

The compound described in the Embodiment 217 wherein $R^8$ represents an oxazolyl group which may have one or more substituents selected from Group L.

Embodiment 222

The compound described in the Embodiment 217 wherein $R^8$ represents an isoxazoly group which may have one or more substituents selected from Group L.

Embodiment 223

The compound described in the Embodiment 217 wherein $R^8$ represents an isothiazolyl group which may have one or more substituents selected from Group L.

Embodiment 224

The compound described in the Embodiment 217 wherein $R^8$ represents a triazolyl group which may have one or more substituents selected from Group L.

Embodiment 225

The compound described in the Embodiment 217 wherein $R^8$ represents an oxadiazolyl group which may have one or more substituents selected from Group L.

Embodiment 226

The compound described in the Embodiment 217 wherein $R^8$ represents a thiadiazolyl group which may have one or more substituents selected from Group L.

Embodiment 227

The compound described in the Embodiment 217 wherein $R^8$ represents a tetrazolyl group which may have one or more substituents selected from Group L.

Embodiment 228

The compound described in the Embodiment 217 wherein $R^8$ represents a pyrimidinyl group which may have one or more substituents selected from Group L.

Embodiment 229

The compound described in the Embodiment 217 wherein $R^8$ represents a pyrazinyl group which may have one or more substituents selected from Group L.

Embodiment 230

The compound described in the Embodiment 217 wherein $R^8$ represents a pyridazinyl group which may have one or more substituents selected from Group L.

Embodiment 231

The compound described in the Embodiment 217 wherein $R^8$ represents a benzofuranyl group which may have one or more substituents selected from Group L.

Embodiment 232

The compound described in the Embodiment 217 wherein $R^8$ represents an indolyl group which may have one or more substituents selected from Group L.

Embodiment 233

The compound described in the Embodiment 217 wherein $R^8$ represents an isoindolyl group which may have one or more substituents selected from Group L.

Embodiment 234

The compound described in the Embodiment 217 wherein $R^8$ represents an indolizinyl group which may have one or more substituents selected from Group L.

Embodiment 235

The compound described in the Embodiment 217 wherein $R^8$ represents an indazolyl group which may have one or more substituents selected from Group L.

Embodiment 236

The compound described in the Embodiment 217 wherein $R^8$ represents a benzimidazolyl group which may have one or more substituents selected from Group L.

Embodiment 237

The compound described in the Embodiment 217 wherein $R^8$ represents a benzothiazolyl group which may have one or more substituents selected from Group L.

Embodiment 238

The compound described in the Embodiment 217 wherein $R^8$ represents a benzoxazolyl group which may have one or more substituents selected from Group L.

Embodiment 239

The compound described in the Embodiment 217 wherein $R^8$ represents a benzisothiazolyl group which may have one or more substituents selected from Group L.

Embodiment 240

The compound described in the Embodiment 217 wherein $R^8$ represents a benzisoxazolyl group which may have one or more substituents selected from Group L.

Embodiment 241

The compound described in the Embodiment 217 wherein $R^8$ represents a 2,3-dihydrobenzofuranyl group which may have one or more substituents selected from Group L.

Embodiment 242

The compound described in the Embodiment 217 wherein $R^8$ represents a 2,3-dihydrobenzothienyl group which may have one or more substituents selected from Group L.

Embodiment 243

The compound described in the Embodiment 217 wherein $R^8$ represents a 3,4-dihydrobenzopyranyl group which may have one or more substituents selected from Group L.

Embodiment 244

The compound described in the Embodiment 217 wherein $R^8$ represents a 1,3-benzodioxolyl group which may have one or more substituents selected from Group L.

Embodiment 245

The compound described in the Embodiment 217 wherein $R^8$ represents a quinolyl group which may have one or more substituents selected from Group L.

Embodiment 246

The compound described in the Embodiment 217 wherein $R^8$ represents an isoquinolyl group which may have one or more substituents selected from Group L.

Embodiment 247

The compound described in the Embodiment 217 wherein $R^8$ represents a cinnolinyl group which may have one or more substituents selected from Group L.

Embodiment 248

The compound described in the Embodiment 217 wherein $R^8$ represents a phthalazinyl group which may have one or more substituents selected from Group L.

Embodiment 249

The compound described in the Embodiment 217 wherein $R^8$ represents a quinazolinyl group which may have one or more substituents selected from Group L.

Embodiment 250

The compound described in the Embodiment 217 wherein $R^8$ represents a quinoxalinyl group which may have one or more substituents selected from Group L.

Embodiment 251

The compound described in the Embodiment 217 wherein $R^8$ represents a naphthyridinyl group which may have one or more substituents selected from Group L.

Embodiment 252

The compound described in the Embodiment 217 wherein $R^8$ represents a benzothienyl group which may have one or more substituents selected from Group L.

Embodiment 253

The compound described in the Embodiment 217 wherein $R^8$ represents $—CR^4$=$CR^4$—O—$R^{12}$.

Embodiment 254

The compound described in the Embodiment 217 wherein $R^8$ represents $—CR^{11}$=N—N($R^{19}R^{20}$).

Embodiment 255

The compound described in the Embodiment 217 wherein $R^8$ represents $—CR^{11}$=N—O—$R^{12}$.

Embodiment 256

The present compound wherein $W^2$ represents a C1-C6 chain hydrocarbon group, $W^1$ represents an oxygen atom, u is 0, E represents #—C($Z^1$)=N—N=C($Z^3$)—O—$CH_2$—, each of $Z^1$ and $Z^3$, which are identical to or different from each other, independently represents, a C1-C6 chain hydrocarbon group, G represents $R^8$-$T^3$-, $R^8$ represents a benzofuranyl group which may have one or more substituents selected from Group L, and $T^3$ represents a single bond.

Embodiment 257

The compound described in the Embodiment 256 wherein $R^{15}$ represents a halogen atom.

Embodiment 258

The compound described in the Embodiment 256 wherein $R^{15}$ represents a C3-C4 cycloalkyl group which may have one or more halogen atoms.

Embodiment 259

The compound described in the Embodiment 256 wherein $R^{15}$ represents a C1-C3 alkoxy group which may have one or more halogen atoms.

Embodiment 260

The compound described in the Embodiment 256 wherein $R^{15}$ represents a C3-C4 cycloalkyl group which may have one or more halogen atoms.

Embodiment 261

The present compound wherein $W^2$ represents a methyl group, $W^1$ represents an oxygen atom, $R^{15}$ represents a methyl group, an ethyl group, a fluorine atom, a chlorine atom, a bromine atom or cyclopropyl group, u is 0, E represents #—N=C($Z^1$)—S—$CH_2$— or #—N=C($Z^1$)—O—$CH_2$—, $Z^1$ represents a methoxy group or a methylthio group, G represents $R^1$-$T^2$-, $R^1$ represents a C6-C10 aromatic hydrocarbon group or a 5 to 10 membered aromatic heterocyclic group {the C6-C10 aromatic hydrocarbon group and the 5 to 10 membered aromatic heterocyclic group may have one or more substituents selected from Group P}, and $T^2$ represents a single bond.

Embodiment 262

The present compound wherein $W^2$ represents a methyl group, $W^1$ represents an oxygen atom, $R^{15}$ represents a methyl group, an ethyl group, a fluorine atom, a chlorine atom, a bromine atom or a cyclopropyl group, u is 0, E represents #—N=C($Z^1$)—S—$CH_2$—, $Z^1$ represents a methylthio group, G represents $R^1$-$T^2$-, $R^1$ represents a phenyl group, a pyridyl group, a pyrazolyl group, a thienyl group, a benzoisoxazolyl group, an isoxazolopyridyl group, an imidazopyridyl group or benzothiazolyl group {the phenyl group, the pyridyl group, the pyrazolyl group, the thienyl group, the benzoisoxazolyl group, the isoxazolopyridyl group, the imidazopyridyl group and the benzothiazolyl group may have one or more substituents selected from Group P}, $T^2$ represents a single bond, $—(CR^2R^3)_n—$, $—O—(CR^2R^3)_{n+1}—*$, $—CR^4$=$CR^5$— or $—CR^4$=$CR^5—CR^2R^3—*$, $R^2$ represents a hydrogen atom, and $R^3$ represents a hydrogen atom.

Embodiment 263

The present compound wherein $W^2$ represents a methyl group, $W^1$ represents an oxygen atom, $R^{15}$ represents a methyl group, an ethyl group, a fluorine atom, a chlorine atom, a bromine atom or cyclopropyl group, u is 0, E represents #—N=C($Z^1$)—O—$CH_2$—, $Z^1$ represents a methoxy group, G represents $R^1$-$T^2$-, $R^1$ represents a phenyl group, a pyridyl group, a pyrazolyl group, a thienyl group, a benzoisoxazolyl group, an isoxazolopyridyl group, an imidazopyridyl group or a benzothiazolyl group {the phenyl group, the pyridyl group, the pyrazolyl group, the thienyl group, the benzoisoxazolyl group, the isoxazolopyridyl group, the imidazopyridyl group and the benzothiazolyl group may have one or more substituents selected from Group P}, $T^2$ represents a single bond, $—(CR^2R^3)_n—$, $—O—(CR^2R^3)_{n+1}—*$, $—CR^4$=$CR^5$— or $—CR^4$=$CR^5—CR^2R^3—*$, $R^2$ represents a hydrogen atom, and $R^3$ represents a hydrogen atom.

Embodiment 264

The present compound wherein $W^2$ represents a methyl group, $W^1$ represents an oxygen atom, $R^{15}$ represents a methyl group, an ethyl group, a fluorine atom, a chlorine atom, a bromine atom or a cyclopropyl group, u is 0, E represents #—N=C($Z^1$)—O—CH$_2$—, $Z^1$ represents a methylthio group, G represents $R^1$-$T^2$-, $R^1$ represents a phenyl group, a pyridyl group, a pyrazolyl group, a thienyl group, a benzoisoxazolyl group, an isoxazolopyridyl group, an imidazopyridyl group or a benzothiazolyl group {the phenyl group, the pyridyl group, the pyrazolyl group, the thienyl group, the benzoisoxazolyl group, the isoxazolopyridyl group, the imidazopyridyl group and the benzothiazolyl group may have one or more substituents selected from Group P}, $T^2$ represents a single bond, —(CR$^2$R$^3$)$_n$—, —O—(CR$^2$R$^3$)$_{n+1}$—*, —CR$^4$=CR$^5$— or —CR$^4$=CR$^5$—CR$^2$R$^3$—*, $R^2$ represents a hydrogen atom, and $R^3$ represents hydrogen atom.

Embodiment 265

The present compound wherein $W^2$ represents a methyl group, $W^1$ represents an oxygen atom, $R^{15}$ represents a methyl group, an ethyl group, a fluorine atom, a chlorine atom, a bromine atom or a cyclopropyl group, u is 0, E represents #—N=C($Z^1$)—S—CH$_2$—, $Z^1$ represents a methoxy group, G represents $R^1$-$T^2$-, $R^1$ represents a phenyl group, a pyridyl group, a pyrazolyl group, a thienyl group, a benzoisoxazolyl group, an isoxazolopyridyl group, an imidazopyridyl group or a benzothiazolyl group {the phenyl group, the pyridyl group, the pyrazolyl group, the thienyl group, the benzoisoxazolyl group, the isoxazolopyridyl group, the imidazopyridyl group and the benzothiazolyl group may have one or more substituents selected from Group P}, $T^2$ represents a single bond, —(CR$^2$R$^3$)$_n$—, —O—(CR$^2$R$^3$)$_{n+1}$—*, —CR$^4$=CR$^5$— or —CR$^4$=CR$^5$—CR$^2$R$^3$—*, $R^2$ represents a hydrogen atom, and $R^3$ represents a hydrogen atom.

Embodiment 266

The present compound wherein $W^2$ represents a methyl group, $W^1$ represents an oxygen atom, $R^{15}$ represents a methyl group, an ethyl group, a fluorine atom, a chlorine atom, a bromine atom or a cyclopropyl group, u is 0, E represents #—N=C($Z^1$)—S—CH$_2$—, $Z^1$ represents a methylthio group, G represents $R^1$-$T^2$-, $R^1$ represents a phenyl group, a pyridyl group, a pyrazolyl group, a thienyl group, a benzoisoxazolyl group, an isoxazolopyridyl group, an imidazopyridyl group or a benzothiazolyl group {the phenyl group, the pyridyl group, the pyrazolyl group, the thienyl group, the benzoisoxazolyl group, the isoxazolopyridyl group, the imidazopyridyl group and the benzothiazolyl group may have one or more substituents selected from Group P}, $T^2$ represents a single bond, $R^2$ represents a hydrogen atom, and $R^3$ represents a hydrogen atom.

Embodiment 267

The present compound wherein $W^2$ represents a methyl group, $W^1$ represents an oxygen atom, $R^{15}$ represents a methyl group, an ethyl group, a fluorine atom, a chlorine atom, a bromine atom or a cyclopropyl group, u is 0, E represents #—N=C($Z^1$)—O—CH$_2$—, $Z^1$ represents a methylthio group, G represents $R^1$-$T^2$-, $R^1$ represents a phenyl group, a pyridyl group, a pyrazolyl group, a thienyl group, a benzoisoxazolyl group, an isoxazolopyridyl group, an imidazopyridyl group or a benzothiazolyl group {the phenyl group, the pyridyl group, the pyrazolyl group, the thienyl group, the benzoisoxazolyl group, the isoxazolopyridyl group, the imidazopyridyl group and the benzothiazolyl group may have one or more substituents selected from Group P}, $T^2$ represents a single bond, $R^2$ represents a hydrogen atom, and $R^3$ represents a hydrogen atom.

Embodiment 268

The present compound wherein $W^2$ represents a methyl group, $W^1$ represents an oxygen atom, $R^{15}$ represents a methyl group, an ethyl group, a fluorine atom, a chlorine atom, a bromine atom or a cyclopropyl group, u is 0, E represents #—N=C($Z^1$)—O—CH$_2$—, $Z^1$ represents a methoxy group, G represents $R^1$-$T^2$-, $R^1$ represents a phenyl group, a pyridyl group, a pyrazolyl group, a thienyl group, a benzoisoxazolyl group, an isoxazolopyridyl group, an imidazopyridyl group or a benzothiazolyl group {the phenyl group, the pyridyl group, the pyrazolyl group, the thienyl group, the benzoisoxazolyl group, the isoxazolopyridyl group, the imidazopyridyl group and the benzothiazolyl group may have one or more substituents selected from Group P}, $T^2$ represents a single bond, $R^2$ represents a hydrogen atom, and $R^3$ represents a hydrogen atom.

Embodiment 269

The present compound wherein $W^2$ represents a methyl group, $W^1$ represents an oxygen atom, $R^{15}$ represents a methyl group, u is 0, E represents #—N=C($Z^1$)—S—CH$_2$—, $Z^1$ represents a methylthio group, G represents $R^1$-$T^2$-, $R^1$ represents a phenyl group, a pyridyl group, a pyrazolyl group, a thienyl group, a benzoisoxazolyl group, an isoxazolopyridyl group, an imidazopyridyl group or a benzothiazolyl group {the phenyl group, the pyridyl group, the pyrazolyl group, the thienyl group, the benzoisoxazolyl group, the isoxazolopyridyl group, the imidazopyridyl group and the benzothiazolyl group may have one or more substituents selected from Group P}, $T^2$ represents a single bond, $R^2$ represents a hydrogen atom, and $R^3$ represents a hydrogen atom.

Embodiment 270

The present compound wherein $R^{15}$ represents a methyl group, an ethyl group, a fluorine atom, a chlorine atom, a bromine atom or a cyclopropyl group, $W^2$ represents a C1-C6 chain hydrocarbon group, $W^1$ represents an oxygen atom, u is 0, E represents #—C($Z^1$)=N—N=C($Z^3$)—O—CH$_2$—, each of $Z^1$ and $Z^3$, which are identical to or different from each other, independently represents a C1-C6 chain hydrocarbon group, G represents $R^8$-$T^3$-, $R^8$ represents —CR$^{11}$=N—O—R$^{12}$, and $T^3$ represents a single bond.

Embodiment 271

The compound described in the Embodiment 270 wherein $R^{11}$ represents a phenyl group which may have one or more substituents selected from Group N.

Embodiment 272

The compound described in the Embodiment 270 wherein $R^{11}$ represents a benzyl group which may have one or more substituents selected from Group N.

Embodiment 273

The compound described in the Embodiment 270 wherein $R^{11}$ represents a hydrogen atom.

Embodiment 274

The compound described in the Embodiment 270 wherein $R^{11}$ represents a halogen atom.

Embodiment 275

The compound described in the Embodiment 270 wherein $R^{11}$ represents a nitro group.

Embodiment 276

The compound described in the Embodiment 270 wherein $R^{11}$ represents a cyano group.

Embodiment 277

The compound described in the Embodiment 270 wherein $R^{11}$ represents a C1-C6 alkyl group which may have one or more halogen atoms.

Embodiment 278

The compound described in the Embodiment 270 wherein $R^{11}$ represents a C3-C6 cycloalkyl group which may have one or more halogen atoms.

Embodiment 279

The compound described in the Embodiment 270 wherein $R^{11}$ represents a C1-C6 alkoxy group which may have one or more halogen atoms.

Embodiment 280

The compound described in the Embodiment 270 wherein $R^{11}$ represents a C1-C6 alkylthio group which may have one or more halogen atoms.

Embodiment 281

The compound described in the Embodiment 270 wherein $R^{12}$ represents a phenyl group which may have one or more substituents selected from Group N.

Embodiment 282

The compound described in the Embodiment 270 wherein $R^{12}$ represents a benzyl group which may have one or more substituents selected from Group N.

Embodiment 283

The compound described in the Embodiment 270 wherein $R^{12}$ represents a pyridyl group which may have one or more substituents selected from Group N.

Embodiment 284

The compound described in the Embodiment 270 wherein $R^{12}$ represents a pyrazolyl group which may have one or more substituents selected from Group N.

Embodiment 285

The compound described in the Embodiment 270 wherein $R^{12}$ represents a pyrimidinyl group which may have one or more substituents selected from Group N.

Embodiment 286

The compound described in the Embodiment 270 wherein $R^{12}$ represents a hydrogen atom.

Embodiment 287

The compound described in the Embodiment 270 wherein $R^{12}$ represents a C1-C6 chain hydrocarbon group which have one or more halogen atoms.

Embodiment 288

The compound described in the Embodiment 270 wherein $R^{12}$ represents a C3-C6 cycloalkyl group which may have one or more halogen atoms.

Embodiment 289

The compound described in the Embodiment 270 wherein $R^{12}$ represents a (C3-C6 cycloalkyl)C1-C6 alkyl group which may have one or more halogen atoms.

Embodiment 290

The compound described in the Embodiment 270 wherein $R^{12}$ represents a (C1-C6 alkoxy)C2-C6 alkyl group which may have one or more halogen atoms.

Embodiment 291

The compound described in the Embodiment 270 wherein $R^{12}$ represents a (C1-C6 alkylthio)C2-C6 alkyl group which may have one or more halogen atoms.

Embodiment 292

The compound described in the Embodiment 277 wherein $R^{12}$ represents a phenyl group which may have one or more substituents selected from Group N.

Embodiment 293

The compound described in the Embodiment 277 wherein $R^{12}$ represents a benzyl group which may have one or more substituents selected from Group N.

Embodiment 294

The compound described in the Embodiment 277 wherein $R^{12}$ represents a pyridyl group which may have one or more substituents selected from Group N.

Embodiment 295

The compound described in the Embodiment 277 wherein $R^{12}$ represents a pyrazolyl group which may have one or more substituents selected from Group N.

Embodiment 296

The compound described in the Embodiment 277 wherein $R^{12}$ represents a pyrimidinyl group which may have one or more substituents selected from Group N.

Embodiment 297

The compound described in the Embodiment 277 wherein $R^{12}$ represents a hydrogen atom.

Embodiment 298

The compound described in the Embodiment 277 wherein $R^{12}$ represents a C1-C6 chain hydrocarbon group which have one or more halogen atoms.

Embodiment 299

The compound described in the Embodiment 277 wherein $R^{12}$ represents a C3-C6 cycloalkyl group which have one or more halogen atoms.

Embodiment 300

The compound described in the Embodiment 277 wherein $R^{12}$ represents a (C3-C6 cycloalkyl)C1-C6 alkyl group which have one or more halogen atoms.

Embodiment 301

The compound described in the Embodiment 277 wherein $R^{12}$ represents a (C1-C6 alkoxy)C2-C6 alkyl group which have one or more halogen atoms.

Embodiment 302

The compound described in the Embodiment 277 wherein $R^{12}$ represents a (C1-C6 alkylthio)C2-C6 alkyl group which have one or more halogen atoms.

Embodiment 303

The present compound wherein $R^{15}$ represents a methyl group, an ethyl group, a fluorine atom, a chlorine atom, a bromine atom or a cyclopropyl group, $W^2$ represents a methyl group, WI represents an oxygen atom, u is 0, E represents #—C($Z^1$)=N—N=C($Z^3$)—O—CH$_2$—, G and $Z^1$ together with carbon atoms to which they are bound form a C3-C10 alicyclic hydrocarbon group which may have one or more substituents selected from Group U.

Embodiment 304

The present compound wherein $R^{15}$ represents a methyl group, an ethyl group, a fluorine atom, a chlorine atom, a bromine atom or a cyclopropyl group, $W^2$ represents a methyl group, $W^1$ represents an oxygen atom, u is 0, E represents #—C($Z^1$)=N—N=C($Z^3$)—O—CH$_2$—, G and $Z^1$ together with carbon atoms to which they are bound form a 3 to 10 membered non-aromatic heterocyclic group which may have one or more substituents selected from Group U.

Embodiment 305

The present compound wherein $R^{15}$ represents a methyl group, $W^2$ represents a methyl group, $W^1$ represents an oxygen atom, u is 0, E represents #—C($Z^1$) =N—N=C($Z^3$)—O—CH$_2$—, and G and $Z^1$ together with carbon atoms to which they are bound form a C3-C10 alicyclic hydrocarbon group which may have one or more substituents selected from Group U.

Embodiment 306

The present compound wherein $R^{15}$ represents a methyl group, $W^2$ represents a methyl group, $W^1$ represents an oxygen atom, u is 0, E represents #—C($Z^1$) =N—N=C($Z^3$)—O—CH$_2$—, and G and $Z^1$ together with carbon atoms to which they are bound form a 3 to 10 membered non-aromatic heterocyclic group which may have one or more substituents selected from Group U.

Embodiment 366

The compound described in the Embodiment 217 wherein $R^8$ represents a dihydrobenzofuranyl group which may have one or more substituents selected from Group L.

Embodiment 368

The compound described in the Embodiment 217 wherein $R^8$ represents a dihydrobenzopyranyl group which may have one or more substituents selected from Group L.

Embodiment 369

The compound described in the Embodiment 217 wherein $R^8$ represents a tetrahydronaphthyl group which may have one or more substituents selected from Group L.

Embodiment 370

The compound described in the Embodiment 217 wherein $R^8$ represents an indanyl group which may have one or more substituents selected from Group L.

Embodiment 371

The compound described in the Embodiment 217 wherein $R^8$ represents an oxazolopyridyl group which may have one or more substituents selected from Group L.

Embodiment 372

The compound described in the Embodiment 217 wherein $R^8$ represents a thiazolopyridyl group which may have one or more substituents selected from Group L.

Embodiment 373

The compound described in the Embodiment 217 wherein $R^8$ represents an isoxazolopyridyl group which may have one or more substituents selected from Group L.

Embodiment 374

The compound described in the Embodiment 217 wherein $R^8$ represents an isothiazolopyridyl group which may have one or more substituents selected from Group L.

Embodiment 375

The compound described in the Embodiment 217 wherein $R^8$ represents a tetrahydroindazoly group which may have one or more substituents selected from Group L.

Embodiment 376

The compound described in the Embodiment 217 wherein $R^8$ represents a cyclopentapyrazolyl group which may have one or more substituents selected from Group L.

Embodiment 377

The present compound wherein $R^{15}$ represents a halogen atom, a methyl group, a cyclopropyl group or a methoxy group, $W^2$ represents a methyl group, $W^1$ represents an oxygen atom, u is 0, E represents #—C($Z^1$)=N—N=C($Z^3$)—O—$CH_2$—, $Z^3$ represents an ethyl group, G and $Z^1$ together with carbon atoms to which they are bound form an indan-1-ylidene group, a 1,2,3,4-tetrahydronaphthalen-1-ylidene group, a 2,3-dihydrobenzofuran-3-ylidene group, a 3,4-dihydro-2H-1-benzopyran-4-ylidene group or a 1,1-dioxo-3,4-dihydro-2H-1-benzothiopyran-4-ylidene group {the indan-1-ylidene group, the 1,2,3,4-tetrahydronaphthalen-1-ylidene group, the 2,3-dihydrobenzofuran-3-ylidene group, the 3,4-dihydro-2H-1-benzopyran-4-ylidene group and the 1,1-dioxo-3,4-dihydro-2H-1-benzothiopyran-4-ylidene group may have one or more substituents selected from Group U}.

Embodiment 378

The present compound wherein $R^{15}$ represents a halogen atom, a methyl group, a cyclopropyl group or a methoxy group, $W^2$ represents a methyl group, $W^1$ represents an oxygen atom, u is 0, E represents #—C($Z^1$)=N—N=C($Z^3$)—O—$CH_2$—, $Z^3$ represents an ethyl group, G and $Z^1$ together with carbon atoms to which they are bound form an indan-1-ylidene group, a 1,2,3,4-tetrahydronaphthalen-1-ylidene group, a 2,3-dihydrobenzofuran-3-ylidene group, a 3,4-dihydro-2H-1-benzopyran-4-ylidene group or a 1,1-dioxo-3,4-dihydro-2H-1-benzothiopyran-4-ylidene group {the indan-1-ylidene group, the 1,2,3,4-tetrahydronaphthalen-1-ylidene group, the 2,3-dihydrobenzofuran-3-ylidene group, the 3,4-dihydro-2H-1-benzopyran-4-ylidene group and the 1,1-dioxo-3,4-dihydro-2H-1-benzothiopyran-4-ylidene group may have one or more substituents selected from the group consisting of a halogen atom, a C1-C3 alkyl group which may have one or more halogen atoms, and a C1-C3 alkoxy group which may have one or more halogen atoms.

Embodiment 379

The present compound wherein $R^{15}$ represents a halogen atom, a methyl group, a cyclopropyl group or a methoxy group, $W^2$ represents a methyl group, $W^1$ represents an oxygen atom, u is 0, E represents #—C($Z^1$)=N—N=C($Z^3$)—O—$CH_2$—, $Z^3$ represents an ethyl group, G and $Z^1$ together with carbon atoms to which they are bound form a 3,4-dihydro-2H-1-benzopyran-4-ylidene group which may have one or more substituents selected from the group consisting of a halogen atom, a C1-C3 alkyl group which may have one or more halogen atoms, and a C1-C3 alkoxy group which may have one or more halogen atoms.

Embodiment 380

The present compound wherein $R^{15}$ represents a halogen atom, a C1-C6 chain hydrocarbon group, a C3-C6 cycloalkyl group or a C1-C6 alkoxy group {the C1-C6 chain hydrocarbon group, the C3-C6 cycloalkyl group or the C1-C6 alkoxy group may have one or more substituents selected from Group I}, $W^2$ represents a C1-C6 chain hydrocarbon group, $W^1$ represents an oxygen atom, u is 0, E represents #—C($Z^1$)=N—N=C($Z^3$)—O—$CH_2$—, $Z^3$ represents a C1-C6 chain hydrocarbon group which may have one or more substituents selected from Group I, G and $Z^1$ together with carbon atoms to which they are bound form an indan-1-ylidene group, a 1,2,3,4-tetrahydronaphthalen-1-ylidene group, a 2,3-dihydrobenzofuran-3-ylidene group, a 2,3-dihydrobenzothiophen-3-ylidene group, a 3,4-dihydro-2H-1-benzopyran-4-ylidene group, a 1-oxo-3,4-dihydro-2H-1-benzothiopyran-4-ylidene group, a 1,1-dioxo-3,4-dihydro-2H-1-benzothiopyran-4-ylidene group or a 3,4-dihydro-2H-1-benzothiopyran-4-ylidene group {the indan-1-ylidene group, the 1,2,3,4-tetrahydronaphthalen-1-ylidene group, the 2,3-dihydrobenzofuran-3-ylidene group, the 2,3-dihydrobenzothiophen-3-ylidene group, the 3,4-dihydro-2H-1-benzopyran-4-ylidene group, the 1-oxo-3,4-dihydro-2H-1-benzothiopyran-4-ylidene group, the 1,1-dioxo-3,4-dihydro-2H-1-benzothiopyran-4-ylidene group and the 3,4-dihydro-2H-1-benzothiopyran-4-ylidene group may have one or more substituents selected from Group U}.

Embodiment 381

The present compound wherein $W^1$ represents an oxygen atom, $W^2$ represents a methyl group, u is 0, $R^{15}$ represents a methyl group, E represents #—C($Z^1$)=N—N=C($Z^3$)—O—$CH_2$—, G represents $R^8$-$T^3$-, $Z^1$ represents a methyl group, $Z^3$ represents an ethyl group, $T^3$ represents a single bond, $R^8$ represents a furanyl group, a pyrazolyl group, a pyrimidinyl group, a pyrazinyl group, a benzofuranyl group, a benzothienyl group, an indolyl group, an indazolyl group, a benzimidazolyl group, a benzothiazolyl group, a benzoxazolyl group, a dihydrobenzofuranyl group, a quinolyl group, a quinoxalinyl group, a tetrahydronaphthyl group, an indanyl group, a 1,3-benzodioxolyl group, a pyrrolopyridyl group {the furanyl group, the pyrazolyl group, the pyrimidinyl group, the pyrazinyl group, the benzofuranyl group, the benzothienyl group, the indolyl group, the indazolyl group, the benzimidazolyl group, the benzothiazolyl group, the benzoxazolyl group, the dihydrobenzofuranyl group, the quinolyl group, the quinoxalinyl group, the tetrahydronaphthyl group, the indanyl group, the 1,3-benzodioxolyl group and the pyrrolopyridyl group may have one or more substituents selected from the group consisting of a C1-C6 chain hydrocarbon group which may have one or more halogen atoms and a halogen atom}, or —$CR^{11}$=N—O—$R^2$, $R^{11}$ represents a methyl group, $R^{12}$ represents a benzyl group {the benzyl group may have one or more substituents selected from the group consisting of a C1-C3 alkyl group and a C1-C3 alkoxy group}, a C1-C6 chain hydrocarbon group, a (C3-C6 cycloalkyl)C1-C6 alkyl group, a (C1-C6 alkoxy)C2-C6 alkyl group, a cyano(C1-C6 alkyl) group or a hydrogen atom.

Embodiment 382

The present compound wherein $W^1$ represents an oxygen atom, $W^2$ represents a methyl group, u is 0, $R^{15}$ represents a methyl group, E represents #—C($Z^1$)=N—N=C($Z^3$)—O—$CH_2$—, G represents $R^8$-$T^3$-, $Z^1$ represents a methyl group, $Z^3$ represents an ethyl group, $T^3$ represents a single bond, $R^8$ represents a furanyl group, a pyrazolyl group, a pyrimidinyl group, a pyrazinyl group, a benzofuranyl group, a benzothienyl group, an indolyl group, an indazolyl group, a benzimidazolyl group, a benzothiazolyl group, a benzoxazolyl group, a dihydrobenzofuranyl group, a quinolyl group, a quinoxalinyl group, a tetrahydronaphthyl group, an indanyl group, a 1,3-benzodioxolyl group, a pyrrolopyridyl group {the furanyl group, the pyrazolyl group, the pyrimidinyl group, the pyrazinyl group, the benzofuranyl group, the benzothienyl group, the indolyl group, the indazolyl group, the benzimidazolyl group, the benzothiazolyl group, the benzoxazolyl group, the dihydrobenzofuranyl group, the quinolyl group, the quinoxalinyl group, the tetrahydronaphthyl group, the indanyl group, the 1,3-benzodioxolyl group and the pyrrolopyridyl group may have one or more substituents selected from the group consisting of a methyl group and a halogen atom}, or —$CR^{11}$=N—O—$R^{12}$, $R^{11}$ represents a methyl group, $R^{12}$ represents a benzyl group {the benzyl group may have one or more substituents selected from the group consisting of a methyl group and a methoxy group}, a C1-C6 chain hydrocarbon group, a (C3-C6 cycloalkyl)C1-C6 alkyl group, a (C1-C6 alkoxy)C2-C6 alkyl group, a cyano(C1-C6 alkyl) group or a hydrogen atom.

Embodiment 383

The present compound wherein $W^1$ represents an oxygen atom, $W^2$ represents a methyl group, u is 0, $R^{15}$ represents a methyl group, E represents #—C($Z^1$)=N—N=C($Z^3$)—O—$CH_2$—, G represents $R^8$-$T^3$-, $Z^1$ represents a methyl group, $Z^3$ represents an ethyl group, $T^3$ represents a single bond, $R^8$ represents a partially unsaturated or aromatic 8 to 10 membered fused heterocyclic group which may have one or more substituents selected from the group consisting of a methyl group and a halogen atom, or —$CR^{11}$=N—O—$R^{12}$, $R^{11}$ represents a methyl group, $R^{12}$ represents a benzyl group {the benzyl group may have one or more substituents selected from the group consisting of a methyl group and a methoxy group}, a C1-C6 chain hydrocarbon group, a (C3-C6 cycloalkyl)C1-C6 alkyl group, a (C1-C6 alkoxy)C2-C6 alkyl group, a cyano(C1-C6 alkyl) group or a hydrogen atom.

Embodiment 384

The present compound wherein $W^1$ represents an oxygen atm, $W^2$ represents a methyl group, u is 0, $R^{15}$ represents a methyl group, E represents #—C($Z^1$)=N—N=C($Z^3$)—O—$CH_2$—, G represents $R^8$-$T^3$-, $Z^1$ represents a methyl group, $Z^3$ represents an ethyl group, $T^3$ represents a single bond, $R^8$ represents a benzofuranyl group, a benzothienyl group, an indolyl group, an indazolyl group, a benzimidazolyl group, a benzothiazolyl group, a benzoxazolyl group, a dihydrobenzofuranyl group, a quinolyl group, a quinoxalinyl group, a tetrahydronaphthyl group, an indanyl group, a 1,3-benzodioxolyl group, a pyrrolopyridyl group {the benzofuranyl group, the benzothienyl group, the indolyl group, the indazolyl group, the benzimidazolyl group, the benzothiazolyl group, the benzoxazolyl group, the dihydrobenzofuranyl group, the quinolyl group, the quinoxalinyl group, the tetrahydronaphthyl group, the indanyl group, the 1,3-benzodioxolyl group and the pyrrolopyridyl group may have one or more substituents selected from the group consisting of a methyl group and a halogen atom}, or —$CR^{11}$=N—O—$R^{12}$, $R^{11}$ represents a methyl group, $R^{12}$ represents a benzyl group {the benzyl group may have one or more substituents selected from the group consisting of a methyl group and a methoxy group}, a C1-C6 chain hydrocarbon group, a (C3-C6 cycloalkyl)C1-C6 alkyl group, a (C1-C6 alkoxy)C2-C6 alkyl group, a cyano(C1-C6 alkyl) group or a hydrogen atom.

Embodiment 385

The present compound wherein $W^1$ represents an oxygen atom, $W^2$ represents a methyl group, u is 0, $R^{15}$ represents a halogen atom, a methyl group, a cyclopropyl group or a methoxy group, E represents #—C($Z^1$)=N—N=C($Z^3$)—O—$CH_2$—, G represents $R^8$-$T^3$-, $Z^1$ represents a C1-C3 alkyl group, $Z^3$ represents a C1-C3 alkyl group, $T^3$ represents a single bond, $R^8$ represents a furanyl group, a pyrazolyl group, a pyrimidinyl group, a pyrazinyl group, a benzofuranyl group, a benzothienyl group, an indolyl group, an indazolyl group, a benzimidazolyl group, a benzothiazolyl group, a benzoxazolyl group, a dihydrobenzofuranyl group, a quinolyl group, a quinoxalinyl group, a tetrahydronaphthyl group, an indanyl group, a 1,3-benzodioxolyl group, a pyrrolopyridyl group {the furanyl group, the pyrazolyl group, the pyrimidinyl group, the pyrazinyl group, the benzofuranyl group, the benzothienyl group, the indolyl group, the indazolyl group, the benzimidazolyl group, the benzothiazolyl group, the benzoxazolyl group, the dihydrobenzofuranyl group, the quinolyl group, the quinoxalinyl group, the tetrahydronaphthyl group, the indanyl group, the 1,3-benzodioxolyl group and the pyrrolopyridyl group may have one or more substituents selected from the group consisting of a C1-C6 chain hydrocarbon group which may have one or more halogen atoms and a halogen atom}, or —$CR^{11}$=N—O—$R^{12}$, $R^{11}$ represents a C1-C3 alkyl group, $R^{12}$ represents a benzyl group {the benzyl group may have one or more substituents selected from the group consisting of a C1-C6 alkyl group and a C1-C6 alkoxy group}, a C1-C6 chain hydrocarbon group, a (C3-C6 cycloalkyl)C1-C6 alkyl group, a (C1-C6 alkoxy)C2-C6 alkyl group, a cyano(C1-C6 alkyl) group or a hydrogen atom.

Embodiment 386

The present compound wherein $W^2$ represents a methyl group, $R^{15}$ represents a halogen atom, a methyl group, a cyclopropyl group or a methoxy group, u is 0, E represents #—C($Z^1$)=N—N=C($Z^3$)—O—$CH_2$—, G represents $R^8$-$T^3$-, $Z^1$ represents a C1-C3 alkyl group, $T^3$ represents a single bond, $R^8$ represents a furanyl group, a pyrazolyl group, a pyrimidinyl group, a pyrazinyl group, a benzofuranyl group, a benzothienyl group, an indolyl group, an indazolyl group, a benzimidazolyl group, a benzothiazolyl group, a benzoxazolyl group, a dihydrobenzofuranyl group, a quinolyl group, a quinoxalinyl group, a tetrahydronaphthyl group, an indanyl group, a 1,3-benzodioxolyl group, a pyrrolopyridyl group {the furanyl group, the pyrazolyl group, the pyrimidinyl group, the pyrazinyl group, the benzofuranyl group, the benzothienyl group, the indolyl group, the indazolyl group, the benzimidazolyl group, the benzothiazolyl group, the benzoxazolyl group, the dihydrobenzofuranyl group, the quinolyl group, the quinoxalinyl group, the tetrahydronaphthyl group, the indanyl group, the 1,3-benzodioxolyl group and the pyrrolopyridyl group may have one or more substituents selected from the group consisting of a C1-C6 chain hydrocarbon group which may have one or more halogen atoms and a halogen atom}, or —$CR^{11}$=N—O—$R^{12}$, $R^{11}$ represents a C1-C6 alkyl group, $R^{12}$ represents a benzyl group {the benzyl group may have one or more substituents selected from the group consisting of a C1-C6 alkyl group and a C1-C6 alkoxy group}, a C1-C6 chain hydrocarbon group, a C3-C6 cycloalkyl group, a (C1-C6 alkoxy)C2-C6 alkyl group, a cyano(C1-C6 alkyl) group {the C1-C6 chain hydrocarbon group, the C3-C6 cycloalkyl group, the (C1-C6 alkoxy)C2-C6 alkyl group and the cyano(C1-C6 alkyl) group may have one or more halogen atoms} or a hydrogen atom, and $Z^3$ represents a C1-C6 chain hydrocarbon group which may have one or more halogen atoms.

Embodiment 387

The present compound wherein $W^1$ represents an oxygen atom, $W^2$ represents a methyl group, u is 0, $R^{15}$ represents a halogen atom, a methyl group, a cyclopropyl group or a methoxy group, E represents #—C($Z^1$)=N—N=C($Z^3$)—O—CH$_2$—, G represents $R^8$-$T^3$-, $Z^1$ represents a C1-C3 alkyl group, $Z^3$ represents a C1-C3 alkyl group, $T^3$ represents a single bond, $R^8$ represents a furanyl group, a pyrazolyl group, a pyrimidinyl group, a pyrazinyl group, a benzofuranyl group, a benzothienyl group, an indolyl group, an indazolyl group, a benzimidazolyl group, a benzothiazolyl group, a benzoxazolyl group, a dihydrobenzofuranyl group, a quinolyl group, a quinoxalinyl group, a tetrahydronaphthyl group, an indanyl group, a 1,3-benzodioxolyl group, a pyrrolopyridyl group {the furanyl group, the pyrazolyl group, the pyrimidinyl group, the pyrazinyl group, the benzofuranyl group, the benzothienyl group, the indolyl group, the indazolyl group, the benzimidazolyl group, the benzothiazolyl group, the benzoxazolyl group, the dihydrobenzofuranyl group, the quinolyl group, the quinoxalinyl group, the tetrahydronaphthyl group, the indanyl group, the 1,3-benzodioxolyl group and the pyrrolopyridyl group may have one or more substituents selected from Group L}, or —CR$^{11}$=N—O—R$^{12}$, R$^{11}$ represents a C1-C3 alkyl group, R$^{12}$ represents a benzyl group {the benzyl group may have one or more substituents selected from the group consisting of a C1-C6 alkyl group and a C1-C6 alkoxy group}, a C1-C6 chain hydrocarbon group, a (C3-C6 cycloalkyl)C1-C6 alkyl group, a (C1-C6 alkoxy)C2-C6 alkyl group, a cyano(C1-C6 alkyl) group or hydrogen atom.

Embodiment 388

The present compound wherein $W^1$ represents an oxygen atom, $W^2$ represents a methyl group, u is 0, $R^{15}$ represents a methyl group, E represents #—C($Z^1$)=N—N=C($Z^3$)—O—CH$_2$—, G represents $R^8$-$T^3$-, $Z^1$ represents a methyl group, $Z^3$ represents an ethyl group, $T^3$ represents a single bond, $R^8$ represents a furanyl group, a pyrazolyl group, a pyrimidinyl group, a pyrazinyl group, a benzofuranyl group, a benzothienyl group, an indolyl group, an indazolyl group, a benzimidazolyl group, a benzothiazolyl group, a benzoxazolyl group, a dihydrobenzofuranyl group, a quinolyl group, a quinoxalinyl group, a tetrahydronaphthyl group, an indanyl group, a 1,3-benzodioxolyl group, a pyrrolopyridyl group {the furanyl group, the pyrazolyl group, the pyrimidinyl group, the pyrazinyl group, the benzofuranyl group, the benzothienyl group, the indolyl group, the indazolyl group, the benzimidazolyl group, the benzothiazolyl group, the benzoxazolyl group, the dihydrobenzofuranyl group, the quinolyl group, the quinoxalinyl group, the tetrahydronaphthyl group, the indanyl group, the 1,3-benzodioxolyl group and the pyrrolopyridyl group may have one or more substituents selected from Group L}, or —CR$^{11}$=N—O—R$^{12}$, R$^{11}$ represents a C1-C3 alkyl group, R$^{12}$ represents a benzyl group {the benzyl group may have one ore more substituents selected from the group consisting of a C1-C6 alkyl group and a C1-C6 alkoxy group}, a C1-C6 chain hydrocarbon group, a (C3-C6 cycloalkyl)C1-C6 alkyl group, a (C1-C6 alkoxy)C2-C6 alkyl group, a cyano(C1-C6 alkyl) group or a hydrogen atom.

Embodiment 389

The present compound wherein $W^1$ represents an oxygen atom, $W^2$ represents a methyl group, u is 0, $R^{15}$ represents a methyl group, E represents #—C($Z^1$)=N—N=C($Z^3$)—O—CH$_2$—, G represents $R^8$-$T^3$-, $Z^1$ represents a methyl group, $Z^3$ represents an ethyl group, $T^3$ represents a single bond, $R^8$ represents a furanyl group, a pyrazolyl group, a pyrimidinyl group, a pyrazinyl group, a benzofuranyl group, a benzothienyl group, an indolyl group, an indazolyl group, a benzimidazolyl group, a benzothiazolyl group, a benzoxazolyl group, a dihydrobenzofuranyl group, a quinolyl group, a quinoxalinyl group, a tetrahydronaphthyl group, an indanyl group, a 1,3-benzodioxolyl group, or a pyrrolopyridyl group {the furanyl group, the pyrazolyl group, the pyrimidinyl group, the pyrazinyl group, the benzofuranyl group, the benzothienyl group, the indolyl group, the indazolyl group, the benzimidazolyl group, the benzothiazolyl group, the benzoxazolyl group, the dihydrobenzofuranyl group, the quinolyl group, the quinoxalinyl group, the tetrahydronaphthyl group, the indanyl group, the 1,3-benzodioxolyl group and the pyrrolopyridyl group may have one or more substituents selected from Group L}, R$^{12}$ represents a benzyl group {the benzyl group may have one or more substituents selected from the group consisting of a C1-C6 alkyl group and a C1-C6 alkoxy group}, a C1-C6 chain hydrocarbon group, a (C3-C6 cycloalkyl)C1-C6 alkyl group, a (C1-C6 alkoxy)C2-C6 alkyl group, a cyano(C1-C6 alkyl) group or a hydrogen atom.

Embodiment 390

The present compound wherein $W^1$ represents an oxygen atom, $W^2$ represents a methyl group, u is 0, $R^{15}$ represents a methyl group, E represents #—C($Z^1$)=N—N=C($Z^3$)—O—CH$_2$—, G represents $R^8$-$T^3$-, $Z^1$ represents a methyl group, $Z^3$ represents an ethyl group, $T^3$ represents a single bond, $R^8$ represents a furanyl group, a pyrazolyl group, a pyrimidinyl group, a pyrazinyl group, a benzofuranyl group, a benzothienyl group, an indolyl group, indazolyl group, a benzimidazolyl group, a benzothiazolyl group, a benzoxazolyl group, a dihydrobenzofuranyl group, a quinolyl group, a quinoxalinyl group, a tetrahydronaphthyl group, an indanyl group, a 1,3-benzodioxolyl group, or a pyrrolopyridyl group {the furanyl group, the pyrazolyl group, the pyrimidinyl group, the pyrazinyl group, the benzofuranyl group, the benzothienyl group, the indolyl group, the indazolyl group, the benzimidazolyl group, the benzothiazolyl group, the benzoxazolyl group, the dihydrobenzofuranyl group, the quinolyl group, the quinoxalinyl group, the tetrahydronaphthyl group, the indanyl group, the 1,3-benzodioxolyl group and the pyrrolopyridyl group may have one or more substituents selected from the group consisting of C1-C6 chain hydrocarbon group which may have one or more halogen atoms, a halogen atom, and (C1-C3 alkoxy)C1-C3 alkyl group.

Embodiment 391

The present compound wherein $W^1$ represents an oxygen atom, $W^2$ represents a methyl group, u is 0, $R^{15}$ represents a methyl group, E represents #—C($Z^1$)=N—N=C($Z^3$)—

O—CH$_2$—, G represents R$^8$-T$^3$-, Z$^1$ represents a methyl group, Z$^3$ represents a methyl group, T$^3$ represents a single bond, R$^8$ represents a furanyl group, a pyrazolyl group, a pyrimidinyl group, a pyrazinyl group, a benzofuranyl group, a benzothienyl group, an indolyl group, an indazolyl group, a benzimidazolyl group, a benzothiazolyl group, a benzoxazolyl group, a dihydrobenzofuranyl group, a quinolyl group, a quinoxalinyl group, a tetrahydronaphthyl group, an indanyl group, a 1,3-benzodioxolyl group, a pyrrolopyridyl group {the furanyl group, the pyrazolyl group, the pyrimidinyl group, the pyrazinyl group, the benzofuranyl group, the benzothienyl group, the indolyl group, the indazolyl group, the benzimidazolyl group, the benzothiazolyl group, the benzoxazolyl group, the dihydrobenzofuranyl group, the quinolyl group, the quinoxalinyl group, the tetrahydronaphthyl group, the indanyl group, the 1,3-benzodioxolyl group and the pyrrolopyridyl group may have one or more substituents selected from the group consisting of a methyl group and a halogen atom}, or —CR$^{11}$=N—O—R$^{12}$, R$^{11}$ represents a methyl group, R$^{12}$ represents a benzyl group {the benzyl group may have one or more substituents selected from the group consisting of a methyl group and a halogen atom}, a C1-C6 chain hydrocarbon group, a (C3-C6 cycloalkyl) C1-C3 alkyl group, a (C1-C3 alkoxy)C2-C3 alkyl group, a (C1-C3 alkylthio)C1-C3 alkyl group, a cyano (C1-C6 alkyl) group or a hydrogen atom.

Embodiment 392

A present compound wherein R$^{15}$ represents a halogen atom, a methyl group, a cyclopropyl group or a methoxy group, W$^2$ represents a methyl group, W$^1$ represents an oxygen atom, u is 0, E represents #—C(Z$^1$)=N—N=C (Z$^3$)—O—CH$_2$—, Z$^3$ represents an ethyl group, G and Z$^1$ together with carbon atoms to which they are bound form a 3,4-dihydro-2H-1-benzopyran-4-ylidene group {the 3,4-dihydro-2H-1-benzopyran-4-ylidene group may have one ore more substituents selected from the group consisting of a halogen atom, a C1-C3 alkyl group and a C1-C3 alkoxy group}.

Embodiment 393

The present compound wherein W$^1$ represents an oxygen atom, W$^2$ represents a methyl group, R$^{15}$ represents a C1-C3 alkyl group which may have one or more halogen atoms, a C3-C6 cycloalkyl group, a C1-C6 alkoxy group, or a halogen atom, u is 0, E represents #—C(Z$^1$)=N—N=C(Z$^3$)—O—CH$_2$—, Z$^3$ represents a C1-C3 alkyl group, G and Z$^1$ together with carbon atoms to which they are bound form a C3-C10 alicyclic hydrocarbon group or a 3 to 10 membered non-aromatic heterocyclic group {the C3-C10 alicyclic hydrocarbon group and the 3 to 10 membered non-aromatic heterocyclic group may have one or more substituents selected from Group U}.

Next, the method for preparing the present compound is explained.

The present compound may be prepared, for example, by the below-mentioned process.

Process A

A compound represented by formula (A-1) (hereinafter, referred to as Compound (A-1)) may be prepared by reacting a compound represented by formula (A-2) (hereinafter, referred to as Compound (A-2)) and a compound represented by formula (AA1) (hereinafter, referred to as Compound (AA1)) or salts thereof in the presence of a base.

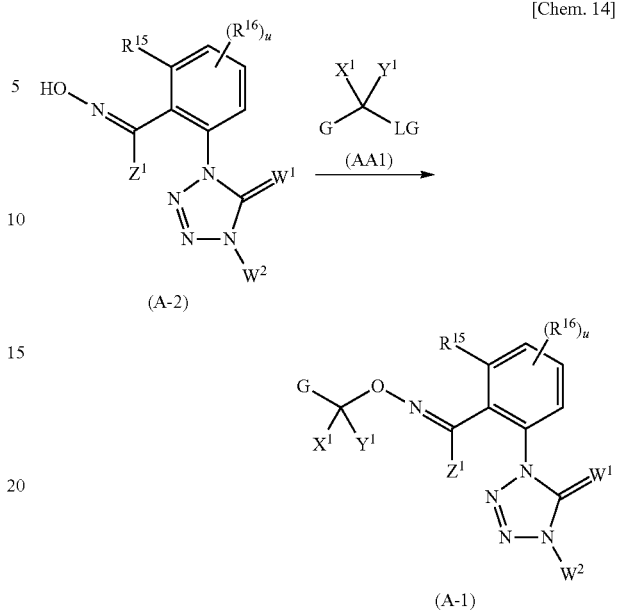

[Chem. 14]

wherein, LG represents a halogen atom, a mesyloxy group, a tosyloxy group, a trifuoromethanesulfonyloxy group, or an acetoxy group, and the other symbols are the same as defined above.

The reaction is usually carried out in a solvent. Examples of the solvent to be used in the reaction include hydrocarbon such as n-hexane, cyclohexane, toluene, and xylene (hereinafter, hydrocarbons); ether such as diethyl ether, tetrahydrofuran, 1,4-dioxane, ethyleneglycol dimethyl ether, methyl tert-butyl ether (hereinafter, referred to as MTBE), and diisopropyl ether (hereinafter, ethers); halogenated hydrocarbon such as chloroform, dichloromethane, chlorobenzene (hereinafter, referred to as halogenated hydrocarbons); amide such as dimethylformamide (hereinafter, referred to as DMF), 1,3-dimethyl-2-imidazolidinone, and N-methylpyrrolidone (hereinafter, referred to as amides); ester such as ethyl acetate and methyl acetate (hereinafter, referred to as esters); nitrile such as acetonitrile and propionitrile (hereinafter, referred to as nitriles); and mixtures thereof.

Examples of the base to be used in the reaction include organic base such as triethylamine, pyridine, 2,2'-bipyridine, and diazabicycloundecene (hereinafter, referred to as organic bases); metallic organic acid salt such as lithium formate, lithium acetate, sodium formate, sodium acetate, potassium formate, potassium acetate (hereinafter, referred to as metallic organic acid salts); metal nitrate such as silver nitrate, and sodium nitrate (hereinafter, referred to as metal nitrates); alkali-metal carbonate such as lithium carbonate, sodium carbonate, potassium carbonate, and cesium carbonate (hereinafter, referred to as alkali-metal carbonates); alkali-metal bicarbonate such as lithium bicarbonate, sodium bicarbonate, potassium bicarbonate, and cesium bicarbonate (hereinafter, referred to as alkali-metal bicarbonates); alkali-metal hydroxide such as lithium hydroxide, sodium hydroxide, potassium hydroxide, and cesium hydroxide (hereinafter, referred to as alkali-metal hydroxides); alkali metal alkoxide such as sodium methoxide, sodium ethoxide, sodium tert-butoxide, and potassium tert-butoxide (hereinafter, referred to as alkali metal alkoxides);

and alkali metal hydride such as sodium hydride (hereinafter, referred to as alkali metal hydrides); and mixtures thereof.

Examples of salts of Compound (AA1) include hydrochloride salt and hydrobromide salt thereof.

In the reaction, Compound (AA1) is used usually within a range of 1 to 10 molar ratio(s), and the base is usually used within a range of 1 to 20 molar ratio(s), as opposed to 1 mole of Compound (A-2).

The reaction temperature is usually within a range of –20 to 150° C. The reaction period of the reaction is usually within a range of 0.1 to 120 hours.

When the reaction is completed, water is added to the reaction mixtures, the reaction mixtures are extracted with organic solvent(s), and the resulting organic layers are worked up (for example, drying and concentration) to isolate Compound (A-1).

The compound (AA1) or salts thereof may be the publicly known compound, or may be prepared according to the similar method to the publicly known method.

Process B

The compound represented by formula (B-1) (hereinafter, referred to as Compound (B-1)) may be prepared by using a compound represented by formula (B-2) (hereinafter, referred to as Compound (B-2)) and Compound (AA1) or salts thereof according to the similar method to Process A.

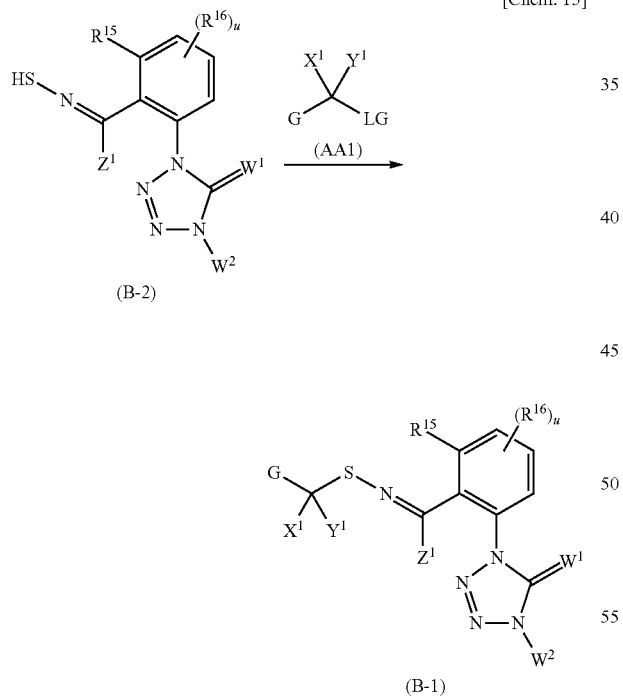

wherein the symbols are the same as defined above.

Process E

The compound represented by formula (E-1) (hereinafter, referred to as Compound (E-1)) may be prepared by using a compound represented by formula (E-2) (hereinafter, referred to as Compound (E-2)) and Compound (AA1) or salts thereof according to the similar method to Process A.

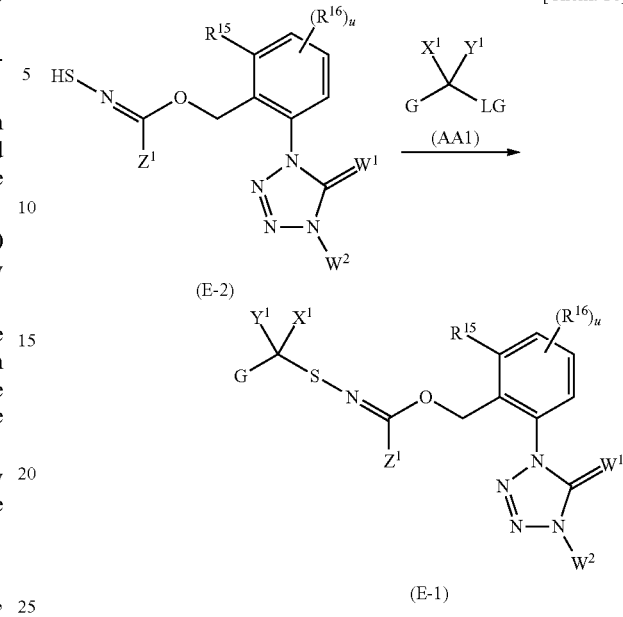

wherein the symbols are the same as defined above.

Process F

The compound represented by formula (F-1) (hereinafter referred to as Compound (F-1)) may be prepared by using a compound represented by formula (F-2)) (hereinafter, referred to as Compound (F-2)) and Compound (AA1) or salts thereof according to the similar method to Process A.

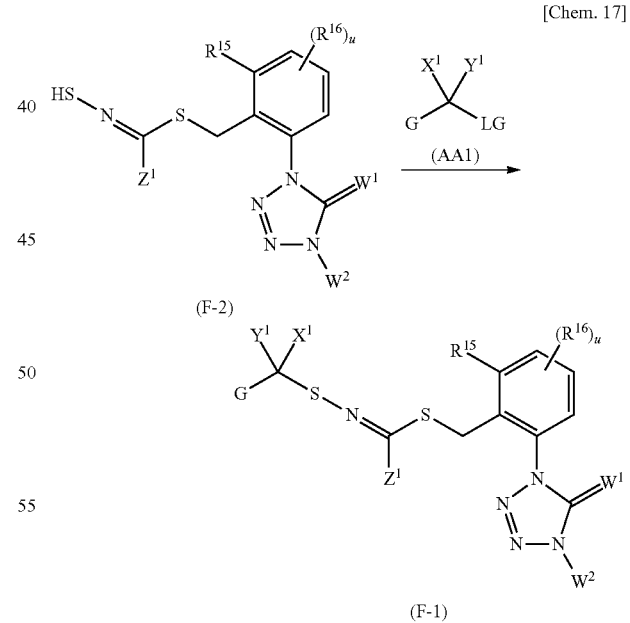

wherein the symbols are the same as defined above.

Process C

A compound represented by formula (C-1) (hereinafter referred to as Compound (C-1)) may be prepared by reacting a compound represented by formula (C-2) (hereinafter, referred to as Compound (C-2)) and a compound represented by formula (CC1) (hereinafter, referred to as Compound (CC1)) or salts thereof in the presence of a base.

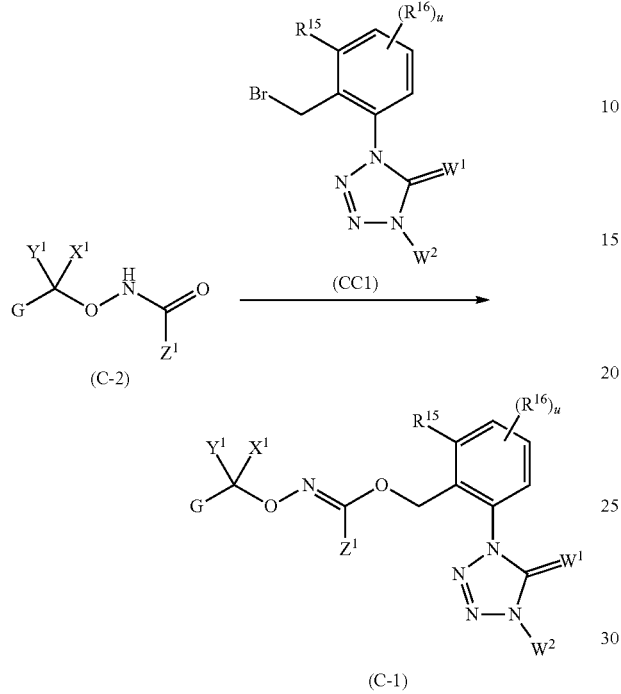

(C-2)

(CC1) →

(C-1)

wherein the symbols are the same as defined above.

The reaction is usually carried out in a solvent. Examples of the solvent to be used in the reaction include hydrocarbons, ethers, hydrogenated hydrocarbons, amides, esters, nitriles, and mixtures thereof.

Examples of the base to be used in the reaction include organic bases, metallic organic acid salts, metal nitrates, alkali-metal hydroxides, alkali metal alkoxides, alkali metal bicarbonates, alkali metal hydrides, and mixtures thereof.

Examples of the salts of Compound (CC1) include hydrochloride salts and hydrobromide salts thereof.

In the reaction, Compound (CC1) is usually used within a range of 1 to 10 molar ratio(s), and the base is usually used within a range of 1 to 20 molar ratio(s), as opposed to 1 mole of Compound (C-2).

The reaction temperature is usually within a range of −20 to 150° C. The reaction period of the reaction is usually within a range of 0.1 to 120 hours.

When the reaction is completed, water is added to the reaction mixtures, the reaction mixtures are extracted with organic solvent(s), and the resulting organic layers are worked up (for example, drying and concentration) to isolate Compound (C-1).

Compound (CC1) or salts thereof may be prepared by the similar method to those described in WO 2013/162072 A1.

Compound (C-2) may be a publicly known compound, or may be prepared according to the similar method to the publicly known method.

Process D

A compound represented by formula (D-1) (hereinafter, referred to as Compound (D-1)) may be prepared by using a compound represented by formula (D-2) (hereinafter, referred to as Compound (D-2)) and Compound (CC1) according to the similar method to Process C.

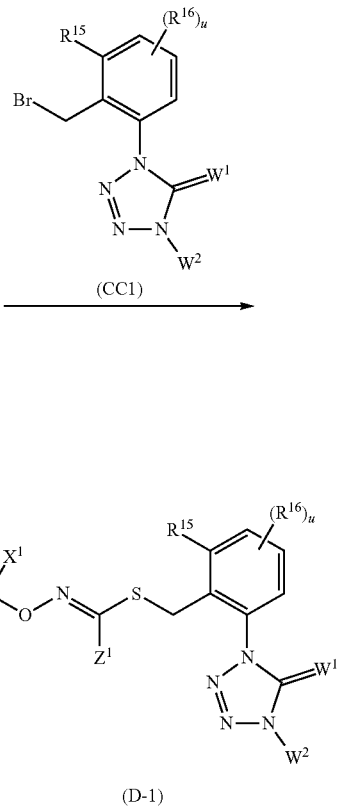

(D-2)

(CC1) →

(D-1)

wherein the symbols are the same as defined above.

Process H

A compound represented by formula (H-1) (hereinafter, referred to as Compound (H-1)) may be prepared by using a compound represented by formula (H-2) (hereinafter, referred to as Compound (H-2)) and Compound (CC1) according to the similar method to Process C.

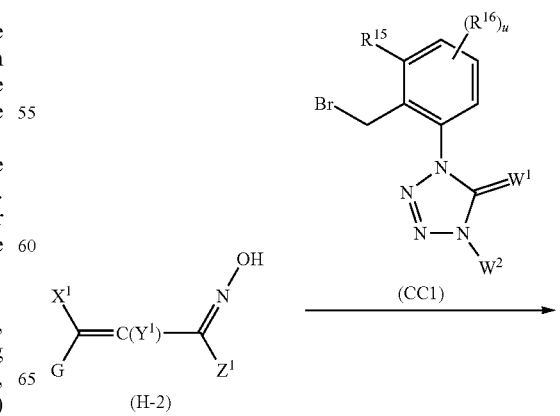

(H-2)

(CC1) →

-continued

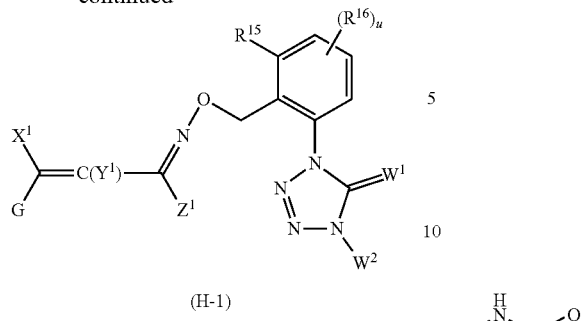

(H-1)

wherein the symbols are the same as defined above.

Process J

A compound represented by formula (J-1) (hereinafter, referred to as Compound (J-1)) may be prepared by reacting a compound (J-2) (hereinafter, referred to as Compound (J-2)) and Compound (CC1) according to the similar method to Process C.

[Chem. 21]

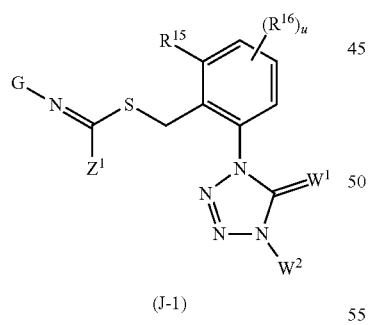

(J-2)

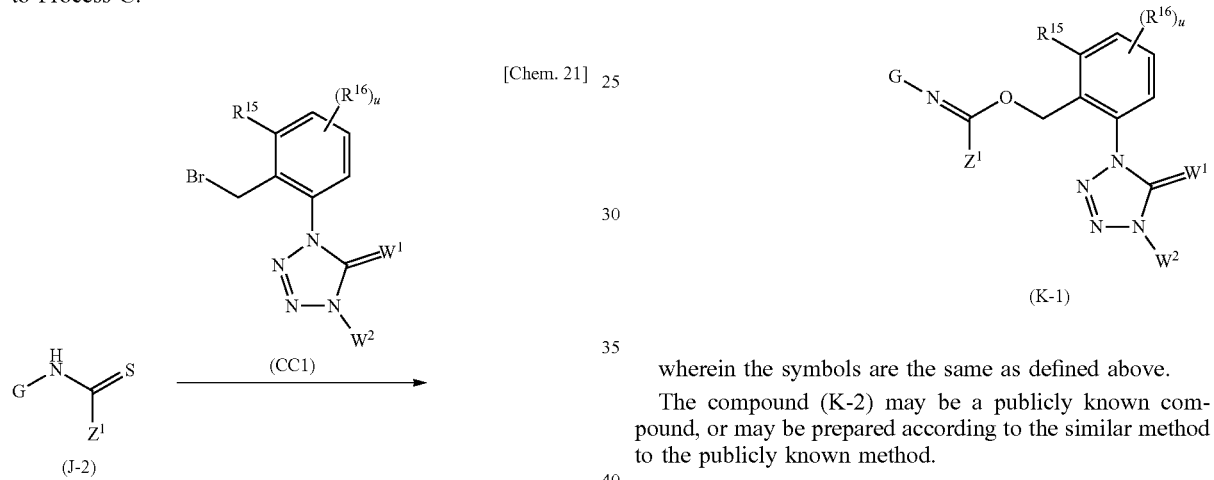

(J-1)

wherein the symbols are the same as defined above.

The compound (J-2) may be a publicly known compound, or may be prepared according to the similar method to the publicly known method.

Process K

The compound represented by formula (K-1) (hereinafter, referred to as Compound (K-1)) may be prepared by using a compound represented by formula (K-2)) (hereinafter, referred to as Compound (K-2)) and Compound (CC1) according to the similar method to Process C.

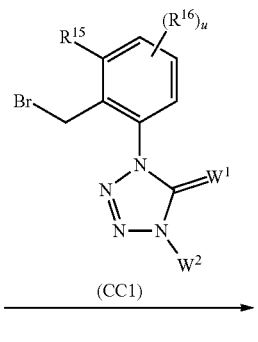

(K-2)

[Chem. 22]

wherein the symbols are the same as defined above.

The compound (K-2) may be a publicly known compound, or may be prepared according to the similar method to the publicly known method.

Process L

A compound represented by formula (L-1) (hereinafter, referred to as Compound (L-1)) may be prepared by reacting a compound represented by formula (L-2)) (hereinafter, referred to as Compound (L-2)) and Compound (CC1) according to the similar method to Process C.

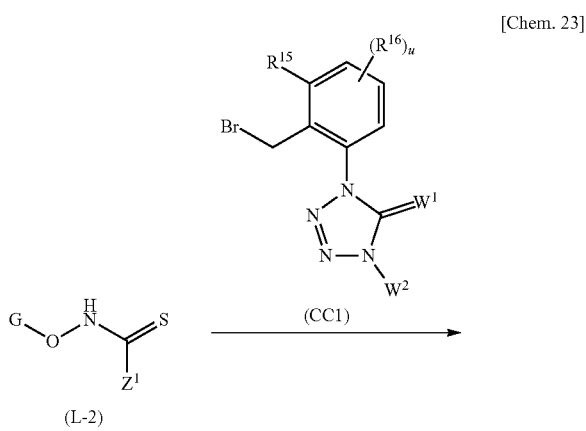

(L-2)

[Chem. 23]

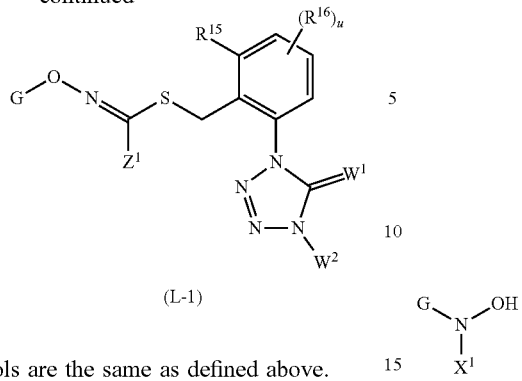

(L-1)

wherein the symbols are the same as defined above.

Compound (L-2) may be a publicly known compound, or may be prepared by the similar method to the publicly known method.

Process M

A compound represented by formula (M-1) (hereinafter, referred to as Compound (M-1)) may be prepared by using a compound (M-2)) (hereinafter, referred to as Compound (M-2)) and Compound (CC1) according to the similar method to the process C.

[Chem. 24]

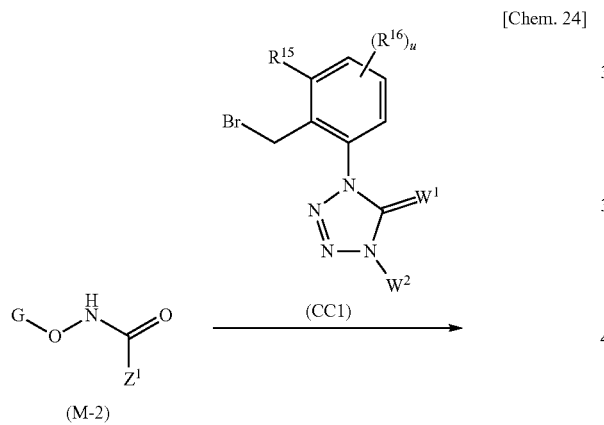

(M-2)

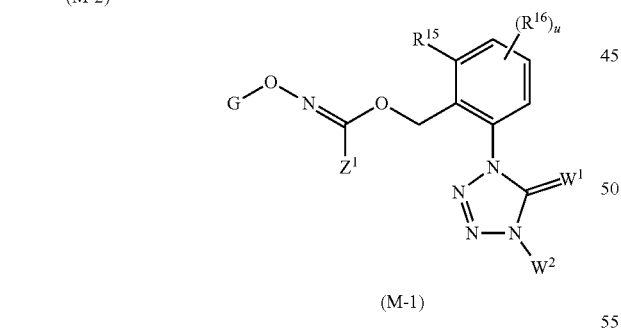

(M-1)

wherein the symbols are the same as defined above.

The compound (M-2) may be a publicly known compound, or may be prepared according to the similar method to the publicly known method.

Process N

A compound represented by formula (N-1) (hereinafter, referred to Compound (N-1)) may be prepared by using a compound represented by formula (N-2)) (hereinafter, referred to as Compound (N-2)) and Compound (CC1) according to the similar method to Process C.

[Chem. 25]

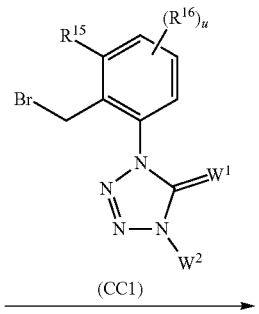

(CC1)

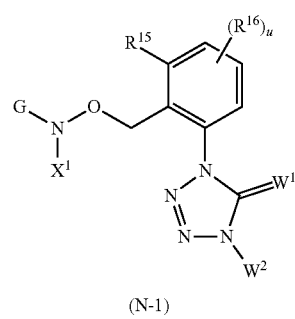

(N-2)

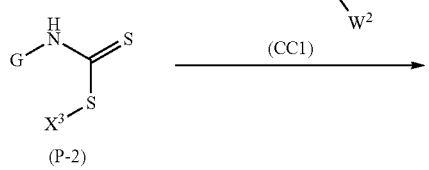

(N-1)

wherein the symbols are the same as defined above.

The compound (N-2) may be a publicly known compound, or may be prepared according to the similar method to the publicly known method.

Process P

A compound represented by formula (P-1) (hereinafter, referred to as Compound (P-1)) may be prepared by using a compound represented by formula (P-2) (hereinafter, referred to as Compound (P-2)) and Compound (CC1) according to the similar method to Process C.

[Chem. 26]

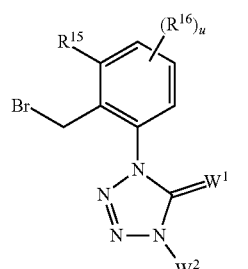

(P-2)

-continued

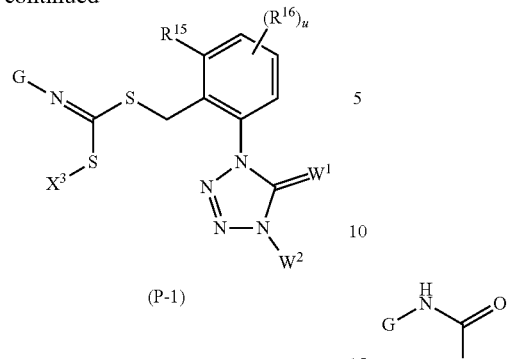

(P-1)

wherein the symbols are the same as defined above.

The compound (P-2) may be a publicly known compound, or may be prepared according to the similar method to the publicly known method.

Process Q

A compound represented by formula (Q-1) (hereinafter, referred to as Compound (Q-1)) may be prepared by using a compound represented by formula (Q-2)) (hereinafter, referred to as Compound (Q-2)) and Compound (CC1) according to the similar method to Process C.

[Chem. 27]

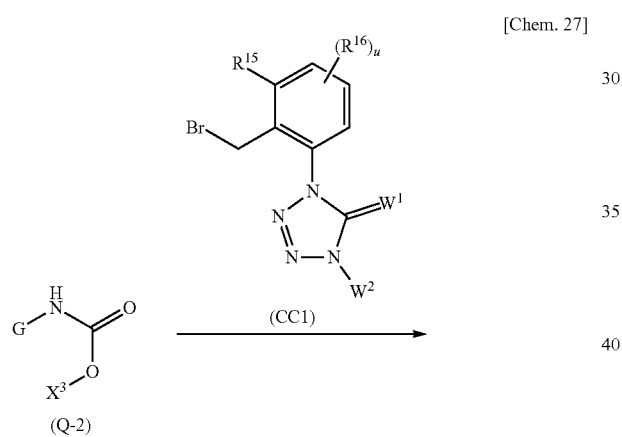

(Q-1)

wherein the symbols are the same as defined above.

Compound (Q-2) may be a publicly known compound, or may be prepared according to the similar method to the publicly known method.

Process R

A compound represented by formula (R-1) (hereinafter referred to as Compound (R-1)) may be prepared by using a compound represented by formula (R-2)) (hereinafter, referred to as Compound (R-2)) and Compound (CC1) according to the similar method to Process C.

[Chem. 28]

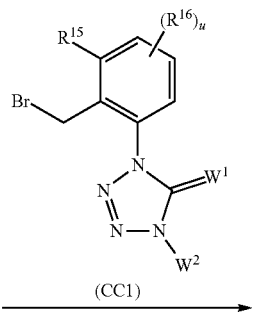

(R-2)

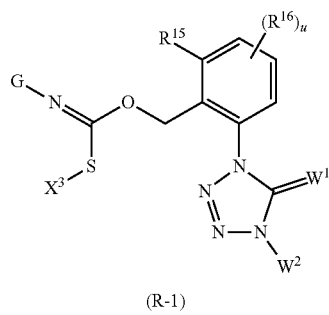

(R-1)

wherein the symbols are the same as defined above.

Compound (R-2) may be a publicly known compound, or may be prepared according to the similar method to the publicly known method.

Process S

A compound represented by formula (S-1) (hereinafter, referred to as Compound (S-1)) may be prepared by using a compound represented by formula (S-2)) (hereinafter, referred to as Compound (S-2)) and Compound (CC1) according to the similar method to Process C.

[Chem. 29]

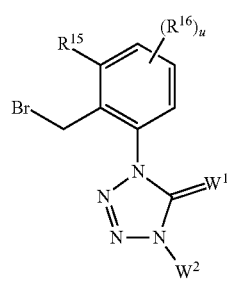

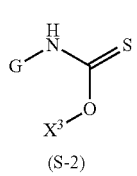

(S-2)

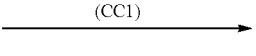

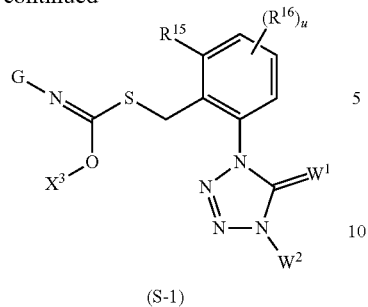

(S-1)

wherein the symbols are the same as defined above.

Compound (S-2) may be a publicly known compound, or may be prepared by the similar method to the publicly method.

Process V

A compound represented by formula (V-1) (hereinafter, referred to as Compound (V-1)) may be prepared by using a compound represented by formula (V-2) (hereinafter, referred to as Compound (V-2)) and Compound (CC1) according to the similar method to Process C.

[Chem. 30]

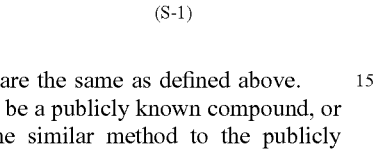

(V-2)

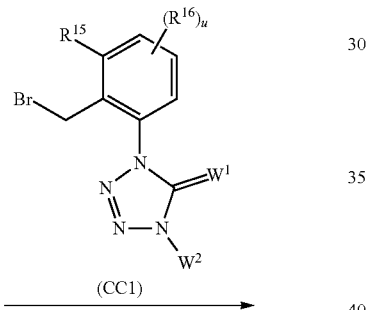

(V-1)

wherein the symbols are the same as defined above.

Process W

A compound represented by formula (W-1) (hereinafter, referred to as Compound (W-1)) may be prepared by using a compound represented by formula (W-2) (hereinafter, referred to as Compound (W-2)) and Compound (CC1) according to the similar method to Process C.

[Chem. 31]

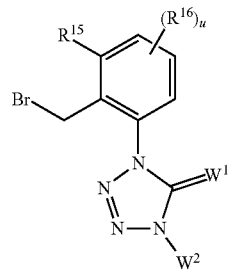

(W-2)

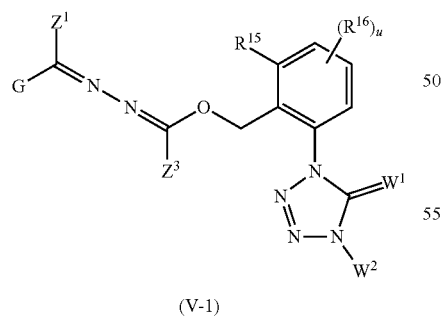

(W-1)

wherein the symbols are the same as defined above.

Process G

A compound represented by formula (G-1) (hereinafter, referred to as Compound (G-1)) may be prepared by reacting a compound represented by formula (G-2) (hereinafter, referred to as Compound (G-2)) and Compound (GG1) in the presence of an acid.

[Chem. 32]

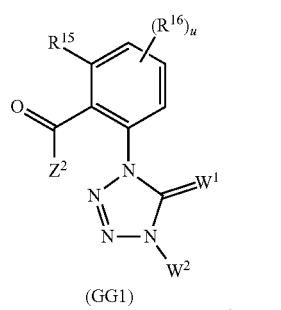

(G-2)

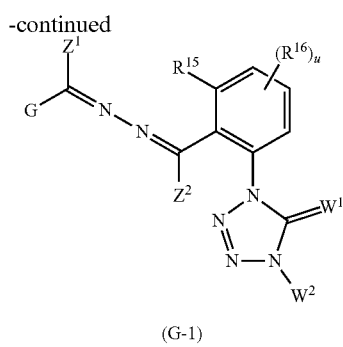

(G-1)

wherein the symbols are the same as defined above.

The reaction may be conducted according to the similar method to those described in Tetrahedron letters, 1987, 28, 4312-4322 or WO2016/088747 A1.

Compound (G-2) may be a publicly known compound, or may be prepared according to the similar method to the publicly known method.

Compound (GG1) may be prepared by the similar method to Reference process A-2.

Process O

A compound represented by formula (O-1) (hereinafter, referred to as Compound (O-1)) may be prepared by reacting a compound represented by formula (O-2) (hereinafter, referred to as Compound (O-2)) and a compound represented by formula (II2) (hereinafter, referred to as Compound (II2)) or salts thereof in the presence of a base.

[Chem. 33]

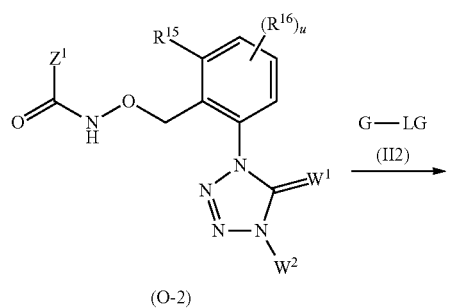

(O-2)

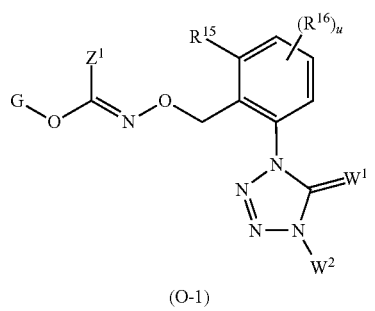

(O-1)

wherein the symbols are the same as defined above.

The reaction is usually carried out in a solvent. Examples of the solvent to be used in the reaction include hydrocarbons, ethers, hydrogenated hydrocarbons, amides, esters, nitriles, and mixtures thereof.

Examples of the base to be used in the reaction include organic bases, metallic organic acid salts, metal nitrates, alkali-metal hydroxides, alkali metal alkoxides, alkali metal bicarbonates, alkali metal hydrides, and mixtures thereof.

Examples of salts of Compound (II2) include hydrochloride salts and hydrobromide salts thereof.

In the reaction, Compound (II2) is usually used within a range of 1 to 10 molar ratio(s), and the base is usually used within a range of 1 to 20 molar ratio(s), as opposed to 1 mole of Compound (O-2).

The reaction temperature is usually within a range of −20 to 150° C. The reaction period of the reaction is usually within a range of 0.1 to 120 hours.

When the reaction is completed, water is added to the reaction mixtures, the reaction mixtures are extracted with organic solvent(s), and the resulting organic layers are worked up (for example, drying and concentration) to isolate Compound (O-1).

Compound (II2) may be a publicly known compound, or may be prepared according to the similar method to the publicly known method.

Process T

A compound represented by formula (T-1)) (hereinafter, referred to as Compound (T-1)) may be prepared by using a compound represented by formula (T-2)) (hereinafter, referred to as Compound (T-2)) and Compound (II2) according to the similar method to Process O.

[Chem. 34]

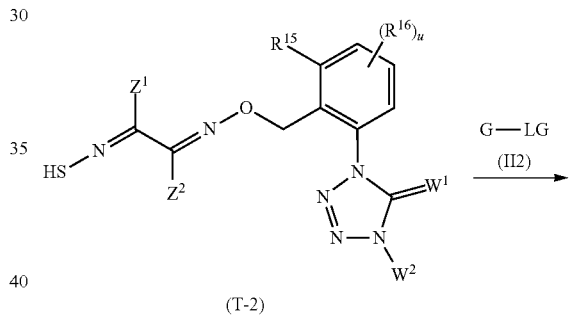

(T-2)

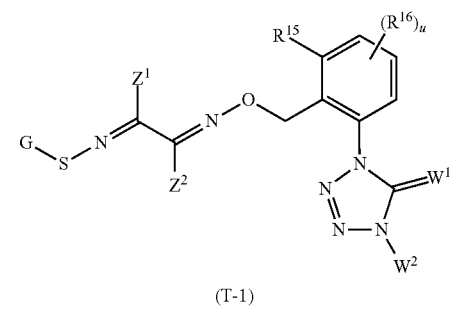

(T-1)

wherein the symbols are the same as defined above.

Process I

A compound represented by formula (I-1) (hereinafter, referred to as Compound (I-1)) may be prepared by using a compound represented by formula (I-2)) (hereinafter, referred to as Compound (I-2)) and Compound (II2) according to the similar method to Process O.

[Chem. 35]

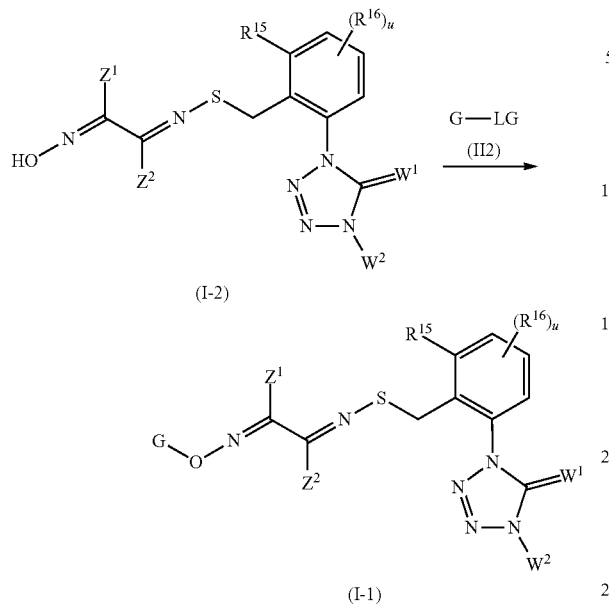

wherein the symbols are the same as defined above.

Process U

A compound represented by formula (U-1) (hereinafter, referred to as Compound (U-1)) may be prepared by using a compound represented by formula (U-2) (hereinafter, referred to as Compound (U-2)) according to the similar method to Process O.

[Chem. 36]

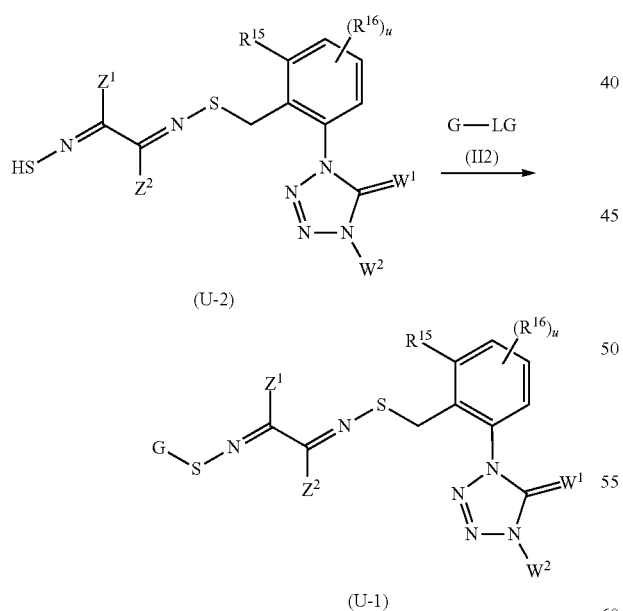

wherein the symbols are the same as defined above.

Process X1

A compound represented by formula (X-1) (hereinafter, referred to as Compound (X-1)) may be prepared by reacting a compound represented by formula (X-2)) (hereinafter, referred to Compound (X-2)) and a compound represented by formula (XX1) (hereinafter, referred to as Compound (XX1)) in the presence of a base.

[Chem. 37]

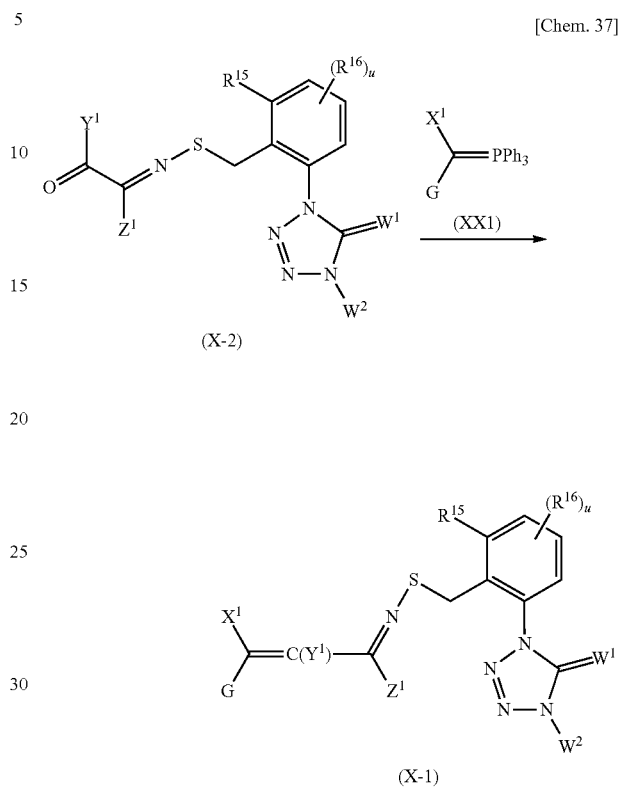

wherein the symbols are the same as defined above.

The reaction may be conducted according to the similar method to those described in Angew. Chem. Int. Ed. 1966, 5, 126, or Chem. Rev. 1989, 89, 863.

Compound (XX1) may be a publicly known compound, or may be prepared according to the similar method to the publicly known method.

Process X2

A compound represented by formula (X-1) maybe prepared by using a compound represented by formula (X-3)) (hereinafter, referred to as Compound (X-3)) and Compound (CC1) according to the similar method to Process C.

[Chem. 38]

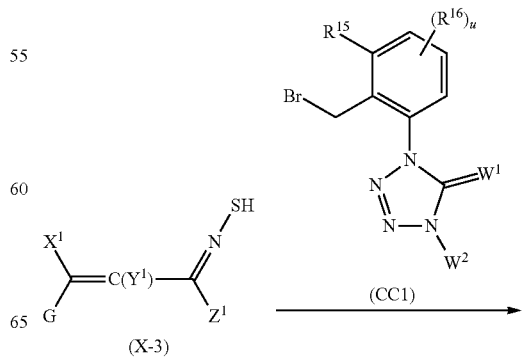

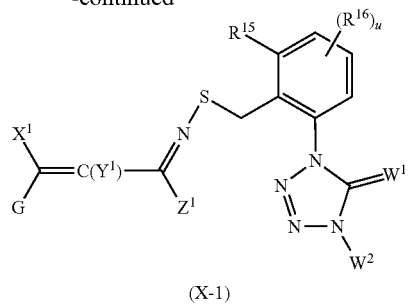

(X-1)

wherein the symbols are the same as defined above.

Process Y

A compound represented by formula (Y-1) (hereinafter, referred to as Compound (Y-1)) may be prepared by using a compound represented by formula (Y-2)) (hereinafter, referred to as Compound (Y-2)) and Compound (CC1) according to the similar method to Process C.

[Chem. 39]

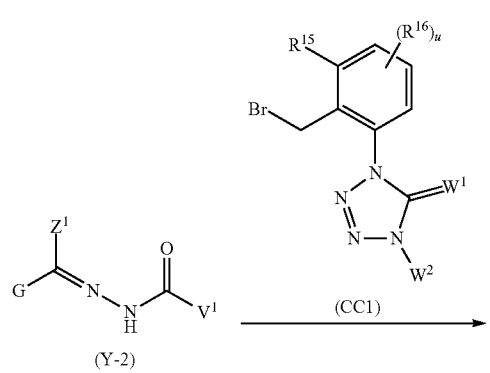

wherein the symbols are the same as defined above.

Compound (Y-2) may be prepared by the similar method to Reference process V-1.

Process Z

A compound represented by formula (Z-1) (hereinafter, referred to as Compound (Z-1)) may be prepared by using a compound represented by formula (Z-2)) (hereinafter, referred to as Compound (Z-2)) and Compound (CC1) according to the similar method to Process C.

[Chem. 40]

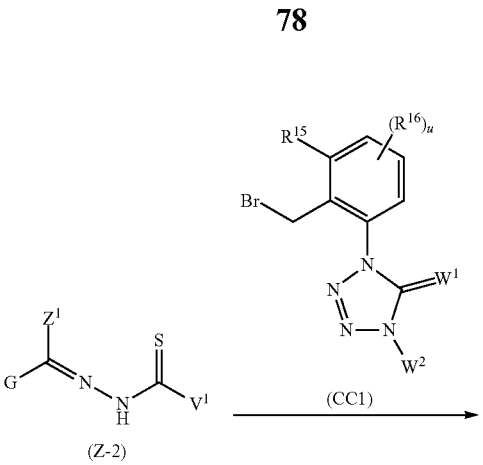

wherein the symbols are the same as defined above.

Compound (Z-2) may be prepared according to the similar method to Reference process W-1.

Process ZA

A compound represented by formula (ZA-1) (hereinafter, referred to as Compound (ZA-1)) may be prepared by reacting a compound represented by formula (ZA-2) (hereinafter, referred to as Compound (ZA-2)) and Compound (ZZ1).

[Chem. 41]

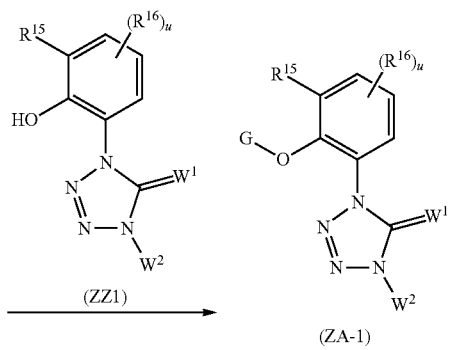

wherein, X represents a halogen atom, and the other symbols are the same as defined above.

The reaction may be conducted according to the similar method to those described in, for example, Journal of Organic Chemistry, 2016, 81, 7315-7325.

Compound (ZA-2) may be a publicly known compound, or may be prepared according to the similar method to the publicly known method.

Compound (ZZ1) may be prepared according to the method described in WO 2015/064727 A1.

Process ZB

A compound represented by formula (ZB-1) (hereinafter, referred to as Compound (ZB-1)) may be prepared by using the compound (ZA-2) and Compound (ZZ2) according to the similar method to the process ZA.

[Chem. 42]

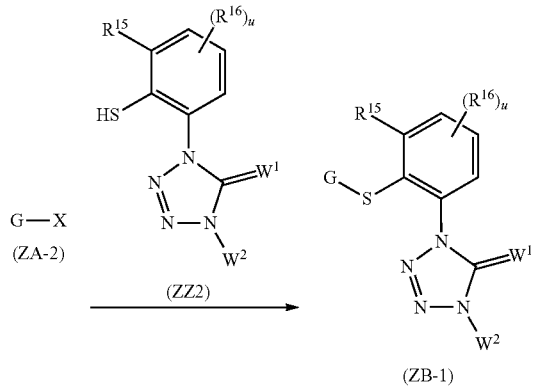

wherein the symbols are the same as defined above.

Reference Process A-1

Compound (A-2) may be prepared by reacting a compound represented by formula (A-3) (hereinafter, referred to as Compound (A-3)) and a compound represented by formula (AA2) (hereinafter, referred to as Compound (AA2)) or salts thereof in the presence of an acid.

[Chem. 43]

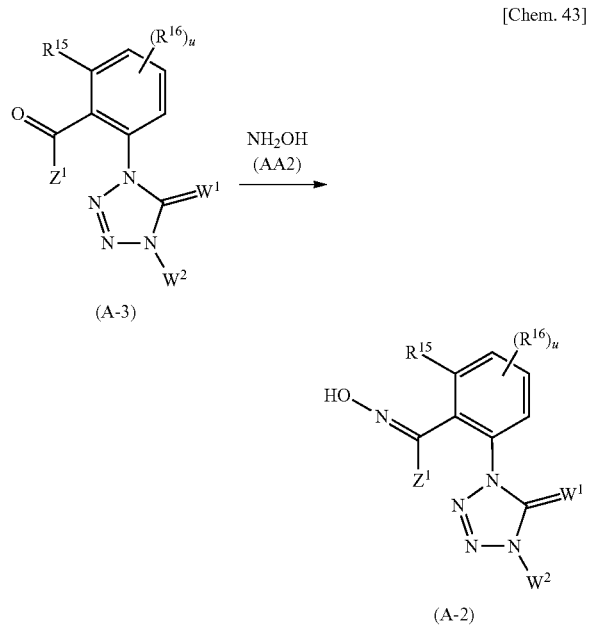

wherein the symbols are the same as defined above.

The reaction may be conducted according to the similar method to those described in, for example, Tetrahedron Letters, 2001, 58, 10043-10046.

The compound (AA2) is a publicly known compound.

Reference Process A-2

Compound (A-3) may be prepared by reacting a compound represented by formula (A-4) (hereinafter, referred to as Compound (A-4)) and an oxidizing agent.

[Chem. 44]

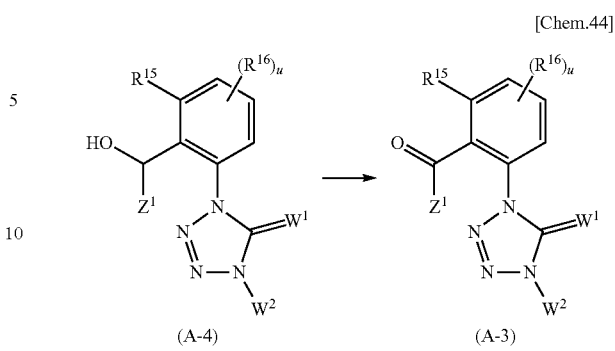

wherein the symbols are the same as defined above.

The reaction is usually carried out in a solvent. Examples of the solvent to be used in the reaction include hydrocarbons, ethers, hydrogenated hydrocarbons, amides, esters, sulfoxides, nitriles, water, and mixtures thereof.

Examples of the oxidizing agent to be used in the reaction include chromate salts such as chromic acid, PDC, and PCC; iodate salts such as Dess-Martin periodinane and IBX; DMSO oxidation such as DMSO-oxalyl chloride, and DMSO-acetic anhydride; ammonium oxide oxidizing agent such as NMO; $SO_3$ pyridine complexes; manganese dioxide.

A base may be added to the reaction, and examples of the base include organic bases, alkali metal carbonates, and alkali metal bicarbonates such as sodium bicarbonate.

An additive agent may be added to the reaction, and examples of the additive agent include trifluoroacetic acid, ruthenium trichloride•hydrates.

In the reaction, the oxidizing agent is usually used within a range of 1 to 10 molar ratio(s) as opposed to 1 mole of Compound (A-4).

The reaction temperature is usually within a range of −20 to 150° C. The reaction period of the reaction is usually within a range of 0.1 to 120 hours.

When the reaction is completed, water is added to the reaction mixtures, the reaction mixtures are extracted with organic solvent(s), and the resulting organic layers are worked up (for example, drying and concentration) to isolate Compound (A-3).

Reference Process A-3

Compound (A-4) may be prepared by reacting a compound represented by formula (A-5) (hereinafter, referred to as Compound (A-5)) and water in the presence of a base.

[Chem. 45]

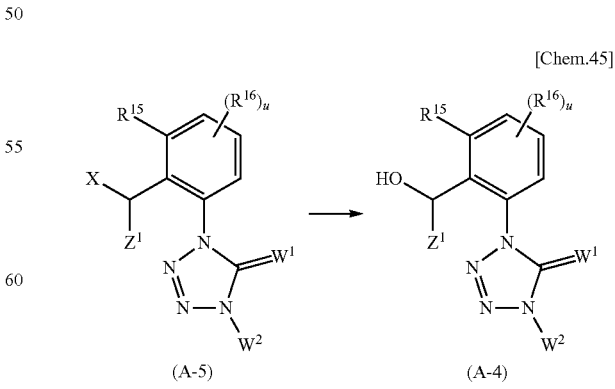

wherein X represents a halogen atom, and the other symbols are the same as defined above.

The reaction is usually carried out in a solvent. Examples of the solvent to be used in the reaction include hydrocarbons, ethers, hydrogenated hydrocarbons, amides, esters, nitriles, alcohol such as methanol, ethanol, and 2-propanol (hereinafter, referred to as alcohols), water, and mixtures thereof.

Examples of the base to be used in the reaction include organic bases, alkali metal carbonates, metallic nitrates, alkali metal hydroxides, alkali metal alkoxides, alkali metal bicarbonates such as sodium carbonates, and mixtures thereof.

An additive agent may be added to the reaction, and examples of the additive agent include quaternary ammonium salt such as tetrabutylammonium bromide, and crown ether.

In the reaction, an excess amount of water is added, and the base is usually used within the rage of 0.1 to 20 molar ratio(s), as opposed to 1 mole of Compound (A-5).

The reaction temperature is usually within a range of −20 to 150° C. The reaction period of the reaction is usually within a range of 0.1 to 120 hours.

When the reaction is completed, water is further added to the reaction mixtures, the reaction mixtures are extracted with organic solvent(s), and the resulting organic layers are worked up (for example, drying and concentration) to isolate Compound (A-4).

Compound (A-5) or salts thereof may be a publicly known compound, or may be prepared according to the publicly known method.

Reference Process B-1

Compound (B-2) may be prepared by reacting a compound represented by formula (B-3) (hereinafter, referred to as Compound (B-3)) and a sulfurizing agent in the presence of a base.

[Chem.46]

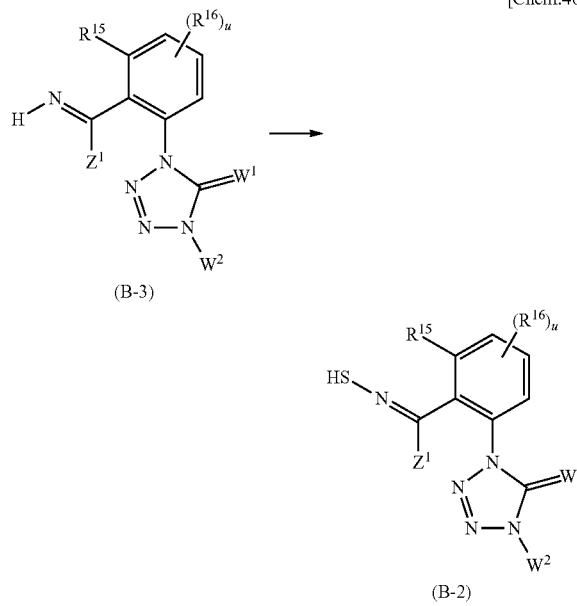

(B-3)

(B-2)

wherein the symbols are the same as defined above.

The reaction may be conducted according to the similar method to those described in, for example, Tetrahedron Letters, 1980, 21, 4989-4990.

Reference Process B-2

Compound (B-3) may be prepared by reacting Compound (A-3) and a compound represented by formula (BB1) (hereinafter, referred to as Compound (BB1)) or salts thereof.

[Chem. 47]

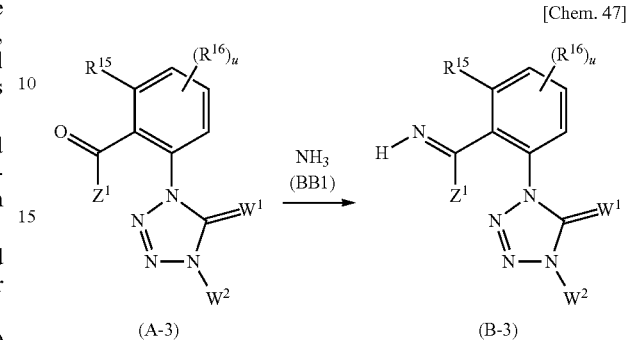

(A-3)  (B-3)

wherein the symbols are the same as defined above.

The reaction may be conducted according to the similar method to those described in, for example, Organic Letters, 2010, 12, 4705-4707.

Compound (BB1) is a publicly known compound.

Reference Process D-1

Compound (D-2) may be prepared by reacting Compound (C-2) and a sulfurizing agent.

[Chem.48]

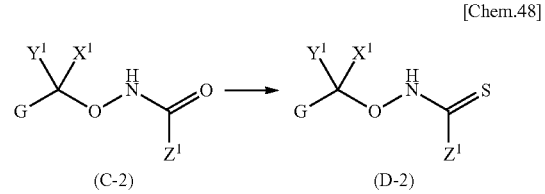

(C-2)  (D-2)

wherein, the symbols are the defined as above.

The reaction may be conducted according to the similar method to those described in, for example, Australian Journal of Chemistry, 2004, 57, 549-552.

Reference Process E-1

Compound (E-2) may be prepared by using a compound represented by formula (E-3) (hereinafter, referred to as Compound (E-3)) and a sulfurizing agent according to the similar method to Reference process B-1.

[Chem.49]

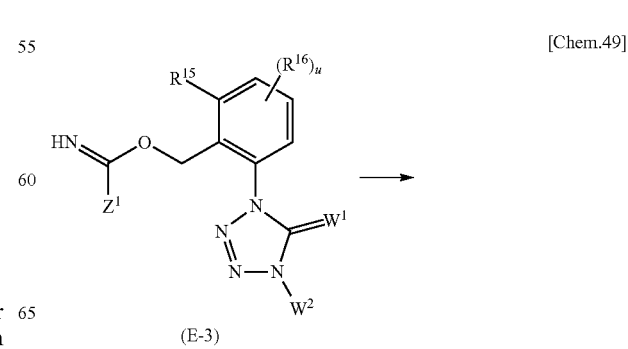

(E-3)

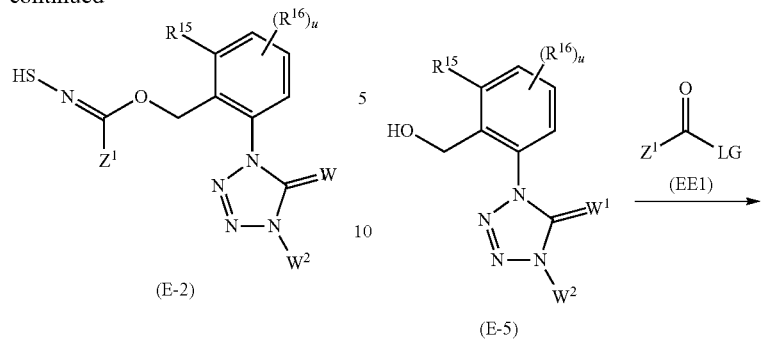

(E-2)

wherein the symbols are the same as defined above.

Reference Process E-2

Compound (E-3) may be prepared by reacting a compound represented by formula (E-4) (hereinafter, referred to as Compound (E-4)) and Compound (BB1) or salts thereof according to the similar method to Reference process B-2.

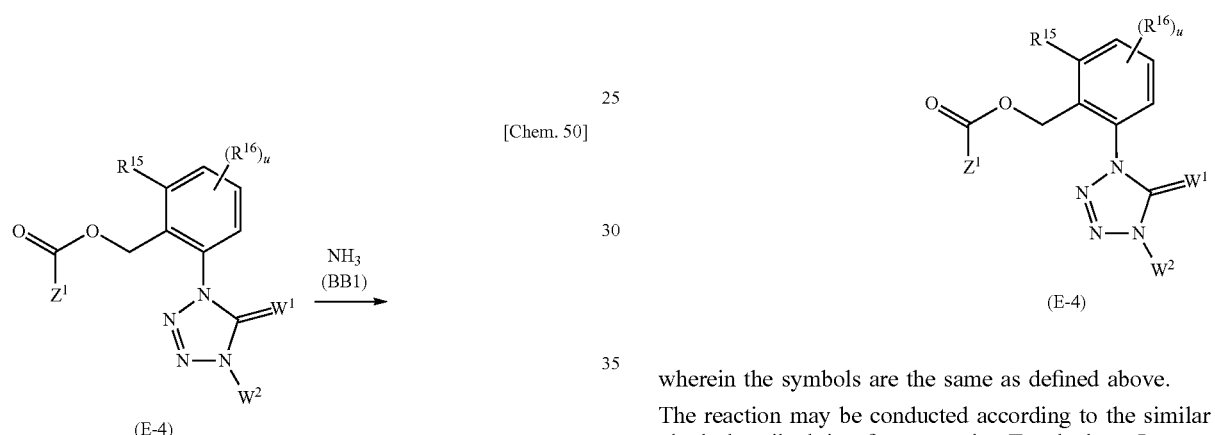

wherein the symbols are the same as defined above.

Reference Process E-3

Compound (E-4) may be prepared by reacting a compound represented by formula (E-5) (hereinafter, referred to as Compound (E-5)) and a compound represented by formula (EE1) (hereinafter, referred to as Compound (EE1)) or salts thereof.

wherein the symbols are the same as defined above.

The reaction may be conducted according to the similar method described in, for example, Tetrahedron Letters, 2003, 59, 7661-7668 or Journal of Organic Chemistry, 2004, 69, 577-580.

Compound (EE1) may be a publicly known compound, or may be prepared according to the similar method to the publicly known method.

Compound (E-5) may be prepared according to the similar method to Reference process A-3.

Reference Process F-1

Compound (F-2) may be prepared by using a compound represented by formula (F-3) (hereinafter, referred to as Compound (F-3)) and a sulfurizing agent according to the similar method to Reference process B-1.

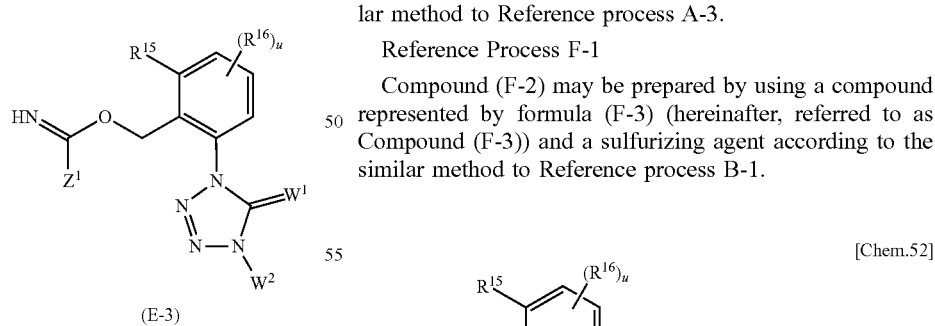

(F-3)

-continued

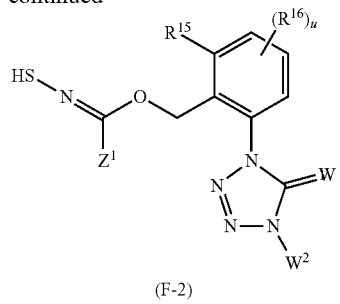

(F-2)

wherein the symbols are the same as defined above.

Reference Process F-2

Compound (F-3) may be prepared by using Compound (E-4) and Compound (BB1) or salts thereof according to the similar method to Reference process B-2.

[Chem. 53]

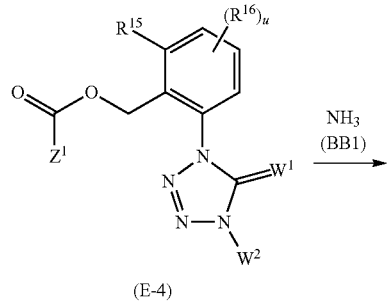

(E-4)

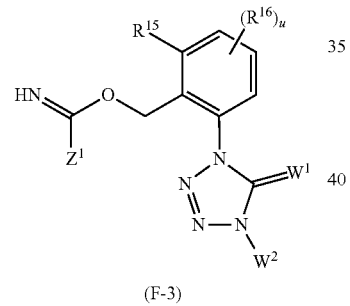

(F-3)

wherein the symbols are the same as defined above.

Reference Process H-1

Compound (H-2) may be prepared by using a compound represented by formula (H-3) (hereinafter, referred to as Compound (H-3)) and Compound (AA2) or salts thereof according to the similar method to Reference process A-1.

[Chem.54]

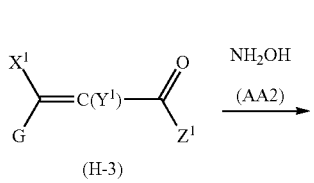 → 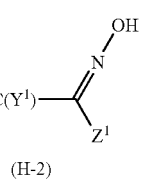

(H-3)　　(H-2)

wherein the symbols are the same as defined above.

The compound (H-3) may be a publicly known compound, or may be prepared according to the similar method to the publicly known method.

Reference I-1

Compound (I-2) may be prepared by using a compound represented by formula (I-3) (hereinafter, referred to as Compound (I-3)) and Compound (AA2) or salts thereof according to the similar method to Reference process A-1.

[Chem.55]

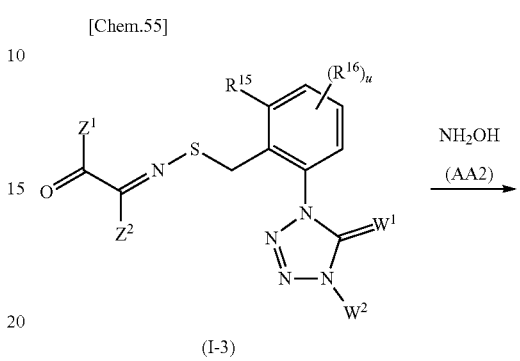

(I-3)

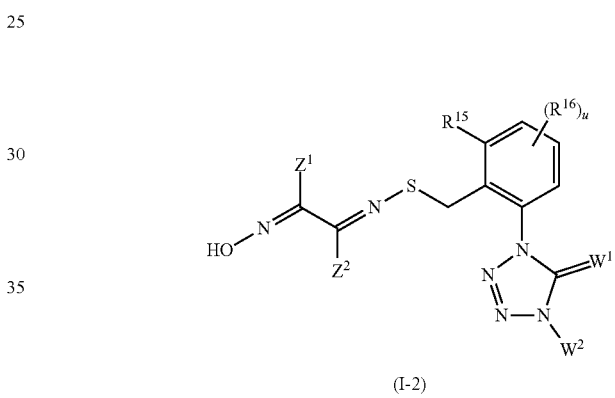

(I-2)

wherein the symbols are the same as defined above.

Reference Process I-2

Compound (I-3) may be prepared by using a compound represented by formula (I-4) (hereinafter, referred to as Compound (I-4)) and Compound (CCI) or salts thereof according to the similar method to the process C.

[Chem.56]

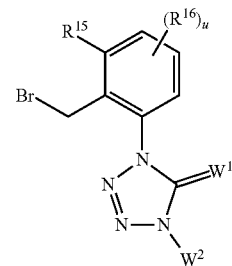

(I-4)

-continued

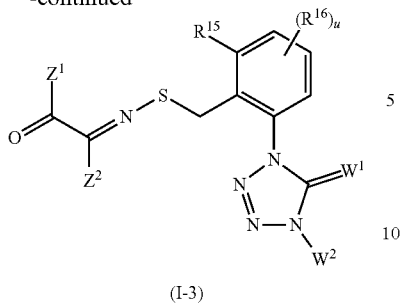

(I-3)

wherein the symbols are the same as defined above.

Reference Process I-3

Compound (I-4) may be prepared by using a compound represented by formula (I-5) (hereinafter, referred to as Compound (I-5)) and a sulfurizing agent according to the similar method to Reference process B-1.

[Chem.57]

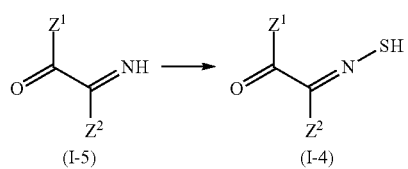

(I-5)    (I-4)

wherein the symbols are the same as defined above.

Compound (I-5) may be a publicly known compound, or may be prepared according to the similar method to the publicly known method.

Reference process O-1

Compound (O-2) may be prepared by using a compound represented by formula (O-3) (hereinafter, referred to as Compound (O-3)) and Compound (CC1) or salts thereof according to the similar method to Process C.

[Chem.58]

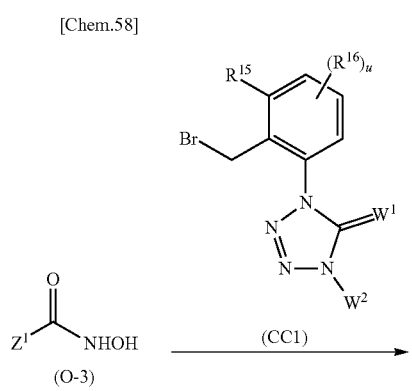

(O-3)    (CC1)

-continued

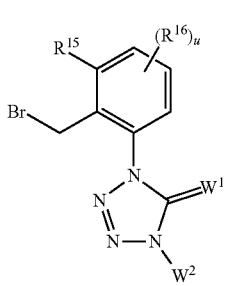

(O-2)

wherein the symbols are the same as defined above.

Compound (O-3) or salts thereof may be a publicly known compound, or may be prepared according to the similar method to the publicly known method.

Reference Process T-1

Compound (T-2) may be prepared by using a compound represented by formula (T-3) (hereinafter, referred to as Compound (T-3)) and a sulfurizing agent according to the similar method to Reference process B-1.

[Chem.59]

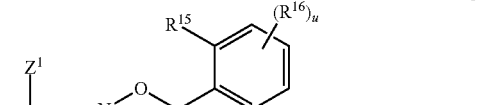

(T-3)

(T-2)

wherein the symbols are the same as defined above.

Reference Process T-2

Compound (T-3) may be prepared by using a compound represented by formula (T-4) (hereinafter, referred to as Compound (T-4)) and Compound (BB1) or salts thereof according to the similar method to Reference process B-2.

[Chem.60]

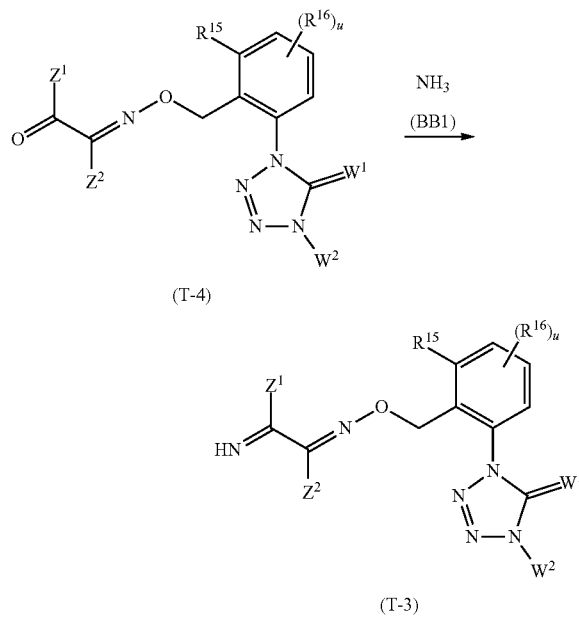

wherein the symbols are the same as defined above.

Reference Process T-3

Compound (T-4) may be prepared by using a compound represented by formula (T-5) (hereinafter, referred to as Compound (T-5)) and Compound (CC1) or salts thereof according to the similar method to Process C.

[Chem.61]

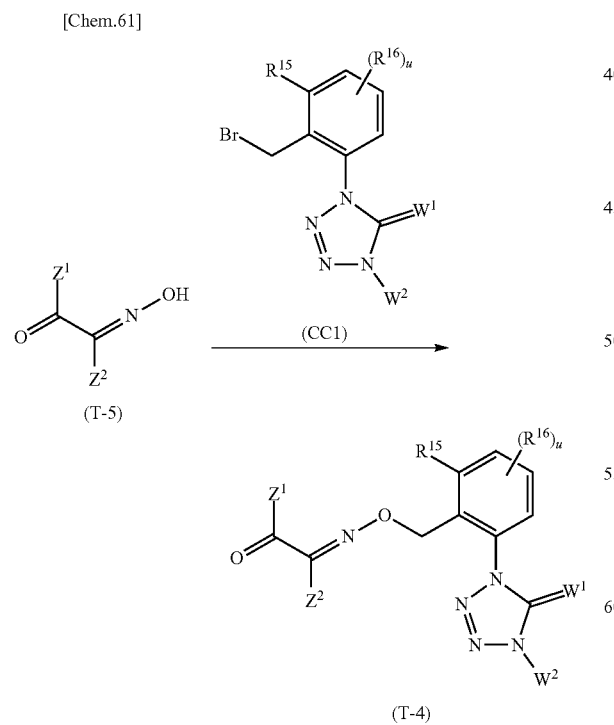

wherein the symbols are the same as defined above.

Reference Process T-4

Compound (T-5) may be prepared by using a compound represented by formula (T-6) (hereinafter, referred to as Compound (T-6)) and Compound (AA2) or salts thereof according to the similar method to Reference process A-1.

[Chem.62]

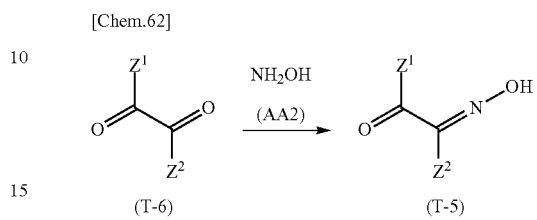

wherein the symbols are the same as defined above.

Compound (T-6) may be a publicly known compound, or may be prepare according to the similar method to the publicly known method.

Reference Process U-1

Compound (U-2) may be prepared by using a compound represented by formula (U-3) (hereinafter, referred to as Compound (U-3)) and a sulfurizing agent according to the similar method to Reference process B-1.

[Chem.63]

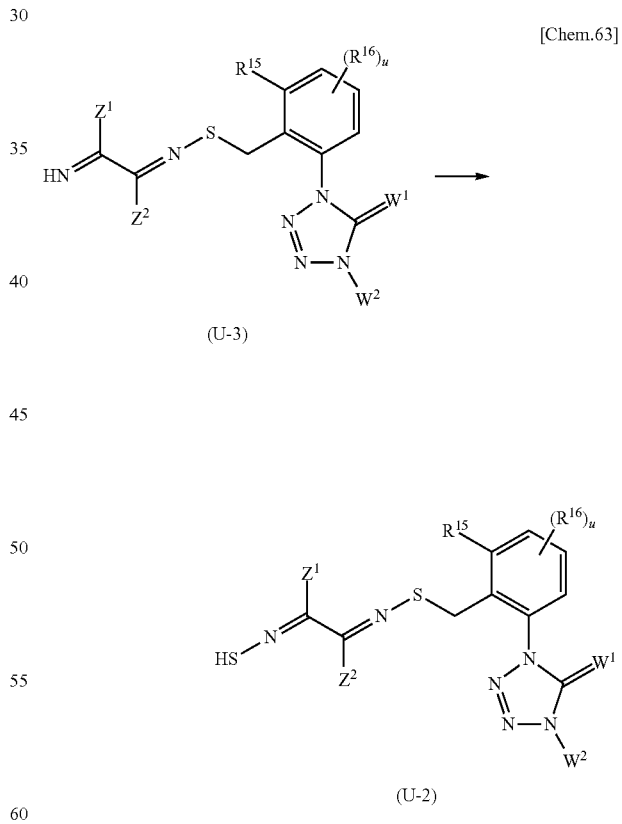

wherein, the symbols are the same as defined above.

Reference Process U-2

Compound (U-3) may be prepared by using the compound (1-3) and Compound (BB1) or salts thereof according to the similar method to Reference process B-2.

[Chem.64]

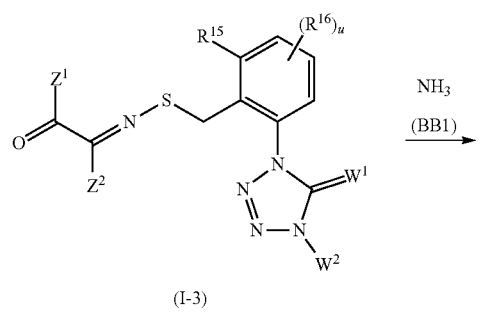

[Chem.66]

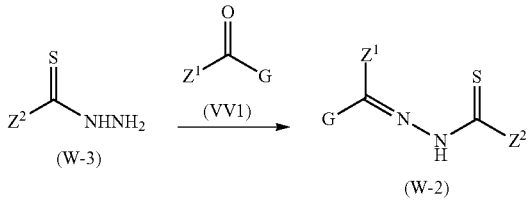

wherein the symbols are the same as defined above.

Compound (W-3) may be a publicly known compound, or may be prepared according to the publicly known method.

Reference Process X-1

A compound represented by formula (X-2) (hereinafter, referred to as Compound (X-2)) may be prepared by using Compound (I-4) and Compound (CC1) according to the similar method to Process C.

[Chem.67]

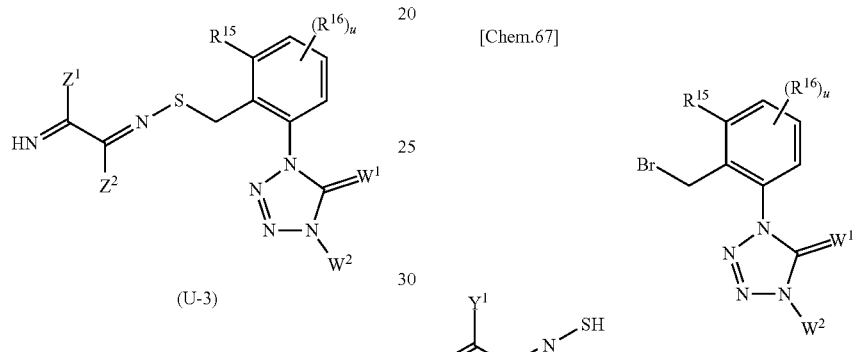

wherein the symbols are the same as defined above.

Reference Process V-1

Compound (V-2) may be prepared by reacting a compound represented by formula (V-3) (hereinafter, referred to as Compound (V-3)) and a compound represented by formula (VV1) (hereinafter, referred to as Compound (VV1)) or salts thereof in the presence of an acid.

[Chem.65]

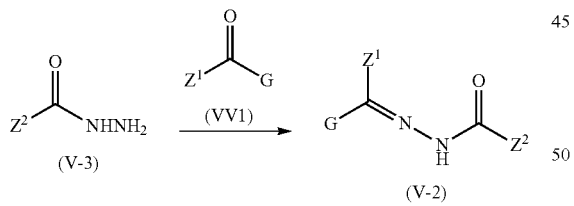

wherein the symbols are the same as defined above.

The reaction may be conducted according to the similar method to those described in, for example, Tetrahedron letters, 1987, 28, 4312-4322 or WO 2016/088747 A1.

Compound (V-3) and Compound (VV1) may be publicly known compounds, or may be prepared according to the similar method to the publicly known method.

Reference Process W-1

Compound (W-2) may be prepared by using a compound represented by formula (W-3) (hereinafter, referred to as Compound (W-3)) and Compound (VV1) or salts thereof according to the similar method to Reference process V-1.

wherein the symbols are the same as defined above.

Reference Process X-2

Compound (X-3) may be prepared by using a compound represented by formula (X-4) (hereinafter, referred to as Compound (X-4)) and a sulfurizing agent according to the similar method to Reference process B-1.

[Chem.68]

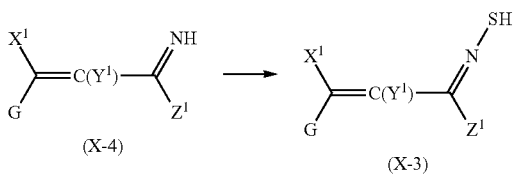

wherein the symbols are the same as defined above.

Reference Process X-3

Compound (X-4) may be prepared by using the compound (H-3) and Compound (BB1) or salts thereof according to Reference process B-2.

[Chem.69]

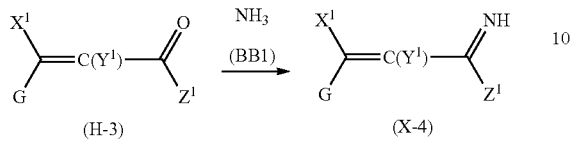

(H-3) → (X-4)

wherein the symbols are the same as defined above.

Reference Process ZB-1

Compound (ZZ2) may be prepared by reacting a compound represented by formula (ZB-2) (hereinafter, referred to as Compound (ZB-2)) in the presence of a base.

[Chem.70]

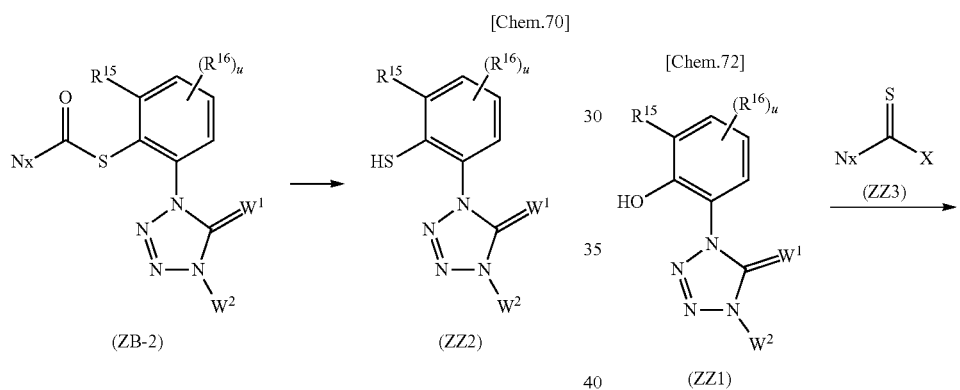

(ZB-2) → (ZZ2)

wherein, Nx represents a di(C1-C6 alkyl)amino group, and the other symbols are the same as defined above.

The reaction may be conducted according to the similar method to those described in, for example, Angew. Chem. Int. Ed. 2009, 48, 7612-7615 or Tetrahedron, 2007, 63, 4120-4125.

Reference Process ZB-2

Compound (ZB-2) may be prepared from a compound represented by formula (ZB-3) (hereinafter, referred to as Compound (ZB-3)).

[Chem.71]

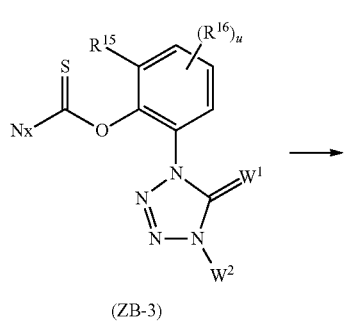

(ZB-3) →

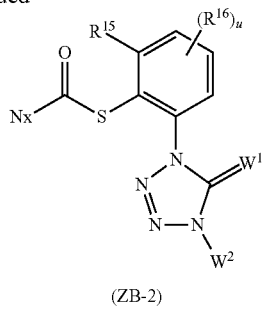

(ZB-2)

wherein the symbols are the same as defined above.

The reaction may be conducted according to the similar method to those described, for example, Angew. Chem. Int. Ed. 2009, 48, 7612-7615, or Tetrahedron, 2007, 63, 420-4125.

Reference Process ZB-3

Compound (ZB-3) may be prepared by reacting Compound (ZZ1) and a compound represented by formula (ZZ3) (hereinafter, referred to as Compound (ZZ3)) in the presence of a base.

[Chem.72]

(ZZ1) + (ZZ3) → (ZB-3)

wherein the symbols are the same as defined above.

The reaction may be prepared according to the similar method described in, for example, Angew. Chem. Int. Ed. 2009, 48, 7612-7615, or Tetrahedron, 2007, 63, 420-4125.

Compound (ZZ3) may be a publicly known compound, or may be prepared according to the similar method to the publicly known method.

Reference Process ZC-1

Compound (V-2) may be prepared by reacting a compound represented by formula (ZC-1) (hereinafter, referred to as Compound (ZC-1)) and a compound represented by formula (ZC-2) (hereinafter, referred to as Compound (ZC-2)) in the presence of a base.

[Chem.73]

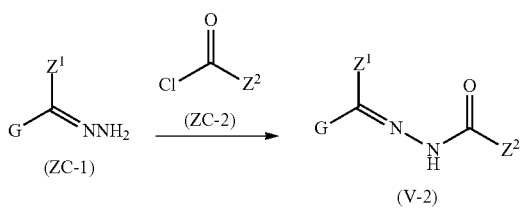

wherein the symbols are the same as defined above.

The reaction may be conducted according to the similar method to those described in, for example, Asian Journal of Organic Chemistry, 2016, 5, 1438-1441.

Compound (ZC-1) may be a publicly known compound, or may be prepared according to the similar method to those described in WO 2000/27822 A1. Compound (ZC-2) is a publicly known compound.

With respect to a use form of the present compound, the present compound may be used singly, however, may be mixed with solid carrier, liquid carrier and/or surfactants and the like, and if necessary, may be added by auxiliary agents for formulation such as stickers, dispersers, and stabilizers, to formulate into wettable powders, water dispersible granules, flowables, granules, dry flowables, emulsifiable concentrates, wettable powders, aqueous solutions, oil solutions, smoking agents, aerosols, microcapsules, poison baits, resin formulations, shampoo formulations, pastes, foams, carbon dioxide gas formulations, tablets or the like. These formulations may be processed into mosquito coil, electric mosquito mat, electric mosquito liquid, smoking agent, fumigant, sheet, spot-on pesticide, or oral pesticide, and may be then used. These formulations usually contain 0.1 to 99% by weight, preferably 0.2 to 90% by weight of the present compound.

Examples of the solid carrier include fine powders or granules of clays (for example, kaolin clay, diatomaceous earth, Fubasami clay, bentonite, or acid white clay), talcs, other inorganic minerals (for example, sericite, quartz powder, sulfur powder, activated charcoal, calcium carbonate or hydrated silica) and the like.

Examples of the liquid carriers include water, alcohols, ketones (for example, acetone, methyl ethyl ketone or cyclohexanone); aromatic hydrocarbons (for example, benzene, toluene, xylene, ethyl benzene, methylnaphthalene), aliphatic hydrocarbons (for example, n-hexane, or kerosene), esters, nitriles, ethers, amides, and halogenated hydrocarbons.

Examples of the surfactants include alkyl sulfates, alkyl sulfonates, alkyl aryl sulfonates, alkyl aryl ethers and polyoxyethylenated compounds thereof, polyethylene glycol ethers, polyol esters and sugar alcohol derivatives Examples of the other auxiliary agents for formulation include stickers, dispersers, and stabilizers. Specific examples include casein, gelatin, polysaccharides (for example, starch, gum arabic, cellulose derivatives and alginic acid), lignin derivatives, bentonite, sugars, water-soluble synthetic polymers (for example, polyvinyl alcohol, polyvinyl pyrrolidone and polyacrylic acids), PAP (acidic isopropyl phosphate), NHT (2,6-di-tert-butyl-4-methylphenol), BHA (a mixture of 2-tert-butyl-4-methoxyphenol and 3-tert-butyl-4-methoxyphenol), vegetable oils, mineral oils, fatty acids os esters thereof, and the others.

Also, the present compound may combined with each type of oils such as mineral oils and vegetable oils, or surfactants, and may be then used to control pests. Specific examples oils that are used in combination with the present compound include Nimbus (registered trademark), Assist (registered trademark), Aureo (registered trademark), Iharol (registered trademark), Silwet L-77 (registered trademark), BreakThru (registered trademark), Sundancell (registered trademark), Induce (registered trademark), Penetrator (registered trademark), AgriDex (registered trademark), Lutensol A8 (registered trademark), NP-7 (registered trademark), Triton (registered trademark), Nufilm (registered trademark), Emulgator NP7 (registered trademark), Emulad (registered trademark), TRITON X 45 (registered trademark), AGRAL 90 (registered trademark), AGROTIN (registered trademark), ARPON (registered trademark), EnSpray N (registered trademark), and BANOLE (registered trademark).

Examples of base material of the resin formulation include polyvinyl chloride polymers, polyurethane and the others. A plasticizer such as phthalate esters (for example, dimethyl phthalate, or dioctyl phthalate), adipic acid esters and stearic acid and the others may be added to these base materials, if necessary. The resin formulation can be prepared by mixing the present compound with the above-mentioned base material, and kneading the mixture, followed by molding it by injection molding, extrusion molding or pressure molding and the like. The resultant resin formulation can be subjected to further molding or cutting procedure and the like, if necessary, to be processed into shapes such as a plate, film, tape, net or string shape. These resin formulations may be processed into animal collars, animal ear tags, sheet products, trap strings, gardening supports and other products.

Examples of a base material for the poison baits include grain powder, vegetable oil, saccharide and crystalline cellulose, and if necessary, with addition of antioxidants such as dibutylhydroxytoluene and nordihydroguaiaretic acid, preservatives such as dehydroacetic acid, accidental ingestion inhibitors for children and pets such as a chili powder, insect attraction fragrances such as cheese flavor, onion flavor and peanut oil.

The application dose of the present compound may be varied depending on a climate condition, a formulation form, an application period, an application method, an application site, a target disease, a target pest, a target crop, and the like, and the dose of the present compound in the present control pest agent is within the range of 1 to 500 g, preferably 2 to 200 g per 1,000 m$^2$. The emulsfiable concentrates, the wettable powders, or the suspensions and the like are usually applied by diluting them with water. In this case, the concentration of the present compound is usually within a range of 0.0005 to 2% by weight, preferably 0.005 to 2% by weight. The dusts or the granules, ant the like are usually applied as itself without diluting them.

The method for applying the present compound is not particularly limited, as far as the applying form is a form by which the present compound may be applied substantially, and includes, for example, an application to plants such as a foliage application; an application to area for cultivating plants such as a submerged treatment; and an application to soil such as seed disinfection. The resin preparation which is processed into a sheet or a string may be applied by winding a crop with a sheet or a string of the resin preparation, putting a string of the resin preparation around a crop so that the crop is surrounded by the string, or laying a sheet of the resin preparation on the soil surface near the root of a crop.

When the present compound is applied to stems and leaves of plants or soils for cultivating plants, the dose of the present compound is usually within a range of 1 to 500 g per 1,000 m² of the soil. Also, when the present compound is applied to seeds, the dose of the present compound is usually within a range of 0.001 to 100 g, preferably 0.01 to 50 g as opposed to 1 kg of seeds.

The emulsfiable concentrates, the wettable powders, or flowables and the like are usually applied by diluting them with water, and then spreading them. In this case, the concentration of the present compound is usually within a range of 0.0005 to 2% by weight. The dusts or the granules, and the like are usually applied as itself without diluting them.

When the present compound is used to control pests in indoor, the application dose is usually within a range of 0.01 to 1,000 mg as the present compound per 1 m² in the case of application for plane surface, and 0.01 to 500 mg as the present compound per 1 m³ in the case of application for space. When the present pest control agent is formulated into the emulsfiable concentrates, the wettable powders, or the flowables, the present compound is diluted with water such that the concentration of the present compound is within a range of 0.1 to 10,000 ppm, and may be then applied. The oil solutions, the aerosols, the smoking agents and the poison baits are applied as itself without diluting them.

When the present compound is sued for controlling external parasites of livestock such as cows, horses, pigs, sheep, goats and chickens and small animals such as dogs, cats, rats and mice, the present compound can be applied to the animals by a known method in the veterinary field. Specifically, when systemic control is intended, the present compound is administered to the animals as a tablet, a mixture with feed, a suppository, or by injection (including intramuscular, subcutaneous, intravenous and intraperitoneal injections). On the other hand, when when non-systemic control is intended, the present compound is applied to the animals by means of spraying of the oil solution or aqueous solution, pour-on or spot-on treatment, or washing of the animal with a shampoo formulation, or by putting a collar or ear tag made of the resin formulations to the animal. In the case of administering to a livestock or a small animal, the dose of the present compound is usually with the range of 0.1 to 1,000 mg per 1 kg of an animal body weight.

Also, the present compound can be used as a plant disease control agent in farmlands such as fields, paddy fields, lawn lands or orchards, and the like. The present compound can control the diseases in the farmlands in the farmlands for growing the below-mentioned plants.

Agricultural crops: corn, rice, wheat, barley, rye, oat, sorghum, cotton, soybean, peanut, sarrazin, sugar beet, rapeseed, sunflower, sugar cane, and tobacco;
Vegetables:
Solanaceae vegetables (e.g., eggplant, tomato, green pepper, hot pepper, and potato),
Cucurbitaceae vegetables (e.g., cucumber, pumpkin, zucchini, watermelon, and melon),
Cruciferae vegetables (e.g., Japanese radish, turnip, horseradish, kohlrabi, Chinese cabbage, cabbage, brown mustard, broccoli, and cauliflower),
Compositae vegetables (e.g., burdock, garland *chrysanthemum*, artichoke, and lettuce),
Liliaceae vegetables (e.g., Welsh onion, onion, garlic, and asparagus),
Umbelliferae vegetables (e.g., carrot, parsley, celery, and parsnip),
Chenopodiaceae vegetables (e.g., spinach, and Swiss chard),
Labiatae vegetables (e.g., Japanese basil, mint, and basil),
Strawberry, sweat potato, yam, aroid, flowers, foliage plants, Fruit trees:
Pomaceous fruits (e.g., apple, common pear, Japanese pear, Chinese quince, and quince),
Stone fleshy fruits (e.g., peach, plum, nectarine, Japanese plum, cherry, apricot, and prune),
Citrus plants (e.g., Satsuma mandarin, orange, lemon, lime, and grapefruit),
Nuts (e.g., chestnut, walnut, hazel nut, almond, pistachio, cashew nut, and macadamia nut),
Berry fruits (e.g., blueberry, cranberry, blackberry, and raspberry),
Grape, persimmon, olive, loquat, banana, coffee, date, coconut palm, oil palm, and the like.
Trees other fruit trees:
Tea, mulberry, flowering trees, street trees (e.g., ash tree, birch, dogwood, eucalyptus, ginkgo, lilac, maple tree, oak, poplar, cercis, Chinese sweet gum, plane tree, zelkova, Japanese arborvitae, fir tree, Japanese hemlock, needle juniper, pine, spruce, Japanese yew), The above-mentioned plants include genetically modified crops.

Examples of the pests that can be controlled by the present compound include plant pathogens, harmful arthropods, harmful nematodes, harmful mollucs, and the like. Specific examples thereof include the followings, but which are not limited to them.

Specific examples of the plant diseases due to the plant pathogens include the followings. The descriptions in the below-mentioned parenthesis represent a scientific name of the plant pathogenic bacteria which causes the corresponding plant diseases.

Rice diseases: blast (*Magnaporthe grisea*), brown spot (*Cochliobolus miyabeanus*), sheath blight (*Rhizoctonia solani*), bakanae disease (*Gibberella fujikuroi*), and downy mildew (*Sclerophthora macrospora*);
Wheat diseases: powdery mildew (*Erysiphe graminis*), fusarium Head blight (*Fusarium graminearum, Fusarium avenaceum, Fusarium culmorum, Microdochium nivale*), yellow rust (*Puccinia striiformis, Puccinia graminis, Puccinia recondita*), pink snow mold (*Micronectriella nivale, M. majus*), Snow mold small rot (*Typhula* sp.), loose smut (*Ustilago tritici*), stinking smut (*Tilletia caries, Tilletia controversa*), eyespot (*Pseudocercosporella herpotrichoides*), leaf blotch (*Septoria tritici*), glume blotch (*Stagonospora nodorum*), tan spot (*Pyrenophora tritici-repentis*), damping-off caused by *rhizoctonia* fungus (*Rhizoctonia solani*), and damping-off (*Gaeumannomyces graminis*);
Barley diseases: powdery mildew (*Erysiphe graminis*), loose smut (*Fusarium graminearum, Fusarium avenaceum, Fusarium culmorum, Microdochium nivale*), yellow rust (*Puccinia striiformis, Puccinia graminis, Puccinia hordei*), loose smut (*Ustilago nuda*), scald (*Rhynchosporium secalis*), net blotch (*Pyrenophora teres*), spot blotch (*Cochliobolus sativus*), leaf stripe (*Pyrenophora graminea*), Ramuraria leaf spot disease (*Ramularia collo-cygni*), and damping-off caused by *rhizoctonia* fungus (*Rhizoctonia solani*);
Corn diseases: rust (*Puccinia sorghi*), southern rust (*Puccinia polysora*), northern leaf blight (*Setosphaeria turcica*), tropical rust (*Physopella zeae*), southern leaf blight (*Cochliobolus heterostrophus*), anthracnose (*Colletotrichum graminicola*), gray leaf spot (*Cercospora zeae-maydis*), eyespot (*Kabatiella zeae*), Faeosufa area leaf spot disease (*Phaeosphaeria maydis*), Diplodia disease (*Stenocarpella maydis, Stenocarpella macrospora*), stalk rot disease (*Fusarium graminearum*, *Fusarium verticilioides*, *Colletotrichum graminicola*), and smut (*Ustilago maydis*);

Cotton diseases: anthracnose (*Colletotrichum gossypii*), Areolate mildew (Ramuraria areola), leaf spot (*Alternaria macrospora*, *Alternaria gossypii*), and Black root rot caused by *Thielaviopsis* fungus (*Thielaviopsis basicola*);

Coffee diseases: rust (*Hemileia vastatrix*) and leaf spot (*Cercospora coffeicola*);

Rapeseed diseases: *sclerotinia* rot (*Sclerotinia sclerotiorum*), alternaria leaf spot (*Alternaria brassicae*), and root rot (*Phoma lingam*);

Sugarcane diseases: rust (*Puccinia melanocephela*, *Puccinia kuehnii*), and smut (*Ustilago scitaminea*);

Sunflower diseases: rust (*Puccinia helianthi*) and downy mildew (*Plasmopara halstedii*);

Citrus diseases: melanose (*Diaporthe citri*), scab (*Elsinoe fawcetti*), fruit rot (*Penicillium digitatum*, *Penicillium italicum*), and *Phytophthora* disease (*Phytophthora parasitica*, *Phytophthora citrophthora*);

Apple diseases: blossom blight (*Monilinia mali*), canker (*Valsa ceratosperma*), powdery mildew (*Podosphaera leucotricha*), *Alternaria* leaf spot (*Alternaria alternata* apple pathotype), scab (*Venturia inaequalis*), anthracnose (*Glomerella cingulata*), blotch (*Diplocarpon mali*), ring rot (*Botryosphaeria berengeriana*), and crown rot (*Phytophthora cactorum*);

Pear diseases: scab (*Venturia nashicola*, *Venturia pirina*), black spot (*Alternaria alternata* Japanese pear pathotype), and rust (*Gymnosporangium haraeanum*);

Peach diseases: brown rot (*Monilinia fructicola*), scab (*Cladosporium carpophilum*), and *Phomopsis* rot (*Phomopsis* sp.);

Grapes diseases: anthracnose (*Elsinoe ampelina*), ripe rot (*Glomerella cingulata*), powdery mildew (*Uncinula necator*), rust (*Phakopsora ampelopsidis*), black rot (*Guignardia bidwellii*), downy mildew (*Plasmopara viticola*);

Diseases of Japanese persimmon: anthracnose (*Gloeosporium kaki*) and leaf spot (*Cercospora kaki*, *Mycosphaerella nawae*);

Diseases of Cucurbitaceae: anthracnose (*Colletotrichum lagenarium*), powdery mildew (*Sphaerotheca fuliginea*), gummy stem blight (*Didymella bryoniae*), *corynespora* leaf spot (*Corynespora cassiicola*), *Fusarium* wilt (*Fusarium oxysporum*), downy mildew (*Pseudoperonospora cubensis*), *Phytophthora* rot (*Phytophthora* sp.), and damping-off (*Pythium* sp.);

Tomato diseases: early blight (*Alternaria solani*), leaf mold (*Cladosporium fulvum*), cercospora leaf mold (*Pseudocercospora fuligena*), late blight (*Phytophthora infestans*), and powdery mildew (*Leveillula taurica*);

Eggplant disease: brown spot (*Phomopsis vexans*) and powdery mildew (*Erysiphe cichoracearum*);

Diseases of brassica family: *Alternaria* leaf spot (*Alternaria japonica*), white spot (*Cercosporella brassicae*), clubroot (*Plasmodiophora brassicae*), and downy mildew (*Peronospora parasitica*);

Welsh onion diseases: rust (*Puccinia allii*);

Soybean diseases: purple stain (*Cercospora kikuchii*), Sphaceloma scad (*Elsinoe glycines*), pod and stem blight (*Diaporthe phaseolorum* var. *sojae*), rust (*Phakopsora pachyrhizi*), target spot (*Corynespora cassiicola*), anthracnose (*Colletotrithum glycines*, *Colletotrichum truncatum*), *Rhizoctonia* rot (*Rhizoctonia solani*), septoria brown spot (*Septoria glycines*), cercospora leaf spot (*Cercospora sojina*), sclerotinia rot (*Sclerotinia sclerotiorum*), powdery mildew (*Microsphaera diffusa*), phytophthora root and stem rot (*Phytophthora sojae*), downy mildew (*Peronospora manshurica*), and sudden death syndrome (*Fusarium virguliforme*);

Kidney bean diseases: stem rot (*Sclerotinia sclerotiorum*), rust (*Uromyces appendiculatus*), angular leaf spot (*Phaeoisariopsis griseola*), and anthracnose (*Colletotrichum lindemuthianum*);

Peanut diseases: leaf spot (*Cercospora personata*), brown leaf spot (*Cercospora arachidicola*), and southern blight (*Sclerotium rolfsii*);

Garden pea diseases: powdery mildew (*Erysiphe pisi*);

Potato diseases: early blight (*Alternaria solani*), late blight (*Phytophthora infestans*), pink rot (*Phytophthora erythroseptica*), powdery scab (*Spongospora subterranea* f. sp. *subterranea*), and *Verticillium* wilt (*Verticillium albo-atrum*, *Verticillium dahliae*, *Verticillium nigrescens*);

Strawberry diseases: powdery mildew (*Sphaerotheca humuli*);

Tea diseases: net blister blight (*Exobasidium reticulatum*), white scab (*Elsinoe leucospila*), gray blight (*Pestalotiopsis* sp.), and anthracnose (*Colletotrichum theaesinensis*);

Tabacco diseases: brown spot (*Alternaria longipes*), anthracnose (*Colletotrichum tabacum*), downy mildew (*Peronospora tabacina*), and black shank (*Phytophthora nicotianae*);

Sugar beet diseases: *cercospora* leaf spot (*Cercospora beticola*), leaf blight (*Thanatephorus cucumeris*), root rot (*Thanatephorus cucumeris*), and *aphanomyces* root rot (*Aphanomyces cochlioides*);

Rose diseases: blackspot (*Diplocarpon rosae*) and powdery mildew (*Sphaerotheca pannosa*);

Chrysanthemum and Asteraceae vegetable diseases: leaf blight (*Septoria chrysanthemi-indici*) and white rust (*Puccinia horiana*);

Onion diseases: *Botrytis* leaf blight (*Botrytis cinerea*, *Botrytis byssoidea*, *Botrytis squamosa*), neck rot (*Botrytis alli*), and small sclerotial (*Botrytis squamosa*);

Various plants diseases: Gray molds (*Botrytis cinerea*) and *Sclerotinia* rot (*Sclerotinia sclerotiorum*);

Japanese radish diseases: *Alternaria* leaf spot (*Alternaria brassicicola*);

Turfgrass diseases: dollar spot (*Sclerotinia homoeocarpa*), and brown patch and large patch (*Rhizoctonia solani*);

Banana diseases: Sigatoka disease (*Mycosphaerella fijiensis*, *Mycosphaerella musicola*);

Seed diseases or diseases in the early stages of the growth of various plants caused by bacteria of *Aspergillus* spp., *Penicillium* spp., *Fusarium* spp., *Gibberella* spp., *Tricoderma* spp., *Thielaviopsis* spp., *Rhizopus* spp., *Mucor* spp., *Corticium* spp., *Phoma* spp., *Rhizoctonia* spp., *Diplodia* spp., and the others; Viral diseases of various plants mediated by *Polymyxa* spp., *Olpidium* spp., or the others; and Rice bacterial seedling blight (*Burkholderia plantarii*);

Cucumber angular leaf spot (*Pseudomonas syringae* pv. *Lachrymans*);

Eggplant bacterial wilt (*Ralstonia solanacearum*);

Citrus canker (*Xanthomonas citri*);

Chinese cabbage bacterial soft rot (*Erwinia carotovora*); and the others.

The present compound can exert sufficient control efficacies against plant pathogens that acquired a resistance to existing fungicides, and thereby can use.

With respect to the plant pathogens that acquired a resistance, the present compound can use to control plant pathogens that contains mutations being capable of conferring mitochondrial cytochrome b gene on a resistance to Qo inhibitor.

Examples of the mutations being capable of conferring mitochondrial cytochrome b gene on a resistance to Qo inhibitor include G143A, F129L, and G137 R.

Among the genes encoding cytochrome b, QoI resitant strains in which its nucleotide sequence is mutated such that a glycine as the 143th amino acid residues of cytochrome b being replaced with an alanine is included, and specific examples thereof includes *Alternaria* alternate, *Alternaria arborescens, Alternaria mali, Alternaria tenussima, Ascochyta rabiei, Blumeria graminis* f. sp. *hordei, Blumeria graminis* f. sp. *tritici, Botrytis cinerea, Cercospora beticola, Cercospora sojina, Cladosporium carpophilum, Colletotrichum gloeosporioides, Colletotrichum graminicola, Corynespora cassiicola, Didymella bryoniae, Erysiphe necator, Glomerella cingulata, Microdochium majus, Microdochium nivale, Monilinia fruciigena, Mycosphaerella fijiensis, Mycosphaerella musicola, Mycovellosiella nattrassii, Pestalotiopsis longiseta, Phaeosphaeria nodorum, Plasmopara viticola, Podosphaera xanthii, Pseudocercospora vitis, Pseudoperonospora cubensis, Pyrenophora tritici-repentis, Pyricularia grisea, Pyricularia oryzae, Ramularia areola, Ramularia collo-cygni, Rhynchosporium secalis, Septoria tritici, Sphaerotheca aphanis, Stemphylium vesicarium, Ustilago maydis, Venturia inaequalis, Venturia pirina.*

Among the genes encoding cytochrome b, QoI resistant strains in which its nucleotide sequence is mutated such that a phenylalanine as the 129th amino acid residues of cytochrome b being replaced with leucine is included, and specific examples thereof includes *Alternaria solani, Fulvia fulva, Phakopsora pachyrhizi, Plasmopara viticola, Pyrenophora teres, Pyrenophora tritici-repentis, Pyricularia grisea, Pythium aphanidermatum, Rhizoctonia solani, Septoria tritici.*

Among the genes encoding cytochrome b, QoI resistant strains in which its nucleotide sequence is mutated such that a glycine as the 137th amino acid residues of cytochrome b being replaced with arginine is included, and specific examples thereof includes *Pyrenophora tritici-repentis.*

Examples of arthropod pests include the followings.

Hemiptera:

Delphacidae such as *Laodelphax striatellus, Nilaparvata lugens, Sogatella furcifera, Peregrinus maidis, Javesella pellucida, Perkinsiella saccharicida*, and *Tagosodes orizicolus;*

Cicadellidae such as *Nephotettix cincticeps, Nephotettix virescens, Nephotettix nigropictus, Recilia dorsalis, Empoasca onukii, Empoasca fabae, Dalbulus maidis*, and *Cofana spectra;*

Cercopidae such as *Mahanarva posticata*, and *Mahanarva fimbriolata;*

Aphididae such as *Aphis fabae, Aphis glycines, Aphis gossypii, Aphis pomi, Aphis spiraecola, Myzus persicae, Brachycaudus helichrysi, Brevicoryne brassicae*, Rosy apple aphid (*Dysaphis plantaginea*), *Lipaphis erysimi, Macrosiphum euphorbiae, Aulacorthum solani, Nasonovia ribisnigri, Rhopalosiphum padi, Rhopalosiphum maidis, Toxoptera citricida, Hyalopterus pruni, Melanaphis sacchari, Tetraneura nigriabdominalis, Ceratovacuna lanigera, Eriosoma lanigerum;*

Phylloxeridae such as *Daktulosphaira vitifoliae*, Pecan *phylloxera* (*Phylloxera devastatrix*), Pecan leaf *phylloxera* (*Phylloxera notabilis*), Southern pecan leaf *phylloxera* (*Phylloxera russellae*);

Adelgidae such as *Adelges tsugae, Adelges piceae, Aphrastasia pectinatae;*

Pentatomidae such as *Scotinophara lurida*, Malayan rice black bug (*Scotinophara coarctata*), *Nezara antennata, Eysarcoris aeneus, Eysarcoris lewisi, Eysarcoris ventralis, Eysarcoris annamita, Halyomorpha halys, Nezara viridula*, Brown stink bug (*Euschistus heros*), Red banded stink bug (*Piezodorus guildinii*), *Oebalus pugnax*, and *Dichelops melacanthus;*

Cydnidae such as Burrower brown bug (*Scaptocoris castanea*);

Alydidae such as *Riptortus pedestris, Leptocorisa chinensis*, and *Leptocorisa acuta;*

Coreidae such as *Cletus punctiger*, and *Leptoglossus australis;*

Lygaeidae such as *Caverelius saccharivorus, Togo hemipterus*, and *Blissus leucopterus;*

Miridae such as *Trigonotylus caelestialium, Stenotus rubrovittatus, Stenodema calcarata*, and *Lygus lineolaris;*

Aleyrodidae such as *Trialeurodes vaporariorum, Bemisia tabaci, Dialeurodes citri, Aleurocanthus spiniferus, Aleurocanthus camelliae*, and *Pealius euryae;*

Diaspididae such as *Abgrallaspis cyanophylli, Aonidiella aurantii, Diaspidiotus perniciosus, Pseudaulacaspis pentagona, Unaspis yanonensis*, and *Unaspis citri;*

Coccidae such as *Ceroplastes rubens;*

Margarodidae such as *Icerya purchasi*, and *Icerya seychellarum;*

Pseudococcidae such as *Phenacoccus solani, Phenacoccus solenopsis, Planococcus kraunhiae, Pseudococcus comstocki, Planococcus citri, Pseudococcus calceolariae, Pseudococcus longispinus*, and *Brevennia rehi;*

Psyllidae such as *Diaphorina citri, Trioza erytreae, Cacopsylla pyrisuga, Cacopsylla chinensis, Bactericera cockerelli*, and Pear psylla (*Cacopsylla pyricola*);

Tingidae such as *Corythucha ciliata, Corythucha marmorata, Stephanitis nashi*, and *Stephanitis pyrioides;*

Cimicidae such as *Cimex lectularius;*

Cicadidae such as Giant Cicada (*Quesada gigas*); and *Triatoma* spp. such as *Triatoma infestans.*

Lepidoptera:

Crambidae such as *Chilo suppressalis*, Darkheaded stem borer (*Chilo polychrysus*), White stem borer (*Scirpophaga innotata*), *Scirpophaga incertulas, Rupela albina, Cnaphalocrocis medinalis, Marasmia patnalis, Marasmia exigua, Notarcha derogata, Ostrinia furnacalis*, European corn borer (*Ostrinia nubilalis*), *Hellula undalis, Herpetogramma luctuosale, Pediasia teterrellus, Nymphula depunctalis*, and Sugarcane borer (*Diatraea saccharalis*);

Pyralidae such as *Elasmopalpus lignosellus, Plodia interpunctella*, and *Euzophera batangensis;*

Noctuidae such as *Spodoptera litura, Spodoptera exigua, Mythimna separata, Mamestra brassicae, Sesamia inferens, Spodoptera mauritia, Naranga aenescens, Spodoptera frugiperda, Spodoptera exempta, Agrotis ipsilon, Autographa nigrisigna, Plusia festucae*, Soybean looper (*Chrysodeixis includens*), *Trichoplusia* spp., *Heliothis* spp. (for example, *Heliothis virescens*), *Helicoverpa* spp. (for example, *Helicoverpa armigera* or *Helicoverpa zea*), Velvetbean caterpillar (*Anticarsia gemmatalis*), Cotton leafworm (*Alabama argillacea*), Hop vine borer (*Hydraecia immanis*);

Pieridae such as *Pieris rapae;*

Tortricidae such as *Grapholita molesta, Grapholita dimorpha, Leguminivora glycinivorella, Matsumuraeses azukivora, Adoxophyes orana fasciata, Adoxophyes honmai, Homona magnanima, Archips fuscocupreanus, Cydia pomonella, Tetramoera schistaceana*, Bean Shoot Borer (*Epinotia aporema*), and Citrus fruit borer (*Ecdytolopha aurantiana*);

Gracillariidae such as *Caloptilia theivora*, and *Phyllonorycter ringoniella*;

Carposinidae such as *Carposina sasakii*;

Lyonetiidae such as Coffee Leaf miner (*Leucoptera coffeella*), *Lyonetia clerkella*, and *Lyonetia prunifoliella*;

Lymantriidae such as *Lymantria* spp. (for example, *Lymantria dispar*), and *Euproctis* spp. (for example, *Euproctis pseudoconspersa*), Plutellidae such as *Plutella xylostella*;

Gelechiidae such as *Anarsia lineatella*, *Helcystogramma triannulella*, *Pectinophora gossypiella*, *Phthorimaea operculella*, and *Tuta absoluta*;

Arctiidae such as *Hyphantria cunea*;

Castniidae such as Giant Sugarcane borer (*Telchin licus*);

Cossidae such as *Cossus insularis*;

Geometridae such as *Ascotis selenaria*;

Limacodidae such as *Parasa lepida*;

Stathmopodidae such as *Stathmopoda masinissa*;

Sphingidae such as *Acherontia lachesis*;

Sesiidae such as *Nokona feralis*, *Synanthedon hector*, and *Synanthedon tenuis*;

Hesperiidae such as *Parnara guttata*;

Tinedae such as *Tinea translucens* and *Tineola bisselliella*.

Thysanoptera;

Thripidae such as *Frankliniella occidentalis*, *Thrips palmi*, *Scirtothrips dorsalis*, *Thrips tabaci*, *Frankliniella intonsa*, *Stenchaetothrips biformis*, and *Echinothrips americanus*; and Phlaeothripidae such as *Haplothrips aculeatus*.

Diptera:

Anthomyiidae such as *Delia platura*, *Delia antiqu*, and *Pegomya cunicularia*;

Ulidiidae such as *Tetanops myopaeformis*;

Agromyzidae such as *Agromyza oryzae*, *Liriomyza sativae*, *Liriomyza trifolii*, and *Chromatomyia horticola*;

Chloropidae such as *Chlorops oryzae*;

Tephritidae such as *Bactrocera cucurbitae*, *Bactrocera dorsalis*, *Bactrocera latifrons*, *Bactrocera oleae*, *Bactrocera tryoni*, *Ceratitis capitata*, *Rhagoletis pomonella*, and *Rhacochlaena japonica*;

Ephydridae such as *Hydrellia griseola*, *Hydrellia philippina*, and *Hydrellia sasakii*;

Drosophilidae such as *Drosophila suzukii*;

Phoridae such as *Megaselia spiracularis*;

Psychodidae such as *Clogmia albipunctata*;

Sciaridae such as *Bradysia difformis*;

Cecidomyiidae such as *Mayetiola destructor*, and *Orseolia oryzae*;

Diopsidae such as *Diopsis macrophthalma*;

Tipulidae such as *Tipula aino*, Common cranefly (*Tipula oleracea*), and European cranefly (*Tipula paludosa*);

Culicidae such as *Culex pipiens pallens*, *Aedes aegypti*, *Aedes albopicutus*, *Anopheles hyracanus sinesis*, *Culex quinquefasciatus*, *Culex pipiens molestus* Forskal, and *Culex quinquefasciatus*;

Simulidae such as *Prosimulium yezoensis* and *Simulium ornatum*;

Tabanidae such as *Tabanus trigonus*;

Muscidae such as *Muscadomestica*, *Muscina stabulans*, *Stomoxys calcitrans*, and *Haematobia irritans*;

Tabanidae such as *Tabanus trigonus* Coquillett;

Calliphoridae;

Sarcophagidae;

Chironomidae such as *Chironomus plumosus*, *Chironomus yoshimatsui*, and *Glyptotendipes tokunagai*;

Fannidae; and

Simulidae.

Coleoptera:

Chrysomelidae such as *Diabrotica virgifera virgifera*, *Diabrotica undecimpunctata howardi*, *Diabrotica barberi*, *Diabrotica virgifera zeae*, *Diabrotica balteata*, Cucurbit Beetle (*Diabrotica speciosa*), *Cerotoma trifurcata*, *Oulema melanopus*, *Aulacophora femoralis*, *Phyllotreta striolata*, Cabbage flea beetle (*Phyllotreta cruciferae*), Western black flea beetle (*Phyllotreta pusilla*), Cabbage stem flea beetle (*Psylliodes chrysocephala*), *Leptinotarsa decemlineata*, *Oulema oryzae*, *Colaspis brunnea*, *Chaetocnema pulicaria*, *Chaetocnema confinis*, *Epitrix cucumeris*, *Dicladispa armigera*, Grape *Colaspis* (*Colaspis brunnea*), southern corn leaf beetle (*Myochrous denticollis*), *Laccoptera quadrimaculata*, and *Epitrix hirtipennis*;

Carabidae such as Seedcorn beetle (*Stenolophus lecontei*), and Slender seedcorn beetle (*Clivina impressifrons*);

Scarabaeidae such as *Anomala cuprea*, *Anomala rufocuprea*, *Anomala albopilosa*, *Popillia japonica*, *Heptophylla picea*, European Chafer (*Rhizotrogus majalis*), *Tomarus gibbosus*, *Holotrichia* spp., *Phyllophaga* spp. (for example, *Phyllophaga crinita*), and *Diloboderus* spp. (for example, *Diloboderus abderus*);

Curculionidae such as *Araecerus coffeae*, *Cylas formicarius*, *Euscepes postfasciatus*, *Hypera postica*, *Sitophilus zeamais*, *Echinocnemus squameus*, *Lissorhoptrus oryzophilus*, *Rhabdoscelus lineatocollis*, *Anthonomus grandis*, *Sphenophorus venatus*, Southern Corn Billbug (*Sphenophorus callosus*), Soybean stalk weevil (*Sternechus subsignatus*), Sugarcane weevil (*Sphenophorus levis*), *Scepticus griseus*, *Scepticus uniformis*, *Zabrotes subfasciatus*, *Tomicus piniperda*, Coffee Berry Borer (*Hypothenemus hampei*), *Aracanthus* spp. (for example, *Aracanthus mourei*), and cotton root borer (*Eutinobothrus brasiliensis*);

Tenebrionidae such as *Tribolium castaneum*, and *Tribolium confusum*;

Coccinellidae such as *Epilachna vigintioctopunctata*;

Bostrychidae such as *Lyctus brunneus*;

Ptinidae;

Cerambycidae such as *Anoplophora malasiaca* and *Migdolus fryanus*; *Agriotes* sp., *Aelous* sp., *Anchastus* sp., *Melanotus* sp., *Limonius* sp., *Conoderus* sp., or *Ctenicera* sp. such as *Melanotus okinawensis*, *Agriotes fuscicollis*, and *Melanotus legatus*;

Staphylinidae such as *Paederus fuscipes*;

Dermestidae such as *Anthrenus verbasci* and *Dermestes maculates*; and

Anobidae such as *Lasioderma serricorne* and *Stegobium paniceum*.

Orthoptera:

Acrididae such as *Locusta migratoria*, *Dociostaurus maroccanus*, *Chortoicetes terminifera*, *Nomadacris septemfasciata*, Brown Locust (*Locustana pardalina*), Tree Locust (*Anacridium melanorhodon*), Italian Locust (*Calliptamus italicus*), Differential grasshopper (*Melanoplus differentialis*), Two striped grasshopper (*Melanoplus bivittatus*), Migratory grasshopper (*Melanoplus sanguinipes*), Red-Legged grasshopper (*Melanoplus femurrubrum*), Clearwinged grasshopper (*Camnula pellucida*), *Schistocerca gregaria*, Yellow-winged locust (*Gastrimargus musicus*), Spur-throated locust (*Austracris guttulosa*), *Oxya yezoensis*, *Oxya japonica*, and *Patanga succincta*;

Gryllotalpidae such as *Gryllotalpa orientalis*;

Gryllidae such as *Acheta domestica*, and *Teleogryllus emma*;

Tettigoniidae such as Mormon cricket (*Anabrus simplex*).

Hymenoptera:
Tenthredinidae such as *Athalia rosae*, and *Athalia japonica*;
*Solenopsis* spp. such as *Solenopsis invicta* and *Solenopsis geminata*;
*Atta* spp. such as Brown leaf-cutting ant (*Atta capiguara*); *Acromyrmex* spp.;
*Camponotus* spp. such as *Paraponera clavata, Ochetellus glaber, Monomorium pharaonis, Linepithema humile, Formica fusca japonica, Pristomyrmex punctutus, Pheidole noda, Pheidole megacephala, Camponotus japonicus, Camponotus obscuripes*;
*Pogonomyrmex* spp. such as *Pogonomyrmex occidentalis*;
*Wasmania* spp. such as *Wasmania auropunctata*;
Formicidae such as *Anoplolepis gracilipes*;
Vespidae such as *Vespa mandarinia japonica, Vespa simillima, Vespa analis* Fabriciusi, *Vespa velutina*, and *Polistes jokahamae*;
Siricidae such as *Urocerus gigas*; and
Bethylidae.
Blattodea:
Blattellidae such as *Blattella germanica*;
Blattidae such as *Periplaneta fuliginosa, Periplaneta americana, Periplaneta brunnea*, and *Blatta orientalis*;
Termitidae such as *Reticulitermes speratus, Coptotermes formosanus, Incisitermes minor, Cryptotermes domesticus, Odontotermes formosanus, Neotermes koshunensis, Glyptotermes satsumensis, Glyptotermes nakajimai, Glyptotermes fuscus, Hodotermopsis sjostedti, Coptotermes guangzhouensis, Reticulitermes amamianus, Reticulitermes miyatakei, Reticulitermes kanmonensis, Nasutitermes takasagoensis, Pericapritermes nitobei, Sinocapritermes mushae*, and *Cornitermes cumulans*.
Siphonaptera:
*Ctenocephalides felis, Ctenocephalides canis, Pulex irritans, Xenopsylla cheopis, Tunga penetrans, Echidnophaga gallinacea*, and *Nosopsyllus fasciatus*.
Anoplura:
*Haematopinus suis, Haematopinus eurysternus, Dalmalinia ovis, Linognathus seypsus, Pediculus humanis, Pediculuc humanus corporis, Pediculus humanus humanus*, and *Phthirus pubis*.
Mallophagida:
*Louse* spp. that is parasitic on the kitchen such as *Dalmalinia bovis*, and *Lipeurus caponis*;
*Dalmalinia ovis*;
*Trichodectes canis*;
*Felicola subrostrata*.
Acari:
Tetranychidae such as *Tetranychus urticae, Tetranychus kanzawai, Tetranychus evansi, Panonychus citri, Panonychus ulmi*, and *Oligonychus* spp.;
Eriophyidae such as *Aculops pelekassi, Phyllocoptruta citri, Aculops lycopersici, Calacarus carinatus, Acaphylla theavagrans, Eriophyes chibaensis, Aculus schlechtendali, Aceria diospyri, Aceria tosichella, Shevtchenkella* sp.;
Tarsonemidae such as *Polyphagotarsonemus latus*;
Tenuipalpidae such as *Brevipalpus phoenicis*;
Tuckerellidae;
Ixodidae such as *Haemaphysalis longicomis, Haemaphysalis flava, Dermacentor taiwanensis, Dermacentor variabilis, Dermacentor andersoni, Ixodes ovatus, Ixodes persulcatus, Ixodes ricinus, Ixodes scapularis, Amblyomma americanum, Ambryomma maculatum, Boophilus microplus, Boophilus annulatus*, and *Rhipicephalus sanguineu*;

Acaridae such as *Tyrophagus putrescentiae* and *Tyrophagus similis*;
Pyroglyphidae such as *Dermatophagoides farinae* and *Dermatophagoides pteronyssinus*;
Cheyletidae such as *Cheyletus eruditus, Cheyletus malaccensis, Cheyletus moorei*, and *Cheyletiella yasguri*;
Sarcoptidae such as *Otodectes cynotis*, and *Sarcoptes scabiei*;
Demodicidae such as *Demodex canis*;
Listrophoridae;
Haplochthoniidae;
Macronyssidae such as *Ornithonyssus bacoti* and *Ornithonyssus sylviarum*;
Dermanyssidae such as *Dermanyssus gallinae*; and
Trombiculidae such as *Leptotrombidium akamushi*.
Araneae:
Eutichuridae such as *Cheiracanthium japonicum*; and
Theridiidae such as *Latrodectus hasseltii*.
Polydesmida;
Paradoxosomatidae such as *Oxidus gracilis* and *Nedyopus tambanus*.
Isopoda:
Armadillidiidae such as *Armadillidium vulgare*.
Chilopoda:
Scutigeridae such as *Thereuonema hilgendorfi*;
Scolopendridae such as *Scolopendra subspinipes*; and
Ethopolidae such as *Bothropolys rugosus*.
Gastropoda:
Limacidae such as *Limax marginatus* and *Limax flavus*.
Philomycidae such as *Meghimatium bilineatum*;
Ampullariidae such as *Pomacea canaliculata*; and
Lymnaeidae such as *Austropeplea ollula*.
Nematoda:
Aphelenchoididae such as *Aphelenchoides besseyi*;
Pratylenchidae such as *Pratylenchus coffeae, Pratylenchus brachyurus, Pratylenchus neglectus*, and *Radopholus similis*;
Heteroderidae such as *Meloidogyne javanica, Meloidogyne incognita, Meloidogyne hapla, Heterodera glycines, Globodera rostochiensis*, and *Globodera pallida*;
Hoplolaimidae such as *Rotylenchulus reniformis*;
Anguinidae such as *Nothotylenchus acris*, and *Ditylenchus dipsaci*;
Tylenchulidae such as *Tylenchulus semipenetrans*;
Longidoridae such as *Xiphinema index*;
Trichodoridae; and
Parasitaphelenchidae such as *Bursaphelenchus xylophilus*.

EXAMPLES

Hereinafter, the present invention is explained in more detail by using Production examples, Reference Production examples, Formulation examples, Test examples, however, the present invention should not be limited to these examples.

Production Example 1

A mixture of 2-acetylfuran 0.38 g, propionic acid hydradide 0.30 g, ethanol 5 mL and acetic acid 0.5 mL was heated under reflux for three hours. The reaction solutions were cooled to room temperature, and concentrated under reduced pressure. The resulting solids were washed with water, and dried to obtain the residues 0.21 g. To the mixture solutions of the resulting residues and DMF 7 mL was added potassium tert-butoxide 0.13 g at room temperature, and the mixture was stirred at room temperature for 10 minutes. 1-{2-(Bromomethyl)-3-methylphenyl}-4-methyl-4,5-dihydrotetrazol-5-one 0.32 g, which was prepared according to the similar method to those described in WO 2013/162072, was added to the mixture solutions, and the mixture was stirred for additional four hours. To the reaction mixture was added water, and the mixture was extracted with ethyl acetate. The resulting organic layer was washed with saturated brine and dried over anhydrous magnesium sulfate, and concentrated under reduced pressure. The resulting residues were subjected to silica gel column chromatography (n-hexane:ethyl acetate=2:1) to give 0.37 g of the Present compound 1-1 as below-mentioned.

Present Compound 1-1

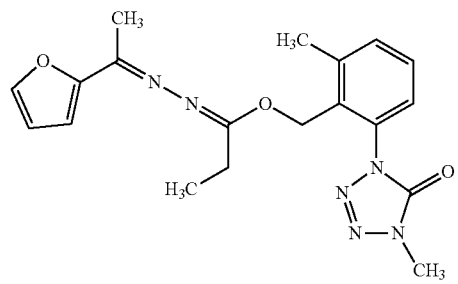

[Chem.74]

Present compound 1-1: $^1$H-NMR (CDCl$_3$) δ: 7.49 (1H, dd, J=1.8, 0.7 Hz), 7.39-7.8 (2H, m), 7.26-7.25 (1H, m), 6.76 (1H, dd, J=3.4, 0.7 Hz), 6.45 (1H, dd, J=3.4, 1.8 Hz), 5.22 (2H, s), 3.68 (3H, s), 2.54 (2H, q, J=7.6 Hz), 2.50 (3H, s), 2.19 (3H, s), 1.04 (3H, t, J=7.6 Hz).

The compounds that were prepared according to the similar method to those described in Production example 1 and its physical properties are indicated below. Also, the solvents that were used for silica gel column chromatography were indicated in parenthesis below a structural formula. Further, when a compound is a mixture of isomers, the isomeric ratio thereof is also indicated below the compound.

Present Compound 1-2

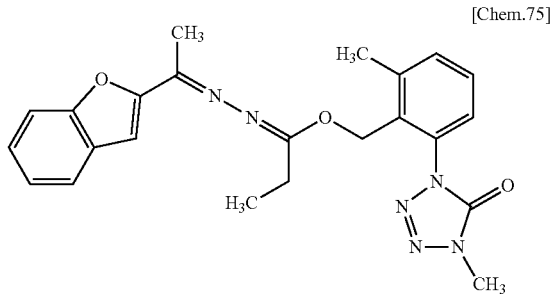 [SMILES: CCC(=NN=C(C)c1cc2ccccc2o1)OCc1c(C)cccc1-n1nnn(C)c1=O]

[Chem.75]

(n-hexane:ethyl acetate=2:1)

Present compound 1-2: $^1$H-NMR (CDCl$_3$) δ: 7.59-7.56 (1H, m), 7.51 (1H, dd, J=8.3, 0.9 Hz), 7.40-7.35 (2H, m), 7.33-7.29 (1H, m), 7.25-7.19 (2H, m), 7.09 (1H, d, J=0.9 Hz), 5.23 (2H, s), 3.67 (3H, s), 2.57 (2H, q, J=7.6 Hz), 2.49 (3H, s), 2.27 (3H, s), 1.04 (3H, t, J=7.6 Hz).

Present Compound 1-3

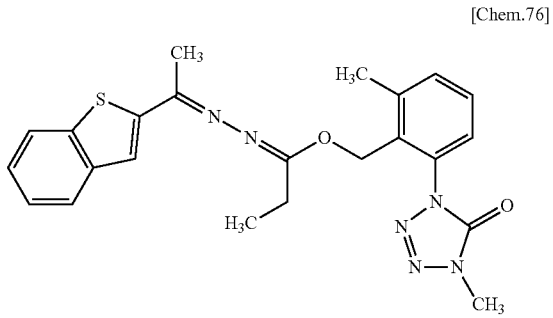 [SMILES: CCC(=NN=C(C)c1cc2ccccc2s1)OCc1c(C)cccc1-n1nnn(C)c1=O]

[Chem.76]

(n-hexane:ethyl acetate=2:1)

Present compound 1-3: $^1$H-NMR (CDCl$_3$) δ: 7.79-7.74 (2H, m), 7.54 (1H, s), 7.41-7.38 (2H, m), 7.35-7.30 (2H, m), 7.27-7.26 (1H, m), 5.26 (2H, s), 3.68 (3H, s), 2.60 (2H, q, J=7.6 Hz), 2.51 (3H, s), 2.38 (3H, s), 1.09 (3H, t, J=7.6 Hz).

Present Compound 1-4

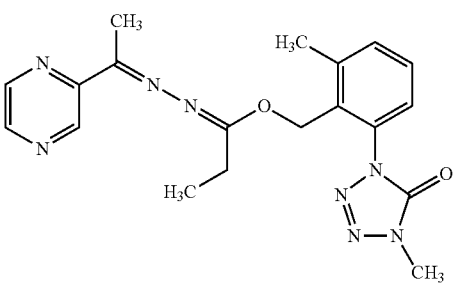

[Chem.77]

(n-hexane:ethyl acetate=2:1)

Present compound 1-4: $^1$H-NMR (CDCl$_3$) δ: 9.37 (1H, d, J=1.4 Hz), 8.54 (1H, dd, J=2.6, 1.4 Hz), 8.52 (1H, d, J=2.6 Hz), 7.44-7.39 (2H, m), 7.28-7.27 (1H, m), 5.28 (2H, s), 3.69 (3H, s), 2.58 (2H, q, J=7.6 Hz), 2.53 (3H, s), 2.37 (3H, s), 1.08 (3H, t, J=7.6 Hz).

Present Compound 1-5

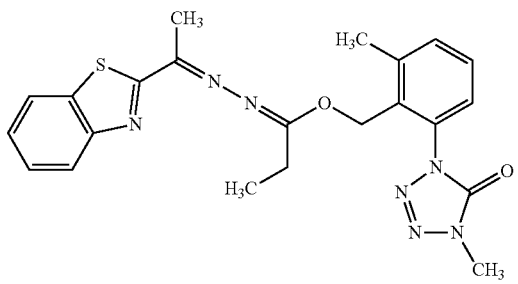

[Chem.78]

(n-hexane:ethyl acetate=2:1)

Present compound 1-5: $^1$H-NMR (CDCl$_3$) δ: 8.06-8.01 (1H, m), 7.86 (1H, dd, J=7.8, 0.7 Hz), 7.50-7.39 (4H, m), 7.27-7.26 (1H, m), 5.30 (2H, s), 3.69 (3H, s), 2.62 (2H, q, J=7.6 Hz), 2.53 (3H, s), 2.50 (3H, s), 1.11 (3H, t, J=7.6 Hz).

Present Compound 1-6

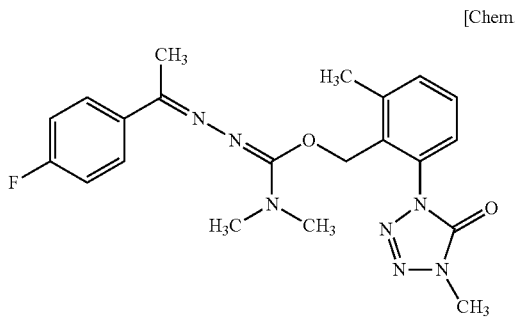

(n-hexane:ethyl acetate=1:2)

Present compound 1-6: $^1$H-NMR (CDCl$_3$) δ: 7.68 (2H, dd, J=8.7, 5.5 Hz), 7.31-7.26 (2H, m), 7.16 (1H, dd, J=6.2, 3.0 Hz), 7.06-7.02 (2H, m), 4.86 (2H, s), 3.58 (3H, s), 2.65 (6H, s), 2.50 (3H, s), 1.85 (3H, s).

Present Compound 1-8

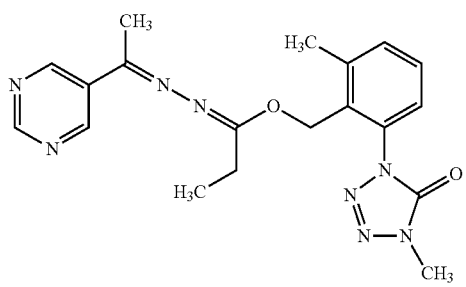

(n-hexane:ethyl acetate=1:2)

Present compound 1-8: $^1$H-NMR (CDCl$_3$) δ: 9.20 (1H, s), 9.14 (2H, s), 7.42-7.40 (2H, m), 7.28-7.26 (1H, m), 5.26 (2H, s), 3.69 (3H, s), 2.58 (2H, q, J=7.6 Hz), 2.52 (3H, s), 2.32 (3H, s), 1.07 (3H, t, J=7.6 Hz).

Present Compound 1-9

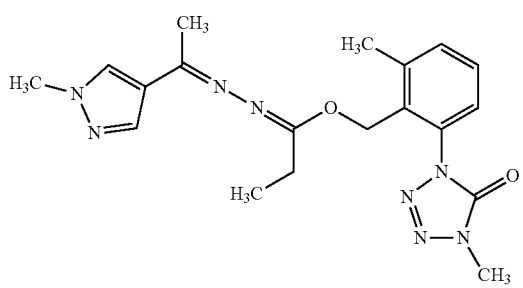

(n-hexane:ethyl acetate=1:1)

Present compound 1-9: $^1$H-NMR (CDCl$_3$) δ: 7.80 (1H, s), 7.69 (1H, s), 7.41-7.37 (2H, m), 7.28-7.24 (1H, m), 5.20 (2H, s), 3.92 (3H, s), 3.68 (3H, s), 2.51 (2H, q, J=7.6 Hz), 2.50 (3H, s), 2.17 (3H, s), 1.04 (3H, t, J=7.6 Hz).

Present Compound 1-10

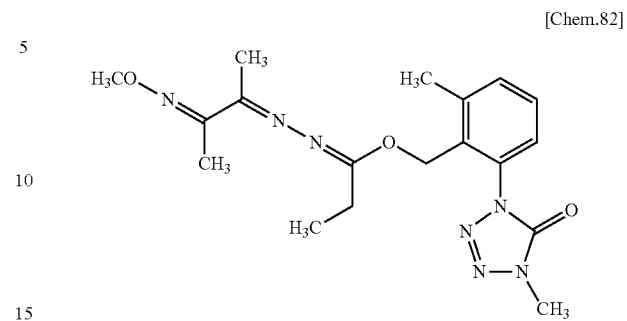

(n-hexane:ethyl acetate=1:1)

Present compound 1-10: $^1$H-NMR (CDCl$_3$) δ: 7.41-7.36 (2H, m), 7.26-7.24 (1H, m), 5.21 (2H, s), 3.98 (3H, s), 3.68 (3H, s), 2.50 (3H, s), 2.45 (2H, q, J=7.6 Hz), 2.07 (3H, s), 2.05 (3H, s), 1.02 (3H, t, J=7.6 Hz).

Production Example 3

To mixture of phenethylamine 0.8 g and dimethylsulfoxide 22 mL was added 20 N aqueous sodium hydroxide solution 0.31 mL at room temperature, and the mixture was stirred for 5 minutes. To the reaction solutions was added carbon disulfide 1.26 g at room temperature, and the mixture was stirred at room temperature for additional 1 hours. The reaction solutions were cooled to 0° C., and thereto was added iodoethane 2.1 g, and the mixture was stirred at room temperature for 1 hour. To the reaction solutions was added water, and the mixture was extracted with ethyl acetate, and washed with water. The resulting organic layer was dried over anhydrous magnesium sulfate, and concentrated under reduced pressure to obtain the residues 1.35 g. To the mixture of the resulting residues, 1-{2-(bromomethyl)-3-methylphenyl}-4-methyl-4,5-dihydrotetrazol-5-one 1.70 g and toluene 12 mL were added successively tetrabutylammonium bromide 0.19 g and 8 N aqueous sodium hydroxide solution 6 mL at 0° C., and the mixture was stirred at 0° C. for 2 hours. To the reaction solutions were added water 20 mL, and the mixures were extracted with ethyl acetate. The resulting organic layer was dried over anhydrous magnesium sulfate, and concentrated under reduced pressure. The resulting residues were subjected to silica gel column chromatography (n-hexane:ethyl acetate=2:1) to give 1.40 g of the Present compound 3-1 as below-mentioned.

Present Compound 3-1

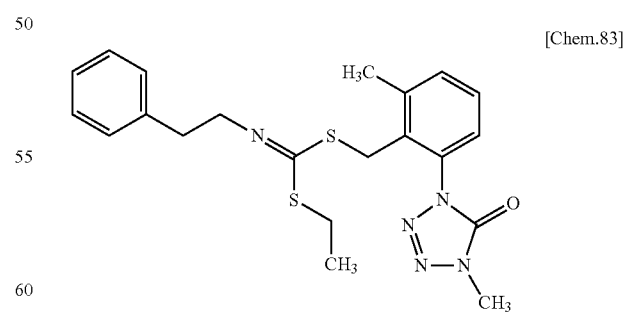

Present compound 3-1: $^1$H-NMR (CDCl$_3$) δ: 7.32 (2H, t, J=6.2 Hz), 7.28 (1H, d, J=7.0 Hz), 7.25 (3H, d, J=5.0 Hz), 7.20 (2H, d, J=5.7 Hz), 4.25 (2H, s), 3.70 (3H, s), 3.66 (2H, t, J=7.2 Hz), 3.00-2.92 (4H, m), 2.39 (3H, s), 1.26 (3H, t, J=7.2 Hz).

The compounds that were prepared according to the similar method to those described in Production example 3 and the physical properties thereof are indicated below. Also, the solvents that were used for silica gel column chromatography were indicated in parenthesis below a structural formula.

Present Compound 3-2

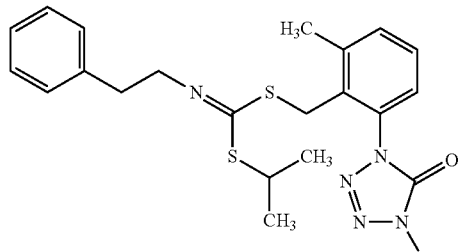
[Chem. 84]

(n-hexane:ethyl acetate=2:1)

Present compound 3-2: $^1$H-NMR (CDCl$_3$) δ: 7.33-7.30 (2H, m), 7.29-7.27 (1H, m), 7.24-7.20 (5H, m), 4.25 (2H, s), 3.70 (3H, s), 3.69-3.63 (3H, m), 2.93 (2H, t, J=7.4 Hz), 2.40 (3H, s), 1.27 (6H, d, J=6.4 Hz).

Present Compound 3-3

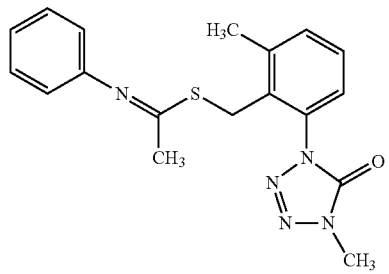
[Chem. 85]

(n-hexane:ethyl acetate=3:1)

Present compound 3-3: $^1$H-NMR (CDCl$_3$) δ: 7.35-7.29 (4H, m), 7.20 (1H, d, J=7.6 Hz), 7.06 (1H, dd, J=7.6, 7.6 Hz), 6.69 (2H, d, J=7.6 Hz), 4.41 (2H, s), 3.35 (3H, s), 2.49 (3H, s), 1.92 (3H, s).

Present Compound 3-4

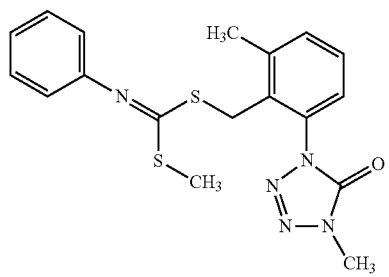
[Chem. 86]

(n-hexane:ethyl acetate=2:1)

Present compound 3-4: $^1$H-NMR (CDCl$_3$) δ: 7.36-7.29 (4H, m), 7.22-7.20 (1H, m), 7.10-7.07 (1H, m), 6.82 (2H, d, J=7.3 Hz), 4.47 (2H, s), 3.46 (3H, s), 2.50 (3H, s), 2.42 (3H, s).

Present Compound 3-5

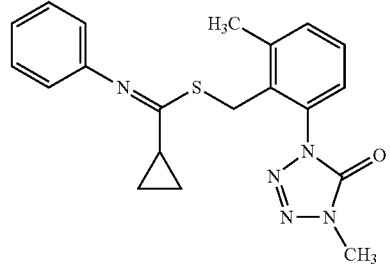
[Chem. 87]

(n-hexane:ethyl acetate=3:1)

Present compound 3-5: $^1$H-NMR (CDCl$_3$) δ: 7.34-7.28 (4H, m), 7.19-7.17 (1H, m), 7.05 (1H, t, J=7.6 Hz), 6.81 (2H, d, J=7.6 Hz), 4.33 (2H, s), 3.39 (3H, s), 2.47 (3H, s), 1.73-1.67 (1H, m), 0.96 (2H, d, J=5.9 Hz), 0.70 (2H, d, J=7.2 Hz).

Present Compound 3-6

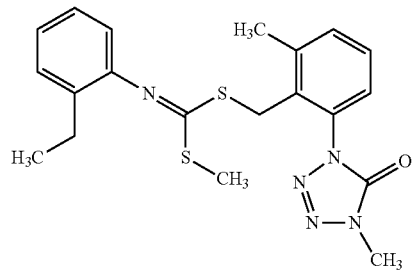
[Chem. 88]

(n-hexane:ethyl acetate=2:1)

Present compound 3-6: $^1$H-NMR (CDCl$_3$) δ: 7.34-7.32 (2H, m), 7.21-7.19 (2H, m), 7.13 (1H, dd, J=7.5, 7.5 Hz), 7.04 (1H, dd, J=7.5, 7.5 Hz), 6.71 (1H, d, J=7.5 Hz), 4.42 (2H, s), 3.49 (3H, s), 2.50 (3H, s), 2.46-2.42 (5H, m), 1.14 (3H, t, J=7.6 Hz).

Present Compound 3-7

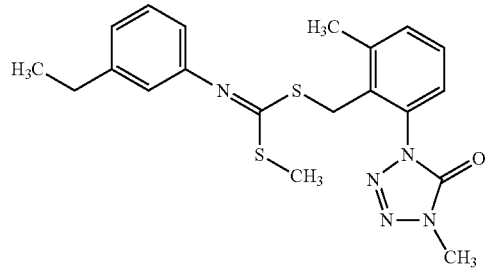
[Chem. 89]

(n-hexane:ethyl acetate=2:1)

Present compound 3-7: $^1$H-NMR (CDCl$_3$) δ: 7.34-7.30 (2H, m), 7.24-7.20 (2H, m), 6.92 (1H, d, J=7.9 Hz), 6.68-6.63 (2H, m), 4.47 (2H, s), 3.45 (3H, s), 2.63 (2H, q, J=8.0 Hz), 2.49 (3H, s), 2.41 (3H, s), 1.24 (3H, t, J=8.0 Hz).

Present Compound 3-8

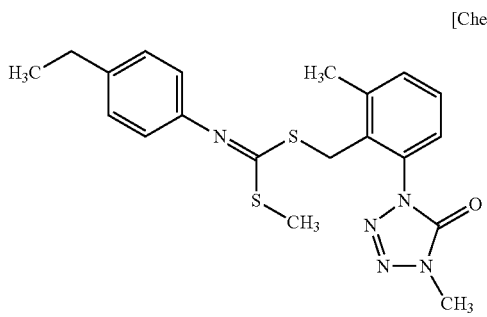

(n-hexane:ethyl acetate=2:1)

Present compound 3-8: ¹H-NMR (CDCl₃) δ: 7.34-7.30 (2H, m), 7.21 (1H, d, J=7.7 Hz), 7.14 (2H, d, J=8.2 Hz), 6.75 (2H, d, J=8.2 Hz), 4.47 (2H, s), 3.45 (3H, s), 2.62 (2H, q, J=7.2 Hz), 2.49 (3H, s), 2.41 (3H, s), 1.22 (3H, t, J=7.2 Hz).

Present Compound 3-9

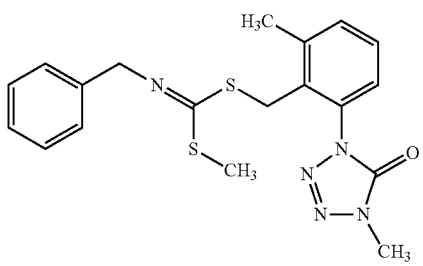

(n-hexane:ethyl acetate=2:1) E/Z mixture, Isomeric ratio 2:1

Present compound 3-9: ¹H-NMR (CDCl₃) δ: 7.36-7.31 (6H, m), 7.29-7.16 (2H, m), 4.60 (1.33H, s), 4.56 (0.67H, s), 4.39 (0.67H, s), 4.37 (1.33H, s), 3.69 (1H, s), 3.54 (2H, s), 2.52 (1H, s), 2.51 (2H, s), 2.44 (1H, s), 2.43 (2H, s).

Present Compound 3-10

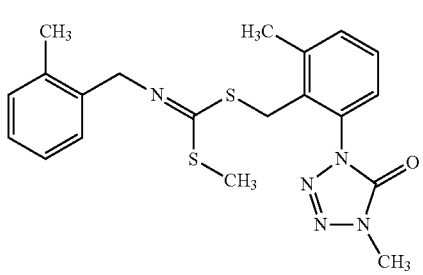

(n-hexane:ethyl acetate=2:1) E/Z mixture, Isomeric ratio 2:1

Present compound 3-10: ¹H-NMR (CDCl₃) δ: 7.37-7.15 (7H, m), 4.55 (1.33H, s), 4.50 (0.67H, s), 4.40 (0.67H, s), 4.35 (1.33H, s), 3.69 (1H, s), 3.54 (2H, s), 2.51 (3H, s), 2.42 (1H, s), 2.41 (2H, s), 2.31 (2H, s), 2.27 (1H, s).

Present Compound 3-11

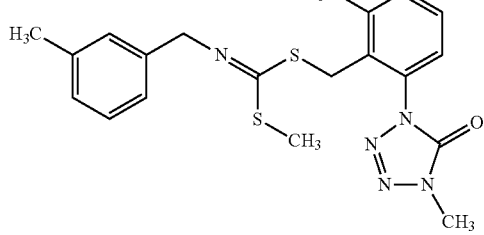

(n-hexane:ethyl acetate=2:1) E/Z mixture, Isomeric ratio 2:1

Present compound 3-11: ¹H-NMR (CDCl₃) δ: 7.35-7.03 (7H, m), 4.57 (1.33H, s), 4.53 (0.67H, s), 4.39 (0.67H, s), 4.37 (1.33H, s), 3.69 (1H, s), 3.54 (2H, s), 2.52 (1H, s), 2.51 (2H, s), 2.44 (2H, s), 2.43 (1H, s), 2.37 (2H, s), 2.34 (1H, s).

Present Compound 3-12

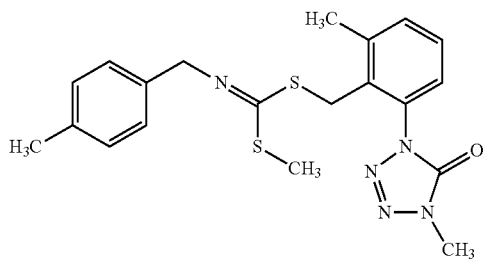

(n-hexane:ethyl acetate=2:1) E/Z mixture, Isomeric ratio 2:1

Present compound 3-12: ¹H-NMR (CDCl₃) δ: 7.35-7.10 (7H, m), 4.56 (1.33H, s), 4.52 (0.67H, s), 4.38 (0.67H, s), 4.35 (1.33H, s), 3.69 (1H, s), 3.56 (2H, s), 2.52 (1H, s), 2.50 (2H, s), 2.43 (2H, s), 2.42 (1H, s), 2.34 (2H, s), 2.33 (1H, s).

Present Compound 3-13

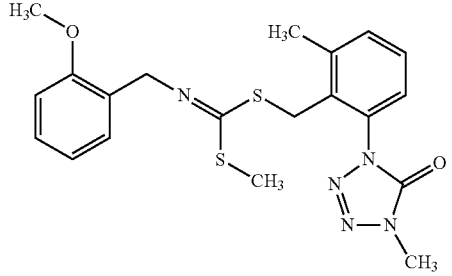

(n-hexane:ethyl acetate=2:1) E/Z mixture, Isomeric ratio 2:1

Present compound 3-13: ¹H-NMR (CDCl₃) δ: 7.43-7.17 (5H, m), 6.99-6.82 (2H, m), 4.59 (1.33H, s), 4.55 (0.67H, s), 4.39 (2H, s), 3.85 (2H, s), 3.80 (1H, s), 3.69 (1H, s), 3.54 (2H, s), 2.52 (1H, s), 2.51 (2H, s), 2.46 (1H, s), 2.44 (2H, s).

Present Compound 3-14

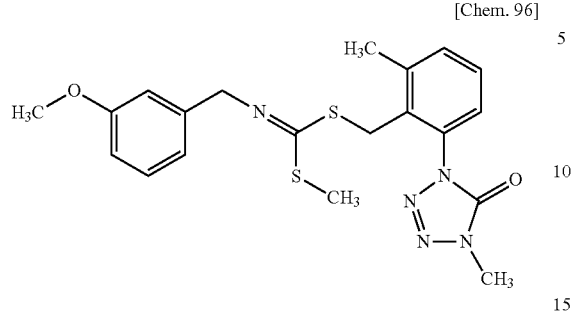

(n-hexane:ethyl acetate=2:1) E/Z mixture, Isomeric ratio 2:1

Present compound 3-14: $^1$H-NMR (CDCl$_3$) δ: 7.36-7.16 (4H, m), 6.95-6.89 (2H, m), 6.81-6.76 (1H, m), 4.57 (1.33H, s), 4.53 (0.67H, s), 4.39 (0.67H, s), 4.37 (1.33H, s), 3.82 (2H, s), 3.80 (1H, s), 3.69 (1H, s), 3.54 (2H, s), 2.51 (1H, s), 2.51 (2H, s), 2.44 (3H, s).

Present Compound 3-15

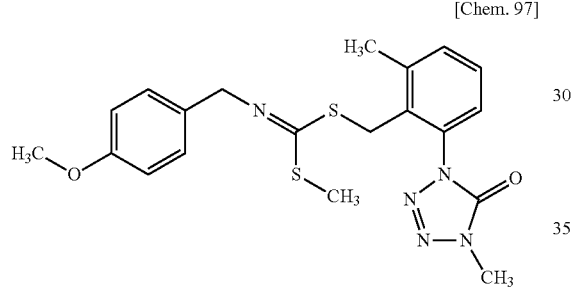

(n-hexane:ethyl acetate=2:1) E/Z mixture, Isomeric ratio 2:1

Present compound 3-15: $^1$H-NMR (CDCl$_3$) δ: 7.35-7.16 (5H, m), 6.88-6.86 (2H, m), 4.54 (1.33H, s), 4.50 (0.67H, s), 4.39 (0.67H, s), 4.35 (1.33H, s), 3.81 (2H, s), 3.79 (1H, s), 3.69 (1H, s), 3.57 (2H, s), 2.52 (1H, s), 2.50 (2H, s), 2.42 (2H, s), 2.41 (1H, s).

Present Compound 3-16

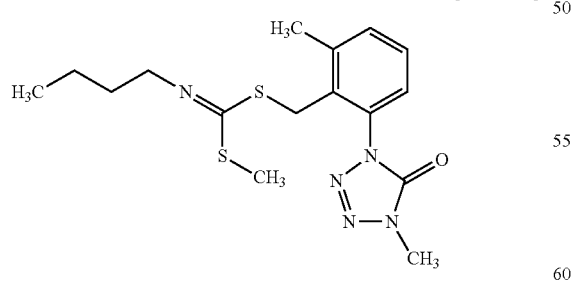

(n-hexane:ethyl acetate=2:1) E/Z mixture, Isomeric ratio 2:1

Present compound 3-16: $^1$H-NMR (CDCl$_3$) δ: 7.34-7.28 (2H, m), 7.21-7.16 (1H, m), 4.33 (0.67H, s), 4.27 (1.33H, s), 3.72 (1H, s), 3.71 (2H, s), 3.37 (1.33H, t, J=6.8 Hz), 3.34 (0.67H, t, J=7.0 Hz), 2.51 (1H, s), 2.46 (2H, s), 2.45 (2H, s), 2.35 (1H, s), 1.66-1.50 (2H, m), 1.44-1.28 (2H, m), 0.94 (2H, t, J=7.4 Hz), 0.89 (1H, t, J=7.4 Hz).

Present Compound 3-17

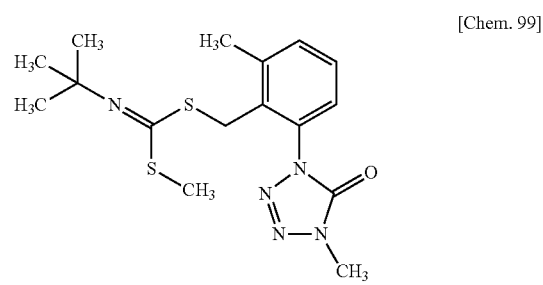 [SMILES: CSC(=NC(C)(C)C)SCc1c(C)cccc1-n1nnn(C)c1=O]

(n-hexane:ethyl acetate=2:1)

Present compound 3-17: $^1$H-NMR (CDCl$_3$) δ: 7.35-7.28 (2H, m), 7.18 (1H, d, J=7.2 Hz), 4.21 (2H, br s), 3.71 (3H, s), 2.45 (6H, br s), 1.33 (9H, br s).

Present Compound 3-18

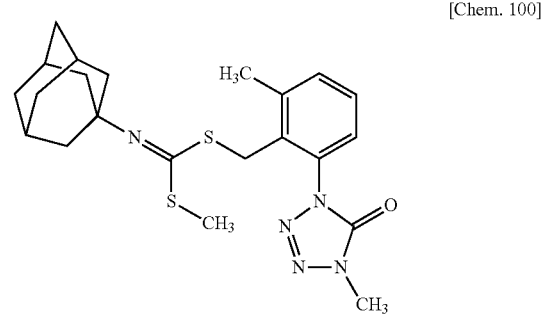 [SMILES: CSC(=NC12CC3CC(CC(C3)C1)C2)SCc1c(C)cccc1-n1nnn(C)c1=O]

(n-hexane:ethyl acetate=3:1)

Present compound 3-18: $^1$H-NMR (CDCl$_3$) δ: 7.34-7.28 (2H, m), 7.17 (1H, dd, J=7.4, 1.5 Hz), 4.25 (2H, br s), 3.72 (3H, s), 2.45 (6H, br s), 2.07 (3H, br s), 1.98 (6H, br s), 1.66 (6H, br s).

Present Compound 3-19

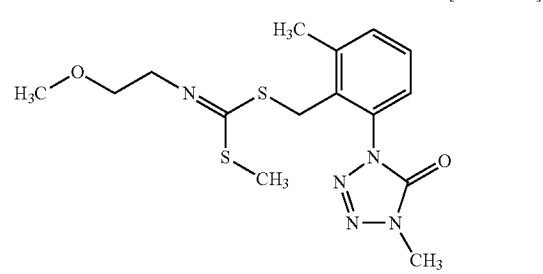

(n-hexane:ethyl acetate=2:1) E/Z mixture, Isomeric ratio 2:1

Present compound 3-19: $^1$H-NMR (CDCl$_3$) δ: 7.34-7.28 (2H, m), 7.20-7.17 (1H, m), 4.34 (0.67H, s), 4.28 (1.33H, s), 3.72 (1H, s), 3.71 (2H, s), 3.67-3.64 (1.33H, m), 3.60-3.50 (2.67H, m), 3.40 (2H, s), 3.36 (1H, s), 2.51 (1H, s), 2.47 (2H, s), 2.45 (2H, s), 2.37 (1H, s).

Present Compound 3-20

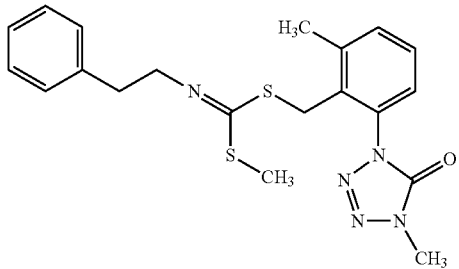
[Chem. 102]

(n-hexane:ethyl acetate=2:1) E/Z mixture, Isomeric ratio 2:1

Present compound 3-20: ¹H-NMR (CDCl₃) δ: 7.34-7.17 (8H, m), 4.30 (0.67H, s), 4.25 (1.33H, s), 3.71 (2H, s), 3.68 (1H, s), 3.64-3.57 (2H, m), 2.95 (1.33H, t, J=7.4 Hz), 2.87 (0.67H, t, J=7.5 Hz), 2.48 (1H, s), 2.44 (2H, s), 2.39 (2H, s), 2.35 (1H, s).

Present Compound 3-21

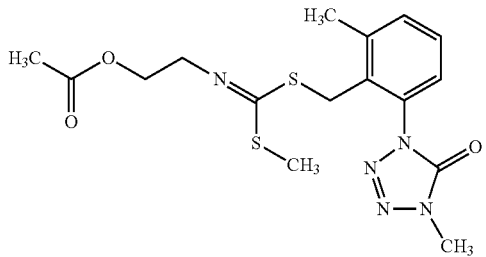
[Chem. 103]

(n-hexane:ethyl acetate=1:1) E/Z mixture, Isomeric ratio 2:1

Present compound 3-21: ¹H-NMR (CDCl₃) δ: 7.35-7.29 (2H, m), 7.22-7.16 (1H, m), 4.35 (0.67H, s), 4.22 (1.33H, s), 3.73 (1H, s), 3.72 (2H, s), 3.70 (2H, s), 3.67 (1H, s), 3.64 (1.33H, t, J=6.9 Hz), 3.59 (0.67H, t, J=6.9 Hz), 2.67 (1.33H, t, J=6.9 Hz), 2.60 (0.67H, t, J=6.9 Hz), 2.51 (1H, s), 2.47 (2H, s), 2.43 (2H, s), 2.32 (1H, s).

Present Compound 3-22

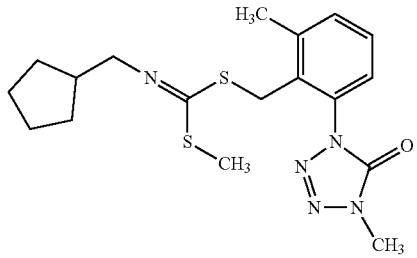
[Chem. 104]

(n-hexane:ethyl acetate=2:1) E/Z mixture, Isomeric ratio 2:1

Present compound 3-22: ¹H-NMR (CDCl₃) δ: 7.34-7.28 (2H, m), 7.21-7.16 (1H, m), 4.33 (0.67H, s), 4.26 (1.33H, s), 3.72 (1H, s), 3.71 (2H, s), 3.31 (1.33H, d, J=6.9 Hz), 3.27 (0.67H, d, J=6.9 Hz), 2.51 (1H, s), 2.46 (2H, s), 2.45 (2H, s), 2.35 (1H, s), 2.25-2.18 (0.67H, m), 2.15-2.08 (0.33H, m), 1.77-1.50 (6H, m), 1.31-1.17 (2H, m).

Present Compound 3-23

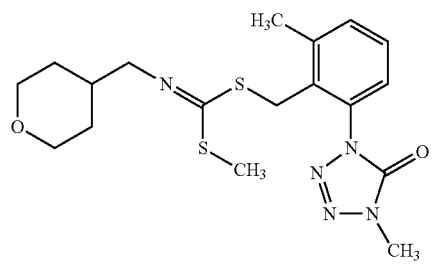
[Chem. 105]

(n-hexane:ethyl acetate=2:1) E/Z mixture, Isomeric ratio 2:1

Present compound 3-23: ¹H-NMR (CDCl₃) δ: 7.36-7.29 (2H, m), 7.21-7.18 (1H, m), 4.34 (0.67H, s), 4.26 (1.33H, s), 4.01-3.94 (2H, m), 3.72 (1H, s), 3.71 (2H, s), 3.45-3.34 (2H, m), 3.24 (1.33H, d, J=6.6 Hz), 3.20 (0.67H, d, J=6.3 Hz), 2.51 (1H, s), 2.47 (2H, s), 2.45 (2H, s), 2.35 (1H, s), 1.95-1.75 (1H, m), 1.69-1.60 (2H, m), 1.44-1.29 (2H, m).

Present Compound 3-24

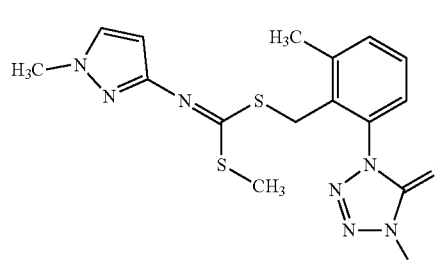
[Chem. 106]

(n-hexane:ethyl acetate=1:1)

Present compound 3-24: ¹H-NMR (CDCl₃) δ: 7.34-7.18 (4H, m), 6.10-6.05 (1H, br m), 4.43 (2H, s), 3.86-3.82 (3H, br m), 3.71-3.64 (3H, br m), 2.50 (6H, s).

Present Compound 3-25

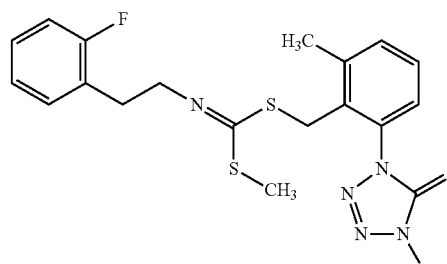
[Chem. 107]

(n-hexane:ethyl acetate=2:1) E/Z mixture, Isomeric ratio 2:1

Present compound 3-25: ¹H-NMR (CDCl₃) δ: 7.34-7.28 (2H, m), 7.24-7.13 (3H, m), 7.08-6.96 (2H, m), 4.30 (0.67H, s), 4.23 (1.33H, s), 3.71 (2H, s), 3.70 (1H, s), 3.61 (1.33H, t, J=7.1 Hz), 3.57 (0.67H, d, J=7.1 Hz), 3.00 (1.33H, t, J=7.1 Hz), 2.93 (0.67H, t, J=7.1 Hz), 2.48 (1H, s), 2.44 (2H, s), 2.38 (2H, s), 2.33 (1H, s).

Present Compound 3-26

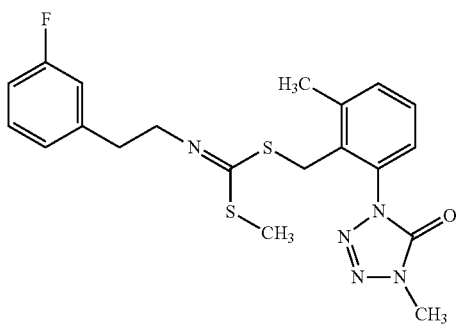

[Chem. 108]

(n-hexane:ethyl acetate=2:1) E/Z mixture, Isomeric ratio 2:1

Present compound 3-26: $^1$H-NMR (CDCl$_3$) δ: 7.34-7.31 (2H, m), 7.21 (2H, ddd, J=16.5, 10.4, 4.4 Hz), 7.02-6.85 (3H, m), 4.31 (0.67H, s), 4.24 (1.33H, s), 3.71 (2H, s), 3.69 (1H, s), 3.61 (1.33H, t, J=7.2 Hz), 3.57 (0.67H, t, J=7.2 Hz), 2.96 (1.33H, t, J=7.2 Hz), 2.87 (0.67H, t, J=7.2 Hz), 2.48 (1H, s), 2.44 (2H, s), 2.38 (2H, s), 2.34 (1H, s).

Present Compound 3-27

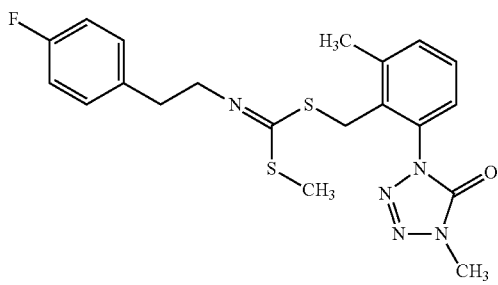

[Chem. 109]

(n-hexane:ethyl acetate=2:1) E/Z mixture, Isomeric ratio 2:1

Present compound 3-27: $^1$H-NMR (CDCl$_3$) δ: 7.34-7.29 (2H, m), 7.21-7.12 (3H, m), 6.99-6.91 (2H, m), 4.31 (0.67H, s), 4.23 (1.33H, s), 3.71 (2H, s), 3.69 (1H, s), 3.58 (1.33H, t, J=7.2 Hz), 3.55 (0.67H, t, J=7.2 Hz), 2.93 (1.33H, t, J=7.2 Hz), 2.84 (0.67H, t, J=7.2 Hz), 2.47 (1H, s), 2.44 (2H, s), 2.39 (2H, s), 2.34 (1H, s).

Present Compound 3-28

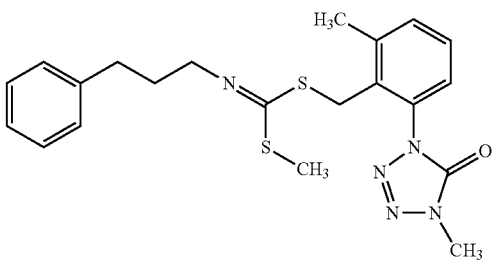

[Chem. 110]

(n-hexane:ethyl acetate=2:1) E/Z mixture, Isomeric ratio 2:1

Present compound 3-28: $^1$H-NMR (CDCl$_3$) δ: 7.36-7.16 (8H, m), 4.34 (0.67H, s), 4.30 (1.33H, s), 3.70 (1H, s), 3.64 (2H, s), 3.39 (1.33H, t, J=6.8 Hz), 3.37 (0.67H, t, J=6.8 Hz), 2.71 (1.33H, t, J=6.8 Hz), 2.66 (0.67H, t, J=6.8 Hz), 2.50 (1H, s), 2.47 (2H, s), 2.46 (2H, s), 2.37 (1H, s), 2.01-1.93 (1.33H, m), 1.92-1.85 (0.67H, m).

Present Compound 3-29

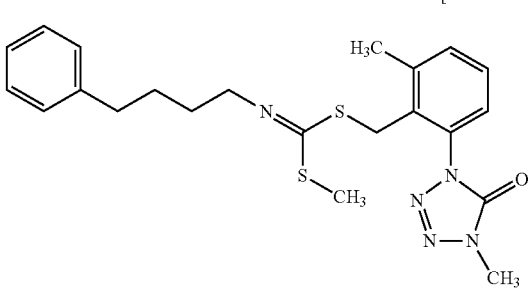

[Chem. 111]

(n-hexane:ethyl acetate=2:1) E/Z mixture, Isomeric ratio 2:1

Present compound 3-29: $^1$H-NMR (CDCl$_3$) δ: 7.36-7.15 (8H, m), 4.33 (0.67H, s), 4.26 (1.33H, s), 3.70 (1H, s), 3.66 (2H, s), 3.39 (1.33H, t, J=6.3 Hz), 3.36 (0.67H, t, J=6.3 Hz), 2.66 (1.33H, t, J=6.3 Hz), 2.61 (0.67H, t, J=6.3 Hz), 2.50 (1H, s), 2.46 (2H, s), 2.43 (2H, s), 2.35 (1H, s), 1.74-1.61 (4H, m).

Present Compound 3-30

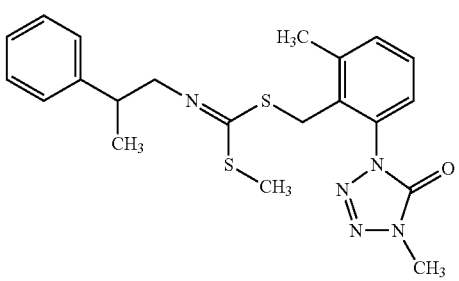

[Chem. 112]

(n-hexane:ethyl acetate=2:1)

Present compound 3-30: $^1$H-NMR (CDCl$_3$) δ: 7.34-7.17 (8H, m), 4.15 (2H, s), 3.62 (3H, s), 3.57 (1H, dd, J=13.6, 6.3 Hz), 3.50 (1H, dd, J=13.6, 7.4 Hz), 3.15-3.06 (1H, m), 2.50 (3H, s), 2.24 (3H, s), 1.34 (3H, d, J=7.1 Hz).

Present Compound 3-31

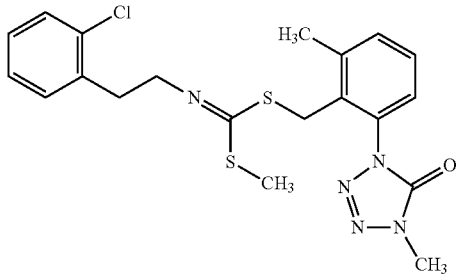

[Chem. 113]

(n-hexane:ethyl acetate=2:1) E/Z mixture, Isomeric ratio 2:1

Present compound 3-31: $^1$H-NMR (CDCl$_3$) δ: 7.35-7.10 (7H, m), 4.30 (0.67H, s), 4.24 (1.33H, s), 3.71 (2H, s), 3.70 (1H, s), 3.64 (1.33H, t, J=7.2 Hz), 3.60 (0.67H, t, J=7.2 Hz), 3.09 (1.33H, t, J=7.2 Hz), 3.02 (0.67H, t, J=7.2 Hz), 2.48 (1H, s), 2.43 (2H, s), 2.39 (2H, s), 2.34 (1H, s).

Present Compound 3-32

[Chem.114]

(n-hexane:ethyl acetate=2:1) E/Z mixture, Isomeric ratio 2:1

Present compound 3-32: $^1$H-NMR (CDCl$_3$) δ: 7.34-7.06 (7H, m), 4.31 (0.67H, s), 4.24 (1.33H, s), 3.71 (2H, s), 3.69 (1H, s), 3.60 (1.33H, t, J=7.1 Hz), 3.55 (0.67H, t, J=7.1 Hz), 2.94 (1.33H, t, J=7.1 Hz), 2.85 (0.67H, t, J=7.0 Hz), 2.48 (1H, s), 2.45 (2H, s), 2.39 (2H, s), 2.35 (1H, s).

Present Compound 3-33

[Chem.115]

(n-hexane:ethyl acetate=2:1) E/Z mixture, Isomeric ratio 2:1

Present compound 3-33: $^1$H-NMR (CDCl$_3$) δ: 7.38-7.11 (7H, m), 4.31 (0.67H, s), 4.22 (1.33H, s), 3.69 (2H, s), 3.69 (1H, s), 3.58 (1.33H, t, J=7.1 Hz), 3.55 (0.67H, t, J=7.1 Hz), 2.93 (1.33H, t, J=7.1 Hz), 2.84 (0.67H, t, J=7.1 Hz), 2.47 (1H, s), 2.44 (2H, s), 2.38 (2H, s), 2.34 (1H, s).

Present Compound 3-34

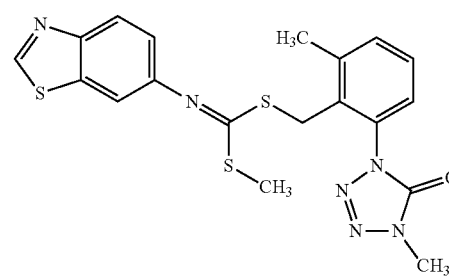

[Chem.116]

(n-hexane:ethyl acetate=1:1)

Present compound 3-34: $^1$H-NMR (CDCl$_3$) δ: 8.89 (1H, s), 8.06 (1H, d, J=8.2 Hz), 7.37-7.34 (3H, m), 7.21 (1H, d, J=6.0 Hz), 7.01 (1H, dd, J=8.7, 1.8 Hz), 4.49 (2H, br s), 3.45 (3H, br s), 2.51 (3H, br s), 2.45 (3H, br s).

Present Compound 3-35

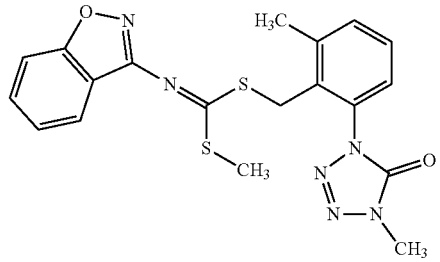

[Chem.117]

(n-hexane:ethyl acetate=1:1)

Present compound 3-35: $^1$H-NMR (CDCl$_3$) δ: 7.89 (1H, dd, J=7.8, 1.8 Hz), 7.39-7.32 (3H, m), 7.24 (1H, dd, J=7.3, 1.8 Hz), 7.06 (1H, td, J=7.6, 1.1 Hz), 6.98 (1H, dd, J=8.2, 0.9 Hz), 5.21 (2H, s), 3.58 (3H, s), 2.67 (3H, s), 2.51 (3H, s).

Present Compound 3-36

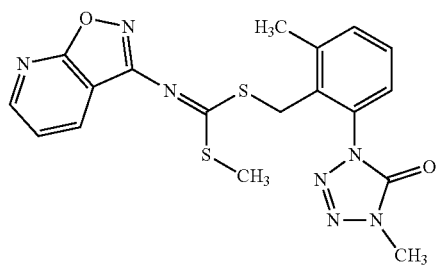

[Chem.118]

(n-hexane:ethyl acetate=1:9)

Present compound 3-36: $^1$H-NMR (CDCl$_3$) δ: 8.37 (1H, dd, J=7.1, 2.3 Hz), 7.49-7.42 (2H, m), 7.31 (1H, dd, J=7.6, 1.2 Hz), 7.24 (1H, dd, J=6.8, 2.3 Hz), 6.21 (1H, t, J=7.0 Hz), 5.21 (2H, s), 3.69 (3H, s), 2.77 (3H, s), 2.30 (3H, s).

Production Example 4

To mixture of 3-trifluoromethylaniline 0.87 g and dimethylsulfoxide 18 mL were added 20 N aqueous sodium hydroxide solution 0.4 mL and carbon disulfide 1.02 g successively at room temperature, and the mixture was stirred at room temperature for 1 hour. The reaction solutions were cooled to 0° C., and thereto was added iodoethane 1.52 g, and the mixture was stirred at room temperature for 1 hour. To the reaction solutions was added water, and the mixture was extracted with chloroform. The resulting organic layer was dried over anhydrous magnesium sulfate and concentrated under reduced pressure to obtain residues. To mixture of the resulting residues, 1-{2-(bromomethyl)-3-methylphenyl}-4-methyl-4,5-dihydrotetrazol-5-one 1.69 g, and THF 30 mL was added sodium hydride (oily, 60%) 0.39 g at 0° C., and the mixture was stirred at room temperature for 2 hours. To the reaction solutions was added water, and the mixture was extracted with ethyl acetate. The resulting organic layer was washed with saturated brine, dried over anhydrous magnesium sulfate and concentrated under reduced pressure. The resulting residues were subjected to silica gel column chromatography (n-hexane:ethyl acetate: 2:1) to obtain 1.92 g of the Present compound 4-1 as below-mentioned.

Present Compound 4-1

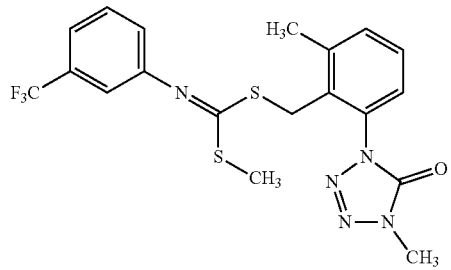

[Chem.119]

Present compound 4-1: $^1$H-NMR (CDCl$_3$) δ: 7.42-7.35 (4H, m), 7.23-7.21 (1H, m), 7.08 (1H, s), 6.99 (1H, d, J=7.6 Hz), 4.45 (2H, s), 3.52 (3H, s), 2.49 (3H, s), 2.45 (3H, s).

The compounds that were prepared according to the similar method to those described in Production example 4, and physical properties thereof are indicated below. Also, the solvents that were used for silica gel column chromatography were indicated in parenthesis below a structural formula. Further, when a compound is a mixture of isomers, the isomeric ratio thereof is also indicated below the compound.

Present Compound 4-2

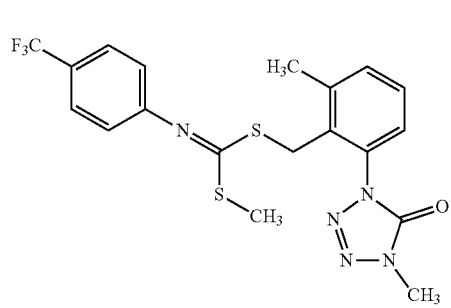

[Chem.120]

(n-hexane:ethyl acetate=2:1)

Present compound 4-2: $^1$H-NMR (CDCl$_3$) δ: 7.56 (2H, d, J=8.4 Hz), 7.35-7.34 (2H, m), 7.24-7.22 (1H, m), 6.90 (2H, d, J=8.4 Hz), 4.42 (2H, s), 3.53 (3H, s), 2.49 (3H, s), 2.45 (3H, s).

Present Compound 4-3

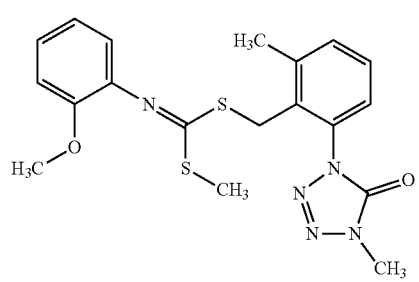

[Chem.121]

(n-hexane:ethyl acetate=2:1)

Present compound 4-3: $^1$H-NMR (CDCl$_3$) δ: 7.34-7.32 (2H, m), 7.21 (2H, s), 6.64 (1H, d, J=6.8 Hz), 6.43-6.40 (1H, m), 6.39-6.38 (1H, m), 4.45 (2H, s), 3.80 (3H, s), 3.49 (3H, s), 2.49 (3H, s), 2.42 (3H, s).

Present Compound 4-4

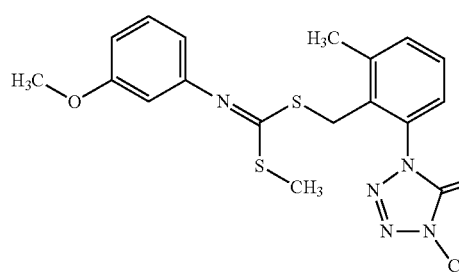

[Chem.122]

(n-hexane:ethyl acetate=2:1)

Present compound 4-4: $^1$H-NMR (CDCl$_3$) δ: 7.38-7.36 (1H, m), 7.34-7.32 (1H, m), 7.24-7.19 (2H, m), 6.64 (1H, d, J=7.2 Hz), 6.43-6.41 (1H, m), 6.40-6.38 (1H, m), 4.42 (2H, s), 3.80 (3H, s), 3.49 (3H, s), 2.49 (3H, s), 2.43 (3H, s).

Present Compound 4-5

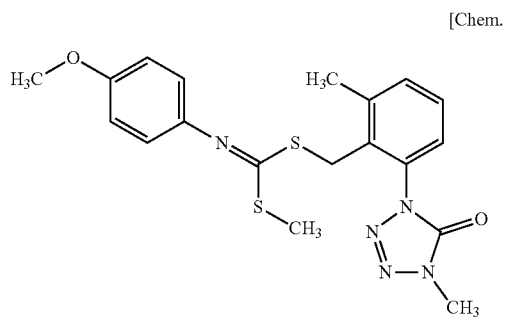

[Chem.123]

(n-hexane:ethyl acetate=2:1)

Present compound 4-5: ¹H-NMR (CDCl₃) δ: 7.35-7.31 (2H, m), 7.23-7.20 (1H, m), 6.88 (2H, d, J=8.8 Hz), 6.79 (2H, d, J=8.8 Hz), 4.48 (2H, s), 3.80 (3H, s), 3.46 (3H, s), 2.50 (3H, s), 2.40 (3H, s).

Present Compound 4-6

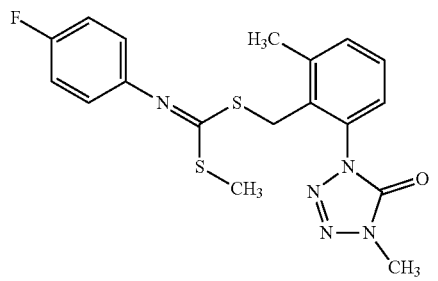

[Chem.124]

(n-hexane:ethyl acetate=2:1)

Present compound 4-6: ¹H-NMR (CDCl₃) δ: 7.35-7.32 (2H, m), 7.21 (1H, d, J=9.3 Hz), 7.04-6.99 (2H, m), 6.80-6.77 (2H, m), 4.47 (2H, s), 3.48 (3H, s), 2.50 (3H, s), 2.42 (3H, s).

Present Compound 4-7

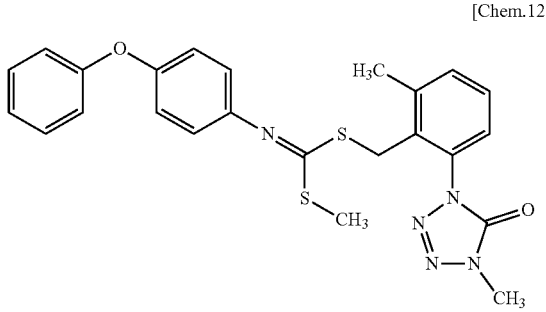

[Chem.125]

(n-hexane:ethyl acetate=2:1)

Present compound 4-7: ¹H-NMR (CDCl₃) δ: 7.34-7.30 (4H, m), 7.22-7.20 (1H, m), 7.09-7.06 (1H, m), 7.00-6.98 (4H, m), 6.82 (2H, d, J=8.8 Hz), 4.47 (2H, s), 3.52 (3H, s), 2.50 (3H, s), 2.43 (3H, s).

Present Compound 4-8

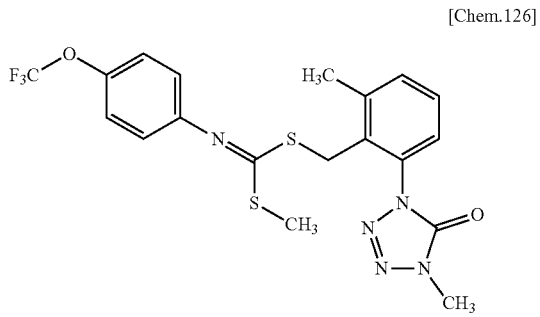 [SMILES: CSC(=Nc1ccc(OC(F)(F)F)cc1)SCc1c(C)cccc1-n1nnn(C)c1=O]

[Chem.126]

(n-hexane:ethyl acetate=2:1)

Present compound 4-8: ¹H-NMR (CDCl₃) δ: 7.35-7.33 (2H, m), 7.23-7.15 (3H, m), 6.83 (2H, d, J=8.6 Hz), 4.46 (2H, s), 3.46 (3H, s), 2.49 (3H, s), 2.43 (3H, s).

Present Compound 4-9

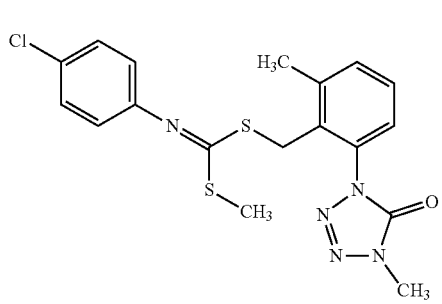

[Chem.127]

(n-hexane:ethyl acetate=2:1)

Present compound 4-9: ¹H-NMR (CDCl₃) δ: 7.35-7.29 (3H, m), 7.23-7.21 (2H, m), 6.76 (2H, d, J=8.6 Hz), 4.45 (2H, s), 3.49 (3H, s), 2.48 (3H, s), 2.43 (3H, s).

Present Compound 4-10

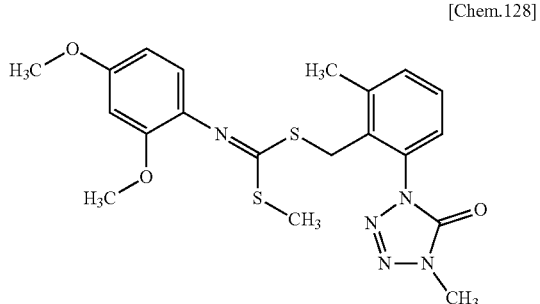

[Chem.128]

(n-hexane:ethyl acetate=2:1)

Present compound 4-10: ¹H-NMR (CDCl₃) δ: 7.33-7.30 (3H, m), 7.20 (1H, s), 6.67 (1H, d, J=8.4 Hz), 6.50 (1H, s), 4.50 (2H, s), 3.79 (3H, s), 3.78 (3H, s), 3.59 (3H, s), 2.51 (3H, s), 2.41 (3H, s).

Present Compound 4-11

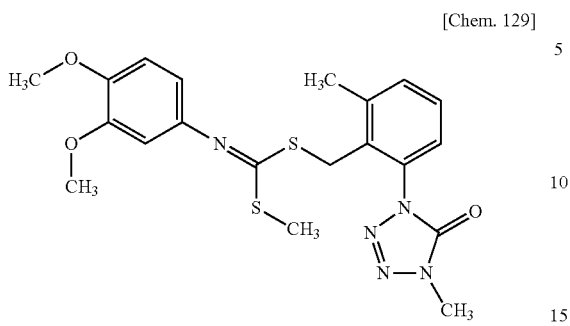

(n-hexane:ethyl acetate=2:1)

Present compound 4-11: $^1$H-NMR (CDCl$_3$) δ: 7.35-7.33 (2H, m), 7.22-7.20 (1H, m), 6.83 (1H, d, J=9.1 Hz), 6.45 (1H, d, J=2.3 Hz), 6.41-6.39 (1H, m), 4.49 (2H, s), 3.87 (6H, s), 3.44 (3H, s), 2.51 (3H, s), 2.41 (3H, s).

Present Compound 4-12

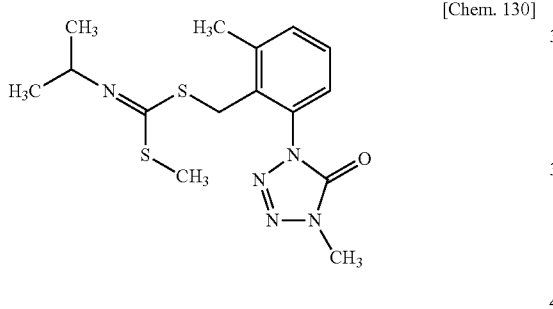

(n-hexane:ethyl acetate=2:1)

Present compound 4-12: $^1$H-NMR (CDCl$_3$) δ: 7.34-7.28 (2H, m), 7.21-7.17 (1H, m), 4.28 (2H, s), 3.86 (1H, t, J=6.2 Hz), 3.71 (3H, s), 2.46 (3H, s), 2.45 (3H, s), 1.13 (6H, d, J=6.2 Hz).

Production Example 5

To mixture of 1 g of the intermediate compound 1-1 and DMF 7 mL was added sodium hydride (oily, 60%) 0.32 g at 0° C. under nitrogen atmosphere, and the mixture were stirred at room temperature for 1 hour. The reaction solutions were cooled to 0° C. and thereto was then added 2-phenylethyl bromide 4.0 g, and the mixture were stirred at room temperatures for 2 hours, and then at 50° C. for 8 hours. The reaction solutions were cooled to room temperature, and thereto was then added water, and the mixture was extracted with ethyl acetate. The resulting organic layer was washed with water, and saturated brine successively, and dried over sodium sulfate. The solutions were concentrated under reduced pressure and the resulting residues were subjected to silica gel column chromatography (n-hexane:ethyl acetate=3:7) to give 2.51 g of the Present compound 5-1 as below-mentioned.

Present Compound 5-1

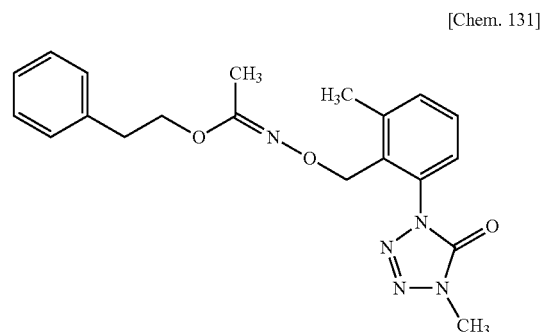 [SMILES: CC(=NOCc1c(C)cccc1-n1nnn(C)c1=O)OCCc1ccccc1]

Present compound 5-1: $^1$H-NMR (CDCl$_3$) δ: 7.48-7.41 (2H, m), 7.30-7.14 (6H, m), 4.89 (2H, s), 3.67 (3H, s), 3.64 (2H, br s), 2.79 (2H, t, J=7.9 Hz), 2.56 (3H, s), 1.92 (3H, br s).

The compounds that were prepared according to the similar method to those described in Production example 5 and physical properties thereof are indicated below. Also, the solvents that were used for silica gel column chromatography were indicated in parenthesis below a structural formula.

Present Compound 5-2

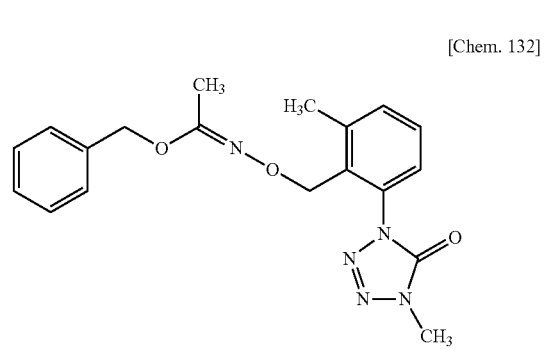 [SMILES: CC(=NOCc1c(C)cccc1-n1nnn(C)c1=O)OCc1ccccc1]

(n-hexane:ethyl acetate=3:7)

Present compound 5-2: $^1$H-NMR (CDCl$_3$) δ: 7.42 (1H, t, J=7.8 Hz), 7.35 (1H, d, J=7.8 Hz), 7.31-7.18 (6H, m), 4.90 (2H, s), 4.68 (2H, s), 3.64 (3H, s), 2.38 (3H, s), 2.01 (3H, s).

Present Compound 5-3

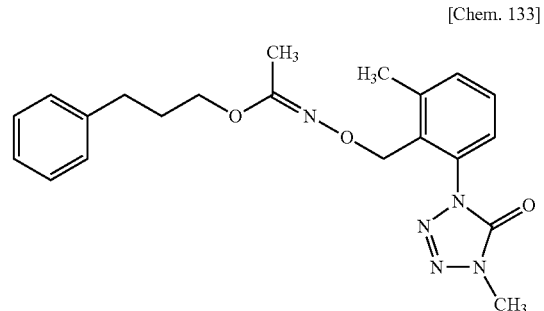

(n-hexane:ethyl acetate=3:7)

Present compound 5-3: $^1$H-NMR (CDCl$_3$) δ: 7.45-7.37 (2H, m), 7.28-7.24 (3H, m), 7.19-7.13 (3H, m), 4.87 (2H, s), 3.68 (3H, s), 3.48 (2H, br s), 2.55 (2H, t, J=7.8 Hz), 2.47 (3H, s), 1.94 (3H, s), 1.87-1.80 (2H, m).

Present Compound 5-4

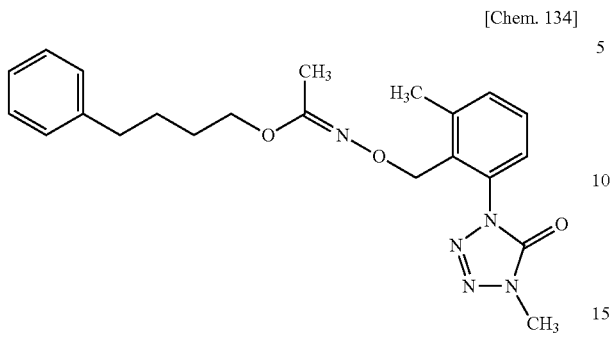

[Chem. 134]

(n-hexane:ethyl acetate=3:7)

Present compound 5-4: $^1$H-NMR (CDCl$_3$) δ: 7.46-7.38 (2H, m), 7.28-7.24 (3H, m), 7.19-7.13 (3H, m), 4.88 (2H, s), 3.70 (3H, s), 3.46 (2H, br s), 2.59-2.56 (2H, m), 2.51 (3H, s), 1.96 (3H, s), 1.56-1.52 (4H, m).

Present Compound 5-5

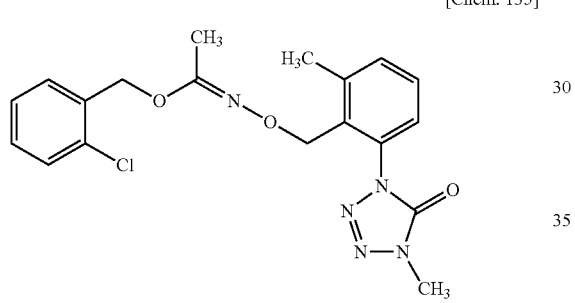

[Chem. 135]

(n-hexane:ethyl acetate=3:7)

Present compound 5-5: $^1$H-NMR (CDCl$_3$) δ: 7.41 (1H, t, J=7.7 Hz), 7.36-7.33 (2H, m), 7.23-7.18 (3H, m), 7.14-7.12 (1H, m), 4.94 (2H, s), 4.83 (2H, br s), 3.61 (3H, s), 2.37 (3H, s), 2.05 (3H, s).

Present Compound 5-6

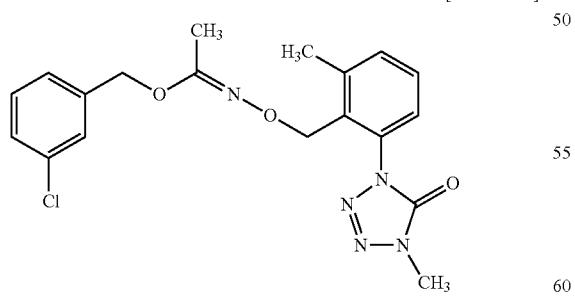

[Chem. 136]

(n-hexane:ethyl acetate=3:7)

Present compound 5-6: $^1$H-NMR (CDCl$_3$) δ: 7.42 (1H, t, J=7.8 Hz), 7.36-7.33 (1H, m), 7.27-7.15 (4H, m), 7.07 (1H, dt, J=5.9, 2.0 Hz), 4.92 (2H, s), 4.62 (2H, s), 3.67 (3H, s), 2.39 (3H, s), 2.04 (3H, s).

Present Compound 5-7

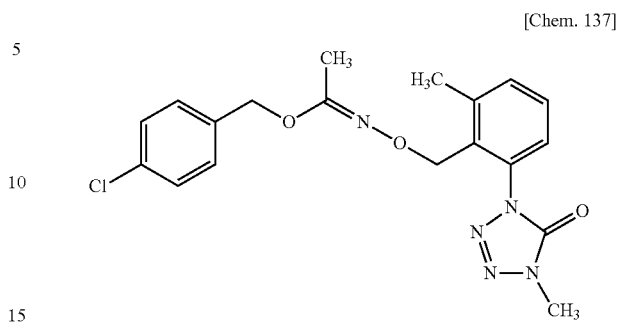

[Chem. 137]

(n-hexane:ethyl acetate=3:7)

Present compound 5-7: $^1$H-NMR (CDCl$_3$) δ: 7.43 (1H, t, J=7.7 Hz), 7.35 (1H, d, J=7.5 Hz), 7.26-7.23 (3H, m), 7.12 (2H, d, J=8.2 Hz), 4.91 (2H, s), 4.61 (2H, s), 3.66 (3H, s), 2.39 (3H, s), 2.02 (3H, s).

Present Compound 5-8

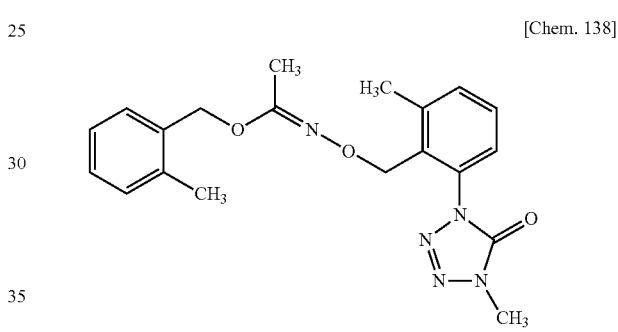

[Chem. 138]

(n-hexane:ethyl acetate=3:7)

Present compound 5-8: $^1$H-NMR (CDCl$_3$) δ: 7.40 (1H, t, J=7.8 Hz), 7.32 (1H, d, J=7.2 Hz), 7.22-7.11 (4H, m), 7.06 (1H, d, J=7.2 Hz), 4.89 (2H, s), 4.71 (2H, br s), 3.57 (3H, s), 2.30 (3H, s), 2.26 (3H, s), 2.03 (3H, s).

Present Compound 5-9

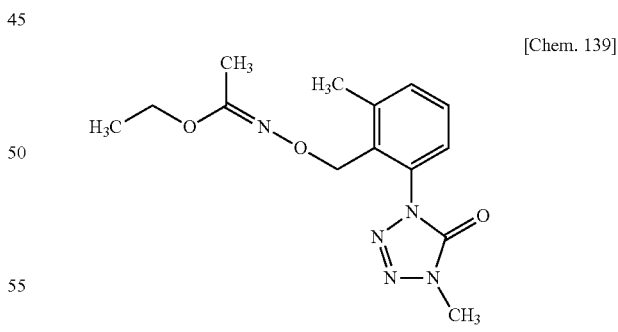

[Chem. 139]

(n-hexane:ethyl acetate=2:8)

Present compound 5-9: $^1$H-NMR (CDCl$_3$) δ: 7.38-7.33 (2H, m), 7.24-7.18 (1H, m), 4.47 (2H, s), 3.72 (3H, s), 3.37 (2H, q, J=7.0 Hz), 2.48 (3H, s), 1.60 (3H, s), 1.11 (3H, t, J=7.0 Hz).

Production Example 6

To mixture of 0.5 g of the intermediate compound 2-3 and DMF 4 mL was added to sodium hydride (oily, 60%) 0.1 g at 0° C. under nitrogen atmosphere, and the mixture was stirred at room temperature for 1 hour. The reaction solutions were cooled to 0° C., and thereto was the added 1-chloro-2-(3-bromopropyl)benzene 1.5 g, and the mixture was stirred at room temperature for 3 hours. To the reaction solutions was added water, the mixture was extracted with ethyl acetate. The resulting organic layer was washed with water, and saturated brine successively, and dried over sodium sulfate. The reactions were concentrated under reduced pressure to obtain the residues, and the resulting residues were subjected to silica gel column chromatography (n-hexane:ethyl acetate=6:4) to obtain 2.5 g of the Present compound 6-1.

Present Compound 6-1

[Chem. 140]

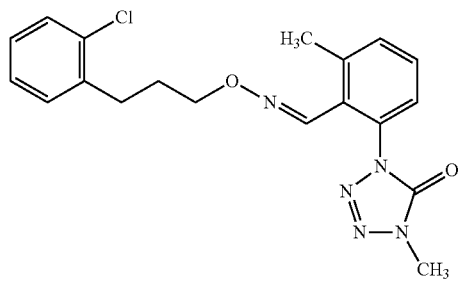

Present compound 6-1: $^1$H-NMR (CDCl$_3$) δ: 8.22 (1H, s), 7.42-7.27 (4H, m), 7.24-7.12 (3H, m), 4.03 (2H, t, J=6.6 Hz), 3.61 (3H, s), 2.79 (2H, t, J=7.7 Hz), 2.50 (3H, s), 1.97-1.90 (2H, m).

The compound that were prepared according to the similar method to those described in Production example 6 and physical properties thereof were indicated below. Also, the solvents that were used for silica gel column chromatography were indicated in parenthesis below a structural formula.

Present Compound 6-2

[Chem. 141]

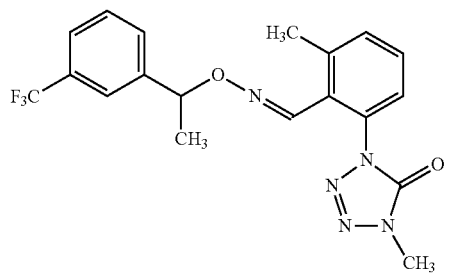

(n-hexane:ethyl acetate 6:4)

Present compound 6-2: $^1$H-NMR (CDCl$_3$) δ: 8.26 (1H, s), 7.56-7.45 (4H, m), 7.40-7.34 (2H, m), 7.24 (1H, dd, J=7.6, 1.7 Hz), 5.19 (1H, q, J=6.7 Hz), 3.56 (3H, s), 2.39 (3H, s), 1.53 (3H, d, J=6.7 Hz).

Present Compound 6-3

[Chem. 142]

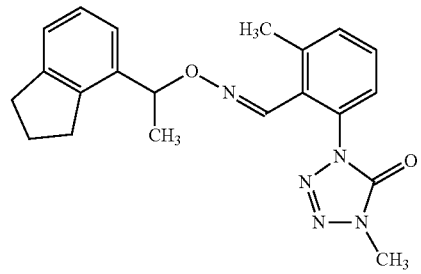

(n-hexane:ethyl acetate=6:4)

Present compound 6-3: $^1$H-NMR (CDCl$_3$) δ: 8.24 (1H, s), 7.39-7.33 (2H, m), 7.24 (1H, dd, J=7.2, 2.0 Hz), 7.17-7.11 (3H, m), 5.23 (1H, q, J=6.6 Hz), 3.55 (3H, s), 2.99-2.81 (4H, m), 2.40 (3H, s), 2.11-2.04 (2H, m), 1.50 (3H, d, J=6.6 Hz).

Present Compound 6-4

[Chem. 143]

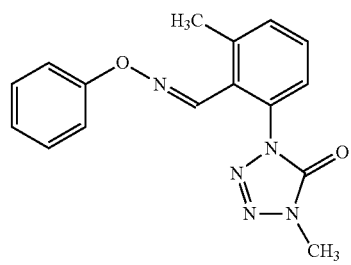

(n-hexane:ethyl acetate=6:4)

Present compound 6-4: $^1$H-NMR (CDCl$_3$) δ: 8.56 (1H, s), 7.50-7.26 (5H, m), 7.06-7.01 (3H, m), 3.55 (3H, s), 2.58 (3H, s).

Present Compound 6-5

[Chem. 144]

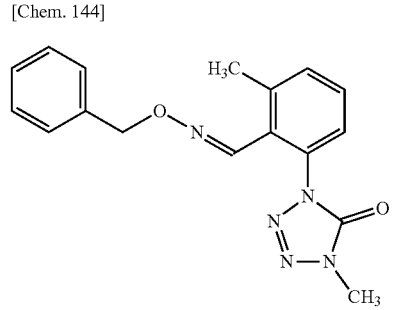 [SMILES: Cc1cccc(-n2nnn(C)c2=O)c1C=NOCc1ccccc1]

(n-hexane:ethyl acetate=6:4)

Present compound 6-5: $^1$H-NMR (CDCl$_3$) δ: 8.26 (1H, s), 7.41-7.28 (8H, m), 5.04 (2H, s), 3.55 (3H, s), 2.45 (3H, s).

Present Compound 6-6

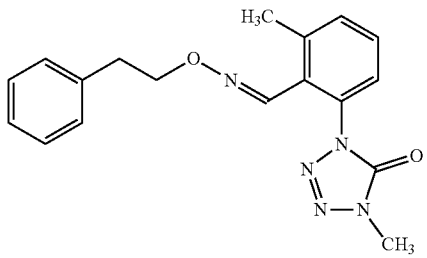

Present compound 6-6: ¹H-NMR (CDCl₃) δ: 8.21 (1H, s), 7.43-7.37 (2H, m), 7.32-7.29 (3H, m), 7.24-7.20 (3H, m), 4.20 (2H, t, J=7.2 Hz), 3.64 (3H, s), 2.91 (2H, t, J=7.2 Hz), 2.49 (3H, s).

Present Compound 6-7

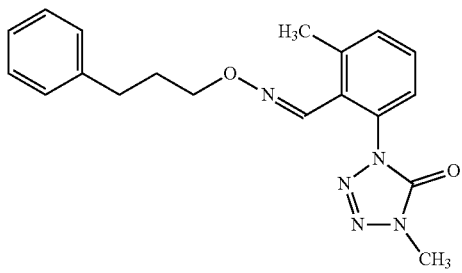

(n-hexane:ethyl acetate=6:4)

Present compound 6-7: ¹H-NMR (CDCl₃) δ: 8.21 (1H, s), 7.42-7.36 (2H, m), 7.31-7.27 (3H, m), 7.20-7.17 (3H, m), 4.00 (2H, t, J=6.6 Hz), 3.56 (3H, s), 2.67 (2H, t, J=7.7 Hz), 2.49 (3H, s), 1.96-1.88 (2H, m).

Present Compound 6-8

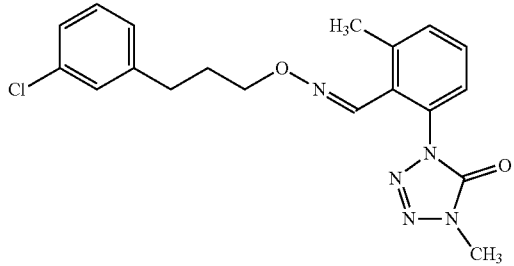

(n-hexane:ethyl acetate=6:4)

Present compound 6-8: ¹H-NMR (CDCl₃) δ: 8.21 (1H, s), 7.42-7.37 (2H, m), 7.29 (1H, dd, J=6.7, 2.6 Hz), 7.24-7.15 (3H, m), 7.07 (1H, d, J=7.5 Hz), 4.00 (2H, t, J=6.5 Hz), 3.60 (3H, s), 2.65 (2H, t, J=7.7 Hz), 2.49 (3H, s), 1.95-1.87 (2H, m).

Present Compound 6-9

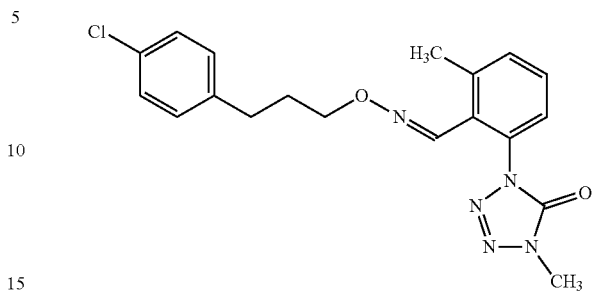

(n-hexane:ethyl acetate=6:4)

Present compound 6-9: ¹H-NMR (CDCl₃) δ: 8.20 (1H, s), 7.42-7.37 (2H, m), 7.27 (2H, tt, J=9.4, 2.7 Hz), 7.13-7.11 (3H, m), 3.98 (2H, t, J=6.5 Hz), 3.59 (3H, s), 2.64 (2H, t, J=7.8 Hz), 2.49 (3H, s), 1.93-1.84 (2H, m).

Present Compound 6-10

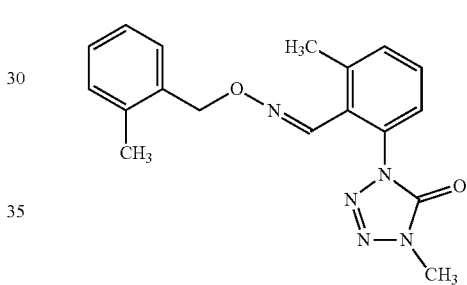

(n-hexane:ethyl acetate=6:4)

Present compound 6-10: ¹H-NMR (CDCl₃) δ: 8.25 (1H, s), 7.41-7.35 (2H, m), 7.28-7.26 (2H, m), 7.24-7.17 (3H, m), 5.06 (2H, s), 3.57 (3H, s), 2.45 (3H, s), 2.34 (3H, s).

Present Compound 6-11

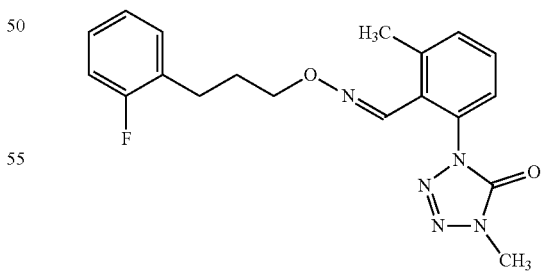

(n-hexane:ethyl acetate=6:4)

Present compound 6-11: ¹H-NMR (CDCl₃) δ: 8.20 (1H, s), 7.42-7.36 (2H, m), 7.28 (1H, dd, J=6.7, 2.4 Hz), 7.22-7.15 (2H, m), 7.08-6.98 (2H, m), 4.01 (2H, t, J=6.6 Hz), 3.61 (3H, s), 2.70 (2H, t, J=7.6 Hz), 2.49 (3H, s), 1.96-1.88 (2H, m).

Present Compound 6-12

[Chem. 151]

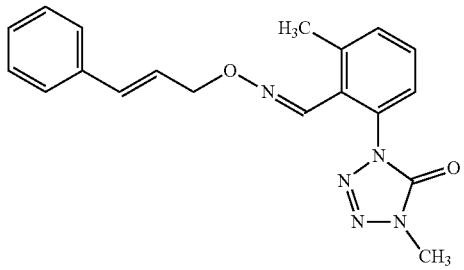

(n-hexane:ethyl acetate=6:4)

Present compound 6-12: $^{1}$H-NMR (CDCl$_{3}$) δ: 8.26 (1H, s), 7.42-7.14 (8H, m), 6.61 (1H, d, J=15.9 Hz), 6.31 (1H, dt, J=15.9, 6.3 Hz), 4.66 (2H, dd, J=6.3, 1.4 Hz), 3.55 (3H, s), 2.49 (3H, s).

Production Example 7

A mixture of N-benzyloxyacetamide 5.0 g, 1-{2-(bromomethyl)-3-methylphenyl}-4-methyl-4,5-dihydrotetrazol-5-one 8.5 g, potassium carbonate 5.0 g, N,N-dimethyl-4-aminopyridine 0.1 g and acetonitrile 30 mL was stirred under reflux for 9 hours. The mixture was cooled to room temperature, and thereto was then added water, and the mixture was extracted with ethyl acetate. The resulting mixture was washed with water and saturated brine successively, and dried over sodium sulfate. The resulting solutions were concentrated under reduced pressure, and the resulting residues were recrystallized, and the crystals were filtered. The filtrates were concentrated under reduced pressure to obtain the residues. The resulting residues were subjected to silica gel column chromatography (n-hexane:ethyl acetate=4:6) to give 1.7 g of the Present compound 7-1 as below mentioned.

Present Compound 7-1

[Chem. 152]

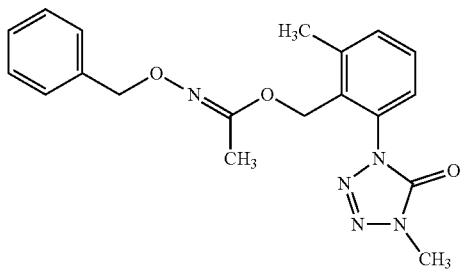

(n-hexane:ethyl acetate=6:4)

Present compound 7-1: $^{1}$H-NMR (CDCl$_{3}$) δ: 7.41-7.25 (8H, m), 5.22 (2H, s), 4.90 (2H, s), 3.60 (3H, s), 2.48 (3H, s), 1.84 (3H, s).

The compound that were prepared according to the similar method to those described in Production example 1 and physical properties thereof are indicated below. Also, the solvents that were used for silica gel column chromatography were indicated in parenthesis below a structural formula.

Present Compound A-2

[Chem. 153]

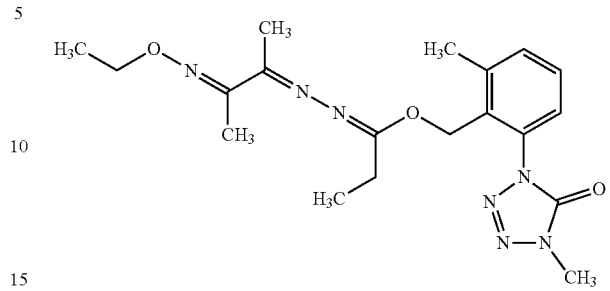

(n-hexane:ethyl acetate=1:1)

Present compound A-2: $^{1}$H-NMR (CDCl$_{3}$) δ: 7.41-7.36 (2H, m), 7.27-7.24 (1H, m), 5.21 (2H, s), 4.22 (2H, q, J=7.1 Hz), 3.68 (3H, s), 2.50 (3H, s), 2.45 (2H, q, J=7.6 Hz), 2.08 (3H, s), 2.05 (3H, s), 1.31 (3H, t, J=7.1 Hz), 1.02 (3H, t, J=7.6 Hz).

Present Compound A-3

[Chem. 154]

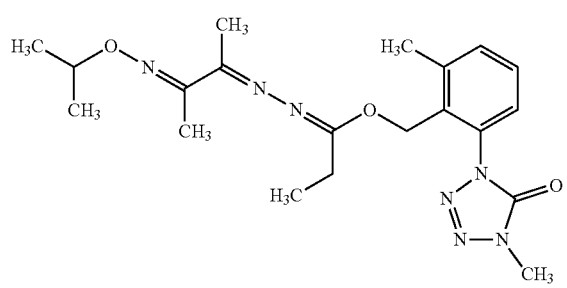

(n-hexane:ethyl acetate=3:2)

Present compound A-3: $^{1}$H-NMR (CDCl$_{3}$) δ: 7.41-7.36 (2H, m), 7.26-7.24 (1H, m), 5.21 (2H, s), 4.42 (1H, sept, J=6.2 Hz), 3.68 (3H, s), 2.50 (3H, s), 2.45 (2H, q, J=7.6 Hz), 2.07 (3H, s), 2.05 (3H, s), 1.29 (6H, d, J=6.2 Hz), 1.02 (3H, t, J=7.7 Hz).

Production Example B

To mixture of 10.0 g of the intermediate compound AA-1 and ethanol 140 mL was added 1 N aqueous sodium hydroxide solution 56 mL and hydroxylamine hydrochloride salt 2.9 g, and the mixture was stirred at room temperature for 1 hour. The mixture was concentrated under reduced pressure, and thereto were added ethyl acetate and water, and the mixture was extracted with ethyl acetate. The resulting organic layer was washed with water and saturated brine, dried over anhydrous magnesium sulfate, and concentrated under reduced pressure. The resulting residues were recrystallized from hexane and ethyl acetate to give 7.9 g of the Present compound B-1.

Present Compound B-1

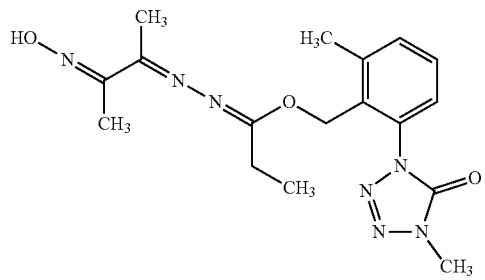
[Chem. 154]

Present compound B-1: $^1$H-NMR (CDCl$_3$) δ: 7.42-7.37 (2H, m), 7.26-7.24 (1H, m), 5.21 (2H, s), 3.68 (3H, s), 2.50-2.44 (5H, m), 2.13 (3H, s), 2.05 (3H, s), 1.03 (3H, t, J=7.6 Hz).

Production Example C

To mixture of 0.30 g of the Present compound B-1 and DMF 1.6 mL was added potassium carbonate 0.22 g and benzyl bromide 0.21 g, and the mixture was stirred at room temperature for 1.5 hours. The resulting mixture was subjected to silica gel column chromatography to give 0.39 g of the Present compound C-1.

Present Compound C-1

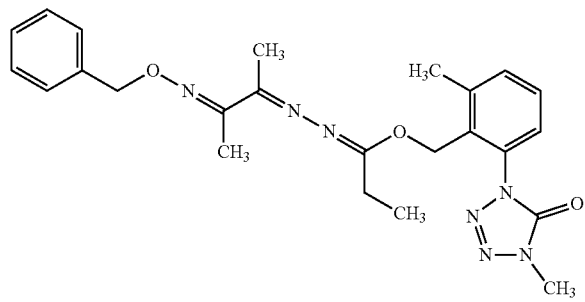
[Chem. 156]

(n-hexane:ethyl acetate=2:1)
Present compound C-1: $^1$H-NMR (CDCl$_3$) δ: 7.41-7.29 (7H, m), 7.25-7.23 (1H, m), 5.21 (2H, s), 5.20 (2H, s), 3.67 (3H, s), 2.49 (3H, s), 2.44 (2H, q, J=7.6 Hz), 2.11 (3H, s), 2.04 (3H, s), 1.01 (3H, t, J=7.6 Hz).

The compounds that were prepared according to the similar method to those described in Production example C and physical properties thereof are indicated below. When the physical properties of the compound was LCMS, the retention time (RT/min) and measured molecular ion values (M+H)$^+$ are indicated below.

LCMS Measurement Condition
Spectra were measured with LCMS-2020 (SHIMADZU).
Column types: L-column2 ODS (4.6×35 mm), column temperate: 40° C., Solvent gradient: flows with [Water 90% (containing 0.1% HCOOH)] and [acetonitrile 10% (containing 0.1% HCOOH)] for 2 minutes, then flows with [Acetonitrile 100% (containing 0.1% HCCOH)] for 2 minutes. Flow rate: 2.0 mL/min, Detection wavelength: 190-400 nm. Also, the solvents that were used for silica gel column chromatography were indicated in parenthesis below a structural formula.

Present Compound C-2

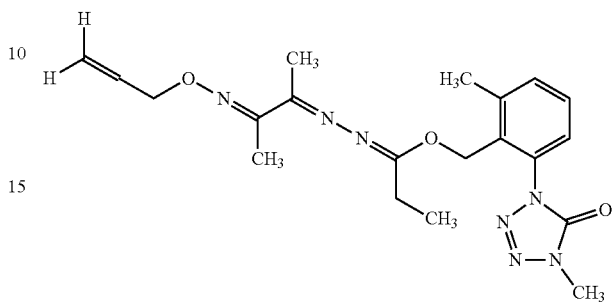
[Chem. 157]

(n-hexane:ethyl acetate=1:1)
Present compound C-2: $^1$H-NMR (CDCl$_3$) δ: 7.41-7.36 (2H, m), 7.29-7.24 (1H, m), 6.09-5.99 (1H, m), 5.32 (1H, dq, J=17.2, 1.6 Hz), 5.23 (1H, dq, J=10.4, 1.1 Hz), 5.21 (2H, s), 4.68 (2H, dt, J=5.7, 1.5 Hz), 3.68 (3H, s), 2.49 (3H, s), 2.45 (2H, q, J=7.6 Hz), 2.10 (3H, s), 2.04 (3H, s), 1.02 (3H, t, J=7.6 Hz).

Present Compound C-3

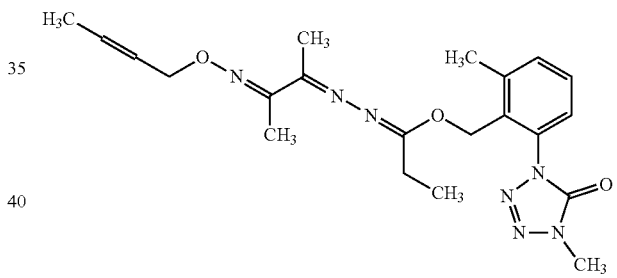
[Chem. 158]

(n-hexane:ethyl acetate=1:1)
Present compound C-3: $^1$H-NMR (CDCl$_3$) δ: 7.41-7.36 (2H, m), 7.27-7.24 (1H, m), 5.85-5.67 (2H, m), 5.20 (2H, s), 4.76-4.59 (2H, m), 3.68 (3H, s), 2.49 (3H, s), 2.44 (2H, q, J=7.6 Hz), 2.08 (3H, s), 2.05 (3H, s), 1.76-1.73 (3H, m), 1.01 (3H, t, J=7.6 Hz).

Present Compound C-4

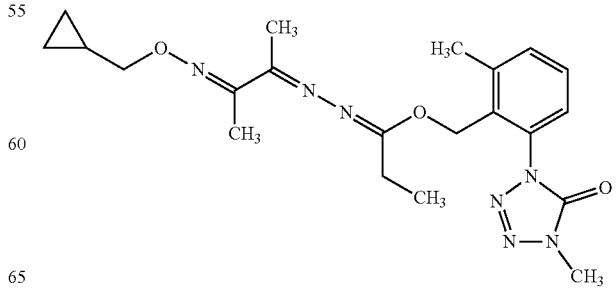
[Chem.159]

(n-hexane:ethyl acetate=1:1)
Present compound C-4: ¹H-NMR (CDCl₃) δ: 7.41-7.36 (2H, m), 7.27-7.24 (1H, m), 5.21 (2H, s), 3.99 (2H, d, J=7.2 Hz), 3.68 (3H, s), 2.50 (3H, s), 2.45 (2H, q, J=7.6 Hz), 2.10 (3H, s), 2.05 (3H, s), 1.24-1.14 (1H, m), 1.02 (3H, t, J=7.6 Hz), 0.58-0.54 (2H, m), 0.33-0.30 (2H, m).
Present Compound C-5

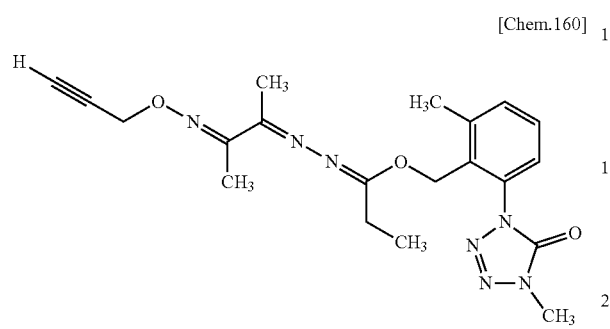

[Chem.160]

(n-hexane:ethyl acetate=1:1)
Present compound C-5: ¹H-NMR (CDCl₃) δ: 7.41-7.36 (2H, m), 7.26-7.24 (1H, m), 5.21 (2H, s), 4.77 (2H, d, J=2.5 Hz), 3.68 (3H, s), 2.49 (3H, s), 2.48 (1H, t, J=2.5 Hz), 2.45 (2H, q, J=7.6 Hz), 2.11 (3H, s), 2.06 (3H, s), 1.02 (3H, t, J=7.6 Hz).
Present Compound C-6

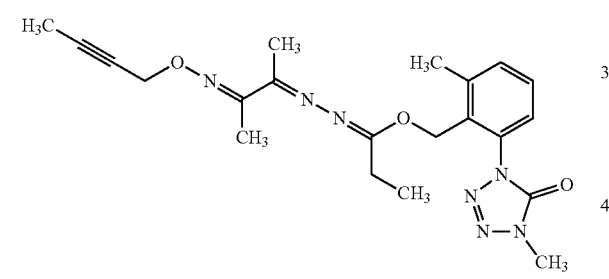

[Chem.161]

(n-hexane:ethyl acetate=1:1)
Present compound C-6: ¹H-NMR (CDCl₃) δ: 7.41-7.36 (2H, m), 7.25-7.24 (1H, m), 5.21 (2H, s), 4.74 (2H, q, J=2.3 Hz), 3.68 (3H, s), 2.49 (3H, s), 2.45 (2H, q, J=7.6 Hz), 2.11 (3H, s), 2.06 (3H, s), 1.89 (3H, t, J=2.4 Hz), 1.02 (3H, t, J=7.7 Hz).
Present Compound C-7

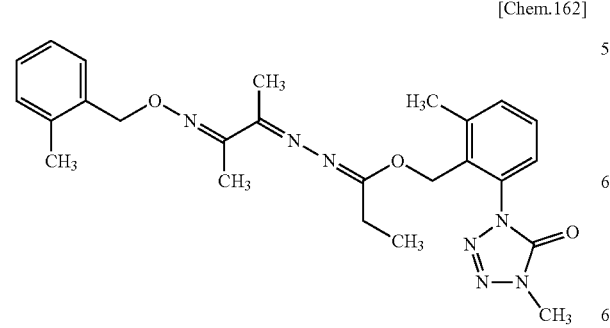

[Chem.162]

(n-hexane:ethyl acetate=3:2)
Present compound C-7: ¹H-NMR (CDCl₃) δ: 7.41-7.34 (3H, m), 7.27-7.17 (4H, m), 5.23 (2H, s), 5.20 (2H, s), 3.67 (3H, s), 2.49 (3H, s), 2.44 (2H, q, J=7.5 Hz), 2.39 (3H, s), 2.10 (3H, s), 2.04 (3H, s), 1.01 (3H, t, J=7.6 Hz).
Present Compound C-8

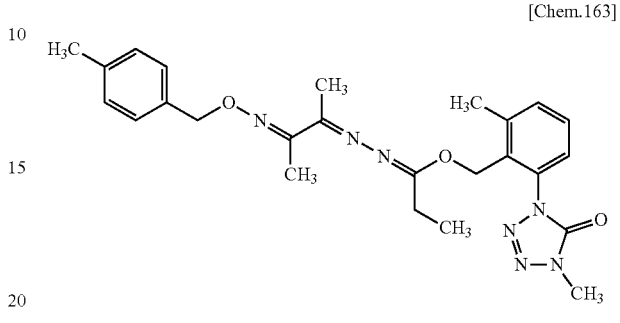

[Chem.163]

(n-hexane:ethyl acetate=3:2)
Present compound C-8: ¹H-NMR (CDCl₃) δ: 7.41-7.36 (2H, m), 7.29-7.25 (3H, m), 7.17 (2H, d, J=7.8 Hz), 5.20 (2H, s), 5.17 (2H, s), 3.67 (3H, s), 2.49 (3H, s), 2.44 (2H, q, J=7.6 Hz), 2.36 (3H, s), 2.09 (3H, s), 2.04 (3H, s), 1.01 (3H, t, J=7.6 Hz).
Present Compound C-9

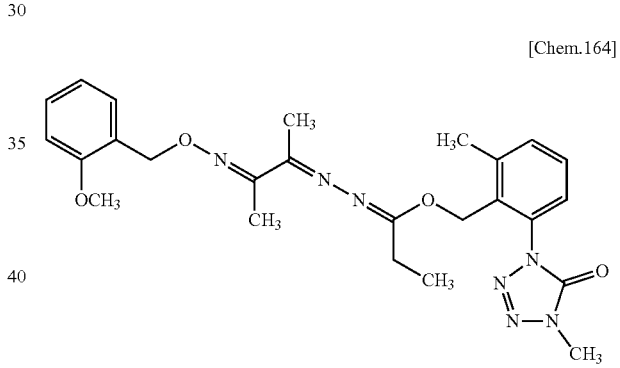

[Chem.164]

(n-hexane:ethyl acetate=1:1)
Present compound C-9: ¹H-NMR (CDCl₃) δ: 7.41-7.35 (3H, m), 7.31-7.23 (2H, m), 6.95 (1H, t, J=7.5 Hz), 6.90 (1H, d, J=8.4 Hz), 5.28 (2H, s), 5.20 (2H, s), 3.86 (3H, s), 3.67 (3H, s), 2.49 (3H, s), 2.44 (2H, q, J=7.6 Hz), 2.13 (3H, s), 2.04 (3H, s), 1.01 (3H, t, J=7.6 Hz).
Present Compound C-10

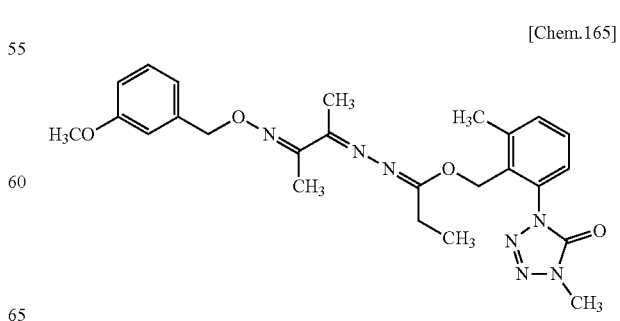

[Chem.165]

(n-hexane:ethyl acetate=1:1)

Present compound C-10: $^1$H-NMR (CDCl$_3$) δ: 7.41-7.36 (2H, m), 7.30-7.24 (2H, m), 7.00-6.93 (2H, m), 6.86 (1H, dd, J=8.3, 2.6 Hz), 5.20 (2H, s), 5.19 (2H, s), 3.82 (3H, s), 3.67 (3H, s), 2.49 (3H, s), 2.44 (2H, q, J=7.6 Hz), 2.11 (3H, s), 2.04 (3H, s), 1.01 (3H, t, J=7.6 Hz).

Present Compound C-11

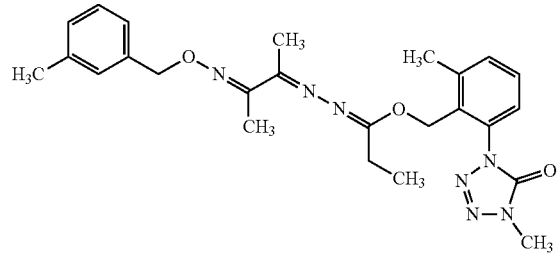

(n-hexane:ethyl acetate=3:2)

Present compound C-11: $^1$H-NMR (CDCl$_3$) δ: 7.41-7.36 (2H, m), 7.27-7.24 (2H, m), 7.20 (2H, d, J=7.8 Hz), 7.13 (1H, d, J=7.3 Hz), 5.20 (2H, s), 5.18 (2H, s), 3.67 (3H, s), 2.49 (3H, s), 2.44 (2H, q, J=7.6 Hz), 2.37 (3H, s), 2.10 (3H, s), 2.05 (3H, s), 1.01 (3H, t, J=7.6 Hz).

Present Compound C-12

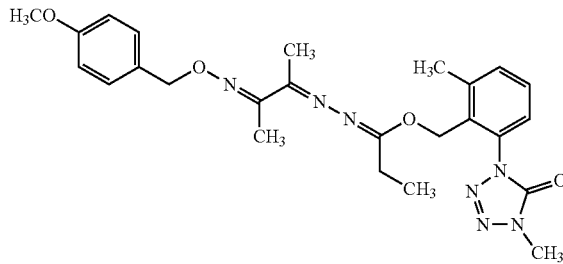

(n-hexane:ethyl acetate=1:1)

Present compound C-12: $^1$H-NMR (CDCl$_3$) δ: 7.41-7.22 (4H, m), 6.91-6.88 (3H, m), 5.20 (2H, s), 5.13 (2H, s), 3.82 (3H, s), 3.67 (3H, s), 2.49 (3H, s), 2.43 (2H, q, J=7.6 Hz), 2.08 (3H, s), 2.05 (3H, s), 1.01 (3H, t, J=7.6 Hz).

Present Compound C-13

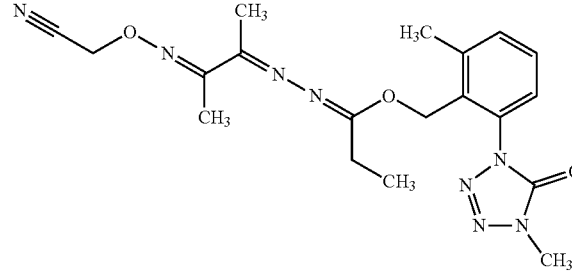

(n-hexane:ethyl acetate=1:1)

Present compound C-13: $^1$H-NMR (CDCl$_3$) δ: 7.42-7.36 (2H, m), 7.27-7.24 (1H, m), 5.22 (2H, s), 4.81 (2H, s), 3.69 (3H, s), 2.50 (3H, s), 2.46 (2H, q, J=7.6 Hz), 2.11 (3H, s), 2.06 (3H, s), 1.03 (3H, t, J=7.6 Hz).

Present Compound C-14

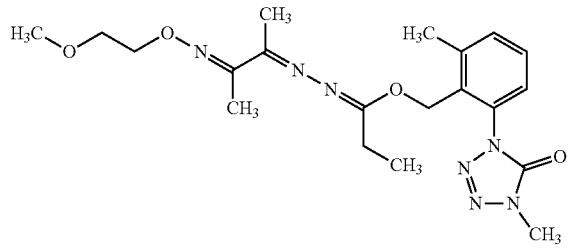

(n-hexane:ethyl acetate=1:1)

Present compound C-14: $^1$H-NMR (CDCl$_3$) δ: 7.42-7.36 (2H, m), 7.27-7.24 (1H, m), 5.21 (2H, s), 4.32 (2H, t, J=4.8 Hz), 3.69 (2H, t, J=4.6 Hz), 3.68 (3H, s), 3.41 (3H, s), 2.50 (3H, s), 2.45 (2H, q, J=7.6 Hz), 2.10 (3H, s), 2.05 (3H, s), 1.02 (3H, t, J=7.6 Hz).

Present Compound C-15

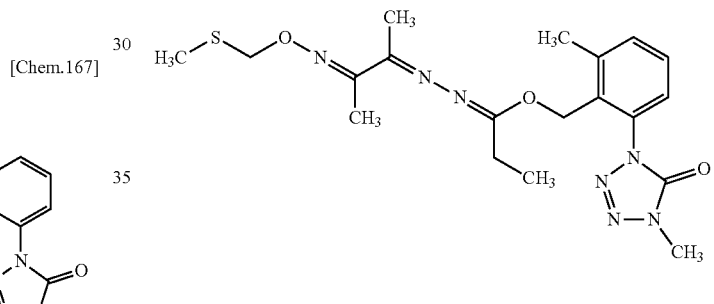

(n-hexane:ethyl acetate=1:1)

Present compound C-15: LCMS: RT=2.30, 434 [M+H$^+$].

The compound that were prepared according to the similar method to those described in Production example 1 and physical properties thereof are indicated below. Also, the solvents that were used for silica gel column chromatography were indicated in parenthesis below a structural formula.

Present Compound D-1

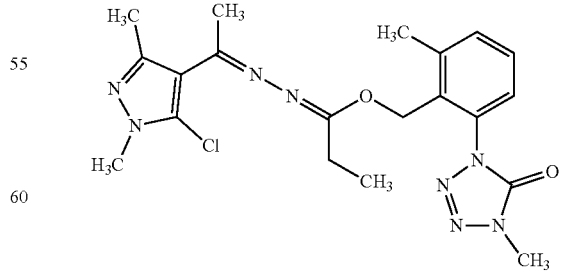

(n-hexane:ethyl acetate=1:1)

Present compound D-1: $^1$H-NMR (CDCl$_3$) δ: 7.40-7.37 (2H, m), 7.25-7.24 (1H, m), 5.21 (2H, s), 3.79 (3H, s), 3.69

(3H, s), 2.55-2.51 (2H, m), 2.51 (3H, s), 2.38 (3H, s), 2.28 (3H, s), 1.05 (3H, t, J=7.6 Hz).
Present Compound D-2

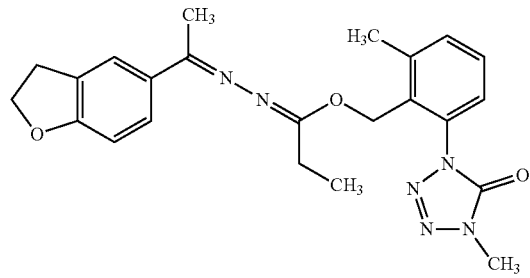

(n-hexane:ethyl acetate=1:1)
Present compound D-2: ¹H-NMR (CDCl₃) δ: 7.76 (1H, s), 7.59 (1H, d, J=8.5 Hz), 7.42-7.37 (2H, m), 7.26-7.24 (1H, m), 6.78 (1H, d, J=8.5 Hz), 5.23 (2H, s), 4.61 (2H, t, J=8.7 Hz), 3.68 (3H, s), 3.24 (2H, t, J=8.7 Hz), 2.54 (2H, q, J=7.6 Hz), 2.51 (3H, s), 2.26 (3H, s), 1.14 (2H, s), 1.05 (3H, t, J=7.6 Hz).
Present Compound D-3

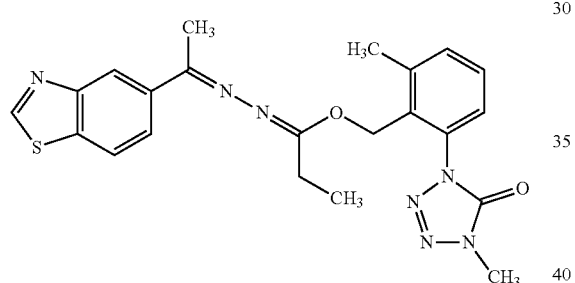

(n-hexane:ethyl acetate=2:3)
Present compound D-3: ¹H-NMR (CDCl₃) δ: 9.02 (1H, s), 8.52 (1H, d, J=1.4 Hz), 8.09 (1H, dd, J=8.6, 1.6 Hz), 7.95 (1H, d, J=8.6 Hz), 7.42-7.38 (2H, m), 7.29-7.27 (1H, m), 5.27 (2H, s), 3.69 (3H, s), 2.60 (2H, q, J=7.7 Hz), 2.53 (3H, s), 2.41 (3H, s), 1.09 (3H, t, J=7.6 Hz).
Present Compound D-4

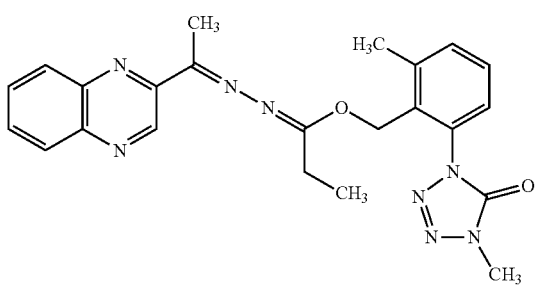

(n-hexane:ethyl acetate=2:3)
Present compound D-4: ¹H-NMR (CDCl₃) δ: 9.69 (1H, s), 8.12-8.10 (2H, m), 7.79-7.73 (2H, m), 7.45-7.40 (2H, m), 7.31-7.26 (1H, m), 5.32 (2H, s), 3.70 (3H, s), 2.62 (2H, q, J=7.7 Hz), 2.55 (3H, s), 2.50 (3H, s), 1.11 (3H, t, J=7.7 Hz).
Present Compound D-5

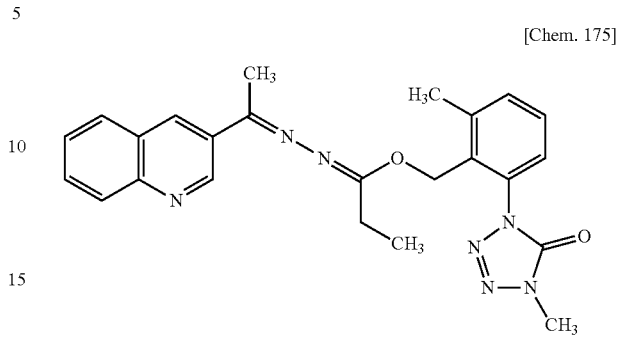

(n-hexane:ethyl acetate=1:1)
Present compound D-5: ¹H-NMR (CDCl₃) δ: 9.57 (1H, d, J=2.3 Hz), 8.37 (1H, d, J=2.3 Hz), 8.12 (1H, d, J=8.4 Hz), 7.87 (1H, d, J=7.9 Hz), 7.75-7.71 (1H, m), 7.59-7.55 (1H, m), 7.44-7.39 (2H, m), 7.32-7.27 (1H, m), 5.28 (2H, s), 3.69 (3H, s), 2.62 (2H, q, J=7.6 Hz), 2.53 (3H, s), 2.42 (3H, s), 1.10 (3H, t, J=7.6 Hz).
Present Compound D-6

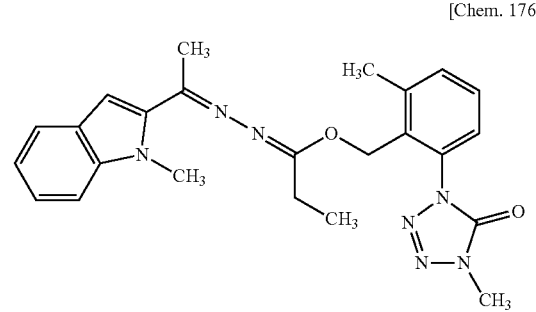

(n-hexane:ethyl acetate=1:1)
Present compound D-6: ¹H-NMR (CDCl₃) δ: 8.04 (1H, d, J=1.1 Hz), 7.89 (1H, dd, J=8.7, 1.7 Hz), 7.40-7.38 (2H, m), 7.31 (1H, d, J=8.8 Hz), 7.26-7.25 (1H, m), 7.06 (1H, d, J=2.9 Hz), 6.53 (1H, dd, J=3.1, 0.8 Hz), 5.25 (2H, s), 3.81 (3H, s), 3.68 (3H, s), 2.58 (2H, q, J=7.6 Hz), 2.53 (3H, s), 2.38 (3H, s), 1.07 (3H, t, J=7.6 Hz).
Present Compound D-7

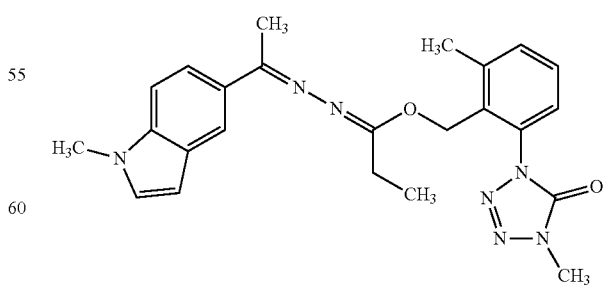

(n-hexane:ethyl acetate=1:1)
Present compound D-7: ¹H-NMR (CDCl₃) δ: 7.62 (1H, d, J=7.9 Hz), 7.42-7.34 (2H, m), 7.30-7.26 (2H, m), 7.12-7.08

(2H, m), 6.89 (1H, d, J=0.9 Hz), 5.26 (2H, s), 4.09 (3H, s), 3.68 (3H, s), 2.56 (2H, q, J=7.6 Hz), 2.53 (3H, s), 2.39 (3H, s), 1.08 (3H, t, J=7.6 Hz).
Present Compound D-8

[Chem. 178]

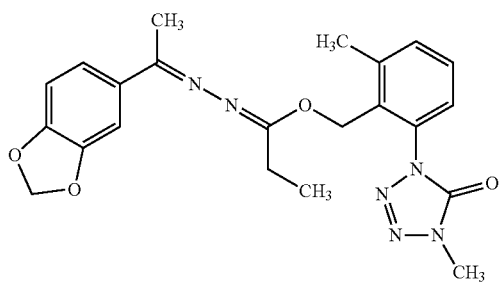

(n-hexane:ethyl acetate=7:3)
Present compound D-8: $^1$H-NMR (CDCl$_3$) δ: 7.46 (1H, d, J=1.8 Hz), 7.42-7.19 (4H, m), 6.81 (1H, d, J=8.2 Hz), 5.99 (2H, s), 5.23 (2H, s), 3.68 (3H, s), 2.54 (2H, q, J=7.7 Hz), 2.51 (3H, s), 2.26 (3H, s), 1.05 (3H, t, J=7.7 Hz).
Present Compound D-9

[Chem. 179]

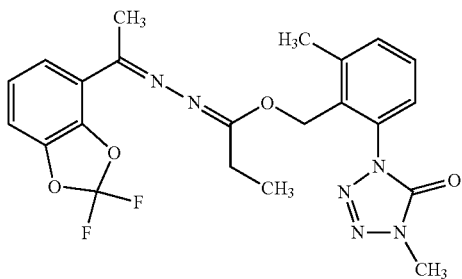

(n-hexane:ethyl acetate=7:3)
Present compound D-9: $^1$H-NMR (CDCl$_3$) δ: 7.52 (1H, dd, J=7.2, 2.0 Hz), 7.41-7.38 (2H, m), 7.29-7.25 (1H, m), 7.10-7.04 (2H, m), 5.25 (2H, s), 3.69 (3H, s), 2.56 (2H, t, J=7.6 Hz), 2.52 (3H, s), 2.33 (3H, s), 1.06 (3H, t, J=7.6 Hz).
Present Compound D-10

[Chem. 180]

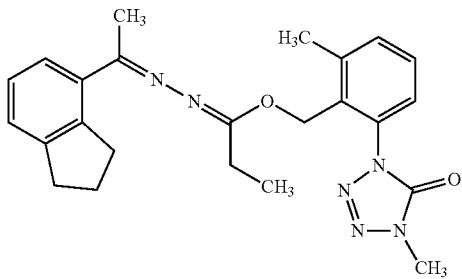

(n-hexane:ethyl acetate=7:3)
Present compound D-10: $^1$H-NMR (CDCl$_3$) δ: 7.42-7.38 (2H, m), 7.33 (1H, d, J=7.3 Hz), 7.27-7.16 (3H, m), 5.23 (2H, s), 3.69 (3H, s), 3.15 (2H, t, J=7.3 Hz), 2.93 (2H, t, J=7.4 Hz), 2.53 (2H, q, J=8.0 Hz), 2.52 (3H, s), 2.29 (3H, s), 2.08-2.02 (2H, m), 1.05 (3H, t, J=7.7 Hz).
Present Compound D-11

[Chem. 181]

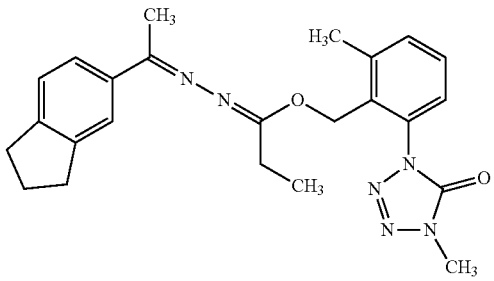

(n-hexane:ethyl acetate=7:3)
Present compound D-11: $^1$H-NMR (CDCl$_3$) δ: 7.70 (1H, s), 7.61-7.59 (1H, m), 7.40-7.35 (2H, m), 7.28-7.22 (2H, m), 5.24 (2H, s), 3.67 (3H, s), 2.95-2.90 (4H, m), 2.57-2.50 (5H, m), 2.28 (3H, s), 2.12-2.04 (2H, m), 1.05 (3H, t, J=7.6 Hz).
Present Compound D-12

[Chem. 182]

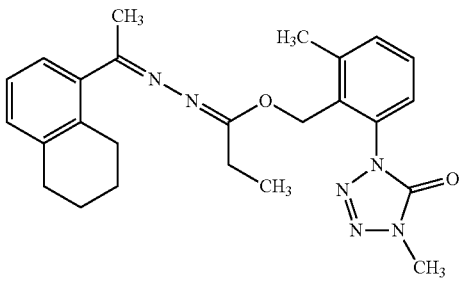

(n-hexane:ethyl acetate=7:3)
Present compound D-12: $^1$H-NMR (CDCl$_3$) δ: 7.42-7.38 (2H, m), 7.14-7.04 (4H, m), 5.22 (2H, s), 3.70 (3H, s), 2.83-2.74 (4H, m), 2.52 (3H, s), 2.47 (2H, q, J=7.6 Hz), 2.17 (3H, s), 1.81-1.76 (4H, m), 1.02 (3H, t, J=7.7 Hz).
Present Compound D-13

[Chem. 183]

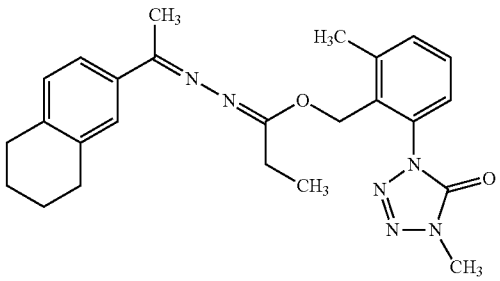

(n-hexane:ethyl acetate=7:3)
Present compound D-13: $^1$H-NMR (CDCl$_3$) δ: 7.56 (1H, dd, J=8.0, 1.9 Hz), 7.51 (1H, s), 7.42-7.37 (2H, m), 7.28-7.24 (1H, m), 7.07 (1H, d, J=8.2 Hz), 5.23 (2H, s), 3.68 (3H, s), 2.82-2.77 (4H, m), 2.52 (2H, q, J=7.6 Hz), 2.51 (3H, s), 2.25 (3H, s), 1.82-1.79 (4H, m), 1.04 (3H, t, J=7.6 Hz).

Present Compound D-14

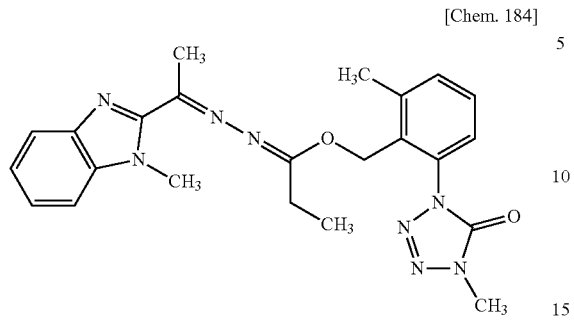

(n-hexane:ethyl acetate=7:3)

Present compound D-14: $^1$H-NMR (CDCl$_3$) δ: 7.83 (1H, d, J=7.8 Hz), 7.44-7.27 (6H, m), 5.29 (2H, s), 4.12 (3H, s), 3.69 (3H, s), 2.56 (3H, s), 2.55 (2H, d, J=7.6 Hz), 2.54 (3H, s), 1.09 (3H, t, J=7.7 Hz).

Present Compound D-15

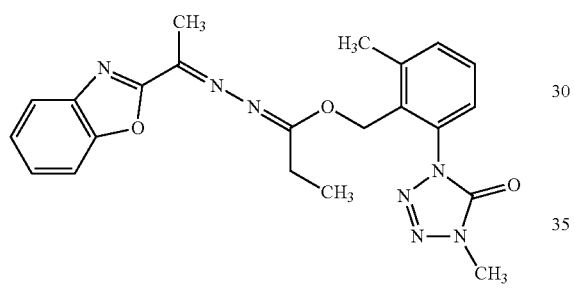

(n-hexane:ethyl acetate=7:3)

Present compound D-15: $^1$H-NMR (CDCl$_3$) δ: 7.84-7.80 (1H, m), 7.65 (1H, d, J=8.0 Hz), 7.45-7.28 (4H, m), 7.13 (1H, d, J=7.1 Hz), 5.11 (2H, s), 3.63 (3H, s), 2.62 (2H, q, J=7.6 Hz), 2.50 (3H, s), 1.99 (3H, s), 1.29-1.24 (3H, m).

Present Compound D-16

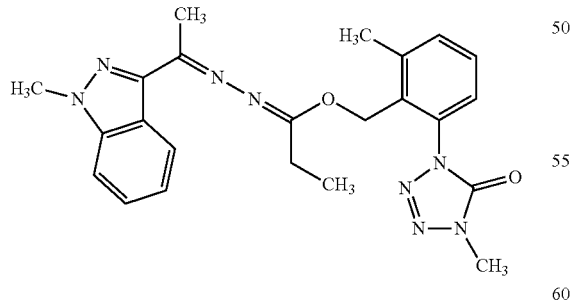

(n-hexane:ethyl acetate=7:3)

Present compound D-16: $^1$H-NMR (CDCl$_3$) δ: 8.43 (1H, d, J=8.2 Hz), 7.44-7.37 (4H, m), 7.30-7.27 (1H, m), 7.24-7.20 (1H, m), 5.29 (2H, s), 4.10 (3H, s), 3.68 (3H, s), 2.66 (2H, q, J=7.6 Hz), 2.54 (3H, s), 2.49 (3H, s), 1.13 (3H, t, J=7.6 Hz).

Present Compound D-17

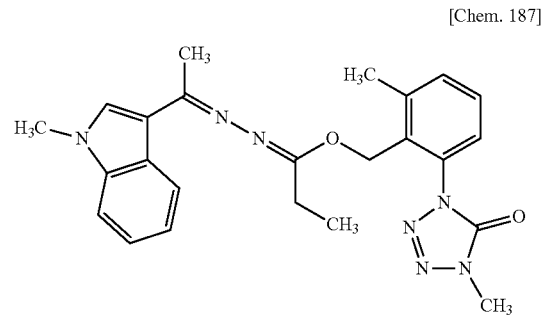 [SMILES: CCC(=NN=C(C)c1cn(C)c2ccccc12)OCc1c(C)cccc1-n1nnn(C)c1=O]

(n-hexane:ethyl acetate=7:3)

Present compound D-17: $^1$H-NMR (CDCl$_3$) δ: 8.49 (1H, dt, J=7.8, 1.0 Hz), 7.40-7.37 (3H, m), 7.33-7.19 (4H, m), 5.25 (2H, s), 3.80 (3H, s), 3.66 (3H, s), 2.68 (2H, q, J=7.6 Hz), 2.52 (3H, s), 2.34 (3H, s), 1.13 (3H, t, J=7.6 Hz).

Present Compound D-18

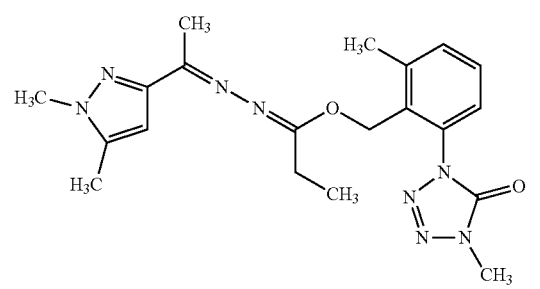

(n-hexane:ethyl acetate=4:6)

Present compound D-18: $^1$H-NMR (CDCl$_3$) δ: 7.41-7.36 (2H, m), 7.27-7.23 (1H, m), 6.48 (1H, d, J=0.9 Hz), 5.21 (2H, s), 3.80 (3H, s), 3.67 (3H, s), 2.50 (3H, s), 2.49 (2H, q, J=7.6 Hz), 2.27 (3H, d, J=0.7 Hz), 2.26 (3H, s), 1.02 (3H, t, J=7.7 Hz).

Present Compound D-19

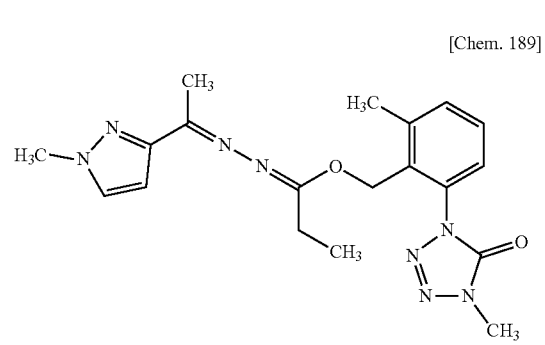 [SMILES: CCC(=NN=C(C)c1ccn(C)n1)OCc1c(C)cccc1-n1nnn(C)c1=O]

(n-hexane:ethyl acetate=4:6)

Present compound D-19: $^1$H-NMR (CDCl$_3$) δ: 7.39-7.37 (2H, m), 7.32 (1H, d, J=2.3 Hz), 7.27-7.23 (1H, m), 6.71 (1H, d, J=2.3 Hz), 5.22 (2H, s), 3.93 (3H, s), 3.68 (3H, s), 2.54-2.48 (5H, m), 2.29 (3H, s), 1.03 (3H, t, J=7.7 Hz).

Present Compound D-20

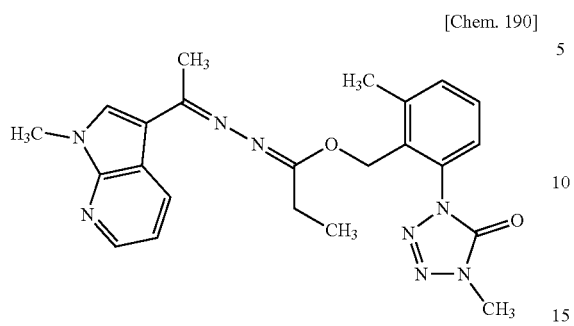

(n-hexane:ethyl acetate=3:7)

Present compound D-20: $^1$H-NMR (CDCl$_3$) δ: 8.69 (1H, dd, J=7.8, 1.7 Hz), 8.37 (1H, dd, J=4.8, 1.6 Hz), 7.49 (1H, s), 7.41-7.38 (2H, m), 7.29-7.27 (1H, m), 7.15 (1H, dd, J=7.8, 4.6 Hz), 5.25 (2H, s), 3.92 (3H, s), 3.67 (3H, s), 2.66 (2H, q, J=7.6 Hz), 2.53 (3H, s), 2.33 (3H, s), 1.13 (3H, t, J=7.7 Hz).

Present Compound D-21

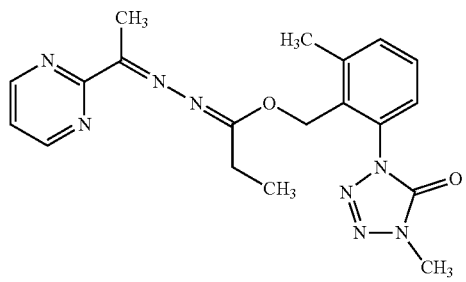

(ethyl acetate)

Present compound D-21: $^1$H-NMR (CDCl$_3$) δ: 8.83 (2H, d, J=5.0 Hz), 7.42-7.37 (2H, m), 7.32-7.26 (2H, m), 5.27 (2H, s), 3.70 (3H, s), 2.59-2.48 (5H, m), 2.37 (3H, s), 1.01 (3H, t, J=7.6 Hz).

Production Example D-1

A mixture of 16.0 g of the Intermediate compound AA-1, N,N-dimethylformamide dimethyl acetal 12 mL, and DMF 40 mL was stirred at 110° C. for 10 hours. The resulting mixture was allowed to cool to room temperature, and thereto was added water and saturated brine, and the mixture was extracted with ethyl acetate. The resulting organic layer was washed with saturated brine, dried over anhydrous magnesium sulfate, and concentrated under reduced pressure to obtain the residues. To the mixture of the resulting residues and ethanol 140 mL was added dropwise hydrazine monohydrate 5 mL, and the mixture was stirred at room temperature for 12 hours. To the resulting mixture was added water, and the mixture was extracted with ethyl acetate. The resulting organic layer was washed with saturated brine, dried over anhydrous magnesium sulfate, and concentrated under reduced pressure to obtain the residues. The resulting residues were subjected to silica gel column chromatography (ethyl acetate) to give 10.0 g of Present compound D-22 as below mentioned.

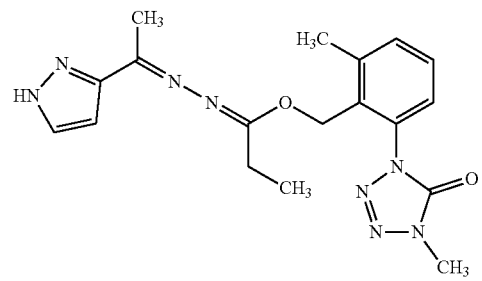

Present compound D-22: $^1$H-NMR (CDCl$_3$) δ: 7.58 (1H, d, J=1.8 Hz), 7.42-7.37 (2H, m), 7.27-7.25 (1H, m), 6.57 (1H, bs), 5.23 (2H, s), 3.68 (3H, s), 2.56-2.50 (5H, m), 2.25 (3H, s), 1.05 (3H, t, J=7.7 Hz).

Production Example D-2

To sodium hydride (oily, 60%) 0.07 g was added DMF 6 mL under nitrogen atmosphere, and thereto was added dropwise gradually mixture solutions of Present compound D-22 at 0° C., and the mixture was stirred for 10 m min. To the reaction solutions were added iodoethane 0.16 mL, and the mixture was stirred at room temperature for additional 3 hours. To the reaction solutions was added water and saturated brine, and the mixture was extracted with ethyl acetate. The organic layer was washed with saturated brine, dried over anhydrous magnesium sulfate, and concentrated under reduced pressure. The resulting residues were subjected to silica gel column chromatography (n-hexane:ethyl acetate=1:1) to give 0.28 g of the Present compound D-23 and 0.06 g of the Present compound D-24 as below mentioned.

Present Compound D-23

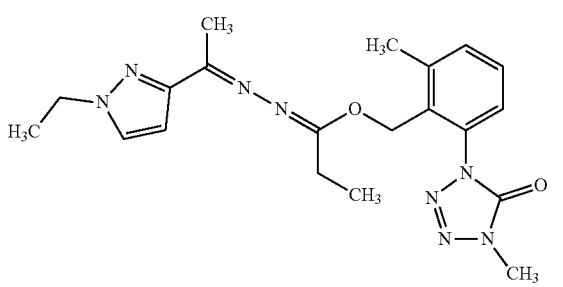

Present compound D-23: $^1$H-NMR (CDCl$_3$) δ: 7.41-7.38 (2H, m), 7.35 (1H, d, J=2.3 Hz), 7.27-7.24 (1H, m), 6.71 (1H, d, J=2.3 Hz), 5.22 (2H, s), 4.20 (2H, q, J=7.3 Hz), 3.68 (3H, s), 2.53-2.48 (5H, m), 2.30 (3H, s), 1.50 (3H, t, J=7.2 Hz), 1.03 (3H, t, J=7.6 Hz).

Present Compound D-24

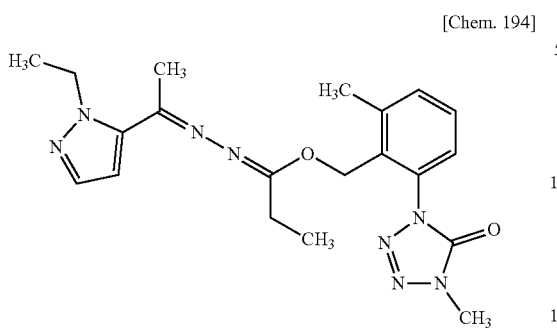

[Chem. 194]

Present compound D-24: $^1$H-NMR (CDCl$_3$) δ: 7.47 (1H, d, J=2.0 Hz), 7.43-7.38 (2H, m), 7.28-7.25 (1H, m), 6.50 (1H, d, J=2.0 Hz), 5.24 (2H, s), 4.62 (2H, q, J=7.2 Hz), 3.68 (3H, s), 2.55-2.49 (5H, m), 2.28 (3H, s), 1.41 (3H, t, J=7.1 Hz), 1.07 (3H, t, J=7.6 Hz).

The compounds that were prepared according to the similar method to those described in Production example D-2, and physical properties thereof are indicated below. Also, the solvents that were used for silica gel column chromatography were indicated in parenthesis below a structural formula. Further, when a compound is a mixture of isomers, the isomeric ratio thereof is also indicated below the compound.

Present Compound D-25

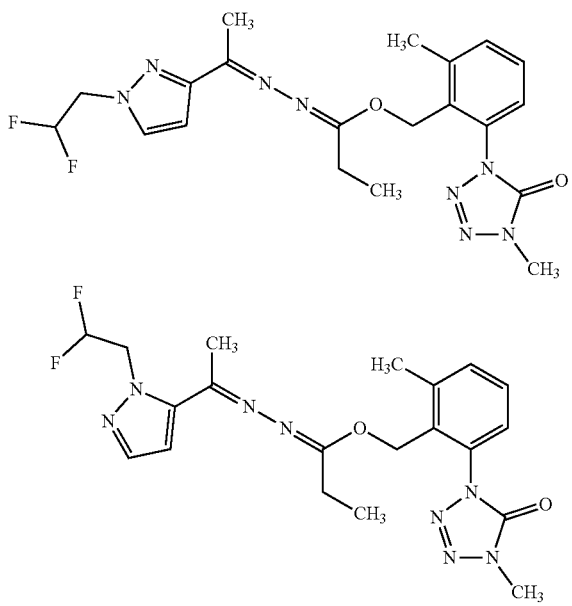

[Chem. 195]

(n-hexane:ethyl acetate=1:1) Isomeric ratio 1:1

Present compound D-25: $^1$H-NMR (CDCl$_3$) δ: 7.55 (0.5H, d, J=2.1 Hz), 7.43-7.37 (2.5H, m), 7.28-7.24 (1H, m), 6.77 (0.5H, d, J=2.5 Hz), 6.57 (0.5H, d, J=1.8 Hz), 6.30-5.96 (1H, m), 5.23 (2H, s), 5.04 (1H, td, J=13.1, 4.6 Hz), 4.47 (1H, td, J=13.5, 4.4 Hz), 3.69 (1.5H, s), 3.68 (1.5H, s), 2.53-2.46 (5H, m), 2.29 (1.5H, s), 2.28 (1.5H, s), 1.09-1.01 (3H, m).

Present Compound D-26

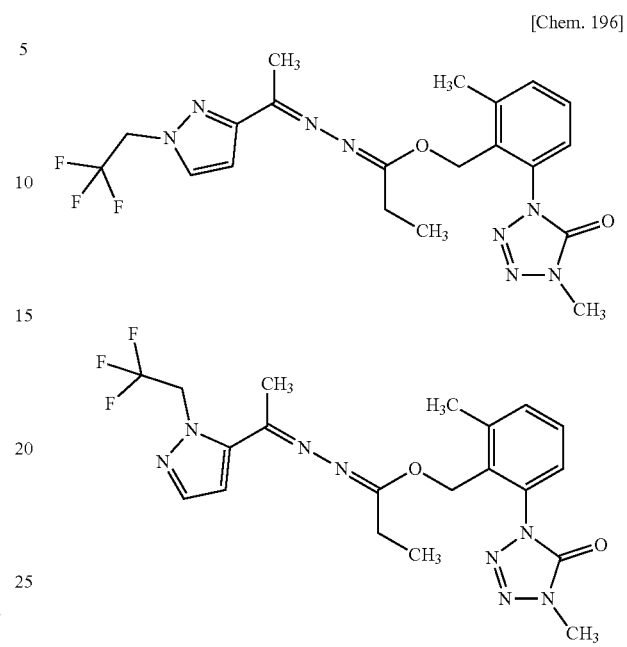

[Chem. 196]

(n-hexane:ethyl acetate=1:1) Isomeric ratio 9:1

Present compound D-26: $^1$H-NMR (CDCl$_3$) δ: 7.59 (0.1H, d, J=2.0 Hz), 7.46 (0.9H, d, J=2.5 Hz), 7.42-7.37 (2H, m), 7.28-7.24 (1H, m), 6.82 (0.9H, d, J=2.5 Hz), 6.59 (0.1H, d, J=2.0 Hz), 5.23 (2H, s), 3.68 (3H, s), 2.54-2.47 (5H, m), 2.29 (3H, s), 1.08-1.02 (3H, m).

Present Compound D-27

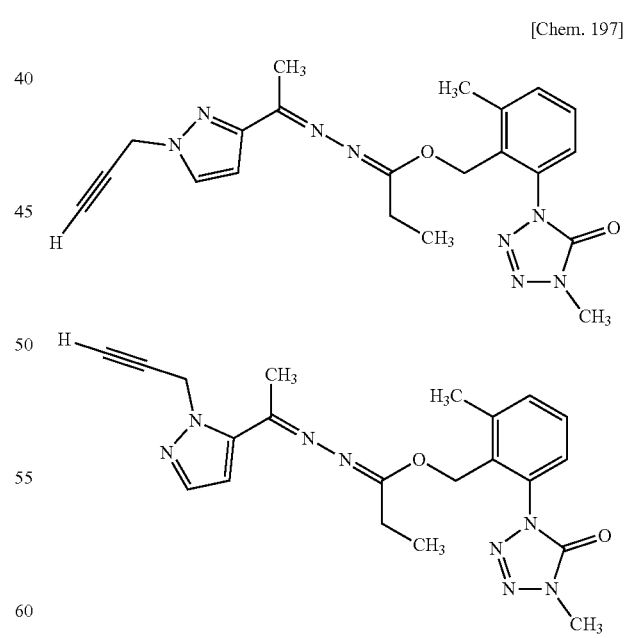

[Chem. 197]

(n-hexane:ethyl acetate=1:1) Isomeric ratio 1:1

Present compound D-27: $^1$H-NMR (CDCl$_3$) δ: 7.59 (0.5H, d, J=2.5 Hz), 7.53 (0.5H, d, J=2.0 Hz), 7.41-7.38 (2H, m), 7.28-7.24 (1H, m), 6.77 (0.5H, d, J=2.3 Hz), 6.55 (0.5H, d, J=2.0 Hz), 5.45 (1H, d, J=2.5 Hz), 5.24 (1H, s), 5.22 (1H, s), 4.96 (1H, d, J=2.5 Hz), 3.68 (1.5H, s), 3.68 (1.5H, s), 2.60 (1H, q, J=7.7 Hz), 2.55-2.47 (4.5H, m), 2.31 (0.5H, t, J=2.5 Hz), 2.29 (1.5H, s), 2.28 (1.5H, s), 1.08 (1.5H, t, J=7.6 Hz), 1.03 (1.5H, t, J=7.6 Hz).

Present Compound D-28

[Chem. 198]

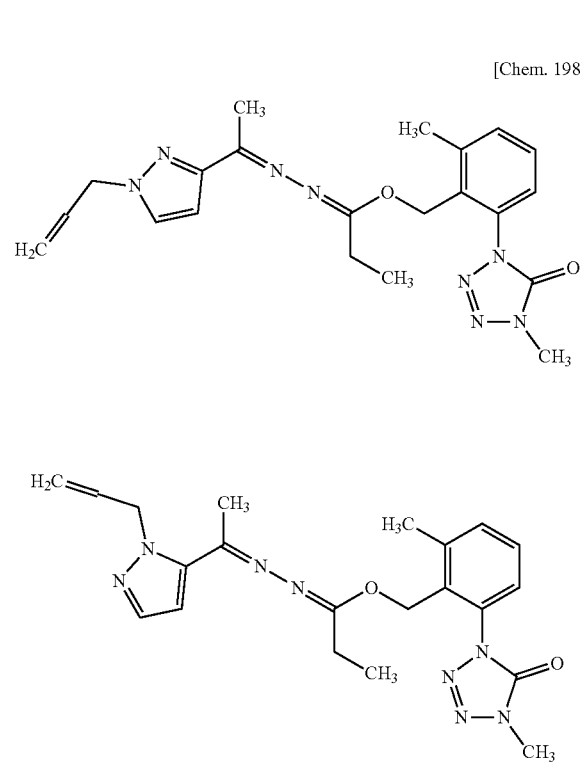

(n-hexane:ethyl acetate=1:1) Isomeric ratio 9:1

Present compound D-28: ¹H-NMR (CDCl₃) δ: 7.51 (0.1H, d, J=1.8 Hz), 7.41-7.36 (2.9H, m), 7.27-7.24 (1H, m), 6.75 (0.9H, d, J=2.3 Hz), 6.54 (0.1H, d, J=2.1 Hz), 6.09-5.99 (1H, m), 5.29-5.20 (4H, m), 4.84-4.76 (2H, m), 3.68 (3H, s), 2.54-2.48 (5H, m), 2.30 (2.7H, s), 2.28 (0.3H, s), 1.07-1.01 (3H, m).

Present Compound D-29

[Chem. 199]

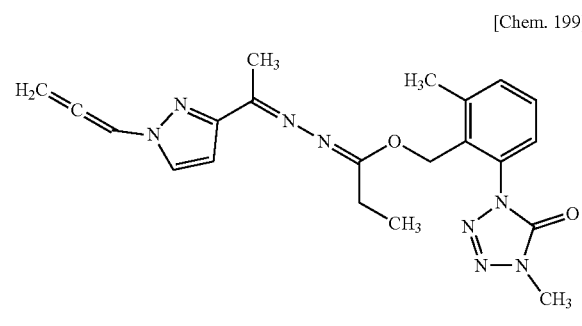

(n-hexane:ethyl acetate=1:1)

Present compound D-29: ¹H-NMR (CDCl₃) δ: 7.54 (1H, d, J=2.5 Hz), 7.42-7.36 (2H, m), 7.22 (1H, t, J=6.6 Hz), 6.83 (1H, d, J=2.5 Hz), 5.63 (2H, d, J=6.6 Hz), 5.23 (2H, s), 3.68 (3H, s), 2.54-2.48 (5H, m), 2.30 (3H, s), 1.03 (3H, t, J=7.7 Hz).

Present Compound D-30

[Chem. 200]

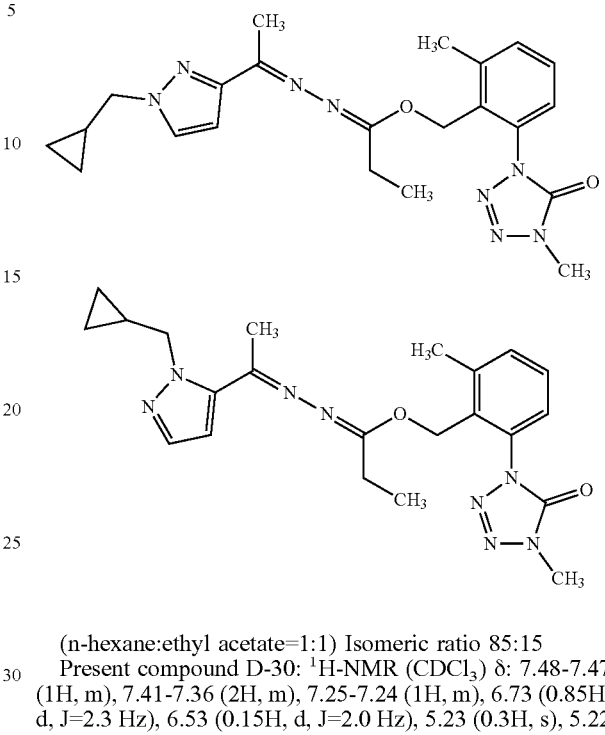

(n-hexane:ethyl acetate=1:1) Isomeric ratio 85:15

Present compound D-30: ¹H-NMR (CDCl₃) δ: 7.48-7.47 (1H, m), 7.41-7.36 (2H, m), 7.25-7.24 (1H, m), 6.73 (0.85H, d, J=2.3 Hz), 6.53 (0.15H, d, J=2.0 Hz), 5.23 (0.3H, s), 5.22 (1.7H, s), 4.47 (0.3H, d, J=7.0 Hz), 4.01 (1.7H, d, J=7.0 Hz), 3.68 (0.45H, s), 3.68 (2.55H, s), 2.55-2.48 (5H, m), 2.29 (3H, s), 1.34-1.27 (1H, m), 1.09-1.01 (3H, m), 0.68-0.63 (1.7H, m), 0.51-0.47 (0.3H, m), 0.40-0.36 (2H, m).

Production Example E-1

To mixture of 0.39 g of the intermediate compound 6-1 and DMF 10 mL was added potassium tert-butoxide 0.22 g at room temperature, and the mixture was stirred at room temperature for 10 minutes. 1-{2-(Bromomethyl)-3-methylphenyl}-4-methyl-4,5-dihydrotetrazol-5-one 0.50 g was added to the mixture solutions, and the mixture was stirred for additional 10 hours. To the mixture was added water, and the mixture was extracted with ethyl acetate. The resulting organic layer was washed with saturated brine, dried over anhydrous magnesium sulfate, and concentrated under reduced pressure. The resulting residues were subjected to silica gel column chromatography (hexane:ethyl acetate=1:1) to give 0.14 g of Present compound E-1 as belowmentioned.

[Chem. 201]

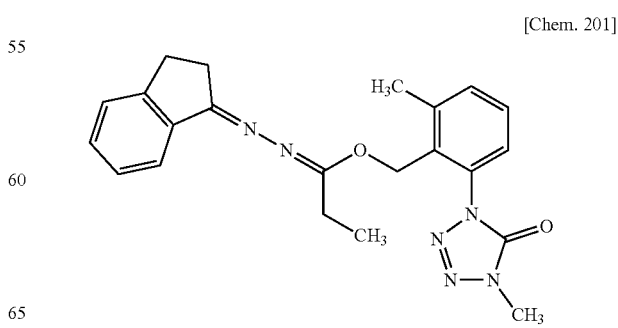

Present compound E-1: ¹H-NMR (CDCl$_3$) δ: 7.82 (1H, d), 7.38-7.34 (2H, m), 7.33-7.30 (2H, m), 7.28-7.24 (2H, m), 5.23 (2H, s), 3.65 (3H, s), 3.03 (2H, t), 2.86-2.83 (2H, m), 2.58 (2H, q), 2.50 (3H, s), 1.08-1.04 (3H, m).

Production Example E-2

The compounds that were prepared according to the similar method to those described in Production example E-1 and physical properties thereof are indicated below.

Present Compound E-2

[Chem. 202]

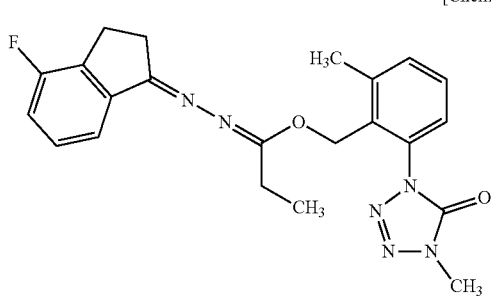

Present compound E-2: ¹H-NMR (CDCl$_3$) δ: 7.60 (1H, d), 7.40-7.37 (2H, m), 7.28-7.23 (2H, m), 7.03 (1H, t), 5.22 (2H, s), 3.68 (3H, s), 3.07-3.03 (2H, m), 2.90-2.87 (2H, m), 2.58 (2H, q), 2.51 (3H, s), 1.06 (3H, t).

Present Compound E-3

[Chem. 203]

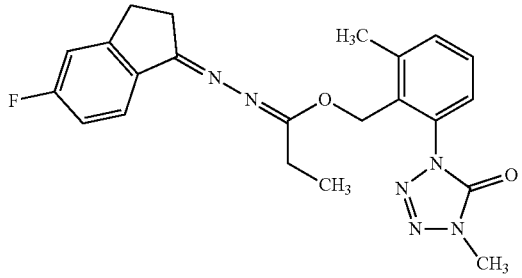

Present compound E-3: ¹H-NMR (CDCl$_3$) δ: 7.78 (1H, dd), 7.42-7.37 (1H, m), 7.28-7.24 (2H, m), 7.01-6.95 (2H, m), 5.21 (2H, s), 3.68 (3H, s), 3.04-3.01 (2H, m), 2.89-2.86 (2H, m), 2.58 (2H, q), 2.51 (3H, s), 1.07 (3H, t).

Present Compound E-4

[Chem. 204]

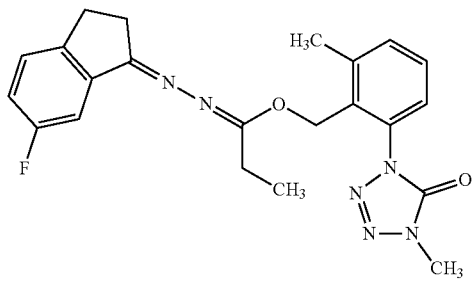

Present compound E-4: ¹H-NMR (CDCl$_3$) δ:7.46 (1H, dd), 7.42-7.37 (2H, m), 7.28-7.24 (2H, m), 7.05 (1H, td), 5.22 (2H, s), 3.68 (3H, s), 3.01-2.97 (2H, m), 2.91-2.87 (2H, m), 2.58 (2H, q), 2.51 (3H, s), 1.06 (3H, t).

Present Compound E-5

[Chem. 205]

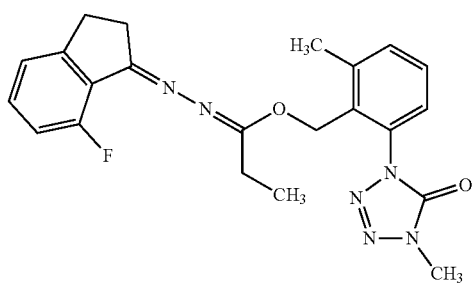

Present compound E-5: ¹H-NMR (CDCl$_3$) δ: 7.41-7.37 (2H, m), 7.32-7.24 (2H, m), 7.10 (1H, d), 6.94 (1H, t), 5.21 (2H, s), 3.68 (3H, s), 3.07-3.04 (2H, m), 2.90-2.86 (2H, m), 2.58 (2H, q), 2.51 (3H, s), 1.06 (3H, t).

Present Compound E-6

[Chem. 206]

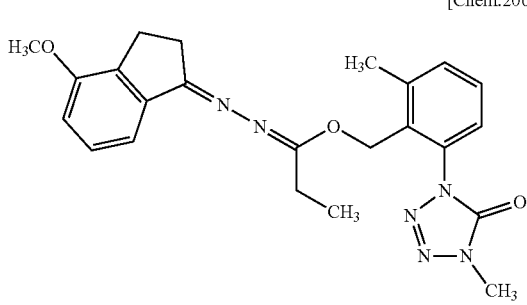

Present compound E-6: ¹H-NMR (CDCl$_3$) δ: 7.42 (1H, d), 7.40-7.38 (2H, m), 7.28-7.24 (2H, m), 6.84 (1H, d), 5.21 (2H, s), 3.87 (3H, s), 3.67 (3H, s), 2.97-2.93 (2H, m), 2.87-2.83 (2H, m), 2.57 (2H, q), 2.51 (3H, s), 1.05 (3H, t).

Present Compound E-7

[Chem. 207]

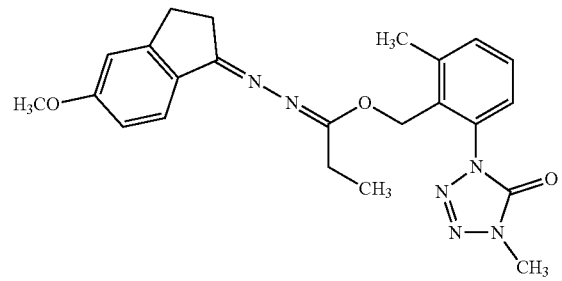

Present Compound E-7:
¹H-NMR (CDCl$_3$) δ: 7.73 (1H, d), 7.39-7.35 (2H, m), 7.27-7.23 (1H, m), 6.84-6.81 (2H, m), 5.22 (2H, s), 3.81 (3H, s), 3.65 (3H, s), 3.00-2.97 (2H, m), 2.86-2.83 (2H, m), 2.58 (2H, q), 2.50 (3H, s), 1.06 (3H, t).

Present Compound E-8

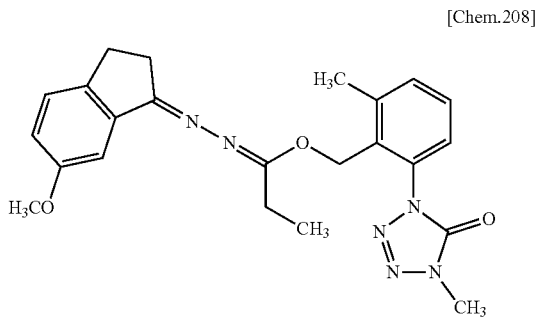 [SMILES: CCC(=NN=C1CCc2ccc(OC)cc21)OCc1c(C)cccc1-n1nnn(C)c1=O]

Present Compound E-8:
¹H-NMR (CDCl₃) δ: 7.40-7.38 (2H, m), 7.29 (1H, d), 7.26-7.24 (1H, m), 7.21 (1H, d), 6.96 (1H, dd), 5.22 (2H, s), 3.85 (3H, s), 3.68 (3H, s), 2.98-2.94 (2H, m), 2.88-2.84 (2H, m), 2.58 (2H, q), 2.51 (3H, s), 1.06 (3H, t).

Present Compound E-9

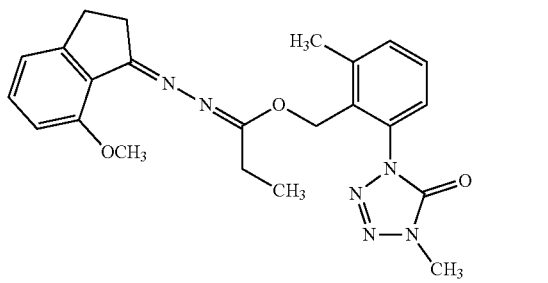

Present compound E-9: ¹H-NMR (CDCl₃) δ: 7.43-7.37 (2H, m), 7.31-7.23 (2H, m), 6.92 (1H, d), 6.77 (1H, d), 5.21 (2H, s), 3.93 (3H, s), 3.68 (3H, s), 3.01-2.98 (2H, m), 2.87-2.84 (2H, m), 2.62-2.56 (2H, m), 2.50 (3H, s), 1.06 (3H, t).

Present Compound E-10

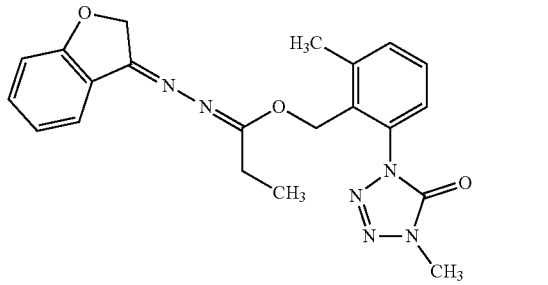

Present compound E-10: ¹H-NMR (CDCl₃) δ: 7.72-7.70 (1H, m), 7.41-7.34 (3H, m), 7.27-7.25 (1H, m), 7.01-6.95 (2H, m), 5.17 (2H, s), 5.07 (2H, s), 3.68 (3H, s), 2.62 (2H, q), 2.50 (3H, s), 1.07 (3H, t).

Present Compound E-11

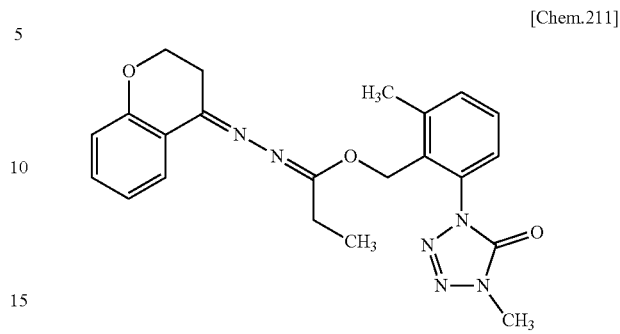

Present compound E-11: ¹H-NMR (CDCl₃) δ: 8.11 (1H, dd), 7.42-7.37 (2H, m), 7.29-7.24 (2H, m), 6.98-6.94 (1H, m), 6.91-6.89 (1H, m), 5.21 (2H, s), 4.27 (2H, t), 3.68 (3H, s), 2.95 (2H, t), 2.59 (2H, q), 2.50 (3H, s), 1.07 (3H, t).

Present Compound E-12

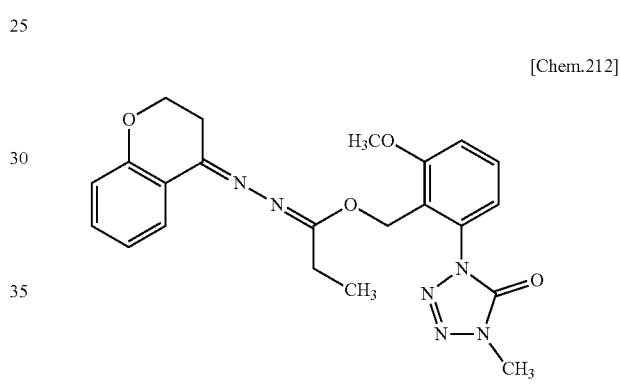

Present compound E-12: ¹H-NMR (CDCl₃) δ: 8.11 (1H, dd), 7.46 (1H, t), 7.29-7.24 (1H, m), 7.09-7.03 (2H, m), 6.97-6.93 (1H, m), 6.90-6.88 (1H, m), 5.33 (2H, s), 4.29-4.25 (2H, m), 3.91 (3H, s), 3.65 (3H, s), 3.01 (2H, t), 2.56 (2H, q), 1.03 (3H, t).

Present Compound E-13

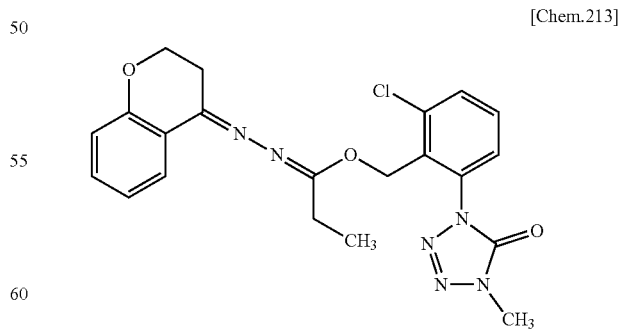

Present compound E-13: ¹H-NMR (CDCl₃) δ: 8.10 (1H, dd), 7.59 (1H, dd), 7.44 (1H, t), 7.38-7.36 (1H, m), 7.29-7.24 (1H, m), 6.97-6.93 (1H, m), 6.89 (1H, dd), 5.42 (2H, s), 4.26 (2H, t), 3.67 (3H, s), 2.98 (2H, t), 2.57 (2H, q), 1.05 (3H, t).

Present Compound E-14

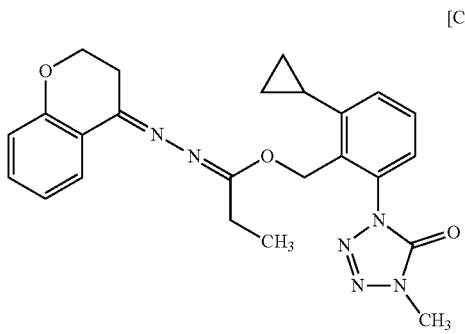

[Chem.214]

Present compound E-14: ¹H-NMR (CDCl₃) δ: 8.11 (1H, dd), 7.41 (1H, t), 7.30-7.23 (3H, m), 6.98-6.94 (1H, m), 6.90 (1H, dd), 5.42 (2H, s), 4.27 (2H, t), 3.67 (3H, s), 2.98 (2H, t), 2.60 (2H, q), 2.17-2.10 (1H, m), 1.07 (3H, t), 1.03-0.99 (2H, m), 0.79-0.75 (2H, m).

Present Compound E-15

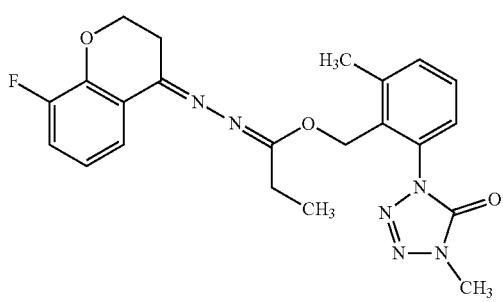

[Chem.215]

Present compound E-15: ¹H-NMR (CDCl₃) δ: 7.87 (1H, dt), 7.43-7.38 (2H, m), 7.27-7.25 (1H, m), 7.10-7.05 (1H, m), 6.90-6.84 (1H, m), 5.21 (2H, s), 4.35 (2H, t), 3.68 (3H, s), 2.99 (2H, t), 2.59 (2H, q), 2.50 (3H, s), 1.07 (3H, t).

Present Compound E-16

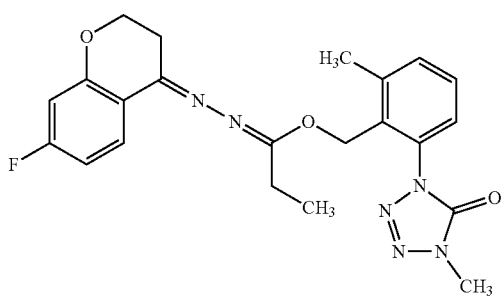

[Chem.216]

Present compound E-16: ¹H-NMR (CDCl₃) δ: 8.09 (1H, dd), 7.42-7.37 (2H, m), 7.27-7.24 (1H, m), 6.70-6.65 (1H, m), 6.60 (1H, dd), 5.20 (2H, s), 4.27 (2H, t), 3.68 (3H, s), 2.94 (2H, t), 2.59 (2H, q), 2.49 (3H, s), 1.07 (3H, t).

Present Compound E-17

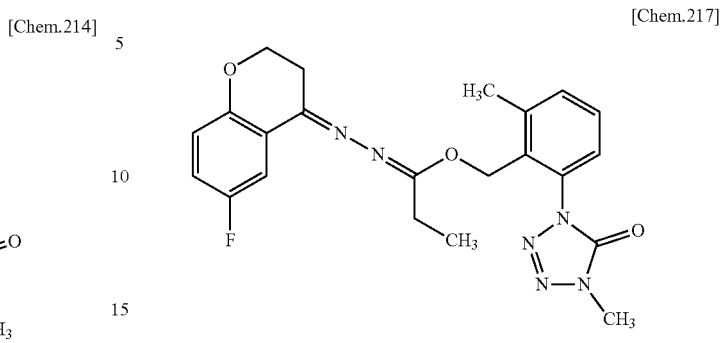

[Chem.217]

Present compound E-17: ¹H-NMR (CDCl₃) δ: 7.76 (1H, dd), 7.43-7.37 (2H, m), 7.27-7.24 (1H, m), 7.00-6.95 (1H, m), 6.85 (1H, dd), 5.21 (2H, s), 4.24 (2H, t), 3.68 (3H, s), 2.93 (2H, t), 2.60 (2H, q), 2.50 (3H, s), 1.08 (3H, t).

Present Compound E-18

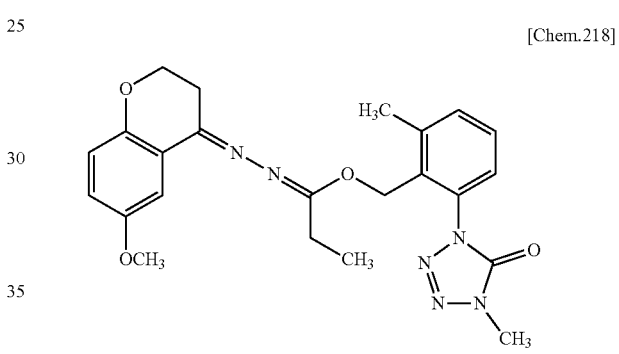

[Chem.218]

Present compound E-18: ¹H-NMR (CDCl₃) δ: 7.60 (1H, d), 7.42-7.37 (2H, m), 7.26 (1H, dd), 6.90-6.87 (1H, m), 6.85-6.82 (1H, m), 5.21 (2H, s), 4.22 (2H, t), 3.80 (3H, s), 3.68 (3H, s), 2.91 (2H, t), 2.58 (2H, q), 2.50 (3H, s), 1.07 (3H, t).

Present Compound E-19

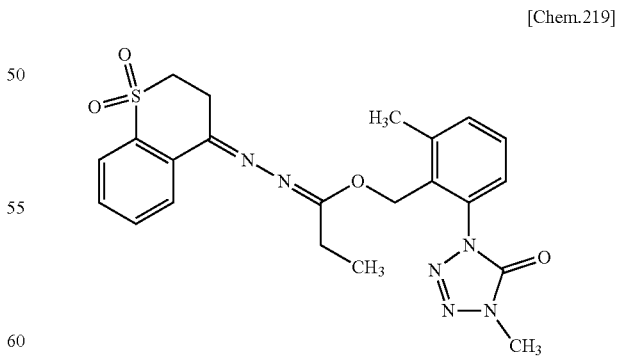

[Chem.219]

Present compound E-19: ¹H-NMR (CDCl₃) δ: 8.34-8.31 (1H, m), 7.98-7.96 (1H, m), 7.63-7.55 (2H, m), 7.44-7.38 (2H, m), 7.28-7.26 (1H, m), 5.25 (2H, s), 3.69 (3H, s), 3.50-3.46 (2H, m), 3.41-3.38 (2H, m), 2.61 (2H, q), 2.51 (3H, s), 1.09 (3H, t).

Present Compound E-20

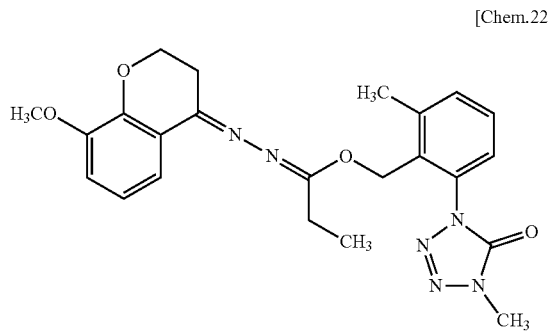
[Chem.220]

Present compound E-20: ¹H-NMR (CDCl₃) δ: 7.72 (1H, dd), 7.42-7.37 (2H, m), 7.26-7.24 (1H, m), 6.92-6.86 (2H, m), 5.21 (2H, s), 4.36 (2H, t), 3.89 (3H, s), 3.67 (3H, s), 2.97 (2H, t), 2.59 (2H, q), 2.50 (3H, s), 1.07 (3H, t).

Present Compound E-21

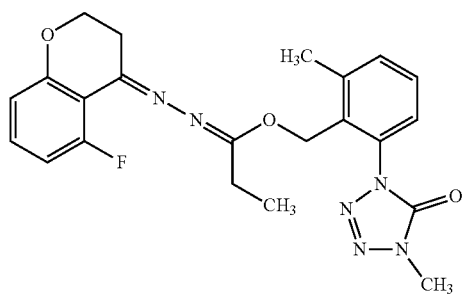
[Chem.221]

Present compound E-21: ¹H-NMR (CDCl₃) δ: 7.42-7.37 (2H, m), 7.26-7.24 (1H, m), 7.21-7.15 (1H, m), 6.72-6.67 (2H, m), 5.21 (2H, s), 4.24 (2H, t), 3.68 (3H, s), 2.98 (2H, t), 2.58 (2H, q), 2.50 (3H, s), 1.06 (3H, t).

Present Compound E-22

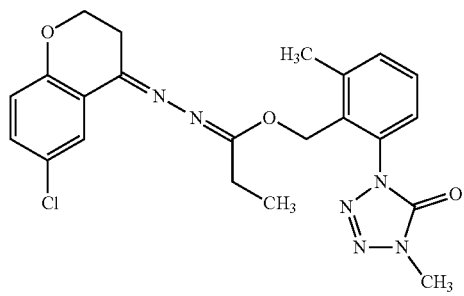
[Chem.222]

Present compound E-22: ¹H-NMR (CDCl₃) δ: 8.05 (1H, d), 7.43-7.38 (2H, m), 7.27-7.25 (1H, m), 7.21 (1H, dd), 6.84 (1H, d), 5.21 (2H, s), 4.25 (2H, t), 3.68 (3H, s), 2.94 (2H, t), 2.61 (2H, q), 2.50 (3H, s), 1.08 (3H, t).

Present Compound E-23

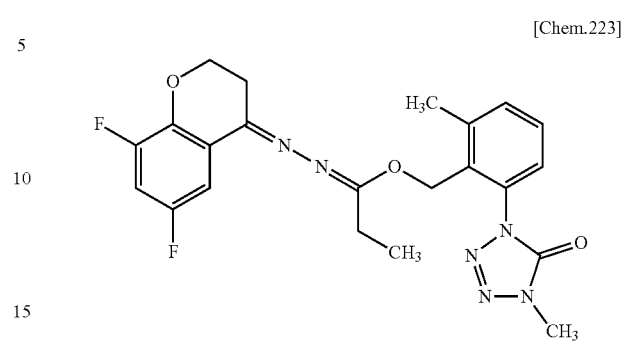
[Chem.223]

Present compound E-23: ¹H-NMR (CDCl₃) δ: 7.59-7.55 (1H, m), 7.43-7.38 (2H, m), 7.27-7.25 (1H, m), 6.89-6.84 (1H, m), 5.21 (2H, s), 4.32 (2H, t), 3.68 (3H, s), 2.98 (2H, t), 2.59 (2H, q), 2.50 (3H, s), 1.08 (3H, t).

Present Compound E-24

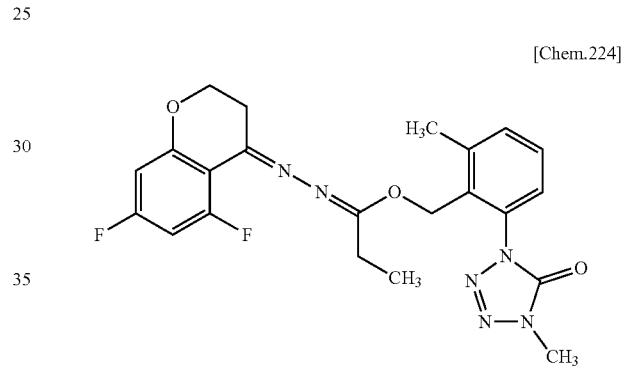
[Chem.224]

Present compound E-24: ¹H-NMR (CDCl₃) δ: 7.42-7.37 (2H, m), 7.27-7.24 (1H, m), 6.50-6.44 (2H, m), 5.20 (2H, s), 4.24 (2H, t), 3.68 (3H, s), 2.97 (2H, t), 2.57 (2H, q), 2.49 (3H, s), 1.06 (3H, t).

Present Compound E-25

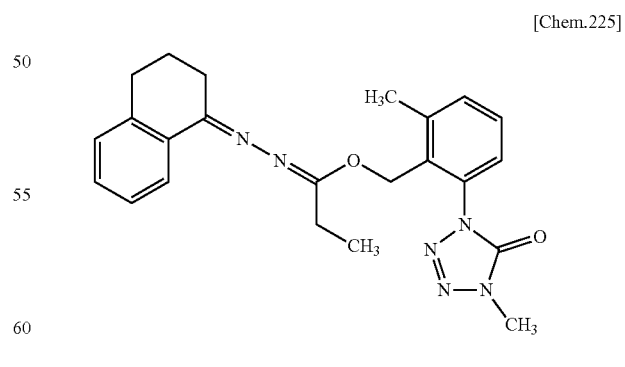
[Chem.225]

Present compound E-25: ¹H-NMR (CDCl₃) δ: 8.23-8.21 (1H, m), 7.42-7.37 (2H, m), 7.29-7.20 (3H, m), 7.16-7.13 (1H, m), 5.22 (2H, s), 3.68 (3H, s), 2.81 (2H, t), 2.74 (2H, t), 2.58-2.53 (2H, m), 2.51 (3H, s), 1.92-1.85 (2H, m), 1.06 (3H, t).

Present Compound E-26

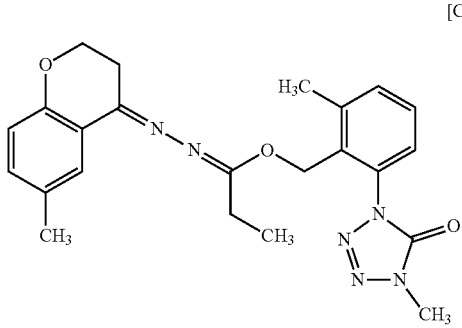

[Chem.226]

Present compound E-26: ¹H-NMR (CDCl₃) δ: 7.89-7.88 (1H, m), 7.42-7.37 (2H, m), 7.26-7.24 (1H, m), 7.10-7.07 (1H, m), 6.80 (1H, d), 5.21 (2H, s), 4.23 (2H, t), 3.67 (3H, s), 2.92 (2H, t), 2.60 (2H, q), 2.50 (3H, s), 2.31 (3H, s), 1.07 (3H, t).

Present Compound E-27

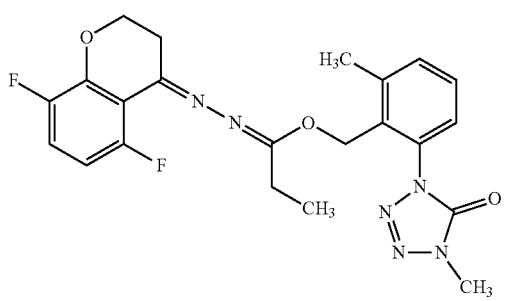

[Chem.227]

Present compound E-27: ¹H-NMR (CDCl₃) δ: 7.43-7.37 (2H, m), 7.27-7.25 (1H, m), 7.04-6.98 (1H, m), 6.66-6.59 (1H, m), 5.21 (2H, s), 4.34 (2H, t), 3.69 (3H, s), 3.02 (2H, t), 2.58 (2H, q), 2.50 (3H, s), 1.06 (3H, t).

Present Compound E-28

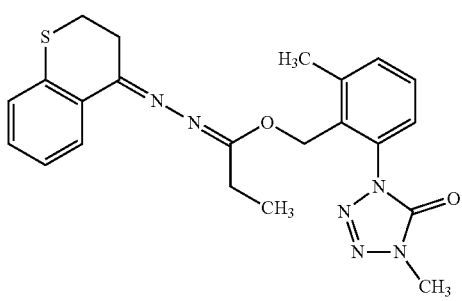

[Chem.228]

Present compound E-28: ¹H-NMR (CDCl₃) δ: 8.24-8.22 (1H, m), 7.42-7.37 (2H, m), 7.27-7.25 (1H, m), 7.23-7.20 (2H, m), 7.14-7.09 (1H, m), 5.22 (2H, s), 3.68 (3H, s), 3.13-3.10 (2H, m), 3.01-2.97 (2H, m), 2.56 (2H, q), 2.50 (3H, s), 1.06 (3H, t).

Present Compound E-30

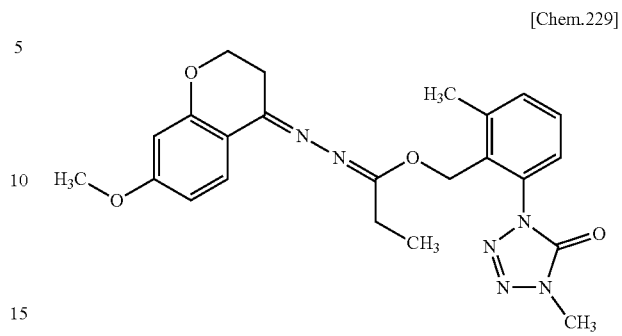

[Chem.229]

Present compound E-30: ¹H-NMR (CDCl₃) δ: 8.02 (1H, d), 7.42-7.37 (2H, m), 7.26-7.24 (1H, m), 6.55 (1H, dd), 6.40 (1H, d), 5.19 (2H, s), 4.26 (2H, t), 3.80 (3H, s), 3.67 (3H, s), 2.93 (2H, t), 2.58 (2H, q), 2.49 (3H, s), 1.06 (3H, t).

Production Example E-29

To mixture of Present compound E-28 1.1 g and chloroform 50 mL was added m-chloroperbenzoic acid 0.58 g at room temperature, and the mixture was stirred at room temperature for 1 hour. To the mixture was added saturated aqueous sodium bisulfite solution 30 mL, and the mixture was extracted with ethyl acetate. The resulting organic layer was dried over anhydrous magnesium sulfate, and concentrated under reduced pressure. The resulting residues were subjected to silica gel column chromatography to give 0.81 g of Present compound E-29 as below-mentioned.

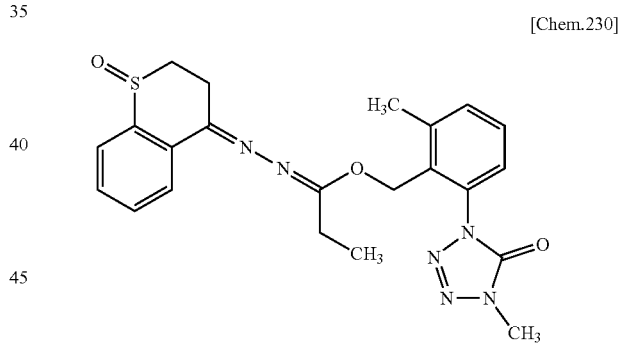

[Chem.230]

Present compound E-29: ¹H-NMR (CDCl₃) δ: 8.32-8.30 (1H, m), 7.81-7.79 (1H, m), 7.57-7.52 (2H, m), 7.44-7.38 (2H, m), 7.28-7.26 (1H, m), 5.29-5.21 (2H, m), 3.69 (3H, s), 3.46-3.39 (1H, m), 3.21-3.08 (3H, m), 2.63-2.56 (2H, m), 2.51 (3H, s), 1.08 (3H, t).

Reference Production Example 1

To sodium hydride (oily, 60%) 2.54 g was added DMF 50 mL under nitrogen atmosphere, and thereto was added dropwise gradually mixture solutions of acetohydroxamic acid 7.95 g and DMF 50 mL at 0° C., and the mixture was stirred at room temperature for 1 hour. The reaction solutions were cooled to 0° C. and thereto was then added 1-{2-(bromomethyl)-3-methylphenyl}-4-methyl-4,5-dihydrotetrazol-5-one 15.0 g, and the mixture was stirred at room temperature for additional 2 hours. To the reaction solutions was added water, and the mixture was extracted with ethyl acetate. The organic layer was washed with water and saturated brine, dried over sodium sulfate, and concentrated under reduced pressure. The resulting solids were washed with hexane to give 2.51 g of the intermediate compound 1-1.

Intermediate Compound 1-1

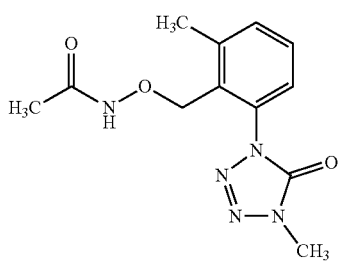

[Chem.231]

Intermediate Compound 1-1:
$^1$H-NMR (CDCl$_3$) δ: 8.31 (1H, br s), 7.43 (2H, dd, J=13.7, 6.9 Hz), 7.23-7.22 (1H, m), 4.97 (2H, s), 3.72 (3H, s), 2.51 (3H, s), 1.81 (3H, s).

Reference Production Example 2-1

A mixture of 1-{2-(bromomethyl)-3-methylphenyl}-4-methyl-4,5-dihydrotetrazol-5-one 30 g, 1N aqueous sodium hydroxide solution 500 mL, and tetrahydrofuran 300 mL was heated under reflux for 8 hours while stirring. The mixture was concentrated under reduced pressure, and to the resulting residues was added water, and the mixture was extracted with ethyl acetate. The organic layer was washed with water and saturated brine, dried over sodium sulfate, and concentrated under reduced pressure. The resulting solids were recrystallized from ethyl acetate to give 20 g of the Intermediate compound 2-1.

Intermediate Compound 2-1

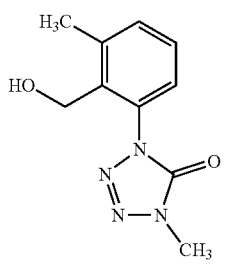

[Chem.232]

Intermediate compound 2-1: $^1$H-NMR (CDCl$_3$) δ: 7.39-7.34 (2H, m), 7.21 (1H, dd, J=6.4, 3.0 Hz), 4.48 (2H, d, J=7.1 Hz), 3.75 (3H, s), 3.75 (1H, t, J=7.1 Hz), 2.57 (3H, s).

Reference Production Example 2-2

A mixture of 16 g of the Intermediate compound 2-1, sodium hydrogen carbonate 24 g, and ethyl acetate 300 mL was added Dess-Martin periodinane 36 g at room temperature under nitrogen atmosphere, and the mixture was stirred at room temperature for 2 hours. To the mixture was added saturated aqueous sodium thiosulfate solution, and the mixture was extracted with ethyl acetate. The organic layer was washed with water and saturated brine successively, dried over sodium sulfate, and concentrated under reduced pressure to give 10 g of Intermediate compound 2-2 as crude product.

Intermediate Compound 2-2

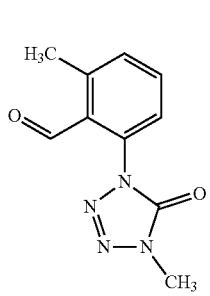

[Chem.233]

Reference Production Example 4-3

A mixture of Intermediate compound 2-2 as crude product 5 g, hydroxylamine hydrochloride 3.2 g, sodium hydroxide 1.8 g, ethanol 46 mL and water 23 mL was heated under reflux for 9 hours while stirring. The mixture was cooled to room temperature, and thereto was added water, and the mixture was extracted with ethyl acetate. The organic layer was washed with water and saturated brine, dried over sodium sulfate, and concentrated under reduced pressure. The resulting solids were recrystallized from ethyl acetate to give 2.5 g of the Intermediate compound 2-3.

Intermediate Compound 2-3

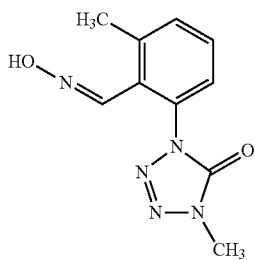

[Chem. 234]

Intermediate compound 2-3: $^1$H-NMR (CDCl$_3$) δ: 8.24 (1H, s), 7.63 (1H, br s), 7.44-7.37 (2H, m), 7.29 (1H, dd, J=7.3, 1.8 Hz), 3.70 (3H, s), 2.49 (3H, s).

Reference Production Example 5-1

To mixture of indanone 3.0 g and ethanol 10 mL was added hydrazine monohydrate 15 mL and acetic acid 0.2 mL successively, and the mixture was stirred at 90° C. for 8 hours. The mixtures were allowed to cool to room temperature, and thereto was added water 10 mL, and the mixture was extracted with ethyl acetate. The resulting organic layer was washed with saturated brine, dried over anhydrous magnesium sulfate, and concentrated under reduced pressure to give 3.1 g of the Intermediate compound 5-1.

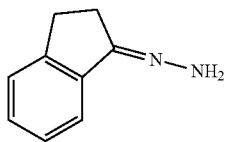

Intermediate compound 5-1: $^1$H-NMR (CDCl$_3$) δ: 7.65-7.63 (1H, m), 7.28-7.25 (3H, m), 5.15 (2H, s), 3.13-3.10 (2H, m), 2.70-2.66 (2H, m).

Reference Production Example 5-2

The compounds that were prepared according to the similar method to those described in Reference Production example 5-1 and physical properties thereof are indicated below.

Intermediate Compound 5-2

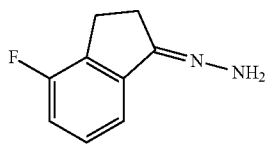

Intermediate compound 5-2: $^1$H-NMR (CDCl$_3$) δ: 7.42 (1H, d), 7.25-7.20 (1H, m), 6.96 (1H, t), 5.21 (2H, s), 3.14-3.11 (2H, m), 2.73-2.70 (2H, m).

Intermediate Compound 5-3

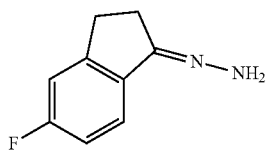

Intermediate compound 5-3: $^1$H-NMR (CDCl$_3$) δ: 7.59 (1H, dd), 6.98-6.93 (2H, m), 5.12 (2H, s), 3.11-3.08 (2H, m), 2.72-2.68 (2H, m).

Intermediate Compound 5-4

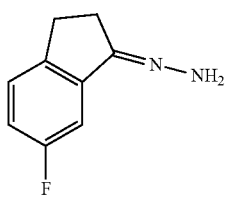

Intermediate compound 5-4: $^1$H-NMR (CDCl$_3$) δ: 7.30-7.26 (1H, m), 7.21 (1H, dd), 6.97 (1H, td), 5.20 (2H, s), 3.07-3.05 (2H, m), 2.72-2.68 (2H, m).

Intermediate Compound 5-5

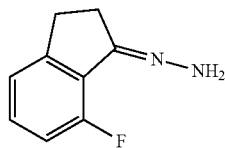

Intermediate compound 5-5: $^1$H-NMR (CDCl$_3$) δ: 7.25-7.19 (1H, m), 7.07 (1H, d), 6.96-6.91 (1H, m), 5.28 (2H, s), 3.16-3.12 (2H, m), 2.73-2.70 (2H, m).

Intermediate Compound 5-6

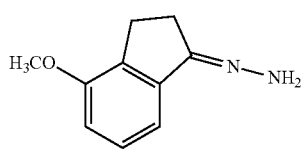

Intermediate compound 5-6: $^1$H-NMR (CDCl$_3$) δ: 7.26-7.23 (2H, m), 6.77 (1H, dd), 5.14 (2H, s), 3.86 (3H, s), 3.04-3.01 (2H, m), 2.69-2.66 (2H, m).

Intermediate Compound 5-7

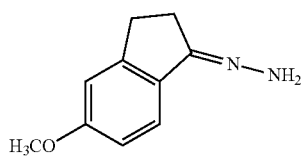

Intermediate compound 5-7: $^1$H-NMR (CDCl$_3$) δ: 7.55 (1H, d), 6.84-6.81 (2H, m), 5.04 (2H, s), 3.82 (3H, s), 3.09-3.05 (2H, m), 2.70-2.67 (2H, m).

Intermediate Compound 5-8

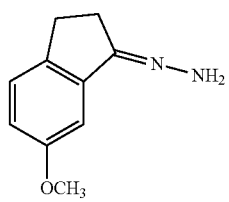

Intermediate compound 5-8: $^1$H-NMR (CDCl$_3$) δ: 7.18 (1H, dd), 7.14 (1H, d), 6.88 (1H, dd), 5.15 (2H, s), 3.82 (3H, s), 3.06-3.03 (2H, m), 2.71-2.68 (2H, m).

Intermediate Compound 5-9

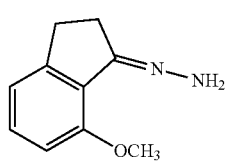

Intermediate compound 5-9: ¹H-NMR (CDCl₃) δ: 7.24 (1H, t), 6.90 (1H, dd), 6.77 (1H, d), 5.19 (2H, s), 3.95 (3H, s), 3.10-3.07 (2H, m), 2.72-2.69 (2H, m).

Intermediate Compound 5-10

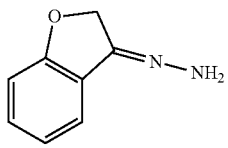

[Chem. 244]

Intermediate compound 5-10: ¹H-NMR (CDCl₃) δ: 7.57 (1H, d), 7.31-7.29 (1H, m), 7.01-6.94 (2H, m), 5.05 (2H, s), 5.00 (2H, s).

Intermediate Compound 5-11

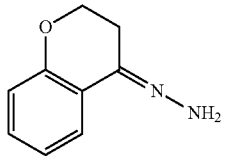

[Chem. 245]

Intermediate compound 5-11: ¹H-NMR (CDCl₃) δ: 7.90 (1H, dd), 7.20-7.18 (1H, m), 6.97-6.93 (1H, m), 6.89-6.87 (1H, m), 5.28 (2H, s), 4.28 (2H, t), 2.68 (2H, t).

Intermediate Compound 5-12

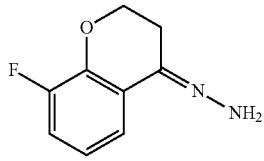

[Chem. 246]

Intermediate compound 5-12: ¹H-NMR (CDCl₃) δ: 7.66 (1H, dt), 7.02-6.97 (1H, m), 6.86 (1H, td), 5.36 (2H, s), 4.36 (2H, t), 2.70 (2H, t).

Intermediate Compound 5-13

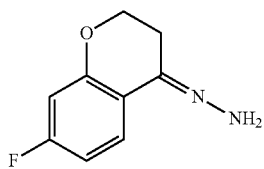

[Chem. 247]

Intermediate compound 5-13: ¹H-NMR (CDCl₃) δ: 7.87 (1H, dd), 6.67 (1H, td), 6.59 (1H, dd), 5.25 (2H, s), 4.28 (2H, t), 2.66 (2H, t).

Intermediate Compound 5-14

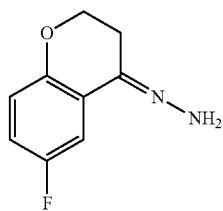

[Chem. 248]

Intermediate compound 5-14: ¹H-NMR (CDCl₃) δ: 7.57 (1H, dd), 6.91-6.88 (1H, m), 6.84-6.81 (1H, m), 5.35 (2H, s), 4.25 (2H, t), 2.64 (2H, t).

Intermediate Compound 5-15

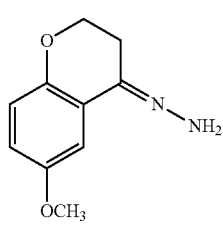

[Chem.249]

Intermediate compound 5-15: ¹H-NMR (DMSO-D₆) δ: 7.27 (1H, d), 6.77-6.70 (2H, m), 6.44 (2H, s), 4.12 (2H, t), 3.69 (3H, s), 2.57 (2H, t).

Intermediate Compound 5-16

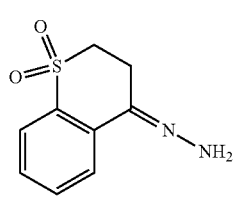

[Chem.250]

Intermediate compound 5-16: ¹H-NMR (DMSO-D₆) δ: 7.99 (1H, dd), 7.75 (1H, dt), 7.61-7.57 (1H, m), 7.47-7.43 (1H, m), 7.17 (2H, s), 3.61 (2H, t), 2.96 (2H, t).

Intermediate Compound 5-17

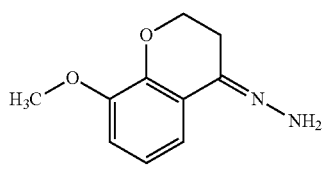

[Chem.251]

Intermediate compound 5-17: ¹H-NMR (DMSO-D₆) δ: 7.38-7.33 (1H, m), 6.81 (2H, d), 6.39 (2H, s), 4.17 (2H, t), 3.73 (3H, s), 2.59 (2H, t).

Intermediate Compound 5-18

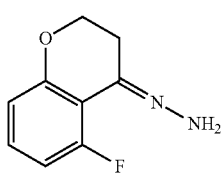

Intermediate compound 5-18: ¹H-NMR (DMSO-D$_6$) δ: 7.12-7.07 (1H, m), 6.76-6.73 (1H, m), 6.71-6.69 (1H, m), 6.60 (2H, s), 4.18 (2H, t), 2.63 (2H, t).

Intermediate Compound 5-19

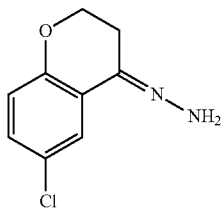

Intermediate compound 5-19: ¹H-NMR (DMSO-D$_6$) δ: 7.70 (1H, d), 7.13 (1H, dd), 6.87 (1H, d), 6.64 (2H, s), 4.19 (2H, t), 2.60 (2H, t).

Intermediate Compound 5-20

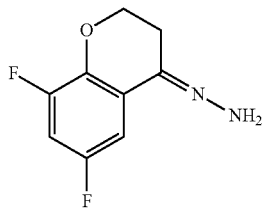

Intermediate compound 5-20: ¹H-NMR (DMSO-D$_6$) δ: 7.29-7.25 (1H, m), 7.14-7.09 (1H, m), 6.81 (2H, s), 4.26 (2H, t), 2.64 (2H, t).

Intermediate Compound 5-21

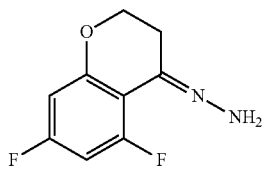

Intermediate compound 5-21: ¹H-NMR (DMSO-D$_6$) δ: 6.80-6.74 (1H, m), 6.66-6.62 (1H, m), 6.59 (2H, s), 4.22 (2H, t), 2.63 (2H, t)

Intermediate Compound 5-22

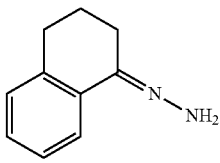

Intermediate compound 5-22: ¹H-NMR (DMSO-D$_6$) δ: 7.82-7.80 (1H, m), 7.14-7.09 (3H, m), 6.29 (2H, s), 2.66 (2H, t), 2.40 (2H, t), 1.82-1.75 (2H, m).

Intermediate Compound 5-23

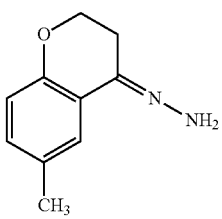

Intermediate compound 5-23: ¹H-NMR (DMSO-D$_6$) δ: 7.57 (1H, d), 6.94-6.91 (1H, m), 6.71 (1H, d), 6.36 (2H, s), 4.13 (2H, t), 2.58 (2H, t), 2.21 (3H, s).

Intermediate Compound 5-24

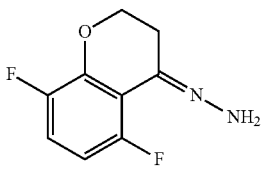

Intermediate compound 5-24: ¹H-NMR (DMSO-D$_6$) δ: 7.11-7.05 (1H, m), 6.79 (2H, s), 6.76-6.70 (1H, m), 4.28 (2H, t), 2.66 (2H, t).

Intermediate Compound 5-25

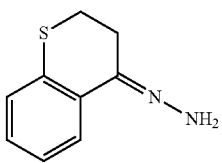

Intermediate compound 5-25: ¹H-NMR (DMSO-D$_6$) δ: 7.88-7.86 (1H, m), 7.18-7.15 (1H, m), 7.12-7.06 (2H, m), 6.54 (2H, s), 2.99 (2H, t), 2.74 (2H, t).

Intermediate Compound 5-26

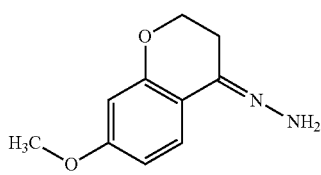

Intermediate compound 5-26: ¹H-NMR (DMSO-D$_6$) δ: 7.67 (1H, d), 6.51 (1H, dd), 6.39 (1H, d), 6.17 (2H, s), 4.17 (2H, t), 3.71 (3H, s), 2.58 (2H, t).

Reference Production Example 6-1

A mixture of 3.1 g of the Intermediate compound 5-1 and tetrahydrofuran 50 mL was cooled to 0° C., and thereto were added triethylamine 4.5 mL and propionyl chloride 2.3 mL successively. The mixture was stirred at room temperature for 14 hours. To the mixture was added water 50 mL, and the mixture was concentrated under reduced pressure. The resulting solids were filtered, and washed with water and hexane successively. The resulting solids were concentrated under reduced pressure to give 2.5 g the Intermediate compound 6-1.

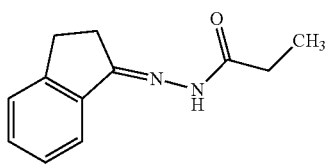

Intermediate compound 6-1: ¹H-NMR (DMSO-D$_6$) δ: 10.22 (0.6H, s), 10.15 (0.4H, s), 7.63 (1H, t), 7.39-7.36 (2H, m), 7.30-7.29 (1H, m), 3.09-3.04 (2H, m), 2.82-2.76 (2H, m), 2.65 (1.2H, q), 2.31 (0.8H, q), 1.08 (3H, t).

Reference Production Example 6-2

The compounds that were prepared according to the similar method to those defined in Reference Production example 6-1 and physical properties thereof are indicated below.

Intermediate Compound 6-2

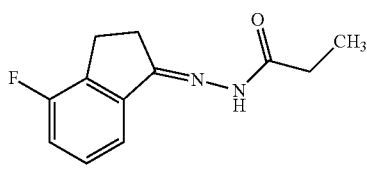

Intermediate compound 6-2: ¹H-NMR (DMSO-D$_6$) δ: 10.33 (0.6H, s), 10.18 (0.4H, s), 7.48-7.44 (1H, m), 7.38-7.31 (1H, m), 7.22-7.16 (1H, m), 3.09-3.05 (2H, m), 2.87-2.81 (2H, m), 2.65 (1.2H, q), 2.31 (0.8H, q), 1.08 (3H, t).

Intermediate Compound 6-3

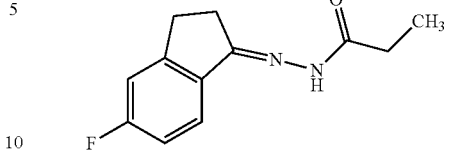

Intermediate compound 6-3: ¹H-NMR (DMSO-D$_6$) δ: 10.22 (0.6H, s), 10.10 (0.4H, s), 7.66-7.60 (1H, m), 7.23-7.21 (1H, m), 7.14-7.10 (1H, m), 3.07-3.04 (2H, m), 2.84-2.78 (2H, m), 2.68-2.61 (1.2H, m), 2.29 (0.8H, q), 1.07 (3H, t).

Intermediate Compound 6-4

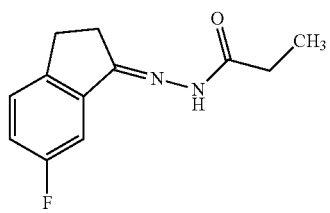

Intermediate Compound 6-4:
¹H-NMR (DMSO-D$_6$) δ: 10.31 (0.6H, s), 10.18 (0.4H, s), 7.42-7.38 (1H, m), 7.31-7.29 (1H, m), 7.24-7.17 (1H, m), 3.04-3.00 (2H, m), 2.86-2.80 (2H, m), 2.68-2.63 (1.2H, m), 2.31 (0.8H, q), 1.09-1.02 (3H, m).

Intermediate Compound 6-5

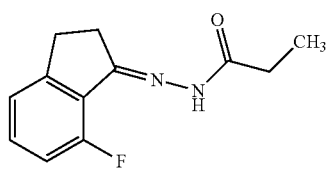

Intermediate compound 6-5: ¹H-NMR (DMSO-D$_6$) δ: 10.24 (0.7H, s), 10.09 (0.3H, s), 7.40-7.33 (1H, m), 7.22-7.18 (1H, m), 7.10-7.04 (1H, m), 3.11-3.08 (2H, m), 2.85-2.80 (2H, m), 2.64-2.58 (1.4H, m), 2.33-2.30 (0.6H, m), 1.09-1.02 (3H, m).

Intermediate Compound 6-6

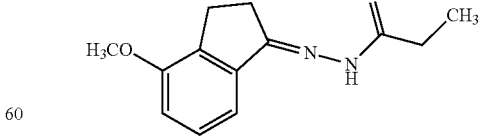

Intermediate compound 6-6: ¹H-NMR (DMSO-D$_6$) δ: 10.21 (0.6H, s), 10.07 (0.4H, s), 7.31-7.25 (1H, m), 7.21 (1H, t), 6.96 (1H, t), 3.83-3.81 (3H, m), 2.93-2.90 (2H, m), 2.80-2.75 (2H, m), 2.64 (1.2H, q), 2.29 (0.8H, q), 1.07 (3H, t).

Intermediate Compound 6-7

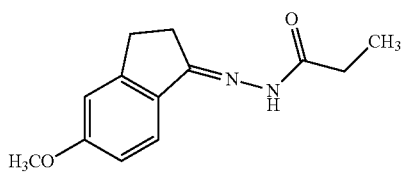

Intermediate compound 6-7: ¹H-NMR (DMSO-D$_6$) δ: 10.08 (0.6H, s), 9.98 (0.4H, s), 7.52 (1H, t), 6.95-6.92 (1H, m), 6.88-6.86 (1H, m), 3.79-3.78 (3H, m), 3.04-3.00 (2H, m), 2.80-2.75 (2H, m), 2.62 (1.2H, q), 2.27 (0.8H, q), 1.06 (3H, t).

Intermediate Compound 6-8

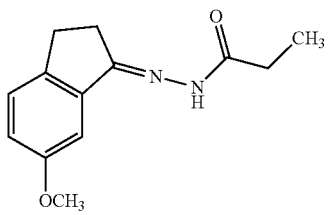

Intermediate compound 6-8: ¹H-NMR (DMSO-D$_6$) δ: 10.21 (0.6H, s), 10.09 (0.4H, s), 7.28-7.26 (1H, m), 7.08 (1H, t), 6.98-6.94 (1H, m), 3.78-3.77 (3H, m), 2.98-2.95 (2H, m), 2.83-2.77 (2H, m), 2.66 (1.2H, q), 2.30 (0.8H, q), 1.07 (3H, t).

Intermediate Compound 6-9

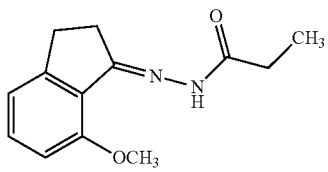

Intermediate compound 6-9: ¹H-NMR (DMSO-D$_6$) δ: 10.01 (0.7H, s), 9.87 (0.3H, s), 7.34-7.28 (1H, m), 6.95-6.91 (1H, m), 6.89-6.85 (1H, m), 3.82-3.81 (3H, m), 3.02-2.98 (2H, m), 2.78-2.71 (2H, m), 2.65-2.59 (1.4H, m), 2.27 (0.6H, q), 1.1-1.03 (3H, m).

Intermediate Compound 6-10

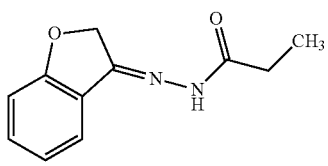

Intermediate compound 6-10: ¹H-NMR (DMSO-D$_6$) δ: 10.42 (0.5H, s), 10.28 (0.5H, s), 7.60-7.55 (1H, m), 7.43-7.37 (1H, m), 7.07-7.02 (2H, m), 5.13-5.12 (2H, m), 2.64 (1H, q), 2.27 (1H, q), 1.09-1.02 (3H, m).

Intermediate Compound 6-11

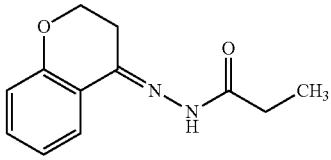

Intermediate compound 6-11: ¹H-NMR (DMSO-D$_6$) δ: 10.47 (0.6H, s), 10.35 (0.4H, s), 7.94-7.90 (1H, m), 7.30-7.25 (1H, m), 7.00-6.96 (1H, m), 6.89 (1H, d), 4.26-4.21 (2H, m), 2.83-2.80 (2H, m), 2.68 (1.3H, q), 2.30 (0.7H, q), 1.10-1.05 (3H, m).

Intermediate Compound 6-12

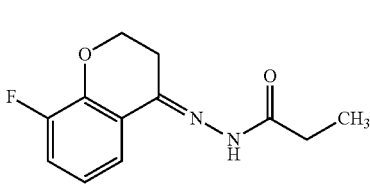

Intermediate compound 6-12: ¹H-NMR (DMSO-D$_6$) δ: 10.58 (0.6H, s), 10.44 (0.4H, s), 7.74-7.70 (1H, m), 7.24-7.20 (1H, m), 6.98-6.92 (1H, m), 4.35-4.30 (2H, m), 2.87-2.84 (2H, m), 2.68 (1.3H, q), 2.32 (0.7H, q), 1.08 (3H, t).

Intermediate Compound 6-13

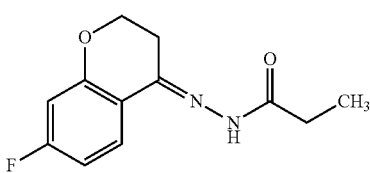

Intermediate compound 6-13: ¹H-NMR (DMSO-D$_6$) δ: 10.49 (0.6H, s), 10.38 (0.4H, s), 7.98-7.92 (1H, m), 6.87-6.77 (2H, m), 4.30-4.25 (2H, m), 2.82 (2H, t), 2.67 (1.2H, q), 2.30 (0.8H, q), 1.08 (3H, t).

Intermediate Compound 6-14

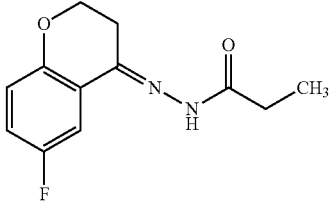

Intermediate compound 6-14: ¹H-NMR (DMSO-D$_6$) δ: 10.55-10.45 (1H, m), 7.59 (1H, dd), 7.15-7.10 (1H, m), 6.96-6.91 (1H, m), 4.24-4.20 (2H, m), 2.82-2.79 (2H, m), 2.72-2.67 (1.3H, m), 2.32 (0.7H, q), 1.10-1.02 (3H, m).

Intermediate Compound 6-15

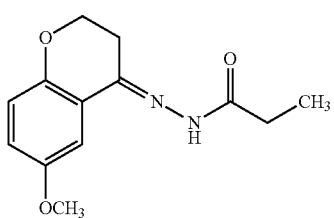

Intermediate compound 6-15: ¹H-NMR (DMSO-D$_6$) δ: 10.48 (0.6H, s), 10.36 (0.4H, s), 7.41-7.38 (1H, m), 6.91-6.83 (2H, m), 4.20-4.15 (2H, m), 3.72 (3H, s), 2.79-2.76 (2H, m), 2.69 (1.2H, q), 2.30 (0.8H, q), 1.11-1.06 (3H, m).

Intermediate compound 6-16

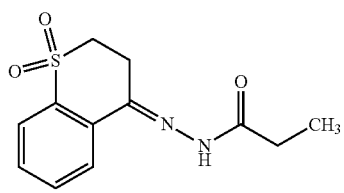

Intermediate compound 6-16: ¹H-NMR (DMSO-D$_6$) δ: 10.78 (1H, br s), 8.15 (1H, d), 7.86-7.84 (1H, m), 7.73 (1H, t), 7.64 (1H, t), 3.72-3.68 (2H, m), 3.23-3.18 (2H, m), 2.78-2.70 (1.4H, m), 2.40-2.36 (0.6H, m), 1.11-1.03 (3H, m).

Intermediate Compound 6-17

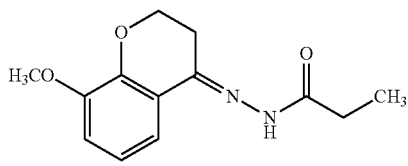

Intermediate compound 6-17: ¹H-NMR (DMSO-D$_6$) δ: 10.46 (0.6H, s), 10.33 (0.4H, s), 7.51-7.46 (1H, m), 6.97-6.87 (2H, m), 4.25-4.20 (2H, m), 3.76 (3H, s), 2.80 (2H, t), 2.71-2.64 (1.2H, m), 2.33-2.29 (0.8H, m), 1.08 (3H, t).

Intermediate Compound 6-18

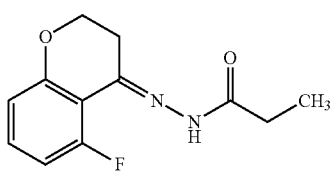

Intermediate compound 6-18: ¹H-NMR (DMSO-D$_6$) δ: 10.51 (0.8H, s), 10.35 (0.2H, s), 7.28-7.23 (1H, m), 6.83-6.75 (2H, m), 4.23 (2H, t), 2.83 (2H, t), 2.62 (1.6H, q), 2.33-2.28 (0.4H, m), 1.07 (3H, t).

Intermediate Compound 6-19

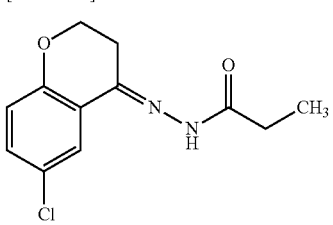

Intermediate compound 6-19: ¹H-NMR (DMSO-D$_6$) δ: 10.56 (1H, s), 7.85 (1H, d), 7.32-7.29 (1H, m), 6.95 (1H, d), 4.26-4.23 (2H, m), 2.83-2.81 (2H, m), 2.69 (1.3H, q), 2.33-2.29 (0.7H, m), 1.08 (3H, t).

Intermediate Compound 6-20

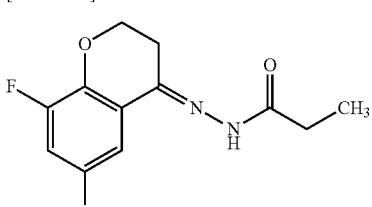

Intermediate compound 6-20: ¹H-NMR (DMSO-D$_6$) δ: 10.64 (1H, s), 7.45-7.43 (1H, m), 7.36-7.30 (1H, m), 4.35-4.29 (2H, m), 2.87-2.84 (2H, m), 2.69 (1.3H, q), 2.32 (0.7H, q), 1.08 (3H, t).

Intermediate Compound 6-21

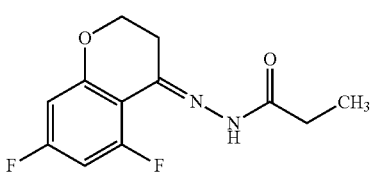

Intermediate compound 6-21: ¹H-NMR (DMSO-D$_6$) δ: 10.53 (1H, s), 6.89-6.84 (1H, m), 6.73-6.71 (1H, m), 4.26 (2H, t), 2.82 (2H, t), 2.60 (1.3H, q), 2.31-2.30 (0.7H, m), 1.06 (3H, t).

Intermediate Compound 6-22

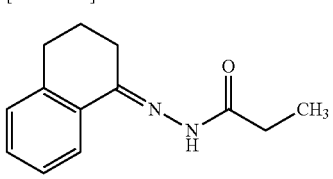

Intermediate compound 6-22: ¹H-NMR (DMSO-D$_6$) δ: 10.33 (0.7H, s), 10.23 (0.3H, s), 8.02-7.97 (1H, m), 7.26-7.17 (3H, m), 2.74-2.58 (5.3H, m), 2.35-2.29 (0.7H, m), 1.83-1.79 (2H, m), 1.08 (3H, t).

Intermediate Compound 6-23

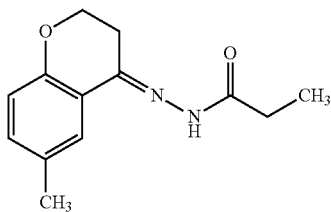

Intermediate compound 6-23: ¹H-NMR (DMSO-D$_6$) δ: 10.44 (0.6H, s), 10.33 (0.4H, s), 7.71 (1H, d), 7.11-7.07 (1H, m), 6.80-6.78 (1H, m), 4.22-4.16 (2H, m), 2.80-2.77 (2H, m), 2.69 (1.2H, q), 2.33-2.25 (3.8H, m), 1.10-1.05 (3H, m).

Intermediate Compound 6-24

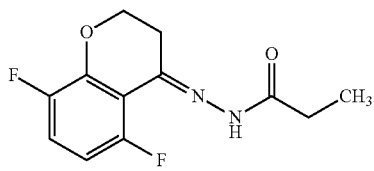

Intermediate compound 6-24: ¹H-NMR (DMSO-D$_6$) δ: 10.63 (0.8H, s), 10.44 (0.2H, s), 7.29-7.23 (1H, m), 6.84-6.78 (1H, m), 4.33 (2H, t), 2.87 (2H, t), 2.62 (1.6H, q), 2.33-2.31 (0.4H, m), 1.06 (3H, t).

Intermediate Compound 6-25

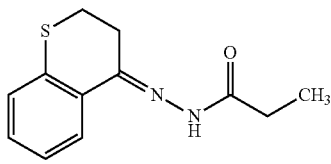

Intermediate compound 6-25: ¹H-NMR (DMSO-D$_6$) δ: 10.46 (0.6H, s), 10.34 (0.4H, s), 8.07-8.01 (1H, m), 7.24-7.24 (2H, m), 7.20-7.15 (1H, m), 3.07-3.02 (2H, m), 2.97-2.91 (2H, m), 2.68 (1.3H, q), 2.35-2.30 (0.7H, m), 1.08 (3H, t).

Intermediate Compound 6-26

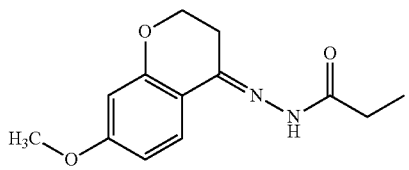

Intermediate compound 6-26: ¹H-NMR (DMSO-D$_6$) δ: 10.36 (0.6H, s), 10.25 (0.4H, s), 7.82 (1H, t), 6.60-6.57 (1H, m), 6.45-6.44 (1H, m), 4.25-4.20 (2H, m), 3.75-3.75 (3H, m), 2.77 (2H, t), 2.65 (1.2H, q), 2.30-2.26 (0.8H, m), 1.09-1.04 (3H, m).

Intermediate compound AA-1 was prepared according to the similar method to those described in Production example 1, and physical properties thereof are indicated below.

Intermediate Compound AA-1

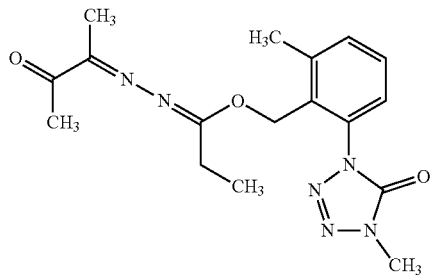

(n-hexane:ethyl acetate=2:1)

Intermediate compound AA-1: ¹H-NMR (CDCl$_3$) δ: 7.43-7.36 (2H, m), 7.28-7.25 (1H, m), 5.26 (2H, s), 3.69 (3H, s), 2.54-2.48 (5H, m), 2.43 (3H, s), 1.96 (3H, s), 1.06 (3H, t, J=7.6 Hz).

Reference Production Example 7-1

To mixture of toluene 10 mL, 2,2-difluoro-1,3-benzodioxol-4-carboxylic acid 5.0 g, a catalytic amount of DMF was added dropwise thionyl chloride 8.9 mL at room temperature. The mixture was stirred at 70° C. for 3 hours, and thereto was added toluene, and the mixture was concentrated under reduced pressure. To the resulting residues were added tetrahydrofuran 54 mL and triethylamine 7.6 mL. To the mixture was added N,O-dimethyl hydroxylamine hydrochloride 2.5 g, and the mixture was stirred at room temperature overnight. To the mixture was added 2N hydrochloric acid, and the mixture was stirred, and extracted with ethyl acetate. The resulting mixture was washed with sodium hydrogen carbonate and saturated brine successively, dried over sodium sulfate, and concentrated under reduced pressure. To mixture of the resulting residues and tetrahydrofuran 36 mL was added dropwise 1M methyl magnesium bromide of tetrahydrofuran solution 27 mL at 0° C., and the mixture was stirred at room temperature for 3 hours. To the mixture was added saturated aqueous ammonium chloride solution, and the mixture was extracted with ethyl acetate three times. The resulting organic layer was dried over magnesium sulfate, and concentrated under reduced pressure. The resulting residues were subjected to silica gel column chromatography (n-hexane:ethyl acetate=5:1) to give 3.2 g of Intermediate compound 7-1 as below-mentioned.

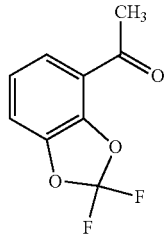

Intermediate compound 7-1: ¹H-NMR (CDCl₃) δ: 7.64 (1H, dd, J=8.1, 1.3 Hz), 7.26 (1H, dd, J=8.0, 1.4 Hz), 7.17 (1H, t, J=8.1 Hz), 2.67 (3H, s).

Reference Production Example 8

To mixture of DMF 20 mL, 3-acetyl-7-azaindole 1.00 g, and 60% sodium hydride 0.27 g was added dropwise methyl iodide 0.97 g at 0° C., and the mixture was stirred at room temperature for 3 hours. To the mixture was added water 20 mL, and extracted with ethyl acetate five times. The resulting organic layer was dried over magnesium sulfate, and concentrated under reduced pressure to give 1.1 g of Intermediate compound 8-1 as below-mentioned.

[Chem.289]

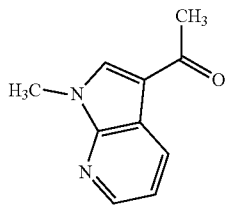

Intermediate compound 8-1: ¹H-NMR (CDCl₃) δ: 8.62 (1H, dd, J=7.9, 2.0 Hz), 8.41 (1H, dd, J=4.8, 1.6 Hz), 7.87-7.85 (1H, m), 7.26-7.22 (1H, m), 3.96 (3H, s), 2.53 (3H, s).

According to the above-mentioned process, the following compounds (hereianfter, collectively referred to as Present compound Z) can be obtained.

Present compound AA-D1-G1~AA-D1-G1943, AA-D2-G1~AA-D2-G1943, AA-D3-G1~AA-D3-G1943, AA-D4-G1~AA-D4-G1943, AA-D5-G1~AA-D5-G1943, AA-D6-G1~AA-D6-G1943, AA-D7-G1~AA-D7-G1943, AA-D8-G1~AA-D8-G1943, AA-D9-G1~AA-D9-G1943, AA-D10-G1~AA-D10-G1943, AA-D11-G1~AA-D11-G1943, BB-D1-G1~BB-D1-G1943, BB-D2-G1~BB-D2-G1943, BB-D3-G1~BB-D3-G1943, BB-D4-G1~BB-D4-G1943, BB-D5-G1~BB-D5-G1943, BB-D6-G1~BB-D6-G1943, BB-D7-G1~BB-D7-G1943, BB-D8-G1~BB-D8-G1943, BB-D9-G1~BB-D9-G1943, BB-D10-G1~BB-D10-G1943, BB-D11-G1~BB-D11-G1943, CC-D1-G1~CC-D1-G1943, CC-D2-G1~CC-D2-G1943, CC-D3-G1~CC-D3-G1943, CC-D4-G1~CC-D4-G1943, CC-D5-G1~CC-D5-G1943, CC-D6-G1~CC-D6-G1943, CC-D7-G1~CC-D7-G1943, CC-D8-G1~CC-D8-G1943, CC-D9-G1~CC-D9-G1943, CC-D10-G1~CC-D10-G1943, CC-D11-G1~CC-D11-G1943, DD-D1-G1~DD-D1-G1943, DD-D2-G1~DD-D2-G1943, DD-D3-G1~DD-D3-G1943, DD-D4-G1~DD-D4-G1943, DD-D5-G1~DD-D5-G1943, DD-D6-G1~DD-D6-G1943, DD-D7-G1~DD-D7-G1943, DD-D8-G1~DD-D8-G1943, DD-D9-G1~DD-D9-G1943, DD-D10-G1~DD-D10-G1943, DD-D11-G1~DD-D11-G1943, EE-F1-G1~EE-F1-G1943, EE-F2-G1~EE-F2-G1943, EE-F3-G1~EE-F3-G1943, EE-F4-G1~EE-F4-G1943, EE-F5-G1~EE-F5-G1943, EE-F6-G1~EE-F6-G1943, EE-F7-G1~EE-F7-G1943, EE-F8-G1~EE-F8-G1943, EE-F9-G1~EE-F9-G1943, EE-F10-G1~EE-F10-G1943, EE-F11-G1~EE-F11-G1943, EE-F12-G1~EE-F12-G1943, EE-F13-G1~EE-F13-G1943, EE-F14-G1~EE-F14-G1943, EE-F15-G1~EE-F15-G1943, EE-F16-G1~EE-F16-G1943, EE-F17-G1~EE-F17-G1943, EE-F18-G1~EE-F18-G1943, EE-F19-G1~EE-F19-G1943, EE-F20-G1~EE-F20-G1943, EE-F21-G1~EE-F21-G1943,
FF-F1-G1~FF-F1-G1943, FF-F2-G1~FF-F2-G1943, FF-F3-G1~FF-F3-G1943, FF-F4-G1~FF-F4-G1943, FF-F5-G1~FF-F5-G1943, FF-F6-G1~FF-F6-G1943, FF-F7-G1~FF-F7-G1943, FF-F8-G1~FF-F8-G1943, FF-F9-G1~FF-F9-G1943, FF-F10-G1~FF-F10-G1943, FF-F11-G1~FF-F11-G1943, FF-F12-G1~FF-F12-G1943, FF-F13-G1~FF-F13-G1943, FF-F14-G1~FF-F14-G1943, FF-F15-G1~FF-F15-G1943, FF-F16-G1~FF-F16-G1943, FF-F17-G1~FF-F17-G1943, FF-F18-G1~FF-F18-G1943, FF-F19-G1~FF-F19-G1943, FF-F20-G1~FF-F20-G1943, FF-F19-G1~FF-F19-G1943, FF-F20-G1~FF-F20-G1943, GG-F2-G1~GG-F2-G1943, GG-F3-G1~GG-F3-G1943, GG-F4-G1~GG-F4-G1943, GG-F5-G1~GG-F5-G1943, GG-F6-G1~GG-F6-G1943, GG-F7-G1~GG-F7-G1943, GG-F8-G1~GG-F8-G1943, GG-F9-G1~GG-F9-G1943, GG-F10-G1~GG-F10-G1943, GG-F11-G1~GG-F11-G1943, GG-F12-G1~GG-F12-G1943, GG-F13-G1~GG-F13-G1943, GG-F14-G1~GG-F14-G1943, GG-F15-G1~GG-F15-G1943, GG-F16-G1~GG-F16-G1943, GG-F17-G1~GG-F17-G1943, GG-F18-G1~GG-F18-G1943, GG-F19-G1~GG-F19-G1943, GG-F20-G1~GG-F20-G1943, GG-F21-G1~GG-F21-G1943, HH-F1-G1~HH-F1-G1943, HH-F2-G1~HH-F2-G1943, HH-F3-G1~HH-F3-G1943, HH-F4-G1~HH-F4-G1943, HH-F5-G1~HH-F5-G1943, HH-F6-G1~HH-F6-G1943, HH-F7-G1~HH-F7-G1943, HH-F8-G1~HH-F8-G1943, HH-F9-G1~HH-F9-G1943, HH-F10-G1~HH-F10-G1943, HH-F11-G1~HH-F11-G1943, HH-F12-G1~HH-F12-G1943, HH-F13-G1~HH-F13-G1943, HH-F14-G1~HH-F14-G1943, HH-F15-G1~HH-F15-G1943, HH-F16-G1~HH-F16-G1943, HH-F17-G1~HH-F17-G1943, HH-F18-G1~HH-F18-G1943, HH-F19-G1~HH-F19-G1943, HH-F20-G1~HH-F20-G1943, HH-F21-G1~HH-F21-G1943,
II-D1-E1-H1~II-D1-E1-H1888, II-D1-E2-H1~II-D1-E2-H1888, II-D1-E3-H1~II-D1-E3-H1888, II-D1-E4-H1~II-D1-E4-H1888, II-D1-E5-H1~II-D1-E5-H1888, II-D1-E6-H1~II-D1-E6-H1888, II-D1-E7-H1~II-D1-E7-H1888, II-D1-E8-H1~II-D1-E8-H1888, II-D1-E9-H1~II-D1-E9-H1888, II-D1-E10-H1~II-D1-E10-H1888, II-D1-E11-H1~II-D1-E11-H1888, II-D2-E1-H1~II-D2-E1-H1888, II-D2-E2-H1~II-D2-E2-H1888, II-D2-E3-H1~II-D2-E3-H1888, II-D2-E4-H1~II-D2-E4-H1888, II-D2-E5-H1~II-D2-E5-H1888, II-D2-E6-H1~II-D2-E6-H1888, II-D2-E7-H1~II-D2-E7-H1888, II-D2-E8-H1~II-D2-E8-H1888, II-D2-E9-H1~II-D2-E9-H1888, II-D2-E10-H1~II-D2-E10-H1888, II-D2-E11-H1~II-D2-E11-H1888, II-D3-E1-H1~II-D3-E1-H1888, II-D3-E2-H1~II-D3-E2-H1888, II-D3-E3-H1~II-D3-E3-H1888, II-D3-E4-H1~II-D3-E4-H1888, II-D3-E5-H1~II-D3-E5-H1888, II-D3-E6-H1~II-D3-E6-H1888, II-D3-E7-H1~II-D3-E7-H1888, II-D3-E8-H1~II-D3-E8-H1888, II-D3-E9-H1~II-D3-E9-H1888, II-D3-E10-H1~II-D3-E10-H1888, II-D3-E11-H1~II-D3-E11-H1888, II-D4-E1-H1~II-D4-E1-H1888, II-D4-E2-H1~II-D4-E2-H1888, II-D4-E3-H1~II-D4-E3-H1888, II-D4-E4-H1~II-D4-E4-H1888, II-D4-E5-H1~II-D4-E5-H1888, II-D4-E6-H1~II-D4-E6-H1888, II-D4-E7-H1~II-D4-E7-H1888, II-D4-E8-H1~II-D4-E8-H1888, II-D4-E9-H1~II-D4-E9-H1888, II-D4-E10-H1~II-D4-E10-H1888, II-D4-E11-H1~II-D4-E11-H1888, II-D5-E1-H1~II-D5-E1-H1888, II-D5-E2-H1~II-D5-E2-H1888, II-D5-E3-H1~II-D5-E3-H1888, II-D5-E4-H1~II-D5-E4-H1888, II-D5-E5-H1~II-D5-E5-H1888, II-D5-E6-H1~II-D5-E6-H1888, II-D5-E7-H1~II-D5-E7-H1888, II-D5-E8-H1~II-D5-E8-H1888, II-D5-E9-H1~II-D5-E9-H1888, II-D5-E10-H1~II-D5-E10-H1888, II-D5-E11-H1~II-D5-E11-H1888, II-D6-E1-H1~II-D6-E1-H1888, II-D6-E2-H1~II-D6-E2-H1888, II-D6-E3-H1~II-D6-E3-H1888, II-D6-E4-H1~II-D6-E4-H1888, II-D6-E5-H1~II-D6-E5-H1888, II-D6-E6-H1~II-D6-E6-H1888, II-D6-E7-H1~II-D6-E7-H1888, II-D6-E8-H1~II-D6-E8-H1888, II-D6-E9-H1~II-D6-E9-H1888, II-D6-E10-H1~II-D6-E10-H1888, II-D6-E11-H1~II-D6-E11-H1888, II-D7-E1-H1~II-D7-E1-H1888, II-D7-E2-H1~II-D7-E2-H1888, II-D7-E3-H1~II-D7-E3-H1888, II-D7-E4-H1~II-D7-E4-H1888, II-D7-E5-H1~II-D7-E5-H1888, II-D7-E6-H1~II-D7-E6-H1888, II-D7-E7-H1~II-D7-E7-H1888, II-D7-E8-H1~II-D7-E8-H1888, II-D7-E9-H1~II-D7-E9-H1888, II-D7-E10-H1~II-D7-E10-H1888, II-D7-E11-H1~II-D7-E11-H1888, II-D8-E1-H1~II-D8-E1-H1888, II-D8-E2-H1~II-D8-E2-H1888, II-D8-E3-H1~II-D8-E3-H1888, II-D8-E4-H1~II-D8-E4-H1888, II-D8-E5-H1~II-D8-E5-H1888, II-D8-E6-H1~II-D8-E6-H1888, II-D8-E7-H1~II-D8-E7-H1888, II-D8-E8-H1~II-D8-E8-H1888, II-D8-E9-H1~II-D8-E9-H1888, II-D8-E10-H1~II-D8-E10-H1888, II-D8-E11-H1~II-D8-E11-H1888, II-D9-E1-H1~II-D9-E1-H1888, II-D9-E2-H1~II-D9-E2-H1888, II-D9-E3-H1~II-D9-E3-H1888, II-D9-E4-H1~II-D9-E4-H1888, II-D9-E5-H1~II-D9-E5-H1888, II-D9-E6-H1~II-D9-E6-H1888, II-D9-E7-H1~II-D9-E7-H1888, II-D9-E8-H1~II-D9-E8-H1888, II-D9-E9-H1~II-D9-E9-H1888, II-D9-E10-H1~II-D9-E10-H1888, II-D9-E11-H1~II-D9-E11-H1888, II-D10-E1-H1~II-D10-E1-H1888, II-D10-E2-H1~II-D10-E2-H1888, II-D10-E3-H1~II-D10-E3-H1888, II-D10-E4-H1~II-D10-E4-H1888, II-D10-E5-H1~II-D10-E5-H1888, II-D10-E6-H1~II-D10-E6-H1888, II-D10-E7-H1~II-D10-E7-H1888, II-D10-E8-H1~II-D10-E8-H1888, II-D10-E9-H1~II-D10-E9-H1888, II-D10-E10-H1~II-D10-E10-H1888, II-D10-E11-H1~II-D10-E11-H1888, II-D11-E1-H1~II-D11-E1-H1888, II-D11-E2-H1~II-D11-E2-H1888, II-D11-E3-H1~II-D11-E3-H1888, II-D11-E4-H1~II-D11-E4-H1888, II-D11-E5-H1~II-D11-E5-H1888, II-D11-E6-H1~II-D11-E6-H1888, II-D11-E7-H1~II-D11-E7-H1888, II-D11-E8-H1~II-D11-E8-H1888, II-D11-E9-H1~II-D11-E9-H1888, II-D11-E10-H1~II-D11-E10-H1888, II-D11-E11-H1~II-D11-E11-H1888, JJ-D1-E1-H1~JJ-D1-E1-H1888, JJ-D1-E2-H1~JJ-D1-E2-H1888, JJ-D1-E3-H1~JJ-D1-E3-H1888, JJ-D1-E4-H1~JJ-D1-E4-H1888, JJ-D1-E5-H1~JJ-D1-E5-H1888, JJ-D1-E6-H1~JJ-D1-E6-H1888, JJ-D1-E7-H1~JJ-D1-E7-H1888, JJ-D1-E8-H1~JJ-D1-E8-H1888, JJ-D1-E9-H1~JJ-D1-E9-H1888, JJ-D1-E10-H1~JJ-D1-E10-H1888, JJ-D1-E11-H1~JJ-D1-E11-H1888, JJ-D2-E1-H1~JJ-D2-E1-H1888, JJ-D2-E2-H1~JJ-D2-E2-H1888, JJ-D2-E3-H1~JJ-D2-E3-H1888, JJ-D2-E4-H1~JJ-D2-E4-H1888, JJ-D2-E5-H1~JJ-D2-E5-H1888, JJ-D2-E6-H1~JJ-D2-E6-H1888, JJ-D2-E7-H1~JJ-D2-E7-H1888, JJ-D2-E6-H1888, JJ-D2-E7-H1~JJ-D2-E7-H1888~JJ-D2-E9-H1888, JJ-D2-E10-H1~JJ-D2-E10-H1888, JJ-D2-E11-H1~JJ-D2-E11-H1888, JJ-D3-E1-H1~JJ-D3-E1-H1888, JJ-D3-E2-H1~JJ-D3-E2-H1888, JJ-D3-E3-H1~JJ-D3-E3-H1888, JJ-D3-E4-H1~JJ-D3-E4-H1888, JJ-D3-E5-H1~JJ-D3-E5-H1888, JJ-D3-E6-H1~JJ-D3-E6-H1888, JJ-D3-E7-H1~JJ-D3-E7-H1888, JJ-D3-E8-H1~JJ-D3-E8-H1888, JJ-D3-E9-H1~JJ-D3-E9-H1888, JJ-D3-E10-H1~JJ-D3-E10-H1888, JJ-D3-E11-H1~JJ-D3-E11-H1888, JJ-D4-E1-H1~JJ-D4-E1-H1888, JJ-D4-E2-H1~JJ-D4-E2-H1888, JJ-D4-E3-H1~JJ-D4-E3-H1888, JJ-D4-E4-H1~JJ-D4-E4-H1888, JJ-D4-E5-H1~JJ-D4-E5-H1888, JJ-D4-E6-H1~JJ-D4-E6-H1888, JJ-D4-E7-H1~JJ-D4-E7-H1888, JJ-D4-E8-H1~JJ-D4-E8-H1888, JJ-D4-E9-H1~JJ-D4-E9-H1888, JJ-D4-E10-H1~JJ-D4-E10-H1888, JJ-D4-E11-H1~JJ-D4-E11-H1888, JJ-D5-E1-H1~JJ-D5-E1-H1888, JJ-D5-E2-H1~JJ-D5-E2-H1888, JJ-D5-E3-H1~JJ-D5-E3-H1888, JJ-D5-E4-H1~JJ-D5-E4-H1888, JJ-D5-E5-H1~JJ-D5-E5-H1888, JJ-D5-E6-H1~JJ-D5-E6-H1888, JJ-D5-E7-H1~JJ-D5-E7-H1888, JJ-D5-E8-H1~JJ-D5-E8-H1888, JJ-D5-E9-H1~JJ-D5-E9-H1888, JJ-D5-E10-H1~JJ-D5-E10-H1888, JJ-D5-E11-H1~JJ-D5-E11-H1888, JJ-D6-E1-H1~JJ-D6-E1-H1888, JJ-D6-E2-H1~JJ-D6-E2-H1888, JJ-D6-E3-H1~JJ-D6-E3-H1888, JJ-D6-E4-H1~JJ-D6-E4-H1888, JJ-D6-E5-H1~JJ-D6-E5-H1888, JJ-D6-E6-H1~JJ-D6-E6-H1888, JJ-D6-E7-H1~JJ-D6-E7-H1888, JJ-D6-E8-H1~JJ-D6-E8-H1888, JJ-D6-E9-H1~JJ-D6-E9-H1888, JJ-D6-E10-H1~JJ-D6-E10-H1888, JJ-D6-E11-H1~JJ-D6-E11-H1888, JJ-D7-E1-H1~JJ-D7-E1-H1888, JJ-D7-E2-H1~JJ-D7-E2-H1888, JJ-D7-E3-H1~JJ-D7-E3-H1888, JJ-D7-E4-H1~JJ-D7-E4-H1888, JJ-D7-E5-H1~JJ-D7-E5-H1888, JJ-D7-E6-H1~JJ-D7-E6-H1888, JJ-D7-E7-H1~JJ-D7-E7-H1888, JJ-D7-E8-H1~JJ-D7-E8-H1888, JJ-D7-E9-H1~JJ-D7-E9-H1888, JJ-D7-E10-H1~JJ-D7-E10-H1888, JJ-D7-E11-H1~JJ-D7-E11-H1888, JJ-D8-E1-H1~JJ-D8-E1-H1888, JJ-D8-E2-H1~JJ-D8-E2-H1888, JJ-D8-E3-H1~JJ-D8-E3-H1888, JJ-D8-E4-H1~JJ-D8-E4-H1888, JJ-D8-E5-H1~JJ-D8-E5-H1888, JJ-D8-E6-H1~JJ-D8-E6-H1888, JJ-D8-E7-H1~JJ-D8-E7-H1888, JJ-D8-E8-H1~JJ-D8-E8-H1888, JJ-D8-E9-H1~JJ-D8-E9-H1888, JJ-D8-E10-H1~JJ-D8-E10-H1888, JJ-D8-E11-H1~JJ-D8-E11-H1888, JJ-D9-E1-H1~JJ-D9-E1-H1888, JJ-D9-E2-H1~JJ-D9-E2-H1888, JJ-D9-E3-H1~JJ-D9-E3-H1888, JJ-D9-E4-H1~JJ-D9-E4-H1888, JJ-D9-E5-H1~JJ-D9-E5-H1888, JJ-D9-E6-H1~JJ-D9-E6-H1888, JJ-D9-E7-H1~JJ-D9-E7-H1888, JJ-D9-E8-H1~JJ-D9-E8-H1888, JJ-D9-E9-H1~JJ-D9-E9-H1888, JJ-D9-E10-H1~JJ-D9-E10-H1888, JJ-D9-E11-H1~JJ-D9-E11-H1888, JJ-D10-E1-H1~JJ-D10-E1-H1888, JJ-D10-E2-H1~JJ-D10-E2-H1888, JJ-D10-E3-H1~JJ-D10-E3-H1888, JJ-D10-E4-H1~JJ-D10-E4-H1888, JJ-D10-E5-H1~JJ-D10-E5-H1888, JJ-D10-E6-H1~JJ-D10-E6-H1888, JJ-D10-E7-H1~JJ-D10-E7-H1888, JJ-D10-E8-H1~JJ-D10-E8-H1888, JJ-D10-E9-H1~JJ-D10-E9-H1888, JJ-D10-E10-H1~JJ-D10-E10-H1888, JJ-D10-E11-H1~JJ-D10-E11-H1888, JJ-D11-E1-H1~JJ-D11-E1-H1888, JJ-D11-E2-H1~JJ-D11-E2-H1888, JJ-D11-E3-H1~JJ-D11-E3-H1888, JJ-D11-E4-H1~JJ-D11-E4-H1888, JJ-D11-E5-H1~JJ-D11-E5-H1888, JJ-D11-E6-H1~JJ-D11-E6-H1888, JJ-D11-E7-H1~JJ-D11-E7-H1888, JJ-D11-E8-H1~JJ-D11-E8-H1888, JJ-D11-E9-H1~JJ-D11-E9-H1888, JJ-D11-E10-H1~JJ-D11-E10-H1888, JJ-D11-E11-H1~JJ-D11-E11-H1888, KK-D1-J1~KK-D1-J20, KK-D2-J1~KK-D2-J20, KK-D3-J KK-D3-J20, KK-D4-J1~KK-D4-J20, KK-D5-J1~KK-D5-J20, KK-D6-J1~KK-D6-J20, KK-D7-J1~KK-D7-J20, KK-D8-J1~KK-D8-J20, KK-D9-J1~KK-D9-J20, KK-D10-J1~KK-D10-J20, KK-D11-J1~KK-D11-J20, LL-D1-J1~LL-D1-J20, LL-D2-J1~LL-D2-J20, LL-D3-J1~LL-D3-J20, LL-D4-J1~LL-D4-J20, LL-D5-J1~LL-D5-J20, LL-D6-J1~LL-D6-J20, LL-D7-J1~LL-D7-J20, LL-D8-J1~LL-D8-J20, LL-D9-J1~LL-D9-J20, LL-D10-J1~LL-D10-J20, LL-D11-J1~LL-D11-J20, MM-L1-M1-N1-K1~MM-L1-M1-N1-K45, MM-L2-M1-N1-K1~MM-L2-M1-N1-K45, MM-L3-M1-N1-K1~MM-L3-M1-N1-K45, MM-L4-M1-N1-K1~MM-L4-M1-N1-K45, MM-L5-M1-N1-K1~MM-L5-M1-N1-K45, MM-L6-M1-N1-K1~MM-L6-M1-N1-K45, MM-L7-M1-N1-K1~MM-L7-M1-N1-K45, MM-L1-M2-N1-K1~MM-L1-M2-N1-K45, MM-L2-M2-N1-K1~MM-L2-M2-N1-K45, MM-L3-M2-N1-K1~MM-L3-M2-N1-K45, MM-L4-M2-N1-K1~MM-L4-M2-N1-K45, MM-L5-M2-N1-K1~MM-L5-M2-N1-K45, MM-L6-M2-N1-K1~MM-L6-M2-N1-K45, MM-L7-M2-N1-K1~MM-L7-M2-N1-K45, MM-L1-

M3-N1-K1~MM-L1-M3-N1-K45, MM-L2-M3-N1-K1~MM-L2-M3-N1-K45, MM-L3-M3-N1-K1~MM-L3-M3-N1-K45, MM-L4-M3-N1-K1~MM-L4-M3-N1-K45, MM-L5-M3-N1-K1~MM-L5-M3-N1-K45, MM-L6-M3-N1-K1~MM-L6-M3-N1-K45, MM-L7-M3-N1-K1~MM-L7-M3-N1-K45, MM-L1-M4-N1-K1~MM-L1-M4-N1-K45, MM-L2-M4-N1-K1~MM-L2-M4-N1-K45, MM-L3-M4-N1-K1~MM-L3-M4-N1-K45, MM-L4-M4-N1-K1~MM-L4-M4-N1-K45, MM-L5-M4-N1-K1~MM-L5-M4-N1-K45, MM-L6-M4-N1-K1~MM-L6-M4-N1-K45, MM-L7-M4-N1-K1~MM-L7-M4-N1-K45, MM-L1-M5-N1-K1~MM-L1-M5-N1-K45, MM-L2-M5-N1-K1~MM-L2-M5-N1-K45, MM-L3-M5-N1-K1~MM-L3-M5-N1-K45, MM-L4-M5-N1-K1~MM-L4-M5-N1-K45, MM-L5-M5-N1-K1~MM-L5-M5-N1-K45, MM-L6-M5-N1-K1~MM-L6-M5-N1-K45, MM-L7-M5-N1-K1~MM-L7-M5-N1-K45, MM-L1-M6-N1-K1~MM-L1-M6-N1-K45, MM-L2-M6-N1-K1~MM-L2-M6-N1-K45, MM-L3-M6-N1-K1~MM-L3-M6-N1-K45, MM-L4-M6-N1-K1~MM-L4-M6-N1-K45, MM-L5-M6-N1-K1~MM-L5-M6-N1-K45, MM-L6-M6-N1-K1~MM-L6-M6-N1-K45, MM-L7-M6-N1-K1~MM-L7-M6-N1-K45, MM-L1-M7-N1-K1~MM-L1-M7-N1-K45, MM-L2-M7-N1-K1~MM-L2-M7-N1-K45, MM-L3-M7-N1-K1~MM-L3-M7-N1-K45, MM-L4-M7-N1-K1~MM-L4-M7-N1-K45, MM-L5-M7-N1-K1~MM-L5-M7-N1-K45, MM-L6-M7-N1-K1~MM-L6-M7-N1-K45, MM-L7-M7-N1-K1~MM-L7-M7-N1-K45, MM-L1-M1-N2-K1~MM-L1-M1-N2-K45, MM-L2-M1-N2-K1~MM-L2-M1-N2-K45, MM-L3-M1-N2-K1~MM-L3-M1-N2-K45, MM-L4-M1-N2-K1~MM-L4-M1-N2-K45, MM-L5-M1-N2-K1~MM-L5-M1-N2-K45, MM-L6-M1-N2-K1~MM-L6-M1-N2-K45, MM-L7-M1-N2-K1~MM-L7-M1-N2-K45, MM-L1-M2-N2-K1~MM-L1-M2-N2-K45, MM-L2-M2-N2-K1~MM-L2-M2-N2-K45, MM-L3-M2-N2-K1~MM-L3-M2-N2-K45, MM-L4-M2-N2-K1~MM-L4-M2-N2-K45, MM-L5-M2-N2-K1~MM-L5-M2-N2-K45, MM-L6-M2-N2-K1~MM-L6-M2-N2-K45, MM-L7-M2-N2-K1~MM-L7-M2-N2-K45, MM-L1-M3-N2-K1~MM-L1-M3-N2-K45, MM-L2-M3-N2-K1~MM-L2-M3-N2-K45, MM-L3-M3-N2-K1~MM-L3-M3-N2-K45, MM-L4-M3-N2-K1~MM-L4-M3-N2-K45,

MM-L5-M3-N2-K1~MM-L5-M3-N2-K45, MM-L6-M3-N2-K1~MM-L6-M3-N2-K45, MM-L7-M3-N2-K1~MM-L7-M3-N2-K45, MM-L1-M4-N2-K1~MM-L1-M4-N2-K45, MM-L2-M4-N2-K1~MM-L2-M4-N2-K45, MM-L3-M4-N2-K1~MM-L3-M4-N2-K45, MM-L4-M4-N2-K1~MM-L4-M4-N2-K45, MM-L5-M4-N2-K1~MM-L5-M4-N2-K45, MM-L6-M4-N2-K1~MM-L6-M4-N2-K45, MM-L7-M4-N2-K1~MM-L7-M4-N2-K45, MM-L1-M5-N2-K1~MM-L1-M5-N2-K45, MM-L2-M5-N2-K1~MM-L2-M5-N2-K45, MM-L3-M5-N2-K1~MM-L3-M5-N2-K45, MM-L4-M5-N2-K1~MM-L4-M5-N2-K45, MM-L5-M5-N2-K1~MM-L5-M5-N2-K45, MM-L6-M5-N2-K1~MM-L6-M5-N2-K45, MM-L7-M5-N2-K1~MM-L7-M5-N2-K45, MM-L1-M6-N2-K1~MM-L1-M6-N2-K45, MM-L2-M6-N2-K1~MM-L2-M6-N2-K45, MM-L3-M6-N2-K1~MM-L3-M6-N2-K45, MM-L4-M6-N2-K1~MM-L4-M6-N2-K45, MM-L5-M6-N2-K1~MM-L5-M6-N2-K45, MM-L6-M6-N2-K1~MM-L6-M6-N2-K45, MM-L7-M6-N2-K1~MM-L7-M6-N2-K45, MM-L1-M7-N2-K1~MM-L1-M7-N2-K45, MM-L2-M7-N2-K1~MM-L2-M7-N2-K45, MM-L3-M7-N2-K1~MM-L3-M7-N2-K45, MM-L4-M7-N2-K1~MM-L4-M7-N2-K45, MM-L5-M7-N2-K1~MM-L5-M7-N2-K45, MM-L6-M7-N2-K1~MM-L6-M7-N2-K45, MM-L7-M7-N2-K1~MM-L7-M7-N2-K45, MM-L1-M1-N3-K1~MM-L1-M1-N3-K45, MM-L2-M1-N3-K1~MM-L2-M1-N3-K45, MM-L3-M1-N3-K1~MM-L3-M1-N3-K45, MM-L4-M1-N3-K1~MM-L4-M1-N3-K45, MM-L5-M1-N3-K1~MM-L5-M1-N3-K45, MM-L6-M1-N3-K1~MM-L6-M1-N3-K45, MM-L7-M1-N3-K1~MM-L7-M1-N3-K45, MM-L1-M2-N3-K1~MM-L1-M2-N3-K45, MM-L2-M2-N3-K1~MM-L2-M2-N3-K45, MM-L3-M2-N3-K1~MM-L3-M2-N3-K45, MM-L4-M2-N3-K1~MM-L4-M2-N3-K45, MM-L5-M2-N3-K1~MM-L5-M2-N3-K45, MM-L6-M2-N3-K1~MM-L6-M2-N3-K45, MM-L7-M2-N3-K1~MM-L7-M2-N3-K45, MM-L1-M3-N3-K1~MM-L1-M3-N3-K45, MM-L2-M3-N3-K1~MM-L2-M3-N3-K45, MM-L3-M3-N3-K1~MM-L3-M3-N3-K45, MM-L4-M3-N3-K1~MM-L4-M3-N3-K45, MM-L5-M3-N3-K1~MM-L5-M3-N3-K45, MM-L6-M3-N3-K1~MM-L6-M3-N3-K45, MM-L7-M3-N3-K1~MM-L7-M3-N3-K45, MM-L1-M4-N3-K1~MM-L1-M4-N3-K45, MM-L2-M4-N3-K1~MM-L2-M4-N3-K45, MM-L3-M4-N3-K1~MM-L3-M4-N3-K45, MM-L4-M4-N3-K1~MM-L4-M4-N3-K45, MM-L5-M4-N3-K1~MM-L5-M4-N3-K45, MM-L6-M4-N3-K1~MM-L6-M4-N3-K45, MM-L7-M4-N3-K1~MM-L7-M4-N3-K45, MM-L1-M5-N3-K1~MM-L1-M5-N3-K45, MM-L2-M5-N3-K1~MM-L2-M5-N3-K45, MM-L3-M5-N3-K1~MM-L3-M5-N3-K45, MM-L4-M5-N3-K1~MM-L4-M5-N3-K45, MM-L3-M5-N3-K45, MM-L4-M5-N3-K1~MM-L4-M5-N3-K45~MM-L6-M5-N3-K45, MM-L7-M5-N3-K1~MM-L7-M5-N3-K45, MM-L1-M6-N3-K1~MM-L1-M6-N3-K45,

MM-L2-M6-N3-K1~MM-L2-M6-N3-K45, MM-L3-M6-N3-K1~MM-L3-M6-N3-K45, MM-L4-M6-N3-K1~MM-L4-M6-N3-K45, MM-L5-M6-N3-K1~MM-L5-M6-N3-K45, MM-L6-M6-N3-K1~MM-L6-M6-N3-K45, MM-L7-M6-N3-K1~MM-L7-M6-N3-K45, MM-L1-M7-N3-K1~MM-L1-M7-N3-K45, MM-L2-M7-N3-K1~MM-L2-M7-N3-K45, MM-L3-M7-N3-K1~MM-L3-M7-N3-K45, MM-L4-M7-N3-K1~MM-L4-M7-N3-K45, MM-L5-M7-N3-K1~MM-L5-M7-N3-K45, MM-L6-M7-N3-K1~MM-L6-M7-N3-K45, MM-L7-M7-N3-K1~MM-L7-M7-N3-K45, MM-L1-M1-N4-K1~MM-L1-M1-N4-K45, MM-L2-M1-N4-K1~MM-L2-M1-N4-K45, MM-L3-M1-N4-K1~MM-L3-M1-N4-K45, MM-L4-M1-N4-K1~MM-L4-M1-N4-K45, MM-L5-M1-N4-K1~MM-L5-M1-N4-K45, MM-L6-M1-N4-K1~MM-L6-M1-N4-K45, MM-L7-M1-N4-K1~MM-L7-M1-N4-K45, MM-L1-M2-N4-K1~MM-L1-M2-N4-K45, MM-L2-M2-N4-K1~MM-L2-M2-N4-K45, MM-L3-M2-N4-K1~MM-L3-M2-N4-K45, MM-L4-M2-N4-K1~MM-L4-M2-N4-K45, MM-L5-M2-N4-K1~MM-L5-M2-N4-K45, MM-L6-M2-N4-K1~MM-L6-M2-N4-K45, MM-L7-M2-N4-K1~MM-L7-M2-N4-K45, MM-L1-M3-N4-K1~MM-L1-M3-N4-K45, MM-L2-M3-N4-K1~MM-L2-M3-N4-K45, MM-L3-M3-N4-K1~MM-L3-M3-N4-K45, MM-L4-M3-N4-K1~MM-L4-M3-N4-K45, MM-L5-M3-N4-K1~MM-L5-M3-N4-K45, MM-L6-M3-N4-K1~MM-L6-M3-N4-K45, MM-L7-M3-N4-K1~MM-L7-M3-N4-K45, MM-L1-M4-N4-K1~MM-L1-M4-N4-K45, MM-L2-M4-N4-K1~MM-L2-M4-N4-K45, MM-L3-M4-N4-K1~MM-L3-M4-N4-K45, MM-L4-M4-N4-K1~MM-L4-M4-N4-K45, MM-L5-M4-N4-K1~MM-L5-M4-N4-K45, MM-L6-M4-N4-K1~MM-L6-M4-N4-K45, MM-L7-M4-N4-K1~MM-L7-M4-N4-K45, MM-L1-M5-N4-K1~MM-L1-M5-N4-K45, MM-L2-M5-N4-K1~MM-L2-M5-N4-K45, MM-L3-M5-N4-K1~MM-L3-M5-N4-K45, MM-L4-M5-N4-K1~MM-L4-M5-N4-K45, MM-L5-M5-N4-K1~MM-L5-M5-N4-K45, MM-L6-M5-N4-K1~MM-L6-M5-N4-K45, MM-L7-M5-N4-K1~MM-L7-M5-N4-K45, MM-L1-M6-N4-K1~MM-L1-M6-N4-K45, MM-L2-M6-N4-K1~MM-L2-M6-N4-K45, MM-L3-

M6-N4-K1~MM-L3-M6-N4-K45, MM-L4-M6-N4-K1~MM-L4-M6-N4-K45, MM-L5-M6-N4-K1~MM-L5-M6-N4-K45, MM-L6-M6-N4-K1~MM-L6-M6-N4-K45, MM-L7-M6-N4-K1~MM-L7-M6-N4-K45, MM-L1-M7-N4-K1~MM-L1-M7-N4-K45, MM-L2-M7-N4-K1~MM-L2-M7-N4-K45, MM-L3-M7-N4-K1~MM-L3-M7-N4-K45, MM-L4-M7-N4-K1~MM-L4-M7-N4-K45, MM-L5-M7-N4-K1~MM-L5-M7-N4-K45, MM-L6-M7-N4-K1~MM-L6-M7-N4-K45, MM-L7-M7-N4-K1~MM-L7-M7-N4-K45, MM-L1-M1-N5-K1~MM-L1-M1-N5-K45, MM-L2-M1-N5-K1~MM-L2-M1-N5-K45, MM-L3-M1-N5-K1~MM-L3-M1-N5-K45, MM-L4-M1-N5-K1~MM-L4-M1-N5-K45, MM-L5-M1-N5-K1~MM-L5-M1-N5-K45,

MM-L6-M1-N5-K1~MM-L6-M1-N5-K45, MM-L7-M1-N5-K1~MM-L7-M1-N5-K45, MM-L1-M2-N5-K1~MM-L1-M2-N5-K45, MM-L2-M2-N5-K1~MM-L2-M2-N5-K45, MM-L3-M2-N5-K1~MM-L3-M2-N5-K45, MM-L4-M2-N5-K1~MM-L4-M2-N5-K45, MM-L5-M2-N5-K1~MM-L5-M2-N5-K45, MM-L6-M2-N5-K1~MM-L6-M2-N5-K45, MM-L7-M2-N5-K1~MM-L7-M2-N5-K45, MM-L1-M3-N5-K1~MM-L1-M3-N5-K45, MM-L2-M3-N5-K1~MM-L2-M3-N5-K45, MM-L3-M3-N5-K1~MM-L3-M3-N5-K45, MM-L4-M3-N5-K1~MM-L4-M3-N5-K45, MM-L5-M3-N5-K1~MM-L5-M3-N5-K45, MM-L6-M3-N5-K1~MM-L6-M3-N5-K45, MM-L7-M3-N5-K1~MM-L7-M3-N5-K45, MM-L1-M4-N5-K1~MM-L1-M4-N5-K45, MM-L2-M4-N5-K1~MM-L2-M4-N5-K45, MM-L3-M4-N5-K1~MM-L3-M4-N5-K45, MM-L4-M4-N5-K1~MM-L4-M4-N5-K45, MM-L5-M4-N5-K1~MM-L5-M4-N5-K45, MM-L6-M4-N5-K1~MM-L6-M4-N5-K45, MM-L7-M4-N5-K1~MM-L7-M4-N5-K45, MM-L1-M5-N5-K1~MM-L1-M5-N5-K45, MM-L2-M5-N5-K1~MM-L2-M5-N5-K45, MM-L3-M5-N5-K1~MM-L3-M5-N5-K45, MM-L4-M5-N5-K1~MM-L4-M5-N5-K45, MM-L5-M5-N5-K1~MM-L5-M5-N5-K45, MM-L6-M5-N5-K1~MM-L6-M5-N5-K45, MM-L7-M5-N5-K1~MM-L7-M5-N5-K45, MM-L1-M6-N5-K1~MM-L1-M6-N5-K45, MM-L2-M6-N5-K1~MM-L2-M6-N5-K45, MM-L3-M6-N5-K1~MM-L3-M6-N5-K45, MM-L4-M6-N5-K1~MM-L4-M6-N5-K45, MM-L5-M6-N5-K1~MM-L5-M6-N5-K45, MM-L6-M6-N5-K1~MM-L6-M6-N5-K45, MM-L7-M6-N5-K1~MM-L7-M6-N5-K45, MM-L1-M7-N5-K1~MM-L1-M7-N5-K45, MM-L2-M7-N5-K1~MM-L2-M7-N5-K45, MM-L3-M7-N5-K1~MM-L3-M7-N5-K45, MM-L4-M7-N5-K1~MM-L4-M7-N5-K45, MM-L5-M7-N5-K1~MM-L5-M7-N5-K45, MM-L6-M7-N5-K1~MM-L6-M7-N5-K45, MM-L7-M7-N5-K1~MM-L7-M7-N5-K45, MM-L1-M1-N6-K1~MM-L1-M1-N6-K45, MM-L2-M1-N6-K1~MM-L2-M1-N6-K45, MM-L3-M1-N6-K1~MM-L3-M1-N6-K45, MM-L4-M1-N6-K1~MM-L4-M1-N6-K45, MM-L5-M1-N6-K1~MM-L5-M1-N6-K45, MM-L6-M1-N6-K1~MM-L6-M1-N6-K45, MM-L7-M1-N6-K1~MM-L7-M1-N6-K45, MM-L1-M2-N6-K1~MM-L1-M2-N6-K45, MM-L2-M2-N6-K1~MM-L2-M2-N6-K45, MM-L3-M2-N6-K1~MM-L3-M2-N6-K45, MM-L4-M2-N6-K1~MM-L4-M2-N6-K45, MM-L5-M2-N6-K1~MM-L5-M2-N6-K45, MM-L6-M2-N6-K1~MM-L6-M2-N6-K45, MM-L7-M2-N6-K1~MM-L7-M2-N6-K45,

MM-L1-M3-N6-K1~MM-L1-M3-N6-K45, MM-L2-M3-N6-K1~MM-L2-M3-N6-K45, MM-L3-M3-N6-K1~MM-L3-M3-N6-K45, MM-L4-M3-N6-K1~MM-L4-M3-N6-K45, MM-L5-M3-N6-K1~MM-L5-M3-N6-K45, MM-L6-M3-N6-K1~MM-L6-M3-N6-K45, MM-L7-M3-N6-K1~MM-L7-M3-N6-K45, MM-L1-M4-N6-K1~MM-L1-M4-N6-K45, MM-L2-M4-N6-K1~MM-L2-M4-N6-K45, MM-L3-M4-N6-K1~MM-L3-M4-N6-K45, MM-L4-M4-N6-K1~MM-L4-M4-N6-K45, MM-L5-M4-N6-K1~MM-L5-M4-N6-K45, MM-L6-M4-N6-K1~MM-L6-M4-N6-K45, MM-L7-M4-N6-K1~MM-L7-M4-N6-K45, MM-L1-M5-N6-K1~MM-L1-M5-N6-K45, MM-L2-M5-N6-K1~MM-L2-M5-N6-K45, MM-L3-M5-N6-K1~MM-L3-M5-N6-K45, MM-L4-M5-N6-K1~MM-L4-M5-N6-K45, MM-L5-M5-N6-K1~MM-L5-M5-N6-K45, MM-L6-M5-N6-K1~MM-L6-M5-N6-K45, MM-L7-M5-N6-K1~MM-L7-M5-N6-K45, MM-L1-M6-N6-K1~MM-L1-M6-N6-K45, MM-L2-M6-N6-K1~MM-L2-M6-N6-K45, MM-L3-M6-N6-K1~MM-L3-M6-N6-K45, MM-L4-M6-N6-K1~MM-L4-M6-N6-K45, MM-L5-M6-N6-K1~MM-L5-M6-N6-K45, MM-L6-M6-N6-K1~MM-L6-M6-N6-K45, MM-L7-M6-N6-K1~MM-L7-M6-N6-K45, MM-L1-M7-N6-K1~MM-L1-M7-N6-K45, MM-L2-M7-N6-K1~MM-L2-M7-N6-K45, MM-L3-M7-N6-K1~MM-L3-M7-N6-K45, MM-L4-M7-N6-K1~MM-L4-M7-N6-K45, MM-L5-M7-N6-K1~MM-L5-M7-N6-K45, MM-L6-M7-N6-K1~MM-L6-M7-N6-K45, MM-L7-M7-N6-K1~MM-L7-M7-N6-K45, MM-L1-M1-N7-K1~MM-L1-M1-N7-K45, MM-L2-M1-N7-K1~MM-L2-M1-N7-K45, MM-L3-M1-N7-K1~MM-L3-M1-N7-K45, MM-L4-M1-N7-K1~MM-L4-M1-N7-K45, MM-L5-M1-N7-K1~MM-L5-M1-N7-K45, MM-L6-M1-N7-K1~MM-L6-M1-N7-K45, MM-L7-M1-N7-K1~MM-L7-M1-N7-K45, MM-L1-M2-N7-K1~MM-L1-M2-N7-K45, MM-L2-M2-N7-K1~MM-L2-M2-N7-K45, MM-L3-M2-N7-K1~MM-L3-M2-N7-K45, MM-L4-M2-N7-K1~MM-L4-M2-N7-K45, MM-L5-M2-N7-K1~MM-L5-M2-N7-K45, MM-L6-M2-N7-K1~MM-L6-M2-N7-K45, MM-L7-M2-N7-K1~MM-L7-M2-N7-K45, MM-L1-M3-N7-K1~MM-L1-M3-N7-K45, MM-L2-M3-N7-K1~MM-L2-M3-N7-K45, MM-L3-M3-N7-K1~MM-L3-M3-N7-K45, MM-L4-M3-N7-K1~MM-L4-M3-N7-K45, MM-L5-M3-N7-K1~MM-L5-M3-N7-K45, MM-L6-M3-N7-K1~MM-L6-M3-N7-K45, MM-L7-M3-N7-K1~MM-L7-M3-N7-K45, MM-L1-M4-N7-K1~MM-L1-M4-N7-K45, MM-L2-M4-N7-K1~MM-L2-M4-N7-K45, MM-L3-M4-N7-K1~MM-L3-M4-N7-K45, MM-L4-M4-N7-K1~MM-L4-M4-N7-K45, MM-L5-M4-N7-K1~MM-L5-M4-N7-K45, MM-L6-M4-N7-K1~MM-L6-M4-N7-K45, MM-L7-M4-N7-K1~MM-L7-M4-N7-K45, MM-L1-M5-N7-K1~MM-L1-M5-N7-K45, MM-L2-M5-N7-K1~MM-L2-M5-N7-K45, MM-L3-M5-N7-K1~MM-L3-M5-N7-K45, MM-L4-M5-N7-K1~MM-L4-M5-N7-K45, MM-L5-M5-N7-K1~MM-L5-M5-N7-K45, MM-L6-M5-N7-K1~MM-L6-M5-N7-K45, MM-L7-M5-N7-K1~MM-L7-M5-N7-K45, MM-L1-M6-N7-K1~MM-L1-M6-N7-K45, MM-L2-M6-N7-K1~MM-L2-M6-N7-K45, Mm-L3-M6-N7-K1~MM-L3-M6-N7-K45, MM-L4-M6-N7-K1~MM-L4-M6-N7-K45, MM-L5-M6-N7-K1~MM-L5-M6-N7-K45, MM-L6-M6-N7-K1~MM-L6-M6-N7-K45, MM-L7-M6-N7-K1~MM-L7-M6-N7-K45, MM-L1-M7-N7-K1~MM-L1-M7-N7-K45, MM-L2-M7-N7-K1~MM-L2-M7-N7-K45, MM-L3-M7-N7-K1~MM-L3-M7-N7-K45, MM-L4-M7-N7-K1~MM-L4-M7-N7-K45, MM-L5-M7-N7-K1~MM-L5-M7-N7-K45, MM-L6-M7-N7-K1~MM-L6-M7-N7-K45, MM-L7-M7-N7-K1~MM-L7-M7-N7-K45, III-GG1-O1~III-GG665-O1, III-GG1-O2~III-GG665-O2, III-GG1-O3~III-GG665-O3, III-GG1-O4~III-GG665-O4, III-GG1-O5~III-GG665-O5, IIII-GGG1-O1~IIII-GGG365-O1, IIII-GGG1-O2~IIII-GGG365-O2, IIII-GGG1-O3~IIII-GGG365-O3, IIII-GGG1-O4~IIII-GGG365-O4, and IIII-GGG1-O5~IIII-GGG365-O5.

Herein, Me represents methyl group, Et represents ethyl group, Pr represents propyl group, iPr represents isopropyl group, cPr represents cyclopropyl group, Bu represents butyl group, tBu represents t-butyl group, cBu represents cyclobutyl group, cPen represents cyclopentyl group, (1,2,3,6-tetrapy-1) represents 1,2,3,6-tetrahydropyrazin-1-yl group, Ph represents phenyl group, 1-pyr represents pyrazol-1-yl group, 3-pyr represents pyrazol-3-yl group, 4-pyr represents pyrazol-4-yl group, 5-pyr represents pyrazol-5-yl group, 2-Im represents imidazol-2-yl group, 4-Im represents imidazol-4-yl group, 5-Im represents imidazol-5-yl group, 2-Th represents thiazol-2-yl group, 3-Ith represents isothiazol-3-yl group, 4-Ith represents isothiazol-4-yl group, 5-Ith represents isothiazol-5-yl group, 3-IO represents isoxazol-3-yl group, 4-IO represents isoxazol-4-yl group, 5-IO represents isoxazol-5-yl group, 2-Py represents pyridin-2-yl group, 3-Py represents pyridin-3-yl group, 4-Py represents pyridin-4-yl group, 2-Pm represents pyrimidin-2-yl group, 4-Pm represents pyrimidin-4-yl group, 5-Pm represents pyrimidin-5-yl group, 3-Prd represents pyridazin-3-yl group, 4-Prd represents pyridazin-4-yl group, 2-Pra represents pyrazin-2-yl group, (1,2,3-tri-1) represents 1,2,3-triazol-1-yl group, (1,2,4-tri-1) represents 1,2,4-triazol-1-yl group, (1,2,4-Oxa-3) represents 1,2,4-oxadiazolyl-3-yl group, (1,2,5-Oxa-3) represents 1,2,5-oxadiazolyl-3-yl group, (1,2,4-Oxa-5) represents 1,2,4-oxadiazolyl-5-yl group, (1,2,4-Thia-3) represents 1,2,4-thiadiazolyl-3-yl group, (1,2,3-Thia-4) represents 1,2,3-thiadiazolyl-4-yl group, (1,2,3-Thia-5) represents 1,2,3-thiadiazolyl-5-yl group, (1,2,4-Thia-5) represents 1,2,4-thiadiazolyl-5-yl group, tet-1 represents (1H)-tetrazolyl-1-yl group, tet-5 represents (1H)-tetrazolyl-5-yl group, 2-Fra represents furan-2-yl group, 3-Fra represents furan-3-yl group, 2-Bf represents benzofuran-2-yl group, 3-Bf represents benzofuran-3-yl group, 4-Bf represents benzofuran-4-yl group, 2-Bt represents benzothiophen-2-yl group, 4-Bt represents benzothiophen-4-yl group, 5-Bt represents benzothiophen-5-yl group, 6-Bt represents benzothiophen-6-yl group, 2-Bet represents benzothiazol-2-yl group, 1-Adam represents adamanthyl-2-yl group, 3-BI represents 1,2-benzisoxazol-3-yl group, 3-ISP represents isoxazolo[5,4-b]pyridin-3-yl group, and 4-IND represents indan-4-yl group.

The substituent Nos. D1 to D11 indicated in [Table 1] represents substituent $Z^1$ in the compound represented by formula (AA), the compound represented by formula (BB), the compound represented by formula (CC), the compound represented by formula (DD), the compound represented by formula (II), the compound represented by formula (JJ), the compound represented by formula (KK), or the compound represented by formula (LL).

TABLE 1

| Substituent No. | $Z^1$ |
| --- | --- |
| D1 | Me |
| D2 | Et |
| D3 | $CHF_2$ |
| D4 | $CF_3$ |
| D5 | cPr |
| D6 | OMe |
| D7 | OEt |
| D8 | $OCHF_2$ |
| D9 | $OCF_3$ |
| D10 | SMe |
| D11 | SEt |

The substituent Nos. E1 to E11 indicated in [Table 2] represent substituent $Z^3$ in the compound represented by formula (II) to the compound represented by formula (JJ).

TABLE 2

| Substituent No. | $Z^3$ |
| --- | --- |
| E1 | Me |
| E2 | Et |
| E3 | $CHF_2$ |
| E4 | $CF_3$ |
| E5 | cPr |
| E6 | OMe |
| E7 | OEt |
| E8 | $OCHF_2$ |
| E9 | $OCF_3$ |
| E10 | SMe |
| E11 | SEt |

The substituent Nos. E1 to E21 indicated in [Table 3] represents substituent $X^3$ in the compound represented by formula (EE), the compound represented by formula (FF), the compound represented by formula (GG), or the compound represented by formula (HH).

TABLE 3

| Substituent No. | $X^3$ |
| --- | --- |
| F1 | H |
| F2 | $CH=CH_2$ |
| F3 | $CH_2CH=CH_2$ |
| F4 | $C\equiv CH$ |
| F5 | $CH_2C\equiv CH$ |
| F6 | $C(O)CH_3$ |
| F7 | $CH_2CHO$ |
| F8 | $CH_2NO_2$ |
| F9 | $CH_2CN$ |
| F10 | $CH_2OH$ |
| F11 | cPr |
| F12 | cBu |
| F13 | cPen |
| F14 | cHex |
| F15 | $CH_2CN$ |
| F16 | $CH_2CH_2CN$ |
| F17 | Ph |
| F18 | $CH_2Ph$ |
| F19 | 2-Py |
| F20 | 3-Py |
| F21 | 4-Py |

The below-mentioned substituent Nos. G1 to G1943 represents substituent $G^1$ in the compound represented by formula (BB), the compound represented by formula (CC), the compound represented by formula (DD), the compound represented by formula (EE), the compound represented by formula (FF), the compound represented by formula (GG), or the compound represented by formula (HH).

<Substituent No.; $G^1$>

[G1;Ph], [G2;4-F-Ph], [G3;4-Cl-Ph], [G4;4-Br-Ph], [G5;4-I-Ph], [G6;4-Me-Ph], [G7;4-Et-Ph], [G8;4-Pr-Ph], [G9;4-iPr-Ph], [G10;4-$CF_3$-Ph], [G11;4-$CHF_2$-Ph], [G2;4-OMe-Ph], [G13;4-OEt-Ph], [G14;4-$OCF_3$-Ph], [G15;4-$OCHF_2$-Ph], [G16;4-$OCH_2CHF_2$-Ph], [G17;4-CN-Ph], [G18;4-SMe-Ph], [G19;4-SEt-Ph], [G20;4-cPr-Ph], [G21;2-F-Ph], [G22;2-Cl-Ph], [G23;2-Br-Ph], [G24;2-I-Ph], [G25;2-Me-Ph], [G26;2-Et-Ph], [G27;2-Pr-Ph], [G28;2-iPr-Ph], [G29;2-$CF_3$-Ph], [G30;2-$CHF_2$-Ph], [G31;2-OMe-Ph], [G32;2-OEt-Ph], [G33;2-$OCF_3$-Ph], [G34;2-$OCHF_2$-Ph], [G35;2-$OCH_2CHF_2$-Ph], [G36;2-CN-Ph], [G37;2-SMe-Ph], [G38;2-SEt-Ph], [G39;2-cPr-Ph], [G40;3-F-Ph], [G41;3-Cl-Ph], [G42;3-Br-Ph], [G43;3-I-Ph], [G44;3-Me-Ph], [G45;3-Et-Ph], [G46;3-Pr-Ph], [G47;3-iPr-Ph], [G48;3-$CF_3$-Ph], [G49;3-$CHF_2$-Ph], [G50;3-OMe-Ph], [G51;3-OEt-Ph], [G52;3-$OCF_3$-Ph], [G53;3-$OCHF_2$-Ph], [G54;3-$OCH_2CHF_2$-Ph],

[G55;3-CN-Ph], [G56;3-SMe-Ph], [G57;3-SEt-Ph], [G58;3-cPr-Ph], [G59;2,3-diMeO-Ph], [G60;2,4-diMeO-Ph], [G61;2-Im], [G62;4-F-2-Im], [G63;4-Cl-2-Im], [G64;4-Br-2-Im], [G65;4-I-2-Im], [G66;4-Me-2-Im], [G67;4-Et-2-Im], [G68;4-Pr-2-Im], [G69;4-iPr-2-Im], [G70;4-CF$_3$-2-Im], [G71;4-CHF$_2$-2-Im], [G72;4-OMe-2-Im], [G73;4-OEt-2-Im], [G74;4-OCF$_3$-2-Im], [G75;4-OCHF$_2$-2-Im], [G76;4-OCH$_2$CHF$_2$-2-Im], [G77;4-CN-2-Im], [G78;4-SMe-2-Im], [G79;4-SEt-2-Im], [G80;4-cPr-2-Im], [G81;5-F-2-Im], [G82;5-Cl-2-Im], [G83;5-Br-2-Im], [G84;5-I-2-Im], [G85;5-Me-2-Im], [G86;5-Et-2-Im], [G87;5-Pr-2-Im], [G88;5-iPr-2-Im], [G89;5-CF$_3$-2-Im], [G90;5-CHF$_2$-2-Im], [G91;5-OMe-2-Im], [G92;5-OEt-2-Im], [G93;5-OCF$_3$-2-Im], [G94;5-OCHF$_2$-2-Im], [G95;5-OCH$_2$CHF$_2$-2-Im], [G96;5-CN-2-Im], [G97;5-SMe-2-Im], [G98;5-SEt-2-Im], [G99;5-cPr-2-Im], [G100;4-Im], [G101;2-F-4-Im], [G102;2-Cl-4-Im], [G103;2-Br-4-Im], [G104;2-I-4-Im], [G105;2-Me-4-Im], [G106;2-Et-4-Im], [G107;2-Pr-4-Im], [G108;2-iPr-4-Im], [G109;2-CF$_3$-4-Im], [G100;2-CHF$_2$-4-Im], [G111;2-OMe-4-Im], [G112;2-OEt-4-Im], [G113;2-OCF$_3$-4-Im], [G114;2-OCHF$_2$-4-Im], [G115;2-OCH$_2$CHF$_2$-4-Im], [G116;2-CN-4-Im], [G117;2-SMe-4-Im], [G118;2-SEt-4-Im], [G119;2-cPr-4-Im], [G120;5-F-4-Im], [G121;5-Cl-4-Im], [G122;5-Br-4-Im], [G123;5-I-4-Im], [G124;5-Me-4-Im], [G125;5-Et-4-Im], [G126;5-Pr-4-Im], [G127;5-iPr-4-Im], [G128;5-CF$_3$-4-Im], [G129;5-CHF$_2$-4-Im], [G130;5-OMe-4-Im], [G131;5-OEt-4-Im], [G132;5-OCF$_3$-4-Im], [G133;5-OCHF$_2$-4-Im], [G134;5-OCH$_2$CHF$_2$-4-Im], [G135;5-CN-4-Im], [G136;5-SMe-4-Im], [G137;5-SEt-4-Im], [G138;5-cPr-4-Im], [G139;5-Im], [G140;2-F-5-Im], [G141;2-Cl-5-Im], [G142;2-Br-5-Im], [G143;2-I-5-Im], [G144;2-Me-5-Im], [G145;2-Et-5-Im], [G146;2-Pr-5-Im], [G147;2-iPr-5-Im], [G148;2-CF$_3$-5-Im], [G149;2-CHF$_2$-5-Im], [G150;2-OMe-5-Im], [G151;2-OEt-5-Im], [G152;2-OCF$_3$-5-Im], [G153;2-OCHF$_2$-5-Im], [G154;2-OCH$_2$CHF$_2$-5-Im], [G155;2-CN-5-Im], [G156;2-SMe-5-Im], [G157;2-SEt-5-Im], [G158;2-cPr-5-Im], [G159;4-F-5-Im], [G160;4-Cl-5-Im], [G161;4-Br-5-Im], [G162;4-I-5-Im], [G163;4-Me-5-Im], [G164;4-Et-5-Im], [G165;4-Pr-5-Im], [G166;4-iPr-5-Im], [G167;4-CF$_3$-5-Im], [G168;4-CHF$_2$-5-Im], [G169;4-OMe-5-Im], [G170;4-OEt-5-Im], [G171;4-OCF$_3$-5-Im], [G172;4-OCHF$_2$-5-Im], [G173;4-OCH$_2$CHF$_2$-5-Im], [G174;4-CN-5-Im], [G175;4-SMe-5-Im], [G176;4-SEt-5-Im], [G177;4-cPr-5-Im], [G178;3-Ith], [G179;4-F-3-Ith], [G180;4-Cl-3-Ith], [G181;4-Br-3-Ith], [G182;4-I-3-Ith], [G183;4-Me-3-Ith], [G184;4-Et-3-Ith], [G185;4-Pr-3-Ith], [G186;4-iPr-3-Ith], [G187;4-CF$_3$-3-Ith], [G188;4-CHF$_2$-3-Ith], [G189;4-OMe-3-Ith], [G190;4-OEt-3-Ith], [G191;4-OCF$_3$-3-Ith], [G192;4-OCHF$_2$-3-Ith], [G193;4-OCH$_2$CHF$_2$-3-Ith], [G194;4-CN-3-Ith], [G195;4-SMe-3-Ith], [G196;4-SEt-3-Ith], [G197;4-cPr-3-Ith], [G198;5-F-3-Ith], [G199;5-Cl-3-Ith],

[G200;5-Br-3-Ith], [G201;5-I-3-Ith], [G202;5-Me-3-Ith], [G203;5-Et-3-Ith], [G204;5-Pr-3-Ith], [G205;5-iPr-3-Ith], [G206;5-CF$_3$-3-Ith], [G207;5-CHF$_2$-3-Ith], [G208;5-OMe-3-Ith], [G209;5-OEt-3-Ith], [G210;5-OCF$_3$-3-Ith], [G211;5-OCHF$_2$-3-Ith], [G212;5-OCH$_2$CHF$_2$-3-Ith], [G213;5-CN-3-Ith], [G214;5-SMe-3-Ith], [G215;5-SEt-3-Ith], [G216;5-cPr-3-Ith], [G217;4-Ith], [G218;3-F-4-Ith], [G219;3-Cl-4-Ith], [G220;3-Br-4-Ith], [G221;3-J-4-Ith], [G222;3-Me-4-Ith], [G223;3-Et-4-Ith], [G224;3-Pr-4-Ith], [G225;3-iPr-4-Ith], [G226;3-CF$_3$-4-Ith], [G227;3-CHF$_2$-4-Ith], [G228;3-OMe-4-Ith], [G229;3-OEt-4-Ith], [G230;3-OCF$_3$-4-Ith], [G231;3-OCHF$_2$-4-Ith], [G232;3-OCH$_2$CHF$_2$-4-Ith], [G233;3-CN-4-Ith], [G234;3-SMe-4-Ith], [G235;3-SEt-4-Ith], [G236;3-cPr-4-Ith], [G237;5-F-4-Ith], [G238;5-Cl-4-Ith], [G239;5-Br-4-Ith], [G240;5-J-4-Ith], [G241;5-Me-4-Ith], [G242;5-Et-4-Ith], [G243;5-Pr-4-Ith], [G244;5-iPr-4-Ith], [G245;5-CF$_3$-4-Ith], [G246;5-CHF$_2$-4-Ith], [G247;5-OMe-4-Ith], [G248;5-OEt-4-Ith], [G249;5-OCF$_3$-4-Ith], [G250;5-OCHF$_2$-4-Ith], [G251;5-OCH$_2$CHF$_2$-4-Ith], [G252;5-CN-4-Ith], [G253;5-SMe-4-Ith], [G254;5-SEt-4-Ith], [G255;5-cPr-4-Ith], [G256;5-Ith], [G257;3-F-5-Ith], [G258;3-Cl-5-Ith], [G259;3-Br-5-Ith], [G260;3-J-5-Ith], [G261;3-Me-5-Ith], [G262;3-Et-5-Ith], [G263;3-Pr-5-Ith], [G264;3-iPr-5-Ith], [G265;3-CF$_3$-5-Ith], [G266;3-CHF$_2$-5-Ith], [G267;3-OMe-5-Ith], [G268;3-OEt-5-Ith], [G269;3-OCF$_3$-5-Ith], [G27;3-OCHF$_2$-5-Ith], [G271;3-OCH$_2$CHF$_2$-5-Ith], [G272;3-CN-5-Ith], [G273;3-SMe-5-Ith], [G274;3-SEt-5-Ith], [G275;3-cPr-5-Ith], [G276;4-F-5-Ith], [G277;4-Cl-5-Ith], [G278;4-Br-5-Ith], [G279;4-J-5-Ith], [G280;4-Me-5-Ith], [G281;4-Et-5-Ith], [G282;4-Pr-5-Ith], [G283;4-iPr-5-Ith], [G284;4-CF$_3$-5-Ith], [G285;4-CHF$_2$-5-Ith], [G286;4-OMe-5-Ith], [G287;4-OEt-5-Ith], [G288;4-OCF$_3$-5-Ith], [G289;4-OCHF$_2$-5-Ith], [G290;4-OCH$_2$CHF$_2$-5-Ith], [G291;4-CN-5-Ith], [G292;4-SMe-5-Ith], [G293;4-SEt-5-Ith], [G294;4-cPr-5-Ith], [G295;3-IO], [G296;4-F-3-IO], [G297;4-Cl-3-IO], [G298;4-Br-3-IO], [G299;4-J-3-IO], [G300;4-Me-3-IO], [G301;4-Et-3-IO], [G302;4-Pr-3-IO], [G303;4-iPr-3-IO], [G304;4-CF$_3$-3-IO], [G305;4-CHF$_2$-3-IO], [G306;4-OMe-3-IO], [G307;4-OEt-3-IO], [G308;4-OCF$_3$-3-IO], [G309;4-OCHF$_2$-3-IO], [G310;4-OCH$_2$CHF$_2$-3-IO], [G311;4-CN-3-IO], [G312;4-SMe-3-IO], [G313;4-SEt-3-IO], [G314;4-cPr-3-IO], [G315;5-F-3-IO], [G316;5-Cl-3-IO], [G317;5-Br-3-IO], [G318;5-J-3-IO], [G319;5-Me-3-IO], [G320;5-Et-3-IO], [G312;5-Pr-3-IO], [G322;5-iPr-3-IO], [G323;5-CF$_3$-3-IO], [G324;5-CHF$_2$-3-IO], [G325;5-OMe-3-IO], [G326;5-OEt-3-IO], [G327;5-OCF$_3$-3-IO], [G328;5-OCHF$_2$-3-IO], [G329;5-OCH$_2$CHF$_2$-3-IO], [G330;5-CN-3-IO], [G331;5-SMe-3-IO], [G332;5-SEt-3-IO], [G333;5-cPr-3-IO], [G334;4-IO], [G335;3-F-4-IO], [G336;3-Cl-4-IO], [G337;3-Br-4-IO], [G338;3-J-4-IO], [G339;3-Me-4-IO], [G340;3-Et-4-IO], [G341;3-Pr-4-IO], [G342;3-iPr-4-IO], [G343;3-CF$_3$-4-IO], [G344;3-CHF$_2$-4-IO], [G345;3-OMe-4-IO], [G346;3-OEt-4-IO], [G347;3-OCF$_3$-4-IO], [G348;3-OCHF$_2$-4-IO], [G349;3-OCH$_2$CHF$_2$-4-IO], [G350;3-CN-4-IO], [G351;3-SMe-4-IO], [G352;3-SEt-4-IO], [G353;3-cPr-4-IO], [G354;5-F-4-IO], [G355;5-Cl-4-IO], [G356;5-Br-4-IO], [G357;5-I-4-IO], [G358;5-Me-4-IO], [G359;5-Et-4-IO], [G360;5-Pr-4-IO], [G361;5-iPr-4-IO], [G362;5-CF$_3$-4-IO], [G363;5-CHF$_2$-4-IO], [G364;5-OMe-4-IO], [G365;5-OEt-4-IO], [G366;5-OCF$_3$-4-IO], [G367;5-OCHF$_2$-4-IO], [G368;5-OCH$_2$CHF$_2$-4-IO], [G369;5-CN-4-IO], [G370;5-SMe-4-IO], [G371;5-SEt-4-IO], [G372;5-cPr-4-IO], [G373;5-IO], [G374;3-F-5-IO], [G375;3-Cl-5-IO], [G376;3-Br-5-IO], [G377;3-J-5-IO], [G378;3-Me-5-IO], [G379;3-Et-5-IO], [G380;3-Pr-5-IO], [G381;3-iPr-5-IO], [G382;3-CF$_3$-5-IO], [G383;3-CHF$_2$-5-IO], [G384;3-OMe-5-IO], [G385;3-OEt-5-IO], [G386;3-OCF$_3$-5-IO], [G387;3-OCHF$_2$-5-IO], [G388;3-OCH$_2$CHF$_2$-5-IO], [G389;3-CN-5-IO], [G390;3-SMe-5-IO], [G391;3-SEt-5-IO], [G392;3-cPr-5-IO], [G393;4-F-5-IO], [G394;4-Cl-5-IO], [G395;4-Br-5-IO], [G396;4-J-5-IO], [G397;4-Me-5-IO], [G398;4-Et-5-IO], [G399;4-Pr-5-IO],

[G400;4-iPr-5-IO], [G401;4-CF$_3$-5-IO], [G402;4-CHF$_2$-5-IO], [G403;4-OMe-5-IO], [G404;4-OEt-5-IO], [G405;4-OCF$_3$-5-IO], [G406;4-OCHF$_2$-5-IO], [G407;4-OCH$_2$CHF$_2$-5-IO], [G408;4-CN-5-IO], [G409;4-SMe-5-IO], [G410;4-SEt-5-IO], [G411;4-cPr-5-IO], [G412;2-Pm], [G413;4-F-2-Pm], [G414;4-Cl-2-Pm], [G415;4-Br-2-Pm], [G416;4-J-2-Pm], [G417;4-Me-2-Pm], [G418;4-Et-2-Pm], [G419;4-Pr-2-Pm], [G420;4-iPr-2-Pm], [G421;4-CF$_3$-2-Pm], [G422;4-CHF$_2$-2-Pm], [G423;4-OMe-2-Pm], [G424;4-OEt-2-Pm], [G425;4-OCF$_3$-2-Pm], [G426;4-OCHF$_2$-2-Pm], [G427;4-CN-2-Pm], [G428;4-SMe-2-Pm], [G429;4-SEt-2-Pm],

[G430;4-cPr-2-Pm], [G431;5-F-2-Pm], [G432;5-Cl-2-Pm], [G433;5-Br-2-Pm], [G434;5-J-2-Pm], [G435;5-Me-2-Pm], [G436;5-Et-2-Pm], [G437;5-Pr-2-Pm], [G438;5-iPr-2-Pm], [G439;5-CF$_3$-2-Pm], [G440;5-CHF$_2$-2-Pm], [G441;5-OMe-2-Pm], [G442;5-OEt-2-Pm], [G443;5-OCF$_3$-2-Pm], [G444;5-OCHF$_2$-2-Pm], [G445;5-CN-2-Pm], [G446;5-SMe-2-Pm], [G447;5-SEt-2-Pm], [G448;5-cPr-2-Pm], [G449;4-Pm], [G450;2-F-4-Pm], [G451;2-Cl-4-Pm], [G452;2-Br-4-Pm], [G453;2-J-4-Pm], [G454;2-Me-4-Pm], [G455;2-Et-4-Pm], [G456;2-Pr-4-Pm], [G457;2-iPr-4-Pm], [G458;2-CF$_3$-4-Pm], [G459;2-CHF$_2$-4-Pm], [G460;2-OMe-4-Pm], [G461;2-OEt-2-Pm], [G462;2-OCF$_3$-4-Pm], [G463;2-OCHF$_2$-4-Pm], [G464;2-CN-4-Pm], [G465;2-SMe-4-Pm], [G466;2-SEt-4-Pm], [G467;2-cPr-4-Pm], [G468;5-F-4-Pm], [G469;5-Cl-4-Pm], [G470;5-Br-4-Pm], [G471;5-J-4-Pm], [G472;5-Me-4-Pm], [G473;5-Et-4-Pm], [G474;5-Pr-4-Pm], [G475;5-iPr-4-Pm], [G476;5-CF$_3$-4-Pm], [G477;5-CHF$_2$-4-Pm], [G478;5-OMe-4-Pm], [G479;5-OEt-4-Pm], [G480;5-OCF$_3$-4-Pm], [G481;5-OCHF$_2$-4-Pm], [G482;5-CN-4-Pm], [G483;5-SMe-4-Pm], [G484;5-SEt-4-Pm], [G485;5-cPr-4-Pm], [G486;6-F-4-Pm], [G487;6-Cl-4-Pm], [G488;6-Br-4-Pm], [G489;6-J-4-Pm], [G490;6-Me-4-Pm], [G491;6-Et-4-Pm], [G492;6-Pr-4-Pm], [G493;6-iPr-4-Pm], [G494;6-CF$_3$-4-Pm], [G495;6-CHF$_2$-4-Pm], [G496;6-OMe-4-Pm], [G497;6-OEt-4-Pm], [G498;6-OCF$_3$-4-Pm], [G499;6-OCHF$_2$-4-Pm], [G500;6-CN-4-Pm], [G501;6-SMe-4-Pm], [G502;6-SEt-4-Pm], [G503;6-cPr-4-Pm], [G504;5-Pm], [G505;2-F-5-Pm], [G506;2-Cl-5-Pm], [G507;2-Br-5-Pm], [G508;2-I-5-Pm], [G509;2-Me-5-Pm], [G510;2-Et-5-Pm], [G511;2-Pr-5-Pm], [G512;2-iPr-5-Pm], [G513;2-CF$_3$-5-Pm], [G514;2-CHF$_2$-5-Pm], [G515;2-OMe-5-Pm], [G516;2-OEt-5-Pm], [G517;2-OCF$_3$-5-Pm], [G518;2-OCHF$_2$-5-Pm], [G519;2-CN-5-Pm], [G520;2-SMe-5-Pm], [G521;2-SEt-5-Pm], [G522;2-cPr-5-Pm], [G523;4-F-5-Pm], [G524;4-Cl-5-Pm], [G525;4-Br-5-Pm], [G526;4-I-5-Pm], [G527;4-Me-5-Pm], [G528;4-Et-5-Pm], [G529;4-Pr-5-Pm], [G530;4-iPr-5-Pm], [G531;4-CF$_3$-5-Pm], [G532;4-CHF$_2$-5-Pm], [G533;4-OMe-5-Pm], [G534;4-OEt-5-Pm], [G535;4-OCF$_3$-5-Pm], [G536;4-OCHF$_2$-5-Pm], [G537;4-CN-5-Pm], [G538;4-SMe-5-Pm], [G539;4-SEt-5-Pm], [G540;4-cPr-5-Pm], [G541;3-Prd], [G542;4-F-3-Prd], [G543;4-Cl-3-Prd], [G544;4-Br-3-Prd], [G545;4-I-3-Prd], [G546;4-Me-3-Prd], [G547;4-Et-3-Prd], [G548;4-Pr-3-Prd], [G549;4-iPr-3-Prd], [G550;4-CF$_3$-3-Prd], [G551;4-CHF$_2$-3-Prd], [G552;4-OMe-3-Prd], [G553;4-OEt-3-Prd], [G554;4-OCF$_3$-3-Prd], [G555;4-OCHF$_2$-3-Prd], [G556;4-CN-3-Prd], [G557;4-SMe-3-Prd], [G558;4-SEt-3-Prd], [G559;4-cPr-3-Prd], [G560;5-F-3-Prd], [G561;5-Cl-3-Prd], [G562;5-Br-3-Prd], [G563;5-I-3-Prd], [G564;5-Me-3-Prd], [G565;5-Et-3-Prd], [G566;5-Pr-3-Prd], [G567;5-iPr-3-Prd], [G568;5-CF$_3$-3-Prd], [G569;5-CHF$_2$-3-Prd], [G570;5-OMe-3-Prd], [G571;5-OEt-3-Prd], [G572;5-OCF$_3$-3-Prd], [G573;5-OCHF$_2$-3-Prd], [G574;5-CN-3-Prd], [G575;5-SMe-3-Prd], [G576;5-SEt-3-Prd], [G577;5-cPr-3-Prd], [G578;6-F-3-Prd], [G579;6-Cl-3-Prd], [G580;6-Br-3-Prd], [G581;6-I-3-Prd], [G582;6-Me-3-Prd], [G583;6-Et-3-Prd], [G584;6-Pr-3-Prd], [G585;6-iPr-3-Prd], [G586;6-CF$_3$-3-Prd], [G587;6-CHF$_2$-3-Prd], [G588;6-OMe-3-Prd], [G589;6-OEt-3-Prd], [G590;6-OCF$_3$-3-Prd], [G591;6-OCHF$_2$-3-Prd], [G592;6-CN-3-Prd], [G593;6-SMe-3-Prd], [G594;6-SEt-3-Prd], [G595;6-cPr-3-Prd], [G596;4-Prd], [G597;3-F-4-Prd], [G598;3-Cl-4-Prd], [G599;3-Br-4-Prd],

[G600;3-I-4-Prd], [G601;3-Me-4-Prd], [G602;3-Et-4-Prd], [G6603;3-Pr-4-Prd], [G604;3-iPr-4-Prd], [G605;3-CF$_3$-4-Prd], [G606;3-CHF$_2$-4-Prd], [G607;3-OMe-4-Prd], [G608;3-OEt-4-Prd], [G609;3-OCF$_3$-4-Prd], [G610;3-OCHF$_2$-4-Prd], [G611;3-CN-4-Prd], [G612;3-SMe-4-Prd], [G613;3-SEt-4-Prd], [G614;3-cPr-4-Prd], [G615;5-F-4-Prd], [G616;5-Cl-4-Prd], [G617;5-Br-4-Prd], [G618;5-I-4-Prd], [G619;5-Me-4-Prd], [G620;5-Et-4-Prd], [G621;5-Pr-4-Prd], [G622;5-iPr-4-Prd], [G623;5-CF$_3$-4-Prd], [G624;5-CHF$_2$-4-Prd], [G626;5-OMe-4-Prd], [G626;5-OEt-4-Prd], [G627;5-OCF$_3$-4-Prd], [G628;5-OCHF$_2$-4-Prd], [G629;5-CN-4-Prd], [G630;5-SMe-4-Prd], [G631;5-SEt-4-Prd], [G632;5-cPr-4-Prd], [G633;6-F-4-Prd], [G634;6-Cl-4-Prd], [G635;6-Br-4-Prd], [G636;6-I-4-Prd], [G637;6-Me-4-Prd], [G638;6-Et-4-Prd], [G639;6-Pr-4-Prd], [G640;6-iPr-4-Prd], [G641;6-CF$_3$-4-Prd], [G642;6-CHF$_2$-4-Prd], [G643;6-OMe-4-Prd], [G644;6-OEt-4-Prd], [G645;6-OCF$_3$-4-Prd], [G646;6-OCHF$_2$-4-Prd], [G647;6-CN-4-Prd], [G648;6-SMe-4-Prd], [G649;6-SEt-4-Prd], [G650;6-cPr-4-Prd], [G651;2-Pra], [G652;2-F-2-Pra], [G653;2-Cl-2-Pra], [G654;2-Br-2-Pra], [G655;2-I-2-Pra], [G6656;2-Me-2-Pra], [G657;2-Et-2-Pra], [G658;2-Pr-2-Pra], [G659;2-iPr-2-Pra], [G660;2-CF$_3$-2-Pra], [G661;2-CHF$_2$-2-Pra], [G662;2-OMe-2-Pra], [G663;2-OEt-2-Pra], [G664;2-OCF$_3$-2-Pra], [G665;2-OCHF$_2$-2-Pra], [G666;2-CN-2-Pra], [G667;2-SMe-2-Pra], [G668;2-SEt-2-Pra], [G669;2-cPr-2-Pra], [G670;5-F-2-Pra], [G671;5-Cl-2-Pra], [G672;5-Br-2-Pra], [G673;5-I-2-Pra], [G674;5-Me-2-Pra], [G675;5-Et-2-Pra], [G676;5-Pr-2-Pra], [G677;5-iPr-2-Pra], [G678;5-CF$_3$-2-Pra], [G679;5-CHF$_2$-2-Pra], [G680;5-OMe-2-Pra], [G681;5-OEt-2-Pra], [G682;5-OCF$_3$-2-Pra], [G683;5-OCHF$_2$-2-Pra], [G684;5-CN-2-Pra], [G685;5-SMe-2-Pra], [G686;5-SEt-2-Pra], [G687;5-cPr-2-Pra], [G688;6-F-2-Pra], [G689;6-Cl-2-Pra], [G690;6-Br-2-Pra], [G691;6-I-2-Pra], [G692;6-Me-2-Pra], [G693;6-Et-2-Pra], [G694;6-Pr-2-Pra], [G695;6-iPr-2-Pra], [G696;6-CF$_3$-2-Pra], [G697;6-CHF$_2$-2-Pra], [G698;6-OMe-2-Pra], [G699;6-OEt-2-Pra], [G700;6-OCF$_3$-2-Pra], [G701;6-OCHF$_2$-2-Pra], [G702;6-CN-2-Pra], [G703;6-SMe-2-Pra], [G704;6-SEt-2-Pra], [G705;6-cPr-2-Pra], [G706;(1,2,3-tri-1)], [G707;4-F-(1,2,3-tri-1)], [G708;4-Cl-(1,2,3-tri-1)], [G709;4-Br-(1,2,3-tri-1)], [G710;4-I-(1,2,3-tri-1)], [G711;4-Me-(1,2,3-tri-1)], [G712;4-Et-(1,2,3-tri-1)], [G713;4-Pr-(1,2,3-tri-1)], [G714;4-iPr-(1,2,3-tri-1)], [G715;4-CF$_3$-(1,2,3-tri-1)], [G716;4-CHF$_2$-(1,2,3-tri-1)], [G717;4-OMe-(1,2,3-tri-1)], [G718;4-OEt-(1,2,3-tri-1)], [G719;4-OCF$_3$-(1,2,3-tri-1)], [G720;4-OCHF$_2$-(1,2,3-tri-1)], [G721;4-CN-(1,2,3-tri-1)], [G722;4-SMe-(1,2,3-tri-1)], [G723;4-SEt-(1,2,3-tri-1)], [G724;4-cPr-(1,2,3-tri-1)], [G725;5-F-(1,2,3-tri-1)], [G726;5-Cl-(1,2,3-tri-1)], [G727;5-Br-(1,2,3-tri-1)], [G728;5-I-(1,2,3-tri-1)], [G729;5-Me-(1,2,3-tri-1)], [G730;5-Et-(1,2,3-tri-1)], [G731;5-Pr-(1,2,3-tri-1)], [G732;5-iPr-(1,2,3-tri-1)], [G733;5-CF$_3$-(1,2,3-tri-1)], [G734;5-CHF$_2$-(1,2,3-tri-1)], [G735;5-OMe-(1,2,3-tri-1)], [G736;5-OEt-(1,2,3-tri-1)], [G737;5-OCF$_3$-(1,2,3-tri-1)], [G738;5-OCHF$_2$-(1,2,3-tri-1)], [G739;5-CN-(1,2,3-tri-1)], [G740;5-SMe-(1,2,3-tri-1)], [G741;5-SEt-(1,2,3-tri-1)], [G742;5-cPr-(1,2,3-tri-1)], [G743;(1,2,4-tri-1)], [G744;3-F-(1,2,4-tri-1)], [G745;3-Cl-(1,2,4-tri-1)], [G746;3-Br-(1,2,4-tri-1)], [G747;3-I-(1,2,4-tri-1)], [G748;3-Me-(1,2,4-tri-1)], [G749;3-Et-(1,2,4-tri-1)], [G750;3-Pr-(1,2,4-tri-1)], [G751;3-iPr-(1,2,4-tri-1)], [G752;3-CF$_3$-(1,2,4-tri-1)], [G753;3-CHF$_2$-(1,2,4-tri-1)], [G754;3-OMe-(1,2,4-tri-1)], [G755;3-OEt-(1,2,4-tri-1)], [G756;3-OCF$_3$-(1,2,4-tri-1)], [G757;3-OCHF$_2$-(1,2,4-tri-1)], [G758;3-CN-(1,2,4-tri-1)], [G759;3-SMe-(1,2,4-tri-1)], [G760;3-SEt-(1,2,4-tri-1)], [G761;3-cPr-(1,2,4-tri-1)], [G762;5-F-(1,2,4-tri-1)], [G763;5-Cl-(1,2,4-tri-1)], [G764;5-Br-(1,2,4-tri-1)], [G765;5-I-(1,2,4-tri-1)], [G766;5-Me-(1,2,4-tri-1)], [G767;5-Et-(1,2,4-tri-1)], [G768;5-Pr-(1,2,4-tri-1)], [G769;5-iPr-(1,2,4-tri-1)], [G770;5-CF$_3$-(1,2,4-tri-1)], [G771;5-CHF$_2$-(1,2,4-tri-1)], [G772;5-OMe-(1,2,4-tri-1)], [G773;5-OEt-(1,2,4-tri-1)], [G774;5-OCF$_3$-(1,2,4-tri-1)], [G775;5-OCHF$_2$-(1,2,4-tri-1)], [G776;5-CN-(1,2,4-tri-1)], [G777;5-

SMe-(1,2,4-tri-1)], [G778;5-SEt-(1,2,4-tri-1)], [G779;5-cPr-(1,2,4-tri-1)], [G780;(1,2,5-Oxa-3)], [G781;5-F-(1,2,5-Oxa-3)], [G782;5-Cl-(1,2,5-Oxa-3)], [G783;5-Br-(1,2,5-Oxa-3)], [G784;5-I-(1,2,5-Oxa-3)], [G785;5-Me-(1,2,5-Oxa-3)], [G786;5-Et-(1,2,5-Oxa-3)], [G787;5-Pr-(1,2,5-Oxa-3)], [G788;5-iPr-(1,2,5-Oxa-3)], [G789;5-CF$_3$-(1,2,5-Oxa-3)], [G790;5-CHF$_2$-(1,2,5-Oxa-3)], [G791;5-OMe-(1,2,5-Oxa-3)], [G792;5-OEt-(1,2,5-Oxa-3)], [G793;5-OCF$_3$-(1,2,5-Oxa-3)], [G794;5-OCHF$_2$-(1,2,5-Oxa-3)], [G795;5-CN-(1,2,5-Oxa-3)], [G796;5-SMe-(1,2,5-Oxa-3)], [G797;5-SEt-(1,2,5-Oxa-3)], [G798;5-cPr-(1,2,5-Oxa-3)], [G799;(1,2,4-Oxa-5)],

[G800;3-F-(1,2,4-Oxa-5)], [G801;3-Cl-(1,2,4-Oxa-5)], [G802;3-Br-(1,2,4-Oxa-5)], [G803;3-I-(1,2,4-Oxa-5)], [G8804;3-Me-(1,2,4-Oxa-5)], [G805;3-Et-(1,2,4-Oxa-5)], [G806;3-Pr-(1,2,4-Oxa-5)], [G807;3-iPr-(1,2,4-Oxa-5)], [G808;3-CF$_3$-(1,2,4-Oxa-5)], [G809;3-CHF$_2$-(1,2,4-Oxa-5)], [G810;3-OMe-(1,2,4-Oxa-5)], [G811;3-OEt-(1,2,4-Oxa-5)], [G812;3-OCF$_3$-(1,2,4-Oxa-5)], [G813;3-OCHF$_2$-(1,2,4-Oxa-5)], [G814;3-CN-(1,2,4-Oxa-5)], [G815;3-SMe-(1,2,4-Oxa-5)], [G816;3-SEt-(1,2,4-Oxa-5)], [G817;3-cPr-(1,2,4-Oxa-5)], [G818;(1,2,4-Oxa-3)], [G819;5-F-(1,2,4-Oxa-3)], [G820;5-Cl-(1,2,4-Oxa-3)], [G821;5-Br-(1,2,4-Oxa-3)], [G822;5-I-(1,2,4-Oxa-3)], [G823;5-Me-(1,2,4-Oxa-3)], [G824;5-Et-(1,2,4-Oxa-3)], [G825;5-Pr-(1,2,4-Oxa-3)], [G826;5-iPr-(1,2,4-Oxa-3)], [G827;5-CF$_3$-(1,2,4-Oxa-3)], [G828;5-CHF$_2$-(1,2,4-Oxa-3)], [G829;5-OMe-(1,2,4-Oxa-3)], [G830;5-OEt-(1,2,4-Oxa-3)], [G831;5-OCF$_3$-(1,2,4-Oxa-3)], [G832;5-OCHF$_2$-(1,2,4-Oxa-3)], [G833;5-CN-(1,2,4-Oxa-3)], [G834;5-SMe-(1,2,4-Oxa-3)], [G835;5-SEt-(1,2,4-Oxa-3)], [G836;5-cPr-(1,2,4-Oxa-3)], [G837;(1,2,3-Thia-4)], [G838;5-F-(1,2,3-Thia-4)], [G839;5-Cl-(1,2,3-Thia-4)], [G840;5-Br-(1,2,3-Thia-4)], [G841;5-I-(1,2,3-Thia-4)], [G842;5-Me-(1,2,3-Thia-4)], [G843;5-Et-(1,2,3-Thia-4)], [G844;5-Pr-(1,2,3-Thia-4)], [G845;5-iPr-(1,2,3-Thia-4)], [G846;5-CF$_3$-(1,2,3-Thia-4)], [G847;5-CHF$_2$-(1,2,3-Thia-4)], [G848;5-OMe-(1,2,3-Thia-4)], [G849;5-OEt-(1,2,3-Thia-4)], [G850;5-OCF$_3$-(1,2,3-Thia-4)], [G851;5-OCHF$_2$-(1,2,3-Thia-4)], [G852;5-CN-(1,2,3-Thia-4)], [G853;5-SMe(1,2,3-Thia-4)], [G854;5-SEt-(1,2,3-Thia-4)], [G855;5-cPr-(1,2,3-Thia-4)], [G856;(1,2,3-Thia-5)], [G857;4-F-(1,2,3-Thia-5)], [G858;4-Cl-(1,2,3-Thia-5)], [G859;4-Br-(1,2,3-Thia-5)], [G860;4-J-(1,2,3-Thia-5)], [G861;4-Me-(1,2,3-Thia-5)], [G862;4-Et-(1,2,3-Thia-5)], [G863;4-Pr-(1,2,3-Thia-5)], [G864;4-iPr-(1,2,3-Thia-5)], [G865;4-CF$_3$-(1,2,3-Thia-5)], [G866;4-CHF$_2$-(1,2,3-Thia-5)], [G867;4-OMe-(1,2,3-Thia-5)], [G868;4-OEt-(1,2,3-Thia-5)], [G869;4-OCF$_3$-(1,2,3-Thia-5)], [G870;4-OCHF$_2$-(1,2,3-Thia-5)], [G871;4-CN-(1,2,3-Thia-5)], [G872;4-SMe-(1,2,3-Thia-5)], [G873;4-SEt-(1,2,3-Thia-5)], [G874;4-cPr-(1,2,3-Thia-5)], [G875;(1,2,4-Thia-5)], [G876;3-F-(1,2,4-Thia-5)], [G877;3-Cl-(1,2,4-Thia-5)], [G878;3-Br-(1,2,4-Thia-5)], [G879;3-I-(1,2,4-Thia-5)], [G880;3-Me-(1,2,4-Thia-5)], [G881;3-Et-(1,2,4-Thia-5)], [G882;3-Pr-(1,2,4-Thia-5)], [G883;3-iPr-(1,2,4-Thia-5)], [G884;3-CF$_3$-(1,2,4-Thia-5)], [G885;3-CHF$_2$-(1,2,4-Thia-5)], [G886;3-OMe-(1,2,4-Thia-5)], [G887;3-OEt-(1,2,4-Thia-5)], [G888;3-OCF$_3$-(1,2,4-Thia-5)], [G889;3-OCHF$_2$-(1,2,4-Thia-5)], [G890;3-CN-(1,2,4-Thia-5)], [G891;3-SMe-(1,2,4-Thia-5)], [G892;3-SEt-(1,2,4-Thia-5)], [G893;3-cPr-(1,2,4-Thia-5)], [G894;(1,2,4-Thia-3)], [G895;5-F-(1,2,4-Thia-3)], [G896;5-Cl-(1,2,4-Thia-3)], [G897;5-Br-(1,2,4-Thia-3)], [G898;5-I-(1,2,4-Thia-3)], [G899;5-Me-(1,2,4-Thia-3)], [G900;5-Et-(1,2,4-Thia-3)], [G901;5-Pr-(1,2,4-Thia-3)], [G902;5-iPr-(1,2,4-Thia-3)], [G903;5-CF$_3$-(1,2,4-Thia-3)], [G904;5-CHF$_2$-(1,2,4-Thia-3)], [G905;5-OMe-(1,2,4-Thia-3)], [G906;5-OEt-(1,2,4-Thia-3)], [G907;5-OCF$_3$-(1,2,4-Thia-3)], [G908;5-OCHF$_2$-(1,2,4-Thia-3)], [G909;5-CN-(1,2,4-Thia-3)], [G910;5-SMe-(1,2,4-Thia-3)], [G911;5-SEt-(1,2,4-Thia-3)], [G912;5-cPr-(1,2,4-Thia-3)], [G913;(1,2,4-tet-1)], [G914;5-F-(1,2,4-tet-1)], [G915;5-Cl-(1,2,4-tet-1)], [G916;5-Br-(1,2,4-tet-1)], [G917;5-I-(1,2,4-tet-1)], [G918;5-Me-(1,2,4-tet-1)], [G919;5-Et-(1,2,4-tet-1)], [G920;5-Pr-(1,2,4-tet-1)], [G921;5-iPr-(1,2,4-tet-1)], [G922;5-CF$_3$-(1,2,4-tet-1)], [G923;5-CHF$_2$-(1,2,4-tet-1)], [G924;5-OMe-(1,2,4-tet-1)], [G925;5-OEt-(1,2,4-tet-1)], [G9926;5-OCF$_3$-(1,2,4-tet-1)], [G927;5-OCHF$_2$-(1,2,4-tet-1)], [G928;5-CN-(1,2,4-tet-1)], [G929;5-SMe-(1,2,4-tet-1)], [G930;5-SEt-(1,2,4-tet-1)], [G931;5-cPr-(1,2,4-tet-1)], [G932;tet-5], [G933;1-F-tet-5], [G934;1-Cl-tet-5], [G935;1-Br-tet-5], [G936;1-I-tet-5], [G937;1-Me-tet-5], [G938;1-Et-tet-5], [G939;1-Pr-tet-5], [G940;1-iPr-tet-5], [G941;1-CF$_3$-tet-5], [G942;1-CHF$_2$-tet-5], [G943;1-OMe-tet-5], [G944;1-OEt-tet-5], [G945;1-OCF$_3$-tet-5], [G946;1-OCHF$_2$-tet-5], [G947;1-CN-tet-5], [G948;1-SMe-tet-5], [G949;1-SEt-tet-5], [G950;1-cPr-tet-5], [G951;3-Fra], [G952;2-F-3-Fra], [G953;2-Cl-3-Fra], [G954;2-Me-3-Fra], [G955;2-Et-3-Fra], [G956;2-iPr-3-Fra], [G957;2-CF$_3$-3-Fra], [G958;2-CHF$_2$-3-Fra], [G959;2-OMe-3-Fra], [G960;2-OEt-3-Fra], [G961;2-OCF$_3$-3-Fra], [G962;2-OCHF$_2$-3-Fra], [G963;2-CN-3-Fra], [G964;2-SMe-3-Fra], [G965;2-SEt-3-Fra], [G966;2-cPr-3-Fra], [G967;4-F-3-Fra], [G968;4-Cl-3-Fra], [G969;4-Me-3-Fra], [G970;4-ET-3-Fra], [G971;4-iPr-3-Fra], [G972;4-CF$_3$-3-Fra], [G973;4-CHF$_2$-3-Fra], [G974;4-OMe-3-Fra], [G975;4-OEt-3-Fra], [G976;4-OCF$_3$-3-Fra], [G977;4-OCHF$_2$-3-Fra], [G978;4-CN-3-Fra], [G979;4-SMe-3-Fra], [G980;4-SEt-3-Fra], [G981;4-cPr-3-Fra], [G982;5-F-3-Fra], [G983;5-Cl-3-Fra], [G984;5-Me-3-Fra], [G985;5-ET-3-Fra], [G986;5-iPr-3-Fra], [G987;5-CF$_3$-3-Fra], [G988;5-CHF$_2$-3-Fra], [G989;5-OMe-3-Fra], [G990;5-OEt-3-Fra], [G991;5-OCF$_3$-3-Fra], [G992;5-OCHF$_2$-3-Fra], [G993;5-CN-3-Fra], [G994;5-SMe-3-Fra], [G995;5-SEt-3-Fra], [G996;5-cPr-3-Fra], [G997;2-Fra], [G998;3-F-2-Fra], [G999;3-Cl-2-Fra],

[G1000;3-Me-2-Fra], [G1001;3-ET-2-Fra], [G1002;3-iPr-2-Fra], [G1003;3-CF$_3$-2-Fra], [G1004;3-CHF$_2$-2-Fra], [G1005;3-OMe-2-Fra], [G1006;3-OEt-2-Fra], [G1007;3-OCF$_3$-2-Fra], [G1008;3-OCHF$_2$-2-Fra], [G1009;3-CN-2-Fra], [G1010;3-SMe-2-Fra], [G1011;3-SEt-2-Fra], [G1012;3-cPr-2-Fra], [G1013;4-F-2-Fra], [G1014;4-Cl-2-Fra], [G1015;4-Me-2-Fra], [G1016;4-ET-2-Fra], [G1017;4-iPr-2-Fra], [G1018;4-CF$_3$-2-Fra], [G1019;4-CHF$_2$-2-Fra], [G1020;4-OMe-2-Fra], [G1021;4-OEt-2-Fra], [G1022;4-OCF$_3$-2-Fra], [G1023;4-OCHF$_2$-2-Fra], [G1024;4-CN-2-Fra], [G1025;4-SMe-2-Fra], [G1026;4-SEt-2-Fra], [G1027;4-cPr-2-Fra], [G1028;5-F-2-Fra], [G1029;5-Cl-2-Fra], [G1030;5-Me-2-Fra], [G1031;5-ET-2-Fra], [G1032;5-iPr-2-Fra], [G1033;5-CF$_3$-2-Fra], [G1034;5-CHF$_2$-2-Fra], [G1035;5-OMe-2-Fra], [G1036;5-OEt-2-Fra], [G1037;5-OCF$_3$-2-Fra], [G1038;5-OCHF$_2$-2-Fra], [G1039;5-CN-2-Fra], [G1040;5-SMe-2-Fra], [G1041;5-SEt-2-Fra], [G1042;5-cPr-2-Fra], [G1043;2-Bf], [G1044;3-Bf], [G1045;2-F-3-Bf], [G1046;2-Cl-3-Bf], [G1047;2-Me-3-Bf], [G1048;2-ET-3-Bf], [G1049;2-iPr-3-Bf], [G1050;2-CF$_3$-3-Bf], [G1051;2-CHF$_2$-3-Bf], [G1052;2-OMe-3-Bf], [G1053;2-OEt-3-Bf], [G1054;2-OCF$_3$-3-Bf], [G1055;2-OCHF$_2$-3-Bf], [G1056;2-CN-3-Bf], [G1057;2-SMe-3-Bf], [G1058;2-SEt-3-Bf], [G1059;2-cPr-3-Bf], [G1060;4-F-3-Bf], [G1061;4-Cl-3-Bf], [G1062;4-Me-3-Bf], [G1063;4-ET-3-Bf], [G1064;4-iPr-3-Bf], [G1065;4-CF$_3$-3-Bf], [G1066;4-CHF$_2$-3-Bf], [G1067;4-OMe-3-Bf], [G1068;4-OEt-3-Bf], [G1069;4-OCH$_3$-3-Bf], [G1070;4-OCHF$_2$-3-Bf], [G1071;4-CN-3-Bf], [G1072;4-SMe-3-Bf], [G1073;4-SEt-3-Bf], [G1074;4-cPr-3-Bf], [G1075;5-F-3-Bf], [G1076;5-Cl-3-Bf], [G1077;5-Me-3-Bf], [G1078;5-Et-3-Bf], [G1079;5-iPr-3-Bf], [G1080;5-CF$_3$-3-

Bf], [G1081;5-CHF$_2$-3-Bf], [G1082;5-OMe-3-Bf], [G1083; 5-OEt-3-Bf], [G1084;5-OCF$_3$-3-Bf], [G1085;5-OCHF$_2$-3-Bf], [G1086;5-CN-3-Bf], [G1087;5-SMe-3-Bf], [G1088;5-SEt-3-Bf], [G1089;5-cPr-3-Bf], [G1090;6-F-3-Bf], [G1091; 6-Cl-3-Bf], [G1092;6-Me-3-Bf], [G10936;6-Et-3-Bf], [G1094;6-iPr-3-Bf], [G1095;6-CF$_3$-3-Bf], [G1096;6-CHF$_2$-3-Bf], [G1097;6-OMe-3-Bf], [G1098;6-OEt-3-Bf], [G1099; 6-OCF$_3$-3-Bf], [G1100;6-OCHF$_2$-3-Bf], [G1101;6-CN-3-Bf], [G1102;6-SMe-3-Bf], [G1103;6-SEt-3-Bf], [G1104;6-cPr-3-Bf], [G1105;7-F-3-Bf], [G1106;7-Cl-3-Bf], [G1107; 7-Me-3-Bf], [G1108;7-Et-3-Bf], [G1109;7-iPr-3-Bf], [G1110;7-CF$_3$-3-Bf], [G1111;7-CHF$_2$-3-Bf], [G1112;7-OMe-3-Bf], [G1113;7-OEt-3-Bf], [G1114;7-OCF$_3$-3-Bf], [G1115;7-OCHF$_2$-3-Bf], [G1116;7-CN-3-Bf], [G1117;7-SMe-3-Bf], [G1118;7-SEt-3-Bf], [G1119;7-cPr-3-Bf], [G1120;3-F-2-Bf], [G1121;3-Cl-2-Bf], [G1122;3-Me-2-Bf], [G1123;3-Et-2-Bf], [G1124;3-iPr-2-Bf], [G1125;3-CF$_3$-2-Bf], [G1126;3-CHF$_2$-2-Bf], [G1127;3-OMe-2-Bf], [G1128; 3-OEt-2-Bf], [G1129;3-OCF$_3$-2-Bf], [G1130;3-OCHF$_2$-2-Bf], [G1131;3-CN-2-Bf], [G1132;3-SMe-2-Bf], [G1133;3-SEt-2-Bf], [G1134;3-cPr-2-Bf], [G1135;4-F-2-Bf], [G1136; 4-Cl-2-Bf], [G1137;4-Me-2-Bf], [G1138;4-Et-2-Bf], [G1139;4-iPr-2-Bf], [G1140;4-CF$_3$-2-Bf], [G1141;4-CHF$_2$-2-Bf], [G1142;4-OMe-2-Bf], [G1143;4-OEt-2-Bf], [G1144; 4-OCF$_3$-2-Bf], [G1145;4-OCHF$_2$-2-Bf], [G1146;4-CN-2-Bf], [G1147;4-SMe-2-Bf], [G1148;4-SEt-2-Bf], [G1149;4-cPr-2-Bf], [G1150;5-F-2-Bf], [G1151;5-Cl-2-Bf], [G1152; 5-Me-2-Bf], [G1153;5-Et-2-Bf], [G1154;5-iPr-2-Bf], [G1155;5-CF$_3$-2-Bf], [G1156;5-CHF$_2$-2-Bf], [G1157;5-OMe-2-Bf], [G1158;5-OEt-2-Bf], [G1159;5-OCF$_3$-2-Bf], [G1160;5-OCHF$_2$-2-Bf], [G1161;5-CN-2-Bf], [G1162;5-SMe-2-Bf], [G1163;5-SEt-2-Bf], [G1164;5-cPr-2-Bf], [G1165;6-F-2-Bf], [G1166;6-Cl-2-Bf], [G1167;6-Me-2-Bf], [G1168;6-Et-2-Bf], [G1169;6-iPr-2-Bf], [G1170;6-CF$_3$-2-Bf], [G1171;6-CHF$_2$-2-Bf], [G1172;6-OMe-2-Bf], [G1173; 6-OEt-2-Bf], [G1174;6-OCF$_3$-2-Bf], [G1175;6-OCHF$_2$-2-Bf], [G1176;6-CN-2-Bf], [G1177;6-SMe-2-Bf], [G1178;6-SEt-2-Bf], [G1179;6-cPr-2-Bf], [G1180;7-F-2-Bf], [G1181; 7-Cl-2-Bf], [G1182;7-Me-2-Bf], [G1183;7-Et-2-Bf], [G1184;7-iPr-2-Bf], [G1185;7-CF$_3$-2-Bf], [G1186;7-CHF$_2$-2-Bf], [G1187;7-OMe-2-Bf], [G1188;7-OEt-2-Bf], [G1189; 7-OCF$_3$-2-Bf], [G1190;7-OCHF$_2$-2-Bf], [G1191;7-CN-2-Bf], [G1192;7-SMe-2-Bf], [G1193;7-SEt-2-Bf], [G1194;7-cPr-2-Bf], [G1195;6-F-4-Bf], [G1196;3-F-4-Bf], [G1197;3-Cl-4-Bf], [G1198;3-Me-4-Bf], [G1199;3-Et-4-Bf],

[G1200;3-iPr-4-Bf], [G1201;3-CF$_3$-4-Bf], [G1202;3-CHF$_2$-4-Bf], [G1203;3-OMe-4-Bf], [G1204;3-OEt-4-Bf], [G1205;3-OCF$_3$-4-Bf], [G1206;3-OCHF$_2$-4-Bf], [G1207;3-CN-4-Bf], [G1208;3-SMe-4-Bf], [G1209;3-SEt-4-Bf], [G1210;3-cPr-4-Bf], [G1211;5-F-4-Bf], [G1212;5-Cl-4-Bf], [G1213;5-Me-4-Bf], [G1214;5-Et-4-Bf], [G1215;5-iPr-4-Bf], [G1216;5-CF$_3$-4-Bf], [G1217;5-CHF$_2$-4-Bf], [G1218; 5-OMe-4-Bf], [G1219;5-OEt-4-Bf], [G1220;5-OCF$_3$-4-Bf], [G1221;5-OCHF$_2$-4-Bf], [G1222;5-CN-4-Bf], [G1223;5-SMe-4-Bf], [G1224;5-SEt-4-Bf], [G1225;5-cPr-4-Bf], [G1226;6-F-4-Bf], [G1227;6-Cl-4-Bf], [G1228;6-Me-4-Bf], [G1229;6-Et-4-Bf], [G1230;6-iPr-4-Bf], [G1231;6-CF$_3$-4-Bf], [G1232;6-CHF$_2$-4-Bf], [G1233;6-OMe-4-Bf], [G1234; 6-OEt-4-Bf], [G1235;6-OCF$_3$-4-Bf], [G1236;6-OCHF$_2$-4-Bf], [G1237;6-CN-4-Bf], [G1238;6-SMe-4-Bf], [G1239;6-SEt-4-Bf], [G1240;6-cPr-4-Bf], [G1241;2-Bt], [G1242;4-F-2-Bt], [G1243;4-Cl-2-Bt], [G1244;4-Me-2-Bt], [G1245;4-Et-2-Bt], [G1246;4-iPr-2-Bt], [G1247;4-CF$_3$-2-Bt], [G1248; 4-CHF$_2$-2-Bt], [G1249;4-OMe-2-Bt], [G1250;4-OEt-2-Bt], [G1251;4-OCF$_3$-2-Bt], [G1252;4-OCHF$_2$-2-Bt], [G1253;4-CN-2-Bt], [G1254;4-SMe-2-Bt], [G1255;4-SEt-2-Bt], [G1256;4-cPr-2-Bt], [G11257;7-F-2-Bt], [G1258;7-Cl-2-Bt], [G1259;7-Me-2-Bt], [G1260;7-Et-2-Bt], [G1261;7-iPr-2-Bt], [G1262;7-CF$_3$-2-Bt], [G1263;7-CHF$_2$-2-Bt], [G1264; 7-OMe-2-Bt], [G1265;7-OEt-2-Bt], [G1266;7-OCF$_3$-2-Bt], [G1267;7-OCHF$_2$-2-Bt], [G1268;7-CN-2-Bt], [G1269;7-SMe-2-Bt], [G1270;7-SEt-2-Bt], [G1271;7-cPr-2-Bt], [G1272;4-Bt], [G1273;2-F-4-Bt], [G1274;2-Cl-4-Bt], [G1275;2-Me-4-Bt], [G1276;2-Et-4-Bt], [G1277;2-iPr-4-Bt], [G1278;2-CF$_3$-4-Bt], [G1279;2-CHF$_2$-4-Bt], [G1280;2-OMe-4-Bt], [G1281;2-OEt-4-Bt], [G1282;2-OCF$_3$-4-Bt], [G1283;2-OCHF$_2$-4-Bt], [G1284;2-CN-4-Bt], [G1285;2-SMe-4-Bt], [G1286;2-SEt-4-Bt], [G1287;2-cPr-4-Bt], [G1288;5-F-4-Bt], [G1289;5-Cl-4-Bt], [G1290;5-Me-4-Bt], [G1291;5-Et-4-Bt], [G1292;5-iPr-4-Bt], [G1293;5-CF$_3$-4-Bt], [G1294;5-CHF$_2$-4-Bt], [G1295;5-OMe-4-Bt], [G1296; 5-OEt-4-Bt], [G1297;5-OCF$_3$-4-Bt], [G1298;5-OCHF$_2$-4-Bt], [G1299;5-CN-4-Bt], [G1300;5-SMe-4-Bt], [G1301;5-SEt-4-Bt], [G1302;5-cPr-4-Bt], [G1303;6-F-4-Bt], [G1304; 6-Cl-4-Bt], [G1305;6-Me-4-Bt], [G1306;6-Et-4-Bt], [G1307;6-iPr-4-Bt], [G1308;6-CF$_3$-4-Bt], [G1309;6-CHF$_2$-4-Bt], [G1310;6-OMe-4-Bt], [G1311;6-OEt-4-Bt], [G1312; 6-OCF$_3$-4-Bt], [G1313;6-OCHF$_2$-4-Bt], [G1314;6-CN-4-Bt], [G1315;6-SMe-4-Bt], [G1316;6-SEt-4-Bt], [G1317;6-cPr-4-Bt], [G1318;7-F-4-Bt], [G1319;7-Cl-4-Bt], [G1320;7-Me-4-Bt], [G1321;7-Et-4-Bt], [G1322;7-iPr-4-Bt], [G1323; 7-CF$_3$-4-Bt], [G1324;7-CHF$_2$-4-Bt], [G1325;7-OMe-4-Bt], [G1326;7-OEt-4-Bt], [G1327;7-OCF$_3$-4-Bt], [G1328;7-OCHF$_2$-4-Bt], [G1329;7-CN-4-Bt], [G1330;7-SMe-4-Bt], [G1331;7-SEt-4-Bt], [G1332;7-cPr-4-Bt], [G1333;5-Bt], [G1334;5-F-5-Bt], [G1335;5-Cl-5-Bt], [G1336;5-Me-5-Bt], [G1337;5-Et-5-Bt], [G1338;5-iPr-5-Bt], [G1339;5-CF$_3$-5-Bt], [G1340;5-CHF$_2$-5-Bt], [G1341;5-OMe-5-Bt], [G1342; 5-OEt-5-Bt], [G1343;5-OCF$_3$-5-Bt], [G1344;5-OCHF$_2$-5-Bt], [G1345;5-CN-5-Bt], [G1346;5-SMe-5-Bt], [G1347;5-SEt-5-Bt], [G1348;5-cPr-5-Bt], [G1349;6-F-5-Bt], [G1350; 6-Cl-5-Bt], [G1351;6-Me-5-Bt], [G1352;6-Et-5-Bt], [G1353;6-iPr-5-Bt], [G1354;6-CF$_3$-5-Bt], [G1355;6-CHF$_2$-5-Bt], [G1356;6-OMe-5-Bt], [G1357;6-OEt-5-Bt], [G1358; 6-OCF$_3$-5-Bt], [G1359;6-OCHF$_2$-5-Bt], [G1360;6-CN-5-Bt], [G1361;6-SMe-5-Bt], [G1362;6-SEt-5-Bt], [G1363;6-cPr-5-Bt], [G1364;6-Bt], [G1365;5-F-4-Bt], [G1366;5-Cl-4-Bt], [G1367;5-Me-4-Bt], [G1368;5-Et-4-Bt], [G1369;5-iPr-4-Bt], [G1370;5-CF$_3$-4-Bt], [G1371;5-CHF$_2$-4-Bt], [G1372; 5-OMe-4-Bt], [G1373;5-OEt-4-Bt], [G1374;5-OCF$_3$-4-Bt], [G1375;5-OCHF$_2$-4-Bt], [G1376;5-CN-4-Bt], [G1377;5-SMe-4-Bt], [G1378;5-SEt-4-Bt], [G1379;5-cPr-4-Bt], [G1380;6-F-4-Bt], [G1381;6-Cl-4-Bt], [G1382;6-Me-4-Bt], [G1383;6-Et-4-Bt], [G1384;6-iPr-4-Bt], [G1385;6-CF$_3$-4-Bt], [G1386;6-CHF$_2$-4-Bt], [G1387;6-OMe-4-Bt], [G1388; 6-OEt-4-Bt], [G1389;6-OCF$_3$-4-Bt], [G1390;6-OCHF$_2$-4-Bt], [G1391;6-CN-4-Bt], [G1392;6-SMe-4-Bt], [G1393;6-SEt-4-Bt], [G1394;6-cPr-4-Bt], [G1395;1-Pyr], [G1396;4-F-1-Pyr], [G1397;4-Cl-1-Pyr], [G1398;4-Me-1-Pyr], [G1399;4-Et-1-Pyr],

[G1400;4-iPr-1-Pyr], [G1401;4-CF$_3$-1-Pyr], [G1402;4-CHF$_2$-1-Pyr], [G1403;4-OMe-1-Pyr], [G1404;4-OCF$_3$-1-Pyr], [G1405;4-OCHF$_2$-1-Pyr], [G1406;4-OCH$_2$CHF$_2$-1-Pyr], [G1407;4-CN-1-Pyr], [G1408;4-SMe-1-Pyr], [G1409; 4-cPr-1-Pyr], [G1410;5-F-1-Pyr], [G1411;5-Cl-1-Pyr], [G1412;5-Me-1-Pyr], [G1413;5-Et-1-Pyr], [G1414;5-iPr-1-Pyr], [G1415;5-CF$_3$-1-Pyr], [G1416;5-CHF$_2$-1-Pyr], [G1417;5-OMe-1-Pyr], [G1418;5-OCF$_3$-1-Pyr], [G1419;5-OCHF$_2$-1-Pyr], [G1420;5-OCH$_2$CHF$_2$-1-Pyr], [G1421;5-CN-1-Pyr], [G1422;5-SMe-1-Pyr], [G1423;5-cPr-1-Pyr], [G1424;5-F-5-F-1-Pyr], [G1425;4-F-5-Cl-1-Pyr], [G1426; 4-F-5-Me-1-Pyr], [G1427;4-F-5-Et-1-Pyr], [G1428;4-F-5-iPr-1-Pyr], [G1429;4-F-5-CF$_3$-1-Pyr], [G1430;4-F-5-CHF$_2$-1-Pyr], [G1431;4-F-5-OMe-1-Pyr], [G1432;4-F-5-OCF$_3$-1-

Pyr], [G1433;4-F-5-OCHF$_2$-1-Pyr], [G1434;4-F-5-OCH$_2$CHF$_2$-1-Pyr], [G1435;4-F-5-CN-1-Pyr], [G1436;4-F-5-SMe-1-Pyr], [G1437;4-F-5-cPr-1-Pyr], [G1438;4-Cl-5-F-1-Pyr], [G1439;4-Cl-5-Cl-1-Pyr], [G1440;4-Cl-5-Me-1-Pyr], [G1441;4-Cl-5-Et-1-Pyr], [G1442;4-Cl-5-iPr-1-Pyr], [G1443;4-Cl-5-CF$_3$-1-Pyr], [G1444;4-Cl-5-CHF$_2$-1-Pyr], [G1445;4-Cl-5-OMe-1-Pyr], [G1446;4-Cl-5-OCF$_3$-1-Pyr], [G1447;4-Cl-5-OCHF$_2$-1-Pyr], [G1448;4-Cl-5-OCH$_2$CHF$_2$-1-Pyr], [G1449;4-Cl-5-CN-1-Pyr], [G1450;4-Cl-5-SMe-1-Pyr], [G1451;4-Cl-5-cPr-1-Pyr], [G1452;4-Me-5-F-1-Pyr], [G1453;4-Me-5-Cl-1-Pyr], [G1454;4-Me-5-Me-1-Pyr], [G1455;4-Me-5-Et-1-Pyr], [G1456;4-Me-5-iPr-1-Pyr], [G1457;4-Me-5-CF$_3$-1-Pyr], [G1458;4-Me-5-CHF$_2$-1-Pyr], [G1459;4-Me-5-OMe-1-Pyr], [G1460;4-Me-5-OCF$_3$-1-Pyr], [G1461;4-Me-5-OCHF$_2$-1-Pyr], [G1462;4-Me-5-OCH$_2$CHF$_2$-1-Pyr], [G1463;4-Me-5-CN-1-Pyr], [G1464;4-Me-5-SMe-1-Pyr], [G1465;4-Me-5-cPr-1-Pyr], [G1466;4-Et-5-F-1-Pyr], [G1467;4-Et-5-Cl-1-Pyr], [G1468;4-Et-5-Me-1-Pyr], [G1469;4-Et-5-Et-1-Pyr], [G1470;4-Et-5-iPr-1-Pyr], [G11471;4-Et-5-CF$_3$-1-Pyr], [G1472;4-Et-5-CHF$_2$-1-Pyr], [G1473;4-Et-5-OMe-1-Pyr], [G1474;4-Et-5-OCF$_3$-1-Pyr], [G1475;4-Et-5-OCHF$_2$-1-Pyr], [G1476;4-Et-5-OCH$_2$CHF$_2$-1-Pyr], [G1477;4-Et-5-CN-1-Pyr], [G1478;4-Et-5-SMe-1-Pyr], [G1479;4-Et-5-cPr-1-Pyr], [G1480;4-CF$_3$-5-F-1-Pyr], [G1481;44-CF$_3$-5-Cl-1-Pyr], [G1482;4-CF$_3$-5-Me-1-Pyr], [G1483;4-CF$_3$-5-Et-1-Pyr], [G1484;4-CF$_3$-5-iPr-1-Pyr], [G1485;4-CF$_3$-5-CF$_3$-1-Pyr], [G1486;4-CF$_3$-5-CHF$_2$-1-Pyr], [G1487;4-CF$_3$-5-OMe-1-Pyr], [G1488;4-CF$_3$-5-OCF$_3$-1-Pyr], [G1489;4-CF$_3$-5-OCHF$_2$-1-Pyr], [G1490;4-CF$_3$-5-OCH$_2$CHF$_2$-1-Pyr], [G1491;4-CF$_3$-5-CN-1-Pyr], [G1492;4-CF$_3$-5-SMe-1-Pyr], [G1493;4-CF$_3$-5-cPr-1-Pyr], [G1494;4-OMe-5-F-1-Pyr], [G1495;4-OMe-5-Cl-1-Pyr], [G1496;4-OMe-5-Me-1-Pyr], [G1497;4-OMe-5-Et-1-Pyr], [G1498;4-OMe-5-iPr-1-Pyr], [G1499;4-OMe-5-CF$_3$-1-Pyr], [G1500;4-OMe-5-CHF$_2$-1-Pyr], [G1501;4-OMe-5-OMe-1-Pyr], [G1502;4-OMe-5-OCF$_3$-1-Pyr], [G1503;4-OMe-5-OCHF$_2$-1-Pyr], [G1504;4-OMe-5-OCH$_2$CHF$_2$-1-Pyr], [G1505;4-OMe-5-CN-1-Pyr], [G1506;4-OMe-5-SMe-1-Pyr], [G1507;4-OMe-5-cPr-1-Pyr], [G1508;4-SMe-5-F-1-Pyr], [G1509;4-SMe-5-Cl-1-Pyr], [G1510;4-SMe-5-Me-1-Pyr], [G1511;4-SMe-5-Et-1-Pyr], [G1512;4-SMe-5-iPr-1-Pyr], [G1513;4-SMe-5-CF$_3$-1-Pyr], [G1514;4-SMe-5-CHF$_2$-1-Pyr], [G1515;4-SMe-5-OMe-1-Pyr], [G1516;4-SMe-5-OCF$_3$-1-Pyr], [G1517;4-SMe-5-OCHF$_2$-1-Pyr], [G1518;4-SMe-5-OCH$_2$CHF$_2$-1-Pyr], [G1519;4-SMe-5-CN-1-Pyr], [G1520;4-SMe-5-SMe-1-Pyr], [G1521;4-SMe-5-cPr-1-Pyr], [G1522;4-Pyr], [G1523;2-F-4-Pyr], [G1524;2-Cl-4-Pyr], [G1525;2-Me-4-Pyr], [G1526;2-Et-4-Pyr], [G1527;2-iPr-4-Pyr], [G1528;2-CF$_3$-4-Pyr], [G1529;2-CHF$_2$-4-Pyr], [G1530;2-OMe-4-Pyr], [G1531;2-OCF$_3$-4-Pyr], [G1532;2-OCHF$_2$-4-Pyr], [G1533;2-OCH$_2$CHF$_2$-4-Pyr], [G1534;2-CN-4-Pyr], [G1535;2-SMe-4-Pyr], [G1536;2-cPr-4-Pyr], [G1537;5-F-4-Pyr], [G1538;5-Cl-4-Pyr], [G1539;5-Me-4-Pyr], [G1540;5-Et-4-Pyr], [G1541;5-iPr-4-Pyr], [G1542;5-CF$_3$-4-Pyr], [G1543;5-CHF$_2$-4-Pyr], [G1544;5-OMe-4-Pyr], [G1545;5-OCF$_3$-4-Pyr], [G1546;5-OCHF$_2$-4-Pyr], [G1547;5-OCH$_2$CHF$_2$-4-Pyr], [G1548;5-CN-4-Pyr], [G1549;5-SMe-4-Pyr], [G1550;5-cPr-4-Pyr], [G1551;2-F-5-F-4-Pyr], [G1552;2-F-5-Cl-4-Pyr], [G1553;2-F-5-Me-4-Pyr], [G1554;2-F-5-Et-4-Pyr], [G1555;2-F-5-iPr-4-Pyr], [G1556;2-F-5-CF$_3$-4-Pyr], [G1557;2-F-5-CHF$_2$-4-Pyr], [G1558;2-F-5-OMe-4-Pyr], [G1559;2-F-5-OCF$_3$-4-Pyr], [G1560;2-F-5-OCHF$_2$-4-Pyr], [G1561;2-F-5-OCH$_2$CHF$_2$-4-Pyr], [G1562;2-F-5-CN-4-Pyr], [G1563;2-F-5-SMe-4-Pyr], [G1564;2-F-5-cPr-4-Pyr], [G1565;2-Cl-5-F-4-Pyr], [G1566;2-Cl-5-Cl-4-Pyr], [G1567;2-Cl-5-Me-4-Pyr], [G1568;2-Cl-5-Et-4-Pyr], [G1569;2-Cl-5-iPr-4-Pyr], [G1570;2-Cl-5-CF$_3$-4-Pyr], [G1571;2-Cl-5-CHF$_2$-4-Pyr], [G1572;2-Cl-5-OMe-4-Pyr], [G1573;2-Cl-5-OCF$_3$-4-Pyr], [G1574;2-Cl-5-OCHF$_2$-4-Pyr], [G1575;2-Cl-5-OCH$_2$CHF$_2$-4-Pyr], [G1576;2-Cl-5-CN-4-Pyr], [G1577;2-Cl-5-SMe-4-Pyr], [G1578;2-Cl-5-cPr-4-Pyr], [G1579;2-Me-5-F-4-Pyr], [G1580;2-Me-5-Cl-4-Pyr], [G1581;2-Me-5-Me-4-Pyr], [G1582;2-Me-5-Et-4-Pyr], [G1583;2-Me-5-iPr-4-Pyr], [G1584;2-Me-5-CF$_3$-4-Pyr], [G1585;2-Me-5-CHF$_2$-4-Pyr], [G1586;2-Me-5-OMe-4-Pyr], [G1587;2-Me-5-OCF$_3$-4-Pyr], [G1588;2-Me-5-OCHF$_2$-4-Pyr], [G1589;2-Me-5-OCH$_2$CHF$_2$-4-Pyr], [G1590;2-Me-5-CN-4-Pyr], [G1591;2-Me-5-SMe-4-Pyr], [G1592;2-Me-5-cPr-4-Pyr], [G1593;2-Et-5-F-4-Pyr], [G1594;2-Et-5-Cl-4-Pyr], [G1595;2-Et-5-Me-4-Pyr], [G1596;2-Et-5-Et-4-Pyr], [G1597;2-Et-5-iPr-4-Pyr], [G1598;2-Et-5-CF$_3$-4-Pyr], [G1599;2-Et-5-CHF$_2$-4-Pyr], [G1600;2-Et-5-OMe-4-Pyr], [G1601;2-Et-5-OCF$_3$-4-Pyr], [G1602;2-Et-5-OCHF$_2$-4-Pyr], [G1603;2-Et-5-OCH$_2$CHF$_2$-4-Pyr], [G1604;2-Et-5-CN-4-Pyr], [G1605;2-Et-5-SMe-4-Pyr], [G1606;2-Et-5-cPr-4-Pyr], [G1607;2-CF$_3$-5-F-4-Pyr], [G1608;2-CF$_3$-5-Cl-4-Pyr], [G1609;2-CF$_3$-5-Me-4-Pyr], [G1610;2-CF$_3$-5-Et-4-Pyr], [G1611;2-CF$_3$-5-iPr-4-Pyr], [G1612;2-CF$_3$-5-CF$_3$-4-Pyr], [G1613;2-CF$_3$-5-CHF$_2$-4-Pyr], [G1614;2-CF$_3$-5-OMe-4-Pyr], [G1615;2-CF$_3$-5-OCF$_3$-4-Pyr], [G1616;2-CF$_3$-5-OCHF$_2$-4-Pyr], [G1617;2-CF$_3$-5-OCH$_2$CHF$_2$-4-Pyr], [G1618;2-CF$_3$-5-CN-4-Pyr], [G1619;2-CF$_3$-5-SMe-4-Pyr], [G1620;2-CF$_3$-5-cPr-4-Pyr], [G1621;2-OMe-5-F-4-Pyr], [G1622;2-OMe-5-Cl-4-Pyr], [G1623;2-OMe-5-Me-4-Pyr], [G1624;2-OMe-5-Et-4-Pyr], [G1625;2-OMe-5-iPr-4-Pyr], [G1626;2-OMe-5-CF$_3$-4-Pyr], [G1627;2-OMe-5-CHF$_2$-4-Pyr], [G1628;2-OMe-5-OMe-4-Pyr], [G1629;2-OMe-5-OCF$_3$-4-Pyr], [G1630;2-OMe-5-OCHF$_2$-4-Pyr], [G1631;2-OMe-5-OCH$_2$CHF$_2$-4-Pyr], [G1632;2-OMe-5-CN-4-Pyr], [G1633;2-OMe-5-SMe-4-Pyr], [G1634;2-OMe-5-cPr-4-Pyr], [G1635;2-SMe-5-F-4-Pyr], [G1636;2-SMe-5-Cl-4-Pyr], [G1637;2-SMe-5-Me-4-Pyr], [G1638;2-SMe-5-Et-4-Pyr], [G1639;2-SMe-5-iPr-4-Pyr], [G1640;2-SMe-5-CF$_3$-4-Pyr], [G1641;2-SMe-5-CHF$_2$-4-Pyr], [G1642;2-SMe-5-OMe-4-Pyr], [G1643;2-SMe-5-OCF$_3$-4-Pyr], [G1644;2-SMe-5-OCHF$_2$-4-Pyr], [G1645;2-SMe-5-OCH$_2$CHF$_2$-4-Pyr], [G1646;2-SMe-5-CN-4-Pyr], [G1647;2-SMe-5-SMe-4-Pyr], [G1648;2-SMe-5-cPr-4-Pyr], [G1649;5-Pyr], [G1650;2-F-5-Pyr], [G1651;2-Cl-5-Pyr], [G1652;2-Me-5-Pyr], [G1653;2-Et-5-Pyr], [G1654;2-CF$_3$-5-Pyr], [G1655;2-CHF$_2$-5-Pyr], [G1656;2-OMe-5-Pyr], [G1657;2-OCF$_3$-5-Pyr], [G1658;2-OCHF$_2$-5-Pyr], [G1659;2-OCH$_2$CHF$_2$-5-Pyr], [G1660;2-CN-5-Pyr], [G1661;2-SMe-5-Pyr], [G1662;2-cPr-5-Pyr], [G1663;4-F-5-Pyr], [G1664;4-Cl-5-Pyr], [G1665;4-Me-5-Pyr], [G1666;4-Et-5-Pyr], [G1667;4-iPr-5-Pyr], [G1668;4-CF$_3$-5-Pyr], [G1669;4-CHF$_2$-5-Pyr], [G1670;4-OMe-5-Pyr], [G1671;4-OCF$_3$-5-Pyr], [G1672;4-OCHF$_2$-5-Pyr], [G1673;4-OCH$_2$CHF$_2$-5-Pyr], [G1674;4-CN-5-Pyr], [G1675;4-SMe-5-Pyr], [G1676;4-cPr-5-Pyr], [G1677;2-F-4-F-5-Pyr], [G1678;2-F-4-Cl-5-Pyr], [G1679;2-F-4-Me-5-Pyr], [G1680;2-F-4-Et-5-Pyr], [G1681;2-F-4-iPr-5-Pyr], [G1682;2-F-4-CF$_3$-5-Pyr], [G1683;2-F-4-CHF$_2$-5-Pyr], [G1684;2-F-4-OMe-5-Pyr], [G1685;2-F-4-OCF$_3$-5-Pyr], [G1686;2-F-4-OCHF$_2$-5-Pyr], [G1687;2-F-4-OCH$_2$CHF$_2$-5-Pyr], [G1688;2-F-4-CN-5-Pyr], [G1689;2-F-4-SMe-5-Pyr], [G1690;2-F-4-cPr-5-Pyr], [G1691;2-Cl-4-F-5-Pyr], [G1692;2-Cl-4-Cl-5-Pyr], [G1693;2-Cl-4-Me-5-Pyr], [G1694;2-Cl-4-Et-5-Pyr], [G1695;2-Cl-4-iPr-5-Pyr], [G1696;2-Cl-4-CF$_3$-5-Pyr], [G1697;2-Cl-4-CHF$_2$-5-Pyr], [G1698;2-Cl-4-OMe-5-Pyr], [G1699;2-Cl-4-OCF$_3$-5-Pyr], [G1700;2-Cl-4-OCHF$_2$-5-Pyr], [G1701;2-Cl-4-OCH$_2$CHF$_2$-5-Pyr], [G1702;2-Cl-4-CN-5-Pyr], [G1703;2-

Cl-4-SMe-5-Pyr], [G1704;2-Cl-4-cPr-5-Pyr], [G1705;2-Me-4-F-5-Pyr], [G1706;2-Me-4-Cl-5-Pyr], [G1707;2-Me-4-Me-5-Pyr], [G1708;2-Me-4-Et-5-Pyr], [G1709;2-Me-4-iPr-5-Pyr], [G1710;2-Me-4-CF$_3$-5-Pyr], [G1711;2-Me-4-CHF$_2$-5-Pyr], [G1712;2-Me-4-OMe-5-Pyr], [G1713;2-Me-4-OCF$_3$-5-Pyr], [G1714;2-Me-4-OCHF$_2$-5-Pyr], [G1715;2-Me-4-OCH$_2$CHF$_2$-5-Pyr], [G1716;2-Me-4-CN-5-Pyr], [G1717;2-Me-4-SMe-5-Pyr], [G1718;2-Me-4-cPr-5-Pyr], [G1719;2-Et-4-F-5-Pyr], [G1720;2-Et-4-Cl-5-Pyr], [G1721;2-Et-4-Me-5-Pyr], [G1722;2-Et-4-Et-5-Pyr], [G1723;2-Et-4-iPr-5-Pyr], [G1724;2-Et-4-CF$_3$-5-Pyr], [G1725;2-Et-4-CHF$_2$-5-Pyr], [G1726;2-Et-4-OMe-5-Pyr], [G1727;2-Et-4-OCF$_3$-5-Pyr], [G1728;2-Et-4-OCHF$_2$-5-Pyr], [G1729;2-Et-4-OCH$_2$CHF$_2$-5-Pyr], [G1730;2-Et-4-CN-5-Pyr], [G1731;2-Et-4-SMe-5-Pyr], [G1732;2-Et-4-cPr-5-Pyr], [G1733;2-CF$_3$-4-F-5-Pyr], [G1734;2-CF$_3$-4-Cl-5-Pyr], [G1735;2-CF$_3$-4-Me-5-Pyr], [G1736;2-CF$_3$-4-Et-5-Pyr], [G1737;2-CF$_3$-4-iPr-5-Pyr], [G1738;2-CF$_3$-4-CF$_3$-5-Pyr], [G1739;2-CF$_3$-4-CHF$_2$-5-Pyr], [G1740;2-CF$_3$-4-OMe-5-Pyr], [G1741;2-CF$_3$-4-OCF$_3$-5-Pyr], [G1742;2-CF$_3$-4-OCHF$_2$-5-Pyr], [G1743;2-CF$_3$-4-OCH$_2$CHF$_2$-5-Pyr], [G1744;2-CF$_3$-4-CN-5-Pyr], [G1745;2-CF$_3$-4-SMe-5-Pyr], [G1746;2-CF$_3$-4-cPr-5-Pyr], [G1747;2-OMe-4-F-5-Pyr], [G1748;2-OMe-4-Cl-5-Pyr], [G1749;2-OMe-4-Me-5-Pyr], [G1750;2-OMe-4-Et-5-Pyr], [G1751;2-OMe-4-iPr-5-Pyr], [G1752;2-OMe-4-CF$_3$-5-Pyr], [G1753;2-OMe-4-CHF$_2$-5-Pyr], [G1754;2-OMe-4-OMe-5-Pyr], [G1755;2-OMe-4-OCF$_3$-5-Pyr], [G1756;2-OMe-4-OCHF$_2$-5-Pyr], [G1757;2-OMe-4-OCH$_2$CHF$_2$-5-Pyr], [G1758;2-OMe-4-CN-5-Pyr], [G1759;2-OMe-4-SMe-5-Pyr], [G1760;2-OMe-4-cPr-5-Pyr], [G1761;2-SMe-4-F-5-Pyr], [G1762;2-SMe-4-Cl-5-Pyr], [G1763;2-SMe-4-Me-5-Pyr], [G1764;2-SMe-4-Et-5-Pyr], [G1765;2-SMe-4-iPr-5-Pyr], [G1766;2-SMe-4-CF$_3$-5-Pyr], [G1767;2-SMe-4-CHF$_2$-5-Pyr], [G1768;2-SMe-4-OMe-5-Pyr], [G1769;2-SMe-4-OCF$_3$-5-Pyr], [G1770;2-SMe-4-OCHF$_2$-5-Pyr], [G1771;2-SMe-4-OCH$_2$CHF$_2$-5-Pyr], [G1772;2-SMe-4-CN-5-Pyr], [G1773;2-SMe-4-SMe-5-Pyr], [G1774;2-SMe-4-cPr-5-Pyr], [G1775;3-Pyr], [G1776;1-Me-3-Pyr], [G1777;1-Et-3-Pyr], [G1778;1-iPr-3-Pyr], [G1779;1-CF$_3$-3-Pyr], [G1780;1-CHF$_2$-3-Pyr], [G1781;1-CH$_2$CHF$_2$-3-Pyr], [G1782;2-CN-3-Pyr], [G1783;2-SMe-3-Pyr], [G1784;2-cPr-3-Pyr], [G1785;2-F-3-Pyr], [G1786;2-Cl-3-Pyr], [G1787;2-Me-3-Pyr], [G1788;2-Et-3-Pyr], [G1789;2-iPr-3-Pyr], [G1790;2-CF$_3$-3-Pyr], [G1791;2-CHF$_2$-3-Pyr], [G1792;2-OMe-3-Pyr], [G1793;2-OCF$_3$-3-Pyr], [G1794;2-OCHF$_2$-3-Pyr], [G1795;2-OCH$_2$CHF$_2$-3-Pyr], [G1796;2-CN-3-Pyr], [G1797;2-SMe-3-Pyr], [G1798;2-cPr-3-Pyr], [G1799;4-F-3-Pyr],

[G1800;4-Cl-3-Pyr], [G1801;4-Me-3-Pyr], [G1802;4-Et-3-Pyr], [G1803;4-iPr-3-Pyr], [G1804;4-CF$_3$-3-Pyr], [G1805;4-CHF$_2$-3-Pyr], [G1806;4-OMe-3-Pyr], [G1807;4-OCF$_3$-3-Pyr], [G1808;4-OCHF$_2$-3-Pyr], [G1809;4-OCH$_2$CHF$_2$-3-Pyr], [G1810;4-CN-3-Pyr], [G1811;4-SMe-3-Pyr], [G1812;4-cPr-3-Pyr], [G1813;2-F-4-F-3-Pyr], [G1814;2-F-4-Cl-3-Pyr], [G1815;2-F-4-Me-3-Pyr], [G1816;2-F-4-Et-3-Pyr], [G1817;2-F-4-iPr-3-Pyr], [G1818;2-F-4-CF$_3$-3-Pyr], [G1819;2-F-4-CHF$_2$-3-Pyr], [G1820;2-F-4-OMe-3-Pyr], [G1821;2-F-4-OCF$_3$-3-Pyr], [G1822;2-F-4-OCHF$_2$-3-Pyr], [G1823;2-F-4-OCH$_2$CHF$_2$-3-Pyr], [G824;2-F-4-CN-3-Pyr], [G1825;2-F-4-SMe-3-Pyr], [G1826;2-F-4-cPr-3-Pyr], [G1827;2-Cl-4-F-3-Pyr], [G1828;2-Cl-4-Cl-3-Pyr], [G1829;2-Cl-4-Me-3-Pyr], [G830;2-Cl-4-Et-3-Pyr], [G1831;2-Cl-4-iPr-3-Pyr], [G1832;2-Cl-4-CF$_3$-3-Pyr], [G1833;2-Cl-4-CHF$_2$-3-Pyr], [G1834;2-Cl-4-OMe-3-Pyr], [G1835;2-Cl-4-OCF$_3$-3-Pyr], [G836;2-Cl-4-OCHF$_2$-3-Pyr], [G1837;2-Cl-4-OCH$_2$CHF$_2$-3-Pyr], [G1838;2-Cl-4-CN-3-Pyr], [G1839;2-Cl-4-SMe-3-Pyr], [G1840;2-Cl-4-cPr-3-Pyr], [G1841;2-Me-4-F-3-Pyr], [G1842;2-Me-4-Cl-3-Pyr], [G1843;2-Me-4-Me-3-Pyr], [G1844;2-Me-4-Et-3-Pyr], [G1845;2-Me-4-iPr-3-Pyr], [G1846;2-Me-4-CF$_3$-3-Pyr], [G1847;2-Me-4-CHF$_2$-3-Pyr], [G1848;2-Me-4-OMe-3-Pyr], [G1849;2-Me-4-OCF$_3$-3-Pyr], [G1850;2-Me-4-OCHF$_2$-3-Pyr], [G1851;2-Me-4-OCH$_2$CHF$_2$-3-Pyr], [G1852;2-Me-4-CN-3-Pyr], [G1853;2-Me-4-SMe-3-Pyr], [G1854;2-Me-4-cPr-3-Pyr], [G1855;2-Et-4-F-3-Pyr], [G1856;2-Et-4-Cl-3-Pyr], [G1857;2-Et-4-Me-3-Pyr], [G1858;2-Et-4-Et-3-Pyr], [G1859;2-Et-4-iPr-3-Pyr], [G1860;2-Et-4-CF$_3$-3-Pyr], [G1861;2-Et-4-CHF$_2$-3-Pyr], [G1862;2-Et-4-OMe-3-Pyr], [G1863;2-Et-4-OCF$_3$-3-Pyr], [G1864;2-Et-4-OCHF$_2$-3-Pyr], [G1865;2-Et-4-OCH$_2$CHF$_2$-3-Pyr], [G1866;2-Et-4-CN-3-Pyr], [G1867;2-Et-4-SMe-3-Pyr], [G1868;2-Et-4-cPr-3-Pyr], [G1869;2-CF$_3$-4-F-3-Pyr], [G1870;2-CF$_3$-4-Cl-3-Pyr], [G1871;2-CF$_3$-4-Me-3-Pyr], [G1872;2-CF$_3$-4-Et-3-Pyr], [G1873;2-CF$_3$-4-iPr-3-Pyr], [G1874;2-CF$_3$-4-CF$_3$-3-Pyr], [G1875;2-CF$_3$-4-CHF$_2$-3-Pyr], [G1876;2-CF$_3$-4-OMe-3-Pyr], [G1877;2-CF$_3$-4-OCF$_3$-3-Pyr], [G1878;2-CF$_3$-4-OCHF$_2$-3-Pyr], [G1879;2-CF$_3$-4-OCH$_2$CHF$_2$-3-Pyr], [G1880;2-CF$_3$-4-CN-3-Pyr], [G1881;2-CF$_3$-4-SMe-3-Pyr], [G1882;2-CF$_3$-4-cPr-3-Pyr], [G1883;2-OMe-4-F-3-Pyr], [G1884;2-OMe-4-Cl-3-Pyr], [G1885;2-OMe-4-Me-3-Pyr], [G1886;2-OMe-4-Et-3-Pyr], [G1887;2-OMe-4-iPr-3-Pyr], [G1888;2-OMe-4-CF$_3$-3-Pyr], [G1889;2-OMe-4-CHF$_2$-3-Pyr], [G1890;2-OMe-4-OMe-3-Pyr], [G1891;2-OMe-4-OCF$_3$-3-Pyr], [G1892;2-OMe-4-OCHF$_2$-3-Pyr], [G1893;2-OMe-4-OCH$_2$CHF$_2$-3-Pyr], [G1894;2-OMe-4-CN-3-Pyr], [G1895;2-OMe-4-SMe-3-Pyr], [G1896;2-OMe-4-cPr-3-Pyr], [G1897;2-SMe-4-F-3-Pyr], [G1898;2-SMe-4-Cl-3-Pyr], [G1899;2-SMe-4-Me-3-Pyr], [G1900;2-SMe-4-Et-3-Pyr], [G1901;2-SMe-4-iPr-3-Pyr], [G1902;2-SMe-4-CF$_3$-3-Pyr], [G1903;2-SMe-4-CHF$_2$-3-Pyr], [G1904;2-SMe-4-OMe-3-Pyr], [G1905;2-SMe-4-OCF$_3$-3-Pyr], [G1906;2-SMe-4-OCHF$_2$-3-Pyr], [G1907;2-SMe-4-OCH$_2$CHF$_2$-3-Pyr], [G1908;2-SMe-4-CN-3-Pyr], [G1909;2-SMe-4-SMe-3-Pyr], [G1910;2-SMe-4-cPr-3-Pyr], [G1911;CH$_2$CH$_2$Ph], [G1912;CH$_2$CH$_2$CH$_2$Ph], [G1913;CH$_2$CH(CH$_3$)Ph], [G1914;CH$_2$CH$_2$CH$_2$CH$_2$Ph], [G1915;CH$_2$Ph], [G1916;CH$_2$(2-Me-Ph)], [G1917;CH$_2$(3-Me-Ph)], [G1918;CH$_2$(4-Me-Ph)], [G1919;CH$_2$(2-MeO-Ph)], [G1920;CH$_2$(3-MeO-Ph)], [G1921;CH$_2$(4-MeO-Ph)], [G1922;CH$_2$CH$_2$(2-F-Ph)], [G1923;CH$_2$CH$_2$(3-F-Ph)], [G1924;CH$_2$CH$_2$(4-F-Ph)], [G1925;CH$_2$CH$_2$(2-Cl-Ph)], [G1926;CH$_2$CH$_2$(3-Cl-Ph)], [G1927;CH$_2$CH$_2$(4-Cl-Ph)], [G1928;Bu], [G1929;tBu], [G1930;iPr], [G1931;1-Adam], [G1932;2-Adam], [G1933;CH$_2$CH$_2$OMe], [G1934;CH$_2$CH$_2$OMe], [G1935;CH$_2$CH$_2$OC(O)Me], [G1936;CH$_2$CH$_2$(cPr)], [G1937;CH$_2$CH$_2$(cBu)], [G1938;CH$_2$(cPen)], [G1939;CH$_2$CH$_2$(cPen)], [G1940;CH$_2$(1,2,3,6-tetrapy-1)], [G1941;CH$_2$CH$_2$(1,2,3,6-tetrapy-1)], [G1942;3-BI], [G1943;3-ISP].

The below-mentioned substituent Nos. H1 to H18888 represent G$^2$ substituent in the compound represented by formula (II) or the compounds represented by formula (JJ).

<Substituent No.; G$^2$>

[H1;2-Im], [H2;4-F-2-Im], [H3;4-Cl-2-Im], [H4;4-Br-2-Im], [H5;4-I-2-Im], [H6;4-Me-2-Im], [H7;4-Et-2-Im], [H8;4-Pr-2-Im], [H9;4-iPr-2-Im], [H10;4-CF$_3$-2-Im], [H11;4-CHF$_2$-2-Im], [H12;4-OMe-2-Im], [H13;4-OEt-2-Im], [H14;4-OCF$_3$-2-Im], [H15;4-OCHF$_2$-2-Im], [H16;4-OCH$_2$CHF$_2$-2-Im], [H17;4-CN-2-Im], [H18;4-SMe-2-Im], [H19;4-SEt-2-Im], [H20;4-cPr-2-Im], [H21;5-F-2-Im], [H22;5-Cl-2-Im], [H23;5-Br-2-Im], [H24;5-I-2-Im], [H25;5-Me-2-Im], [H26;5-Et-2-Im], [H27;5-Pr-2-Im], [H28;5-iPr-2-Im], [H29;5-CF$_3$-2-Im], [H30;5-CHF$_2$-2-Im], [H31;5-OMe-2-Im], [H32;5-OEt-2-Im], [H33;5-OCF$_3$-2-Im], [H34;5-OCHF$_2$-2-

Im], [H35;5-OCH₂CHF₂-2-Im], [H36;5-CN-2-Im], [H37;5-SMe-2-Im], [H38;5-SEt-2-Im], [H39;5-cPr-2-Im], [H40;4-Im], [H41;2-F-4-Im], [H42;2-Cl-4-Im], [H43;2-Br-4-Im], [H44;2-I-4-Im], [H45;2-Me-4-Im], [H46;2-Et-4-Im], [H47;2-Pr-4-Im], [H48;2-iPr-4-Im], [H49;2-CF₃-4-Im], [H50;2-CHF₂-4-Im], [H51;2-OMe-4-Im], [H52;2-OEt-4-Im], [H53;2-OCF₃-4-Im], [H54;2-OCHF₂-4-Im], [H55;2-OCH₂CHF₂-4-Im], [H56;2-CN-4-Im], [H57;2-SMe-4-Im], [H58;2-SEt-4-Im], [H59;2-cPr-4-Im], [H60;5-F-4-Im], [H61;5-Cl-4-Im], [H62;5-Br-4-Im], [H63;5-I-4-Im], [H64;5-Me-4-Im], [H65;5-Et-4-Im], [H66;5-Pr-4-Im], [H67;5-iPr-4-Im], [H68;5-CF₃-4-Im], [H69;5-CHF₂-4-Im], [H70;5-OMe-4-Im], [H71;5-OEt-4-Im], [H72;5-OCF₃-4-Im], [H73;5-OCHF₂-4-Im], [H74;5-OCH₂CHF₂-4-Im], [H75;5-CN-4-Im], [H76;5-SMe-4-Im], [H77;5-SEt-4-Im], [H78;5-cPr-4-Im], [H79;5-Im], [H80;2-F-5-Im], [H81;2-Cl-5-Im], [H82;2-Br-5-Im], [H83;2-I-5-Im], [H84;2-Me-5-Im], [H85;2-Et-5-Im], [H86;2-Pr-5-Im], [H87;2-iPr-5-Im], [H88;2-CF₃-5-Im], [H89;2-CHF₂-5-Im], [H90;2-OMe-5-Im], [H91;2-OEt-5-Im], [H92;2-OCF₃-5-Im], [H93;2-OCHF₂-5-Im], [H94;2-OCH₂CHF₂-5-Im], [H95;2-CN-5-Im], [H96;2-SMe-5-Im], [H97;2-SEt-5-Im], [H98;2-cPr-5-Im], [H99;4-F-5-Im], [H100;4-Cl-5-Im], [H101;4-Br-5-Im], [H102;4-I-5-Im], [H103;4-Me-5-Im], [H104;4-Et-5-Im], [H105;4-Pr-5-Im], [H106;4-iPr-5-Im], [H107;4-CF₃-5-Im], [H108;4-CHF₂-5-Im], [H109;4-OMe-5-Im], [H110;4-OEt-5-Im], [H11;4-OCF₃-5-Im], [H112;4-OCHF₂-5-Im], [HI 113;4-OCH₂CHF₂-5-Im], [H114;4-CN-5-Im], [H115;4-SMe-5-Im], [H116;4-SEt-5-Im], [H117;4-cPr-5-Im], [H118;3-Ith], [H119;4-F-3-Ith], [H120;4-Cl-3-Ith], [H121;4-Br-3-Ith], [H122;4-I-3-Ith], [H123;4-Me-3-Ith], [H124;4-Et-3-Ith], [H125;4-Pr-3-Ith], [H126;4-iPr-3-Ith], [H127;4-CF₃-3-Ith], [H128;4-CHF₂-3-Ith], [H129;4-OMe-3-Ith], [H130;4-OEt-3-Ith], [H131;4-OCF₃-3-Ith], [H132;4-OCHF₂-3-Ith], [H133;4-OCH₂CHF₂-3-Ith], [H134;4-CN-3-Ith], [H135;4-SMe-3-Ith], [H136;4-SEt-3-Ith], [H137;4-cPr-3-Ith], [H138;5-F-3-Ith], [H139;5-Cl-3-Ith], [H140;5-Br-3-Ith], [H141;5-I-3-Ith], [H142;5-Me-3-Ith], [H143;5-Et-3-Ith], [H144;5-Pr-3-Ith], [H145;5-iPr-3-Ith], [H146;5-CF₃-3-Ith], [H147;5-CHF₂-3-Ith], [H148;5-OMe-3-Ith], [H149;5-OEt-3-Ith], [H150;5-OCF₃-3-Ith], [H151;5-OCHF₂-3-Ith], [H152;5-OCH₂CHF₂-3-Ith], [H153;5-CN-3-Ith], [H154;5-SMe-3-Ith], [H155;5-SEt-3-Ith], [H156;5-cPr-3-Ith], [H157;4-Ith], [H158;3-F-4-Ith], [H159;3-Cl-4-Ith], [H160;3-Br-4-Ith], [H161;3-I-4-Ith], [H162;3-Me-4-Ith], [H163;3-Et-4-Ith], [H164;3-Pr-4-Ith], [H165;3-iPr-4-Ith], [H166;3-CF₃-4-Ith], [H167;3-CHF₂-4-Ith], [H168;3-OMe-4-Ith], [H169;3-OEt-4-Ith], [H170;3-OCF₃-4-Ith], [H171;3-OCHF₂-4-Ith], [H172;3-OCH₂CHF₂-4-Ith], [H173;3-CN-4-Ith], [H174;3-SMe-4-Ith], [H175;3-SEt-4-Ith], [H176;3-cPr-4-Ith], [H177;5-F-4-Ith], [H178;5-Cl-4-Ith], [H179;5-Br-4-Ith], [H180;5-I-4-Ith], [H181;5-Me-4-Ith], [H182;5-Et-4-Ith], [H183;5-Pr-4-Ith], [H184;5-iPr-4-Ith], [H185;5-CF₃-4-Ith], [H186;5-CHF₂-4-Ith], [H187;5-OMe-4-Ith], [H188;5-OEt-4-Ith], [H189;5-OCF₃-4-Ith], [H190;5-OCHF₂-4-Ith], [H191;5-OCH₂CHF₂-4-Ith], [H192;5-CN-4-Ith], [H193;5-SMe-4-Ith], [H194;5-SEt-4-Ith], [H195;5-cPr-4-Ith], [H196;5-Ith], [H197;3-F-5-Ith], [H198;3-Cl-5-Ith], [H199;3-Br-5-Ith], [H200;3-I-5-Ith], [H201;3-Me-5-Ith], [H202;3-Et-5-Ith], [H203;3-Pr-5-Ith], [H204;3-iPr-5-Ith], [H205;3-CF₃-5-Ith], [H206;3-CHF₂-5-Ith], [H207;3-OMe-5-Ith], [H208;3-OEt-5-Ith], [H209;3-OCF₃-5-Ith], [H210;3-OCHF₂-5-Ith], [H211;3-OCH₂CHF₂-5-Ith], [H212;3-CN-5-Ith], [H213;3-SMe-5-Ith], [H214;3-SEt-5-Ith], [H215;3-cPr-5-Ith], [H216;4-F-5-Ith], [H217;4-Cl-5-Ith], [H218;4-Br-5-Ith], [H219;4-I-5-Ith], [H220;4-Me-5-Ith], [H221;4-Et-5-Ith], [H222;4-Pr-5-Ith], [H223;4-iPr-5-Ith], [H224;4-CF₃-5-Ith], [H225;4-CHF₂-5-Ith], [H226;4-OMe-5-Ith], [H227;4-OEt-5-Ith], [H228;4-OCF₃-5-Ith], [H229;4-OCHF₂-5-Ith], [H230;4-OCH₂CHF₂-5-Ith], [H231;4-CN-5-Ith], [H232;4-SMe-5-Ith], [H233;4-SEt-5-Ith], [H234;4-cPr-5-Ith], [H235;3-IO], [H236;4-F-3-IO], [H237;4-Cl-3-IO], [H238;4-Br-3-IO], [H239;4-I-3-IO], [H240;4-Me-3-IO], [H241;4-Et-3-IO], [H242;4-Pr-3-IO], [H243;4-iPr-3-IO], [H244;4-CF₃-3-IO], [H245;4-CHF₂-3-IO], [H246;4-OMe-3-IO], [H247;4-OEt-3-IO], [H248;4-OCF₃-3-IO], [H249;4-OCHF₂-3-IO], [H250;4-OCH₂CHF₂-3-IO], [H251;4-CN-3-IO], [H252;4-SMe-3-IO], [H253;4-SEt-3-IO], [H254;4-cPr-3-IO], [H255;5-F-3-IO], [H256;5-Cl-3-IO], [H257;5-Br-3-IO], [H258;5-I-3-IO], [H259;5-Me-3-IO], [H260;5-Et-3-IO], [H261;5-Pr-3-IO], [H262;5-iPr-3-IO], [H263;5-CF₃-3-IO], [H264;5-CHF₂-3-IO], [H265;5-OMe-3-IO], [H266;5-OEt-3-IO], [H267;5-OCF₃-3-IO], [H268;5-OCHF₂-3-IO], [H269;5-OCH₂CHF₂-3-IO], [H270;5-CN-3-IO], [H271;5-SMe-3-IO], [H272;5-SEt-3-IO], [H273;5-cPr-3-IO], [H274;4-IO], [H275;3-F-4-IO], [H276;3-Cl-4-IO], [H277;3-Br-4-IO], [H278;3-J-4-IO], [H279;3-Me-4-IO], [H280;3-Et-4-IO], [H281;3-Pr-4-IO], [H282;3-iPr-4-IO], [H283;3-CF₃-4-IO], [H284;3-CHF₂-4-IO], [H285;3-OMe-4-IO], [H286;3-OEt-4-IO], [H287;3-OCF₃-4-IO], [H288;3-OCHF₂-4-IO], [H289;3-OCH₂CHF₂-4-IO], [H290;3-CN-4-IO], [H291;3-SMe-4-IO], [H292;3-SEt-4-IO], [H293;3-cPr-4-IO], [H294;5-F-4-IO], [H295;5-Cl-4-IO], [H296;5-Br-4-IO], [H297;5-J-4-IO], [H298;5-Me-4-IO], [H299;5-Et-4-IO], [H300;5-Pr-4-IO], [H301;5-iPr-4-IO], [H302;5-CF₃-4-IO], [H303;5-CHF₂-4-IO], [H304;5-OMe-4-IO], [H305;5-OEt-4-IO], [H306;5-OCF₃-4-IO], [H307;5-OCHF₂-4-IO], [H308;5-OCH₂CHF₂-4-IO], [H309;5-CN-4-IO], [H310;5-SMe-4-IO], [H311;5-SEt-4-IO], [H312;5-cPr-4-IO], [H313;5-IO], [H314;3-F-5-IO], [H315;3-Cl-5-IO], [H316;3-Br-5-IO], [H317;3-J-5-IO], [H318;3-Me-5-IO], [H319;3-Et-5-IO], [H320;3-Pr-5-IO], [H321;3-iPr-5-IO], [H322;3-CF₃-5-IO], [H323;3-CHF₂-5-IO], [H324;3-OMe-5-IO], [H325;3-OEt-5-IO], [H326;3-OCF₃-5-IO], [H327;3-OCHF₂-5-IO], [H328;3-OCH₂CHF₂-5-IO], [H329;3-CN-5-IO], [H330;3-SMe-5-IO], [H331;3-SEt-5-IO], [H332;3-cPr-5-IO], [H333;4-F-5-IO], [H334;4-Cl-5-IO], [H335;4-Br-5-IO], [H336;4-J-5-IO], [H337;4-Me-5-IO], [H338;4-Et-5-IO], [H339;4-Pr-5-IO], [H340;4-iPr-5-IO], [H341;4-CF₃-5-IO], [H342;4-CHF₂-5-IO], [H343;4-OMe-5-IO], [H344;4-OEt-5-IO], [H345;4-OCF₃-5-IO], [H346;4-OCHF₂-5-IO], [H347;4-OCH₂CHF₂-5-IO], [H348;4-CN-5-IO], [H349;4-SMe-5-IO], [H350;4-SEt-5-IO], [H351;4-cPr-5-IO], [H352;2-Pm], [H353;4-F-2-Pm], [H354;4-Cl-2-Pm], [H355;4-Br-2-Pm], [H356;4-J-2-Pm], [H357;4-Me-2-Pm], [H358;4-Et-2-Pm], [H359;4-Pr-2-Pm], [H360;4-iPr-2-Pm], [H361;4-CF₃-2-Pm], [H362;4-CHF₂-2-Pm], [H363;4-OMe-2-Pm], [H364;4-OEt-2-Pm], [H365;4-OCF₃-2-Pm], [H366;4-OCHF₂-2-Pm], [H367;4-CN-2-Pm], [H368;4-SMe-2-Pm], [H369;4-SEt-2-Pm], [H370;4-cPr-2-Pm], [H371;5-F-2-Pm], [H372;5-Cl-2-Pm], [H373;5-Br-2-Pm], [H374;5-J-2-Pm], [H375;5-Me-2-Pm], [H376;5-Et-2-Pm], [H377;5-Pr-2-Pm], [H378;5-iPr-2-Pm], [H379;5-CF₃-2-Pm], [H380;5-CHF₂-2-Pm], [H381;5-OMe-2-Pm], [H382;5-OEt-2-Pm], [H383;5-OCF₃-2-Pm], [H384;5-OCHF₂-2-Pm], [H385;5-CN-2-Pm], [H386;5-SMe-2-Pm], [H387;5-SEt-2-Pm], [H388;5-cPr-2-Pm], [H389;4-Pm], [H390;2-F-4-Pm], [H391;2-Cl-4-Pm], [H392;2-Br-4-Pm], [H393;2-J-4-Pm], [H394;2-Me-4-Pm], [H395;2-Et-4-Pm], [H396;2-Pr-4-Pm], [H397;2-iPr-4-Pm], [H398;2-CF₃-4-Pm], [H399;2-CHF₂-4-Pm], [H400;2-OMe-4-Pm], [H401;2-OEt-4-Pm], [H402;2-OCF₃-4-Pm], [H403;2-OCHF₂-4-Pm], [H404;2-CN-4-Pm], [H405;2-SMe-4-Pm], [H406;2-SEt-4-Pm], [H407;2-cPr-4-Pm], [H408;5-F-4-Pm],

[H409;5-Cl-4-Pm], [H41;5-Br-4-Pm], [H411;5-J-4-Pm], [H412;5-Me-4-Pm], [H413;5-Et-4-Pm], [H414;5-Pr-4-Pm], [H415;5-iPr-4-Pm], [H416;5-CF$_3$-4-Pm], [H417;5-CHF$_2$-4-Pm], [H418;5-OMe-4-Pm], [H419;5-OEt-4-Pm], [H420;5-OCF$_3$-4-Pm], [H421;5-OCHF$_2$-4-Pm], [H422;5-CN-4-Pm], [H423;5-SMe-4-Pm], [H424;5-SEt-4-Pm], [H425;5-cPr-4-Pm], [H426;6-F-4-Pm], [H427;6-Cl-4-Pm], [H428;6-Br-4-Pm], [H429;6-J-4-Pm], [H430;6-Me-4-Pm], [H431;6-Et-4-Pm], [H432;6-Pr-4-Pm], [H433;6-iPr-4-Pm], [H434;6-CF$_3$-4-Pm], [H435;6-CHF$_2$-4-Pm], [H436;6-OMe-4-Pm], [H437;6-OEt-4-Pm], [H438;6-OCF$_3$-4-Pm], [H439;6-OCHF$_2$-4-Pm], [H440;6-CN-4-Pm], [H441;6-SMe-4-Pm], [H442;6-SEt-4-Pm], [1H443;6-cPr-4-Pm], [H444;5-Pm], [H445;2-F-5-Pm], [H446;2-Cl-5-Pm], [H447;2-Br-5-Pm], [H448;2-J-5-Pm], [H449;2-Me-5-Pm], [H450;2-Et-5-Pm], [H451;2-Pr-5-Pm], [H452;2-iPr-5-Pm], [H453;2-CF$_3$-5-Pm], [H454;2-CHF$_2$-5-Pm], [H455;2-OMe-5-Pm], [H456;2-OEt-5-Pm], [H457;2-OCF$_3$-5-Pm], [H458;2-OCHF$_2$-5-Pm], [H459;2-CN-5-Pm], [H460;2-SMe-5-Pm], [H461;2-SEt-5-Pm], [H462;2-cPr-5-Pm], [H463;4-F-5-Pm], [H464;4-Cl-5-Pm], [H465;4-Br-5-Pm], [H466;4-J-5-Pm], [H467;4-Me-5-Pm], [H468;4-Et-5-Pm], [H469;4-Pr-5-Pm], [H470;4-iPr-5-Pm], [H471;4-CF$_3$-5-Pm], [H472;4-CHF$_2$-5-Pm], [H473;4-OMe-5-Pm], [H474;4-OEt-5-Pm], [H475;4-OCF$_3$-5-Pm], [H476;4-OCHF$_2$-5-Pm], [H477;4-CN-5-Pm], [H478;4-SMe-5-Pm], [H479;4-SEt-5-Pm], [H480;4-cPr-5-Pm], [H481;4-Prd], [H482;4-F-3-Prd], [H483;4-Cl-3-Prd], [H484;4-Br-3-Prd], [H485;4-J-3-Prd], [H486;4-Me-3-Prd], [H487;4-Et-3-Prd], [H488;4-Pr-3-Prd], [H489;4-iPr-3-Prd], [H490;4-CF$_3$-3-Prd], [H491;4-CHF$_2$-3-Prd], [H492;4-OMe-3-Prd], [H493;4-OEt-3-Prd], [H494;4-OCF$_3$-3-Prd], [H495;4-OCHF$_2$-3-Prd], [H496;4-CN-3-Prd], [H497;4-SMe-3-Prd], [H498;4-SEt-3-Prd], [H499;4-cPr-3-Prd], [H500;5-F-3-Prd], [H501;5-Cl-3-Prd], [H502;5-Br-3-Prd], [H503;5-J-3-Prd], [H504;5-Me-3-Prd], [H505;5-Et-3-Prd], [H506;5-Pr-3-Prd], [H507;5-iPr-3-Prd], [H508;5-CF$_3$-3-Prd], [H509;5-CHF$_2$-3-Prd], [H51;5-OMe-3-Prd], [H511;5-OEt-3-Prd], [H512;5-OCF$_3$-3-Prd], [H513;5-OCHF$_2$-3-Prd], [H514;5-CN-3-Prd], [H515;5-SMe-3-Prd], [H516;5-SEt-3-Prd], [H517;5-cPr-3-Prd], [H518;6-F-3-Prd], [H519;6-Cl-3-Prd], [H520;6-Br-3-Prd], [H521;6-J-3-Prd], [H522;6-Me-3-Prd], [H523;6-Et-3-Prd], [H524;6-Pr-3-Prd], [H525;6-iPr-3-Prd], [H526;6-CF$_3$-3-Prd], [H527;6-CHF$_2$-3-Prd], [H528;6-OMe-3-Prd], [H529;6-OEt-3-Prd], [H530;6-OCF$_3$-3-Prd], [H531;6-OCHF$_2$-3-Prd], [H532;6-CN-3-Prd], [H533;6-SMe-3-Prd], [H534;6-SEt-3-Prd], [H535;6-cPr-3-Prd], [H536;4-Prd], [H537;3-F-4-Prd], [H538;3-Cl-4-Prd], [H539;3-Br-4-Prd], [H540;3-J-4-Prd], [H541;3-Me-4-Prd], [H542;3-Et-4-Prd], [H543;3-Pr-4-Prd], [H544;3-iPr-4-Prd], [H545;3-CF$_3$-4-Prd], [H546;3-CHF$_2$-4-Prd], [H547;3-OMe-4-Prd], [H548;3-OEt-4-Prd], [H549;3-OCF$_3$-4-Prd], [H550;3-OCHF$_2$-4-Prd], [H551;3-CN-4-Prd], [H552;3-SMe-4-Prd], [H553;3-SEt-4-Prd], [H554;3-cPr-4-Prd], [H555;5-F-4-Prd], [H556;5-Cl-4-Prd], [H557;5-Br-4-Prd], [H558;5-I-4-Prd], [H559;5-Me-4-Prd], [H560;5-Et-4-Prd], [H561;5-Pr-4-Prd], [H562;5-iPr-4-Prd], [H563;5-CF$_3$-4-Prd], [H564;5-CHF$_2$-4-Prd], [H565;5-OMe-4-Prd], [H566;5-OEt-4-Prd], [H567;5-OCF$_3$-4-Prd], [H568;5-OCHF$_2$-4-Prd], [H569;5-CN-4-Prd], [H570;5-SMe-4-Prd], [H571;5-SEt-4-Prd], [H572;5-cPr-4-Prd], [H573;6-F-4-Prd], [H574;6-Cl-4-Prd], [H575;6-Br-4-Prd], [H576;6-I-4-Prd], [H577;6-Me-4-Prd], [H578;6-Et-4-Prd], [H579;6-Pr-4-Prd], [H580;6-iPr-4-Prd], [H581;6-CF$_3$-4-Prd], [H582;6-CHF$_2$-4-Prd], [H583;6-OMe-4-Prd], [H584;6-OEt-4-Prd], [H585;6-OCF$_3$-4-Prd], [H586;6-OCHF$_2$-4-Prd], [H587;6-CN-4-Prd], [H588;6-SMe-4-Prd], [H589;6-SEt-4-Prd], [H590;6-cPr-4-Prd], [H591;2-Pra], [H592;2-F-2-Pra], [H593;2-Cl-2-Pra], [H594;2-Br-2-Pra], [H595;2-I-2-Pra], [H596;2-Me-2-Pra], [H597;2-Et-2-Pra], [H598;2-Pr-2-Pra], [H599;2-iPr-2-Pra], [H600;2-CF$_3$-2-Pra],

[H60;2-CHF$_2$-2-Pra], [H602;2-OMe-2-Pra], [H603;2-OEt-2-Pra], [H604;2-OCF$_3$-2-Pra], [H605;2-OCHF$_2$-2-Pra], [H606;2-CN-2-Pra], [H607;2-SMe-2-Pra], [H608;2-SEt-2-Pra], [H609;2-cPr-2-Pra], [H610;5-F-2-Pra], [H611;5-Cl-2-Pra], [H612;5-Br-2-Pra], [H613;5-I-2-Pra], [H614;5-Me-2-Pra], [H615;5-Et-2-Pra], [H616;5-Pr-2-Pra], [H617;5-iPr-2-Pra], [H618;5-CF$_3$-2-Pra], [H619;5-CHF$_2$-2-Pra], [H620;5-OMe-2-Pra], [H621;5-OEt-2-Pra], [H6222;5-OCF$_3$-2-Pra], [H623;5-OCHF$_2$-2-Pra], [H624;5-CN-2-Pra], [H625;5-SMe-2-Pra], [H626;5-SEt-2-Pra], [H627;5-cPr-2-Pra], [H628;6-F-2-Pra], [H629;6-Cl-2-Pra], [H630;6-Br-2-Pra], [H631;6-I-2-Pra], [H632;6-Me-2-Pra], [H633;6-Et-2-Pra], [H634;6-Pr-2-Pra], [H635;6-iPr-2-Pra], [H636;6-CF$_3$-2-Pra], [H637;6-CHF$_2$-2-Pra], [H638;6-OMe-2-Pra], [H639;6-OEt-2-Pra], [H640;6-OCF$_3$-2-Pra], [H641;6-OCHF$_2$-2-Pra], [H642;6-CN-2-Pra], [H643;6-SMe-2-Pra], [H644;6-SEt-2-Pra], [H645;6-cPr-2-Pra], [H646;(1,2,3-tri-1], [H647;4-F-(1,2,3-tri-1)], [H648;4-Cl-(1,2,3-tri-1)], [H649;4-Br-(1,2,3-tri-1)], [H650;4-I-(1,2,3-tri-1)], [H651;4-Me-(1,2,3-tri-1)], [H652-4-Et-(1,2,3-tri-1)], [H653;4-Pr-(1,2,3-tri-1)], [H654;4-iPr-(1,2,3-tri-1)], [H655;4-CF$_3$-(1,2,3-tri-1)], [H6564-CHF$_2$-(1-2-3-tri-1)], [H6574-OMe-(1-2-3-tri-1)], [H658;4-OEt-(1,2,3-tri-1)], [H659;4-OCF$_3$-(1,2,3-tri-1)], [H660;4-OCHF$_2$-(1,2,3-tri-1)], [H661;4-CN-(1,2,3-tri-1)], [H662;4-SMe-(1,2,3-tri-1)], [H663;4-SEt-1,2,3-tri-1)], [H664;4-cPr-(1,2,3-tri-1)], [H665;5-F-(1,2,3-tri-1)], [H666;5-Cl-(1,2,3-tri-1)], [H667;5-Br-(1,2,3-tri-1)], [H668;5-I-1,2,3-tri-1)], [H669;5-Me-1,2,3-tri-1)], [H670;5-Et-(1,2,3-tri-1)], [H671;5-Pr-(1,2,3-tri-1)], [H672;5-iPr-(1,2,3-tri-1)], [H673;5-CF$_3$-(1,2,3-tri-1)], [H674;5-CHF$_2$-(1,2,3-tri-1)], [H675;5-OMe-(1,2,3-tri-1)], [H676;5-OEt-(1,2,3-tri-1)], [H677;5-OCF$_3$-(1,2,3-tri-1)], [H678;5-OCHF$_2$-(1,2,3-tri-1)], [H679;5-CN-(1,2,3-tri-1)], [H680;5-SMe-(1,2,3-tri-1)], [H681;5-SEt-1,2,3-tri-1)], [H682;5-cPr-(1,2,3-tri-1)], [H683;(1,2,4-tri-1)], [H684;3-F-(1,2,4-tri-1)], [H68;3-Cl-(1,2,4-tri-1)], [H686;3-Br-(1,2,4-tri-1)], [H687;3-I-(1,2,4-tri-1)], [H688;3-Me-(1,2,4-tri-1)], [H689;3-Et-(1,2,4-tri-1)], [H690;3-Pr-(1,2,4-tri-1)], [H691;3-iPr-(1,2,4-tri-1)], [H692;3-CF$_3$-(1,2,4-tri-1)], [H693;3-CHF$_2$-(1,2,4-tri-1)], [H694;3-OMe-(1,2,4-tri-1)], [H695;3-OEt-(1,2,4-tri-1)], [H696;3-OCF$_3$-(1,2,4-tri-1)], [H697;3-OCHF$_2$-(1,2,4-tri-1)], [H698;3-CN-(1,2,4-tri-1)], [H699;3-SMe-(1,2,4-tri-1)], [H700;3-SEt-(1,2,4-tri-1)], [H701;3-cPr-(1,2,4-tri-1)], [H702;5-F-(1,2,4-tri-1)], [H703;5-Cl-(1,2,4-tri-1)], [H704;5-Br-(1,2,4-tri-1)], [H705;5-I-(1,2,4-tri-1)], [H706;5-Me-(1,2,4-tri-1)], [H707;5-Et-(1,2,4-tri-1)], [H708;5-Pr-(1,2,4-tri-1)], [H7095-iPr-(1-2-4-tri-1)], [H710;5-CF$_3$-(1,2,4-tri-1)], [H711;5-CHF$_2$-(1,2,4-tri-1)], [H712;5-OMe-(1,2,4-tri-1)], [H713;5-OEt-(1,2,4-tri-1)], [H714;5-OCF$_3$-(1,2,4-tri-1)], [H715;5-OCHF$_2$-(1,2,4-tri-1)], [H716;5-CN-(1,2,4-tri-1)], [H717;5-SMe-(1,2,4-tri-1)], [H718;5-SEt-(1,2,4-tri-1)], [H719;5-cPr-(1,2,4-tri-1)], [H720;(1,2,5-Oxa-3)], [H721;5-F-(125-Oxa-3)], [H722;5-Cl-(125-Oxa-3)], [H723;5-Br-(1,2,5-Oxa-3)], [H724;5-I-(1,2,5-Oxa-3)], [H725;5-Me-(1,2,5-Oxa-3)], [H726;5-Et-(1,2,5-Oxa-3)], [H727;5-Pr-(1,2,5-Oxa-3)], [H728;5-iPr-(1,2,5-Oxa-3)], [H729;5-CF$_3$-(1,2,5-Oxa-3)], [H730;5-CHF$_2$-(1,2,5-Oxa-3)], [H731;5-OMe-(1,2,5-Oxa-3)], [H732;5-OEt-(1,2,5-Oxa-3)], [H733;5-OCF$_3$-(1,2,5-Oxa-3)], [H734;5-OCHF$_2$-(1,2,5-Oxa-3)], [H735;5-CN-(1,2,5-Oxa-3)], [H736;5-SMe-(1,2,5-Oxa-3)], [H737;5-SEt-(1,2,5-Oxa-3)], [H738;5-cPr-(1,2,5-Oxa-3)], [H739;(1,2,4-Oxa-5)], [H740;3-F-(1,2,4-Oxa-5)], [H741;3-Cl-(1,2,4-Oxa-5)], [H742;3-Br-(1,2,4-Oxa-5)], [H743;3-I-(1,2,4-Oxa-5)], [H744;3-Me-(1,2,4-Oxa-5)], [H745;3-Et-(1,2,4-Oxa- 5)], [H746;3-Pr-(1,2,4-Oxa-5)], [H747;3-iPr-(1,2,4-Oxa-5)], [H748;3-CF₃-(1,2,4-Oxa-5)], [H749;3-CHF₂-(1,2,4-Oxa-5)], [H750;3-OMe-(1,2,4-Oxa-5)], [H751;3-OEt-(1,2,4-Oxa-5)], [H752;3-OCF₃-(1,2,4-Oxa-5)], [H753;3-OCHF₂-(1,2,4-Oxa-5)], [H754;3-CN-(1,2,4-Oxa-5)], [H755;3-SMe-(1,2,4-Oxa-5)], [H756;3-SEt-(1,2,4-Oxa-5)], [H757;3-cPr-(1,2,4-Oxa-5)], [H758;(1,2,4-Oxa-3)], [H759;5-F-(1,2,4-Oxa-3)], [H760;5-Cl-(1,2,4-Oxa-3)], [H761;5-Br-(1,2,4-Oxa-3)], [H762;5-I-(1,2,4-Oxa-3)], [H763;5-Me-(1,2,4-Oxa-3)], [H764;5-Et-(1,2,4-Oxa-3)], [H765;5-Pr-(1,2,4-Oxa-3)], [H766;5-iPr-(1,2,4-Oxa-3)], [H767;5-CF₃-(1,2,4-Oxa-3)], [H768;5-CHF₂-(1,2,4-Oxa-3)], [H769;5-OMe-(1,2,4-Oxa-3)], [H770;5-OEt-(1,2,4-Oxa-3)], [H771;5-OCF₃-(1,2,4-Oxa-3)], [H772;5-OCHF₂-(1,2,4-Oxa-3)], [H773;5-CN-(1,2,4-Oxa-3)], [H774;5-SMe-(1,2,4-Oxa-3)], [H775;5-SEt-(1,2,4-Oxa-3)], [H776;5-cPr-(1,2,4-Oxa-3)], [H777;(1,2,3-Thia-4)], [H778;5-F-(1,2,3-Thia-4)], [H779;5-Cl-(1,2,3-Thia-4)], [H780;5-Br-(1,2,3-Thia-4)], [H781;5-I-(1,2,3-Thia-4)], [H782;5-Me-(1,2,3-Thia-4)], [H783;5-Et-(1,2,3-Thia-4)], [H784;5-Pr-(1,2,3-Thia-4)], [H785;5-iPr-(1,2,3-Thia-4)], [H786;5-CF₃-(1,2,3-Thia-4)], [H787;5-CHF₂-(1,2,3-Thia-4)], [H788;5-OMe-(1,2,3-Thia-4)], [H789;5-OEt-(1,2,3-Thia-4)], [H790;5-OCF₃-(1,2,3-Thia-4)], [H791;5-OCHF₂-(1,2,3-Thia-4)], [H792;5-CN-(1,2,3-Thia-4)], [H793;5-SMe-(1,2,3-Thia-4)], [H794;5-SEt-(1,2,3-Thia-4)], [H795;5-cPr-(1,2,3-Thia-4)], [H796;(1,2,3-Thia-5)], [H797;4-F-(1,2,3-Thia-5)], [H798;4-Cl-(1,2,3-Thia-5)], [H799;4-Br-(1,2,3-Thia-5)], [H800;4-I-(1,2,3-Thia-5)],

[H801;4-Me-(1,2,3-Thia-5)], [H802;4-Et-(1,2,3-Thia-5)], [H803;4-Pr-(1,2,3-Thia-5)], [H804;4-iPr-(1,2,3-Thia-5)], [H805;4-CF₃-(1,2,3-Thia-5)], [H806;4-CHF₂-(1,2,3-Thia-5)], [H807;4-OMe-(1,2,3-Thia-5)], [H808;4-OEt-(1,2,3-Thia-5)], [H809;4-OCF₃-(1,2,3-Thia-5)], [H810;4-OCHF₂-(1,2,3-Thia-5)], [H811;4-CN-(1,2,3-Thia-5)], [H812;4-SMe-(1,2,3-Thia-5)], [H813;4-SEt-(1,2,3-Thia-5)], [H814;4-cPr-(1,2,3-Thia-5)], [H815;(1,2,4-Thia-5)], [H816;3-F-(1,2,4-Thia-5)], [H817;3-Cl-(1,2,4-Thia-5)], [H818;3-Br-(1,2,4-Thia-5)], [H819;3-I-(1,2,4-Thia-5)], [H820;3-Me-(1,2,4-Thia-5)], [H821;3-Et-(1,2,4-Thia-5)], [H822;3-Pr-(1,2,4-Thia-5)], [H823;3-iPr-(1,2,4-Thia-5)], [H824;3-CF₃-(1,2,4-Thia-5)], [H825;3-CHF₂-(1,2,4-Thia-5)], [H826;3-OMe-(1,2,4-Thia-5)], [H827;3-OEt-(1,2,4-Thia-5)], [H828;3-OCF₃-(1,2,4-Thia-5)], [H829;3-OCHF₂-(1,2,4-Thia-5)], [H839;3-CN-(1,2,4-Thia-5)], [H831;3-SMe-(1,2,4-Thia-5)], [H832;3-SEt-(1,2,4-Thia-5)], [H833;3-cPr-(1,2,4-Thia-5)], [H834;(1,2,4-Thia-3)], [H835;5-F-(1,2,4-Thia-3)], [H836;5-Cl-(1,2,4-Thia-3)], [H837;5-Br-(1,2,4-Thia-3)], [H838;5-I-(1,2,4-Thia-3)], [H839;5-Me-(1,2,4-Thia-3)], [H840;5-Et-(1,2,4-Thia-3)], [H841;5-Pr-(1,2,4-Thia-3)], [H842;5-iPr-(1,2,4-Thia-3)], [H843;5-CF₃-(1,2,4-Thia-3)], [H844;5-CHF₂-(1,2,4-Thia-3)], [H845;5-OMe-(1,2,4-Thia-3)], [H846;5-OEt-(1,2,4-Thia-3)], [H847;5-OCF₃-(1,2,4-Thia-3)], [H848;5-OCHF₂-(1,2,4-Thia-3)], [H849;5-CN-(1,2,4-Thia-3)], [H850;5-SMe-(1,2,4-Thia-3)], [H851;5-SEt-(1,2,4-Thia-3)], [H852;5-cPr-(1,2,4-Thia-3)], [H853;tet], [H854;5-F-tet-1], [H855;5-Cl-tet-1], [H856;5-Br-tet-1], [H857;5-I-tet-1], [H858;5-Me-tet-1], [H859;5-Et-tet-1], [H860;5-Pr-tet-1], [H861;5-iPr-tet-1], [H862;5-CF₃-tet-1], [H863;5-CHF₂-tet-1], [H864;5-OMe-tet-1], [H865;5-OEt-tet-1], [H866;5-OCF₃-tet-1], [H867;5-OCHF₂-tet-1], [H868;5-CN-tet-1], [H869;5-SMe-tet-1], [H870;5-SEt-tet-1], [H871;5-cPr-tet-1], [H872;tet-5], [H873;1-F-tet-5], [H874;1-Cl-tet-5], [H875;1-Br-tet-5], [H876;1-I-tet-5], [H877;1-Me-tet-5], [H878;1-Et-tet-5], [H879;1-Pr-tet-5], [H880;1-iPr-tet-5], [H881;1-CF₃-tet-5], [H882;1-CHF₂-tet-5], [H883;1-OMe-tet-5], [H884;1-OEt-tet-5], [H885;1-OCF₃-tet-5], [H8861-OCHF₂-tet-5], [H887;1-CN-tet-5], [H888;1-SMe-tet-5],

[H889;1-SEt-tet-5], [H890;1-cPr-tet-5], [H891;3-Fra], [H892;2-F-3-Fra], [H893;2-Cl-3-Fra], [H894;2-Me-3-Fra], [H895;2-Et-3-Fra], [H896;2-Pr-3-Fra], [H897;2-iPr-3-Fra], [H898;2-CF₃-3-Fra], [H899;2-CHF₂-3-Fra], [H900;2-OMe-3-Fra], [H901;2-OEt-3-Fra], [H902;2-OCF₃-3-Fra], [H903;2-OCHF₂-3-Fra], [H904;2-CN-3-Fra], [H905;2-SMe-3-Fra], [H906;2-SEt-3-Fra], [H907;2-cPr-3-Fra], [H908;4-F-3-Fra], [H909;4-Cl-3-Fra], [H910;4-Me-3-Fra], [H911;4-Et-3-Fra], [H912;4-Pr-3-Fra], [H913;4-iPr-3-Fra], [H914;4-CF₃-3-Fra], [H915;4-CHF₂-3-Fra], [H916;4-OMe-3-Fra], [H917;4-OEt-3-Fra], [H918;4-OCF₃-3-Fra], [H919;4-OCHF₂-3-Fra], [H920;4-CN-3-Fra], [H921;4-SMe-3-Fra], [H922;4-SEt-3-Fra], [H923;4-cPr-3-Fra], [H924;5-F-3-Fra], [H925;5-Cl-3-Fra], [H926;5-Me-3-Fra], [H927;5-Et-3-Fra], [H928;5-Pr-3-Fra], [H929;5-iPr-3-Fra], [H930;5-CF₃-3-Fra], [H931;5-CHF₂-3-Fra], [H932;5-OMe-3-Fra], [H933;5-OEt-3-Fra], [H934;5-OCF₃-3-Fra], [H935;5-OCHF₂-3-Fra], [H936;5-CN-3-Fra], [H937;5-SMe-3-Fra], [H938;5-SEt-3-Fra], [H939;5-cPr-3-Fra], [H940;2-Fra], [H941;3-F-2-Fra], [H942;3-Cl-2-Fra], [H943;3-Me-2-Fra], [H944;3-Et-2-Fra], [H945;3-Pr-2-Fra], [H946;3-iPr-2-Fra], [H947;3-CF₃-2-Fra], [H948;3-CHF₂-2-Fra], [H949;3-OMe-2-Fra], [H950;3-OEt-2-Fra], [H951;3-OCF₃-2-Fra], [H952;3-OCHF₂-2-Fra], [H953;3-CN-2-Fra], [H954;3-SMe-2-Fra], [H955;3-SEt-2-Fra], [H956;3-cPr-2-Fra], [H957;4-F-2-Fra], [H958;4-Cl-2-Fra], [H959;4-Me-2-Fra], [H960;4-Et-2-Fra], [H961;4-Pr-2-Fra], [H962;4-iPr-2-Fra], [H963;4-CF₃-2-Fra], [H964;4-CHF₂-2-Fra], [H965;4-OMe-2-Fra], [H966;4-OEt-2-Fra], [H967;4-OCF₃-2-Fra], [H968;4-OCHF₂-2-Fra], [H969;4-CN-2-Fra], [H970;4-SMe-2-Fra], [H971;4-SEt-2-Fra], [H972;4-cPr-2-Fra], [H973;5-F-2-Fra], [H974;5-Cl-2-Fra], [H975;5-Me-2-Fra], [H976;5-Et-2-Fra], [H977;5-Pr-2-Fra], [H978;5-iPr-2-Fra], [H979;5-CF₃-2-Fra], [H980;5-CHF₂-2-Fra], [H981;5-OMe-2-Fra], [H982;5-OEt-2-Fra], [H983;5-OCF₃-2-Fra], [H984;5-OCHF₂-2-Fra], [H985;5-CN-2-Fra], [H986;5-SMe-2-Fra], [H987;5-SEt-2-Fra], [H988;5-cPr-2-Fra], [H989;2-Bf], [H990;3-Bf], [H991;2-F-3-Bf], [H992;2-Cl-3-Bf], [H993;2-Me-3-Bf], [H994;2-Et-3-Bf], [H995;2-Pr-3-Bf], [H996;2-iPr-3-Bf], [H997;2-CF₃-3-Bf], [H998;2-CHF₂-3-Bf], [H999;2-OMe-3-Bf], [H1000;2-OEt-3-Bf],

[H1001;2-OCF₃-3-Bf], [H1002;2-OCHF₂-3-Bf], [H1003;2-CN-3-Bf], [H1004;2-SMe-3-Bf], [H1005;2-SEt-3-Bf], [H1006;2-cPr-3-Bf], [H1007;4-F-3-Bf], [H1008;4-Cl-3-Bf], [H1009;4-Me-3-Bf], [H1010;4-Et-3-Bf], [H1011;4-Pr-3-Bf], [H1012;4-iPr-3-Bf], [H1013;4-CF₃-3-Bf], [H1014;4-CHF₂-3-Bf], [H1015;4-OMe-3-Bf], [H1016;4-OEt-3-Bf], [H1017;4-OCF₃-3-Bf], [H1018;4-OCHF₂-3-Bf], [H1019;4-CN-3-Bf], [H1020;4-SMe-3-Bf], [H1021;4-SEt-3-Bf], [H1022;4-cPr-3-Bf], [H1023;5-F-3-Bf], [H1024;5-Cl-3-Bf], [H1025;5-Me-3-Bf], [H1026;5-Et-3-Bf], [H1027;5-Pr-3-Bf], [H1028;5-iPr-3-Bf], [H1029;5-CF₃-3-Bf], [H1030;5-CHF₂-3-Bf], [H1031;5-OMe-3-Bf], [H1032;5-OEt-3-Bf], [H1033;5-OCF₃-3-Bf], [H1034;5-OCHF₂-3-Bf], [H1035;5-CN-3-Bf], [H1036;5-SMe-3-Bf], [H1037;5-SEt-3-Bf], [H1038;5-cPr-3-Bf], [H1039;6-F-3-Bf], [H1040;6-Cl-3-Bf], [H1041;6-Me-3-Bf], [H1042;6-Et-3-Bf], [H1043;6-Pr-3-Bf], [H1044;6-iPr-3-Bf], [H1045;6-CF₃-3-Bf], [H106;6-CHF₂-3-Bf], [H1047;6-OMe-3-Bf], [H1048;6-OEt-3-Bf], [H1049;6-OCF₃-3-Bf], [H1050;6-OCHF₂-3-Bf], [H1051;6-CN-3-Bf], [H1052;6-SMe-3-Bf], [H1053;6-SEt-3-Bf], [H1054;6-cPr-3-Bf], [H1055;7-F-3-Bf], [H1056;7-Cl-3-Bf], [H1057;7-Me-3-Bf], [H1058;7-Et-3-Bf], [H1059;7-Pr-3-Bf], [H1060;7-iPr-3-Bf], [H1061;7-CF₃-3-Bf], [H1062;7-CHF₂-3-Bf], [H1063;7-OMe-3-Bf], [H1064;7-OEt-3-Bf], [H1065;7-OCF₃-3-Bf], [H1066;7-OCHF₂-3-Bf], [H1067;7-CN-3-Bf], [H1068;7-SMe-3-Bf], [H1069;7-SEt-3-Bf],

[H1070;7-cPr-3-Bf], [H1071;3-F-2-Bf], [H1072;3-Cl-2-Bf], [H1073;3-Me-2-Bf], [H1074;3-Et-2-Bf], [H1075;3-Pr-2-Bf], [H1076;3-iPr-2-Bf], [H1077;3-CF$_3$-2-Bf], [H1078;3-CHF$_2$-2-Bf], [H1079;3-OMe-2-Bf], [H1080;3-OEt-2-Bf], [H1081;3-OCF$_3$-2-Bf], [H1082;3-OCHF$_2$-2-Bf], [H1083;3-CN-2-Bf], [H1084;3-SMe-2-Bf], [H1085;3-SEt-2-Bf], [H1086;3-cPr-2-Bf], [H1087;4-F-2-Bf], [H1088;4-Cl-2-Bf], [H1089;4-Me-2-Bf], [H1090;4-Et-2-Bf], [H1091;4-Pr-2-Bf], [H1092;4-iPr-2-Bf], [H1093;4-CF$_3$-2-Bf], [H1094;4-CHF$_2$-2-Bf], [H1095;4-OMe-2-Bf], [H1096;4-OEt-2-Bf], [H1097;4-OCF$_3$-2-Bf], [H1098;4-OCHF$_2$-2-Bf], [H1099;4-CN-2-Bf], [H1100;4-SMe-2-Bf], [H1101;4-SEt-2-Bf], [H1102;4-cPr-2-Bf], [H1103;5-F-2-Bf], [H1104;5-Cl-2-Bf], [H1105;5-Me-2-Bf], [H1106;5-Et-2-Bf], [H1107;5-Pr-2-Bf], [H1108;5-iPr-2-Bf], [H1109;5-CF$_3$-2-Bf], [H1110;5-CHF$_2$-2-Bf], [H1111;5-OMe-2-Bf], [H1112;5-OEt-2-Bf], [H1113;5-OCF$_3$-2-Bf], [H1114;5-OCHF$_2$-2-Bf], [H1115;5-CN-2-Bf], [H1116;5-SMe-2-Bf], [H1117;5-SEt-2-Bf], [H1118;5-cPr-2-Bf], [H1119;6-F-2-Bf], [H1120;6-Cl-2-Bf], [H1121;6-Me-2-Bf], [H1122;6-Et-2-Bf], [H1123;6-Pr-2-Bf], [H1124;6-iPr-2-Bf], [H1125;6-CF$_3$-2-Bf], [H1126;6-CHF$_2$-2-Bf], [H1127;6-OMe-2-Bf], [H1128;6-OEt-2-Bf], [H1129;6-OCF$_3$-2-Bf], [H1130;6-OCHF$_2$-2-Bf], [H1131;6-CN-2-Bf], [H1132;6-SMe-2-Bf], [H1133;6-SEt-2-Bf], [H1134;6-cPr-2-Bf], [H1135;7-F-2-Bf], [H1136;7-Cl-2-Bf], [H1137;7-Me-2-Bf], [H1138;7-Et-2-Bf], [H1139;7-Pr-2-Bf], [H1140;7-iPr-2-Bf], [H1141;7-CF$_3$-2-Bf], [H1142;7-CHF$_2$-2-Bf], [H1143;7-OMe-2-Bf], [H1144;7-OEt-2-Bf], [HI 1145;7-OCF$_3$-2-Bf], [HI 146;7-OCHF$_2$-2-Bf], [H1147;7-CN-2-Bf], [H1148;7-SMe-2-Bf], [H1149;7-SEt-2-Bf], [H1150;7-cPr-2-Bf], [H1151;4-Bf], [H1152;3-F-4-Bf], [H1153;3-Cl-4-Bf], [H1154;3-Me-4-Bf], [H1155;3-Et-4-Bf], [H1156;3-Pr-4-Bf], [H1157;3-iPr-4-Bf], [H1158;3-CF$_3$-4-Bf], [H1159;3-CHF$_2$-4-Bf], [H1160;3-OMe-4-Bf], [H1161;3-OEt-4-Bf], [H1162;3-OCF$_3$-4-Bf], [HI 163;3-OCHF$_2$-4-Bf], [H1164;3-CN-4-Bf], [H1165;3-SMe-4-Bf], [H1166;3-SEt-4-Bf], [H1167;3-cPr-4-Bf], [H1168;5-F-4-Bf], [H1169;5-Cl-4-Bf], [H1170;5-Me-4-Bf], [H1171;5-Et-4-Bf], [H1172;5-Pr-4-Bf], [H1173;5-iPr-4-Bf], [H1174;5-CF$_3$-4-Bf], [H1175;5-CHF$_2$-4-Bf], [H1176;5-OMe-4-Bf], [H1177;5-OEt-4-Bf], [H1178;5-OCF$_3$-4-Bf], [H1179;5-OCHF$_2$-4-Bf], [H1180;5-CN-4-Bf], [H1181;5-SMe-4-Bf], [H1182;5-SEt-4-Bf], [H1183;5-cPr-4-Bf], [H1184;6-F-4-Bf], [H1185;6-Cl-4-Bf], [H1186;6-Me-4-Bf], [H1187;6-Et-4-Bf], [H1188;6-Pr-4-Bf], [H1189;6-iPr-4-Bf], [H1190;6-CF$_3$-4-Bf], [H1191;6-CHF$_2$-4-Bf], [H1192;6-OMe-4-Bf], [H1193;6-OEt-4-Bf], [H1194;6-OCF$_3$-4-Bf], [H1195;6-OCHF$_2$-4-Bf], [H1196;6-CN-4-Bf], [H1197;6-SMe-4-Bf], [H1198;6-SEt-4-Bf], [H1199;6-cPr-4-Bf],

[H1200;2-Bt], [H1201;4-F-2-Bt], [H1202;4-Cl-2-Bt], [H1203;4-Me-2-Bt], [H1204;4-Et-2-Bt], [H1205;4-Pr-2-Bt], [H1206;4-iPr-2-Bt], [H1207;4-CF$_3$-2-Bt], [H1208;4-CHF$_2$-2-Bt], [H1209;4-OMe-2-Bt], [H1210;4-OEt-2-Bt], [H1211;4-OCF$_3$-2-Bt], [H1212;4-OCHF$_2$-2-Bt], [H1213;4-CN-2-Bt], [H1214;4-SMe-2-Bt], [H1215;4-SEt-2-Bt], [H1216;4-cPr-2-Bt], [H1217;7-F-2-Bt], [H1218;7-Cl-2-Bt], [H1219;7-Me-2-Bt], [H1220;7-Et-2-Bt], [H1221;7-Pr-2-Bt], [H1222;7-iPr-2-Bt], [H1223;7-CF$_3$-2-Bt], [H1224;7-CHF$_2$-2-Bt], [H1225;7-OMe-2-Bt], [H1226;7-OEt-2-Bt], [H1227;7-OCF$_3$-2-Bt], [H1228;7-OCHF$_2$-2-Bt], [H1229;7-CN-2-Bt], [H1230;7-SMe-2-Bt], [H1231;7-SEt-2-Bt], [H1232;7-cPr-2-Bt], [H1233;4-Bt], [H1234;2-F-4-Bt], [H1235;2-Cl-4-Bt], [H1236;2-Me-4-Bt], [H1237;2-Et-4-Bt], [H1238;2-Pr-4-Bt], [H1239;2-iPr-4-Bt], [H1240;2-CF$_3$-4-Bt], [H1241;2-CHF$_2$-4-Bt], [H1242;2-OMe-4-Bt], [H1243;2-OEt-4-Bt], [H1244;2-OCF$_3$-4-Bt], [H1245;2-OCHF$_2$-4-Bt], [H1246;2-CN-4-Bt], [H1247;2-SMe-4-Bt], [H1248;2-SEt-4-Bt], [H1249;2-cPr-4-Bt], [H1250;5-F-4-Bt], [H1251;5-Cl-4-Bt], [H1252;5-Me-4-Bt], [H1253;5-Et-4-Bt], [H1254;5-Pr-4-Bt], [H1255;5-iPr-4-Bt], [H12565-CF$_3$-4-Bt], [H1257;5-CHF$_2$-4-Bt], [H1258;5-OMe-4-Bt], [H1259;5-OEt-4-Bt], [H1260;5-OCF$_3$-4-Bt], [H1261;5-OCHF$_2$-4-Bt], [H1262;5-CN-4-Bt], [H1263;5-SMe-4-Bt], [H1264;5-SEt-4-Bt], [H1265;5-cPr-4-Bt], [H1266;6-F-4-Bt], [H1267;6-Cl-4-Bt], [H1268;6-Me-4-Bt], [H1269;6-Et-4-Bt], [H1270;6-Pr-4-Bt], [H1271;6-iPr-4-Bt], [H1272;6-CF$_3$-4-Bt], [H1273;6-CHF$_2$-4-Bt], [H1274;6-OMe-4-Bt], [H1275;6-OEt-4-Bt], [H1276;6-OCF$_3$-4-Bt], [H1277;6-OCHF$_2$-4-Bt], [H1278;6-CN-4-Bt], [H1279;6-SMe-4-Bt], [H1280;6-SEt-4-Bt], [H1281;6-cPr-4-Bt], [H1282;7-F-4-Bt], [H1283;7-Cl-4-Bt], [H1284;7-Me-4-Bt], [H1285;7-Et-4-Bt], [H1286;7-Pr-4-Bt], [H1287;7-iPr-4-Bt], [H1288;7-CF$_3$-4-Bt], [H1289;7-CHF$_2$-4-Bt], [H1290;7-OMe-4-Bt], [H1291;7-OEt-4-Bt], [H1292;7-OCF$_3$-4-Bt], [H1293;7-OCHF$_2$-4-Bt], [H1294;7-CN-4-Bt], [H1295;7-SMe-4-Bt], [H1296;7-SEt-4-Bt], [H1297;7-cPr-4-Bt], [H1298;5-Bt], [H1299;5-F-5-Bt], [H1300;5-Cl-5-Bt], [H1301;5-Me-5-Bt], [H1302;5-Et-5-Bt], [H1303;5-Pr-5-Bt], [H1304;5-iPr-5-Bt], [H1305;5-CF$_3$-5-Bt], [H1306;5-CHF$_2$-5-Bt], [H1307;5-OMe-5-Bt], [H1308;5-OEt-5-Bt], [H1309;5-OCF$_3$-5-Bt], [H1310;5-OCHF$_2$-5-Bt], [H1311;5-CN-5-Bt], [H1312;5-SMe-5-Bt], [H1313;5-SEt-5-Bt], [H1314;5-cPr-5-Bt], [H1315;6-F-5-Bt], [H1316;6-Cl-5-Bt], [H1317;6-Me-5-Bt], [H1318;6-Et-5-Bt], [H1319;6-Pr-5-Bt], [H1320;6-iPr-5-Bt], [H1321;6-CF$_3$-5-Bt], [H1322;6-CHF$_2$-5-Bt], [H1323;6-OMe-5-Bt], [H1324;6-OEt-5-Bt], [H1325;6-OCF$_3$-5-Bt], [H1326;6-OCHF$_2$-5-Bt], [H1327;6-CN-5-Bt], [H1328;6-SMe-5-Bt], [H1329;6-SEt-5-Bt], [H1330;6-cPr-5-Bt], [H1331;6-Bt], [H1332;5-F-4-Bt], [H1333;5-Cl-4-Bt], [H1334;5-Me-4-Bt], [H1335;5-Et-4-Bt], [H1336;5-Pr-4-Bt], [H1337;5-iPr-4-Bt], [H1338;5-CF$_3$-4-Bt], [H1339;5-CHF$_2$-4-Bt], [H1340;5-OMe-4-Bt], [H1341;5-OEt-4-Bt], [H1342;5-OCF$_3$-4-Bt], [H1343;5-OCHF$_2$-4-Bt], [H1344;5-CN-4-Bt], [H1345;5-SMe-4-Bt], [H1346;5-SEt-4-Bt], [H1347;5-cPr-4-Bt], [H1348;6-F-4-Bt], [H1349;6-Cl-4-Bt], [H1350;6-Me-4-Bt], [H1351;6-Et-4-Bt], [H1352;6-Pr-4-Bt], [H1353;6-iPr-4-Bt], [H1354;6-CF$_3$-4-Bt], [H1355;6-CHF$_2$-4-Bt], [H1356;6-OMe-4-Bt], [H1357;6-OEt-4-Bt], [H1358;6-OCF$_3$-4-Bt], [H1359;6-OCHF$_2$-4-Bt], [H1360;6-CN-4-Bt], [H1361;6-SMe-4-Bt], [H1362;6-SEt-4-Bt], [H1363;6-cPr-4-Bt], [H1364;1-Pyr], [H1365;4-F-1-Pyr], [H1366;4-Cl-1-Pyr], [H1367;4-Me-1-Pyr], [H1368;4-Et-1-Pyr], [H1369;4-iPr-1-Pyr], [H1370;4-CF$_3$-1-Pyr], [H1371;4-CHF$_2$-1-Pyr], [H1372;4-OMe-1-Pyr], [H1373;4-OCF$_3$-1-Pyr], [H1374;4-OCHF$_2$-1-Pyr], [H1375;4-OCH$_2$CHF$_2$-1-Pyr], [H1376;4-CN-1-Pyr], [H1377;4-SMe-1-Pyr], [H1378;4-cPr—I-Pyr], [H1379;5-F-1-Pyr], [H1380;5-Cl-1-Pyr], [H1381;5-Me-1-Pyr], [H1382;5-Et-1-Pyr], [H1383;5-iPr-1-Pyr], [H1384;5-CF$_3$-1-Pyr], [H1385;5-CHF$_2$-1-Pyr], [H1386;5-OMe-1-Pyr], [H1387;5-OCF$_3$-1-Pyr], [H1388;5-OCHF$_2$-1-Pyr], [H1389;5-OCH$_2$CH F$_2$-1-Pyr], [H1390;5-CN-1-Pyr], [H1391;5-SMe-1-Pyr], [H1392;5-cPr-1-Pyr], [H1393;4-F-5-F-1-Pyr], [H1394;4-F-5-Cl-1-Pyr], [H1395;4-F-5-Me-1-Pyr], [H1396;4-F-5-Et-1-Pyr], [H1397;4-F-5-iPr-1-Pyr], [H1398;4-F-5-CF$_3$-1-Pyr], [H1399;4-F-5-CHF$_2$-1-Pyr], [H1400;4-F-5-OMe-1-Pyr],

[H1401;4-F-5-OCF$_3$-1-Pyr], [H1402;4-F-5-OCHF$_2$-1-Pyr], [H1403;4-F-5-OCH$_2$CHF$_2$-1-Pyr], [H1404;4-F-5-CN-1-Pyr], [H1405;4-F-5-SMe-1-Pyr], [H1406;4-F-5-cPr-1-Pyr], [H1407;4-Cl-5-F-1-Pyr], [H1408;4-Cl-5-Cl-1-Pyr], [H1409;4-Cl-5-Me-1-Pyr], [H1410;4-Cl-5-Et-1-Pyr], [H1411;4-Cl-5-iPr-1-Pyr], [H1412;4-Cl-5-CF$_3$-1-Pyr], [H1413;4-Cl-5-CHF$_2$-1-Pyr], [H1414;4-Cl-5-OMe-1-Pyr], [H1415;4-Cl-5-OCF$_3$-1-Pyr], [H1416;4-Cl-5-OCHF$_2$-1-

Pyr], [H1417;4-Cl-5-OCH$_2$CHF$_2$-1-Pyr], [H1418;4-Cl-5-CN-1-Pyr], [H1419;4-Cl-5-SMe-1-Pyr], [H1420;4-Cl-5-cPr-1-Pyr], [H1421;4-Me-5-F-1-Pyr], [H1422;4-Me-5-Cl-1-Pyr], [H1423;4-Me-5-Me-1-Pyr], [H1424;4-Me-5-Et-1-Pyr], [H1425;4-Me-5-iPr-1-Pyr], [H1426;4-Me-5-CF$_3$-1-Pyr], [H1427;4-Me-5-CHF$_2$-1-Pyr], [H1428;4-Me-5-OMe-1-Pyr], [H1429;4-Me-5-OCF$_3$-1-Pyr], [H1430;4-Me-5-OCHF$_2$-1-Pyr], [H1431;4-Me-5-OCH$_2$CHF$_2$-1-Pyr], [H1432;4-Me-5-CN-1-Pyr], [H1433;4-Me-5-SMe-1-Pyr], [H1434;4-Me-5-cPr-1-Pyr], [H1435;4-Et-5-F-1-Pyr], [H1436;4-Et-5-Cl-1-Pyr], [H1437;4-Et-5-Me-1-Pyr], [H1438;4-Et-5-Et-1-Pyr], [H1439;4-Et-5-iPr-1-Pyr], [H1440;4-Et-5-CF$_3$-1-Pyr], [H1441;4-Et-5-CHF$_2$-1-Pyr], [H1442;4-Et-5-OMe-1-Pyr], [H1443;4-Et-5-OCF$_3$-1-Pyr], [H1444;4-Et-5-OCHF$_2$-1-Pyr], [H14454-Et-5-OCH$_2$CHF$_2$-1-Pyr], [H1446;4-Et-5-CN-1-Pyr], [H1447;4-Et-5-SMe-1-Pyr], [H1448;4-Et-5-cPr-1-Pyr], [H1449;4-CF$_3$-5-F-1-Pyr], [H1450;4-CF$_3$-5-Cl-1-Pyr], [H1451;4-CF$_3$-5-Me-1-Pyr], [H1452;4-CF$_3$-5-Et-1-Pyr], [H1453;4-CF$_3$-5-iPr-1-Pyr], [H1454;4-CF$_3$-5-CF$_3$-1-Pyr], [H1455;4-CF$_3$-5-CHF$_2$-1-Pyr], [H1456;4-CF$_3$-5-OMe-1-Pyr], [H1457;4-CF$_3$-5-OCF$_3$-1-Pyr], [H1458;4-CF$_3$-5-OCHF$_2$-1-Pyr], [H1459;4-CF$_3$-5-OCH$_2$CHF$_2$-1-Pyr], [H1460;4-CF$_3$-5-CN-1-Pyr], [H1461;4-CF$_3$-5-SMe-1-Pyr], [H1462;4-CF$_3$-5-cPr-1-Pyr], [H1463;4-OMe-5-F-1-Pyr], [H1464;4-OMe-5-Cl-1-Pyr], [H1465;4-OMe-5-Me-1-Pyr], [H1466;4-OMe-5-Et-1-Pyr], [H1467;4-OMe-5-iPr-1-Pyr], [H1468;4-OMe-5-CF$_3$-1-Pyr], [H1469;4-OMe-5-CHF$_2$-1-Pyr], [H1470;4-OMe-5-OMe-1-Pyr], [H1471;4-OMe-5-OCF$_3$-1-Pyr], [H1472;4-OMe-5-OCHF$_2$-1-Pyr], [H1473;4-OMe-5-OCH$_2$CHF$_2$-1-Pyr], [H1474;4-OMe-5-CN-1-Pyr], [H1475;4-OMe-5-SMe-1-Pyr], [H1476;4-OMe-5-cPr-1-Pyr], [H1477;4-SMe-5-F-1-Pyr], [H1478;4-SMe-5-Cl-1-Pyr], [H1479;4-SMe-5-Me-1-Pyr], [H1480;4-SMe-5-Et-1-Pyr], [H1481;4-SMe-5-iPr-1-Pyr], [H1482;4-SMe-5-CF$_3$-1-Pyr], [H1483;4-SMe-5-CHF$_2$-1-Pyr], [H1484;4-SMe-5-OMe-1-Pyr], [H1485;4-SMe-5-OCF$_3$-1-Pyr], [H1486;4-SMe-5-OCHF$_2$-1-Pyr], [H1487;4-SMe-5-OCH$_2$CHF$_2$-1-Pyr], [H1488;4-SMe-5-CN-1-Pyr], [H1489;4-SMe-5-SMe-1-Pyr], [H1490;4-SMe-5-cPr-1-Pyr], [H1491;4-Pyr], [H1492;1-F-4-Pyr], [H1493;1-Cl-4-Pyr], [H1494;1-Me-4-Pyr], [H1495;1-Et-4-Pyr], [H1496;1-iPr-4-Pyr], [H1497;1-CF$_3$-4-Pyr], [H1498;1-CHF$_2$-4-Pyr], [H1499;1-CH$_2$CHF$_2$-4-Pyr], [H1500;1-CH$_2$CF$_3$-4-Pyr], [H1501;1-CF$_2$CF$_3$-4-Pyr], [H1502;1-CH$_2$OMe-4-Pyr], [H1503;1-CH$_2$OEt-4-Pyr], [H1504;1-CH$_2$SMe-4-Pyr], [H1505;1-cPr-4-Pyr], [H1506;5-F-4-Pyr], [H1507;5-Cl-4-Pyr], [H1508;5-Me-4-Pyr], [H1509;5-Et-4-Pyr], [H1510;5-iPr-4-Pyr], [H1511;5-CF$_3$-4-Pyr], [H1512;5-CHF$_2$-4-Pyr], [H1513;5-OMe-4-Pyr], [H1514;5-OCF$_3$-4-Pyr], [H1515;5-OCHF$_2$-4-Pyr], [H1516;5-OCH$_2$CHF$_2$-4-Pyr], [H1517;5-CN-4-Pyr], [H1518;5-SMe-4-Pyr], [H1519;5-cPr-4-Pyr], [H1520;1-CH$_2$CF$_3$-5-F-4-Pyr], [H1521;1-CH$_2$CF$_3$-5-Cl-4-Pyr], [H1522;1-CH$_2$CF$_3$-5-Me-4-Pyr], [H1523;1-CH$_2$CF$_3$-5-Et-4-Pyr], [H1524;1-CH$_2$CF$_3$-5-iPr-4-Pyr], [H1525;1-CH$_2$CF$_3$-5-CF$_3$-4-Pyr], [H1526;1-CH$_2$CF$_3$-5-CHF$_2$-4-Pyr], [H1527;1-CH$_2$CF$_3$-5-OMe-4-Pyr], [H1528;1-CH$_2$CF$_3$-5-OCF$_3$-4-Pyr], [H1529;1-CH$_2$CF$_3$-5-OCHF$_2$-4-Pyr], [H1530;1-CH$_2$CF$_3$-5-OCH$_2$CHF$_2$-4-Pyr], [H1531;1-CH$_2$CF$_3$-5-CN-4-Pyr], [H1532;1-CH$_2$CF$_3$-5-SMe-4-Pyr], [H1533;1-CH$_2$CF$_3$-5-cPr-4-Pyr], [H1534;2-Cl-5-F-4-Pyr], [H1535;2-Cl-5-Cl-4-Pyr], [H1536;2-Cl-5-Me-4-Pyr], [H1537;2-Cl-5-Et-4-Pyr], [H1538;2-Cl-5-iPr-4-Pyr], [H1539;2-Cl-5-CF$_3$-4-Pyr], [H1540;2-Cl-5-CHF$_2$-4-Pyr], [H1541;2-Cl-5-OMe-4-Pyr], [H1542;2-Cl-5-OCF$_3$-4-Pyr], [H1543;2-Cl-5-OCHF$_2$-4-Pyr], [H1544;2-Cl-5-OCH$_2$CHF$_2$-4-Pyr], [H1545;2-Cl-5-CN-4-Pyr], [H1546;2-Cl-5-SMe-4-Pyr], [H1547;2-Cl-5-cPr-4-Pyr], [H1548;1-Me-5-F-4-Pyr], [H1549;1-Me-5-Cl-4-Pyr], [H1550;1-Me-5-Me-4-Pyr], [H1551;1-Me-5-Et-4-Pyr], [H1552;1-Me-5-iPr-4-Pyr], [H1553;1-Me-5-CF$_3$-4-Pyr], [H1554;1-Me-5-CHF$_2$-4-Pyr], [H1555;1-Me-5-OMe-4-Pyr], [H1556;1-Me-5-OCF$_3$-4-Pyr], [H1557;1-Me-5-OCHF$_2$-4-Pyr], [H1558;1-Me-5-OCH$_2$CHF$_2$-4-Pyr], [H1559;1-Me-5-CN-4-Pyr], [H1560;1-Me-5-SMe-4-Pyr], [H1561;1-Me-5-cPr-4-Pyr], [H1562;1-Et-5-F-4-Pyr], [H1563;1-Et-5-Cl-4-Pyr], [H1564;1-Et-5-Me-4-Pyr], [H1565;1-Et-5-Et-4-Pyr], [H1566;1-Et-5-iPr-4-Pyr], [H1567;1-Et-5-CF$_3$-4-Pyr], [H1568;1-Et-5-CHF$_2$-4-Pyr], [H1569;1-Et-5-OMe-4-Pyr], [H1570;1-Et-5-OCF$_3$-4-Pyr], [H1571;1-Et-5-OCHF$_2$-4-Pyr], [H1572;1-Et-5-OCH$_2$CHF$_2$-4-Pyr], [H1573;1-Et-5-CN-4-Pyr], [H1574;1-Et-5-SMe-4-Pyr], [H1575;1-Et-5-cPr-4-Pyr], [H1576;1-CF$_3$-5-F-4-Pyr], [H1577;1-CF$_3$-5-Cl-4-Pyr], [H1578;1-CF$_3$-5-Me-4-Pyr], [H1579;1-CF$_3$-5-Et-4-Pyr], [H1580;1-CF$_3$-5-iPr-4-Pyr], [H1581;1-CF$_3$-5-CF$_3$-4-Pyr], [H1582;1-CF$_3$-5-CHF$_2$-4-Pyr], [H1583;1-CF$_3$-5-OMe-4-Pyr], [H1584;1-CF$_3$-5-OCF$_3$-4-Pyr], [H1585;1-CF$_3$-5-OCHF$_2$-4-Pyr], [H1586;1-CF$_3$-5-OCH$_2$CHF$_2$-4-Pyr], [H1587;1-CF$_3$-5-CN-4-Pyr], [H1588;1-CF$_3$-5-SMe-4-Pyr], [H1589;1-CF$_3$-5-cPr-4-Pyr], [H1590;1-CH$_2$OMe-5-F-4-Pyr], [H1591;1-CH$_2$OMe-5-Cl-4-Pyr], [H1592;1-CH$_2$OMe 5-Me-4-Pyr], [H1593;1-CH$_2$OMe-5-Et-4-Pyr], [H1594;1-CH$_2$OMe-5-iPr-4-Pyr], [H1595;1-CH$_2$OMe-5-CF$_3$-4-Pyr], [H1596;1-CH$_2$OMe-5-CHF$_2$-4-Pyr], [H1597;1-CH$_2$OMe-5-OMe-4-Pyr], [H15981-CH$_2$OMe-5-OCF$_3$-4-Pyr], [H15991-CH$_2$OMe-5-OCHF$_2$-4-Pyr], [H1600;1-CH$_2$OMe-5-OCH$_2$CHF$_2$-4-Pyr], [H1601;1-CH$_2$OMe-5-CN-4-Pyr], [H1602;1-CH$_2$OMe-5-SMe-4-Pyr], [H1603;1-CH$_2$OMe$_3$-5-cPr-4-Pyr], [H1604;1-CH$_2$CHF$_2$-5-F-4-Pyr], [H1605;1-CH$_2$CHF$_2$-5-Cl-4-Pyr], [H1606;1-CH$_2$CHF$_2$-5-Me-4-Pyr], [H1607;1-CH$_2$CHF$_2$-5-Et-4-Pyr], [H1608;1-CH$_2$CHF$_2$-5-iPr-4-Pyr], [H1609;1-CH$_2$CHF$_2$-5-CF$_3$-4-Pyr], [H1610;1-CH$_2$CHF$_2$-5-CHF$_2$-4-Pyr], [H1611;1-CH$_2$CHF$_2$-5-OMe-4-Pyr], [H1612;1-CH$_2$CHF$_2$-5-OCF$_3$-4-Pyr], [H1613;1-CH$_2$CHF$_2$-5-OCHF$_2$-4-Pyr], [H1614;1-CH$_2$CHF$_2$-5-OCH$_2$CHF$_2$-4-Pyr], [H1615;1-CH$_2$CHF$_2$-5-CN-4-Pyr], [H1616;1-CH$_2$CHF$_2$-5-SMe-4-Pyr], [H1617;1-CH$_2$CHF$_2$-5-cPr-4-Pyr], [H1618;5-Pyr], [H1619;2-F-5-Pyr], [H1620;2-Cl-5-Pyr], [H1621;2-Me-5-Pyr], [H1622;2-Et-5-Pyr], [H1623;2-CF$_3$-5-Pyr], [H1624;2-CHF$_2$-5-Pyr], [H1625;2-OMe-5-Pyr], [H1626;2-OCF$_3$-5-Pyr], [H1627;2-OCHF$_2$-5-Pyr], [H1628;2-OCH$_2$CHF$_2$-5-Pyr], [H1629;2-CN-5-Pyr], [H1630;2-SMe-5-Pyr], [H1631;2-cPr-5-Pyr], [H1632;4-F-5-Pyr], [H1633;4-Cl-5-Pyr], [H1634;4-Me-5-Pyr], [H1635;4-Et-5-Pyr], [H1636;4-iPr-5-Pyr], [H1637;4-CF$_3$-5-Pyr], [H1638;4-CHF$_2$-5-Pyr], [H1639;4-OMe-5-Pyr], [H1640;4-OCF$_3$-5-Pyr], [H1641;4-OCHF$_2$-5-Pyr], [H1642;4-OCH$_2$CHF$_2$-5-Pyr], [H1643;4-CN-5-Pyr], [H1644;4-SMe-5-Pyr], [H1645;4-cPr-5-Pyr], [H1646;2-F-4-F-5-Pyr], [H1647;2-F-4-Cl-5-Pyr], [H1648;2-F-4-Me-5-Pyr], [H1649;2-F-4-Et-5-Pyr], [H1650;2-F-4-iPr-5-Pyr], [H1651;2-F-4-CF$_3$-5-Pyr], [H1652;2-F-4-CHF$_2$-5-Pyr], [H1653;2-F-4-OMe-5-Pyr], [H1654;2-F-4-OCF$_3$-5-Pyr], [H1655;2-F-4-OCHF$_2$-5-Pyr], [H1656;2-F-4-OCH$_2$CHF$_2$-5-Pyr], [H1657;2-F-4-CN-5-Pyr], [H1658;2-F-4-SMe-5-Pyr], [H1659;2-F-4-cPr-5-Pyr], [H1660;2-Cl-4-F-5-Pyr], [H1661;2-Cl-4-Cl-5-Pyr], [H1662;2-Cl-4-Me-5-Pyr], [H1663;2-Cl-4-Et-5-Pyr], [H1664;2-Cl-4-iPr-5-Pyr], [H1665;2-Cl-4-CF$_3$-5-Pyr], [H1666;2-Cl-4-CHF$_2$-5-Pyr], [H1667;2-Cl-4-OMe-5-Pyr], [H1668;2-Cl-4-OCF$_3$-5-Pyr], [H1669;2-Cl-4-OCHF$_2$-5-Pyr], [H1670;2-Cl-4-OCH$_2$CHF$_2$-5-Pyr], [H1671;2-Cl-4-CN-5-Pyr], [H1672;2-Cl-4-SMe-5-Pyr], [H1673;2-Cl-4-cPr-5-Pyr], [H1674;2-Me-4-F-5-Pyr], [H1675;2-Me-4-Cl-5-Pyr], [H1676;2-Me-4-Me-5-Pyr], [H1677;2-Me-4-Et-5-Pyr], [H1678;2-Me-4-iPr-

5-Pyr], [H1679;2-Me-4-CF$_3$-5-Pyr], [H1680;2-Me-4-CHF$_2$-5-Pyr], [H1681;2-Me-4-OMe-5-Pyr], [H1682;2-Me-4-OCF$_3$-5-Pyr], [H1683;2-Me-4-OCHF$_2$-5-Pyr], [H1684;2-Me-4-OCH$_2$CHF$_2$-5-Pyr], [H1685;2-Me-4-CN-5-Pyr], [H1686;2-Me-4-SMe-5-Pyr], [H1687;2-Me-4-cPr-5-Pyr], [H1688;2-Et-4-F-5-Pyr], [H1689;2-Et-4-Cl-5-Pyr], [H1690; 2-Et-4-Me-5-Pyr], [H1691;2-Et-4-Et-5-Pyr], [H1692;2-Et-4-iPr-5-Pyr], [H1693;2-Et-4-CF$_3$-5-Pyr], [H1694;2-Et-4-CHF$_2$-5-Pyr], [H1695;2-Et-4-OMe-5-Pyr], [H1696;2-Et-4-OCF$_3$-5-Pyr], [H1697;2-Et-4-OCHF$_2$-5-Pyr], [H1698;2-Et-4-OCH$_2$CHF$_2$-5-Pyr], [H1699;2-Et-4-CN-5-Pyr], [H1700; 2-Et-4-SMe-5-Pyr], [H1701;2-Et-4-cPr-5-Pyr], [H1702;2-CF$_3$-4-F-5-Pyr], [H1703;2-CF$_3$-4-Cl-5-Pyr], [H1704;2-CF$_3$-4-Me-5-Pyr], [H1705;2-CF$_3$-4-Et-5-Pyr], [H1706;2-CF$_3$-4-iPr-5-Pyr], [H1707;2-CF$_3$-4-CF$_3$-5-Pyr], [H1708;2-CF$_3$-4-CHF$_2$-5-Pyr], [H1709;2-CF$_3$-4-OMe-5-Pyr], [H1710;2-CF$_3$-4-OCF$_3$-5-Pyr], [H1711;2-CF$_3$-4-OCHF$_2$-5-Pyr], [H1712;2-CF$_3$-4-OCH$_2$CHF$_2$-5-Pyr], [H1713;2-CF$_3$-4-CN-5-Pyr], [H1714;2-CF$_3$-4-SMe-5-Pyr], [H1715;2-CF$_3$-4-cPr-5-Pyr], [H1716;2-OMe-4-F-5-Pyr], [H1717;2-OMe-4-Cl-5-Pyr], [H1718;2-OMe-4-Me-5-Pyr], [H1719;2-OMe-4-Et-5-Pyr], [H1720;2-OMe-4-iPr-5-Pyr], [H1721;2-OMe-4-CF$_3$-5-Pyr], [H1722;2-OMe-4-CHF$_2$-5-Pyr], [H1723;2-OMe-4-OMe-5-Pyr], [H1724;2-OMe-4-OCF$_3$-5-Pyr], [H1725;2-OMe-4-OCHF$_2$-5-Pyr], [H1726;2-OMe-4-OCH$_2$CHF$_2$-5-Pyr], [H1727;2-OMe-4-CN-5-Pyr], [H1728; 2-OMe-4-SMe-5-Pyr], [H1729;2-OMe-4-cPr-5-Pyr], [H1730;2-SMe-4-F-5-Pyr], [H1731;2-SMe-4-Cl-5-Pyr], [H1732;2-SMe-4-Me-5-Pyr], [H1733;2-SMe-4-Et-5-Pyr], [H1734;2-SMe-4-iPr-5-Pyr], [H1735;2-SMe-4-CF3-5-Pyr], [H1736;2-SMe-4-CHF$_2$-5-Pyr], [H1737;2-SMe-4-OMe-5-Pyr], [H1738;2-SMe-4-OCF$_3$-5-Pyr], [H1739;2-SMe-4-OCHF$_2$-5-Pyr], [H1740;2-SMe-4-OCH$_2$CHF$_2$-5-Pyr], [H1741;2-SMe-4-CN-5-Pyr], [H1742;2-SMe-4-SMe-5-Pyr], [H1743;2-SMe-4-cPr-5-Pyr], [H1744;3-Pyr], [H1745; 1-Me-3-Pyr], [H1746;1-Et-3-Pyr], [H1747;1-iPr-3-Pyr], [H1748;1-CF$_3$-3-Pyr], [H1749;1-CHF$_2$-3-Pyr], [H1750;1-CH$_2$CHF$_2$-3-Pyr], [H1751;1-CH$_2$CF$_3$-3-Pyr], [H1751;1-CH$_2$OCH$_3$-3-Pyr], [H1753;1-CH$_2$CH$_2$OMe-3-Pyr], [H1754;1-CH$_2$OCH$_2$CH$_3$-3-Pyr], [H1755;1-cPr-3-Pyr], [H1756;1-CH$_2$C☐CH-3-Pyr], [H1757;1-CH$_2$C≡CMe-3-Pyr], [H1758;1-CH$_2$CH═CH$_2$-3-Pyr], [H1759;1,5-Me$_2$-3-Pyr], [H1760;1-4-Me$_2$-3-Pyr], [H1761;1,4,5-Me$_3$-3-Pyr], [H1762;1-Me-5-F-3-Pyr], [H1763;1-Me-5-Cl-3-Pyr], [H1764;1-Me-5-OMe-3-Pyr], [H1765;1-4-Me$_2$-5-OMe-3-Pyr], [H1766;1-CF$_2$CF$_3$-3-Pyr], [H1767;1-CH$_2$SMe-3-Pyr], [H1768;1-Me-4-F-5-OMe-3-Pyr], [H1769;1-Me-4-Cl-5-OMe-3-Pyr], [H1770;1-Me-4-Br-5-OMe-3-Pyr], [H1771;1-Me-4-I-5-OMe-3-Pyr], [H1772;1-Me-4-CHF$_2$-5-OMe-3-Pyr], [H1773;4-CF$_3$-3-Pyr], [H1774;4-CHF$_2$-3-Pyr], [H1775;4-OMe-3-Pyr], [H1776;4-OCF$_3$-3-Pyr], [H1777;4-OCHF$_2$-3-Pyr], [H1778;4-OCH$_2$CHF$_2$-3-Pyr], [H1779;4-CN-3-Pyr], [H1780;4-SMe-3-Pyr], [H1781;4-cPr-3-Pyr], [H1782;1-Me-4-F-3-Pyr], [H1783;1-Me-4-Cl-3-Pyr], [H1784;1-Me-4-Me-3-Pyr], [H1785;1-Me-4-Et-3-Pyr], [H1786;1-Me-4-iPr-3-Pyr], [H1787;1-Me-4-CF$_3$-3-Pyr], [H1788;1-Me-4-CHF$_2$-3-Pyr], [H17891-Me-4-OMe-3-Pyr], [H1790;1-Me-4-OCF$_3$-3-Pyr], [H1791;1-Me-4-OCHF$_2$-3-Pyr], [H1792;1-Me-4-OCH$_2$CHF$_2$-3-Pyr], [H1793;1-Me-4-CN-3-Pyr], [H1794;1-Me-4-SMe-3-Pyr], [H1795;1-Me-4-cPr-3-Pyr], [H1796;1-Et-5-Me-3-Pyr], [H1797;1-iPr-5-Me-3-Pyr], [H1798;1-CF$_3$-5-Me-3-Pyr], [H1799;1-CHF$_2$-5-Me-3-Pyr], [H1800;1-CH$_2$CHF$_2$-5-Me-3-Pyr], [H1801;1-CH$_2$CF$_3$-5-Me-3-Pyr], [H1802;1-CH$_2$OCH$_3$-5-Me-3-Pyr], [H1803;1-CH$_2$CH$_2$OMe-5-Me-3-Pyr], [H1804;1-cPr-5-Me-3-Pyr], [H1805;1-CH$_2$C≡CH-5-Me-3-Pyr], [H1806;1-CH$_2$C≡CMe-5-Me-3-Pyr], [H1807;1-CH$_2$CH═CH$_2$-5-Me-3-Pyr], [H1880;1-Me-4-Me-5-Cl-3-Pyr], [H1881;1-Me-4-Cl-5-Cl-3-Pyr], [H1882;1-Me-4-Cl-5-Me-3-Pyr], [H1883;1-Me-4-F-5-Me-3-Pyr], [H1884;1-Me-4-Me-5-F-3-Pyr], [H1885;C(Me)═N—N(Me)$_2$], [H1886;C(Me)═N—N(Et)$_2$], [H1887;C(Et)═N—N(Me)$_2$], [H1888;C≡CPh]

The below-mentioned substituent Nos. J1 to H20 represent substituent G$^3$ in the compound represented by formula (KK) or the compound represented by formula (LL).

<Substituent No.; G$^3$>

It is expressed by

[J1;CH$_2$CH$_2$Ph], [J2;CH$_2$Ph], [J3;CH$_2$CH$_2$CH$_2$Ph], [J4; CH$_2$CH$_2$CH$_2$CH$_2$Ph], [J5;CH$_2$ (2-Cl-Ph)], [J6;CH$_2$(3-Cl-Ph)], [J7;CH$_2$(4-Cl-Ph)], [J8;CH$_2$(2-Me-Ph)], [J9;CH$_2$ (3-Me-Ph)], [J10;CH$_2$(4-Me-Ph)], [J11;Et], [J12; CH$_2$CH$_2$CH$_2$(2-Cl-Ph)], [J13;CH(CH$_3$) Ph], [J14;CH(CH$_3$) Ph], [J154-IND], [J16;Ph], [J17;CH$_2$CH$_2$CH$_2$(3-Cl-Ph)], [J18;CH$_2$CH$_2$CH$_2$(4-Cl-Ph)], [J19;CH$_2$CH$_2$CH$_2$ (2-F-Ph)], [J20;CH$_2$CH═CH-Ph].

The below-mentioned substiutent Nos. K1 to K45 represent substituent G$^4$ in the compound represented by formula (MM).

<Substituent No.; G$^4$>

It is expressed by

[K1;Me], [K2;Et], [K3;iPr], [K4;tBu], [K5;Pr], [K6; CH$_2$CH═CH$_2$], [K7;CH$_2$CH═CHCH$_3$], [K8;CH$_2$CH═C (Me)$_2$], [K9;CH$_2$CH═CHCl], [K10;CH$_2$CH═CCl$_2$], [K11; CH$_2$C≡CH], [K12;CH$_2$C≡CCH$_3$], [K13;CH$_2$(cPr)], [K14; CH$_2$(cBu)], [K15;CH$_2$ (cPent)], [K16;CFH$_2$], [K17;CF$_2$H], [K18;CF$_3$], [K19;CH$_2$CF$_2$H], [K2O;CH$_2$CF$_3$], [K21; CH$_2$CH$_2$OMe], [K22;CH$_2$Ph], [K23;CH$_2$(2-F-Ph)], [K24; CH$_2$(3-F-Ph)], [K25;CH$_2$(4-F-Ph)], [K26;CH$_2$(2-Me-Ph)], [K27;CH$_2$(3-Me-Ph)], [K28;CH$_2$(4-Me-Ph)], [K294-Me-Ph], [K30-3-Me-Ph], [K31-2-Me-Ph], [K3-2-4-Fe-Ph], [K33-3-Fe-Ph], [K34-2-F-Ph], [K354-Cl-Ph], [K363-Cl-Ph], [K372-Cl-Ph], [K384-MeO-Ph], [K393-MeO-Ph], [K40-2-MeO-Ph], [K41;C(O)Me], [K42;cBu], [K43; CF$_2$CF$_3$], [K44;CH$_2$(4-Me-Ph)], [K44;CH$_2$(4-Me-Ph)], [K45;CH$_2$(4-Me-Ph)], [K45;CH(CN)$_2$], [K45;CH$_2$CN].

The substituent Nos. L1 to L7 that are indicated in [Table 4] represent substituent Z$^3$ in the compound represented by formula (MM).

TABLE 4

| Substituent No. | Z$^1$ |
|---|---|
| L1 | Me |
| L2 | Et |
| L3 | CF$_3$ |
| L4 | cPr |
| L5 | OMe |
| L6 | OEt |
| L7 | OCF$_3$ |

The substituent Nos. M1 to M7 that are indicated in [Table 5] represent substituent Z$^4$ in the compound represented by formula (MM).

TABLE 5

| Substituent No. | Z$^1$ |
|---|---|
| M1 | Me |
| M2 | Et |
| M3 | CF$_3$ |
| M4 | cPr |
| M5 | OMe |

TABLE 5-continued

| Substituent No. | $Z^1$ |
|---|---|
| M6 | OEt |
| M7 | $OCF_3$ |

The substituent Nos. Ni to N7 that are indicated in [Table 6] represent substituent $Z^5$ in the compound represented by formula (MM).

TABLE 6

| Substituent No. | $Z^1$ |
|---|---|
| N1 | Me |
| N2 | Et |
| N3 | $CF_3$ |
| N4 | cPr |
| N5 | OMe |
| N6 | OEt |
| N7 | $OCF_3$ |

Present compounds AA-D1-G1~AA-D1-G1943, AA-D2-G1~AA-D2-G1943, AA-D3-G1~AA-D3-G1943, AA-D4-G1~AA-D4-G1943, AA-D5-G1~AA-D5-G1943, AA-D6-G1~AA-D6-G1943, AA-D7-G1~AA-D7-G1943, AA-D8-G1~AA-D8-G1943, AA-D9-G1~AA-D9-G1943, AA-D10-G1~AA-D10-G1943, and AA-D11-G1~AA-D11-G1943 represent the following compounds:

the compounds represented by formula (AA)

[Chem.290]

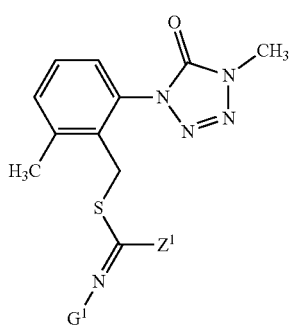

(AA)

wherein the combination of $Z^1$ and $G^1$ represent any combination wherein the $Z^1$ represents a substituent selected from the substituent Nos. D1 to D11, and the $G^1$ represents a substituent selected from the substituent Nos. G1 to G1943.

For example, Present compound AA-D3-G5 represents a compound represented by formula (AA) wherein $Z^1$ represents a substituent No. D3, and $G^1$ represents a substituent No. G5, thereby which represents the following compound.

[Chem.291]

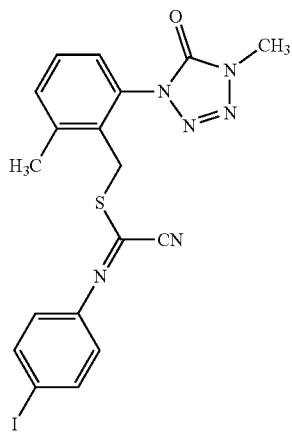

(AA-D3-G5)

Present compounds BB-D1-G1~BB-D1-G1943, BB-D2-G1~BB-D2-G1943, BBD3-G1~BBD3-G1943, BB-D4-G1~BB-D4-G1943, BB-D5-G1~BB-D5-G1943, BB-D6-G1~BB-D6-G1943, BB-D7-G1~BB-D7-G1943, BB-D8-G1~BB-D8-G1943, BB-D9-G1~BB-D9-G1943, BB-D10-G1~BB-D10-G1943, and BB-D11-G1~BB-D11-G1943 represent the following compounds:

the compounds represented by formula (BB)

[Chem.292]

(BB)

wherein the combination of $Z^1$ and $G^1$ represent any combination wherein the $Z^1$ represents a substituent selected from the substituent Nos. D1 to D11, and the $G^1$ represents a substituent selected from the substituent Nos. G1 to G1943.

Present compounds CC-D1-G1~CC-D1-G1943, CC-D2-G1~CC-D2-G1943, CC-D3-G1~CC-D3-G1943, CC-D4-G1~CC-D4-G1943, CC-D5-G1~CC-D5-G1943, CC-D6-G1~CC-D6-G1943, CC-D7-G1~CC-D7-G1943, CC-D8-G1~CC-D8-G1943, CC-D9-G1~CC-D9-G1943, CC-D10-G1~CC-D10-G1943, CC-D11-G1~CC-D11-G1 represent the following compounds:

the compounds represented by formula (CC)

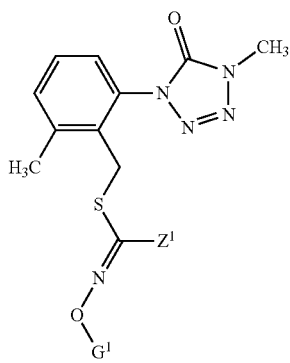

(CC)

wherein the combination of $Z^1$ and $G^1$ represent any combination wherein the $Z^1$ represents a substituent selected from the substituent Nos. D1 to D11, and the $G^1$ represents a substituent selected from the substituent Nos. G1 to G1943.

Present compounds DD-D1-G1~DD-D1-G1943, DD-D2-G1~DD-D2-G1943, DD-D3-G1~DD-D3-G1943, DD-D4-G1~DD-D4-G1943, DD-D5-G1~DD-D5-G1943, DD-D6-G1~DD-D6-G1943, DD-D7-G1~DD-D7-G1943, DD-D8-G1~DD-D8-G1943, DD-D9-G1~DD-D9-G1943, DD-D10-G1~DD-D10-G1943, and DD-D11-G1~DD-D11-G1943 represent the following compounds:

the compounds represented by formula (DD)

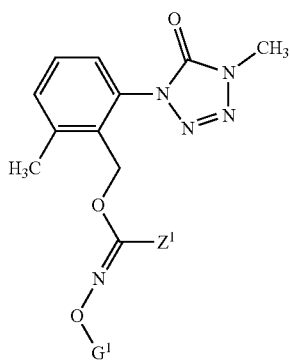

(DD)

wherein the combination of $Z^1$ and $G^1$ represent any combination wherein the $Z^1$ represents a substituent selected from the substituent Nos. D1 to D11, and the $G^1$ represents a substituent selected from the substituent Nos. G1 to G1943.

Present compounds EE-F1-G1~EE-F1-G1943, EE-F2-G1~EE-F2-G1943, EE-F3-G1~EE-F3-G1943, EE-F4-G1~EE-F4-G1943, EE-F5-G1~EE-F5-G1943, EE-F6-G1~EE-F6-G1943, EE-F7-G1~EE-F7-G1943, EE-F8-G1~EE-F8-G1943, EE-F9-G1~EE-F9-G1943, EE-F10-G1~EE-F10-G1943, EE-F11-G1~EE-F11-G1943, EE-F12-G1~EE-F12-G1943, EE-F13-G1~EE-F13-G1943, EE-F14-G1~EE-F14-G1943, EE-F15-G1~EE-F15-G1943, EE-F16-G1~EE-F16-G1943, EE-F17-G1 EE-F17-G1943, EE-F18-G1~EE-F18-G1943, EE-F19-G1~EE-F19-G1943, EE-F20-G1~EE-F20-G1943, and EE-F21-G1~EE-F21-G1943 represent the following compounds:

the compounds represented by formula (EE)

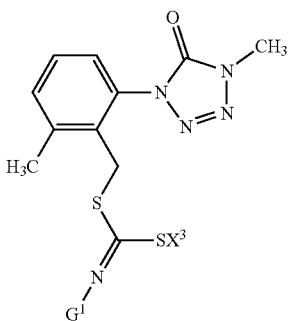

(EE)

wherein the combination of $X^3$ and $G^1$ represent any combination wherein the $X^3$ represents a substituent selected from the substituent Nos. F1 to F21, and the $G^1$ represents a substituent selected from the substituent Nos. G1 to G1943.

Present compounds FF-F1-G1~FF-F1-G1943, FF-F2-G1~FF-F2-G1943, FF-F3-G1~FF-F3-G1943, FF-F4-G1~FF-F4-G1943, FF-F5-G1~FF-F5-G1943, FF-F6-G1~FF-F6-G1943, FF-F7-G1~FF-F7-G1943, FF-F8-G1~FF-F8-G1943, FF-F9-G1~FF-F9-G1943, FF-F10-G1~FF-F10-G1943, FF-F11-G1~FF-F11-G1943, FF-F12-G1~FF-F12-G1943, FF-F13-G1~FF-F13-G1943, FF-F14-G1~FF-F14-G1943, FF-F15-G1~FF-F15-G1943, FF-F16-G1~FF-F16-G1943, FF-F17-G1 FF-F17-G1943, FF-F18-G1~FF-F18-G1943, FF-F19-G1~FF-F19-G1943, FF-F20-G1~FF-F20-G1943, and FF-F21-G1~FF-F21-G1943 represent the following compounds:

the compounds represented by formula (FF)

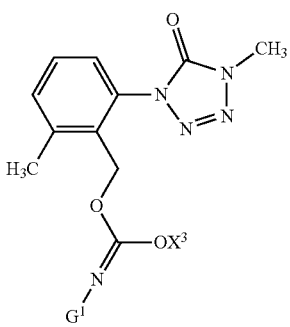

(FF)

wherein the combination of $X^3$ and $G^1$ represent any combination wherein the $X^3$ represents a substituent selected from the substituent Nos. F1 to F21, and the $G^1$ represents a substituent selected from the substituent Nos. G1 to G1943.

Present compounds GG-F1-G1~GG-F1-G1943, GG-F2-G1~GG-F2-G1943, GG-F3-G1~GG-F3-G1943, GG-F4-G1~GG-F4-G1943, GG-F5-G1~GG-F5-G1943, GG-F6-G1~GG-F6-G1943, GG-F7-G1~GG-F7-G1943, GG-F8-G1~GG-F8-G1943, GG-F9-G1~GG-F9-G1943, GG-F10-

G1~GG-F10-G1943, GG-F11-G1~GG-F11-G1943, GG-F12-G1~GG-F12-G1943, GG-F13-G1~GG-F13-G1943, GG-F14-G1~GG-F14-G1943, GG-F15-G1~GG-F15-G1943, GG-F16-G1~GG-F16-G1943, GG-F17-G1~GG-F17-G1943, GG-F18-G1~GG-F18-G1943, GG-F19-G1~GG-F19-G1943, GG-F20-G1~GG-F20-G1943, and GG-F21-G1~GG-F21-G1943 represent the following compounds:

the compounds represented by formula (GG)

[Chem.297]

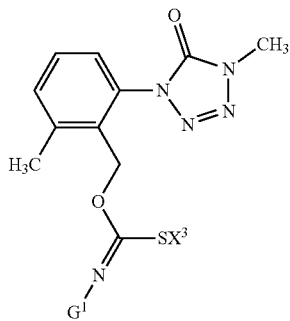

(GG)

wherein the combination of $X^3$ and $G^1$ represent any combination wherein the $X^3$ represents a substituent selected from the substituent Nos. F1 to F21, and the $G^1$ represents a substituent selected from the substituent Nos. G1 to G1943.

Present compounds HH-F1-G1~HH-F1-G1943, HH-F2-G1~HH-F2-G1943, HH-F3-G1~HH-F3-G1943, HH-F4-G1~HH-F4-G1943, HH-F5-G1~HH-F5-G1943, HH-F6-G1~HH-F6-G1943, HH-F7-G1~HH-F7-G1943, HH-F8-G1~HH-F8-G1943, HH-F9-G1~HH-F9-G1943, HH-F10-G1~HH-F10-G1943, HH-F1-G1 HH-F11-G1943, HH-F12-G1~HH-F12-G1943, HH-F13-G1~HH-F13-G1943, HH-F14-G1~HH-F14-G1943, HH-F15-G1~HH-F15-G1943, HH-F16-G1~HH-F16-G1943, HH-F17-G1~HH-F17-G1943, HH-F18-G1~HH-F18-G1943, HH-F19-G1~HH-F19-G1943, HH-F20-G1~HH-F20-G1943, and HH-F21-G1~HH-F21-G1943 represent the following compounds:

the compounds represented by formula (HH

[Chem.298]

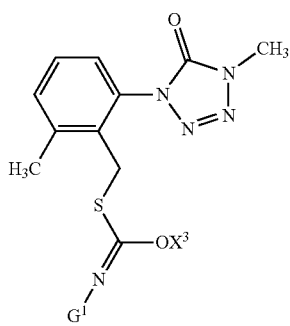

(HH)

wherein the combination of $X^3$ and $G^1$ represent any combination wherein the $X^3$ represents a substituent selected from the substituent Nos. F1 to F21, and the $G^1$ represents a substituent selected from the substituent Nos. G1 to G1943.

Present compounds IID1-E1-H1~IID1-E1-H1888, IID1-E2-H1~IID1-E2-H1888, IID1-E3-H1~IID1-E3-H1888, IID1-E4-H1~IID1-E4-H1888, IID1-E5-H1~IID1-E5-H1888, IID1-E6-H1~IID1-E6-H1888, IID1-E7-H1~IID1-E7-H1888, IID1-E8-H1~IID1-E8-H1888, IID1-E9-H1~IID1-E9-H1888, IID1-E10-H1~IID1-E10-H1888, IID1-E11-H1~IID1-E11-H1888, IID2-E1-H1~IID2-E1-H1888, IID2-E2-H1~IID2-E2-H1888, IID2-E3-H1~IID2-E3-H1888, IID2-E4-H1~IID2-E4-H1888, IID2-E5-H1~IID2-E5-H1888, IID2-E6-H1~IID2-E6-H1888, IID2-E7-H1~IID2-E7-H1888, IID2-E8-H1~IID2-E8-H1888, IID2-E9-H1~IID2-E9-H1888, IID2-E10-H1~IID2-E10-H1888, IID2-E11-H1~IID2-E11-H1888, IID3-E1-H1~IID3-E1-H1888, IID3-E2-H1~IID3-E2-H1888, IID3-E3-H1~IID3-E3-H1888, IID3-E4-H1~IID3-E4-H1888, IID3-E5-H1~IID3-E5-H1888, IID3-E6-H1~IID3-E6-H1888, IID3-E7-H1~IID3-E7-H1888, IID3-E8-H1~IID3-E8-H1888, IID3-E9-H1~IID3-E9-H1888, IID3-E10-H1~IID3-E10-H1888, IID3-E11-H1~IID3-E11-H1888, IID4-E1-H1~IID4-E1-H1888, IID4-E2-H1~IID4-E2-H1888, IID4-E3-H1~IID4-E3-H1888, IID4-E4-H1~IID4-E4-H1888, IID4-E5-H1~IID4-E5-H1888, IID4-E6-H1~IID4-E6-H1888, IID4-E7-H1~IID4-E7-H1888, IID4-E8-H1~IID4-E8-H1888, IID4-E9-H1~IID4-E9-H1888, IID4-E10-H1~IID4-E10-H1888, IID4-E11-H1~IID4-E11-H1888, IID5-E1-H1~IID5-E1-H1888, IID5-E2-H1~IID5-E2-H1888, IID5-E3-H1~IID5-E3-H1888, IID5-E4-H1~IID5-E4-H1888, IID5-E5-H1~IID5-E5-H1888, IID5-E6-H1~IID5-E6-H1888, IID5-E7-H1~IID5-E7-H1888, IID5-E8-H1~II-E8-H1888, IID5-E9-H1~IID5-E9-H1888, IID5-E10-H1~IID5-E10-H1888, IID5-E11-H1 IID5-E11-H1888, IID6-E1-H1~IID6-E1-H1888, IID6-E2-H1~IID6-E2-H1888, IID6-E3-H1~IID6-E3-H1888, IID6-E4-H1~IID6-E4-H1888, IID6-E5-H1 IID6-E5-H1888, IID6-E6-H1~IID6-E6-H1888, IID6-E7-H1~IID6-E7-H1888, IID6-E8-H1~IID6-E8-H1888, IID6-E9-H1~IID6-E9-H1888, IID6-E10-H1 IID6-E10-H1888, IID6-E11-H1~IID6-E11-H1888, IID7-E1-H1~IID7-E1-H1888, IID7-E2-H1~IID7-E2-H1888, IID7-E3-H1~IID7-E3-H1888, IID7-E4-H1 IID7-E4-H1888, IID7-E5-H1~IID7-E5-H1888, IID7-E6-H1~IID7-E6-H1888, IID7-E7-H1~IID7-E7-H1888, IID7-E8-H1~IID7-E8-H1888, IID7-E9-H1 IID7-E9-H1888, IID7-E10-H1~IID7-E10-H1888, IID7-E11-H1~IID7-E11-H1888, IID8-E1-H1~IID8-E1-H1888, IID8-E2-H1~IID8-E2-H1888, IID8-E3-H1 IID8-E3-H1888, IID8-E4-H1~IID8-E4-H1888, IID8-E5-H1~IID8-E5-H1888, IID8-E6-H1~IID8-E6-H1888, IID8-E7-H1~IID8-E7-H1888, IID8-E8-H1 IID8-E8-H1888, IID8-E9-H1~IID8-E9-H1888, IID8-E10-H1~IID8-E10-H1888, IID8-E11-H1~IID8-E11-H1888, IID9-E1-H1~IID9-E1-H1888, IID9-E2-H1 IID9-E2-H1888, IID9-E3-H1~IID9-E3-H1888, IID9-E4-H1~IID9-E4-H1888, IID9-E5-H1~IID9-E5-H1888, IID9-E6-H1~IID9-E6-H1888, IID9-E7-H1 IID9-E7-H1888, IID9-E8-H1~IID9-E8-H1888, IID9-E9-H1~IID9-E9-H1888, IID9-E10-H1~IID9-E10-H1888, IID9-E11-H1~IID9-E11-H1888, IID10-E1-H1 IID10-E1-H1888, IID10-E2-H1~IID10-E2-H1888, IID10-E3-H1~IID10-E3-H1888, IID10-E4-H1~IID10-E4-H1888, IID10-E5-H1~IID10-E5-H1888, IID10-E6-H1 IID10-E6-H1888, IID10-E7-H1~IID10-E7-H1888, IID10-E8-H1~IID10-E8-H1888, IID10-E9-H1~IID10-E9-H1888, IID10-E10-H1~IID10-E10-H1888, IID10-E11-H1 IID10-E11-H1888, IID11-E1-H1~IID11-E1-H1888, IID11-E2-H1 IID11-E2-H1888, IID11-E3-H1~IID11-E3-H1888, IID11-E4-H1~IID11-E4-H1888, IID11-E5-H1~IID11-E5-H1888, IID11-E6-H1~IID11-E6-H1888, IID11-E7-H1 IID11-E7-H1888, IID11-E8-H1~IID11-E8-H1888, IID11-E9-

H1~IID11-E9-H1888, IID11-E10-H1~IID11-E10-H1888, and IID11-E11-H1~IID11-E11-H1888 represent the following compounds:

the compounds represented by formula (II)

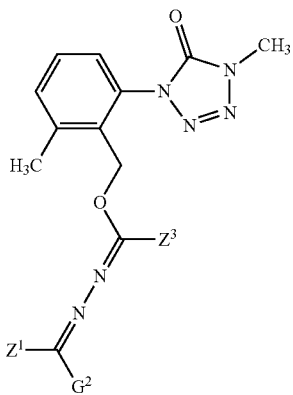

(II)

wherein the combination of $Z^1$, $Z^3$ and $G^2$ represent any combination wherein the $Z^1$ represents a substituent selected from the substituent Nos. D1 to D11, $Z^3$ represents a substituent selected from the substituent Nos. E1 to E11, and the $G^2$ represents a substituent selected from the substituent Nos. H1 to H18888.

Present compounds JJ-D1-E1-H1~JJ-D1-E1-H1888, JJ-D1-E2-H1~JJ-D1-E2-H1888, JJ-D1-E3-H1~JJ-D1-E3-H1888, JJ-D1-E4-H1~JJ-D1-E4-H1888, JJ-D1-E5-H1~JJ-D1-E5-H1888, JJ-D1-E6-H1~JJ-D1-E6-H1888, JJ-D1-E7-H1~JJ-D1-E7-H1888, JJ-D1-E8-H1~JJ-D1-E8-H1888, JJ-D1-E9-H1~JJ-D1-E9-H1888, JJ-D1-E10-H1~JJ-D1-E10-H1888, JJ-D1-E11-H1~JJ-D1-E11-H1888, JJ-D2-E1-H JJ-D2-E1-H1888, JJ-D2-E2-H1~JJ-D2-E2-H1888, JJ-D2-E3-H1~JJ-D2-E3-H1888, JJ-D2-E4-H1~JJ-D2-E4-H1888, JJ-D2-E5-H1~JJ-D2-E5-H1888, JJ-D2-E6-H1~JJ-D2-E6-H1888, JJ-D2-E7-H1~JJ-D2-E7-H1888, JJ-D2-E8-H1~JJ-D2-E8-H1888, JJ-D2-E9-H1~JJ-D2-E9-H1888, JJ-D2-E10-H1~JJ-D2-E10-H1888, JJ-D2-E11-H1~JJ-D2-E11-H1888, JJ-D3-E1-H1~JJ-D3-E1-H1888, JJ-D3-E2-H1~JJ-D3-E2-H1888, JJ-D3-E3-H1~JJ-D3-E3-H1888, JJ-D3-E4-H1~JJ-D3-E4-H1888, JJ-D3-E5-H1~JJ-D3-E5-H1888, JJ-D3-E6-H1~JJ-D3-E6-H1888, JJ-D3-E7-H1~JJ-D3-E7-H1888, JJ-D3-E8-H1~JJ-D3-E8-H1888, JJ-D3-E9-H1~JJ-D3-E9-H1888, JJ-D3-E10-H1~JJ-D3-E10-H1888, JJ-D3-E11-H1~JJ-D3-E11-H1888, JJ-D4-E1-H1~JJ-D4-E1-H1888, JJ-D4-E2-H1~JJ-D4-E2-H1888, JJ-D4-E3-H1~JJ-D4-E3-H1888, JJ-D4-E4-H1~JJ-D4-E4-H1888, JJ-D4-E5-H1~JJ-D4-E5-H1888, JJ-D4-E6-H1~JJ-D4-E6-H1888, JJ-D4-E7-H1~JJ-D4-E7-H1888, JJ-D4-E8-H1~JJ-D4-E8-H1888, JJ-D4-E9-H1~JJ-D4-E9-H1888, JJ-D4-E10-H1~JJ-D4-E10-H1888, JJ-D4-E11-H1~JJ-D4-E11-H1888, JJ-D5-E1-H1~JJ-D5-E1-H1888, JJ-D5-E2-H1~JJ-D5-E2-H1888, JJ-D5-E3-H1~JJ-D5-E3-H1888, JJ-D5-E4-H1~JJ-D5-E4-H1888, JJ-D5-E5-H1~JJ-D5-E5-H1888, JJ-D5-E6-H1~JJ-D5-E6-H1888, JJ-D5-E7-H1~JJ-D5-E7-H1888, JJ-D5-E8-H1~JJ-D5-E8-H1888, JJ-D5-E9-H1~JJ-D5-E9-H1888, JJ-D5-E10-H1~JJ-D5-E10-H1888, JJ-D5-E11-H1~JJ-D5-E11-H1888, JJ-D6-E1-H1~JJ-D6-E1-H1888, JJ-D6-E2-H1~JJ-D6-E2-H1888, JJ-D6-E3-H1~JJ-D6-E3-H1888, JJ-D6-E4-H1~JJ-D6-E4-H1888, JJ-D6-E5-H1~JJ-D6-E5-H1888, JJ-D6-E6-H1~JJ-D6-E6-H1888, JJ-D6-E7-H1~JJ-D6-E7-H1888, JJ-D6-E8-H1~JJ-D6-E8-H1888, JJ-D6-E9-H1~JJ-D6-E9-H1888, JJ-D6-E10-H1~JJ-D6-E10-H1888, JJ-D6-E11-H1~JJ-D6-E11-H1888, JJ-D7-E1-H1~JJ-D7-E1-H1888, JJ-D7-E2-H1~JJ-D7-E2-H1888, JJ-D7-E3-H1~JJ-D7-E3-H1888, JJ-D7-E4-H1~JJ-D7-E4-H1888, JJ-D7-E5-H1~JJ-D7-E5-H1888, JJ-D7-E6-H1~JJ-D7-E6-H1888, JJ-D7-E7-H1~JJ-D7-E7-H1888, JJ-D7-E8-H1~JJ-D7-E8-H1888, JJ-D7-E9-H1~JJ-D7-E9-H1888, JJ-D7-E10-H1~JJ-D7-E10-H1888, JJ-D7-E11-H1~JJ-D7-E11-H1888, JJ-D8-E1-H1~JJ-D8-E1-H1888, JJ-D8-E2-H1~JJ-D8-E2-H1888, JJ-D8-E3-H1~JJ-D8-E3-H1888, JJ-D8-E4-H1~JJ-D8-E4-H1888, JJ-D8-E5-H1~JJ-D8-E5-H1888, JJ-D8-E6-H1~JJ-D8-E6-H1888, JJ-D8-E7-H1~JJ-D8-E7-H1888, JJ-D8-E8-H1~JJ-D8-E8-H1888, JJ-D8-E9-H1~JJ-D8-E9-H1888, JJ-D8-E10-H1~JJ-D8-E10-H1888, JJ-D8-E11-H1~JJ-D8-E11-H1888, JJ-D9-E1-H1~JJ-D9-E1-H1888, JJ-D9-E2-H1~JJ-D9-E2-H1888, JJ-D9-E3-H1~JJ-D9-E3-H1888, JJ-D9-E4-H1~JJ-D9-E4-H1888, JJ-D9-E5-H1~JJ-D9-E5-H1888, JJ-D9-E6-H1~JJ-D9-E6-H1888, JJ-D9-E7-H1~JJ-D9-E7-H1888, JJ-D9-E8-H1~JJ-D9-E8-H1888, JJ-D9-E9-H1~JJ-D9-E9-H1888, JJ-D9-E10-H1~JJ-D9-E10-H1888, JJ-D9-E11-H1~JJ-D9-E11-H1888, JJ-D10-E1-H1~JJ-D10-E1-H1888, JJ-D10-E2-H1~JJ-D10-E2-H1888, JJ-D10-E3-H1~JJ-D10-E3-H1888, JJ-D10-E4-H1~JJ-D10-E4-H1888, JJ-D10-E5-H1~JJ-D10-E5-H1888, JJ-D10-E6-H1~JJ-D10-E6-H1888, JJ-D10-E7-H1~JJ-D10-E7-H1888, JJ-D10-E8-H1~JJ-D10-E8-H1888, JJ-D10-E9-H1~JJ-D10-E9-H1888, JJ-D10-E10-H1~JJ-D10-E10-H1888, JJ-D10-E11-H1~JJ-D10-E11-H1888, JJ-D11-E1-H1~JJ-D11-E1-H1888, JJ-D11-E2-H1~JJ-D11-E2-H1888, JJ-D11-E3-H1~JJ-D11-E3-H1888, JJ-D11-E4-H1~JJ-D11-E4-H1888, JJ-D11-E5-H1~JJ-D11-E5-H1888, JJ-D11-E6-H1~JJ-D11-E6-H1888, JJ-D11-E7-H1~JJ-D11-E7-H1888, JJ-D11-E8-H1~JJ-D11-E8-H1888, JJ-D11-E9-H1~JJ-D11-E9-H1888, JJ-D11-E10-H1~JJ-D11-E10-H1888, and JJ-D11-E11-H1~JJ-D11-E11-H1888 represent the following compounds:

the compounds represented by formula (JJ)

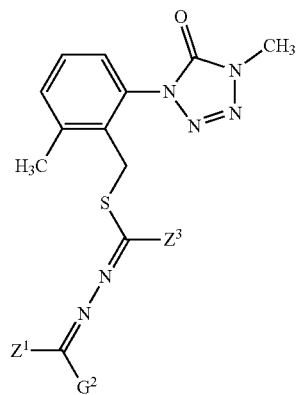

(JJ)

wherein the combination of $Z^1$, $Z^3$ and $G^2$ represent any combination wherein the $Z^1$ represents a substituent selected from the substituent Nos. D1 to D11, $Z^3$ represents a substituent selected from the substituent Nos. E1 to E11, and the $G^2$ represents a substituent selected from the substituent Nos. H1 to H18888.

Present compounds KK-D1-J1~KK-D1-J20, KK-D2-J1~KK-D2-J20, KK-D3-J1~KK-D31-J20, KK-D4-J1~KK- D4-J20, KK-D5-J1~KK-D5-J20, KK-D6-J1~KK-D6-J20, KK-D7-J1~KK-D7-J20, KK-D8-J1~KK-D8-J20, KK-D9-J1~KK-D9-J20, KK-D10-J1~KK-D10-J20, and KK-D11-J1~KK-D11 1-J20 represent the following compounds:

the compounds represented by formula (KK)

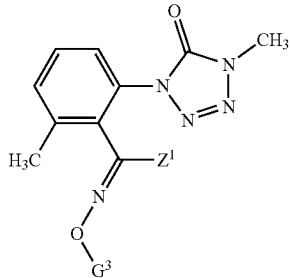

(KK)

wherein the combination of $Z^1$ and $G^3$ represent any combination wherein the $Z^1$ represents a substituent selected from the substituent Nos. D1 to D11, the $G^3$ represents a substituent selected from the substituent Nos. J1 to J20.

Present compounds LL-D1-J1~LL-D1-J20, LL-D2-J1~LL-D2-J20, LL-D3-J1~LL-D3-J20, LL-D4-J1~LL-D4-J20, LL-D5-J1~LL-D5-J20, LL-D6-J1~LL-D6-J20, LL-D7-J1~LL-D7-J20, LL-D8-J1~LL-D8-J20, LL-D9-J1~LL-D9-J20, LL-D10-J1 LL-D10-J20, and LL-D11-J1~LL-D11-J20 represent the following compounds:

the compounds represented by formula (LL)

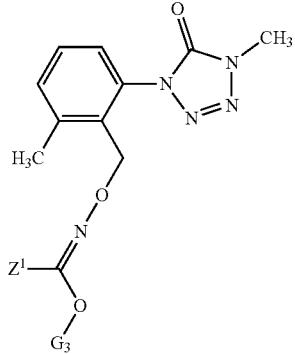

(LL)

wherein the combination of $Z^1$ and $G^3$ represent any combination wherein the $Z^1$ represents a substituent selected from the substituent Nos. D1 to D11, the $G^3$ represents a substituent selected from the substituent Nos. J1 to J20.

Present compounds MM-L1-M1-N1-K1~MM-L1-M1-N1-K45, MM-L2-M1-N1-K1~MM-L2-M1-N1-K45, MM-L3-M1-N1-K1~MM-L3-M1-N1-K45, MM-L4-M1-N1-K1~MM-L4-M1-N1-K45, MM-L5-M1-N1-K1~MM-L5-M1-N1-K45, MM-L6-M1-N1-K1~MM-L6-M1-N1-K45, MM-L7-M1-N1-K1~MM-L7-M1-N1-K45, MM-L1-M2-N1-K1~MM-L1-M2-N1-K45, MM-L2-M1-N1-K1~MM-L2-M1-N1-K45, MM-L3-M21-N1-K1~MM-L3-M2-N1-K45, MM-L4-M2-N1-K1~MM-L4-M2-N1-K45, MM-L5-M2-N1-K1~MM-L5-M2-N1-K45, MM-L6-M2-N1-K1~MM-L6-M2-N1-K45, MM-L7-M2-N1-K1~MM-L7-M2-N1-K45, MM-L1-M3-N1-K1~MM-L1-M3-N1-K45, MM-L2-M3-N1-K1~MM-L2-M3-N1-K45, MM-L3-M3-N1-K1~MM-L3-M3-N1-K45, MM-L4-M3-N1-K1~MM-L4-M3-N1-K45, MM-L5-M3-N1-K1~MM-L5-M3-N1-K45, MM-L6-M3-N1-K1~MM-L6-M3-N1-K45, MM-L7-M3-N1-K1~MM-L7-M3-N1-K45, MM-L1-M4-N1-K1~MM-L1-M4-N1-K45, MM-L2-M4-N1-K1~MM-L2-M4-N1-K45, MM-L3-M4-N1-K1~MM-L3-M4-N1-K45, MM-L4-M4-N1-K1~MM-L4-M4-N1-K45, MM-L5-M4-N1-K1~MM-L5-M4-N1-K45, MM-L6-M4-N1-K1~MM-L6-M4-N1-K45, MM-L7-M4-N1-K1~MM-L7-M4-N1-K45, MM-L1-M5-N1-K1~MM-L1-M5-N1-K45, MM-L2-M5-N1-K1~MM-L2-M5-N1-K45, MM-L3-M5-N1-K1~MM-L3-M5-N1-K45, MM-L4-M5-N1-K1~MM-L4-M5-N1-K45, MM-L5-M5-N1-K1~MM-L5-M5-N1-K45, MM-L6-M5-N1-K1~MM-L6-M5-N1-K45, MM-L7-M5-N1-K1~MM-L5-M5-N1-K45, MM-L1-M6-N1-K1~MM-L1-M6-N1-K45, MM-L2-M6-N1-K1~MM-L2-M6-N1-K45, MM-L3-M6-N1-K1~MM-L3-M6-N1-K45, MM-L4-M6-N1-K1~MM-L4-M6-N1-K45, MM-L5-M6-N1-K1~MM-L5-M6-N1-K45, MM-L6-M6-N1-K1~MM-L6-M6-N1-K45, MM-L7-M6-N1-K1~MM-L7-M6-N1-K45, MM-L1-M7-N1-K1~MM-L1-M7-N1-K45, MM-L2-M7-N1-K1~MM-L2-M7-N1-K45, MM-L3-M7-N1-K1~MM-L3-M7-N1-K45, MM-L4-M7-N1-K1~MM-L4-M7-N1-K45, MM-L5-M7-N1-K1~MM-L5-M7-N1-K45, MM-L6-M7-N1-K1~MM-L6-M7-N1-K45, MM-L7-M7-N1-K1~MM-L7-M7-N1-K45, MM-L1-M1-N2-K1~MM-L1-M1-N2-K45, MM-L2-M1-N2-K1~MM-L2-M1-N2-K45, MM-L3-M1-N2-K1~MM-L3-M1-N2-K45, MM-L4-M1-N2-K1~MM-L4-M1-N2-K45, MM-L5-M1-N2-K1~MM-L5-M1-N2-K45, MM-L6-M1-N2-K1~MM-L6-M1-N2-K45, MM-L7-M1-N2-K1~MM-L7-M1-N2-K45, MM-L1-M2-N2-K1~MM-L1-M2-N2-K45, MM-L2-M2-N2-K1~MM-L2-M2-N2-K45, MM-L3-M2-N2-K1~MM-L3-M2-N2-K45, MM-L4-M2-N2-K1~MM-L4-M2-N2-K45, MM-L5-M2-N2-K1~MM-L5-M2-N2-K45, MM-L6-M2-N2-K1~MM-L6-M2-N2-K45, MM-L7-M2-N2-K1~MM-L7-M2-N2-K45, MM-L1-M3-N2-K1~MM-L1-M3-N2-K45, MM-L2-M3-N2-K1~MM-L2-M3-N2-K45, MM-L3-M3-N2-K1~MM-L3-M3-N2-K45, MM-L4-M3-N2-K1~MM-L4-M3-N2-K45, MM-L5-M3-N2-K1~MM-L5-M3-N2-K45, MM-L6-M3-N2-K1~MM-L6-M3-N2-K45, MM-L7-M3-N2-K1~MM-L7-M3-N2-K45, MM-L1-M4-N2-K1~MM-L1-M4-N2-K45, MM-L2-M4-N2-K1~MM-L2-M4-N2-K45, MM-L3-M4-N2-K1~MM-L3-M4-N2-K45, MM-L4-M4-N2-K1~MM-L4-M4-N2-K45, MM-L5-M4-N2-K1~MM-L5-M4-N2-K45, MM-L6-M4-N2-K1~MM-L6-M4-N2-K45, MM-L7-M4-N2-K1~MM-L7-M4-N2-K45, MM-L1-M5-N2-K1~MM-L1-M5-N2-K45, MM-L2-M5-N2-K1~MM-L2-M5-N2-K45, MM-L3-M5-N2-K1~MM-L3-M5-N2-K45, MM-L4-M5-N2-K1~MM-L4-M5-N2-K45, MM-L5-M5-N2-K1~MM-L5-M5-N2-K45, MM-L6-M5-N2-K1~MM-L6-M5-N2-K45, MM-L7-M5-N2-K1~MM-L7-M5-N2-K45, MM-L1-M6-N2-K1~MM-L1-M6-N2-K45, MM-L2-M6-N2-K1~MM-L2-M6-N2-K45, MM-L3-M6-N2-K1~MM-L3-M6-N2-K45, MM-L4-M6-N2-K1~MM-L4-M6-N2-K45, MM-L5-M6-N2-K1~MM-L5-M6-N2-K45, MM-L6-M6-N2-K1~MM-L6-M6-N2-K45, MM-L7-M6-N2-K1~MM-L7-M6-N2-K45, MM-L1-M7-N2-K1~MM-L1-M7-N2-K45, MM-L2-M7-N2-K1~MM-L2-M7-N2-K45, MM-L3-M7-N2-K1~MM-L3-M7-N2-K45, MM-L4-M7-N2-K1~MM-L4-M7-N2-K45, MM-L5-M7-N2-K1~MM-L5-M7-N2-K45, MM-L6-M7-N2-K1~MM-L6-M7-N2-K45, MM-L7-M7-N2-K1~MM-L7-M7-N2-K45, MM-L1-M1-N3-K1~MM-L1-M1-N3-K45, MM-L2-M1-N3-K1~MM-L2-

M1-N3-K45, MM-L3-M1-N3-K1~MM-L3-M1-N3-K45, MM-L4-M1-N3-K1~MM-L4-M1-N3-K45, MM-L5-M1-N3-K1~MM-L5-M1-N3-K45, MM-L6-M1-N3-K1~MM-L6-M1-N3-K1~MM-L6-M1-N3-K45, MM-L7-M1-N3-K1~MM-L7-M1-N3-K45, MM-L1-M2-N3-K1~MM-L1-M2-N3-K45, MM-L2-M2-N3-K1~MM-L2-M2-N3-K45, MM-L3-M2-N3-K1~MM-L3-M2-N3-K45, MM-L4-M2-N3-K1~MM-L4-M2-N3-K45, MM-L5-M2-N3-K1~MM-L5-M2-N3-K45, MM-L6-M2-N3-K1~MM-L6-M2-N3-K45, MM-L7-M2-N3-K1~MM-L7-M2-N3-K45, MM-L1-M3-N3-K1~MM-L1-M3-N3-K45, MM-L2-M3-N3-K1~MM-L2-M3-N3-K45, MM-L3-M3-N3-K1~MM-L3-M3-N3-K45, MM-L4-M3-N3-K1~MM-L4-M3-N3-K45, MM-L5-M3-N3-K1~MM-L5-M3-N3-K45, MM-L6-M3-N3-K1~MM-L6-M3-N3-K45, MM-L7-M3-N3-K1~MM-L7-M3-N3-K45, MM-L1-M4-N3-K1~MM-L1-M4-N3-K45, MM-L2-M4-N3-K1~MM-L2-M4-N3-K45, MM-L3-M4-N3-K1~MM-L3-M4-N3-K45, MM-L4-M4-N3-K1~MM-L4-M4-N3-K45,

MM-L5-M4-N3-K1~MM-L5-M4-N3-K45, MM-L6-M4-N3-K1~MM-L6-M4-N3-K45, MM-L7-M4-N3-K1~MM-L7-M4-N3-K45, MM-L1-M5-N3-K1~MM-L1-M5-N3-K45, MM-L2-M5-N3-K1~MM-L2-M5-N3-K45, MM-L3-M5-N3-K1~MM-L3-M5-N3-K45, MM-L4-M5-N3-K1~MM-L4-M5-N3-K45, MM-L5-M5-N3-K1~MM-L5-M5-N3-K45, MM-L6-M5-N3-K1~MM-L6-M5-N3-K45, MM-L7-M5-N3-K1~MM-L7-M5-N3-K45, MM-L1-M6-N3-K1~MM-L1-M6-N3-K45, MM-L2-M6-N3-K1~MM-L2-M6-N3-K45, MM-L3-M6-N3-K1~MM-L3-M6-N3-K45, MM-L4-M6-N3-K1~MM-L4-M6-N3-K45, MM-L5-M6-N3-K1~MM-L5-M6-N3-K45, MM-L6-M6-N3-K1~MM-L6-M6-N3-K45, MM-L7-M6-N3-K1~MM-L7-M6-N3-K45, MM-L1-M7-N3-K1~MM-L1-M7-N3-K45, MM-L2-M7-N3-K1~MM-L2-M7-N3-K45, MM-L3-M7-N3-K1~MM-L3-M7-N3-K45, MM-L4-M7-N3-K1~MM-L4-M7-N3-K45, MM-L5-M7-N3-K1~MM-L5-M7-N3-K45, MM-L6-M7-N3-K1~MM-L6-M7-N3-K45, MM-L7-M7-N3-K1~MM-L7-M7-N3-K45, MM-L1-M1-N4-K1~MM-L1-M1-N4-K45, MM-L2-M1-N4-K1~MM-L2-M1-N4-K45, MM-L3-M1-N4-K1~MM-L3-M1-N4-K45, MM-L4-M1-N4-K1~MM-L4-M1-N4-K45, MM-L5-M1-N4-K1~MM-L5-M1-N4-K45, MM-L6-M1-N4-K1~MM-L6-M1-N4-K45, MM-L7-M1-N4-K1~MM-L7-M1-N4-K45, MM-L1-M2-N4-K1~MM-L1-M2-N4-K45, MM-L2-M2-N4-K1~MM-L2-M2-N4-K45, MM-L3-M2-N4-K1~MM-L3-M2-N4-K45, MM-L4-M2-N4-K1~MM-L4-M2-N4-K45, MM-L5-M2-N4-K1~MM-L5-M2-N4-K45, MM-L6-M2-N4-K1~MM-L6-M2-N4-K45, MM-L7-M2-N4-K1~MM-L7-M2-N4-K45, MM-L1-M3-N4-K1~MM-L1-M3-N4-K45, MM-L2-M3-N4-K1~MM-L2-M3-N4-K45, MM-L3-M3-N4-K1~MM-L3-M3-N4-K45, MM-L4-M3-N4-K1~MM-L4-M3-N4-K45, MM-L5-M3-N4-K1~MM-L5-M3-N4-K45, MM-L6-M3-N4-K1~MM-L6-M3-N4-K45, MM-L7-M3-N4-K1~MM-L7-M3-N4-K45, MM-L1-M4-N4-K1~MM-L1-M4-N4-K45, MM-L2-M4-N4-K1~MM-L2-M4-N4-K45, MM-L3-M4-N4-K1~MM-L3-M4-N4-K45, MM-L4-M4-N4-K1~MM-L4-M4-N4-K45, MM-L5-M4-N4-K1~MM-L5-M4-N4-K45, MM-L6-M4-N4-K1~MM-L6-M4-N4-K45, MM-L7-M4-N4-K1~MM-L7-M4-N4-K45, MM-L1-M5-N4-K1~MM-L1-M5-N4-K45, MM-L2-M5-N4-K1~MM-L2-M5-N4-K45, MM-L3-M5-N4-K1~MM-L3-M5-N4-K45, MM-L4-M5-N4-K1~MM-L4-M5-N4-K45, MM-L5-M5-N4-K1~MM-L5-M5-N4-K45, MM-L6-M5-N4-K1~MM-L6-M5-N4-K45,

MM-L7-M5-N4-K1~MM-L7-M5-N4-K45, MM-L1-M6-N4-K1~MM-L1-M6-N4-K45, MM-L2-M6-N4-K1~MM-L2-M6-N4-K45, MM-L3-M6-N4-K1~MM-L3-M6-N4-K45, MM-L4-M6-N4-K1~MM-L4-M6-N4-K45, MM-L5-M6-N4-K1~MM-L5-M6-N4-K45, MM-L6-M6-N4-K1~MM-L6-M6-N4-K45, MM-L7-M6-N4-K1~MM-L7-M6-N4-K45, MM-L1-M7-N4-K1~MM-L1-M7-N4-K45, MM-L2-M7-N4-K1~MM-L2-M7-N4-K45, MM-L3-M7-N4-K1~MM-L3-M7-N4-K45, MM-L4-M7-N4-K1~MM-L4-M7-N4-K45, MM-L5-M7-N4-K1~MM-L5-M7-N4-K45, MM-L6-M7-N4-K1~MM-L6-M7-N4-K45, MM-L7-M7-N4-K1~MM-L7-M7-N4-K45, MM-L1-M1-N5-K1~MM-L1-M1-N5-K45, MM-L2-M1-N5-K1~MM-L2-M1-N5-K45, MM-L3-M1-N5-K1~MM-L3-M1-N5-K45, MM-L4-M1-N5-K1~MM-L4-M1-N5-K45, MM-L5-M1-N5-K1~MM-L5-M1-N5-K45, MM-L6-M1-N5-K1~MM-L6-M1-N5-K45, MM-L7-M1-N5-K1~MM-L7-M1-N5-K45, MM-L1-M2-N5-K1~MM-L1-M2-N5-K45, MM-L2-M2-N5-K1~MM-L2-M2-N5-K45, MM-L3-M2-N5-K1~MM-L3-M2-N5-K45, MM-L4-M2-N5-K1~MM-L4-M2-N5-K45, MM-L5-M2-N5-K1~MM-L5-M2-N5-K45, MM-L6-M2-N5-K1~MM-L6-M2-N5-K45, MM-L7-M2-N5-K1~MM-L7-M2-N5-K45, MM-L1-M3-N5-K1~MM-L1-M3-N5-K45, MM-L2-M3-N5-K1~MM-L2-M3-N5-K45, MM-L3-M3-N5-K1~MM-L3-M3-N5-K45, MM-L4-M3-N5-K1~MM-L4-M3-N5-K45, MM-L5-M3-N5-K1~MM-L5-M3-N5-K45, MM-L6-M3-N5-K1~MM-L6-M3-N5-K45, MM-L7-M3-N5-K1~MM-L7-M3-N5-K45, MM-L1-M4-N5-K1~MM-L1-M4-N5-K45, MM-L2-M4-N5-K1~MM-L2-M4-N5-K45, MM-L3-M4-N5-K1~MM-L3-M4-N5-K45, MM-L4-M4-N5-K1~MM-L4-M4-N5-K45, MM-L5-M4-N5-K1~MM-L5-M4-N5-K45, MM-L6-M4-N5-K1~MM-L6-M4-N5-K45, MM-L7-M4-N5-K1~MM-L7-M4-N5-K45, MM-L1-M5-N5-K1~MM-L1-M5-N5-K45, MM-L2-M5-N5-K1~MM-L2-M5-N5-K45, MM-L3-M5-N5-K1~MM-L3-M5-N5-K45, MM-L4-M5-N5-K1~MM-L4-M5-N5-K45, MM-L5-M5-N5-K1~MM-L5-M5-N5-K45, MM-L6-M5-N5-K1~MM-L6-M5-N5-K45, MM-L7-M5-N5-K1~MM-L7-M5-N5-K45, MM-L1-M6-N5-K1~MM-L1-M6-N5-K45, MM-L2-M6-N5-K1~MM-L2-M6-N5-K45, MM-L3-M6-N5-K1~MM-L3-M6-N5-K45, MM-L4-M6-N5-K1~MM-L4-M6-N5-K45, MM-L5-M6-N5-K1~MM-L5-M6-N5-K45, MM-L6-M6-N5-K1~MM-L6-M6-N5-K45, MM-L7-M6-N5-K1~MM-L7-M6-N5-K45, MM-L1-M7-N5-K1~MM-L1-M7-N5-K45,

MM-L2-M7-N5-K1~MM-L2-M7-N5-K45, MM-L3-M7-N5-K1~MM-L3-M7-N5-K45, MM-L4-M7-N5-K1~MM-L4-M7-N5-K45, MM-L5-M7-N5-K1~MM-L5-M7-N5-K45, MM-L6-M7-N5-K1~MM-L6-M7-N5-K45, MM-L7-M7-N5-K1~MM-L7-M7-N5-K45, MM-L1-M1-N6-K1~MM-L1-M1-N6-K45, MM-L2-M1-N6-K1~MM-L2-M1-N6-K45, MM-L3-M1-N6-K1~MM-L3-M1-N6-K45, MM-L4-M1-N6-K1~MM-L4-M1-N6-K45, MM-L5-M1-N6-K1~MM-L5-M1-N6-K45, MM-L6-M1-N6-K1~MM-L6-M1-N6-K45, MM-L7-M1-N6-K1~MM-L7-M1-N6-K45, MM-L1-M2-N6-K1~MM-L1-M2-N6-K45, MM-L2-M2-N6-K1~MM-L2-M2-N6-K45, MM-L3-M2-N6-K1~MM-L3-M2-N6-K45, MM-L4-M2-N6-K1~MM-L4-M2-N6-K45, MM-L5-M2-N6-K1~MM-L5-M2-N6-K45, MM-L6-M2-N6-K1~MM-L6-M2-N6-K45, MM-L7-M2-N6-K1~MM-L7-M2-N6-K45, MM-L1-M3-N6-K1~MM-L1-M3-N6-K45, MM-L2-M3-N6-K1~MM-L2-M3-N6-K45, MM-L3-M3-N6-K1~MM-L3-M3-N6-K45, MM-L4-M3-N6-K1~MM-L4-M3-N6-K45, MM-L5-M3-N6-K1~MM-L5-M3-N6-K45, MM-L6-M3-N6-K1~MM-L6-M3-N6-K45, MM-L7-M3-N6-K1~MM-L7-M3-N6-K45, MM-L1-M4-N6-K1~MM-L1-M4-N6-K45, MM-L2-M4-N6-K1~MM-L2-M4-N6-K45, MM-L3-M4-N6-K1~MM-

L3-M4-N6-K45, MM-L4-M4-N6-K1~MM-L4-M4-N6-K45, MM-L5-M4-N6-K1~MM-L5-M4-N6-K45, MM-L6-M4-N6-K1~MM-L6-M4-N6-K45, MM-L7-M4-N6-K1~MM-L7-M4-N6-K45, MM-L1-M5-N6-K1~MM-L1-M5-N6-K45, MM-L2-M5-N6-K1~MM-L2-M5-N6-K45, MM-L3-M5-N6-K1~MM-L3-M5-N6-K45, MM-L4-M5-N6-K1~MM-L4-M5-N6-K45, MM-L5-M5-N6-K1~MM-L5-M5-N6-K45, MM-L6-M5-N6-K1~MM-L6-M5-N6-K45, MM-L7-M5-N6-K1~MM-L7-M5-N6-K45, MM-L1-M6-N6-K1~MM-L1-M6-N6-K45, MM-L2-M6-N6-K1~MM-L2-M6-N6-K45, MM-L3-M6-N6-K1~MM-L3-M6-N6-K45, MM-L4-M6-N6-K1~MM-L4-M6-N6-K45, MM-L5-M6-N6-K1~MM-L5-M6-N6-K45, MM-L6-M6-N6-K1~MM-L6-M6-N6-K45, MM-L7-M6-N6-K1~MM-L7-M6-N6-K45, MM-L1-M7-N6-K1~MM-L1-M7-N6-K45, MM-L2-M7-N6-K1~MM-L2-M7-N6-K45, MM-L3-M7-N6-K1~MM-L3-M7-N6-K45, MM-L4-M7-N6-K1~MM-L4-M7-N6-K45, MM-L5-M7-N6-K1~MM-L5-M7-N6-K45, MM-L6-M7-N6-K1~MM-L6-M7-N6-K45, MM-L7-M7-N6-K1~MM-L7-M7-N6-K45, MM-L1-M1-N7-K1~MM-L1-M1-N7-K45, MM-L2-M1-N7-K1~MM-L2-M1-N7-K45, MM-L3-M1-N7-K1~MM-L3-M1-N7-K45, MM-L4-M1-N7-K1~MM-L4-M1-N7-K45, MM-L5-M1-N7-K1~MM-L5-M1-N7-K45, MM-L6-M1-N7-K1~MM-L6-M1-N7-K45, MM-L7-M1-N7-K1~MM-L7-M1-N7-K45, MM-L1-M2-N7-K1~MM-L1-M2-N7-K45, MM-L2-M2-N7-K1~MM-L2-M2-N7-K45, MM-L3-M2-N7-K1~MM-L3-M2-N7-K45, MM-L4-M2-N7-K1~MM-L4-M2-N7-K45, MM-L5-M2-N7-K1~MM-L5-M2-N7-K45,

MM-L6-M2-N7-K1~MM-L6-M2-N7-K45, MM-L7-M2-N7-K1~MM-L7-M2-N7-K45, MM-L1-M3-N7-K1~MM-L1-M3-N7-K45, MM-L2-M3-N7-K1~MM-L2-M3-N7-K45, MM-L3-M3-N7-K1~MM-L3-M3-N7-K45, MM-L4-M3-N7-K1~MM-L4-M3-N7-K45, MM-L5-M3-N7-K1~MM-L5-M3-N7-K45, MM-L6-M3-N7-K1~MM-L6-M3-N7-K45, MM-L7-M3-N7-K1~MM-L7-M3-N7-K45, MM-L1-M4-N7-K1~MM-L1-M4-N7-K45, MM-L2-M4-N7-K1~MM-L2-M4-N7-K45, MM-L3-M4-N7-K1~MM-L3-M4-N7-K45, MM-L4-M4-N7-K1~MM-L4-M4-N7-K45, MM-L5-M4-N7-K1~MM-L5-M4-N7-K45, MM-L6-M4-N7-K1~MM-L6-M4-N7-K45, MM-L7-M4-N7-K1~MM-L7-M4-N7-K45, MM-L1-M5-N7-K1~MM-L1-M5-N7-K45, MM-L2-M5-N7-K1~MM-L2-M5-N7-K45, MM-L3-M5-N7-K1~MM-L3-M5-N7-K45, MM-L4-M5-N7-K1~MM-L4-M5-N7-K45, MM-L5-M5-N7-K1~MM-L5-M5-N7-K45, MM-L6-M5-N7-K1~MM-L6-M5-N7-K45, MM-L7-M5-N7-K1~MM-L7-M5-N7-K45, MM-L1-M6-N7-K1~MM-L1-M6-N7-K45, MM-L2-M6-N7-K1~MM-L2-M6-N7-K45, MM-L3-M6-N7-K1~MM-L3-M6-N7-K45, MM-L4-M6-N7-K1~MM-L4-M6-N7-K45, MM-L5-M6-N7-K1~MM-L5-M6-N7-K45, MM-L6-M6-N7-K1~MM-L6-M6-N7-K45, MM-L7-M6-N7-K1~MM-L7-M6-N7-K45, MM-L1-M7-N7-K1~MM-L1-M7-N7-K45, MM-L2-M7-N7-K1~MM-L2-M7-N7-K45, MM-L3-M7-N7-K1~MM-L3-M7-N7-K45, MM-L4-M7-N7-K1~MM-L4-M7-N7-K45, MM-L5-M7-N7-K1~MM-L5-M7-N7-K45, MM-L6-M7-N7-K1~MM-L6-M7-N7-K45, and MM-L7-M7-N7-K1~MM-L7-M7-N7-K45 represent the following compounds:

the compounds represented by formula (MM)

[Chem.303]

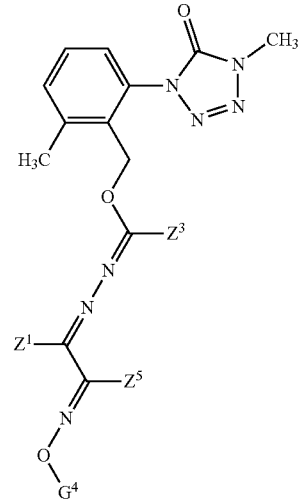

(MM)

wherein the combination of $Z^3$, $Z^4$, $Z^5$ and $G^4$ represent any combination wherein the $Z^3$ represents a substituent selected from the substituent Nos. L1 to L7, the $Z^4$ represents a substituent selected from the substituent Nos. M1 to M7, the $Z^5$ represents a substituent selected from the substituent Nos. N1 to N7, and the $G^4$ represents a substituent selected from the substituent Nos. K1 to K45.

The substituent Nos. ID1~ID9, IZ1~IZ4, BZI1~BZI4, BO1~BO3, QU1, QX1, BD1~BD4, OP1~OP4, XP1~XP4, TI1~TI5, TI5~CP4, YP1~YP6, and IP1~IP4 represent the following structures (wherein, # represents a binding site).

[Chem.304]

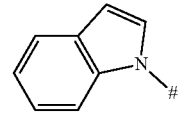

(ID1)

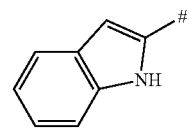

(ID2)

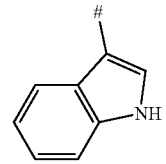

(ID3)

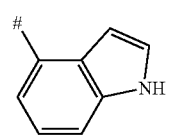

(ID4)

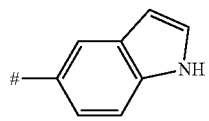 (ID5)
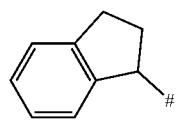 (ID6)
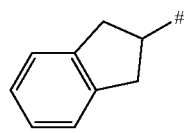 (ID7)
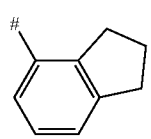 (ID8)
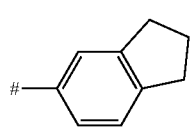 (ID9)
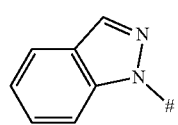 (IZ1)
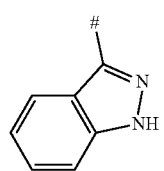 (IZ2)
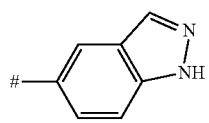 (IZ3)
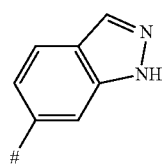 (IZ4)
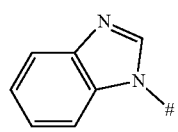 (BI1)
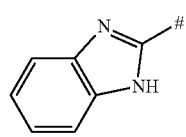 (BZI2)
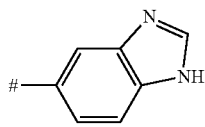 (BZI3)
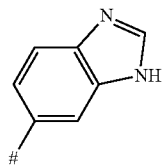 (BZI4)
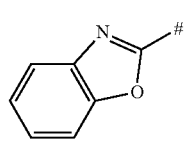 (BO1)
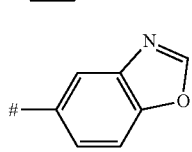 (BO2)
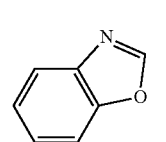 (BO3)
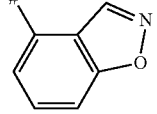 (BO4)
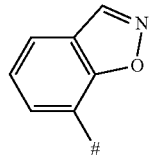 (BO5)
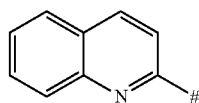 (QU1)
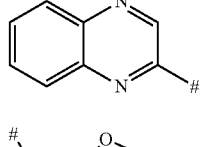 (QX1)
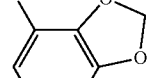 (BD1)
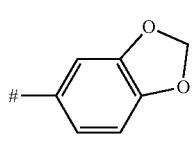 (BD2)

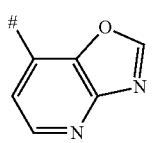 (OP1)
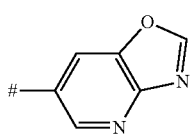 (OP2)
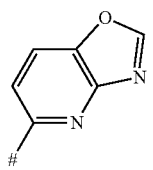 (OP3)
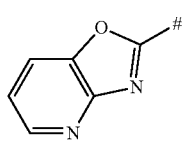 (OP4)
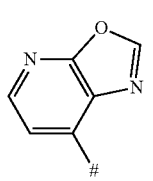 (XP1)
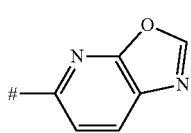 (XP2)
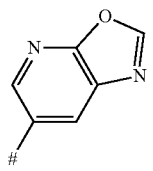 (XP3)
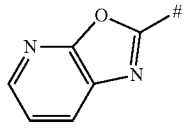 (XP4)
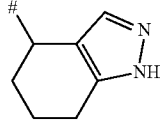 (TI1)
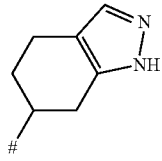 (TI2)
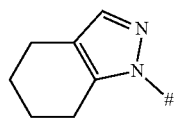 (TI3)
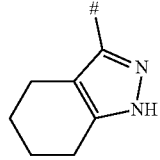 (TI4)
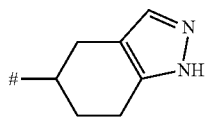 (TI5)
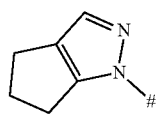 (CP1)
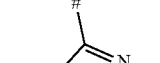 (CP2)
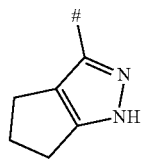 
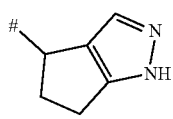 (CP3)
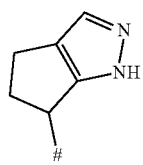 (CP4)
[Chem.305]
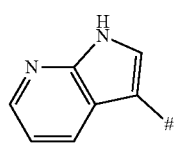 (YP1)
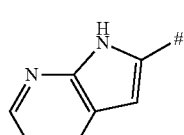 (YP2)
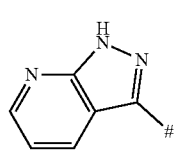 (YP3)

-continued

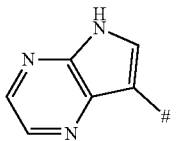 (YP4)

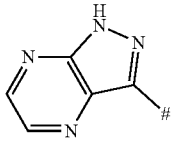 (YP5)

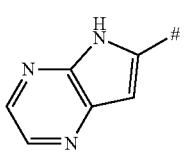 (YP6)

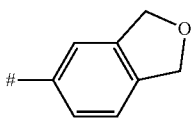 (BD3)

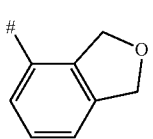 (BD4)

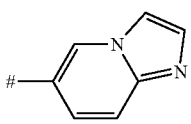 (IP1)

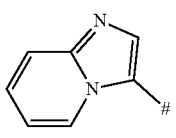 (IP2)

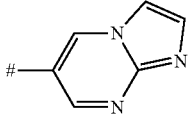 (IP3)

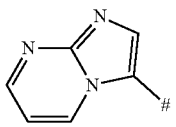 (IP4)

The below-mentioned substituent Nos. GG1 to GG665 represent substituent $G^2$ in the compound represented by formula (III).

[GG1;ID6], [GG2;5-F-ID6], [GG3;5-Cl-ID6], [GG4;5-Me-ID6], [GG5;5-CF$_3$—ID6], [GG6;5-OMe-ID6], [GG7;5-OCF$_3$—ID6], [GG8;5-CN-ID6], [GG9;5-SMe-ID6], [GG10;2-F-ID6], [GG11;2-Cl-ID6], [GG12;2-Me-ID6], [GG13;2-CF$_3$—ID6], [GG14;2-OMe-ID6], [GG15;2-OCF$_3$—ID6], [GG16;2-CN-ID6], [GG17;6-F-ID6], [GG18;6-Cl-ID6], [GG19;6-Me-ID6], [GG20;6-CF$_3$—ID6], [GG21;6-OMe-ID6], [GG22;6-OCF$_3$—ID6], [GG23;6-CN-ID6], [GG24;6-SMe-ID6], [GG25;ID7], [GG26;5-F-ID7], [GG27;5-Cl-ID7], [GG28;5-Me-ID7], [GG29;5-CF$_3$—ID7], [GG30;5-OMe-ID7], [GG31;5-OCF$_3$—ID7], [GG32;5-CN-ID7], [GG33;5-SMe-ID7], [GG34;1-F-ID7], [GG35;1-Cl-ID7], [GG36;1-Me-ID7], [GG37;1-CF$_3$—ID7], [GG38;1-OMe-ID7], [GG39;1-OCF$_3$—ID7], [GG40;1-CN-ID7], [GG41;ID8], [GG42;5-F-ID8], [GG43;5-Cl-ID8], [GG44;5-Me-ID8], [GG45;5-CF$_3$—ID8], [GG46;5-OMe-ID8], [GG47;5-OCF$_3$—ID8], [GG48;5-CN-ID8], [GG49;5-SMe-ID8], [GG50;2-F-ID8], [GG51;2-Cl-ID8], [GG52;2-Me-ID8], [GG53;2-CF$_3$—ID8], [GG54;2-OMe-ID8], [GG55;2-OCF$_3$—ID8], [GG56;2-CN-ID8], [GG57;6-F-ID8], [GG58;6-Cl-ID8], [GG59;6-Me-ID8], [GG60;6-CF$_3$—ID8], [GG61;6-OMe-ID8], [GG62;6-OCF$_3$—ID8], [GG63;6-CN-ID8], [GG64;6-SMe-ID8], [GG65;ID9], [GG66;3-F-ID9], [GG67;3-Cl-ID9], [GG68;3-Me-ID9], [GG69;3-CF$_3$—ID9], [GG70;3-OMe-ID9], [GG71;3-OCF$_3$—ID9], [GG72;3-CN-ID9], [GG73;3-SMe-ID9], [GG74;2-F-ID9], [GG75;2-Cl-ID9], [GG76;2-Me-ID9], [GG77;2-CF$_3$—ID9], [GG78;2-OMe-ID9], [GG80;2-OCF$_3$—ID9], [GG81;2-CN-ID9], [GG82;6-F-ID9], [GG83;6-Cl-ID9], [GG84;6-Me-ID9], [GG85;6-CF$_3$—ID9], [GG86;6-OMe-ID9], [GG87;6-OCF$_3$—ID9], [GG88;6-CN-ID9], [GG89;6-SMe-ID9], [GG90;ID1], [GG91;5-F-ID1], [GG92;5-Cl-ID1], [GG93;5-Me-ID1], [GG94;5-CF$_3$—ID1], [GG95;5-OMe-ID1], [GG96;5-OCF$_3$—ID1], [GG97;5-CN-ID1], [GG98;5-SMe-ID1], [GG99;2-F-ID1], [GG100;2-Cl-ID1], [GG101;2-Me-ID1], [GG102;2-CF$_3$—ID1], [GG103;2-OMe-ID1], [GG104;2-OCF$_3$—ID1], [GG105;2-CN-ID1], [GG106;6-F-ID1], [GG107;6-Cl-ID1], [GG108;6-Me-ID1], [GG109;6-CF$_3$—ID1], [GG110;6-OMe-ID1], [GG111;6-OCF$_3$—ID1], [GG112;6-CN-ID1], [GG113;6-SMe-ID1], [GG114;ID2], [GG115;1-Me-5-F-ID2], [GG116;1-Me-5-Cl-ID2], [GG117;1-Me-5-Me-ID2], [GG118;1-Me-5-CF$_3$—ID2], [GG119;1-Me-5-OMe-ID2], [GG120;1-Me-5-OCF$_3$—ID2], [GG121;1-Me-5-CN-ID2], [GG122;1-Me-5-SMe-ID2], [GG123;1-Me-ID2], [GG124;1-CF$_3$—ID2], [GG125;1-OMe-ID2], [GG126;1-OCF$_3$—ID2], [GG127;1-Me-3-F-ID2], [GG128;1-Me-3-Cl-ID2], [GG129;1-Me-3-Me-ID2], [GG130;1-Me-3-CF$_3$—ID2], [GG131;1-Me-3-OMe-ID2], [GG132;1-Me-3-OCF$_3$—ID2], [GG133;1-Me-3-CN-ID2], [GG134;1-Et-5-F-ID2], [GG135;1-Et-5-Cl-ID2], [GG136;1-Et-5-Me-ID2], [GG137;1-Et-5-CF$_3$—ID2], [GG138;1-Et-5-OMe-ID2], [GG139;1-Et-5-OCF$_3$—ID2], [GG140;1-Et-5-CN-ID2], [GG141;1-Et-5-SMe-ID2], [GG142;1-Et-3-F-ID2], [GG143;1-Et-3-Cl-ID2], [GG144;1-Et-3-Me-ID2], [GG145;1-Et-3-CF$_3$—ID2], [GG1461-Et-3-OMe-ID2], [GG1471-Et-3-OCF$_3$—ID2], [GG1481-Et-3-CN-ID2], [GG149;ID3], [GG150;1-Me-5-F-ID3], [GG151;1-Me-5-Cl-ID3], [GG152;1-Me-5-Me-ID3], [GG153;1-Me-5-CF$_3$—ID3], [GG154;1-Me-5-OMe-ID3], [GG155;1-Me-5-OCF$_3$—ID3], [GG156;1-Me-5-CN-ID3], [GG157;1-Me-5-SMe-ID3], [GG158;1-Me-ID3], [GG159;1-CF$_3$—ID3], [GG160;1-CH$_2$OEt-ID3], [GG161;1-CH$_2$SMe-ID3], [GG162;1-Me-2-F-ID3], [GG163;1-Me-2-Cl-ID3], [GG164;1-Me-2-Me-ID3], [GG165;1-Me-2-CF$_3$—ID3], [GG166;1-Me-2-OMe-ID3], [GG167;1-Me-2-OCF$_3$—ID3], [GG168;1-Me-2-CN-ID3], [GG1691-Et-5-F-ID3], [GG170;1-Et-5-Cl-ID3], [GG171;1-Et-5-Me-ID3], [GG172;1-Et-5-CF$_3$—ID3], [GG173;1-Et-5-OMe-ID3], [GG174;1-Et-5-OCF$_3$—ID3], [GG175;1-Et-5-CN-ID3], [GG176;1-Et-5-SMe-ID3], [GG177;1-Et-2-F-ID3], [GG178;1-Et-2-Cl-ID3], [GG179;1-Et-2-Me-ID3], [GG180;1-Et-2-CF$_3$—ID3], [GG181;1-Et-2-OMe-ID3], [GG182;1-Et-2-OCF$_3$—ID3], [GG183;1-Et-2-CN-ID3], [GG184;ID4], [GG185;1-Me-5-F-ID4], [GG186;1-Me-5-Cl-ID4], [GG187;1-Me-5-Me-ID4], [GG188;1-Me-5-CF$_3$—ID4], [GG189;1-Me-5-OMe-ID4], [GG190;1-Me-5-OCF$_3$—ID4], [GG191;1-Me-5-CN-ID4], [GG192;1-Me-5-SMe-ID4], [GG193;1-Me-ID4],

[GG194;1-CF₃—ID4], [GG195;1-OMe-ID4], [GG196;1-OCF₃-ID4], [GG197;1-Me-2-F-ID4], [GG198;1-Me-2-Cl-ID4], [GG199;1-Me-2-Me-ID4], [GG200;1-Me-2-CF₃—ID4], [GG201;1-Me-2-OMe-ID4], [GG202;1-Me-2-OCF₃—ID4], [GG203;1-Me-2-CN-ID4], [GG204;1-Et-5-F-ID4], [GG205;1-Et-5-Cl-ID4], [GG206;1-Et-5-Me-ID4], [GG207;1-Et-5-CF₃—ID4], [GG208;1-Et-5-OMe-ID4], [GG209;1-Et-5-OCF₃—ID4], [GG210;1-Et-5-CN-ID4], [GG211;1-Et-5-SMe-ID4], [GG212;1-Et-2-F-ID4], [GG213;1-Et-2-Cl-ID4], [GG214;1-Et-2-Me-ID4], [GG215;1-Et-2-CF₃—ID4], [GG216;1-Et-2-OMe-ID4], [GG217;1-Et-2-OCF₃—ID4], [GG218;1-Et-2-CN-ID4], [GG219;ID5], [GG220;1-Me-6-F-ID5], [GG221;1-Me-6-Cl-ID5], [GG222;1-Me-6-Me-ID5], [GG223;1-Me-6-CF₃—ID5], [GG224;1-Me-6-OMe-ID5], [GG225;1-Me-6-OCF₃—ID5], [GG226;1-Me-6-CN-ID5], [GG227;1-Me-6-SMe-ID5], [GG228;1-Me-ID5], [GG229;1-CF₃—ID5], [GG230;1-OMe-ID5], [GG231;1-OCF₃—ID5], [GG232;1-Me-2-F-ID5], [GG233;1-Me-2-Cl-ID5], [GG234;1-Me-2-Me-ID5], [GG235;1-Me-2-CF₃—ID5], [GG236;1-Me-2-OMe-ID5], [GG237;1-Me-2-OCF₃—ID5], [GG238;1-Me-2-CN-ID5], [GG239;1-Et-6-F-ID5], [GG240;1-Et-6-Cl-ID5], [GG241;1-Et-6-Me-ID5], [GG242;1-Et-6-CF₃—ID5], [GG243;1-Et-6-OMe-ID5], [GG244;1-Et-6-OCF₃—ID5], [GG245;1-Et-6-CN-ID5], [GG246;1-Et-6-SMe-ID5], [GG247;1-Et-2-F-ID5], [GG248;1-Et-2-Cl-ID5], [GG249;1-Et-2-Me-ID5], [GG250;1-Et-2-CF₃—ID5],

[GG251;1-Et-2-OMe-ID5], [GG252;1-Et-2-OCF₃—ID5], [GG253;1-Et-2-CN-ID5], [GG254;IZ1], [GG255;5-F-IZ1], [GG256;5-Cl-IZ1], [GG257;5-Me-IZ1], [GG258;5-CF₃—IZ1], [GG259;5-OMe-IZ1], [GG260;5-OCF₃—IZ1], [GG261;5-CN-IZ1], [GG262;5-SMe-IZ1], [GG263;6-F-IZ1], [GG264;6-Cl-IZ1], [GG265;6-Me-IZ1], [GG266;6-CF₃—IZ1], [GG267;6-OMe-IZ1], [GG268;6-OCF₃—IZ1], [GG269;6-CN-IZ1], [GG270;6-SMe-IZ1], [GG271;3-F-IZ1], [GG272;3-Cl-IZ1], [GG273;3-Me-IZ1], [GG274;3-CF₃—IZ1], [GG275;3-OMe-IZ1], [GG276;3-OCF₃—IZ1], [GG277;3-CN-IZ1], [GG278;3-SMe-IZ1], [GG279;IZ2], [GG280;1-Me-5-F-IZ2], [GG281;1-Me-5-Cl-IZ2], [GG282;1-Me-5-Me-IZ2], [GG283;1-Me-5-CF₃—IZ2], [GG284;1-Me-5-OMe-IZ2], [GG285;1-Me-5-OCF₃-IZ2], [GG286;1-Me-5-CN-IZ2], [GG287;1-Me-5-SMe-IZ2], [GG288;1-Me-IZ2], [GG289;1-Et-IZ2], [GG290;1-cPr-IZ2], [GG291;1-iPr-IZ2], [GG292;1-CHF₂-IZ2], [GG293;1-CF₃—IZ2], [GG294;1-CH₂CHF₂—IZ2], [GG295;1-CH₂CF₃-IZ2], [GG296;1-CH₂OMe-IZ2], [GG297;1-CH₂OEt-IZ2], [GG298;1-CH₂SMe-IZ2], [GG299;1-Me-4-F-IZ2], [GG300;1-Me-4-Cl-IZ2], [GG301;1-Me-4-Me-IZ2], [GG302;1-Me-4-CF₃-IZ2], [GG303;1-Me-4-OMe-IZ2], [GG304;1-Me-4-OCF₃-IZ2], [GG305;1-Me-4-CN-IZ2], [GG306;1-Me-4-SMe-IZ2], [GGG307;1-Me-6-F-IZ2], [GG308;1-Me-6-Cl-IZ2], [GG309;1-Me-6-Me-IZ2], [GG310;1-Me-6-CF₃-IZ2], [GG311;1-Me-6-OMe-IZ2], [GG312;1-Me-6-OCF₃—IZ2], [GG313;1-Me-6-CN-IZ2], [GG314;IZ3], [GG315;1-Me-6-F-IZ3], [GG316;1-Me-6-Cl-IZ3], [GG317;1-Me-6-Me-IZ3], [GG318;1-Me-6-CF₃—IZ3], [GG319;1-Me-6-OMe-IZ3], [GG320;1-Me-6-OCF₃-IZ3], [GG321;1-Me-6-CN-IZ3], [GG322;1-Me-6-SMe-IZ3], [GG323;1-Me-IZ3], [GG324;1-CF₃-IZ3], [GG325;1-OMe-IZ3], [GG326;1-OCF₃—IZ3], [GG327;1-Me-2-F-IZ3], [GG328;1-Me-2-Cl-IZ3], [GG329;1-Me-2-Me-IZ3], [GG330;1-Me-2-CF₃-IZ3], [GG331;1-Me-2-OMe-IZ3], [GG332;1-Me-2-OCF₃—IZ3], [GG333;1-Me-2-CN-IZ3], [GG334;1-Et-6-F-IZ3], [GG335;1-Et-6-Cl-IZ3], [GG336;1-Et-6-Me-IZ3], [GG337;1-Et-6-CF₃—IZ3], [GG338;1-Et-6-OMe-IZ3], [GG339;1-Et-6-OCF₃—IZ3], [GG340;1-Et-6-CN-IZ3], [GG341;1-Et-6-SMe-IZ3], [GG342;1-Et-2-F-IZ3], [GG343;1-Et-2-Cl-IZ3], [GG344;1-Et-2-Me-IZ3], [GG345;1-Et-2-CF₃—IZ3], [GG346;1-Et-2-OMe-IZ3], [GG347;1-Et-2-OCF₃-IZ3], [GG348;1-Et-2-CN-IZ3], [GG349;IZ3], [GG350;1-Me-6-F-IZ3], [GG351;1-Me-6-Cl-IZ3], [GG352;1-Me-6-Me-IZ3], [GG353;1-Me-6-CF₃-IZ3], [GG354;1-Me-6-OMe-IZ3], [GG355;1-Me-6-OCF₃—IZ3], [GG356;1-Me-6-CN-IZ3], [GG357;1-Me-6-SMe-IZ3], [GG358;1-Me-IZ3], [GG359;1-CF₃—IZ3], [GG360;1-OMe-IZ3], [GG361;1-OCF₃—IZ3], [GG362;1-Me-2-F-IZ3], [GG363;1-Me-2-Cl-IZ3], [GG364;1-Me-2-Me-IZ3], [GG365;1-Me-2-CF₃-IZ3], [GG366;1-Me-2-OMe-IZ3], [GG367;1-Me-2-OCF₃—IZ3], [GG368;1-Me-2-CN-IZ3], [GG369;1-Et-6-F-IZ3], [GG370;1-Et-6-Cl-IZ3], [GG371;1-Et-6-Me-IZ3], [GG372;1-Et-6-CF₃—IZ3], [GG373;1-Et-6-OMe-IZ3], [GG374;1-Et-6-OCF₃—IZ3], [GG375;1-Et-6-CN-IZ3], [GG376;1-Et-6-SMe-IZ3], [GG377;1-Et-2-F-IZ3], [GG378;1-Et-2-Cl-IZ3], [GG379;1-Et-2-Me-IZ3], [GG380;1-Et-2-CF₃—IZ3], [GG381;1-Et-2-OMe-IZ3], [GG382;1-Et-2-OCF₃—IZ3], [GG383;1-Et-2-CN-IZ3], [GG385;IZ4], [GG386;1-Me-5-F-IZ4], [GG387;1-Me-5-Cl-IZ4], [GG388;1-Me-5-Me-IZ4], [GG389;1-Me-5-CF₃—IZ4], [GG390;1-Me-5-OMe-IZ4], [GG391;1-Me-5-OCF₃—IZ4], [GG392;1-Me-5-CN-IZ4], [GG393;1-Me-5-SMe-IZ4], [GG394;1-Me-IZ4], [GG395;1-CF₃—IZ4], [GG396;1-OMe-IZ4], [GG397;1-OCF₃—IZ4], [GG398;1-Me-3-F-IZ4], [GG399;1-Me-3-Cl-IZ4], [GG400;1-Me-3-Me-IZ4], [GG401;1-Me-3-CF₃—IZ4], [GG402;1-Me-3-OMe-IZ4], [GG403;1-Me-3-OCF₃—IZ4], [GG404;1-Me-3-CN-IZ4], [GG405;BZI1], [GG406;5-F-BZI1], [GG407;5-Cl-BZI1], [GG408;5-Me-BZI1], [GG409;5-CF₃—BZI1], [GG410;5-OMe-BZI1], [GG411;5-OCF₃-BZI1], [GG412;5-CN-BZI1], [GG413;5-SMe-BZI1], [GG414;2-F-BZI1], [GG415;2-Cl-BZI1], [GG416;2-Me-BZI1], [GG417;2-CF₃—BZI1], [GG418;2-OMe-BZI1], [GG419;2-OCF₃—BZI1], [GG420;2-CN-BZI1], [GG421;6-F-BZI1], [GG422;6-Cl-BZI1], [GG423;6-Me-BZI1], [GG424;6-CF₃—BZI1], [GG425;6-OMe-BZI1], [GG426;6-OCF₃—BZI1], [GG427;6-CN-BZI1], [GG428;6-SMe-BZI1], [GG429;BZI2], [GG430;1-Me-5-F-BZI2], [GG431;1-Me-5-Cl-BZI2], [GG432;1-Me-5-Me-BZI2], [GG433;1-Me-5-CF₃—BZI2], [GG434;1-Me-5-OMe-BZI2], [GG435;1-Me-5-OCF₃—BZI2], [GG436;1-Me-5-CN-BZI2], [GG437;1-Me-5-SMe-BZI2], [GG438;1-Me-BZI2], [GG439;1-CF₃—BZI2], [GG440;1-OMe-BZI2], [GG441;1-OCF₃—BZI2], [GG442;1-Et-5-F-BZI2], [GG443;1-Et-5-Cl-BZI2], [GG444;1-Et-5-Me-BZI2], [GG445;1-Et-5-CF₃—BZI2], [GG446;1-Et-5-OMe-BZI2], [GG447;1-Et-5-OCF₃—BZI2], [GG448;1-Et-5-CN-BZI2], [GG449;1-Et-5-SMe-BZI2], [GG450;1-Et-6-F-BZI2], [GG451;1-Me-6-Cl-BZI2], [GG452;1-Me-6-Me-BZI2], [GG453;1-Me-6-CF₃—BZI2], [GG454;1-Me-6-OMe-BZI2], [GG455;1-Me-6-OCF₃—BZI2], [GG456;1-Me-6-CN-BZI2], [GG457;1-Me-6-SMe-BZI2], [GG458;1-Et-6-F-BZI2], [GG459;1-Et-6-Cl-BZI2], [GG460;1-Et-6-Me-BZI2], [GG461;1-Et-6-CF₃—BZI2], [GG462;1-Et-6-OMe-BZI2], [GG463;1-Et-6-OCF₃—BZI2], [GG464;1-Et-6-CN-BZI2], [GG465;1-Et-6-SMe-BZI2], [GG466;BZI4], [GG467;1-Me-BZI4], [GG468;1-CF₃-BZI4], [GG469;1-OMe-BZI4], [GG470;1-OCF₃—BZI4], [GG471;1-Me-6-F-BZI4], [GG472;1-Me-6-Cl-BZI4], [GG473;1-Me-6-Me-BZI4], [GG474;1-Me-6-CF₃—BZI4], [GG475;1-Me-6-OMe-BZI4], [GG476;1-Me-6-OCF₃—BZI4], [GG477;1-Me-6-CN-BZI4], [GG478;1-Me-6-SMe-BZI4], [GG479;1-Et-6-F-BZI4], [GG480;1-Et-6-Cl-BZI4], [GG481;1-Et-6-Me-BZI4], [GG482;1-Et-6-CF₃—BZI4], [GG483;1-Et-6-OMe-BZI4], [GG484;1-Et-6-OCF₃—BZI4], [GG485;1-Et-6-CN-BZI4], [GG468;1-Et-6-SMe-BZI4], [GG487;1-Me-2-F-BZI4], [GG488;1-Me-2-Cl-BZI4], [GG489;1-Me-2-Me-

BZI4], [GG490;1-Me-2-CF₃—BZI4], [GG491;1-Me-2-OMe-BZI4], [GG492;1-Me-2-OCF₃—BZI4], [GG493;1-Me-2-CN-BZI4], [GG494;1-Me-2-SMe-BZI4], [GG495;1-Et-2-F-BZI4], [GG496;1-Et-2-Cl-BZI4], [GG497;1-Et-2-Me-BZI4], [GG498;1-Et-2-CF₃—BZI4], [GG499;1-Et-2-OMe-BZI4], [GG500;1-Et-2-OCF₃—BZI4], [GG501;1-Et-2-CN-BZI4], [GG502;1-Et2-SMe-BZJ4], [GG503;BO1], [GG504;5-F-BO1], [GG505;5-Cl-BO1], [GG506;5-Me-BO1], [GG507;5-CF₃—BO1], [GG508;5-OMe-BO1], [GG509;5-OCF₃-BO1], [GG51;5-CN-BO1], [GG511;5-SMe-BO1], [GG512;6-F-BO1], [GG513;6-Cl-BO1], [GG514;6-Me-BO1], [GG515;6-CF₃—BO1], [GG516;6-OMe-BO1], [GG517;6-OCF₃—BO1], [GG518;6-CN-BO1], [GG519;6-SMe-BO1], [GG520;BO2], [GG521;2-F-B02], [GG522;2-Cl-BO2], [GG523;2-Me-BO2], [GG524;2-CF₃—BO2], [GG525;2-OMe-BO2], [GG526;2-OCF₃-B02], [GG527;2-CN-B02], [GG528;2-SMe-B02], [GG529;6-F-BO2], [GG530;6-Cl-BO2], [GG531;6-Me-B02], [GG532;6-CF₃—BO2], [GG533;6-OMe-B02], [GG534;6-OCF₃—BO2], [GG535;6-CN-B02], [GG536;6-SMe-BO2], [GG537;B03], [GG538;2-F-B03], [GG539;2-Cl-BO3], [GG540;2-Me-BO3], [GG541;2-CF₃—B03], [GG542;2-OMe-BO3], [GG543;2-OCF₃-B03], [GG544;2-CN-BO3], [GG545;2-SMe-B03], [GG546;5-F-BO3], [GG547;5-Cl-B03], [GG548;5-Me-B03], [GG549;5-CF₃—BO3], [GG550;5-OMe-BO3], [GG551;5-OCF₃—BO3], [GG552;5-CN-BO3], [GG553;5-SMe-BO3], [GG554;QU1], [GG555;QX1], [GG558;BD1], [GG559;2,2-diF-BD1], [GG560;BD2], [GG561;OP1], [GG562;OP2], [GG563;OP3], [GG564;OP4], [GG565;XP1], [GG566;XP2], [GG567;XP3], [GG568;XP4], [GG569;T11], [GG570;T12], [GG571;T13], [GG572;T14], [GG573;T15], [GG574;CP1], [GG575;1-Me-CP2], [GG576;1-Me-CP3], [GG577;1-Me-CP4], [GG578;1-Me-T11], [GG579;1-Me-T12], [GG580;YP1], [GG581;1-Me-YP1], [GG582;1-Et-YP1], [GG583;1-CHF₂CH₂—YP1], [GG584;1-CF₃CH₂—YP1], [GG585;1-C₂F₅-YP1], [GG586;1-CH₃OCH₂-YP1], [GG587;YP2], [GG588;1-Me-YP2], [GG589;1-Et-YP2], [GG590;1-CHF₂CH₂-YP2], [GG591;1-CF₃CH₂-YP2], [GG592;1-C₂F₅-YP2], [GG593;1-CH₃OCH₂-YP2], [GG594;YP3], [GG595;1-Me-YP3], [GG5961-Et-YP3], [GG597;1-CHF₂CH₂-YP3], [GG598;1-CF₃CH₂-YP3], [GG599;1-C₂F₅-YP3], [GG600;1-CH₃OCH₂-YP3], [GG601;YP4], [GG602;1-Me-YP4], [GG603;1-Et-YP4], [GG604;1-CHF₂CH₂-YP4], [GG605;1-CF₃CH₂-YP4], [GG606;1-C₂F₅-YP4], [GG607;1-CH₃OCH₂-YP4], [GG608;YP5], [GG609;1-Me-YP5], [GG610;1-Et-YP5], [GG611;1-CHF₂CH₂-YP5], [GG612;1-CF₃CH₂-YP5], [GG613;1-C₂F₅-YP5], [GG614;1-CH₃OCH₂-YP5], [GG615;YP6], [GG616;1-Me-YP6], [GG617;1-Et-YP6], [GG618;1-CHF₂CH₂-YP6], [GG619;1-CF₃CH₂-YP6], [GG620;1-C₂F₅-YP6], [GG621;1-CH₃OCH₂-YP6], [GG622;IP1], [GG623;IP2], [GG624;IP3], [GG625;IP4], [GG626;BD3], [GG627;1-Me-3,3-Me₂-BD3], [GG628;1,1-Me₂-3-Me-BD3], [GG629, 1,1,3,3-F₄-BD3], [GG630;BD4], [GG631;1-Me-3,3-Me₂-BD4], [GG632;1,1-Me₂-3-Me-BD4], [GG633;1,1,3,3-F₄-BD4], [GG634;2-Bet], [GG6354;F-2-Bet], [GG6364;C1-2-Bet], [GG637;4-Me-2-Bet], [GG638;4-CF₃-2-Bet], [GG639;4-OMe-2-Bet], [GG640;5-F-2-Bet], [GG641;5-Cl-2-Bet], [GG642;5-Me-2-Bet], [GG643;5-CF₃-2-Bet], [GG644;5-OMe-2-Bet], [GG645;6-F-2-Bet], [GG646;6-Cl-2-Bet], [GG647;6-Me-2-Bet], [GG648;6-CF₃-2-Bet], [GG649;6-OMe-2-Bet], [GG650;7-F-2-Bet], [GG651;7-Cl-2-Bet], [GG652;7-Me-2-Bet], [GG653;7-CF₃-2-Bet], [GG654;7-OMe-2-Bet], [GG656;1-Et-ID3], [GG657;1-cPr-ID3], [GG658;1-iPr-ID3], [GG659;1-CHF₂—ID3], [GG661;1-CH₂CHF₂—ID3], [GG662;1-CH₂CF₃—ID3], [GG663;1-CH₂OMe-ID3], [GG664;1-Me-T11], [GG665;1-Me-T12], [GG665;1-Me-T14].

Present compounds III-GG1-O1~III-GG665-O1, III-GG1-O2~III-GG665-O2, III-GG1-O3~III-GG665-O3, III-GG1-O4~III-GG665-O4, and III-GG1-O5~III-GG665-O5 represent the following compounds:

the compound represented by formula (III)

[Chem.306]

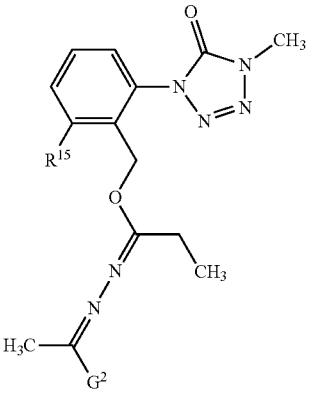

(III)

wherein the combination of G² and R¹⁵ represent any combination wherein the G² represents a substituent selected from the substituent Nos. GG1 to GG665, and the R¹⁵ represents a substituent selected from the substituents 01 to 05.

Hereinafter, THN1 represents 1,2,3,4-tetrahydronaphthalen-1-ylidene group, DIP1 represents 3,4-dihydro-2H-1-benzopyran-4-ylidene group, INDD1 represents indan-1-ylidene group, DIF1 represents 2,3-dihydrobenzofuran-3-ylidene group, DIT1 represents 3,4-dihydro-2H-1-benzothiopyran-4-ylidene group, DIO1 represents 1,1-dioxo-3-4-dihydro-2H-1-benzothiopyran-4-ylidene group, DIP23bP1 represents 3,4-dihydro-2H-pyrano[2-3-b]pyridin-4-ylidene group, DIP32bP1 represents 3,4-dihydro-2H-pyrano[3,2-b]pyridin-4-ylidene group, DIP23cP1 represents 3,4-dihydro-2H-pyrano[2,3-c]pyridin-4-ylidene group, DIP32cP1 represents 3,4-dihydro-2H-pyrano[3,2-c]pyridin-4-ylidene group, and DIP23bPR1 represents 7,8-dihydro-6H-pyrano[2,3-b]pyrazine-8-ylidene group.

Substituent Nos. 01 to 05 indicated in [Table 7] represents a subsituent R¹⁵ in the compounds represented by formula (III) or formula (IIII).

TABLE 7

| Substituent No. | Z¹ |
|---|---|
| O1 | Me |
| O2 | F |
| O3 | Cl |
| O4 | cPr |
| O5 | OMe |

The below-mentioned substituent Nos. GGGG1 to GGGG 365 represent substituent Q in the compound represented by formula (IIII).

[GGG1;INDD1], [GGG2;5-F-INDD1], [GGG3;5-Cl-INDD1], [GGG4;5-Br-INDD1], [GGG5;5-Me-INDD1], [GGG6;5-Et-INDD1], [GGG7;5-iPr-INDD1], [GGG8;5-CF2H-INDD1], [GGG9;5-CF3-INDD1], [GGG10;5-OMe-

INDD1], [GGG11;5-OEt-INDD1], [GGG12;5-OiPr-INDD1], [GGG13;5-OCF3-INDD1], [GGG14;5-OCF2H-INDD1], [GGG15;6-F-INDD1], [GGG16;6-Cl-INDD1], [GGG17;6-Br-INDD1], [GGG18;6-Me-INDD1], [GGG19;6-Et-INDD1], [GGG20;6-iPr-INDD1], [GGG21;6-CF2H-INDD1], [GGG22;6-CF3-INDD1], [GGG23;6-OMe-INDD1], [GGG24;6-OEt-INDD1], [GGG25;6-OiPr-INDD1], [GGG26;6-OCF3-INDD1], [GGG27;6-OCF2H-INDD1], [GGG28;3-F-INDD1], [GGG29;3-Cl-INDD1], [GGG30;3-Br-INDD1], [GGG31;3-Me-INDD1], [GGG32;3-Et-INDD1], [GGG33;3-iPr-INDD1], [GGG34;3-CF2H-INDD1], [GGG35;3-CF3-INDD1], [GGG36;3-OMe-INDD1], [GGG37;3-OEt-INDD1], [GGG38;3-OiPr-INDD1], [GGG39;3-OCF3-INDD1], [GGG40;3-OCF2H-INDD1], [GGG41;3,3-diF-INDD1], [GGG42;3,3-diMe-INDD1], [GGG43;THN1], [GGG44;7-F-THN1], [GGG45;7-Cl-THN1], [GGG46;7-Br-THN1], [GGG47;7-Me-THN1], [GGG48;7-Et-THN1], [GGG49;7-iPr-THN1], [GGG50;7-CF2H-THN1], [GGG51;7-CF3-THN1], [GGG52;7-OMe-THN1], [GGG53;7-OEt-THN1], [GGG54;7-OiPr-THN1], [GGG55;7-OCF3-THN1], [GGG56;7-OCF2H-THN1], [GGG57;6-F-THN1], [GGG58;6-Cl-THN1], [GGG59;6-Br-THN1], [GGG60;6-Me-THN1], [GGG61;6-Et-THN1], [GGG62;6-iPr-THN1], [GGG63;6-CF2H-THN1], [GGG64;6-CF3-THN1], [GGG65;6-OMe-THN1], [GGG66;6-OEt-THN1], [GGG67;6-OiPr-THN1], [GGG68;6-OCF3-THN1], [GGG69;6-OCF2H-THN1], [GGG70;4-F-THN1], [GGG71;4-Cl-THN1], [GGG72;4-Br-THN1], [GGG73;4-Me-THN1], [GGG74;4-Et-THN1], [GGG75;4-iPr-THN1], [GGG76;4-CF2H-THN1], [GGG77;4-CF3-THN1], [GGG78;4-OMe-THN1], [GGG79;4-OEt-THN1], [GGG80;4-OiPr-THN1], [GGG81;4-OCF3-THN1], [GGG82;4-OCF2H-THN1], [GGG83;4-4-diF-THN1], [GGG84;4-4-diMe-THN1], [GGG85;DIF1], [GGG86;5-F-DIF1], [GGG87;5-Cl-DIF1], [GGG88;5-Br-DIF1], [GGG89;5-Me-DIF1], [GGG90;5-Et-DIF1], [GGG91;5-iPr-DIF1], [GGG92;5-CF$_2$H-DIF1], [GGG93;5-CF$_3$-DIF1], [GGG94;5-OMe-DIF1], [GGG95;5-OEt-DIF1], [GGG96;5-OiPr-DIF1], [GGG97;5-OCF$_3$-DIF1], [GGG98;5-OCF$_2$H-DIF1], [GGG99;6-F-DIF1], [GGG100;6-Cl-DIF1], [GGG101;6-Br-DIF1], [GGG102;6-Me-DIF1], [GGG103;6-Et-DIF1], [GGG104;6-iPr-DIF1], [GGG105;6-CF$_2$H-DIF1], [GGG106;6-CF$_3$-DIF1], [GGG107;6-OMe-DIF1], [GGG108;6-OEt-DIF1], [GGG109;6-OiPr-DIF1], [GGG110;6-OCF$_3$-DIF1], [GGG11;6-OCF$_2$H-DIF1], [GGG112;4-F-DIF1], [GGG113;4-Cl-DIF1], [GGG114;4-Br-DIF1], [GGG115;4-Me-DIF1], [GGG116;4-Et-DIF1], [GGG117;4-iPr-DIF1], [GGG118;4-CF$_2$-DIF1], [GGG119;4-CF$_3$-DIF1], [GGG120;4-OMe-DIF1], [GGG121;4-OEt-DIF1], [GGG122;4-OiPr-DIF1], [GGG123;4-OCF$_3$-DIF1], [GGG124;4-OCF$_2$H-DIF1], [GGG125;DIT1], [GGG126;5-F-DIT1], [GGG127;5-Cl-DIT1], [GGG128;5-Br-DIT1], [GGG129;5-Me-DIT1], [GGG130;5-Et-DIT1], [GGG131;5-iPr-DIT1], [GGG132;5-CF$_2$H-DIT1], [GGG133;5-CF$_3$-DIT1], [GGG134;5-OMe-DIT1], [GGG135;5-OEt-DIT1], [GGG136;5-OiPr-DIT1], [GGG137;5-OCF$_3$-DIT1], [GGG138;5-OCF$_2$H-DIT1], [GGG139;6-F-DIT1], [GGG140;6-Cl-DIT1], [GGG141;6-Br-DIT1], [GGG142;6-Me-DIT1], [GGG143;6-Et-DIT1], [GGG144;6-iPr-DIT1], [GGG145;6-CF$_2$H-DIT1], [GGG146;6-CF$_3$-DIT1], [GGG147;6-OMe-DIT1], [GGG148;6-OEt-DIT1], [GGG149;6-OiPr-DIT1], [GGG150;6-OCF$_3$-DIT1], [GGG151;6-OCF$_2$H-DIT1], [GGG152;4-F-DIT1], [GGG153;4-Cl-DIT1], [GGG154;4-Br-DIT1], [GGG155;4-Me-DIT1], [GGG156;4-Et-DIT1], [GGG157;4-iPr-DIT1], [GGG158;4-CF$_2$H-DIT1], [GGG159;4-CF$_3$-DIT1], [GGG160;4-OMe-DIT1], [GGG161;4-OEt-DIT1], [GGG162;4-OiPr-DIT1], [GGG163;4-OCF$_3$-DIT1], [GGG164;4-OCF$_2$H-DIT1], [GGG165;DIP1], [GGG166;5-F-DIP1], [GGG167;5-Cl-DIP1], [GGG168;5-Br-DIP1], [GGG169;5-Me-DIP1], [GGG170;5-Et-DIP1], [GGG171;5-iPr-DIP1], [GGG172;5-CF$_2$H-DIP1], [GGG173;5-CF$_3$-DIP1], [GGG174;5-OMe-DIP1], [GGG175;5-OEt-DIP1], [GGG176;5-OiPr-DIP1], [GGG177;5-OCF$_3$-DIP1], [GGG178;5-OCF$_2$H-DIP1], [GGG179;6-F-DIP1], [GGG180;6-Cl-DIP1], [GGG181;6-Br-DIP1], [GGG182;6-Me-DIP1], [GGG183;6-Et-DIP1], [GGG184;6-iPr-DIP1], [GGG185;6-CF$_2$H-DIP1], [GGG186;6-CF$_3$-DIP1], [GGG187;6-OMe-DIP1], [GGG188;6-OEt-DIP1], [GGG189;6-OiPr-DIP1], [GGG190;6-OCF$_3$-DIP1], [GGG191;6-OCF$_2$H-DIP1], [GGG192;7-F-DIP1], [GGG193;7-Cl-DIP1], [GGG194;7-Br-DIP1], [GGG195;7-Me-DIP1], [GGG196;7-Et-DIP1], [GGG197;7-iPr-DIP1], [GGG198;7-CF$_2$H-DIP1], [GGG199;7-CF$_3$-DIP1], [GGG200;7-OMe-DIP1], [GGG201;7-OEt-DIP1], [GGG202;7-OiPr-DIP1], [GGG203;7-OCF$_3$-DIP1], [GGG204;7-OCF$_2$H-DIP1], [GGG205;DIO1], [GGG206;5-F-DIO1], [GGG207;5-Cl-DIO1], [GGG208;5-Br-DIO1], [GGG209;5-Me-DIO1], [GGG210;5-Et-DIO1], [GGG211;5-iPr-DIO1], [GGG212;5-CF$_2$H-DIO1], [GGG213;5-CF$_3$-DIO1], [GGG214;5-OMe-DIO1], [GGG215;5-OEt-DIO1], [GGG216;5-OiPr-DIO1], [GGG217;5-OCF$_3$-DIO1], [GGG218;5-OCF$_2$H-DIO1], [GGG219;6-F-DIO1], [GGG220;6-Cl-DIO1], [GGG221;6-Br-DIO1], [GGG222;6-Me-DIO1], [GGG223;6-Et-DIO1], [GGG224;6-iPr-DIO1], [GGG225;6-CF$_2$H-DIO1], [GGG226;6-CF$_3$-DIO1], [GGG227;6-OMe-DIO1], [GGG228;6-OEt-DIO1], [GGG229;6-OiPr-DIO1], [GGG230;6-OCF$_3$-DIO1], [GGG231;6-OCF$_2$H-DIO1], [GGG232;7-F-DIO1], [GGG233;7-Cl-DIO1], [GGG234;7-Br-DIO1], [GGG235;7-Me-DIO1], [GGG236;7-Et-DIO1], [GGG237;7-iPr-DIO1], [GGG238;7-CF$_2$H-DIO1], [GGG239;7-CF$_3$-DIO1], [GGG240;7-OMe-DIO1], [GGG241;7-OEt-DIO1], [GGG242;7-OiPr-DIO1], [GGG243;7-OCF$_3$-DIO1], [GGG244;7-OCF$_2$H-DIO1], [GGG245;5-CN-INDD1], [GGG246;6-CN-INDD1], [GGG247;3-CN-INDD1], [GGG248;7-CN-THN1], [GGG249;6-CN-THN1], [GGG250;4-CN-THN1], [GGG251;5-CN-DIF1], [GGG252;6-CN-DIF1], [GGG253;4-CN-DIF1], [GGG254;5-CN-DIT1], [GGG255;6-CN-DIT1], [GGG256;4-CN-DIT1], [GGG257;5-CN-DIP1], [GGG258;6-CN-DIP1], [GGG259;7-CN-DIP1], [GGG260;5-CN-DIO1], [GGG261;6-CN-DIO1], [GGG262;7-CN-DIO1], [GGG263-4-F-INDD1], [GGG264;4-Cl-INDD1], [GGG265;4-Br-INDD1], [GGG266;4-Me-INDD1], [GGG267;4-Et-INDD1], [GGG268;4-iPr-INDD1], [GGG269;4-CF$_2$H-INDD1], [GGG270;4-CF$_3$-INDD1], [GGG271;4-OMe-INDD1], [GGG272;4-OEt-INDD1], [GGG273;4-OiPr-INDD1], [GGG274;4-OCF$_3$-INDD1], [GGG275;4-OCF$_2$H-INDD1], [GGG276;4-CN-INDD1], [GGG277;7-F-INDD1], [GGG278;7-Cl-INDD1], [GGG279;7-Br-INDD1], [GGG280;7-Me-INDD1], [GGG281;7-Et-INDD1], [GGG282;7-iPr-INDD1], [GGG283;7-CF$_2$H-INDD1], [GGG284;7-CF$_3$-INDD1], [GGG285;7-OMe-INDD1], [GGG286;7-OEt-INDD1], [GGG287;7-OiPr-INDD1], [GGG288;7-OCF$_3$-INDD1], [GGG289;7-OCF$_2$H-INDD1], [GGG290;7-CN-INDD1], [GGG263;5-F-THN1], [GGG264;5-Cl-THN1], [GGG265;5-Br-THN1], [GGG266;5-Me-THN1], [GGG267;5-Et-THN1], [GGG268;5-iPr-THN1], [GGG269;5-CF$_2$H-THN1], [GGG270;5-CF$_3$-THN1], [GGG271;5-OMe-THN1], [GGG272;5-OEt-THN1], [GGG273;5-OiPr-THN1], [GGG274;5-OCF$_3$-THN1], [GGG275;5-OCF$_2$H-THN1], [GGG276;5-CN-

THN1], [GGG277;8-F-THN1], [GGG278;8-Cl-THN1], [GGG279;8-Br-THN1], [GGG280;8-Me-THN1], [GGG281;8-Et-THN1], [GGG282;8-iPr-THN1], [GGG283;8-CF$_2$H-THN1], [GGG284;8-CF$_3$-THN1], [GGG285;8-OMe-THN1], [GGG286;8-OEt-THN1], [GGG287;8-OiPr-THN1], [GGG288;8-OCF$_3$-THN1], [GGG289;8-OCF$_2$H-THN1], [GGG290;8-CN-THN1], [GGG291;7-F-DIF1], [GGG292;7-Cl-DIF1], [GGG293;7-Br-DIF1], [GGG294;7-Me-DIF1], [GGG295;7-Et-DIF1], [GGG296;7-iPr-DIF1], [GGG297;7-CF$_2$H-DIF1], [GGG298;7-CF$_3$-DIF1], [GGG299;7-OMe-DIF1], [GGG300;7-OEt-DIF1], [GGG301;7-OiPr-DIF1], [GGG302;7-OCF$_3$-DIF1], [GGG303;7-OCF$_2$H-DIF1], [GGG304;7-CN-DIF1], [GGG305;7-F-DIT1], [GGG306;7-Cl-DIT1], [GGG307;7-Br-DIT1], [GGG308;7-Me-DIT1], [GGG309;7-Et-DIT1], [GGG310;7-iPr-DIT1], [GGG311;7-CF$_2$H-DIT1], [GGG312;7-CF$_3$-DIT1], [GGG313;7-OMe-DIT1], [GGG314;7-OEt-DIT1], [GGG315;7-OiPr-DIT1], [GGG316;7-OCF$_3$-DIT1], [GGG317;7-OCF$_2$H-DIT1], [GGG318;7-CN-DIT1], [GGG319;8-F-DIP1], [GGG320;8-Cl-DIP1], [GGG321;8-Br-DIP1], [GGG322;8-Me-DIP1], [GGG323;8-Et-DIP1], [GGG324;8-iPr-DIP1], [GGG325;8-CF$_2$H-DIP1], [GGG326;8-CF$_3$-DIP1], [GGG327;8-OMe-DIP1], [GGG328;8-OEt-DIP1], [GGG329;8-OiPr-DIP1], [GGG330;8-OCF$_3$-DIP1], [GGG331;8-OCF$_2$H-DIP1], [GGG332;8-CN-DIP1], [GGG333;3-F-DIP1], [GGG334;3-Cl-DIP1], [GGG335;3-Br-DIP1], [GGG336;3-Me-DIP1], [GGG337;3-Et-DIP1], [GGG338;3-iPr-DIP1], [GGG339;3-CF$_2$H-DIP1], [GGG340;3-CF$_3$-DIP1], [GGG341;3-OMe-DIP1], [GGG342;3-OEt-DIP1], [GGG343;3-OiPr-DIP1], [GGG344;3-OCF$_3$-DIP1], [GGG345;3-OCF$_2$H-DIP1], [GGG346;3-CN-DIP1], [GGG347;8-F-DIO1], [GGG348;8-Cl-DIO1], [GGG349;8-Br-DIO1], [GGG350;8-Me-DIO1], [GGG351;8-Et-DIO1], [GGG352;8-iPr-DIO1], [GGG353;8-CF$_2$H-DIO1], [GGG354;8-CF$_3$-DIO1], [GGG355;8-OMe-DIO1], [GGG356;8-OEt-DIO1], [GGG357;8-OiPr-DIO1], [GGG358;8-OCF$_3$-DIO1], [GGG359;8-OCF$_2$H-DIO1], [GGG360;8-CN-DIO1], [GGG361;DIP23bP1], [GGG362;DIP32bP1], [GGG363;DIP23cP1], [GGG364;DIP32cP1], and [GGG365;DIP23bPR1].

Present compounds IIII-GGG1-O1~IIII-GGG365-O1, IIII-GGG1-O2~IIII-GGG365-O2, IIII-GGG1-O3~IIII-GGG365-O3, IIII-GGG1-O4~IIII-GGG365-O4, and IIII-GGG1-O5~IIII-GGG365-O5 represent the following compound:

the compounds represented by formula (IIII)

[Chem.307]

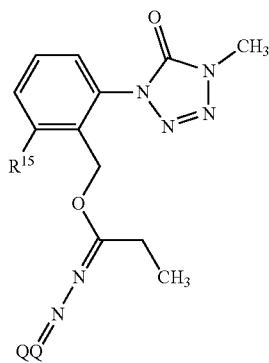

(IIII)

wherein the combination of $R^{15}$ and QQ represent any combination wherein the $R^{15}$ represents a substituent selected from the substituent Nos. 01 to 05, and the QQ represents a substituent selected from the substituent Nos. GGG1 to GGG365.

A composition which comprises one or more ingredients selected from the group consisting of the Present compound, a nematode control ingredient, a plant growth regulator, and the other pest control ingredients (hereinafter collectively referred to as "Present ingredient") can be applied to plants or soils to control pests such as harmful arthropods, harmful nematodes, and plant pathogens. Alternatively, Present compound may be applied separately with Present ingredient to control pests.

The nematode control ingredient represents an ingredient to be used to control harmful nematodes.

The plant growth regulator represents an ingredient to regulate a growth or development of plant, and includes, for example, indole butyric acid.

Examples of the pest control ingredient include plant pathogens and harmful arthropods, and the like.

Examples of the plant pathogens include a fungicidal active ingredient.

The fungicidal active ingredient represents an ingredient for use in protecting a plant from adverse effect by which plant pathogens (for example, flilamentous fungi or bacteria) attack a plant. Examples of the fungicidal active ingredients include those specified by FRAC (Fngicide Resistance Action Committee).

Examples of harmful arthropods include a nonxious insect control ingredient and a mite control ingredient.

Examples of the nonxious insect control ingredient, the mite control ingredient, and the nematode control ingredient include those specified by IRAC (Insecticide Resistance Action Committee).

Hereinafter, a combination of Present compound and Present ingredient. For example, "tebuconazole+SX" indicates the combination of tebuconazole and SX. Here, the abbreviation of "SX" indicates any one compound selected from the group Present compound Z. The abbreviation of "SX" indicates any one compound selected from the Present compound A. Also, the number in a parenthesis represents the CAS registration number.

tebuconazole+SX, prothioconazole+SX, metconazole+SX, ipconazole+SX, triticonazole+SX, difenoconazole+SX, imazalil+SX, triadimenol+SX, tetraconazole+SX, flutriafol+SX, bromuconazole+SX, propiconazole+SX, mefentrifluconazole+SX, ipfentrifluconazole+SX, epoxiconazole+SX, cyproconazole+SX, mandestrobin+SX, azoxystrobin+SX, pyraclostrobin+SX, trifloxystrobin+SX, fluoxastrobin+SX, picoxystrobin+SX, fenamidone+SX, dimoxystrobin+SX, metominostrobin+SX, pyribencarb+SX, sedaxane+SX, penflufen+SX, fluxapyroxad+SX, fluopyram+SX, benzovindiflupyr+SX, boscalid+SX, carboxin+SX, penthiopyrad+SX, flutolanil+SX, bixafen+SX, pydiflumetofen+SX, 3-(difluoromethyl)-N-(7-fluoro-1,1,3-trimethylindan-4-yl)-1-methylpyrazole-4-carboxamide (1383809-87-7), N-cyclopropyl-3-(difluoromethyl)-5-fluoro-N-(5-chloro-2-isopropylbenzyl)-1-methyl-1H-pyrazole-4-carboxamide (1255734-281)+SX, 3-(difluoromethyl)-1-methyl-N-(1,1,3-trimethylindan)-4-yl)pyrazole-4-carboxamide (141573-94-6)+SX, 3-(difluoromethyl)-1-methyl-N-[(3R)-1,1,3-trimethylindan-4-yl]pyrazole-4-carboxamide (1352994-67-2)+SX, metalaxyl+SX, metalaxyl-M+SX, metrafenone+SX, cyflufenamid+SX, proquinazid+SX, 3-chloro-5-phenyl-6-methyl-4-(2,6-difluorophenyl)pyridazine (1358061-55-8)+SX, 1-[2-({[1-(4-chlorophenyl)-1H-pyrazol-3-yl]

oxy}methyl)-3-methylphenyl]-4-ethyl-4,5-dihydrotetrazole-5-one (1472649-01-6)+SX, 4-(2-bromo-4-fluorophenyl)-N-(2-chloro-6-fluorophenyl)-1,3-dimethyl-1H-pyrazole-5-amine (1362477-26-6)+SX, fenpicoxamid+SX, N'-(2,5-dimethyl-4-phenoxyphenyl)-N-ethyl-N-methyl methanimidamide (1052688-31-9)+SX, isotianil+SX, oxolinic acid+SX, ferimzone+SX, phthalide+SX, kasugamycin+SX, tebufloquin+SX, quinofumelin+SX, fenpyrazamine+SX, procymidone+SX, fludioxonil+SX, tolclofos-methyl+SX, thiabendazole+SX, ethaboxam+SX, picarbutrazox+SX, oxathiapiprolin+SX, iminoctadine triacetate+SX, iminoctadine albesilate+SX, fenpropimorph+SX, fenpropidin+SX, spiroxamine+SX, chlorothalonil+SX, folpet+SX, captan+SX, thiram+SX, silthiofam+SX, mancozeb+SX, cartap+SX, clothianidin+SX, thiamethoxam+SX, imidacloprid+SX, thiacloprid+SX, flupyradifurone+SX, sulfoxaflor+SX, triflumezopyrim+SX, dicloromezotiaz+SX, beta-cyfluthrin+SX, tefluthrin+SX, fipronil+SX, chlorantraniliprole+SX, cyantraniliprole+SX, tetraniliprole+SX, thiodicarb+SX, carbofuran+SX, fluxametamide+SX, afoxolaner+SX, fluralaner+SX, broflanilide+SX, abamectin+SX, fluensulfone+SX, fluazaindolizine+SX, tioxazafen+SX, (E)-N-{1-[(6-chloropyridin-3-yl)methyl]pyridin-2(1H)-ylidene}-2,2,2-trifluoroacetamide (1689566-03-7)+SX, Mycorrhizal Fungi+SX, *Bacillus firmus*+SX, *Bacillus amyloliquefaciens*+SX, *Pasteuria nishizawae*+SX, *Pasteuria penetrans*+SX, acephate+SX, acequinocyl+SX, acetamiprid+SX, acrinathrin+SX, acynonapyr+SX, afidopyropen+SX, alanycarb+SX, aldicarb+SX, allethrin+SX, alpha-cypermethrin+SX, alpha-endosulfan+SX, aluminium phosphide+SX, amitraz+SX, azadirachtin+SX, azamethiphos+SX, azinphos-ethyl+SX, azinphos-methyl+SX, azocyclotin+SX, bendiocarb+SX, benfluthrin+SX, benfuracarb+SX, bensultap+SX, benzoximate+SX, benzpyrimoxan+SX, beta-cypermethrin+SX, bifenazate+SX, bifenthrin+SX, bioallethrin+SX, bioresmethrin+SX, bistrifluron+SX, borax+SX, boric acid+SX, bromopropylate+SX, buprofezin+SX, butocarboxim+SX, butoxycarboxim+SX, cadusafos+SX, calcium cyanide+SX, calcium phosphide+SX, carbaryl+SX, carbosulfan+SX, cartap hydrochloride+SX, chinomethionat+SX, chlordane+SX, chlorethoxyfos+SX, chlorfenapyr+SX, chlorfenvinphos+SX, chlorfluazuron+SX, chlormephos+SX, chloropicrin+SX, chlorpyrifos+SX, chlorpyrifos-methyl+SX, chromafenozide+SX, clofentezine+SX, coumaphos+SX, cryolite+SX, cyanophos+SX, cycloniliprole+SX, ycloprothrin+SX, cycloxaprid+SX, cyenopyrafen+SX, cyflumetofen+SX, cyfluthrin+SX, cyhalodiamide+SX, cyhalothrin+SX, cyhexatin+SX, cypermethrin+SX, cyphenothrin+SX, cyromazine+SX, dazomet+SX, deltamethrin+SX, demeton-S-methyl+SX, diafenthiuron+SX, diazinon+SX, dichlorvos+SX, dicofol+SX, dicrotophos+SX, diflovidazin+SX, diflubenzuron+SX, dimefluthrin+SX, dimethoate+SX, dimethylvinphos+SX, dinotefuran+SX, disodium octaborate+SX, disulfoton+SX, DNOC (2-methyl-4,6-dinitrophenol)+SX, doramectin+SX, emamectin-benzoate+SX, empenthrin+SX, endosulfan+SX, EPN (O-ethyl O-(4-nitrophenyl) phenylphosphonothioate)+SX, epsilon-metofluthrin+SX, epsilon-momfluothrin+SX, esfenvalerate+SX, ethiofencarb+SX, ethion+SX, ethiprole+SX, ethoprophos+SX, etofenprox+SX, etoxazole+SX, famphur+SX, fenamiphos+SX, fenazaquin+SX, fenbutatin oxide+SX, fenitrothion+SX, fenobucarb+SX, fenoxycarb+SX, fenpropathrin+SX, fenpyroximate+SX, fenthion+SX, fenvalerate+SX, flometoquin+SX, flonicamid+SX, fluacrypyrim+SX, fluazuron+SX, flubendiamide+SX, flucycloxuron+SX, flucythrinate+SX, flufenoprox+SX, flufenoxuron+SX, flufiprole+SX, flumethrin+SX, fluvalinate+SX, formetanate+SX, fosthiazate+SX, furamethrin+SX, furathiocarb+SX, gamma-cyhalothrin+SX, halfenprox+SX, halofenozide+SX, heptafluthrin+SX, heptenophos+SX, hexaflumuron+SX, hexythiazox+SX, hydramethylnon+SX, hydroprene+SX, imicyafos+SX, imiprothrin+SX, indoxacarb+SX, sofenphos+SX, isoprocarb+SX, isopropyl-O-(methoxyaminothiophosphoryl)salicylate+SX, isoxathion+SX, ivermectin+SX, kadethrin+SX, kappa-tefluthrin+SX, kappa-bifenthrin+SX, kinoprene+SX, lambda-cyhalothrin+SX, lepimectin+SX, lime sulfur+SX, lufenuron+SX, machine oil+SX, malathion+SX, mecarbam+SX, meperfluthrin+SX, metaflumizone+SX, metam+SX, methamidophos+SX, methidathion+SX, methiocarb+SX, methomyl+SX, methoprene+SX, methoxychlor+SX, methoxyfenozide+SX, methyl bromide+SX, metofluthrin+SX, metolcarb+SX, metoxadiazone+SX, mevinphos+SX, milbemectin+SX, milbemycin oxime+SX, momfluorothrin+SX, monocrotophos+SX, moxidectin+SX, naled+SX, nicotine+SX, nicotine-sulfate+SX, nitenpyram+SX, novaluron+SX, noviflumuron+SX, omethoate+SX, oxamyl+SX, oxydemeton-methyl+SX, parathion+SX, parathion-methyl+SX, permethrin+SX, phenothrin+SX, phenthoate+SX, phorate+SX, phosalone+SX, phosmet+SX, phosphamidon+SX, phosphine+SX, phoxim+SX, pirimicarb+SX, pirimiphos-methyl+SX, potassium cyanide+SX, prallethrin+SX, profenofos+SX, profluthrin+SX, propargite+SX, propetamphos+SX, propoxur+SX, prothiofos+SX, pyflubumide+SX, pymetrozine+SX, pyraclofos+SX, pyrethrins+SX, pyridaben+SX, pyridalyl+SX, pyridaphenthion+SX, pyrifluquinazone+SX, pyrimidifen+SX, pyriminostrobin+SX, pyriprole+SX, pyriproxyfen+SX, quinalphos+SX, resmethrin+SX, rotenone+SX selamectin+SX, sigma-cypermethrin+SX, silafluofen+SX, sodium borate+SX, sodium cyanide+SX, sodium metaborate+SX, spinetoram+SX, spinosad+SX, spirodiclofen+SX, spiromesifen+SX, spiropidion+SX, spirotetramat+SX, sulfluramid+SX, sulfotep+SX, sulfur+SX, sulfuryl fluoride+SX, tartar emetic+SX, tau-fluvalinate+SX, tebufenozide+SX, tebufenpyrad+SX, tebupirimfos+SX, teflubenzuron+SX, temephos+SX, terbufos+SX, tetrachlorvinphos+SX, tetradifon+SX, tetramethrin+SX, tetramethylfluthrin+SX, theta-cypermethrin+SX, thiocyclam+SX, thiofanox+SX, thiometon+SX, thiosultap-disodium+SX, thiosultap-monosodium+SX, tolfenpyrad+SX, tralomethrin+SX, transfluthrin+SX, triazamate+SX, triazophos+SX, trichlorfon+SX, triflumezopyrim+SX, triflumuron+SX, trimethacarb+SX, tyclopyrazoflor+SX, vamidothion+SX, XMC (3,5-dimethylphenyl N-methylcarbamate)+SX, xylylcarb+SX, zeta-cypermethrin+SX, zinc phosphide+SX, 3-bromo-N-[2,4-dichloro-6-(methylcarbamoyl)phenyl]-1-(3,5-dichloropyridin-2-yl)-1H-pyrazole-5-carboxamide (1104384-14-6)+SX; N-[3-chloro-1-(pyridin-3-yl)-1H-pyrazol-4-yl]-N-ethyl-3-(3,3,3-trifluoropropanesulfinyl) propaneamide (477923-37-7)+SX, 2-[3-(ethanesulfonyl) pyridin-2-yl]-5-(trifluoromethanesulfonyl)benzoxazole (1616678-32-0)+SX, 4-[5-(3,5-dichlorophenyl)-5-(trifluoromethyl)-4,5-dihydro-1,2-oxazol-3-yl]-2-methyl-N-(1-oxothiethan-3-yl)benzmide (1241050-20-3)+SX, 3-methoxy-N-(5-{5-(trifluoromethyl)-5-[3-(trifluoromethyl)phenyl]-4,5-dihydro-1,2-oxadiazol-3-yl}indan-1-yl) propanamide (1118626-57-5)+SX, N-[2-bromo-6-chloro-4-(1,1,1,2,3,3,3-heptafluoropropan-2-yl)phenyl]-3-{ethyl [(pyridin-4-yl)carbonyl]amino}-2-methoxybenzamide (142951353-0)+SX, N-[2-bromo-6-chloro-4-(1,1,1,2,3,3,3-heptafluoropropan-2-yl)phenyl]-3-[ethyl(4-cyanobenzolyl) amino]-2-methoxybenzamide (1609007-65-9)+SX, N-[2-bromo-6-difluoromethoxy-4-(1,1,1,2,3,3,3-heptafluoropropan-2-yl)phenyl]-3-{meth yl[(pyridin-4-yl)

carbonyl]amino}-2-methoxybenzamide (1630969-78-6)+SX, 1-{2-fluoro-4-methyl-5-[(2,2,2-trifluoroethyl)sulfinyl]phenyl}-3-(trifluoromethyl)-1H-1,2,4-triazole-5-amine (885026-50-6)+SX, BT crop protein CrylAb, BT crop protein CrylAc, BT crop protein CrylFa, BT crop protein CrylA. 105, BT crop protein Cry2Ab, BT crop protein Vip3A, BT crop protein Cry3A, BT crop protein Cry3Ab, BT crop protein Cry3Bb, BT crop protein Cry34Ab1/Cry35Ab1, *Adoxophyes orana* granulosis virus+SX, *Anticarsia gemmatalis* mNPV+SX, *Autographa californica* mNPV FV #11 virus+SX, *Cydia pomonella* GV V15 virus+SX, *Cydia pomonella* GV V22 virus+SX, *Cryptophlebia leucotreta* GV virus+SX, *Dendrolimus punctatus* cypovirus virus+SX, *Helicoverpa armigera* NPV BV-0003+virus SX, *Helicoverpa zea* NPV virus+SX, *Lymantria dispar* NPV virus+SX, *Mamestra brassicae* NPV virus+SX, *Mamestra brassicae* NPV virus+SX, *Neodiprion abietis* NPV virus+SX, *Neodiprion lecontei* NPV virus+SX, *Neodiprion sertifer* NPV virus+SX, *Nosema locustae* virus+SX, *Orgyia pseudotsugata* NPV virus+SX, *Pieris rapae* GV virus+SX, *Plodia interpunctella* GV virus+SX, *Spodoptera exigua* mNPV virus+SX, *Spodoptera littoralis* mNPV virus+SX, *Spodoptera litura* NPV virus+SX, *Arthrobotrys dactyloides* virus+SX, *Bacillus firmus* GB-126 strain+SX, *Bacillus firmus* I-1582 strain+SX, *Bacillus megaterium* strain+SX, *Bacillus* sp. AQ17 strain+SX, *Bacillus* sp. AQ177 strain+SX, *Bacillus* sp. AQ178 strain+SX, *Bacillus sphaericus* 2362 strain+SX, *Bacillus sphaericus* ABTS1743 strain+SX, *Bacillus sphaericus* Serotype H5a5b strain+SX, *Bacillus thuringiensis* AQ52 strain+SX, *Bacillus thuringiensis* BD #32 strain+SX, *Bacillus thuringiensis* CR-371 strain+SX, *Bacillus thuringiensis* subsp. Aizawai ABTS-1857 strain+SX, *Bacillus thuringiensis* subsp. Aizawai AM6552 strain+SX, *Bacillus thuringiensis* subsp. Aizawai GC-91 strain+SX, *Bacillus thuringiensis* subsp. Aizawai Serotype H-7 strain+SX, *Bacillus thuringiensis* subsp. Kurstaki ABTS351 strain+SX, *Bacillus thuringiensis* subsp. Kurstaki BMP123 strain+SX, *Bacillus thuringiensis* subsp. Kurstaki EG234 strain+SX, *Bacillus thuringiensis* subsp. Kurstaki EG7841 strain+SX, *Bacillus thuringiensis* subsp. Kurstaki EVB11319 strain+SX, *Bacillus thuringiensis* subsp. Kurstaki F810 strain+SX, *Bacillus thuringiensis* subsp. Kurstaki HD-1 strain+SX, *Bacillus thuringiensis* subsp. Kurstaki PB54 strain+SX, *Bacillus thuringiensis* subsp. Kurstaki SA-11 strain+SX, *Bacillus thuringiensis* subsp. Kurstaki SA-12 strain+SX, *Bacillus thuringiensis* subsp. Tenebriosis NB176 strain+SX, *Bacillus thuringiensis* subsp. *Thuringiensis* MPPL002 strain+SX, *Bacillus thuringiensis* subsp. *morrisoni* strain+SX, *Bacillus thuringiensis* var. *colmeri* strain+SX, *Bacillus thuringiensis* var. *darmstadiensis* 24-91 strain+SX, *Bacillus thuringiensis* var. *dendrolimus* strain+SX, *Bacillus thuringiensis* var. *galleriae* strain+SX, *Bacillus thuringiensis* var. *israelensis* BMP144 strain+SX, *Bacillus thuringiensis* var. *israelensis* serotypeH-14 strain+SX, *Bacillus thuringiensis* var. *japonensis buibui* A396 strain+SX, *Bacillus thuringiensis* var. san diego strain+SX, *Bacillus thuringiensis* var. 7216 strain+SX, *Bacillus thuringiensis* var. *aegypti* strain+SX, *Bacillus thuringiensis* var. T36 strain+SX, *Beauveria bassiana* ANT-03 strain+SX, *Beauveria bassiana* ATCC74040 strain+SX, *Beauveria bassiana* GHA strain+SX, *Beauveria brongniartii* strain+SX, *Burkholderia rinojensis* A396 strain+SX, *Chromobacterium subtsugae* PRAA4-1T strain+SX, *Dactyllela ellipsospora*+SX, *Dectylaria thaumasia* strain+SX, *Hirsutella minnesotensis* strain+SX, *Hirsutella rhossiliensis* strain+SX, *Hirsutella thompsonii* strain+SX, *Lagenidium giganteum* strain+SX, *Lecanicillium lecanii* KV01 strain+SX, *Metarhizium anisopliae* F52 strain+SX, *Metarhizium flavoviride* strain+SX, *Monacrosporium phymatopagus* strain+SX, *Paecilomyces fumosoroseus* Apopka97 strain+SX, *Paecilomyces fumosoroseus* strain+SX, *Paecilomyces lilacinus* 251 strain+SX, *Paecilomyces lilacinus* strain+SX, *Paecilomyces tenuipes* T1 strain+SX, *Paenibacillus popilliae* strain+SX, *Pasteuria usgae* strain+SX, *Pesteuria thoynei* strain+SX, *Serratia entomophila* strain+SX, *Verticillium chlamydosporium* strain+SX, *Verticillium lecani* NCIM1312 strain+SX, acibenzolar-S-methyl+SX, aldimorph+SX, ametoctradin+SX, aminopyrifen+SX, amisulbrom+SX, anilazine+SX, azaconazole+SX, basic copper chloride+SX, basic copper sulfate+SX, benalaxyl+SX, benalaxyl-M+SX, benodanil+SX, benomyl+SX, benthiavalicarb+SX, benthiavalicarb-isopropyl+SX, binapacryl+SX, biphenyl+SX, bitertanol+SX, blasticidin-S+SX, bupirimate+SX, captafol+SX, carbendazim+SX, carpropamid+SX, chinomethionat+SX, chloroneb+SX, chlozolinate+SX, colletochlorin B+SX, copper(II) hydroxide+SX, coumoxystrobin+SX, cyazofamid+SX, cymoxanil+SX, cyprodinil+SX, dichlobentiazox+SX, dichlofluanid+SX, diclocymet+SX, diclomezine+SX, dicloran+SX, diethofencarb+SX, diflumetorim+SX, dimethachlone+SX, dimethirimol+SX, dimethomorph+SX, diniconazole+SX, diniconazole-M+SX, dinocap+SX, dipymetitrone+SX, dithianon+SX, dodecylbenzenesulphonic acid bisethylenediamine copper(II) salt+SX, dodemorph+SX, dodine+SX, edifenphos+SX, enoxastrobin+SX, etaconazole+SX, ethirimol+SX, etridiazole+SX, famoxadone+SX, fenamidone+SX, fenaminstrobin+SX, fenarimol+SX, fenbuconazole+SX, fenfuram+SX, fenhexamid+SX, fenoxanil+SX, fenpiclonil+SX, fentin acetate+SX, fentin chloride+SX, fentin hydroxide+SX, ferbam+SX, fluazinam+SX, flufenoxystrobin+SX, flumorph+SX, fluopicolide+SX, fluoroimide+SX, fluquinconazole+SX, flusilazole+SX, flusulfamide+SX, flutianil+SX, fosetyl+SX, fuberidazole+SX, furalaxyl+SX, furametpyr+SX, guazatine+SX, hexaconazole+SX, hymexazole+SX, imibenconazole+SX, iminoctadine+SX, iodocarb+SX, iprobenfos+SX, iprodione+SX, iprovalicarb+SX, isofetamid+SX, isoprothiolane+SX, isopyrazam+SX, kresoximmethyl+SX, laminarin+SX, mandipropamid+SX, maneb+SX, mepanipyrim+SX, mepronil+SX, meptyldinocap+SX, methasulfocarb+SX, metiram+SX, myclobutanil+SX, naftifine+SX, nuarimol+SX, octhilinone+SX, ofurace+SX, orysastrobin+SX, oxadixyl+SX, oxpoconazole+SX, oxpoconazole fumarate+SX, oxycarboxin+SX, oxytetracycline+SX, pefurazoate+SX, penconazole+SX, pencycuron+SX, phenamacril+SX, piperalin+SX, polyoxins+SX, probenazole+SX, prochloraz+SX, propamocarb+SX, propineb+SX, prothiocarb+SX, pyrametostrobin+SX, pyraoxystrobin+SX, pyraziflumid+SX, pyrazophos+SX, pyributicarb+SX, pyrifenox+SX, pyrimethanil+SX, pyrimorph+SX, pyriofenone+SX, pyrisoxazole+SX, pyroquilon+SX, quinoxyfen+SX, quintozene+SX, simeconazole+SX, streptomycin+SX, sulfur+SX, teclofthalam+SX, tecnazene+SX, terbinafine+SX, thifluzamide+SX, thiophanate+SX, thiophanate-methyl+SX, tiadinil+SX, tolfenpyrad+SX, tolprocarb+SX, tolylfluanid+SX, triadimefon+SX, triazoxide+SX, triclopyricarb+SX, tricyclazole+SX, tridemorph+SX, triflumizole+SX, triforine+SX, validamycin+SX, valifenalate+SX, vinclozolin+SX, zineb+SX, ziram+SX, zoxamide+SX, 3-(difluoromethyl)-N-methoxy-1-methyl-N-[(1R)-1-methyl-2-(2,4,6-trichlorophenyl)ethyl]pyrazole-4-carboxamide (1639015-48-7)+SX, 3-(difluoromethyl)-N-methoxy-1-methyl-N-[(1S)-1-methyl-2-(2,4,6-trichlorophenyl)ethyl]pyrazole-4-carboxamide (1639015-49-8)+SX, 3-(difluoromethyl)-N-[(3R)-7-fluoro-1,1,3-trimethylindan- 4-yl]-1-methylpyrazole-4-carboxamide (1513466-73-3), N'-[4-({3-[(4-chlorophenyl)methyl]-1,2,4-thiadiazol-5-yl}oxy)-2,5-dimethylphenyl]-N-ethyl-N-methaneimideamide (1202781-91-6)+SX, 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl=methanesulfonate (1360819-11-9)+SX, 2,2-dimethyl-9-fluoro-5-(quinolin-3-yl)-2,3-dihydrobenzo[f][1,4]oxazepine (1207749-50-5)+SX, 2-[6-(3-fluoro-4-methoxyphenyl)-5-methylpyridin-2-yl]quinazoline (1257056-97-5)+SX, 5-fluoro-2-[(4-methylphenyl)methoxy]-4-pyrimidine amine (1174376-25-0)+SX, 5-fluoro-4-imino-3-methyl-1-tosyl-3,4-dihydropyrimidine-2(1H)-one (1616664-98-2)+SX, N'-{4-[(4,5-dichlorothiazol-2-yl)oxy]-2,5-dimethylphenyl}-N-ethyl-N-methyl-methaneimideamide (929908-57-6)+SX, ethyl (2Z)-3-amino-2-cyano-3-phenyl acrylate (39491-78-6)+SX, N-[(2-chlorothiazol-5-yl)methyl]-N-ethyl-6-methoxy-3-nitropyridin-2-amine (1446247-98-8)+SX, α-[3-(4-chloro-2-fluorophenyl)-5-(2,4-difluorophenyl)-4-isoxazolyl]-3-pyridine methanol (1229605-96-2)+SX, (αS)-[3-(4-chloro-2-fluorophenyl)-5-(2,4-difluorophenyl)-4-isoxazolyl]-3-pyridine methanol (1229606-46-5)+SX, 2-{[3-(2-chlorophenyl)-2-(2,4-difluorophenyl)oxiran-2-yl]methyl}-2,4-dihydro-3H-1,2,4-triazole-3-thione (1342260-19-8)+SX, 2-{[(2R,3S)-3-(2-chlorophenyl)-2-(2,4-difluorophenyl)oxiran-2-yl]methyl}-2,4-dihydro-3H-1,2,4-triazole-3-thione (1638897-70-7)+SX, 2-{[(2S,3R)-3-(2-chlorophenyl)-2-(2,4-difluorophenyl)oxiran-2-yl]methyl}-2,4-dihydro-3H-1,2,4-triazole-3-thione (1638897-71-8)+SX, 2-{[(2R,3R)-3-(2-chlorophenyl)-2-(2,4-difluorophenyl)oxiran-2-yl]methyl}-2,4-dihydro-3H-1,2,4-triazole-3-thione (1638897-72-9)+SX, 2-{[(2S,3S)-3-(2-chlorophenyl)-2-(2,4-difluorophenyl)oxiran-2-yl]methyl}-2,4-dihydro-3H-1,2,4-triazole-3-thione (1638897-73-0)+SX, 1-{[3-(2-chlorophenyl)-2-(2,4-difluorophenyl)oxiran-2-yl]methyl}-1H-1,2,4-triazol-5-yl thiocyanate (1342260-26-7)+SX, 1-{[(2R,3S)-3-(2-chlorophenyl)-2-(2,4-difluorophenyl)oxiran-2-yl]methyl}-1H-1,2,4-triazol-5-yl thiocyanate (1638897-82-1)+SX, 1-{[(2S,3R)-3-(2-chlorophenyl)-2-(2,4-difluorophenyl)oxiran-2-yl]methyl}-1H-1,2,4-triazol-5-yl thiocyanate (1638897-84-3)+SX, 1-{[(2R,3R)-3-(2-chlorophenyl)-2-(2,4-difluorophenyl)oxiran-2-yl]methyl}-1H-1,2,4-triazol-5-yl thiocyanate (1638897-86-5)+SX, 1-{[(2S,3S)-3-(2-chlorophenyl)-2-(2,4-difluorophenyl)oxiran-2-yl]methyl}-1H-1,2,4-triazol-5-yl thiocyanate (1638897-89-8)+SX, 5-(4-chlorobenzyl)-2-chloromethyl-2-methyl-1-(1H-1,2,4-triazol-1-ylmethyl)cyclopentanol (1394057-11-4)+SX, (1R,2S,5S)-5-(4-chlorobenzyl)-2-chloromethyl-2-methyl-1-(1H-1,2,4-triazol-1-ylmethyl)cyclopentanol (1801930-06-2)+SX, (1S,2R,5R)-5-(4-chlorobenzyl)-2-chloromethyl-2-methyl-1-(1H-1,2,4-triazol-1-ylmethyl)cyclopentanol (1801930-07-3)+SX, (1R,2R,5R)-5-(4-chlorobenzyl)-2-chloromethyl-2-methyl-1-(1H-1,2,4-triazol-1-ylmethyl)cyclopentanol (1801919-53-8)+SX, (1S,2S,5S)-5-(4-chlorobenzyl)-2-chloromethyl-2-methyl-1-(1H-1,2,4-triazol-1-ylmethyl)cyclopentanol (1801919-54-9)+SX, (1R,2R,5S)-5-(4-chlorobenzyl)-2-chloromethyl-2-methyl-1-(1H-1,2,4-triazol-1-ylmethyl)cyclopentanol (1801919-55-0)+SX, (1S,2S,5R)-5-(4-chlorobenzyl)-2-chloromethyl-2-methyl-1-(1H-1,2,4-triazol-1-ylmethyl)cyclopentanol (1801919-56-1)+SX, (1R,2S,5R)-5-(4-chlorobenzyl)-2-chloromethyl-2-methyl-1-(1H-1,2,4-triazol-1-ylmethyl)cyclopentanol (1801919-57-2)+SX, (1S,2R,5S)-5-(4-chlorobenzyl)-2-chloromethyl-2-methyl-1-(1H-1,2,4-triazol-1-ylmethyl)cyclopentanol (1801919-58-3)+SX, Methyl=3-[4-(chlorophenyl)methyl]-2-hydroxy-1-methyl-2-(1H-1,2,4-triazol-1-ylmethyl)cyclo pentane carboxylate (1791398-02-1)+SX, Methyl=(1R,2S,3S)-3-[(4-chlorophenyl)methyl]-2-hydroxy-1-methyl-2-(1H-1,2,4-triazol-1-ylmethyl)cyclopentane carboxylate+SX, Methyl=(1S,2R,3R)-3-[(4-chlorophenyl)methyl]-2-hydroxy-1-methyl-2-(1H-1,2,4-triazol-1-ylmethyl)cyclopentane carboxylate+SX, Methyl=(1R,2R,3R)-3-[(4-chlorophenyl)methyl]-2-hydroxy-1-methyl-2-(1H-1,2,4-triazol-1-ylmethyl)cyclopentane carboxylate+SX, Methyl=(1S,2S,3S)-3-[(4-chlorophenyl)methyl]-2-hydroxy-1-methyl-2-(1H-1,2,4-triazol-1-ylmethyl)cyclopentane carboxylate+SX, Methyl=(1R,2R,3S)-3-[(4-chlorophenyl)methyl]-2-hydroxy-1-methyl-2-(1H-1,2,4-triazol-1-ylmethyl) cyclopentane carboxylate+SX, Methyl=(1S,2S,3R)-3-[(4-chlorophenyl)methyl]-2-hydroxy-1-methyl-2-(1H-1,2,4-triazol-1-ylmethyl)cyclopentane carboxylate+SX, Methyl=(1R,2S,3R)-3-[(4-chlorophenyl)methyl]-2-hydroxy-1-methyl-2-(1H-1,2,4-triazol-1-ylmethyl)cyclopentane carboxylate+SX, Methyl=(1S,2R,3S)-3-[(4-chlorophenyl)methyl]-2-hydroxy-1-methyl-2-(1H-1,2,4-triazol-1-ylmethyl)cyclopentane carboxylate+SX, 2-chloromethyl-5-(4-fluorobenzyl)-2-methyl-1-(1H-1,2,4-triazol-1-ylmethyl)cyclopentanol (1394057-13-6)+SX, (1R,2S,5S)-2-chloromethyl-5-(4-fluorobenzyl)-2-methyl-1-(1H-1,2,4-triazol-1-ylmethyl)cyclo pentanol (1801930-08-4)+SX, (1S,2R,5R)-2-chloromethyl-5-(4-fluorobenzyl)-2-methyl-1-(1H-1,2,4-triazol-1-ylmethyl)cyclo pentanol (1801930-09-5)+SX, (1R,2R,5R)-2-chloromethyl-5-(4-fluorobenzyl)-2-methyl-1-(1H-1,2,4-triazol-1-ylmethyl)cyclo pentanol (1638898-08-4)+SX, (1S,2S,5S)-2-chloromethyl-5-(4-fluorobenzyl)-2-methyl-1-(1H-1,2,4-triazol-1-ylmethyl)cyclo pentanol (1638898-10-8)+SX, (1R,2R,5S)-2-chloromethyl-5-(4-fluorobenzyl)-2-methyl-1-(1H-1,2,4-triazol-1-ylmethyl)cyclo pentanol (1638898-13-1)+SX, (1S,2S,5R)-2-chloromethyl-5-(4-fluorobenzyl)-2-methyl-1-(1H-1,2,4-triazol-1-ylmethyl)cyclo pentanol (1638898-16-4)+SX, (1R,2S,5R)-2-chloromethyl-5-(4-fluorobenzyl)-2-methyl-1-(1H-1,2,4-triazol-1-ylmethyl)cyclo pentanol (1638898-20-0)+SX, (1S,2R,5S)-2-chloromethyl-5-(4-fluorobenzyl)-2-methyl-1-(1H-1,2,4-triazol-1-ylmethyl)cyclo pentanol (1638898-24-4)+SX, (R)-2-[2-chloro-4-(4-chlorophenoxy)phenyl]-1-(1,2,4-triazol-1-yl)pent-3-yne-2-ol (1801919-59-4)+SX, (R)-2-[4-(4-chlorophenoxy)-2-(trifluoromethyl)phenyl]-1-(1,2,4-triazol-1-yl)propane-2-ol (1616236-94-2)+SX, (R)-1-[4-(4-chlorophenoxy)-2-(trifluoromethyl) phenyl]-1-cyclopropyl-2-(1,2,4-triazol-1-yl)ethanol (1801919-60-7)+SX, (R)-2-[4-(4-chlorophenoxy)-2-(trifluoromethyl)phenyl]-3-methyl-1-(1,2,4-triazol-1-yl) butane-2-ol (1801919-61-8)+SX, 3-[5-(4-chlorophenyl)-2,3-dimethyl-1,2-oxazolydin-3-yl]pyridine (847749-37-5)+SX, *Agrobacterium radiobactor* K1026 strain+SX, *Agrobacterium radiobactor* K84 strain+SX, *Bacillus amyloliquefaciens* AT332 strain+SX, *Bacillus amyloliquefaciens* B3 strain+SX, *Bacillus amyloliquefaciens* D747 strain+SX, *Bacillus amyloliquefaciens* FZB24 strain+SX, *Bacillus amyloliquefaciens* FZB42 strain+SX, *Bacillus amyloliquefaciens* IN937a strain+SX, *Bacillus amyloliquefaciens* MBI600 strain+SX, *Bacillus amyloliquefaciens* PTA-4838 strain+SX, *Bacillus amyloliquefaciens* QST713 strain+SX, *Bacillus licheniformis* HB-2 strain+SX, *Bacillus licheniformis* SB3086 strain+SX, *Bacillus pumilus* AQ717 strain+SX, *Bacillus pumilus* BUF-33 strain+SX, *Bacillus pumilus* GB34 strain+SX, *Bacillus pumilus* QST2808 strain+SX, *Bacillus simplex* CGF2856 strain+SX, *Bacillus subtilis* AQ153 strain+SX, *Bacillus subtilis* AQ743 strain+SX, *Bacillus subtilis* D747 strain+SX, *Bacillus subtilis* DB101 strain+SX, *Bacillus subtilis* GB03 strain+SX, *Bacillus subtilis* HAI0404 strain+SX, *Bacillus subtilis* IAB/BS03 strain+SX, *Bacillus subtilis* MBI600 strain+SX, *Bacillus subtilis* QST30002/AQ30002 strain+SX, *Bacillus subtilis* QST30004/AQ30004 strain+SX, *Bacillus subtilis* QST713 strain+SX, *Bacillus subtilis* QST714 strain+SX, *Bacillus subtilis* var. *Amyloliquefaciens* FZB24 strain and the like+SX, *Bacillus subtilis* Y1336 strain+SX, *Burkholderia cepacia* strain+SX, *Candida oleophila* O strain+SX, *Candida saitoana* strain+SX, *Chaetomium cupreum* strain+SX, *Clonostachys rosea* strain+SX, *Coniothyrium minitans* CGMCC8325 strain+SX, *Coniothyrium minitans* CON/M/91-8 strain+SX, *cryptococcus albidus*+SX, *Erwinia carotovora* CGE234M403 strain+SX, *Fusarium oxysporum* Fo47 strain+SX, *Gliocladium catenulatum* J1446 strain+SX, *Paenibacillus polymyxa* AC-1 strain+SX, *Paenibacillus polymyxa* BS-0105 strain+SX, *Pantoea aGGlomerans* E325 strain+SX, *Phlebiopsis gigantea* strain+SX, *Pseudomonas aureofaciens* TX-1 strain+SX, *Pseudomonas chlororaphis* 63-28 strain+SX, *Pseudomonas chlororaphis* MA342 strain+SX, *Pseudomonas fluorescens* 1629RS strain+SX, *Pseudomonas fluorescens* A506 strain+SX, *Pseudomonas fluorescens* CL145A strain+SX, *Pseudomonas fluorescens* G7090 strain+SX, *Pseudomonas fluorescens* PF-A22 UL strain+SX, *Pseudomonas syringae* 742RS strain+SX, *Pseudomonas syringae* MA-4 strain+SX, *Pseudozyma flocculosa* PF-A22UL strain+SX, *Pseudomonas rhodesiae* HAI-0804 strain+SX, *Pythium oligandrum* DV74 strain+SX, *Streptomyces griseoviridis* K61 strain+SX, *Streptomyces lydicus* WYCD108US strain+SX, *Streptomyces lydicus* WYEC108 strain+SX, *Talaromyces flavus* SAY-Y-94-01 strain+SX, *Talaromyces flavus* SAY-Y-94-01 strain+SX, *Trichoderma asperellum* ICC012 strain+SX, *Trichoderma asperellum* T34 strain+SX, *Trichoderma atroviride* CNCM 11237 strain+SX, *Trichoderma atroviride* SC1 strain+SX, *Trichoderma atroviride* SKT-1 strain+SX, *Trichoderma harzianum* 21 strain+SX, *Trichoderma harzianum* DB104 strain+SX, *Trichoderma harzianum* DSM 14944 strain+SX, *Trichoderma harzianum* ESALQ-1303 strain+SX, *Trichoderma harzianum* ESALQ-1306 strain+SX, *Trichoderma harzianum* IIHR-Th-2 strain+SX, *Trichoderma harzianum* kd strain+SX, *Trichoderma harzianum* MO1 strain+SX, *Trichoderma harzianum* SF strain+SX, *Trichoderma harzianum* T39 strain+SX, *Trichoderma polysporum* EVII 206039 strain+SX, *Trichoderma stromaticum* strain+SX, *Trichoderma viride* GL-21 strain+SX, *Variovorax paradoxus* CGF4526 strain+SX, Harpin protein+SX, 1-methylcyclopropene+SX, 2,3,5-triiodobenzoic acid+SX, IAA (1H-indol-3-yl)acetic acid)+SX, IBA (4-(1H-indol-3-yl)butyric acid)+SX, MCPA (2-(4-chloro-2-methylphenoxy)acetic acid)+SX, MCPB (4-(4-chloro-2-methylphenoxy)butyric acid)+SX, 4-CPA (4-chlorophenoxyacetic acid)+SX, 5-aminolevulinic acid hydrochloride+SX, 6-benzylaminopurine+SX, abscisic acid+SX, AVG (aminoethoxyvinylglycine)+SX, ancymidol+SX, butralin+SX, calcium carbonate+SX, calcium chloride+SX, calcium formate+SX, calcium peroxide+SX, calcium polysulfide+SX, calcium sulfate+SX, chlormequat-chloride+SX, chlorpropham+SX, choline chloride+SX, cloprop+SX, cyanamide+SX, cyclanilide+SX, daminozide+SX, decan-1-ol+SX, dichlorprop+SX, dikegulac+SX, dimethipin+SX, diquat+SX, ethephon+SX, ethychlozate+SX, flumetralin+SX, flurprimidol+SX, forchlorfenuron+SX, Gibberellin A+SX, Gibberellin A3+SX, inabenfide+SX, Kinetin+SX, maleic hydrazide+SX, mefluidide+SX, mepiquatchloride+SX, oxidized glutathione+SX, pacrobutrazol+SX, pendimethalin+SX, prohexandione-calcium+SX, prohydrojasmon+SX, pyraflufen-ethyl+SX, sintofen+SX, sodium 1-naphthaleneacetate+SX, sodium cyanate+SX, streptmycin+SX, thidiazuron+SX, triapenthenol+SX, Tribufos+SX, trinexapac-ethyl+SX, uniconazole-P+SX, 2-(naphthalene-1-yl)acetamide+SX, [4-oxo-4-(2-phenylethyl)amino]butyric acid+SX, Methyl 5-(trifluoromethyl)benzo[b]thiophen-2-carboxylate+SX,

*Glomus* spp. strain+SX, *Glomus intraradices* strain+SX, *Glomus mosseae* strain+SX, *Glomus aggregatum* strain+SX, *Glomus etunicatum* strain+SX, *Bradyrhizobium elkani* strain+SX, *Bradyrhizobium japonicum* strain+SX, *Bradyrhizobium lupini* strain+SX, *Rhizobium leguminosarum* bv. *trifolii* strain+SX, *Rhizobium leguminosarum* bv. *phaseoli* strain+SX, *Rhizobium leguminosarum* bv. *viciae* strain+SX, *Sinorhizobium meliloti* strain+SX, *Rhizobium* spp. strain+SX, allidochlor+SX, benoxacor+SX, cloquintocet+SX, cloquintocet-mexyl+SX, cyometrinil+SX, cyprosulfamide+SX, dichlormid+SX, dicyclonone+SX, dimepiperate+SX, disulfoton+SX, dymron+SX, fenchlorazole+SX, fenchlorazole-ethyl+SX, fenclorim+SX, flurazole+SX, furilazole+SX, fluxofenim+SX, Hexim+SX, isoxadifen+SX, isoxadifen-ethyl+SX, mecoprop+SX, mefenpyr+SX, mefenpyr-ethyl+SX, mefenpyr-diethyl+SX, mephenate+SX, metcamifen+SX, oxabetrinil+SX, 1,8-naphthalic anhydride+SX, 1,8-octamethylene diamine+SX, AD-67 (4-(dichloroacetyl)-1-oxa-4-azaspiro[4.5]decane)+SX, CL-304415 (4-carboxy-3-4-dihydro-2H-1-benzopyran-4-acetic acid)+SX, CSB (1-bromo-4-[(chloromethyl)sulfonyl]benzene)+SX, DKA-24 (2,2-dichloro-N-[2-oxo-2-(2-propenylamino)ethyl]-N-(2-propenyl)acetamide)+SX, MG191 (2-(dichloromethyl)-2-methyl-1-3-dioxolane)+SX, MG-838 (2-propenyl 1-oxa-4-azaspiro[4.5]decane-4-carbodithioate)+SX, PPG-1292 (2,2-dichloro-N-(1,3-dioxan-2-ylmethyl)-N-(2-propenyl)acetamide)+SX, R-28725 (3-(dichloroacetyl)-2,2-dimethyl-1,3-oxazolidine)+SX, R-29148 (3-(dichloroacetyl)-2,2,5-trimethyl-1,3-oxazolidine)+SX, TI-35 (1-(dichloroacetyl)azepane)+SX, 1-dodecyl-1H-imidazole+SX, N-(2-ethylhexyl)-8,9,10-trinorborn-5-ene-2,3-dicarboximide+SX, bucarpolate+SX, N,N-dibutyl-4-chlorobenzenesulfonamide+SX, dietholate+SX, diethylmaleate+SX, piperonyl butoxide+SX, piperonyl cyclonene+SX, piprotal+SX, propyl isome+SX, safroxan+SX, sesamex+SX, sesamolin+SX, sulfoxide+SX, Verbutin+SX, DMC (1,1-bis(4-chlorophenyl)ethanol)+SX, FDMC (1,1-bis(4-chlorophenyl)-2,2-2-trifluoroethanol)+SX, ETN (1,2-epoxy-1,2,3-4-tetrahydronaphthalene)+SX, ETP (1,1,1-trichloro-2,3-expoxypropane)+SX, PSCP (phenylsaligenin cyclic phosphate)+SX, TBPT (S,S,S-tributyl phosphorotrithioate)+SX, TPP (triphenyl phosphate)+SX, anthraquinon+SX, chloralose+SX, acrep+SX, butopyronoxyl+SX, camphor+SX, d-camphor+SX, carboxide+SX, dibutyl phthalate+SX, deet+SX, dimethyl carbate+SX, dimethyl phthalate+SX, dibutyl succinate+SX, dibutyl adipate+SX, ethohexadiol+SX, hexamide+SX, icaridin+SX, methoquinbutyl+SX, methylneodecanamide+SX, 2-(octylthio)ethanol+SX, butoxy(polypropylene glycol+SX, oxamate+SX, quwenzhi+SX, quyingding+SX, zengxiaon+SX, rebemide+SX, copper naphthenate+SX, trimethacarb+SX, zinc naphthenate+SX, bis(tributyltin) oxide+SX, allicin+SX, bromoacetamide+SX, cloethocarb+SX, copper sulfate+SX, fentin+SX, ferric phosphate+SX, metaldehyde+SX, niclosamide+SX, pentachlorophenol+SX, sodium pentachlorophenoxide+SX, tazimcarb+SX, tralopyril+SX, trifenmorph+SX, (E)-2-hexenal+SX, (E)-2-octadecenal+SX, (E)-4-tridecen-1-yl acetate+SX, (E)-5-decen-1-yl acetate+SX, (E)-5-decen-1-ol+SX, (E)-3,3-dimethylcyclohexylidene acetaldehyde+SX, (E)-7-dodecen-1-yl acetate+SX, (E)-8-dodecen-1-yl acetate+SX, (E)-9-dodecen-1-yl acetate+SX, (E)-10-hexadecenal+SX, (E)-1-hexadecen-1-yl acetate+SX, (E)-11-tetradecen-1-yl acetate+SX, (E)-11-tetradecen-1-ol+

SX, (E)-4-tridecen-1-yl acetate+SX, (E)-6-methylhept-2-en-4-ol+SX, (Z)-2-(3,3-dimethylcyclohexylidene)ethanol+SX, (Z)-4-decen-1-yl acetate+SX, (Z)-4-tridecen-1-yl acetate+SX, (Z)-5-decen-1-yl acetate+SX, (Z)-5-decen-1-ol+SX, (Z)-7-tetradecenal+SX, (Z)-7-dodecen-1-yl acetate+SX, (Z)-8-dodecen-1-yl acetate+SX, (Z)-9-dodecen-1-yl acetate+SX, (Z)-8-dodecen-1-ol+SX, (Z)-9-hexadecenal+SX, (Z)-10-hexadecen-1-yl acetate+SX, (Z)-11-hexadecen-1-ol+SX, (Z)-11-hexadecenal+SX, (Z)-11-hexadecen-1-yl acetate+SX, (Z)-11-octadecenal+SX, (Z)-13-octadecenal+SX, (Z)-hexadec-13-en-11-yn-1-yl acetate+SX, (Z)-13-octadecenal+SX, (Z)-icos-13-en-10-one+SX, (Z)-7-tetradecenal+SX, (Z)-tetradec-9-en-1-ol+SX, (Z)-9-tetradecen-1-yl acetate+SX, (Z)-11-tetradecen-1-yl acetate+SX, (Z)-13-icosen-10-one+SX, (Z,E)-7,11-hexadecadien-1-yl acetate+SX, (Z,E)-9,12-tetradecadien-1-yl acetate+SX, (E,Z)-4,10-tetradecadien-1-yl acetate+SX, (E,E)-8,10-dodecadien-1-ol+SX, (E,E)-10,12-hexadecadienal+SX, (E,E)-9,11-tetradecadien-1-yl acetate+SX, (E,Z)-2,13-octadecadien-1-ol+SX, (E,Z)-3,13-octadecadien-1-ol+SX, (E,Z)-2,13-octadecadien-1-yl acetate+SX, (E,Z)-3,13-octadecadien-1-yl acetate+SX, (E,Z)-7,9-dodecadien-1-yl acetate+SX, (E,E)-7,9-dodecadien-1-yl acetate+SX, (Z,E)-9,12-tetradecadien-1-yl acetate+SX, (Z,E)-9,11-tetradecadien-1-yl acetate+SX, (Z,E)-7,11-hexadecadien-1-yl acetate+SX, (Z,Z)-3,13-octadecadien-1-ol+SX, (Z,Z)-4,7-decadien-1-yl acetate+SX, (Z,Z)-3,13-octadecadien-1-yl acetate+SX, (Z,Z)-7,11-hexadecadien-1-yl acetate+SX, (Z,Z,E)-7,11,13-hexadecatrienal+SX, (5R)-5-[(1Z)-1-decen-1-yl]dihydro-2(3H)-furanone+SX, (2R,5R)-ethyl-1,6-dioxaspiro[4,4]nonane+SX, (2R,5S)-ethyl-1,6-dioxaspiro[4,4]nonane+SX, (4R,8R)-4,8-dimethyldecanal+SX, (4R,8S)-4,8-dimethyldecanal+SX, 2-4-dimethyl-5-ethyl-6,8-dioxabicyclo[3,2,1]octane+SX, (–)-4-methyl-3-heptanol+SX, 1,7-dioxaspiro[5,5]undecane+SX, 3-carene+SX, 3-methylcyclohex-2-en-1-one+SX, 14-methyloctadec-1-ene+SX, 4-methylnonan-5-ol+SX, 4-methylnonan-5-one+SX, 4-(3-oxobutyl)phenyl acetate+SX, dodecyl acetate+SX, dodeca-8,10-dien-1-yl acetate+SX, ethyl (2E,4Z)-decadienoate+SX, ethyl-4-methyloctanoate+SX, methyl 2,6,10-trimethyldodecanoate+SX, tetradecan-1-ol+SX, tetradec-11-en-1-ol+SX, tetradec-11-en-1-yl acetate+SX, tridec-4-en-1-yl acetate+SX, (3S,6R)-3-methyl-6-isopropenyl-9-decen-1-yl acetate+SX, (3S,6S)-3-methyl-6-isopropenyl-9-decen-1-yl acetate+SX, alpha-multistriatin+SX, alpha-pinene+SX, endo-brevicomin+SX, exo-brevicomin+SX, camphene+SX, codlelure+SX, codlemone+SX, cuelure+SX, disparlure+SX, dominicalure+SX, eugenol+SX, farnesol+SX, ferrolure+SX, frontalin+SX, gossyplure+SX, grandlure+SX, grandlure I+SX, grandlure II+SX, grandlure III+SX, grandlure IV+SX, hexalure+SX, ipsedienol+SX, ipsenol+SX, japonilure+SX, lineatin+SX, litlue+SX, looplure+SX, medlure+SX, megatomoic acid+SX, methyl eugenol+SX, muscalure+SX, nerolidol+SX, orfralure+SX, oryctalure+SX, ostramone+SX, rhyncolure+SX, siglure+SX, sordidin+SX, sulcatol+SX, trimedlure+SX, trimedlure A+SX, trimedlure B1+SX, trimedlure B2+SX, trimedlure C+SX, trunc-call+SX, (E)-verbenol+SX, (Z)-verbenol+SX, trans-verbenol+SX, and (S)-verbenone+SX.

An application of Present compound can provide an effect of a promotion of the growth of a plant, such as an increase in the rate of seedling establishment, an increase in the number of healthy leaves, an increase in the height of the plant, increase in the weight of the plant, an increase in the leaf area, increase in the number or weight of seeds or fruits, an increase in the number of occasion of flower setting or fruit setting, promoted growth of a root and the like. Also, an application of Present compound can provide an increase of a resistance against an abiotic stress such as a temperature stress (for example, high-temperature stress or low-temperature stress), water stress (for example, drought stress or excess water stress), and a salt stress.

Though the mixed ratio of Present compound to Present ingredient is not particularly limited, examples of the weight ratio (Present compound:Present ingredient) is within a range of 1000:1 to 1:1000, 500:1 to 1:500, 100:1 to 1:100, 50:1 to 1:50, 20:1 to 1:20, 10:1 to 1:10, 3:1 to 1:3, 1:1 to 1:500, 1:1 to 1:100, 1:1 to 1:50, 1:1 to 1:20, and 1:1 to 1:10.

Next, the Formulation Examples are described.

Formulation Example 1

Fifty (50) parts of SX, 3 parts of calcium lignosulfonate, 2 parts of magnesium lauryl sulfate, and 45 parts of synthetic hydrated silicon dioxide are mixed-grinding to obtain a formulation.

Formulation Example 2

Twenty (20) parts of SX, 1.5 parts of sorbitan trioleate are mixed with 28.5 parts of an aqueous solution containing 2 parts of polyvinyl alcohol, and the mixture is then finely-ground by a wet grinding method. To the mixture is then added 40 parts of an aqueous solution containing 0.05 parts of xanthan gum and 0.1 parts of magnesium aluminum silicate, and 10 parts of propylene glycol is further added thereto. The mixture is stirred to obtain a formulation.

Formulation Example 3

Two (2) parts of SX, 88 parts of kaolin clay and 10 parts of talc are mixed-grinding to obtain a formulation.

Formulation Example 4

Five (5) parts of SX, 14 parts of polyoxyethylene styryl phenyl ether, 6 parts of calcium dodecylbenzene sulfonate and 75 parts of xylene are mixed-grinding to obtain a formulation.

Formulation Example 5

Two (2) parts of SX, 1 part of synthetic hydrated silicon dioxide, 2 parts of calcium lignosulfonate, 30 parts of bentonite and 65 parts of kaolin clay are mixed-grinding and thereto is added water, and the mixture is well kneaded and is then granulated and dried to obtain a formulation.

Formulation Example 6

Thirty five (35) parts of a mixture of ammonium polyoxyethylene alkyl ether sulfate and white carbon (weight ratio: 1:1), 20 parts of SX, and 45 parts of water are well mixed to obtain a formulation.

Next, Test Examples are used to show an efficacy of the present compounds on controlling pests.

Test Example 1

Each of plastic pots was filled with soil and thereto soybean (cv: Kurosengoku) seeds were sown and the soybeans were grown in a greenhouse for 10 days, an aqueous suspension of the spores of soybean rust fungi (*Phakopsora pachyrhizi*) was spraying-inoculated. After the inoculation, the soybeans were placed in a greenhouse of 23° C. during daytime and 20° C. during nighttime under a high humidity for 1 day and were then cultivated in the greenhouse for 2 days. Thereafter, any of the present compounds 1-3, 1-5, or 1-10, each of which was made to a formulation according to the similar method to that of Formulation Example 6, was mixed with water so as to be 200 ppm. The mixtures were sprayed to foliar parts so as to adhere adequately on the leaves of the above-mentioned soybean. After the spraying, the soybeans were air-dried, and were then cultivated in the greenhouse for 8 days, and a lesion area was observed. As a result, every of the lesion areas in soybean treated with each of the present compounds showed 30% or less compared to the lesion area in an untreated soybean.

Test Example 2

Each of plastic pots was filled with soil and thereto soybean (cv: Kurosengoku) seeds were sown and the soybens were grown in a greenhouse for 13 days. Thereafter, any of the present compounds 1-2, 1-3, 1-4, 1-5, 1-10, 3-8, or 4-11, each of which was made to a formulation according to the similar method to that of Formulation Example 6, was mixed with water so as to be 200 ppm. The mixtures were sprayed to foliar parts so as to adhere adequately on the leaves of the above-mentioned soybean. After spraying the mixtures, the soybeans were air-dried and after 4 days, an aqueous suspension of the spores of soybean rust fungi (*Phakopsora pachyrhizi*) was spraying-inoculated. After the inoculation, the soybeans were placed in a greenhouse of 23° C. during daytime and 20° C. during nighttime under a high humidity for 1 day and were then cultivated in the greenhouse for 10 days, and a lesion area was observed. As a result, every of the lesion areas in soybean treated with each of the present compounds showed 30% or less compared to the lesion area in an untreated soybean.

Test Example 3

Each of plastic pots was filled with soil and thereto wheat (cv; Apogee) seeds were sown and the wheats were grown in a greenhouse for 10 days. Thereafter, any of the present compounds 1-1, 1-2, 1-3, 1-4, 1-5, 1-10, 1-8, 3-1, 3-16, 3-20, 4-1, 4-2, 4-3, 4-5, 4-8, 4-9, 4-10, 4-12, 6-2, or 6-4, each of which was made to a formulation according to the similar method to that of Formulation Example 6, was mixed with water so as to be 500 ppm. The mixtures were sprayed to foliar parts so as to adhere adequately on the leaves of the above-mentioned wheat. After spraying the mixtures, the wheats were air-dried and after 4 days, an aqueous suspension of the spores of wheat leaf blotch fungi (*Septoria tritici*) was spraying-inoculated. After the inoculation, the wheats were placed at 18° C. under a high humidity for 3 days and then under lighting for 14 to 18 days, and a lesion area was observed. As a result, every of the lesion areas in wheats treated with each of the present compounds showed 30% or less compared to the lesion area in an untreated wheat.

Test Example 4

Each of plastic pots was filled with soil and thereto wheat (cv; SHIROGANE) seeds were sown and the wheats were grown in a greenhouse for 9 days. Any of the present compounds 1-2, 1-5 or 4-12, each of which was made to a formulation according to the similar method to that of Formulation Example 6, was mixed with water so as to be 500 ppm, and the mixtures were sprayed to foliar parts so as to adhere adequately on the leaves of the above-mentioned wheat. After spraying the mixtures, the wheats were air-dried and were then cultivated at 20° C. under lighting for 5 days. The spores of wheat brown rust fungi (*Puccinia recondita*) were sprinkling-inoculated. After the inoculation, the wheats were placed under a dark and humid condition at 23° C. for 1 day and were then cultivated at 20° C. under lighting for 8 days, and a lesion area was observed. As a result, every of the lesion areas in wheats treated with each of the present compounds showed 30% or less compared to the lesion area in an untreated wheat.

Test Example 5

Each of plastic pots was filled with soil and thereto rice (cv; HINOHIKARI) seeds were sown and the plants were grown in a greenhouse for twenty days. Thereafter, any of the present compounds 1-2, 1-3, 1-4, 1-5, 1-8, 1-10, 3-8, 3-16, 3-17, 3-20, 3-28, 3-29, 4-1, 4-8, 4-9, 4-12, or 6-2, each of which was made to a formulation according to the similar method to that of Formulation Example 6, was mixed with water so as to be 500 ppm. The mixtures were sprayed to foliar parts so as to adhere adequately on the leaves of the above-mentioned rice. After spraying the mixtures, the rices were air-dried and were placed at 24° C. during daytime and 20° C. during nighttime under a high humidity for 6 days while the above-mentioned spraying-treated rice were contacted rice seedlings (cv; Hinohikari) infected by rice blast fungi (*Magnaporthe grisea*), and a lesion area was observed. As a result, every of the lesion areas in rices treated with each of the present compounds showed 30% or less compared to the lesion are in an untreated rice.

Test Example 6

Each of plastic pots was filled with soil and thereto barley (cv; MIKAMO GOLDEN) seeds were sown and the barleys were grown in a greenhouse for 7 days. Thereafter, any of the present compounds 1-10, 3-1, 3-3, 3-20, 3-28, 3-29, 4-6, 4-8, or 4-9, each of which was made to a formulation according to the similar method to that of Formulation Example 6, was mixed with water so as to be 200 ppm. The mixtures were sprayed to foliar parts so as to adhere adequately on the leaves of the above-mentioned barley. After spraying the mixtures, the barleys were air-dried and after 2 days, an aqueous suspension of the spores of barley net blotch fungi (*Pyrenophora teres*) was spraying-inoculated. After the inoculation, the barleys were placed at 23° C. during daytime and 20° C. during nighttime under a high humidity for 3 day and then cultivated in a greenhouse for 7 days, and a lesion area was observed. As a result, every of the lesion areas in barleys treated with each of the present compounds showed 30% or less compared to the lesion area in an untreated barley.

Test Example 7

Any of the present compounds 1-4, 1-5, 1-6, 3-9, 3-13, 3-17, 3-23, 3-25, 3-26, 3-29, 3-31, 4-1 or 5-3, each of which was made to a formulation according to the similar method to that of Formulation Example 6, was mixed with water so as to be 500 ppm. The mixtures were sprayed to foliar parts of the cabbage seedling (on the developmental stage of the second to third true leaf) that was planted in a container so as to adhere adequately on the leaves of the above-mentioned cabbage. After the spraying, the stem and leaf of the seedling was cut out and then was installed into the container that was covered with the filter paper. Five heads of cabbage moth (*Plutella xylostella*) at the second instar larval stages were released into the cup. After 5 days, the surviving insects were counted, and the mortality of insects was calculated by the following equation.

Morality (%)={1−the number of the surviving insects/5}×100

As a result, every of the morality treated with each of the present compounds showed 80% or more.

Test Example 8

Each of plastic pots was filled with soils and thereto cucumber (cv; SAGAMIHANJIRO) seeds were sown and the plants were grown in a greenhouse for 12 days. Thereafter, any of the present compounds 1-1, 1-2, 1-3, 1-4, 1-5, 1-10, 3-8, 3-16, 3-28, 3-29, 4-1, 4-6, or 6-2, each of which was made to a formulation according to the similar method to that of Formulation Example 6, was adjusted with water so as to be a prescribed concentration (500 ppm). The adjusted solutions were sprayed to foliar parts so as to adhere adequately on the leaves of the above-mentioned cucumber. After spraying the mixtures, the plants were air-dried and the spores of powdery mildew fungi (*Sphaerotheca fuliginea*; a QoI resistant strains where among the genes coding cytochrome b, a glycine residue as an amino acid residue at the 143rd of the cytochrome b is mutated to an alanine residue) were sprinkling-inoculated. The cucumbers were cultivated in a greenhouse of 24° C. during daytime and 20° C. during nighttime for 8 days, and a lesion area was observed. As a result, every of the lesion areas in cucumbers treated with each of the present compounds showed 30% or less compared to the lesion area in an untreated cucumber.

Test Example 9

Each of plastic pots was filled with soil and thereto Kidney bean (cv; NAGAUZURA SAITO) seeds were sown and the kidney beans were grown in a greenhouse for 8 days. Thereafter, any of the present compounds 1-1, 1-2, 1-3, 1-5, 1-10, 3-16, 3-22, 4-2, 4-3, 4-4, 4-8, or 6-2, each of which was made to a formulation according to the similar method to that of Formulation Example 6, was mixed with water so as to be a prescribed concentration (500 ppm). The adjusted solutions were sprayed to foliar parts so as to adhere adequately on the leaves of the above-mentioned kidney bean. After spraying the mixtures, the kidney beans were air-dried and a PDA medium containing hyphae of kidney bean sclerotinia rot fungi (*Sclerotinia sclerotiorum*) was placed on the leaves of the kidney bean. After the inoculation, all kidney beans were placed under a high humidity during only night and after four days, a lesion area was observed. As a result, every of the lesion areas in kidney beans treated with each of the present compounds showed 30% or less compared to the lesion area in an untreated kidney beans.

Test Example 10

Each of plastic pots was filled with soil and thereto barley (cv; NISHINOHOSHI) seeds were sown and the barleys were grown in a greenhouse for 7 days. Thereafter, any of the present compounds 1-2, 1-3, 1-4, 1-10, 3-6, 3-7, 3-8, 3-20, 3-28, 3-29, 4-3, 4-4, 4-5, 4-7, 4-11, 6-2, or 6-3, each of which was made to a formulation according to the similar method to that of Formulation Example 6, was mixed with water so as to be a prescribed concentration (200 ppm). The mixtures were sprayed to foliar parts so as to adhere adequately on the leaves of the above-mentioned barley. After spraying the mixtures, the barleys were air-dried and after 2 days, an aqueous suspension of the spores of barley scald fungi (*Rhynchosporium secalis*) was spraying-inoculated. After the inoculation, the barleys were placed at 23° C. during daytime and 20° C. during nighttime under a high humidity for 3 day and then cultivated in a greenhouse for 7 days, and a lesion area was observed. As a result, every of the lesion areas in barleys treated with each of the present compounds showed 30% or less compared to the lesion area in an untreated barley.

Test Example 11

Each of plastic pots was filled with soil and thereto cucumber (cv; SAGAMIHANJIRO) seeds were sown and the cucumber were grown in a greenhouse for 19 days. Thereafter, any of the present compounds 3-8, 4-1, 4-5 or 6-2, each of which was made to a formulation according to the similar method to that of Formulation Example 6, was mixed with water so as to be a prescribed concentration (200 ppm). The mixtures were sprayed to foliar parts so as to adhere adequately on the leaves of the above-mentioned cucumber. After spraying the mixtures, the plants were air-dried and after 1 day, an aqueous suspension of the spores of cucumber anthracnose fungi (*Colletotrichum lagenarium*) was spraying-inoculated. After the inoculation, the cucumbers were placed firstly at 23° C. under a high humidity for 1 day and were then cultivated in a greenhouse of 24° C. during daytime and 20° C. during nighttime for 6 days, and a lesion area was observed. As a result, every of the lesion areas in cucumbers treated with each of the present compounds showed 30% or less compared to the lesion area in an untreated cucumber.

Test Example 12

Approximately 30 heads of cotton aphid (*Aphis gossypii*) (all stages of life) were released to cucumber seedling (on the developmental stage of the first true leaf) that was planted in a plastic cup, and the cucumber seedlings were allowed to stand for 1 day. Thereafter, any of the present compounds 1-2, 1-3, 1-4, 3-1, 3-8, 3-11, 3-12, 3-29, 4-6 or 5-3, each of which was mixed with water so as to be 500 ppm as an effective ingredient concentration, and the mixtures were sprayed into the cucumber seedling.

After 6 days, the number of the surviving cotton aphids that were parasitic on the cucumber leaf was examined, ad the controlling value was calculated by the following equation.

Controlling value (%)={1−(Cb×Tai)/(Cai×Tb)}×100 wherein the symbols in the formula represent the following descriptions.

Cb: Number of the test insects in untreated group;
Cai: Number of the surviving insects in untreated group;
Tb: Number of the test insects in treated group;
Tai: Number of the surviving insects in treated group;

Here the "untreated group" represents a group where the test agent solution according to the similar method to those described in the above-mentioned Formulation Examples, which was prepared by diluting a formulation not containing the present compound with the same amount of water as that used in the treated group, were sprayed.

As a result, the controlling value in the treated group treated with each of the present compounds showed 60% or more.

Test Example 13

Each of plastic pots was filled with soil and thereto cucumber (cv; SAGAMIHANJIRO) seeds were sown and the cucumbers were grown in a greenhouse for 19 days. Thereafter, any of the present compounds 1-1, 1-2, 1-5, 3-3, 3-20, 3-28, 4-1, 4-2, 4-3, or 6-2, each of which was made to a formulation according to the similar method to that of Formulation Example 6, was mixed with water so as to be 200 ppm. The mixtures were sprayed to foliar parts so as to adhere adequately on the leaves of the above-mentioned cucumber. After spraying the mixtures, the cucumbers were air-dried and after 1 day, an aqueous suspension of the zoospores of cucumber downy mildew fungi (*Pseudoperonospora cubensis*) was spraying-inoculated. After the inoculation, the cucumbers were placed firstly at 23° C. under a high humidity for 1 day and were then cultivated in a greenhouse of 24° C. during daytime and 20° C. during nighttime for 6 days, and a lesion area was observed. As a result, every of the lesion areas in cucumbers treated with each of the present compounds showed 30% or less compared to the lesion area in an untreated cucumber.

Test Example A

The tests were conducted using Present compound D-1, A-2, A-3, D-2, C-2, C-3, C-4, C-11, C-8, C-13, C-15, D-13, D-11, D-12, D-18, D-19, D-23, D-25, 1-9, 1-10, E-9, E-24, E-26, or E-12 according to Test Example 1, and as a result, every of the lesion areas in soybeans treated with each of the present compounds showed 30% or less compared to the lesion area in an untreated soybean.

Test Example B

The tests were conducted using Present compound 1-1, 3-8, 3-27, D-1, D-8, A-2, A-3, D-3, D-2, D-4, C-1, C-2, C-3, C-4, D-5, D-7, C-6, C-5, C-7, C-11, C-8, C-9, C-10, C-12, C-13, C-14, C-15, D-10, D-13, D-11, D-14, D-12, D-16, D-15, D-17, D-18, D-19, D-20, D-23, D-25, E-1, E-2, E-3, E-4, E-5, E-6, E-7, E-8, E-9, E-11, E-12, E-13, E-14, E-15, E-16, E-17, E-18, E-19, E-20, E-21, E-22, E-23, E-24, E-25, E-26, E-27, E-28, E-29, E-30, or 1-9 according to Test Example 2, and as a result, every of the lesion areas in soybeans treated with each of the present compounds showed 30% or less compared to the lesion area in an untreated soybean.

Test Example C

The tests were conducted using Present compound 3-25, 3-26, 3-27, 3-31, 3-34, D-1, D-8, A-2, A-3, D-3, D-2, D-4, C-1, C-2, C-3, C-4, D-5, D-6, D-7, C-6, C-5, C-7, C-11, C-8, C-9, C-10, C-12, C-13, C-14, D-9, D-18, D-19, D-20, E-8, E-10, E-11, E-3, E-4, E-2, E-5, E-14, E-12, E-6, E-15, E-16, E-17, E-18, E-19, E-20, E-21, E-22, E-23, E-24, E-25, E-26, E-27, E-28, E-29, E-30, or E-13 according to Test Example 3, and as a result, every of the lesion areas in wheats treated with each of the present compounds showed 30% or less compared to the lesion area in an untreated wheat.

Test Example D

The tests were conducted using Present compound D-1, D-8, A-2, A-3, D-3, D-2, C-1, C-2, C-3, C-4, D-5, D-7, D-9, D-19, D-20, C-6, C-5, C-11, C-8, C-12, C-13, C-14, E-8, E-10, E-11, E-3, E-4, E-2, E-5, E-14, E-12, E-6, E-15, E-16, E-17, E-18, E-19, E-21, E-22, E-24, E-25, E-26, E-29, E-30, or E-13 according to Test Example 4, and as a result, every of the lesion areas in wheats treated with each of the present compounds showed 30% or less compared to the lesion area in an untreated wheat.

Test Example E

The tests were conducted using Present compound 3-27, 3-31, 3-32, 3-33, D-1, D-8, A-2, A-3, B-1, D-3, C-1, C-2, C-3, C-4, C-5, C-11, C-8, C-13, C-14, D-9, D-18, D-19, D-20, E-8, E-2, E-5, E-14, E-12, E-6, E-13, E-15, E-16, E-17, E-18, E-19, E-20, E-21, E-22, E-23, E-24, E-25, E-26, E-27, E-28, E-29, or E-30 according to Test Example 5, and as a result, every of the lesion areas in wheats treated with each of the present compounds showed 30% or less compared to the lesion area in an untreated wheat.

Test Example F

The tests were conducted using Present compound 1-4, 1-5, 1-1, 1-2, 1-3, 1-8, 3-4, 3-8, 3-7, 4-1, 4-4, 4-5, 4-7, 3-25, 3-26, 3-27, 3-31, 3-32, 3-33, 4-11, 3-34, D-1, D-8, A-2, A-3, B-1, D-2, D-4, D-9, C-1, C-2, C-3, C-4, D-5, D-6, D-7, C-6, C-5, C-7, C-11, C-8, C-9, C-10, C-12, C-13, C-14, C-15, D-10, D-13, D-11, D-14, D-12, D-16, D-15, D-17, D-18, D-19, D-20, D-23, D-25, E-1, E-7, E-8, E-10, E-3, E-4, E-2, E-9, E-5, E-14, E-12, E-6, E-13, E-15, E-16, E-17, E-18, E-19, E-20, E-21, E-22, E-23, E-24, E-25, E-26, E-27, E-28, E-29, E-30, 1-10, or 1-9 according to Test Example 6, and as a result, every of the lesion areas in barleys treated with each of the present compounds showed 30% or less compared to the lesion area in an untreated barley.

Test Example G

The tests were conducted using Present compound D-1, D-8, A-3, B-1, D-3, D-2, C-1, C-2, C-3, D-5, D-19, C-5, C-11, C-10, C-12, C-13, C-14, E-5, E-14, E-12, E-6, E-21, E-24, E-25, E-26, E-27, E-28, E-29, E-30, or E-13 according to Test Example 7, and as a result, every of the moralities treated with each of the present compounds showed 80% or more.

Test Example H

The tests were conducted using Present compound 3-31, 4-2, D-1, D-8, A-2, A-3, D-3, D-2, D-4, C-1, C-2, C-3, C-4, D-5, D-6, D-7, C-6, C-5, C-7, C-11, C-8, C-9, C-10, C-12, C-13, C-14, D-9, D-18, D-19, D-20, E-8, E-10, E-11, E-3, E-4, E-5, E-14, E-12, E-6, E-13, E-15, E-16, E-17, E-18, E-19, E-20, E-21, E-22, E-23, E-24, E-25, E-26, E-27, E-28, E-29, E-30, or 1-10 according to Test Example 8, and as a result, every of the lesion areas in cucumber treated with each of the present compounds showed 30% or less compared to the lesion area in an untreated cucumber.

Test Example I

The tests were conducted using Present compound 3-25, D-1, D-8, A-2, A-3, D-3, D-2, C-2, C-3, C-4, C-7, C-11, C-8, C-9, C-10, C-14, D-18, D-19, D-20, E-8, E-10, E-11, E-3, E-4, E-2, E-5, E-14, 1-10, E-12, E-6, E-15, E-16, E-17, E-18, E-19, E-20, E-21, E-24, E-25, E-26, E-27, E-28, E-30, or E-13 according to Test Example 9, and as a result, every of the lesion areas in kidney beans treated with each of the present compounds showed 30% or less compared to the lesion area in an untreated kidney bean.

Test Example J

The tests were conducted using Present compound 3-25, 3-26, 3-27, 3-31, 3-32, 3-33, 3-34, D-1, D-8, A-2, A-3, B-1, D-2, D-4, C-1, C-2, C-3, C-4, D-5, D-6, D-7, C-6, C-5, C-7, C-8, C-9, C-10, 1-1, 1-8, or 1-9 according to Test Example 10, and as a result, every of the lesion areas in barleys treated with each of the present compounds showed 30% or less compared to the lesion area in an untreated barley.

Test Example L

The tests were conducted using Present compound D-1, D-8, A-2, A-3, D-3, D-2, C-1, C-2, C-3, D-5, D-6, D-7, C-7, C-11, C-10, C-12, C-14, E-8, E-10, E-11, E-3, E-4, E-2, E-14, E-12, E-6, E-24, E-25, E-26, E-27, E-28, E-29, E-30, or D-9 according to Test Example 12, and as a result, every of the controlling values in the treated groups that were treated with each of the present compounds showed 60% or more.

Test Example M

The tests were conducted using Present compound 3-25, 3-27, 3-32, 3-33, 3-34, D-5, D-6, D-7, C-13, C-14, D-16, D-19, D-23, D-27, D-28, D-30, E-8, E-11, E-3, E-4, E-2, E-9, E-5, E-14, E-12, E-6, E-13, E-15, E-16, E-17, E-18, E-21, E-22, E-23, E-24, E-26, E-27, E-28, E-29, E-30, or 1-10 according to Test Example 13, and as a result, every of the lesion areas in cucumbers treated with each of the present compounds showed 30% or less compared to the lesion area in an untreated cucumber.

Test Example N

Each of plastic pots was filled with soil and thereto cucumber (cv; SAGAMIHANJIRO) seeds were sown and the cucumbers were grown in a greenhouse for 19 days. Thereafter, any of the present compounds 4-1, 3-25, 3-27, 3-28, 3-32, 3-34, D-1, A-2, D-2, D-5, C-6, C-5, C-13, D-10, D-13, E-1, E-8, E-3, E-9, E-5, E-14, E-12, E-15, E-16, E-17, E-18, E-22, E-24, E-26, E-28, E-30, or E-6, each of which was made to a formulation according to the similar method to that of Formulation Example 6, was mixed with water so as to be 50 ppm. The mixtures were sprayed to foliar parts so as to adhere adequately on the leaves of the above-mentioned cucumber. After spraying the mixtures, the cucumbers were air-dried and after 1 day, an aqueous suspension of the zoospores of cucumber downy mildew fungi (*Pseudoperonospora cubensis*) was spraying-inoculated. After the inoculation, the cucumbers were placed firstly at 23° C. under a high humidity for 1 day and were then cultivated in a greenhouse of 24° C. during daytime and 20° C. during nighttime for 6 days, and a lesion area was observed. As a result, every of the lesion areas in cucumbers treated with each of the present compounds showed 30% or less compared to the lesion area in an untreated cucumber.

Test Example O

Each of plastic pots was filled with soil and thereto wheat (cv; APOGEE) seeds were sown and the wheats were grown in a greenhouse for 10 days. Thereafter, any of the present compounds 1-1, 1-2, 1-3, 1-4, 1-5, 1-8, 1-9, 1-10, C-1, C-2, C-3, C-4, C-5, C-6, C-7, C-8, C-9, C-10, C-11, C-12, C-13, C-14, C-15, D-1, D-2, D-5, D-6, D-7, D-8, D-10, D-11, D-12, D-13, D-14, D-15, D-16, D-17, D-18, D-19, D-20, A-2, A-3, B-1, E-1, E-2, E-3, E-4, E-5, E-6, E-7, E-8, E-9, E-11, E-12, E-13, E-14, E-15, E-16, E-17, E-18, E-19, E-20, E-21, E-22, E-23, E-24, E-25, E-26, E-27, E-28, E-29, E-30, 3-1, 3-6, 3-8, 3-7, 4-1, 4-4, 4-5, 4-8, 4-9, 3-20, 3-25, 3-26, 3-27, 3-28, 3-29, 3-30, 3-31, 3-32, 3-33, or 3-34, each of which was made to a formulation according to the similar method to that of Formulation Example 6, was mixed with water so as to be 200 ppm. The mixtures were sprayed to foliar parts so as to adhere adequately on the leaves of the above-mentioned wheat. After spraying the mixtures, the wheats were air-dried and after 4 days, an aqueous suspension of the spores of wheat leaf blotch fungi (*Septoria tritici*) was spraying-inoculated. After the inoculation, the wheats were placed at 18° C. under a high humidity for 3 days and then under lighting for 14 to 18 days, and a lesion area was observed. As a result, every of the lesion areas in wheats treated with each of the present compounds showed 30% or less compared to the lesion area in an untreated wheat.

Test Example P

Each of plastic pots was filled with soil and thereto wheat (cv; APOGEE) seeds were sown and the wheats were grown in a greenhouse for 10 days, and an aqueous suspension of the spores of wheat leaf blotch fungi (*Septoria tritici*) was spraying-inoculated thereto. After the inoculation, the wheats were placed at 18° C. under a high humidity for 3 days. Any of the present compound 1-1, 1-2, 1-3, 1-4, 1-5, 1-8, 1-9, 1-10, C-1, C-2, C-3, C-4, C-5, C-6, C-7, C-8, C-9, C-10, C-11, C-12, C-13, C-14, C-15, D-1, D-2, D-5, D-7, D-8, D-10, D-11, D-12, D-13, D-14, D-15, D-16, D-17, D-18, D-19, D-20, A-2, A-3, E-1, E-2, E-3, E-4, E-5, E-6, E-7, E-8, E-9, E-10, E-11, E-12, E-13, E-14, E-15, E-16, E-17, E-18, E-19, E-20, E-21, E-22, E-23, E-24, E-25, E-26, E-27, E-28, E-29, E-30, 4-1, 4-5, 4-8, 4-9, 3-20, 3-25, 3-26, 3-37, or 3-33, each of which was made to a formulation according to the similar method to that of Formulation Example 6, was mixed with water so as to be 200 ppm. The mixtures were sprayed to foliar parts so as to adhere adequately on the leaves of the above-mentioned wheat. After the spraying, the wheats were air-dried, and placed under lighting for 14 to 18 days, and a lesion area was observed. As a result, every of the lesion areas in wheats treated with each of the present compounds showed 30% or less compared to the lesion area in an untreated wheat.

Test Example Q

Each of plastic pots was filled with soil and thereto wheat (cv; SHIROGANE) seeds were sown and the wheats were grown in a greenhouse for 9 days. Any of the present compound 1-1, 1-2, 1-3, 1-4, 1-5, 1-8, 1-9, 1-10, C-1, C-2, C-3, C-4, C-5, C-6, C-7, C-8, C-9, C-10, C-1, C-2, C-3, C-4, C-5, C-6, C-7, C-8, C-9, C-10, C-11, C-12, C-13, C-14, C-15, D-1, D-2, D-5, D-7, D-8, D-10, D-11, D-12, D-13, D-14, D-15, D-16, D-17, D-18, D-19, D-20, D-23, D-25, A-2, A-3, E-1, E-2, E-3, E-4, E-5, E-6, E-8, E-9, E-10, E-11, E-12, E-13, E-14, E-15, E-16, E-17, E-18, E-19, E-20, E-21, E-22, E-24, E-25, E-26, E-27, E-28, E-29, E-30, 3-1, 3-8, 4-12, 4-9, 3-20, 3-25, 3-26, 3-27, or 3-29, each of which was made to a formulation according to the similar method to that of Formulation Example 6, was mixed with water so as to be 200 ppm, and the mixtures were sprayed to foliar parts so as to adhere adequately on the leaves of the above-mentioned wheat. After spraying the mixtures, the wheats were air-dried and were then cultivated at 20° C. under lighting for 5 days. The spores of wheat brown rust fungi (*Puccinia recondita*) were sprinkling-inoculated. After the inoculation, the wheats were placed under a dark and humid condition at 23° C. for 1 day and were then cultivated at 20° C. under lighting for 8 days, and a lesion area was observed. As a result, every of the lesion areas in wheats treated with each of the present compounds showed 30% or less compared to the lesion area in an untreated wheat.

Test Example R

Each of plastic pots was filled with soil and thereto rice (cv; HINOHIKARI) seeds were sown and the wheats were grown in a greenhouse for 20 days. Any of the present compound 1-1, 1-2, 1-3, 1-4, 1-5, 1-9, 1-10, C-1, C-2, C-3, C-4, C-5, C-6, C-7, C-8, C-9, C-10, C-11, C-12, C-13, C-14, C-15, D-1, D-2, D-5, D-7, D-8, D-10, D-11, D-13, D-16, D-17, D-18, D-19, D-20, D-23, D-25, A-2, A-3, B-1, E-1, E-2, E-3, E-4, E-5, E-6, E-7, E-8, E-9, E-10, E-11, E-13, E-14, E-16, E-17, E-18, E-19, E-20, E-21, E-22, E-23, E-24, E-25, E-26, E-27, E-28, E-29, E-30, 4-1, 4-5, 4-8, 4-9, 3-20, 3-25, 3-26, 3-37, 3-33, 3-1, 3-8, 4-1, 4-5, 4-6, 4-8, 4-9, 3-16, 3-20, 3-25, 3-26, 3-27, 3-28, 3-29, 3-20, 3-31, 3-32, 3-33, or 4-11, each of which was made to a formulation according to the similar method to that of Formulation Example 6, was mixed with water so as to be 200 ppm, and the mixtures were sprayed to foliar parts so as to adhere adequately on the leaves of the above-mentioned rice. After spraying the mixtures, the rices were air-dried and were placed at 24° C. during daytime and 20° C. during nighttime under a high humidity for 6 days while the above-mentioned spraying-treated rice were contacted rice seedlings (cv; Hinohikari) infected by rice blast fungi (*Magnaporthe grisea*), and a lesion area was observed. As a result, every of the lesion areas in plants treated with each of the present compounds showed 30% or less compared to the lesion are in an untreated rice.

Test Example S

Each of plastic pots was filled with soils and thereto cucumber (cv; SAGAMIHANJIRO) seeds were sown and the cucumber were grown in a greenhouse for 12 days. Thereafter, any of the present compound 1-1, 1-2, 1-3, 1-4, 1-5, 1-9, 1-10, C-1, C-2, C-3, C-4, C-5, C-6, C-7, C-8, C-9, C-10, C-11, C-12, C-14, D-1, D-2, D-3, D-4, D-5, D-6, D-7, D-8, D-10, D-11, D-12, D-13, D-14, D-15, D-16, D-17, D-18, D-19, D-20, D-23, D-24, D-25, D-26, D-27, D-28, D-29, D-30, A-2, A-3, E-1, E-2, E-3, E-4, E-5, E-6, E-7, E-8, E-9, E-11, E-12, E-13, E-14, E-15, E-16, E-17, E-18, E-19, E-21, E-22, E-23, E-24, E-25, E-26, E-27, E-28, E-29, E-30, 4-7, or 4-8, each of which was made to a formulation according to the similar method to that of Formulation Example 6, was adjusted with water so as to be 200 ppm. The adjusted solutions were sprayed to foliar parts so as to adhere adequately on the leaves of the above-mentioned cucumber. After spraying the mixtures, the plants were air-dried and the spores of powdery mildew fungi (*Sphaerotheca fuliginea*; a QoI resistant strains where among the genes coding cytochrome b, a glycine residue as an amino acid residue at the 143rd of the cytochrome b is mutated to an alanine residue) were sprinkling-inoculated. The cucumbers were cultivated in a greenhouse of 24° C. during daytime and 20° C. during nighttime for 8 days, and a lesion area was observed. As a result, every of the lesion areas in cucumbers treated with each of the present compounds showed 30% or less compared to the lesion area in an untreated cucumber.

Test Example T

Each of plastic pots was filled with soil and thereto Kidney bean (cv; NAGAUZURA SAITO) seeds were sown and the kidney beans were grown in a greenhouse for 8 days. Thereafter, any of the present compound 1-5, 1-2, 1-3, D-1, A-2, A-3, D-3, C-2, C-7, C-8, C-9, C-10, C-14, C-15, D-10, D-11, D-14, D-12, D-16, D-17, D-18, D-19, D-20, D-23, D-25, D-26, D-27, D-28, D-30, E-1, E-7, E-8, E-11, E-3, E-4, E-2, E-5, E-14, E-12, E-6, E-13, E-15, E-16, E-17, E-21, E-24, E-25, E-26, E-27, E-28, E-30, 3-16, or 4-11, each of which was made to a formulation according to the similar method to that of Formulation Example 6, was mixed with water so as to be 200 ppm. The adjusted solutions were sprayed to foliar parts so as to adhere adequately on the leaves of the above-mentioned kidney bean. After spraying the mixtures, the kidney beans were air-dried and a PDA medium containing hyphae of kidney bean *sclerotinia* rot fungi (*Sclerotinia sclerotiorum*) was placed on the leaves of the kidney bean. After the inoculation, all kidney beans were placed under a high humidity during only night and after four days, a lesion area was observed. As a result, every of the lesion areas in kidney beans treated with each of the present compounds showed 30% or less compared to the lesion area in an untreated kidney beans.

Test Example U

Each of plastic pots was filled with soil and thereto barley (cv; NISHINOHOSHI) seeds were sown and the barleys were grown in a greenhouse for 7 days. Thereafter, any of the present compound 3-6, 4-6, 4-8, 4-12, 4-9, 4-10, 3-16, 3-20, 3-22, 3-25, 3-26, 3-27, 3-28, 3-29, 3-31, 3-32, 3-33, 3-1, 3-34, 3-36, 1-4, 1-5, 1-1, 1-2, 1-3, 1-8, D-1, D-8, 1-10, A-3, D-3, D-2, D-4, C-1, C-2, C-3, C-4, C-5, D-5, D-6, D-7, D-18, D-19, D-20, C-6, C-5, C-11, C-8, C-10, C-12, C-13, C-14, E-8, E-10, E-11, E-3, E-4, E-2, E-5, E-14, E-12, E-6, E-13, E-15, E-16, E-17, E-18, E-19, E-20, E-21, E-22, E-23, E-24, E-25, E-26, E-27, E-28, E-29, E-30, or D-9, each of which was made to a formulation according to the similar method to that of Formulation Example 6, was mixed with water so as to be 500 ppm. The mixtures were sprayed to foliar parts so as to adhere adequately on the leaves of the above-mentioned barley. After spraying the mixtures, the barleys were air-dried and after 2 days, an aqueous suspension of the spores of barley scald fungi (*Rhynchosporium secalis*) was spraying-inoculated. After the inoculation, the barleys were placed at 23° C. during daytime and 20° C. during nighttime under a high humidity for 3 day and then cultivated in a greenhouse for 7 days, and a lesion area was observed. As a result, every of the lesion areas in barleys treated with each of the present compounds showed 30% or less compared to the lesion area in an untreated barley.

Test Example V

Each of plastic pots was filled with soil and thereto soybean (cv: TACHINAGAHA) seeds were sown and the soybens were grown in a greenhouse for 13 days. Thereafter, any of the present compound C-15, D-10, D-13, D-11, D-14, D-12, D-16, D-15, D-17, D-18, D-19, D-20, D-23, D-25, E-1, E-7, E-8, E-10, E-11, E-3, E-4, E-2, E-9, E-5, E-12, E-13, E-14, E-15, E-16, E-17, E-18, E-21, E-22, E-23, E-24, E-25, E-26, E-27, E-28, E-29, E-30, or E-19, each of which was made to a formulation according to the similar method to that of Formulation Example 6, was mixed with water so as to be 200 ppm. The mixtures were sprayed to foliar parts so as to adhere adequately on the leaves of the above-mentioned soybean. After spraying the mixtures, the soybeans were air-dried and after 2 days, an aqueous suspension of the spores of soybean frogeye leaf spot disease fungi (*Cercospora sojina*) was spraying-inoculated. After the inoculation, the soybeans were placed in a greenhouse of 23° C. under a high humidity for 4 days, and were then cultivated in the greenhouse of 23° C. for 15 days, and a lesion area was observed. As a result, every of the lesion areas in soybean treated with each of the present compounds showed 30% or less compared to the lesion area in an untreated soybean.

Test Example W

Each of plastic pots was filled with soil and thereto soybean (cv: TACHINAGAHA) seeds were sown and the soybens were grown in a greenhouse for 13 days. An aqueous suspension of the spores of soybean frogeye leaf spot disease fungi (*Cercospora sojina*) was spraying-inoculated, and after the inoculation, the soybeans were placed in a greenhouse of 23° C. under a high humidity for 4 days. After 5 days of the inoculation, any of the present compound 1-4, 1-2, 1-10, A-2, A-3, D-2, C-1, C-2, C-4, C-6, C-13, 4-8, or 4-9, each of which was made to a formulation according to the similar method to that of Formulation Example 6, was adjusted with water so as to be 200 ppm. The adjusted solutions were sprayed to foliar parts so as to adhere adequately on the leaves of the above-mentioned soybean. The soybeans were air-dried and were then cultivated in the greenhouse for 14 days, and a lesion area was observed. As a result, every of the lesion areas in soybean treated with each of the present compounds showed 30% or less compared to the lesion area in an untreated soybean.

Test Example X

Each of plastic pots was filled with soils and thereto tomato (cv; PATIO) seeds were sown and the cucumber were grown in a greenhouse for 19 days. Thereafter, any of the present compound 1-5, 1-2, 1-3, D-1, 1-9, 1-10, A-2, A-3, D-3, D-2, D-4, C-1, C-2, C-3, D-5, D-7, C-6, C-5, C-7, C-11, C-8, C-9, C-10, C-12, D-18, D-10, D-13, D-11, D-14, D-12, D-16, D-15, D-17, D-18, D-20, D-24, D-25, D-26, D-27, D-29, D-30, E-1, E-7, E-8, E-3, E-2, E-9, E-6, E-13, E-15, E-16, E-17, E-18, E-19, E-22, E-24, E-25, E-26, E-28, E-29, E-30, 3-1, 3-20, or 3-31, each of which was made to a formulation according to the similar method to that of Formulation Example 6, was mixed with water so as to be 200 ppm. The mixtures were sprayed to foliar parts so as to adhere adequately on the leaves of the above-mentioned tomato. After spraying the mixtures, the tomatoes were air-dried and after 1 day, an aqueous suspension of the spores of tomato early blight fungi (*Alternaria solani*; a QoI resistant strains where among the genes coding cytochrome b, a phenylalanine residue as an amino acid residue at the 129th of the cytochrome b is mutated to an leucine residue) were spraying-inoculated. After the inoculation, the tomatoes were placed at 15° C. under a high humidity for 6 days, and a lesion area was observed. As a result, every of the lesion areas in tomatoes treated with each of the present compounds showed 30% or less compared to the lesion area in an untreated tomato.

Test Example Y

Each of plastic pots was filled with soils and thereto soybean (cv; KUROSENGOKU) seeds were sown and the cucumber were grown in a greenhouse for 13 days. Thereafter, the spores of soybean powdery mildew fungi (*Erysiphe diffusa*) was sprinkling-inoculated. After 2 days from the inoculation, any of the present compound C-15, D-10, D-13, D-11, D-14, D-12, D-16, D-15, D-17, D-18, D-19, D-20, D-26, D-27, D-28, D-29, D-30, E-1, E-2, E-3, E-4, E-5, E-6, E-7, E-8, E-9, E-10, E-11, E-12, E-13, E-14, E-15, E-16, E-17, E-18, E-21, E-23, E-24, E-25, E-26, E-27, E-28, E-29, E-30, or E-19, each of which was made to a formulation according to the similar method to that of Formulation Example 6, was mixed with water so as to be 200 ppm. The mixtures were sprayed to foliar parts so as to adhere adequately on the leaves of the above-mentioned soybean. After spraying the mixtures, the soybeans were air-dried and cultivated in a greenhouse for 7 days, and a lesion area was observed. As a result, every of the lesion areas in plants treated with each of the present compounds showed 30% or less compared to the lesion area in an untreated soybean.

Test Example Z

Each of plastic pots was filled with soils and thereto tomato (cv; PATIO) seeds were sown and the cucumber were grown in a greenhouse for 20 days. The present compound E-6, which was made to a formulation according to the similar method to that of Formulation Example 6, was mixed with water so as to be 500 ppm. The mixtures were sprayed to foliar parts so as to adhere adequately on the leaves of the above-mentioned tomato. After spraying the mixtures, the tomatoes were air-dried, and after 1 day, an aqueous suspension of the spores of tomato late blight fungi (*Phytophthora infestans*) was spraying-inoculated. After the inoculation, the tomatoes were were placed firstly at 23° C. under a high humidity for 1 day and were then cultivated in a greenhouse for 4 days, and a lesion area was observed. As a result, every of the lesion areas in tomatoes treated with each of the present compounds showed 30% or less compared to the lesion area in an untreated tomato.

Test Example AA

Any of Present compound 1-2, 1-3, 1-5, D-1, D-8, A-2, A-3, D-3, D-2, D-4, C-1, C-2, C-3, C-4, D-5, D-6, D-7, C-6, C-5, C-7, C-11, C-8, C-9, C-10, C-14, C-15, D-10, D-13, D-11, D-14, D-12, D-16, D-15, D-17, E-1, E-7, E-8, E-10, E-11, E-3, E-4, E-2, E-9, E-5, E-14, E-12, E-6, E-13, D-9, E-17, E-16, E-15, E-18, E-19, E-20, E-21, E-22, E-23, E-24, E-25, E-26, E-27, E-28, E-30, D-18, D-19, D-23, D-26, D-27, D-28, D-29, D-30, or D-20 were diluted with dimethylsulfoxide so as to contain 150 ppm. 1 μL of the dilution solutions were dispensed into titer plate, and thereafter, thereto was then dispensed 150 μL of a potato dextrose broth to which conidia of tomato leaf blight fungus (*Cladosporium fulvum*; a QoI resistant strains where among the genes coding cytochrome b, a phenylalanine residue as an amino acid residue at the 129th of the cytochrome b is mutated to an leucine residue) were inoculated in advance. This plate was cultured at 18° C. for 5 days, thereby allowing tomato leaf blight fungus to undergo proliferation, and the absorbance at 550 nm of each well of the titer plate was then measured to determine a degree of growth of the tomato leaf blight fungus. As a result, every of the growth in tomatoes in treated groups treated with each of the present compounds showed 50% or less compared to the growth in an untreated tomato.

It was clearly found by the tests described in Test Example 8, Test Example H, Test Example S, and Test Example AA that Present compound is useful to control plant pathogens fungus that may contain a mutation for conferring a resistance to Qo inhibitor.

Next, comparative test examples are shown. Comparative test compounds cf1 to cf5 described in WO 2016/088747 are the following compounds.

[Chem.308]

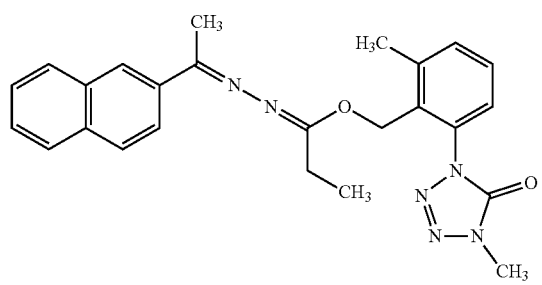

cf1

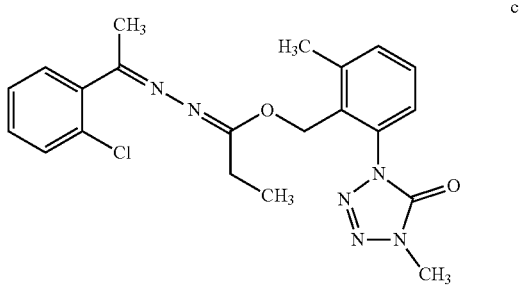

cf2

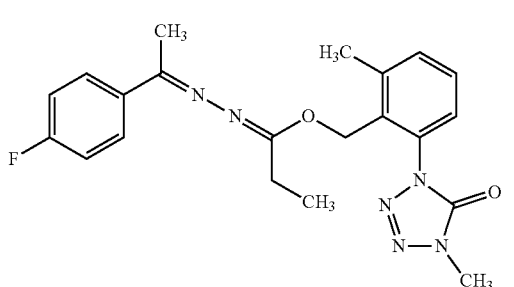

cf3

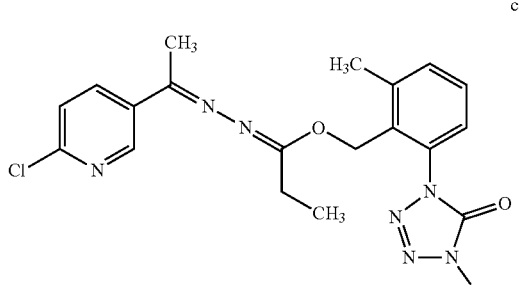

cf4

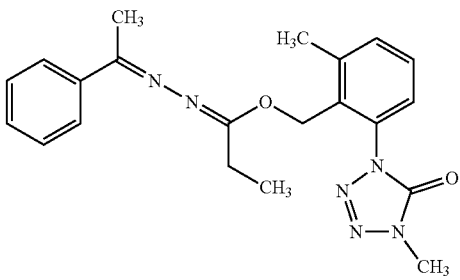

cf5

Comparative Test Example 1

As a result of test using the comparative test compound cf1 according to Test Example T, every of the lesion areas in kidney bean in treated groups treated with the comparative compound showed 50% or more compared to the lesion area in an untreated kidney bean.

Comparative Test Example 2

As a result of test using the comparative test compound cf1 according to Test Example X, every of the lesion areas in tomato in treated groups treated with the comparative compound showed 70% or more compared to the lesion area in an untreated tomato.

Comparative Test Example 3

As a result of test using the comparative test compound cf1 according to Test Example W, every of the lesion areas in soybean in treated groups treated with the comparative compound showed 50% or more compared to the lesion area in an untreated soybean.

Comparative Test Example 4

As a result of test using the comparative test compounds cf1, cf3 or cf4 according to Test Example N, every of the lesion areas in cucumber in treated groups treated with the comparative compound showed 50% or more compared to the lesion area in an untreated cucumber.

Comparative Test Example 5

Each of plastic pots was filled with soil and thereto soybean (cv: Tachinagaha) seeds were sown and the soybens were grown in a greenhouse for 13 days. Thereafter, the comparative test compound cf5, the present compound E-16 or E-21, each of which was made to a formulation according to the similar method to that of Formulation Example 6, was mixed with water so as to be 3.1 ppm. The mixtures were sprayed to foliar parts so as to adhere adequately on the leaves of the above-mentioned soybean. After spraying the mixtures, the soybeans were air-dried and after 2 days, an aqueous suspension of the spores of soybean spot disease fungi (*Cercospora sojina*) was spraying-inoculated. After the inoculation, the soybeans were placed in a greenhouse of 23° C. under a high humidity for 4 days, and were then cultivated in the greenhouse of 23° C. for 15 days, and a lesion area was observed. As a result, the area of lesion on the soybean treated with the comparative compound cf5 was more than 70% of that on an untreated bean, whereas, the area of lesion on the bean treated with the present invented compounds E-16, and E-21 was less than 30% of that on an untreated bean.

Comparative Test Example 6

Each of plastic pots was filled with soil and kidney bean (cultivar: NAGAUZURA SAITO) was sown and grown in a greenhouse for 8 days. Then, the comparative test compound cf5, the present compound E-1, E-3, E-11, or E-16, each of which was made to a formulation according to the similar method to that of Formulation Example 6, was mixed with water so as to be 200 ppm. The mixtures were sprayed to foliar parts so as to adhere adequately on the leaves of the above-mentioned kidney bean. After spraying the mixtures, the kidney beans were air-dried, and placed outside for 6 days. Thereafter, a PDA medium containing hyphae of kidney bean *sclerotinia* rot fungi (*Sclerotinia sclerotiorum*) was placed on the leaves of the kidney bean. After the inoculation, all kidney beans were placed indoors under a high humidity during only night and after six days, a lesion area was observed. As a result, the lesion areas in kidney beans treated with the comparative compound cf5 showed 70% or more compared to the lesion area in an untreated kidney beans, whereas, every of the lesion areas in kidney beans treated with the present compounds E-1, E-3, E-11, and E-16 showed 10% or less compared to the lesion area in an untreated kidney beans.

Comparative Test Example 7

Each of plastic pots was filled with soil and wheat (cultivar: APOGEE) was sown, and the wheats were grown in a greenhouse for 45 days. Then, the comparative test compound cf3, the present compound E-15, or E-16, each of which was made to a formulation according to the similar method to that of Formulation Example 4, was mixed with water so as to be 300 ppm. The mixtures were sprayed to foliar parts of the wheat by the volume of 200 L/ha. After spraying the mixtures, the wheats were air-dried, and placed outside for 4 days. Thereafter, an aqueous suspension of the spores of wheat leaf blotch fungi (*Septoria tritici*) was spraying-inoculated. After the inoculation, the wheats were placed at 15° C. in a greenhouse under a high humidity for 3 days and then under lighting for 23 days, and a lesion area was observed. As a result, the lesion areas in wheats treated with the comparative compound cf3 showed 80% om more compared to the lesion area in an untreated wheats, whereas, every of the lesion areas in wheats treated with the present compounds E-15 and E-16 showed 35% or less compared to the lesion area in an untreated wheat.

INDUSTRIAL APPLICABILITY

The compound of the present invention has efficacies for controlling pests, and is useful as an active ingredient for an agent for controlling pests.

The invention claimed is:
1. A compound represented by a formula (I):

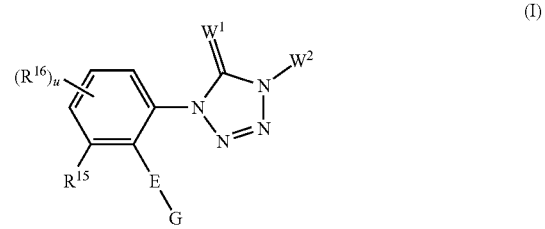

wherein,
$W^1$ represents an oxygen atom or a sulfur atom,
$W^2$ represents a hydrogen atom, a C1-C6 chain hydrocarbon group, a C3-C6 cycloalkyl group, a phenyl group, or a benzyl group, wherein the C1-C6 chain hydrocarbon group and the C3-C6 cycloalkyl group may have one or more substituents selected from Group I, and wherein the phenyl group and the benzyl group may have one or more substituents selected from Group O,
$R^{15}$ represents a halogen atom, a nitro group, a cyano group, a C1-C6 chain hydrocarbon group, a C3-C6 cycloalkyl group, a C1-C6 alkoxy group, a C1-C6 alkylthio group, a C3-C6 cycloalkyloxy group, or a C3-C6 cycloalkylthio group, wherein the C1-C6 chain hydrocarbon group, the C3-C6 cycloalkyl group, the C1-C6 alkoxy group, the C1-C6 alkylthio group, the C3-C6 cycloakyloxy group, and the C3-C6 cycloalkylthio group may have one or more substituents selected from Group I,
$R^{16}$ represents a halogen atom, a nitro group, a cyano group, a formyl group, a carboxy group, a hydroxy group, a sulfanyl group, an amino group, a pentafluorosulfanyl group, a C1-C6 chain hydrocarbon group, a C3-C6 cycloalkyl group, a C1-C6 alkoxy group, a C1-C6 alkylthio group, a C3-C6 cycloakyloxy group, a C3-C6 cycloalkylthio group, a C2-C6 alkenyloxy group, a C2-C6 alkynyloxy group, a C2-C6 alkenylthio group, a C2-C6 alkynylthio group, a (C1-C5 alkyl)carbonyl group, a (C1-C5 alkyl)carbonyloxy group, a (C1-C5 alkyl)carbonylthio group, a (C1-C5 alkoxy)carbonyl group, a C1-C6 alkylamino group, a di(C1-C6 alkyl)amino group, a C1-C4 alkylsulfonyl group, a C1-C4 alkylsulfinyl group, a (C1-C6 alkoxy)C1-C6 alkyl group, or a (C1-C6 alkylthio)C1-C6 alkyl group, wherein the C1-C6 chain hydrocarbon group, the C3-C6 cycloalkyl group, the C1-C6 alkoxy group, the C1-C6 alkylthio group, the C3-C6 cycloakyloxy group, the C3-C6 cycloalkylthio group, the C2-C6 alkenyloxy group, the C2-C6 alkynyloxy group, the C2-C6 alkenylthio group, the C2-C6 alkynylthio group, the (C1-C5 alkyl)carbonyl group, the (C1-C5 alkyl)carbonyloxy group, the (C1-C5 alkyl)carbonylthio group, the (C1-C5 alkoxy)carbonyl group, the C1-C6 alkylamino group, the di(C1-C6 alkyl)amino group, the C1-C4 alkylsulfonyl group, the C1-C4 alkylsulfinyl group, the (C1-C6 alkoxy)C1-C6 alkyl group, and the (C1-C6 alkylthio)C1-C6 alkyl group may have one or more substituents selected from Group I,
u is 0, 1, 2 or 3,
when u is 2 or 3, a plurality of $R^{16}$ may be independently identical to or different from each other,
the combination of E, G, $X^1$, $Y^1$ and $Z^1$ represents any one of the combinations of the following a to i;
a: a combination wherein E represents #—C($X^1$)($Y^1$)—O—N=C($Z^1$)—, #—C($X^1$)($Y^1$)—S—N=C($Z^1$)—,

—C($X^1$)($Y^1$)—O—N=C($Z^1$)—O—CH$_2$—, #—C($X^1$)($Y^1$)—O—N=C($Z^1$)—S—CH$_2$—, #—C($X^1$)($Y^1$)—S—N=C($Z^1$)—O—CH$_2$—, #—C($X^1$)($Y^1$)—S—N=C($Z^1$)—S—CH$_2$—, #—C($X^1$)=C($Y^1$)—C($Z^1$)=N—N=C($Z^2$)—, #—C($X^1$)=C($Y^1$)—C($Z^1$)=N—O—CH$_2$— or #—C($X^1$)=C($Y^1$)—C($Z^1$)=N—S—CH$_2$—,
G represents a C1-C6 chain hydrocarbon group, a (C1-C6 alkoxy)C1-C6 alkyl group, a (C1-C6 alkylthio)C1-C6 alkyl group or $R^1$-$T^1$-, wherein the C1-C6 chain hydrocarbon group, the (C1-C6 alkoxy)C1-C6 alkyl group, and the (C1-C6 alkylthio)C1-C6 alkyl group may have one or more substituents selected from Group S, each of $X^1$ and $Y^1$, which are identical to or different from each other, independently represents substituents selected from Group T, and $Z^1$ represents a substituent selected from Group V;

b: a combination wherein E represents an oxygen atom, #—O—N=C($Z^1$)—C($Z^2$)=N—S—CH$_2$—, #—N=C($Z^1$)—S—CH$_2$—, #—N=C($Z^1$)—O—CH$_2$—, #—O—N=C($Z^1$)—S—CH$_2$—, #—O—N=C($Z^1$)—O—CH$_2$—, #—N($X^1$)—O—CH$_2$—, #—O—C($Z^1$)=N—O—CH$_2$—, #—N=C(S$X^3$)—S—CH$_2$—, #—N=C(O$X^3$)—O—CH$_2$—, #—N=C(S$X^3$)—O—CH$_2$— or #—N=C(O$X^3$)—S—CH$_2$—, G represents a C1-C6 chain hydrocarbon group, a (C1-C6 alkoxy)C1-C6 alkyl group, a (C1-C6 alkylthio)C1-C6 alkyl group or $R^1$-$T^2$, wherein the C1-C6 chain hydrocarbon group, the (C1-C6 alkoxy)C1-C6 alkyl group, and the (C1-C6 alkylthio)C1-C6 alkyl group may have one or more substituents selected from Group S, $X^1$ represents a substituent selected from Group T, and $Z^1$ represents a substituent selected from Group V;

c: a combination wherein E represents a sulfur atom, #—S—N=C($Z^1$)—C($Z^2$)=N—O—CH$_2$— or #—S—N=C($Z^1$)—C($Z^2$)=N—S—CH$_2$—, G represents $R^1$-$T^7$, and $Z^1$ represents a substituent selected from Group V;

d: a combination wherein E represents #—C($Z^1$)=N—N=C($Z^3$)—O—CH$_2$— or #—C($Z^1$)=N—N=C($Z^3$)—S—CH$_2$—, G represents $R^8$-$T^3$-, $R^9$-$T^4$-, $R^{10}$-$T^5$- or $R^{14}$-$T^6$-, and $Z^1$ represents a substituent selected from Group V;

e: a combination wherein E represents #—C($Z^1$)=N—N=C($V^1$)—O—CH$_2$— or #—C($Z^1$)=N—N=C($V^1$)—S—CH$_2$—, G represents $R^1$-$T^1$, and $Z^1$ represents a substituent selected from Group V;

f: a combination wherein E represents #—C($X^1$)($Y^1$)—O—N=C($Z^1$)—, #—C($X^1$)($Y^1$)—S—N=C($Z^1$)—, #—C($X^1$)($Y^1$)—O—N=C($Z^1$)—O—CH$_2$—, #—C($X^1$)($Y^1$)—O—N=C($Z^1$)—S—CH$_2$—, #—C($X^1$)($Y^1$)—S—N=C($Z^1$)—O—CH$_2$— or #—C($X^1$)($Y^1$)—S—N=C($Z^1$)—S—CH$_2$—, G and $X^1$ together with carbon atom(s) to which they are bound form a C3-C10 alicyclic hydrocarbon group or a 3 to 10 membered non-aromatic heterocyclic group, wherein the C3-C10 alicyclic hydrocarbon group, and the 3 to 10 membered non-aromatic heterocyclic group may have one or more substituents selected from Group J, $Y^1$ represents a substituent selected from Group T, and $Z^1$ represents a substituent selected from Group V;

g: a combination wherein E represents #—C($X^1$)($Y^1$)—O—N=C($Z^1$)—, #—C($X^1$)($Y^1$)—S—N=C($Z^1$)—, #—C($X^1$)($Y^1$)—O—N=C($Z^1$)—O—CH$_2$—, #—C($X^1$)($Y^1$)—O—N=C($Z^1$)—S—CH$_2$—, #—C($X^1$)($Y^1$)—S—N=C($Z^1$)—O—CH$_2$— or #—C($X^1$)($Y^1$)—S—N=C($Z^1$)—S—CH$_2$—, G, $X^1$ and $Y^1$ together with carbon atoms to which they are bound form a C6-C10 aromatic hydrocarbon group, or 5 to 10 membered aromatic heterocyclic group, wherein the C6-C10 aromatic hydrocarbon group, and the 5 to 10 membered aromatic heterocyclic group may have one or more substituents selected from Group P, and $Z^1$ represents a substituent selected from Group V;

h: a combination wherein E represents #—C($X^1$)=C($Y^1$)—C($Z^1$)=N—O—CH$_2$—, #—C($X^1$)=C($Y^1$)—C($Z^1$)=N—S—CH$_2$— or #—N($X^1$)—O—CH$_2$—, G and $X^1$ together carbon atoms to which they are bound form, C3-C10 alicyclic hydrocarbon group or 3 to 10 membered non-aromatic heterocyclic group, wherein the C3-C10 alicyclic hydrocarbon group, and the 3 to 10 membered non-aromatic heterocyclic group may have one or more substituents selected from Group J, $Y^1$ represents a substituent selected from Group T, $Z^1$ represents a substituent selected from Group V;

i: a combination wherein E represents #—C($Z^1$)=N—N=C($Z^3$)—O—CH$_2$—, #—C($Z^1$)=N—N=C($Z^3$)—S—CH$_2$—, #—C($Z^1$)=N—N=C($V^1$)—O—CH$_2$— or #—C($Z^1$)=N—N=C($V^1$)—S—CH$_2$—, G and $Z^1$ together with carbon atoms to which they are bound form a C3-C10 alicyclic hydrocarbon group or a 3 to 10 membered non-aromatic heterocyclic group, wherein the C3-C10 alicyclic hydrocarbon group and the 3 to 10 membered non-aromatic heterocyclic group may have one or more substituents selected from Group U;

# represents a binding site to G, $Z^2$ represents a hydrogen atom, a halogen atom, a cyano group, an amino group, a nitro group, a C1-C6 chain hydrocarbon group, a C3-C6 cycloalkyl group, a C1-C6 alkoxy group, a C1-C6 alkylthio group, a (C1-C6 alkoxy)C1-C6 alkyl group, a (C1-C6 alkylthio)C1-C6 alkyl group, a C2-C6 cyanoalkyl group, a C1-C6 alkylamino group, a di(C1-C6 alkyl)amino group, a (C1-C5 alkoxy)carbonyl group, a pyridyl group, an oxetanyl group, a benzyl group, —C(=NO$R^A$)—C(=NO$R^B$)$R^C$ or —C$R^{11}$=N—O—$R^{12}$, wherein the C1-C6 chain hydrocarbon group, the C3-C6 cycloalkyl group, the C1-C6 alkoxy group, the C1-C6 alkylthio group, the (C1-C6 alkoxy)C1-C6 alkyl group, the (C1-C6 alkylthio)C1-C6 alkyl group, the C2-C6 cyanoalkyl group, the C1-C6 alkylamino group, the di(C1-C6 alkyl)amino group and the (C1-C5 alkoxy)carbonyl group may have one or more substituents selected from Group I, and wherein the pyridyl group, the oxetanyl group and the benzyl group may have one or more substituents selected from Group O;

$Z^3$ represents a hydrogen atom, a halogen atom, a cyano group, a nitro group, a C1-C6 chain hydrocarbon group, a C3-C6 cycloalkyl group, a C1-C6 alkoxy group, a C1-C6 alkylthio group, a (C1-C6 alkoxy)C1-C6 alkyl group, a (C1-C6 alkylthio)C1-C6 alkyl group, a C2-C6 cyanoalkyl group, (C1-C5 alkoxy)carbonyl group, a pyridyl group, an oxetanyl group, a benzyl group —C(=NO$R^A$)—C(=NO$R^B$)$R^C$ or —C$R^{11}$=N—O—$R^{12}$, wherein the C1-C6 chain hydrocarbon group, the C3-C6 cycloalkyl group, the C1-C6 alkoxy group, the C1-C6 alkylthio group, the (C1-C6 alkoxy)C1-C6 alkyl group, the (C1-C6 alkylthio)C1-C6 alkyl group, the C2-C6 cyanoalkyl group and the (C1-C5 alkoxy)carbonyl group may have one or more substituents selected from Group I, and wherein the pyridyl group, the oxetanyl group and the benzyl group may have one or more substituents selected from Group O;

$V^1$ represents an amino group, a C1-C6 alkylamino group, a di(C1-C6 alkyl)amino group or —$CR^{11}$=N—O—$R^{12}$, wherein the C1-C6 alkylamino group and the di(C1-C6 alkyl)amino group may have one or more substituents selected from Group I, $R^{11}$ represents a phenyl group, a benzyl group, a hydrogen atom, a halogen atom, a nitro group, a cyano group, a C1-C6 alkyl group, a C3-C6 cycloalkyl group, a C1-C6 alkoxy group or C1-C6 alkylthio group, wherein the phenyl group and the benzyl group may have one or more substituents selected from Group N, and wherein the C1-C6 alkyl group, the C3-C6 cycloalkyl group, the C1-C6 alkoxy group and the C1-C6 alkylthio group may have one or more halogen atoms, each of $R^{12}$, $R^A$, $R^B$, and $R^C$, which are identical to or different from each other, independently represents a phenyl group, a benzyl group, a pyridyl group, a pyrazolyl group, a pyrimidinyl group, a C1-C6 chain hydrocarbon group, a C3-C6 cycloalkyl group, a (C3-C6 cycloalkyl)C1-C6 alkyl group, a (C1-C6 alkoxy)C2-C6 alkyl group, a (C1-C6 alkylthio)C1-C6 alkyl group, a cyano(C1-C6 alkyl) group or a hydrogen atom, wherein the phenyl group, the benzyl group, the pyridyl group, the pyrazolyl group and the pyrimidinyl group may have one or more substituents selected from Group N, and wherein the C1-C6 chain hydrocarbon group, the C3-C6 cycloalkyl group, the (C3-C6 cycloalkyl)C1-C6 alkyl group, the (C1-C6 alkoxy)C2-C6 alkyl group, the (C1-C6 alkylthio)C1-C6 alkyl group and the cyano(C1-C6 alkyl) group may have one or more halogen atoms, $X^3$ represents a C2-C6 alkenyl group, a C2-C6 alkynyl group, a C3-C6 cycloalkyl group, a (C1-C6 alkoxy)C2-C6 alkyl group, a (C1-C6 alkylthio)C2-C6 alkyl group, a C2-C6 cyanoalkyl group, a [(C1-C6 alkyl)amino]C2-C6 alkyl group, a [di(C1-C6 alkyl)amino]C2-C6 alkyl group, a phenyl group, a pyridyl group, a benzyl group, or a hydrogen atom, wherein the C2-C6 alkenyl group, the C2-C6 alkynyl group, the C3-C6 cycloalkyl group, the (C1-C6 alkoxy)C2-C6 alkyl group, the (C1-C6 alkylthio)C2-C6 alkyl group, the C2-C6 cyanoalkyl group, the [(C1-C6 alkyl)amino]C2-C6 alkyl group, and the [di(C1-C6 alkyl)amino]C2-C6 alkyl group may have one or more halogen atoms, and wherein the phenyl group, the pyridyl group and the benzyl group may have one or more substituents selected from Group O, $R^1$ represents a C3-C10 alicyclic hydrocarbon group, a 3 to 10 membered non-aromatic heterocyclic group, a C6-C10 aromatic hydrocarbon group or a 5 to 10 membered aromatic heterocyclic group, wherein the C3-C10 alicyclic hydrocarbon group and the 3 to 10 membered non-aromatic heterocyclic group may have one or more substituents selected from Group J, and wherein the C6-C10 aromatic hydrocarbon group and the 5 to 10 membered aromatic heterocyclic group may have one or more substituents selected from Group P, $T^1$ represents a single bond, an oxygen atom, —$S(O)_m$—, —O—$S(O)_m$—*, —$NR^{11}$—, —$(CR^2R^3)_n$—, —$(CR^2R^3)_n$O—*, —O$(CR^2R^3)_n$—*, —$(CR^2R^3)_nS(O)_m$—*, —$S(O)_m(CR^2R^3)_n$—*, —$C(X^2)$—, —$C(X^2)$—O—*, —O—$C(X^2)$—* or —$CR^4$=$CR^5$—,

* represents a binding site to E,
m is 0, 1 or 2,
n is 1, 2, 3 or 4, when n is 2, 3 or 4, a plurality of $R^2$ are independently identical to or different from each other, and a plurality of $R^3$ are independently identical to or different from each other;

$X^2$ represents an oxygen atom or a sulfur atom, each of $R^2$ and $R^3$, which are identical to or different from each other, independently represents a hydrogen atom, a halogen atom, a nitro group, a cyano group, a C1-C4 chain hydrocarbon group, a C1-C4 alkoxy group, a C1-C4 alkylthio group, a C2-C4 alkenyloxy group, a C2-C4 alkenylthio group, a C2-C4 alkynyloxy group or a C2-C4 alkynylthio group, wherein the C1-C4 chain hydrocarbon group, the C1-C4 alkoxy group, the C1-C4 alkylthio group, the C2-C4 alkenyloxy group, the C2-C4 alkenylthio group, the C2-C4 alkynyloxy group, and the C2-C4 alkynylthio group may have one or more halogen atoms, each of $R^4$ and $R^5$, which are identical to or different from each other, independently represents a C1-C4 chain hydrocarbon group which may have one or more halogen atoms, a hydrogen atom, a halogen atom, a nitro group or a cyano group, $T^2$ represents a single bond, —$S(O)_2$—, —$(CR^2R^3)_n$—, —O—$(CR^2R^3)_{n+1}$—*, —$(CR^2R^3)_n$—$S(O)_2$—*, —$S(O)_m(CR^2R^3)_n$—*, —$CR^4$=$CR^5$—, or —$CR^4$=$CR^5$—$CR^2R^3$—*, $T^7$ represents a single bond, —$(CR^2R^3)_n$—, —O—$(CR^2R^3)_{n+1}$—*, —$S(O)_m$—$(CR^2R^3)_n$—* or —$CR^4$=$CR^5$—$CR^2R^3$—*, $R^8$ represents a 3 to 8 membered non-aromatic heterocyclic group which may have one or more substituents selected from Group M, a partially unsaturated or aromatic 8 to 10 membered fused heterocyclic group, a pyrrolyl group, a furanyl group, a pyrazolyl group, an imidazolyl group, an oxazolyl group, an isoxazolyl group, an isothiazolyl group, a triazolyl group, an oxadiazolyl group, a thiadiazolyl group, a tetrazolyl group, a pyrimidinyl group, a pyrazinyl group, a pyridazinyl group, a tetrahydronaphthyl group, an indanyl group, —$CR^4$=$CR^4$—O—$R^{12}$, —$CR^{11}$=N—N($R^{19}R^{20}$), or —$CR^{11}$=N—O—$R^{12}$, wherein the 8 to 10 membered fused heterocyclic group, the pyrrolyl group, the furanyl group, the pyrazolyl group, the imidazolyl group, the oxazolyl group, the isoxazolyl group, the isothiazolyl group, the triazolyl group, the oxadiazolyl group, the thiadiazolyl group, the tetrazolyl group, the pyrimidinyl group, the pyrazinyl group, the pyridazinyl group, the tetrahydronaphthyl group and the indanyl group may have one or more substituents selected from Group L, $R^9$ represents a phenyl group which may have one or more substituents selected from Group L, $R^{10}$ represents a pyridyl group which may have one or more substituents selected from Group L, $R^{14}$ represents a thienyl group, a thiazolyl group or a naphthyl group wherein the thienyl group, the thiazolyl group and the naphthyl group may have one or more substituents selected from Group L, each of $R^{19}$ and $R^{20}$, which are identical to or different from each other, independently represents a C1-C4 chain hydrocarbon group which may have one or more halogen atoms, a hydrogen atom, a cyano group, a phenyl group, a benzyl group, wherein the phenyl group and the benzyl group may have one or more substituents selected from Group N, $T^3$ represents a single bond, an oxygen atom, —$S(O)_m$—, —$NR^{11}$—, —$(CR^2R^3)_n$—, —$(CR^2R^3)_nO$—*, —O(CR²R³)ₙ—*, —(CR²R³)ₙS(O)ₘ—*, —S(O)ₘ—(CR²R³)ₙ—* or —CR⁴=CR⁵—, T⁴ represents an oxygen atom, —S(O)ₘ—, —NR¹¹—, —(CR²R³)ₙO—*, —(CR²R³)ₙS-(O)ₘ—* or —S(O)ₘ(CR²R³)ₙ—*, T⁵ represents an oxygen atom, —S(O)ₘ—, —NR¹¹—, —(CR²R³)ₙ—, —(CR²R³)ₙO—*, —O(CR²R³)ₙ—*, —(CR²R³)ₙS(O)ₘ—* or —S(O)ₘ(CR²R³)ₙ—*, T⁶ represents an oxygen atom, —S(O)ₘ—, —NR¹¹—, —(CR²R³)ₙ—, —(CR²R³)ₙO—*, —O(CR²R³)ₙ—*, —(CR²R³)ₙS(O)ₘ—*, —S(O)ₘ—(CR²R³)ₙ—* or —CR⁴=CR⁵—;

Group I: a group consisting of a halogen atom, a nitro group, a cyano group, an oxo group, a thioxo group, a carboxy group, a formyl group, a hydroxy group, a sulfanyl group, an amino group, a C1-C4 alkoxy group, a C2-C4 alkenyloxy group, a C2-C4 alkynyloxy group, a (C1-C3 alkyl) carbonyloxy group, a phenyl group, —S(Q)ₚ-Y² and —CR¹¹=N—O—R¹², wherein the C1-C4 alkoxy group, the C2-C4 alkenyloxy group, the C2-C4 alkynyloxy group, the (C1-C3 alkyl) carbonyloxy group and the phenyl group may have one or more halogen atoms;

Q represents an oxygen atom, =N—CN, =N—NO₂, =N—C(O)R¹³ or =N—C(O)OR¹³,

R¹³ represents a C1-C6 chain hydrocarbon group which may have one or more substituents selected from Group R, a phenyl group or a pyridyl group, wherein the phenyl group and the pyridyl group may have one or more substituents selected from Group N, Y² represents NR¹⁸R¹⁷, OR¹⁸, a C1-C6 chain hydrocarbon group, a C3-C6 cycloalkyl group, a phenyl group or a pyridyl group, wherein the C1-C6 chain hydrocarbon group and the C3-C6 cycloalkyl group may have one or more substituents selected from Group R, and wherein the phenyl and the pyridyl group may have one or more substituents selected from Group N, p is 0, 1 or 2, each of R¹⁸ and R¹⁷, which are identical to or different from each other, independently represents a C1-C6 chain hydrocarbon group, a C3-C6 cycloalkyl group, a (C1-C6 alkoxy)C2-C6 alkyl group, a (C1-C6 alkylthio)C2-C6 alkyl group, a C1-C4 alkylsulfinyl group, a C1-C4 alkylsulfonyl group, a (C1-C5 alkyl)carbonyl group, or a hydrogen atom, wherein the C1-C6 chain hydrocarbon group, the C3-C6 cycloalkyl group, the (C1-C6 alkoxy)C2-C6 alkyl group, the (C1-C6 alkylthio)C2-C6 alkyl group, the C1-C4 alkylsulfinyl group, the C1-C4 alkylsulfonyl group and the (C1-C5 alkyl) carbonyl group may have one or more halogen atoms;

Group J: a group consisting of a 3 to 7 membered non-aromatic heterocyclic group, a 5 to 6 membered aromatic heterocyclic group, a phenyl group, a C3-C10 alicyclic hydrocarbon group, a halogen atom, a nitro group, a cyano group, an oxo group, a thioxo group, a formyl group, a carboxy group, a hydroxy group, a sulfanyl group, an amino group, —S(Q)ₚ-Y², —CR¹¹=N—O—R¹², =N—O—R¹², a C1-C4 alkoxy group, a C2-C4 alkenyloxy group and a C2-C4 alkynyloxy group, wherein the 3 to 7 membered non-aromatic heterocyclic group, the 5 to 6 membered aromatic heterocyclic group, the phenyl group and the C3-C10 alicyclic hydrocarbon group may have one or more substituents selected from Group K, and wherein the C1-C4 alkoxy group, the C2-C4 alkenyloxy group and the C2-C4 alkynyloxy group may have one or more halogen atoms;

Group K: a group consisting of a halogen atom, a nitro group, a cyano group, an oxo group, a thioxo group, a formyl group, a carboxy group, a hydroxy group, a sulfanyl group, an amino group, —S(Q)ₚ-Y², —CR¹¹=N—O—R¹², a C1-C4 alkoxy group, a C2-C4 alkenyloxy group and a C2-C4 alkynyloxy group, wherein the C1-C4 alkoxy group, the C2-C4 alkenyloxy group and the C2-C4 alkynyloxy group may have one or more halogen atoms;

Group L: a group consisting of a halogen atom, a nitro group, a cyano group, a formyl group, a hydroxy group, a sulfanyl group, a carboxy group, an amino group, a C1-C6 chain hydrocarbon group, a C3-C6 cycloalkyl group, a C1-C6 alkoxy group, a C2-C6 alkenyloxy group, a C2-C6 alkynyloxy group, a C3-C6 cycloalkoxy group, a C1-C6 alkylthio group, a C2-C6 alkenylthio group, a C2-C6 alkynylthio group, a C1-C6 alkylsulfinyl group, a C2-C6 alkenylsulfinyl group, a C2-C6 alkynylsulfinyl group, a C1-C6 alkylsulfonyl group, a C2-C6 alkenylsulfonyl group, a C2-C6 alkynylsulfonyl group, a C1-C6 alkylamino group, a di(C1-C6 alkyl)amino group, a (C1-C5 alkyl)carbonyl group, a (C1-C5 alkyl)carbonyloxy group, a (C1-C5 alkoxy)carbonyloxy group, an aminocarbony group, a (C1-C6 alkyl)aminocarbony group, a (C1-C6 alkoxy)C1-C6 alkyl group, a (C1-C6 alkylthio)C1-C6 alkyl group, a (C1-C6 alkoxy)C1-C6 alkoxy group, —CR¹¹=N—O—R¹², a phenyl group and a phenoxy group, wherein the C1-C6 chain hydrocarbon group, the C3-C6 cycloalkyl group, the C1-C6 alkoxy group, the C2-C6 alkenyloxy group, the C2-C6 alkynyloxy group, the C3-C6 cycloalkoxy group, the C1-C6 alkylthio group, the C2-C6 alkenylthio group, the C2-C6 alkynylthio group, the C1-C6 alkylsulfinyl group, the C2-C6 alkenylsulfinyl group, the C2-C6 alkynylsulfinyl group, the C1-C6alkylsulfonyl group, the C2-C6 alkenylsulfonyl group, the C2-C6 alkynylsulfonyl group, the C1-C6 alkylamino group, the di(C1-C6 alkyl)amino group, the (C1-C5 alkyl)carbonyl group, the (C1-C5 alkyl)carbonyloxy group, the (C1-C5 alkoxy)carbonyloxy group, the (C1-C6 alkyl)aminocarbony group, the (C1-C6 alkoxy)C1-C6 alkyl group, the (C1-C6 alkylthio)C1-C6 alkyl group, the (C1-C6 alkoxy)C1-C6 alkoxy group, the phenyl group and the phenoxy group may have one or more halogen atoms;

Group M: a group consisting of a halogen atom, a nitro group, a cyano group, a formyl group, a hydroxy group, a sulfanyl group, a carboxy group, an amino group, an oxo group, a thioxo group, a C1-C6 chain hydrocarbon group, a C3-C6 cycloalkyl group, a C1-C6 alkoxy group, a C3-C6 cycloalkoxy group, a C1-C6 alkylthio group, a C2-C6 alkenylthio group, a C1-C6 alkylsulfinyl group, a C1-C6alkylsulfonyl group, a C2-C6 alkenyloxy group, a C2-C6 alkynyloxy group, a (C1-C5 alkyl)carbonyl group, a (C1-C5 alkyl)carbonyloxy group, an aminocarbony group, a (C1-C6 alkyl)aminocarbony group, a (C1-C6 alkoxy)C1-C6 alkyl group, a (C1-C6 alkylthio)C1-C6 alkyl group, a (C1-C6 alkoxy)C1-C6 alkoxy group, a phenyl group and a phenoxy group, wherein the C1-C6 chain hydrocarbon group, the C3-C6 cycloalkyl group, the C1-C6 alkoxy group, the C3-C6 cycloalkoxy group, the C1-C6 alkylthio group, the C2-C6 alkenylthio group, the C1-C6alkylsulfinyl group, the C1-C6 alkylsulfonyl group, the C2-C6 alkenyloxy group, the C2-C6 alkynyloxy group, the (C1-C5 alkyl)carbonyl group, the (C1-C5 alkyl)carbonyloxy group, the (C1-C6 alkyl)

aminocarbony group, the (C1-C6 alkoxy)C1-C6 alkyl group, the (C1-C6 alkylthio)C1-C6 alkyl group, the (C1-C6 alkoxy)C1-C6 alkoxy group, the phenyl group and the phenoxy group may have one or more halogen atoms;

Group N: a group consisting of a halogen atom, a nitro group, a cyano group, a C1-C6 alkyl group, a C3-C6 cycloalkyl group, a C1-C6 alkoxy group, a C3-C6 cycloalkoxy group, a (C1-C6 alkoxy)C1-C6 alkyl group, a (C1-C6 alkylthio)C1-C6 alkyl group, a (C1-C6 alkoxy)C1-C6 alkoxy group and a C1-C6 alkylthio group, wherein the C1-C6 alkyl group, the C3-C6 cycloalkyl group, the C1-C6 alkoxy group, the C3-C6 cycloalkoxy group, the (C1-C6 alkoxy)C1-C6 alkyl group, the (C1-C6 alkylthio)C1-C6 alkyl group, the (C1-C6 alkoxy)C1-C6 alkoxy group and the C1-C6 alkylthio group may have one or more halogen atoms;

Group O: a group consisting of a halogen atom, a nitro group, a cyano group, a carboxy group, a hydroxy group, a sulfanyl group, an amino group, a C1-C6 chain hydrocarbon group, a C1-C4 alkoxy group, a C2-C4 alkenyloxy group, a C2-C4 alkynyloxy group, —S(Q)$_p$-Y$^2$, —CR$^{11}$=N—O—R$^{12}$, a (C1-C3 alkyl)carbonyloxy group and a phenyl group, wherein the C1-C6 chain hydrocarbon group, the C1-C4 alkoxy group, the C2-C4 alkenyloxy group, the C2-C4 alkynyloxy group, the (C1-C3 alkyl) carbonyloxy group and the phenyl group may have one or more halogen atoms;

Group P: a group consisting of a halogen atom, a nitro group, a cyano group, a formyl group, a carboxy group, a hydroxy group, a sulfanyl group, an amino group, —S(Q)$_p$-Y$^2$, —CR$^{11}$=N—O—R$^{12}$, a C1-C6 chain hydrocarbon group, a C1-C4 alkoxy group, a C2-C4 alkenyloxy group, a C2-C4 alkynyloxy group, a 3 to 7 membered non-aromatic heterocyclic group, a 5 to 6 membered aromatic heterocyclic group, a phenyl group, a phenoxy group and a C3-C10 alicyclic hydrocarbon group, wherein the C1-C6 chain hydrocarbon group, the C1-C4 alkoxy group, the C2-C4 alkenyloxy group and the C2-C4 alkynyloxy group may have one or more halogen atoms, and wherein the 3 to 7 membered non-aromatic heterocyclic group, the 5 to 6 membered aromatic heterocyclic group, the phenyl group, the phenoxy group and the C3-C10 alicyclic hydrocarbon group may have one or more substituents selected from Group K;

Group R: a group consisting of a halogen atom, a nitro group, a cyano group, an oxo group, a thioxo group, a carboxy group, a hydroxy group, a sulfanyl group, an amino group, a C1-C4 alkoxy group, a C2-C4 alkenyloxy group, a C2-C4 alkynyloxy group, a (C1-C3 alkyl) carbonyloxy group and a phenyl group, wherein the C1-C4 alkoxy group, the C2-C4 alkenyloxy group and the C2-C4 alkynyloxy group, the (C1-C3 alkyl) carbonyloxy group and the phenyl group may have one or more halogen atoms;

Group S: a group consisting of a halogen atom, a nitro group, a cyano group, an oxo group, a thioxo group, a carboxy group, a hydroxy group, a sulfanyl group, an amino group, a C1-C4 alkoxy group, a C2-C4 alkenyloxy group, a C2-C4 alkynyloxy group and a (C1-C3 alkyl) carbonyloxy group, wherein the C1-C4 alkoxy group, the C2-C4 alkenyloxy group, the C2-C4 alkynyloxy group and the (C1-C3 alkyl) carbonyloxy group may have one or more halogen atoms;

Group T: a group consisting of a hydrogen atom, a halogen atom, a cyano group, a nitro group, a formyl group, a carboxy group, a C1-C6 chain hydrocarbon group, a C3-C6 cycloalkyl group, a (C1-C6 alkoxy) C1-C6 alkyl group, a (C1-C6 alkylthio)C1-C6 alkyl group, a C2-C6 cyanoalkyl group, a (C1-C5 alkyl) carbonyl group, a (C1-C5 alkoxy)carbonyl group, a pyridyl group, an oxetanyl group, benzyl group, —C(=NOR$^A$)—C(=NOR$^B$)R$^C$ and —CR$^{11}$=N—O—R$^{12}$, wherein the C1-C6 chain hydrocarbon group, the C3-C6 cycloalkyl group, the (C1-C6 alkoxy)C1-C6 alkyl group, the (C1-C6 alkylthio)C1-C6 alkyl group, the C2-C6 cyanoalkyl group, the (C1-C5 alkyl)carbonyl group and the (C1-C5 alkoxy)carbonyl group may have one or more substituents selected from Group I, and wherein the pyridyl group, the oxetanyl group and the benzyl group may have one or more substituents selected from Group O;

Group U: a group consisting of a halogen atom, a nitro group, a cyano group, an oxo group, a thioxo group, a carboxy group, a formyl group, a hydroxy group, a sulfanyl group, an amino group, a C1-C4 chain hydrocarbon group, a C3-C6 cycloalkyl group, a C1-C4 alkylthio group, a C1-C4 alkoxy group, a C3-C6 cycloakyloxy group, a C1-C4 alkylsulfonyloxy group, a C3-C6 cycloalkylsulfonyloxy group, a C2-C4 alkenyloxy group, a C2-C4 alkynyloxy group, a (C1-C3 alkyl) carbonyloxy group, a phenyl group, —S(Q)$_p$-Y$^2$, —CR$^{11}$=N—O—R$^{12}$, —C(=NOR$^A$)—C(=NOR$^B$)R$^C$ and =N—O—R$^{12}$, wherein the C1-C4 chain hydrocarbon group, the C3-C6 cycloalkyl group, the C1-C4 alkylthio group, the C1-C4 alkoxy group, the C3-C6 cycloakyloxy group, the C1-C4 alkylsulfonyloxy group, the C3-C6 cycloalkylsulfonyloxy group, the C2-C4 alkenyloxy group, the C2-C4 alkynyloxy group, the (C1-C3 alkyl)carbonyloxy group and the phenyl group may have one or more halogen atoms;

Group V: a group consisting of a hydrogen atom, a halogen atom, a cyano group, an amino group, a nitro group, a C1-C6 chain hydrocarbon group, a C3-C6 cycloalkyl group, a C1-C6 alkoxy group, a C1-C6 alkylthio group, a (C1-C6 alkoxy)C1-C6 alkyl group, a (C1-C6 alkylthio)C1-C6 alkyl group, a C2-C6 cyanoalkyl group, a C1-C6 alkylamino group, a di(C1-C6 alkyl)amino group, a (C1-C5 alkoxy)carbonyl group, a pyridyl group, an oxetanyl group, a benzyl group, —C(=NOR$^A$)—C(=NOR$^B$)R$^C$ and —CR$^{11}$=N—O—R$^{12}$, wherein the C1-C6 chain hydrocarbon group, the C3-C6 cycloalkyl group, the C1-C6 alkoxy group, the C1-C6 alkylthio group, the (C1-C6 alkoxy)C1-C6 alkyl group, the (C1-C6 alkylthio)C1-C6 alkyl group, the C2-C6 cyanoalkyl group, the C1-C6 alkylamino group, the di(C1-C6 alkyl)amino group and the (C1-C5 alkoxy)carbonyl group may have one or more substituents selected from Group I, and wherein the pyridyl group, the oxetanyl group and the benzyl group may have one or more substituents selected from Group O;

or its N-oxide compound.

2. The compound according to claim 1 wherein R$^8$ represents a 3 to 8 membered non-aromatic heterocyclic group which may have one or more substituents selected from Group M, a pyrrolyl group, a furanyl group, a pyrazolyl group, an imidazolyl group, an oxazolyl group, an isoxazolyl group, an isothiazolyl group, a triazolyl group, an oxadiazolyl group, a thiadiazolyl group, a tetrazolyl group, a pyrimidinyl group, a pyrazinyl group, a pyridazinyl group, a benzofuranyl group, a benzothienyl group, an indolyl group, an isoindolyl group, an indolizinyl group, an indazolyl group, a benzimidazolyl group, a benzothiazolyl group, a benzoxazolyl group, a benzisothiazolyl group, a benzisoxazolyl group, a dihydrobenzofuranyl group, a dihydrobenzothienyl group, dihydrobenzopyranyl group, a 1,3-benzodioxolyl group, a quinolyl group, an isoquinolyl group, a cinnolinyl group, a phthalazinyl group, a quinazolinyl group, a quinoxalinyl group, a naphthyridinyl group, a tetrahydronaphthyl group, an indanyl group, an oxazolopyridyl group, a thiazolopyridyl group, an isoxazolopyridyl group, isothiazolopyridyl group, a tetrahydroindazoly group, a cyclopentapyrazolyl group, $-CR^4=CR^4-O-R^{12}$, $-CR^{11}=N-N(R^{19}R^{20})$, or $-CR^{11}=N-O-R^{12}$, wherein the pyrrolyl group, the furanyl group, the pyrazolyl group, the imidazolyl group, the oxazolyl group, the isoxazolyl group, the isothiazolyl group, the triazolyl group, the oxadiazolyl group, the thiadiazolyl group, the tetrazolyl group, the pyrimidinyl group, the pyrazinyl group, the pyridazinyl group, the benzofuranyl group, the benzothienyl group, the indolyl group, the isoindolyl group, the indolizinyl group, the indazolyl group, the benzimidazolyl group, the benzothiazolyl group, the benzoxazolyl group, the benzisothiazolyl group, the benzisoxazolyl group, the dihydrobenzofuranyl group, the dihydrobenzothienyl group, the dihydrobenzopyranyl group, the 1,3-benzodioxolyl group, the quinolyl group, the isoquinolyl group, the cinnolinyl group, the phthalazinyl group, the quinazolinyl group, the quinoxalinyl group, the naphthyridinyl group, the tetrahydronaphthyl group, the indanyl group, the oxazolopyridyl group, the thiazolopyridyl group, the isoxazolopyridyl group, the isothiazolopyridyl group, the tetrahydroindazoly group and the cyclopentapyrazolyl group may have one or more substituents selected from Group L, and Group U represents a group consisting of a halogen atom, a nitro group, a cyano group, an oxo group, a thioxo group, a carboxy group, a formyl group, a hydroxy group, a sulfanyl group, an amino group, a C1-C4 alkoxy group, a C3-C6 cycloakyloxy group, a C1-C4 alkylsulfonyloxy group, a C3-C6 cycloalkylsulfonyloxy group, a C2-C4 alkenyloxy group, a C2-C4 alkynyloxy group, a (C1-C3 alkyl) carbonyloxy group, a phenyl group, $-S(Q)_p-Y^2$, $-CR^{11}=N-O-R^{12}$, $-C(=NOR^A)-C(=NOR^B)R^C$ and $=N-O-R^{12}$, wherein the C1-C4 alkoxy group, the C3-C6 cycloakyloxy group, the C1-C4 alkylsulfonyloxy group, the C3-C6 cycloalkylsulfonyloxy group, the C2-C4 alkenyloxy group, the C2-C4 alkynyloxy group, the (C1-C3 alkyl) carbonyloxy group and the phenyl group may have one or more halogen atoms.

3. The compound according to claim 2 wherein
each of $R^{12}$, $R^A$, $R^B$ and $R^C$, which are identical to or different from each other, independently represents a phenyl group, a benzyl group, a pyridyl group, a pyrazolyl group or a pyrimidinyl group, a C1-C6 chain hydrocarbon group, a C3-C6 cycloalkyl group, a (C3-C6 cycloalkyl)C1-C6 alkyl group, a (C1-C6 alkoxy)C2-C6 alkyl group, a (C1-C6 alkylthio)C2-C6 alkyl group, or a hydrogen atom, wherein the phenyl group, the benzyl group, the pyridyl group, the pyrazolyl group and the pyrimidinyl group may have one or more substituents selected from Group N, and wherein the C1-C6 chain hydrocarbon group, the C3-C6 cycloalkyl group, the (C3-C6 cycloalkyl)C1-C6 alkyl group, the (C1-C6 alkoxy)C2-C6 alkyl group and the (C1-C6 alkylthio)C2-C6 alkyl group may have one or more halogen atoms, $R^8$ represents a 3 to 8 membered non-aromatic heterocyclic group which may have one or more substituents selected from Group M, a pyrrolyl group, a furanyl group, a pyrazolyl group, an imidazolyl group, an oxazolyl group, an isoxazolyl group, an isothiazolyl group, a triazolyl group, an oxadiazolyl group, a thiadiazolyl group, a tetrazolyl group, a pyrimidinyl group, a pyrazinyl group, a pyridazinyl group, a benzofuranyl group, a benzothienyl group, an indolyl group, an isoindolyl group, an indolizinyl group, an indazolyl group, a benzimidazolyl group, a benzothiazolyl group, a benzoxazolyl group, a benzisothiazolyl group, a benzisoxazolyl group, a 2,3-dihydrobenzofuranyl group, a 2,3-dihydrobenzothienyl group, a 3,4-dihydrobenzopyranyl group, a 1,3-benzodioxolyl group, a quinolyl group, an isoquinolyl group, a cinnolinyl group, a phthalazinyl group, a quinazolinyl group, a quinoxalinyl group, a naphthyridinyl group, $-CR^4=CR^4-O-R^{12}$, $-CR^{11}=N-N(R^{19}R^{20})$, or $-CR^{11}=N-O-R^{12}$, wherein the pyrrolyl group, the furanyl group, the pyrazolyl group, the imidazolyl group, the oxazolyl group, the isoxazolyl group, the isothiazolyl group, the triazolyl group, the oxadiazolyl group, the thiadiazolyl group, the tetrazolyl group, the pyrimidinyl group, the pyrazinyl group, the pyridazinyl group, the benzofuranyl group, the benzothienyl group, the indolyl group, the isoindolyl group, the indolizinyl group, the indazolyl group, the benzimidazolyl group, the benzothiazolyl group, the benzoxazolyl group, the benzisothiazolyl group, the benzisoxazolyl group, the 2,3-dihydrobenzofuranyl group, the 2,3-dihydrobenzothienyl group, the 3,4-dihydrobenzopyranyl group, the 1,3-benzodioxolyl group, the quinolyl group, the isoquinolyl group, the cinnolinyl group, the phthalazinyl group, the quinazolinyl group, the quinoxalinyl group and the naphthyridinyl group may have one or more substituents selected from Group L, and Group U represents a group consisting of a halogen atom, a nitro group, a cyano group, an oxo group, a thioxo group, a carboxy group, a formyl group, a hydroxy group, a sulfanyl group, an amino group, a C1-C4 alkoxy group, a C2-C4 alkenyloxy group, a C2-C4 alkynyloxy group, a (C1-C3 alkyl) carbonyloxy group, a phenyl group, $-S(Q)_p-Y^2$, $-CR^{11}=N-O-R^{12}$, $-C(=NOR^A)-C(=NOR^B)R^C$ and $=N-O-R^{12}$, wherein the C1-C4 alkoxy group, the C2-C4 alkenyloxy group, the C2-C4 alkynyloxy group, the (C1-C3 alkyl) carbonyloxy group and the phenyl group may have one or more halogen atoms.

4. The compound according to claim 3 wherein
$W^2$ represents a C1-C6 chain hydrocarbon group,
each of $R^{15}$ and $R^{16}$, which are identical to or different from each other, independently represents a halogen atom, a C1-C3 alkyl group, a C3-C4 cycloalkyl group or a C1-C3 alkoxy group, wherein the C1-C3 alkyl group, the C3-C4 cycloalkyl group and the C1-C3 alkoxy group may have one or more halogen atoms, the combination of E, G and $Z^1$ represents a combination wherein E represents #—$C(Z^1)$=N—N=$C(Z^3)$—O—$CH_2$— or #—$C(Z^1)$=N—N=$C(Z^3)$—S—$CH_2$—, G represents $R^8$-$T^3$-, $R^9$-$T^4$-, $R^{10}$-$T^5$- or $R^{14}$-$T^6$-, $Z^1$ represents a C1-C6 chain hydrocarbon group, a C3-C6 cycloalkyl group, a C1-C6 alkoxy group, a (C1-C6 alkoxy)C1-C6 alkyl group, a (C1-C6 alkoxy)C1-C6 alkoxy group, a C1-C6 alkylthio group, a (C1-C6 alkylthio)C1-C6 alkyl group, a C1-C6 alkylamino group, a di(C1-C6 alkyl)amino group, a hydrogen atom or a halogen atom, wherein the C1-C6 chain hydrocarbon group, the C3-C6 cycloalkyl group, the C1-C6 alkoxy group, the (C1-C6 alkoxy)C1-C6 alkyl group, the (C1-C6 alkoxy)C1-C6 alkoxy group, the C1-C6 alkylthio group, the (C1-C6 alkylthio)C1-C6 alkyl group, the C1-C6 alkylamino group, the di(C1-C6 alkyl)amino group may have one or more halogen atoms, $Z^2$ represents a C1-C6 chain hydrocarbon group, a C3-C6 cycloalkyl group, a C1-C6 alkoxy group, a (C1-C6 alkoxy)C1-C6 alkyl group, a (C1-C6 alkoxy)C1-C6 alkoxy group, a C1-C6 alkylthio group, a (C1-C6 alkylthio)C1-C6 alkyl group, a C1-C6 alkylamino group, a di(C1-C6 alkyl)amino group, a hydrogen atom or a halogen atom, wherein the C1-C6 chain hydrocarbon group, the C3-C6 cycloalkyl group, the C1-C6 alkoxy group, the (C1-C6 alkoxy)C1-C6 alkyl group, the (C1-C6 alkoxy)C1-C6 alkoxy group, the C1-C6 alkylthio group, the (C1-C6 alkylthio)C1-C6 alkyl group, the C1-C6 alkylamino group and the di(C1-C6 alkyl)amino group may have one or more halogen atoms, and $R^2$ and $R^3$ are a hydrogen atom.

5. The compound according to claim 2 or its N-oxide compound wherein the combination of E, G, $X^1$, $Y^1$ and $Z^1$ represents any combination of the following a to i:

a: a combination wherein E represents #—C($X^1$)($Y^1$)—O—N=C($Z^1$)—, #—C($X^1$)($Y^1$)—S—N=C($Z^1$)—, #—C($X^1$)($Y^1$)—O—N=C($Z^1$)—O—CH$_2$—, #—C($X^1$)($Y^1$)—O—N=C($Z^1$)—S—CH$_2$—, #—C($X^1$)($Y^1$)—S—N=C($Z^1$)—O—CH$_2$—, #—C($X^1$)($Y^1$)—S—N=C($Z^1$)—S—CH$_2$—, #—C($Z^1$)=N—N=C($Z^2$)—, or #—C($X^1$)=C($Y^1$)—C($Z^1$)=N—S—CH$_2$—, G represents a C1-C6 chain hydrocarbon group, a (C1-C6 alkoxy)C1-C6 alkyl group, a (C1-C6 alkylthio)C1-C6 alkyl group, or $R^1$-$T^1$-, wherein the C1-C6 chain hydrocarbon group, the (C1-C6 alkoxy)C1-C6 alkyl group and the (C1-C6 alkylthio)C1-C6 alkyl group may have one or more substituents selected from Group S, each of $X^1$ and $Y^1$, which are independently identical to or different from each other, independently represents a substituent selected from Group T, $Z^1$ represents a substituent selected from Group V;

b: a combination wherein E represents an oxygen atom, #—O—N=C($Z^1$)—C($Z^2$)=N—S—CH$_2$—, #—N=C($Z^1$)—S—CH$_2$—, #—N=C($Z^1$)—O—CH$_2$—, #—O—N=C($Z^1$)—S—CH$_2$—, #—O—N=C($Z^1$)—O—CH$_2$—, #—N($X^1$)—O—CH$_2$—, #—N=C(S$X^3$)—S—CH$_2$—, #—N=C(O$X^3$)—O—CH$_2$—, #—N=C(S$X^3$)—O—CH$_2$— or #—N=C(O$X^3$)—S—CH$_2$—, G represents a C1-C6 chain hydrocarbon group, a (C1-C6 alkoxy)C1-C6 alkyl group, (C1-C6 alkylthio)C1-C6 alkyl group, or $R^1$-$T^2$-, wherein the C1-C6 chain hydrocarbon group, the (C1-C6 alkoxy) C1-C6 alkyl group and the (C1-C6 alkylthio)C1-C6 alkyl group may have one or more substituents selected from Group S, $X^1$ represents a substituent selected from Group T, and $Z^1$ represents a substituent selected from Group V;

c: a combination wherein E represents a sulfur atom, #—S—N=C($Z^1$)—C($Z^2$)=N—O—CH$_2$— or #—S—N=C($Z^1$)—C($Z^2$)=N—S—CH$_2$—, G represents $R^1$-$T^7$-, and $Z^1$ represents a substituent selected from Group V;

d: a combination wherein E represents #—C($Z^1$)=N—N=C($Z^3$)—O—CH$_2$— or #—C($Z^1$)=N—N=C($Z^3$)—S—CH$_2$—, G represents $R^8$-$T^3$-, $R^9$-$T^4$-, $R^{10}$-$T^5$- or $R^{14}$-$T^6$-, and $Z^1$ represents a substituent selected from Group V;

e: a combination wherein E represents #—C($Z^1$)=N—N=C($V^1$)—O—CH$_2$— or #—C($Z^1$)=N—N=C($V^1$)—S—CH$_2$—, G represents $R^1$-$T^1$-, and $Z^1$ represents a substituent selected from Group V;

f: a combination wherein E represents #—C($X^1$)($Y^1$)—O—N=C($Z^1$)—, #—C($X^1$)($Y^1$)—S—N=C($Z^1$)—, #—C($X^1$)($Y^1$)—O—N=C($Z^1$)—O—CH$_2$—, #—C($X^1$)($Y^1$)—O—N=C($Z^1$)—S—CH$_2$—, #—C($X^1$)($Y^1$)—S—N=C($Z^1$)—O—CH$_2$— or #—C($X^1$)($Y^1$)—S—N=C($Z^1$)—S—CH$_2$—, G and $X^1$ together with carbon atoms to which they are bound form a C3-C10 alicyclic hydrocarbon group or a 3 to 10 membered non-aromatic heterocyclic group, wherein the C3-C10 alicyclic hydrocarbon group and the 3 to 10 membered non-aromatic heterocyclic group may have one or more substituents selected from Group J, $Y^1$ represents a substituent selected from Group T, and $Z^1$ represents a substituent selected from Group V;

g: a combination wherein E represents #—C($X^1$)($Y^1$)—O—N=C($Z^1$)—, #—C($X^1$)($Y^1$)—S—N=C($Z^1$)—, #—C($X^1$)($Y^1$)—O—N=C($Z^1$)—O—CH$_2$—, #—C($X^1$)($Y^1$)—O—N=C($Z^1$)—S—CH$_2$—, #—C($X^1$)($Y^1$)—S—N=C($Z^1$)—O—CH$_2$— or #—C($X^1$)($Y^1$)—S—N=C($Z^1$)—S—CH$_2$—, G, $X^1$ and $Y^1$ together with carbon atoms to which they are bound form a C6-C10 aromatic hydrocarbon group or a 5 to 10 membered aromatic heterocyclic group, wherein the C6-C10 aromatic hydrocarbon group and the 5 to 10 membered aromatic heterocyclic group may have one or more substituents selected from Group P, and $Z^1$ represents a substituent selected from Group V;

h: a combination wherein E represents #—C($X^1$)=C($Y^1$)—C($Z^1$)=N—O—CH$_2$—, #—C($X^1$)=C($Y^1$)—C($Z^1$)=N—S—CH$_2$— or #—N($X^1$)—O—CH$_2$—, G and $X^1$ together carbon atoms to which they are bound form a C3-C10 alicyclic hydrocarbon group or a 3 to 10 membered non-aromatic heterocyclic group, wherein the C3-C10 alicyclic hydrocarbon group and the 3 to 10 membered non-aromatic heterocyclic group may have one or more substituents selected from Group J, $Y^1$ represents a substituent selected from Group T, and $Z^1$ represents a substituent selected from Group V; and i: a combination wherein E represents #—C($Z^1$)=N—N=C($Z^3$)—O—CH$_2$—, #—C($Z^1$)=N—N=C($Z^3$)—S—CH$_2$—, #—C($Z^1$)=N—N=C($V^1$)—O—CH$_2$— or #—C($Z^1$)=N—N=C($V^1$)—S—CH$_2$—, G and $Z^1$ together with carbon atoms to which they are bound form a C3-C10 alicyclic hydrocarbon group or a 3 to 10 membered non-aromatic heterocyclic group, wherein the C3-C10 alicyclic hydrocarbon group and the 3 to 10 membered non-aromatic heterocyclic group may have one or more substituents selected from Group U.

6. The compound according to claim 5 wherein $W^2$ represents a C1-C6 chain hydrocarbon group, $R^{15}$ represents a C1-C3 alkyl group which may have one or more halogen atoms, u is 0, E represents #—C($Z^1$)=N—N=C($Z^3$)—O—CH$_2$—, G represents $R^8$-$T^3$-, $Z^1$ represents a C1-C6 chain hydrocarbon group which has one or more halogen atoms, or a hydrogen atom, $T^3$ represents a single bond, $R^8$ represents a furanyl group, a pyrazolyl group, a pyrimidinyl group, a pyrazinyl group, a benzofuranyl group, a benzothienyl group, an indolyl group, an indazolyl group, a benzimidazolyl group, a benzothiazolyl group, a benzoxazolyl group, a dihydrobenzofuranyl group, a quinolyl group, a quinoxalinyl group, a tetrahydronaphthyl group, an indanyl group, a 1,3-benzodioxolyl group, an oxazolopyridyl group, a thiazolopyridyl group, an isoxazolopyridyl group, an isothiazolopyridyl group, a tetrahydroindazoly group, a cyclopentapyrazolyl group, or —$CR^{11}$=N—O—$R^{12}$, wherein the furanyl group, the pyrazolyl group, the pyrimidinyl group, the pyrazinyl group, the benzofuranyl group, the benzothienyl group, the indolyl group, the indazolyl group, the benzimidazolyl group, the benzothiazolyl group, the benzoxazolyl group, the dihydrobenzofuranyl group, the quinolyl group, the quinoxalinyl group, the tetrahydronaphthyl group, the indanyl group, the 1,3-benzodioxolyl group, the oxazolopyridyl group, the thiazolopyridyl group, the isoxazolopyridyl group, the isothiazolopyridyl group, the tetrahydroindazoly group and the cyclopentapyrazolyl group may have one or more substituents selected from the group consisting of a C1-C6 chain hydrocarbon group which may have one or more halogen atoms and a halogen atom, $R^{11}$ represents a C1-C6 alkyl group, $R^{12}$ represents a benzyl group, a C1-C6 chain hydrocarbon group, a C3-C6 cycloalkyl group, a (C1-C6 alkoxy)C2-C6 alkyl group, a cyano(C1-C6 alkyl) group, or a hydrogen atom, wherein the benzyl group may have one or more substituents selected from the group consisting of C1-C6 alkyl group and C1-C6 alkoxy group, and wherein the C1-C6 chain hydrocarbon group, the C3-C6 cycloalkyl group, the (C1-C6 alkoxy)C2-C6 alkyl group and the cyano(C1-C6 alkyl) group may have one or more halogen atoms, and $Z^3$ represents a C1-C6 chain hydrocarbon group which may have one or more halogen atoms.

7. The compound according to claim 5 wherein
$W^2$ represents a C1-C6 chain hydrocarbon group,
$R^{15}$ represents a C1-C3 alkyl group which may have one or more halogen atoms, a C3-C6 cycloalkyl group, a C1-C6 alkoxy group, or halogen atom,
u is 0,
E represents #—C($Z^1$)=N—N=C($Z^3$)—O—$CH_2$—,
G and $Z^1$ together with carbon atoms to which they are bound form a C3-C10 alicyclic hydrocarbon group or a 3 to 10 membered non-aromatic heterocyclic group, wherein the C3-C10 alicyclic hydrocarbon group and the 3 to 10 membered non-aromatic heterocyclic group may have one or more substituents selected from Group U, and
$Z^3$ represents a C1-C6 chain hydrocarbon group which may have one or more halogen atoms.

8. The compound according to claim 5 wherein
$W^2$ represents a C1-C6 chain hydrocarbon group,
$R^{15}$ represents a C1-C3 alkyl group which may have one or more halogen atoms,
u is 0,
E represents #—N=C($Z^1$)—S—$CH_2$—,
G represents a C1-C6 chain hydrocarbon group which may have one or more substituents selected from Group S or $R^1$-$T^2$-, $Z^1$ represents a C1-C6 alkylthio group, $T^2$ represents a single bond or —$(CR^2R^3)_n$—, $R^1$ represents a tetrahydrofuranyl group, a tetrahydropyranyl group, a cyclopentyl group, a phenyl group, a pyrazolyl group, a benzoxazolyl group, a benzothiazolyl group or an isoxazolopyridyl group, wherein the tetrahydrofuranyl group, the tetrahydropyranyl group, the cyclopentyl group, the phenyl group, the pyrazolyl group, the benzoxazolyl group, the benzothiazolyl group and the isoxazolopyridyl group may have one or more substituents selected from Group P, n is 1 or 2, and $R^2$ and $R^3$ represent hydrogen atoms.

9. The compound according to claim 1 wherein
$R^{15}$ represents a halogen atom, a methyl group, a cyclopropyl group or a methoxy group,
$W^2$ represents a methyl group,
$W^1$ represents an oxygen atom,
u is 0,
E represents #—C($Z^1$)=N—N=C($Z^3$)—O—$CH_2$—,
$Z^3$ represents an ethyl group,
G and $Z^1$ together with carbon atoms to which they are bound form an indan-1-ylidene group, a 1,2,3,4-tetrahydronaphthalen-1-ylidene group, a 2,3-dihydrobenzofuran-3-ylidene group, a 3,4-dihydro-2H-1-benzopyran-4-ylidene group, or a 3,4-dihydro-2H-1-benzothiopyran-4-ylidene group, wherein the indan-1-ylidene group, the 1,2,3,4-tetrahydronaphthalen-1-ylidene group, the 2,3-dihydrobenzofuran-3-ylidene group, and the 3,4-dihydro-2H-1-benzopyran-4-ylidene group may have one or more substituents selected from the group consisting of a halogen atom, a C1-C3 alkyl group which may have one or more halogen atoms, and a C1-C3 alkoxy group which may have one or more halogen atoms, and wherein the 3,4-dihydro-2H-1-benzothiopyran-4-ylidene group may have one or more substituents selected from the group consisting of an oxo group, a halogen atom, a C1-C3 alkyl group which may have one or more halogen atoms, and a C1-C3 alkoxy group which may have one or more halogen atoms.

10. The compound according to claim 1 wherein
$W^1$ represents an oxygen atom,
$W^2$ represents a methyl group,
u is 0,
$R^{15}$ represents a halogen atom, a methyl group, a cyclopropyl group or a methoxy group,
E represents #—C($Z^1$)=N—N=C($Z^3$)—O—$CH_2$—,
G represents $R^8$-$T^3$-,
$Z^1$ represents a C1-C3 alkyl group,
$Z^3$ represents a C1-C3 alkyl group,
$T^3$ represents a single bond,
$R^8$ represents a furanyl group, a pyrazolyl group, a pyrimidinyl group, a pyrazinyl group, a benzofuranyl group, a benzothienyl group, an indolyl group, an indazolyl group, a benzimidazolyl group, a benzothiazolyl group, a benzoxazolyl group, a dihydrobenzofuranyl group, a quinolyl group, a quinoxalinyl group, a tetrahydronaphthyl group, an indanyl group, a 1,3-benzodioxolyl group, a pyrrolopyridyl group, or —$CR^{11}$=N—O—$R^{12}$, wherein the furanyl group, the pyrazolyl group, the pyrimidinyl group, the pyrazinyl group, the benzofuranyl group, the benzothienyl group, the indolyl group, the indazolyl group, the benzimidazolyl group, the benzothiazolyl group, the benzoxazolyl group, the dihydrobenzofuranyl group, the quinolyl group, the quinoxalinyl group, the tetrahydronaphthyl group, the indanyl group, the 1,3-benzodioxolyl group, and the pyrrolopyridyl group may have one or more substituents selected from the group consisting of C1-C6 chain hydrocarbon group which may have one or more halogen atoms, a (C1-C3alkoxy)C1-C3 alkyl group, and a halogen atom, $R^{11}$ represents a C1-C3 alkyl group, and $R^{12}$ represents a benzyl group, a C1-C6 chain hydrocarbon group, a (C3-C6 cycloalkyl)C1-C3 alkyl group, a (C1-C3 alkoxy)C2-C3 alkyl group, a (C1-C3 alkylthio)C1-C3 alkyl group, a cyano(C1-C6 alkyl) group or a hydrogen atom, wherein the benzyl group may have one or more substituents selected from the group consisting of a halogen atom, a C1-C6 alkyl group, and a C1-C6 alkoxy group.

11. An agent for controlling a pest, said agent comprises the compound according to claim 1.

12. A composition comprising the compound according to claim 1 and one or more ingredients selected from the group consisting of a nematode control ingredient, a plant growth regulating ingredient, and other pest control ingredient.

13. A method for controlling a pest, said method comprises applying an effective amount of the compound according to claim 1 to plant or soil.

\* \* \* \* \*